(12) United States Patent
Dehesh et al.

(10) Patent No.: US 6,770,465 B1
(45) Date of Patent: Aug. 3, 2004

(54) ENGINEERING B-KETOACYL ACP SYNTHASE FOR NOVEL SUBSTRATE SPECIFICITY

(75) Inventors: Katayoon Dehesh, Vacaville, CA (US); Dale Val, Woodland, CA (US)

(73) Assignee: Calgene LLC, Davis California, CA (US)

( * ) Notice: Subject to any disclaimer, the term of this patent is extended or adjusted under 35 U.S.C. 154(b) by 0 days.

(21) Appl. No.: 09/591,279

(22) Filed: Jun. 9, 2000

Related U.S. Application Data

(60) Provisional application No. 60/138,308, filed on Jun. 9, 1999.

(51) Int. Cl.[7] .................................................. C12N 9/10
(52) U.S. Cl. ...................................................... 435/193
(58) Field of Search ........................................ 435/193

(56) References Cited

FOREIGN PATENT DOCUMENTS

| WO | WO 96/36719 | 11/1996 |
|---|---|---|
| WO | WO 98/46776 | 10/1998 |

OTHER PUBLICATIONS

Chothia (1984) Ann Rev Biochem 53:537–572.*
Weijun, H. et al., "Crystal structure of β–ketoacyl–acyl carrier protein synthase II from *E. coli* reveals the molecular architecture of condensing enzymes" The EMBO, 17(5): 1183–1191, (1998).
Val, D. et al. "Re–engineering ketoacyl synthase specificity" Structure, 8(6): 565–566, (2000).
International Search Report for International Application No. PCT/US00/16151, (mailed Jan. 24, 2001).
Structure of the Complex between the Antibiotic Cerulenin and Its Target, ⊖–Kketoacyl–Acyl Carrier Protein Synthase; M. Moche, et al.; The Journal of Biological Chemistry, vol. 274, No. 10, pp. 6031–3034 (Mar. 5, 1999).
A Cuphea β–ketoacyl–ACP synthase shifts the synthesis of fatty acids towards shorter chains in Arabidopsis seeds expressing Cuphea FatB thioesterases; Jeffrey M. Leonard, et al.; The Plant Journal (1998) 13(5) pp. 621–628, (1998).
Kas IV: a 3–ketoacyl–ACP synthase from Cuphea sp. is a medium chain specific condensing enzyme; Katayoon Dehesh, et al.; The Plant Journal 15(3), pp. 383–390, (1998).
Cloning of the fabF gene in an expression vector and in vitro characterization of recombinant fabF and fabB encoded enzymes from *Escherichia coli*; Patricia Edwards, et al.; FEBS Letters 402 pp. 62–66 (1997).
Conversion of a β–Ketoacyl Synthase to a Malonyl Decarboxylase by Replacement of the Active–Site Cysteine with Glutamine; Andrzej Witkowski, et al.; Biochemistry 38, pp. 11643–11650, (aug. 18, 1999).
Reaction mechanism of recombinant 3–oxoacyl–(acyl–carrier–protein) synthase III from Cuphea wrightii enbryo, a fatty acid synthase type II condensing enzyme; Amine Abbadi, et al.; Blochem J. 345, pp. 153–160 (2000).

* cited by examiner

*Primary Examiner*—Rebecca E. Prouty
*Assistant Examiner*—David J. Steadman
(74) *Attorney, Agent, or Firm*—Thomas McBride; Arnold & Porter LLP

(57) ABSTRACT

Methods of altering substrate specificity of beta-ketoacyl-ACP synthase, and engineered beta-ketoacyl-ACP synthases so produced are provided. DNA sequences and constructs for expression of engineered beta-ketoacyl-ACP synthases, as well as the novel beta-ketoacyl-ACP synthases produced therefrom are also provided. Such DNA sequences may be used for expression of the engineered beta-ketoacyl-ACP synthases in host cells, particularly seed cells of oilseed crop plants, for the modification of fatty acid composition.

54 Claims, 113 Drawing Sheets

| | | | | | | | | |
|---|---|---|---|---|---|---|---|---|
| CB | LYS | A | 2 | 5.613 | -3.324 | 2.834 | 1.00 | 59.14 | 6 |
| C | LYS | A | 2 | 6.322 | -2.753 | 4.050 | 1.00 | 61.37 | 6 |
| C | LYS | A | 2 | 5.431 | -1.783 | 4.810 | 1.00 | 63.79 | 6 |
| CE | LYS | A | 2 | 5.988 | -0.370 | 4.758 | 1.00 | 65.75 | 6 |
| NZ | LYS | A | 2 | 6.107 | 0.235 | 6.114 | 1.00 | 67.05 | 7 |
| C | LYS | A | 2 | 7.506 | -2.721 | 1.297 | 1.00 | 54.28 | 6 |
| O | LYS | A | 2 | 8.092 | -3.798 | 1.180 | 1.00 | 55.04 | 8 |
| N | LYS | A | 2 | 5.283 | -3.329 | 0.369 | 1.00 | 55.75 | 7 |
| CA | LYS | A | 2 | 5.997 | -2.678 | 1.505 | 1.00 | 55.55 | 6 |
| N | ARG | A | 3 | 8.133 | -1.550 | 1.248 | 1.00 | 51.95 | 7 |
| CA | ARG | A | 3 | 9.568 | -1.460 | 1.019 | 1.00 | 49.09 | 6 |
| CB | ARG | A | 3 | 9.832 | -0.701 | -0.286 | 1.00 | 45.74 | 6 |
| C | ARG | A | 3 | 9.634 | -1.551 | -1.531 | 1.00 | 42.70 | 6 |
| C | ARG | A | 3 | 9.283 | -0.696 | -2.736 | 1.00 | 39.77 | 6 |
| N | ARG | A | 3 | 10.401 | 0.132 | -3.168 | 1.00 | 37.67 | 7 |
| CZ | ARG | A | 3 | 11.302 | -0.211 | -4.077 | 1.00 | 38.43 | 6 |
| N | ARG | A | 3 | 11.252 | -1.395 | -4.674 | 1.00 | 36.91 | 7 |
| N | ARG | A | 3 | 12.270 | 0.640 | -4.395 | 1.00 | 39.50 | 7 |
| C | ARG | A | 3 | 10.314 | -0.795 | 2.167 | 1.00 | 47.74 | 6 |
| O | ARG | A | 3 | 10.086 | 0.368 | 2.498 | 1.00 | 48.18 | 8 |
| N | ARG | A | 4 | 11.236 | -1.548 | 2.759 | 1.00 | 45.69 | 7 |
| CA | ARG | A | 4 | 12.030 | -1.079 | 3.884 | 1.00 | 43.14 | 6 |
| CB | ARG | A | 4 | 12.459 | -2.265 | 4.753 | 1.00 | 45.59 | 6 |
| C | ARG | A | 4 | 11.299 | -3.046 | 5.351 | 1.00 | 49.39 | 6 |
| C | ARG | A | 4 | 11.719 | -4.453 | 5.750 | 1.00 | 52.07 | 6 |
| N | ARG | A | 4 | 12.975 | -4.463 | 6.482 | 1.00 | 56.09 | 7 |
| CZ | ARG | A | 4 | 13.402 | -5.394 | 7.320 | 1.00 | 57.45 | 6 |
| N | ARG | A | 4 | 12.671 | -6.469 | 7.583 | 1.00 | 58.72 | 7 |
| N | ARG | A | 4 | 14.583 | -5.250 | 7.911 | 1.00 | 58.03 | 7 |
| C | ARG | A | 4 | 13.258 | -0.297 | 3.435 | 1.00 | 40.93 | 6 |
| O | ARG | A | 4 | 13.873 | -0.605 | 2.416 | 1.00 | 40.28 | 8 |
| N | VAL | A | 5 | 13.590 | 0.744 | 4.194 | 1.00 | 38.82 | 7 |
| CA | VAL | A | 5 | 14.729 | 1.598 | 3.891 | 1.00 | 37.38 | 6 |
| CB | VAL | A | 5 | 14.346 | 3.087 | 3.796 | 1.00 | 36.10 | 6 |
| C | VAL | A | 5 | 15.533 | 3.916 | 3.320 | 1.00 | 33.72 | 6 |
| C | VAL | A | 5 | 13.154 | 3.308 | 2.877 | 1.00 | 36.27 | 6 |
| C | VAL | A | 5 | 15.816 | 1.453 | 4.953 | 1.00 | 36.82 | 6 |
| O | VAL | A | 5 | 15.549 | 1.542 | 6.151 | 1.00 | 36.76 | 8 |
| N | VAL | A | 6 | 17.046 | 1.229 | 4.506 | 1.00 | 36.09 | 7 |
| CA | VAL | A | 6 | 18.188 | 1.076 | 5.394 | 1.00 | 35.35 | 6 |
| CB | VAL | A | 6 | 18.784 | -0.343 | 5.351 | 1.00 | 34.87 | 6 |
| C | VAL | A | 6 | 17.864 | -1.358 | 6.013 | 1.00 | 34.92 | 6 |
| C | VAL | A | 6 | 19.087 | -0.767 | 3.921 | 1.00 | 33.83 | 6 |
| C | VAL | A | 6 | 19.280 | 2.084 | 5.044 | 1.00 | 35.02 | 6 |
| O | VAL | A | 6 | 19.291 | 2.649 | 3.954 | 1.00 | 34.67 | 8 |
| N | VAL | A | 7 | 20.190 | 2.324 | 5.981 | 1.00 | 35.45 | 7 |
| CA | VAL | A | 7 | 21.298 | 3.256 | 5.781 | 1.00 | 34.76 | 6 |
| CB | VAL | A | 7 | 21.519 | 4.143 | 7.016 | 1.00 | 34.20 | 6 |
| C | VAL | A | 7 | 22.549 | 5.229 | 6.736 | 1.00 | 35.28 | 6 |
| C | VAL | A | 7 | 20.207 | 4.769 | 7.474 | 1.00 | 33.35 | 6 |
| C | VAL | A | 7 | 22.567 | 2.474 | 5.464 | 1.00 | 34.53 | 6 |
| O | VAL | A | 7 | 23.042 | 1.691 | 6.287 | 1.00 | 34.58 | 8 |
| N | THR | A | 8 | 23.109 | 2.663 | 4.264 | 1.00 | 34.21 | 7 |
| CA | THR | A | 8 | 24.292 | 1.941 | 3.833 | 1.00 | 33.29 | 6 |
| CB | THR | A | 8 | 24.005 | 1.203 | 2.496 | 1.00 | 32.59 | 6 |
| O | THR | A | 8 | 23.817 | 2.189 | 1.470 | 1.00 | 33.02 | 8 |
| C | THR | A | 8 | 22.787 | 0.308 | 2.579 | 1.00 | 29.02 | 6 |
| C | THR | A | 8 | 25.539 | 2.774 | 3.600 | 1.00 | 33.18 | 6 |
| O | THR | A | 8 | 26.490 | 2.253 | 3.004 | 1.00 | 33.39 | 8 |
| N | GLY | A | 9 | 25.560 | 4.034 | 4.005 | 1.00 | 33.20 | 7 |
| CA | GLY | A | 9 | 26.733 | 4.875 | 3.757 | 1.00 | 32.15 | 6 |
| C | GLY | A | 9 | 26.610 | 6.183 | 4.523 | 1.00 | 31.83 | 6 |
| O | GLY | A | 9 | 25.543 | 6.795 | 4.564 | 1.00 | 30.94 | 8 |
| N | LEU | A | 1 | 27.702 | 6.580 | 5.174 | 1.00 | 31.18 | 7 |

| | | | | | | | | |
|---|---|---|---|---|---|---|---|---|
| CA | LEU | A | 1 | 27.715 | 7.796 | 5.976 | 1.00 | 30.88 | 6 |
| CB | LEU | A | 1 | 27.832 | 7.470 | 7.465 | 1.00 | 30.95 | 6 |
| C | LEU | A | 1 | 26.817 | 6.517 | 8.091 | 1.00 | 31.61 | 6 |
| C | LEU | A | 1 | 27.194 | 6.187 | 9.528 | 1.00 | 32.70 | 6 |
| C | LEU | A | 1 | 25.410 | 7.097 | 8.027 | 1.00 | 30.96 | 6 |
| C | LEU | A | 1 | 28.367 | 8.701 | 5.557 | 1.00 | 30.32 | 6 |
| O | LEU | A | 1 | 29.922 | 8.221 | 5.142 | 1.00 | 31.20 | 8 |
| N | GLY | A | 1 | 28.660 | 10.006 | 5.668 | 1.00 | 29.75 | 7 |
| CA | GLY | A | 1 | 29.701 | 10.970 | 5.306 | 1.00 | 29.27 | 6 |
| C | GLY | A | 1 | 29.422 | 12.296 | 6.007 | 1.00 | 28.70 | 6 |
| O | GLY | A | 1 | 28.260 | 12.602 | 6.284 | 1.00 | 28.60 | 8 |
| N | MET | A | 1 | 30.471 | 13.052 | 6.317 | 1.00 | 28.95 | 7 |
| CA | MET | A | 1 | 30.279 | 14.332 | 6.974 | 1.00 | 28.89 | 6 |
| CB | MET | A | 1 | 29.500 | 14.156 | 8.282 | 1.00 | 31.91 | 6 |
| C | MET | A | 1 | 30.318 | 14.051 | 9.554 | 1.00 | 34.60 | 6 |
| SD | MET | A | 1 | 29.290 | 14.107 | 11.033 | 1.00 | 35.65 | 1 |
| CE | MET | A | 1 | 29.116 | 12.360 | 11.381 | 1.00 | 37.75 | 6 |
| C | MET | A | 1 | 31.547 | 15.130 | 7.258 | 1.00 | 28.38 | 6 |
| O | MET | A | 1 | 32.668 | 14.671 | 7.402 | 1.00 | 27.81 | 8 |
| N | LEU | A | 1 | 31.299 | 16.426 | 7.387 | 1.00 | 27.53 | 7 |
| CA | LEU | A | 1 | 32.257 | 17.446 | 7.762 | 1.00 | 27.49 | 6 |
| CB | LEU | A | 1 | 32.577 | 18.409 | 6.630 | 1.00 | 29.94 | 6 |
| C | LEU | A | 1 | 33.334 | 17.830 | 5.431 | 1.00 | 32.91 | 6 |
| C | LEU | A | 1 | 33.043 | 18.630 | 4.173 | 1.00 | 33.46 | 6 |
| C | LEU | A | 1 | 34.828 | 17.784 | 5.721 | 1.00 | 33.17 | 6 |
| C | LEU | A | 1 | 31.597 | 18.185 | 8.933 | 1.00 | 27.03 | 6 |
| O | LEU | A | 1 | 30.438 | 18.586 | 8.823 | 1.00 | 26.86 | 8 |
| N | SER | A | 1 | 32.312 | 18.320 | 10.034 | 1.00 | 27.31 | 7 |
| CA | SER | A | 1 | 31.761 | 18.998 | 11.205 | 1.00 | 28.03 | 6 |
| CB | SER | A | 1 | 31.153 | 17.968 | 12.155 | 1.00 | 28.80 | 6 |
| O | SER | A | 1 | 32.095 | 17.519 | 13.112 | 1.00 | 31.76 | 8 |
| C | SER | A | 1 | 32.860 | 19.787 | 11.895 | 1.00 | 28.55 | 6 |
| O | SER | A | 1 | 34.043 | 19.612 | 11.612 | 1.00 | 28.57 | 8 |
| N | PRO | A | 1 | 32.488 | 20.594 | 12.880 | 1.00 | 29.49 | 7 |
| C | PRO | A | 1 | 31.084 | 20.865 | 13.288 | 1.00 | 29.61 | 6 |
| CA | PRO | A | 1 | 33.426 | 21.371 | 13.665 | 1.00 | 29.78 | 6 |
| CB | PRO | A | 1 | 32.547 | 22.264 | 14.535 | 1.00 | 29.65 | 6 |
| C | PRO | A | 1 | 31.201 | 22.240 | 13.902 | 1.00 | 29.56 | 6 |
| C | PRO | A | 1 | 34.379 | 20.543 | 14.509 | 1.00 | 30.22 | 6 |
| O | PRO | A | 1 | 35.409 | 21.090 | 14.924 | 1.00 | 30.34 | 8 |
| N | VAL | A | 1 | 34.099 | 19.277 | 14.817 | 1.00 | 30.78 | 7 |
| CA | VAL | A | 1 | 35.023 | 18.464 | 15.592 | 1.00 | 31.66 | 6 |
| CB | VAL | A | 1 | 34.400 | 17.804 | 16.836 | 1.00 | 31.11 | 6 |
| C | VAL | A | 1 | 34.067 | 18.850 | 17.890 | 1.00 | 32.88 | 6 |
| C | VAL | A | 1 | 33.175 | 16.980 | 16.477 | 1.00 | 31.36 | 6 |
| C | VAL | A | 1 | 35.695 | 17.376 | 14.761 | 1.00 | 32.04 | 6 |
| O | VAL | A | 1 | 36.346 | 16.500 | 15.340 | 1.00 | 33.52 | 8 |
| N | GLY | A | 1 | 35.563 | 17.410 | 13.440 | 1.00 | 31.84 | 7 |
| CA | GLY | A | 1 | 36.197 | 16.390 | 12.612 | 1.00 | 31.47 | 6 |
| C | GLY | A | 1 | 35.809 | 16.494 | 11.146 | 1.00 | 31.36 | 6 |
| O | GLY | A | 1 | 34.696 | 16.904 | 10.817 | 1.00 | 31.58 | 8 |
| N | ASN | A | 1 | 36.727 | 16.101 | 10.269 | 1.00 | 30.64 | 7 |
| CA | ASN | A | 1 | 36.512 | 16.147 | 8.833 | 1.00 | 30.14 | 6 |
| CB | ASN | A | 1 | 37.798 | 16.560 | 8.113 | 1.00 | 35.19 | 6 |
| C | ASN | A | 1 | 37.969 | 18.057 | 7.977 | 1.00 | 40.02 | 6 |
| O | ASN | A | 1 | 37.973 | 18.798 | 8.961 | 1.00 | 43.84 | 8 |
| N | ASN | A | 1 | 38.133 | 18.535 | 6.748 | 1.00 | 43.10 | 7 |
| C | ASN | A | 1 | 36.017 | 14.824 | 8.269 | 1.00 | 29.28 | 6 |
| O | ASN | A | 1 | 35.843 | 14.691 | 7.058 | 1.00 | 28.86 | 8 |
| N | THR | A | 1 | 35.881 | 13.805 | 9.104 | 1.00 | 29.33 | 7 |
| CA | THR | A | 1 | 35.345 | 12.514 | 8.721 | 1.00 | 28.83 | 6 |
| CB | THR | A | 1 | 36.381 | 11.377 | 8.653 | 1.00 | 27.69 | 6 |
| O | THR | A | 1 | 37.050 | 11.283 | 9.920 | 1.00 | 29.59 | 8 |
| C | THR | A | 1 | 37.397 | 11.575 | 7.548 | 1.00 | 25.58 | 6 |

Figure 1 - 1

| | | | | | | | | |
|---|---|---|---|---|---|---|---|---|
| C | THR | A | 1 | 34.289 | 12.077 | 9.743 | 1.00 | 29.04 | 6 |
| O | THR | A | 1 | 34.219 | 12.625 | 10.840 | 1.00 | 28.85 | 8 |
| N | VAL | A | 2 | 33.567 | 11.013 | 9.417 | 1.00 | 29.52 | 7 |
| CA | VAL | A | 2 | 32.555 | 10.474 | 10.309 | 1.00 | 30.11 | 6 |
| CB | VAL | A | 2 | 31.750 | 9.352 | 9.621 | 1.00 | 28.43 | 6 |
| C | VAL | A | 2 | 30.737 | 8.721 | 10.564 | 1.00 | 26.35 | 6 |
| C | VAL | A | 2 | 31.036 | 9.898 | 8.392 | 1.00 | 27.62 | 6 |
| C | VAL | A | 2 | 33.145 | 9.945 | 11.609 | 1.00 | 31.80 | 6 |
| O | VAL | A | 2 | 32.732 | 10.364 | 12.694 | 1.00 | 33.28 | 8 |
| N | GLU | A | 2 | 34.091 | 9.018 | 11.517 | 1.00 | 32.42 | 7 |
| CA | GLU | A | 2 | 34.703 | 8.414 | 12.692 | 1.00 | 32.57 | 6 |
| CB | GLU | A | 2 | 35.592 | 7.234 | 12.281 | 1.00 | 34.30 | 6 |
| C | GLU | A | 2 | 34.850 | 6.105 | 11.590 | 1.00 | 36.61 | 6 |
| C | GLU | A | 2 | 33.863 | 5.361 | 12.464 | 1.00 | 39.00 | 6 |
| O | GLU | A | 2 | 33.912 | 5.510 | 13.703 | 1.00 | 40.93 | 8 |
| O | GLU | A | 2 | 33.025 | 4.607 | 11.919 | 1.00 | 39.19 | 8 |
| C | GLU | A | 2 | 35.463 | 9.390 | 13.571 | 1.00 | 32.34 | 6 |
| O | GLU | A | 2 | 35.245 | 9.391 | 14.789 | 1.00 | 33.10 | 8 |
| N | SER | A | 2 | 36.257 | 10.293 | 13.005 | 1.00 | 32.05 | 7 |
| CA | SER | A | 2 | 36.967 | 11.289 | 13.805 | 1.00 | 31.37 | 6 |
| CB | SER | A | 2 | 37.958 | 12.083 | 12.967 | 1.00 | 31.88 | 6 |
| O | SER | A | 2 | 37.334 | 12.786 | 11.911 | 1.00 | 33.76 | 8 |
| C | SER | A | 2 | 35.977 | 12.193 | 14.529 | 1.00 | 31.48 | 6 |
| O | SER | A | 2 | 36.173 | 12.531 | 15.698 | 1.00 | 31.98 | 8 |
| N | THR | A | 2 | 34.896 | 12.578 | 13.854 | 1.00 | 30.90 | 7 |
| CA | THR | A | 2 | 33.856 | 13.404 | 14.459 | 1.00 | 29.81 | 6 |
| CB | THR | A | 2 | 32.767 | 13.788 | 13.444 | 1.00 | 24.78 | 6 |
| O | THR | A | 2 | 33.249 | 14.853 | 12.614 | 1.00 | 25.56 | 8 |
| C | THR | A | 2 | 31.476 | 14.246 | 14.101 | 1.00 | 21.14 | 6 |
| C | THR | A | 2 | 33.215 | 12.612 | 15.601 | 1.00 | 30.00 | 6 |
| O | THR | A | 2 | 32.971 | 13.147 | 16.681 | 1.00 | 30.39 | 8 |
| N | TRP | A | 2 | 32.902 | 11.346 | 15.337 | 1.00 | 30.23 | 7 |
| CA | TRP | A | 2 | 32.277 | 10.472 | 16.324 | 1.00 | 31.17 | 6 |
| CB | TRP | A | 2 | 31.999 | 9.093 | 15.721 | 1.00 | 29.55 | 6 |
| C | TRP | A | 2 | 31.238 | 8.158 | 16.610 | 1.00 | 28.53 | 6 |
| C | TRP | A | 2 | 30.034 | 8.432 | 17.335 | 1.00 | 27.77 | 6 |
| CE | TRP | A | 2 | 29.687 | 7.260 | 18.035 | 1.00 | 27.44 | 6 |
| CE | TRP | A | 2 | 29.215 | 9.558 | 17.462 | 1.00 | 27.56 | 6 |
| C | TRP | A | 2 | 31.562 | 6.861 | 16.892 | 1.00 | 28.80 | 6 |
| N | TRP | A | 2 | 30.635 | 6.314 | 17.746 | 1.00 | 27.92 | 7 |
| CZ | TRP | A | 2 | 28.560 | 7.180 | 18.849 | 1.00 | 27.07 | 6 |
| CZ | TRP | A | 2 | 28.096 | 9.478 | 18.269 | 1.00 | 26.86 | 6 |
| C | TRP | A | 2 | 27.776 | 8.295 | 18.952 | 1.00 | 27.23 | 6 |
| C | TRP | A | 2 | 33.115 | 10.362 | 17.592 | 1.00 | 31.45 | 6 |
| O | TRP | A | 2 | 32.600 | 10.554 | 18.694 | 1.00 | 30.70 | 8 |
| N | LYS | A | 2 | 34.404 | 10.082 | 17.456 | 1.00 | 32.86 | 7 |
| CA | LYS | A | 2 | 35.321 | 9.952 | 18.576 | 1.00 | 34.03 | 6 |
| CB | LYS | A | 2 | 36.713 | 9.523 | 18.097 | 1.00 | 39.21 | 6 |
| C | LYS | A | 2 | 36.744 | 8.185 | 17.377 | 1.00 | 44.28 | 6 |
| C | LYS | A | 2 | 38.175 | 7.756 | 17.083 | 1.00 | 48.38 | 6 |
| CE | LYS | A | 2 | 38.218 | 6.354 | 16.497 | 1.00 | 50.26 | 6 |
| NZ | LYS | A | 2 | 39.243 | 5.508 | 17.170 | 1.00 | 53.04 | 7 |
| C | LYS | A | 2 | 35.456 | 11.231 | 19.393 | 1.00 | 33.60 | 6 |
| O | LYS | A | 2 | 35.500 | 11.178 | 20.626 | 1.00 | 33.43 | 8 |
| N | ALA | A | 2 | 35.493 | 12.381 | 18.727 | 1.00 | 32.92 | 7 |
| CA | ALA | A | 2 | 35.574 | 13.661 | 19.422 | 1.00 | 33.42 | 6 |
| CB | ALA | A | 2 | 35.802 | 14.794 | 18.433 | 1.00 | 32.19 | 6 |
| C | ALA | A | 2 | 34.331 | 13.912 | 20.267 | 1.00 | 33.95 | 6 |
| O | ALA | A | 2 | 34.435 | 14.413 | 21.390 | 1.00 | 34.63 | 8 |
| N | LEU | A | 2 | 33.159 | 13.541 | 19.765 | 1.00 | 34.18 | 7 |
| CA | LEU | A | 2 | 31.909 | 13.718 | 20.487 | 1.00 | 34.55 | 6 |
| CB | LEU | A | 2 | 30.710 | 13.432 | 19.585 | 1.00 | 33.95 | 6 |
| C | LEU | A | 2 | 30.303 | 14.460 | 18.534 | 1.00 | 34.29 | 6 |
| C | LEU | A | 2 | 28.879 | 14.174 | 18.065 | 1.00 | 34.02 | 6 |

| | | | | | | | | |
|---|---|---|---|---|---|---|---|---|
| C | LEU | A | 2 | 30.408 | 15.892 | 19.038 | 1.00 | 32.71 | 6 |
| C | LEU | A | 2 | 31.823 | 12.851 | 21.736 | 1.00 | 35.01 | 6 |
| O | LEU | A | 2 | 31.378 | 13.316 | 22.788 | 1.00 | 35.64 | 8 |
| N | LEU | A | 2 | 32.230 | 11.605 | 21.655 | 1.00 | 35.18 | 7 |
| CA | LEU | A | 2 | 32.268 | 10.706 | 22.804 | 1.00 | 35.06 | 6 |
| CB | LEU | A | 2 | 32.555 | 9.268 | 22.371 | 1.00 | 32.51 | 6 |
| C | LEU | A | 2 | 31.525 | 8.585 | 21.467 | 1.00 | 29.72 | 6 |
| C | LEU | A | 2 | 31.961 | 7.165 | 21.133 | 1.00 | 26.45 | 6 |
| C | LEU | A | 2 | 30.142 | 8.573 | 22.099 | 1.00 | 26.27 | 6 |
| C | LEU | A | 2 | 33.238 | 11.148 | 23.891 | 1.00 | 35.21 | 6 |
| O | LEU | A | 2 | 32.966 | 10.952 | 25.078 | 1.00 | 36.74 | 8 |
| N | ALA | A | 2 | 34.305 | 11.857 | 23.540 | 1.00 | 34.68 | 7 |
| CA | ALA | A | 2 | 35.256 | 12.404 | 24.490 | 1.00 | 34.38 | 6 |
| CB | ALA | A | 2 | 36.650 | 12.454 | 23.870 | 1.00 | 33.09 | 6 |
| C | ALA | A | 2 | 34.873 | 13.794 | 24.980 | 1.00 | 34.57 | 6 |
| O | ALA | A | 2 | 35.624 | 14.411 | 25.741 | 1.00 | 35.34 | 8 |
| N | GLY | A | 2 | 33.741 | 14.327 | 24.544 | 1.00 | 34.34 | 7 |
| CA | GLY | A | 3 | 33.263 | 15.629 | 24.953 | 1.00 | 34.46 | 6 |
| C | GLY | A | 3 | 34.078 | 16.803 | 24.446 | 1.00 | 34.66 | 6 |
| O | GLY | A | 3 | 34.082 | 17.863 | 25.078 | 1.00 | 34.44 | 8 |
| N | GLN | A | 3 | 34.706 | 16.668 | 23.283 | 1.00 | 35.27 | 7 |
| CA | GLN | A | 3 | 35.474 | 17.757 | 22.699 | 1.00 | 36.10 | 6 |
| CB | GLN | A | 3 | 36.455 | 17.223 | 21.654 | 1.00 | 40.70 | 6 |
| C | GLN | A | 3 | 37.617 | 16.445 | 22.243 | 1.00 | 46.29 | 6 |
| C | GLN | A | 3 | 38.581 | 15.895 | 21.215 | 1.00 | 48.06 | 6 |
| O | GLN | A | 3 | 38.706 | 16.408 | 20.103 | 1.00 | 48.24 | 8 |
| N | GLN | A | 3 | 39.286 | 14.828 | 21.588 | 1.00 | 49.02 | 7 |
| C | GLN | A | 3 | 34.557 | 18.808 | 22.078 | 1.00 | 36.01 | 6 |
| O | GLN | A | 3 | 33.562 | 18.493 | 21.429 | 1.00 | 35.71 | 8 |
| N | SER | A | 3 | 34.891 | 20.073 | 22.307 | 1.00 | 35.38 | 7 |
| CA | SER | A | 3 | 34.150 | 21.192 | 21.739 | 1.00 | 34.80 | 6 |
| CB | SER | A | 3 | 34.195 | 22.391 | 22.679 | 1.00 | 34.05 | 6 |
| O | SER | A | 3 | 33.564 | 23.531 | 22.140 | 1.00 | 33.64 | 8 |
| C | SER | A | 3 | 34.763 | 21.541 | 20.386 | 1.00 | 35.05 | 6 |
| O | SER | A | 3 | 35.962 | 21.337 | 20.191 | 1.00 | 34.56 | 8 |
| N | GLY | A | 3 | 33.955 | 22.040 | 19.459 | 1.00 | 35.39 | 7 |
| CA | GLY | A | 3 | 34.462 | 22.402 | 18.135 | 1.00 | 35.60 | 6 |
| C | GLY | A | 3 | 34.336 | 23.906 | 17.921 | 1.00 | 35.68 | 6 |
| O | GLY | A | 3 | 34.539 | 24.440 | 16.835 | 1.00 | 36.23 | 8 |
| N | ILE | A | 3 | 34.006 | 24.601 | 19.000 | 1.00 | 36.01 | 7 |
| CA | ILE | A | 3 | 33.746 | 26.031 | 18.997 | 1.00 | 36.55 | 6 |
| CB | ILE | A | 3 | 32.690 | 26.348 | 20.089 | 1.00 | 36.05 | 6 |
| C | ILE | A | 3 | 32.210 | 27.780 | 19.950 | 1.00 | 34.80 | 6 |
| C | ILE | A | 3 | 31.583 | 25.307 | 19.990 | 1.00 | 36.07 | 6 |
| C | ILE | A | 3 | 30.154 | 25.663 | 20.253 | 1.00 | 39.29 | 6 |
| C | ILE | A | 3 | 34.994 | 26.875 | 19.184 | 1.00 | 37.54 | 6 |
| O | ILE | A | 3 | 35.710 | 26.788 | 20.180 | 1.00 | 37.10 | 8 |
| N | SER | A | 3 | 35.253 | 27.735 | 18.204 | 1.00 | 38.80 | 7 |
| CA | SER | A | 3 | 36.422 | 28.593 | 18.154 | 1.00 | 39.48 | 6 |
| CB | SER | A | 3 | 37.337 | 28.135 | 17.008 | 1.00 | 42.02 | 6 |
| O | SER | A | 3 | 38.329 | 27.235 | 17.454 | 1.00 | 46.40 | 8 |
| C | SER | A | 3 | 36.059 | 30.053 | 17.896 | 1.00 | 39.54 | 6 |
| O | SER | A | 3 | 34.918 | 30.363 | 17.558 | 1.00 | 39.54 | 8 |
| N | LEU | A | 3 | 37.045 | 30.937 | 18.011 | 1.00 | 39.16 | 7 |
| CA | LEU | A | 3 | 36.849 | 32.355 | 17.731 | 1.00 | 38.94 | 6 |
| CB | LEU | A | 3 | 37.937 | 33.204 | 18.383 | 1.00 | 41.98 | 6 |
| C | LEU | A | 3 | 37.834 | 33.497 | 19.878 | 1.00 | 43.75 | 6 |
| C | LEU | A | 3 | 39.104 | 34.179 | 20.370 | 1.00 | 44.67 | 6 |
| C | LEU | A | 3 | 36.618 | 34.356 | 20.193 | 1.00 | 44.78 | 6 |
| C | LEU | A | 3 | 36.876 | 32.580 | 16.219 | 1.00 | 38.03 | 6 |
| O | LEU | A | 3 | 37.683 | 31.949 | 15.534 | 1.00 | 38.07 | 8 |
| N | ILE | A | 3 | 36.013 | 33.447 | 15.704 | 1.00 | 37.29 | 7 |
| CA | ILE | A | 3 | 35.993 | 33.709 | 14.264 | 1.00 | 36.95 | 6 |
| CB | ILE | A | 3 | 34.716 | 34.443 | 13.832 | 1.00 | 35.68 | 6 |

Figure 1 - 2

| | | | | | | | | |
|---|---|---|---|---|---|---|---|---|
| C | ILE | A | 3 | 34.806 | 34.938 | 12.395 | 1.00 | 34.35 | 6 |
| C | ILE | A | 3 | 33.494 | 33.531 | 13.991 | 1.00 | 36.19 | 6 |
| C | ILE | A | 3 | 32.184 | 34.280 | 14.122 | 1.00 | 36.40 | 6 |
| C | ILE | A | 3 | 37.223 | 34.525 | 13.874 | 1.00 | 37.25 | 6 |
| O | ILE | A | 3 | 37.552 | 35.503 | 14.546 | 1.00 | 36.69 | 8 |
| N | ASP | A | 3 | 37.870 | 34.153 | 12.772 | 1.00 | 38.29 | 7 |
| CA | ASP | A | 3 | 39.056 | 34.874 | 12.331 | 1.00 | 39.13 | 6 |
| CB | ASP | A | 3 | 40.318 | 34.057 | 12.629 | 1.00 | 43.72 | 6 |
| C | ASP | A | 3 | 40.275 | 32.654 | 12.064 | 1.00 | 47.45 | 6 |
| O | ASP | A | 3 | 41.077 | 32.344 | 11.160 | 1.00 | 49.13 | 8 |
| O | ASP | A | 3 | 39.444 | 31.842 | 12.525 | 1.00 | 52.02 | 8 |
| C | ASP | A | 3 | 39.025 | 35.267 | 10.863 | 1.00 | 38.42 | 6 |
| O | ASP | A | 3 | 39.957 | 35.946 | 10.414 | 1.00 | 38.79 | 8 |
| N | HIS | A | 3 | 37.971 | 34.930 | 10.127 | 1.00 | 37.59 | 7 |
| CA | HIS | A | 3 | 37.943 | 35.229 | 8.696 | 1.00 | 37.01 | 6 |
| CB | HIS | A | 3 | 37.379 | 34.059 | 7.893 | 1.00 | 36.86 | 6 |
| C | HIS | A | 3 | 36.020 | 33.624 | 8.342 | 1.00 | 37.26 | 6 |
| C | HIS | A | 3 | 35.624 | 32.848 | 9.377 | 1.00 | 37.41 | 6 |
| N | HIS | A | 3 | 34.875 | 34.016 | 7.684 | 1.00 | 37.20 | 7 |
| CE | HIS | A | 3 | 33.830 | 33.492 | 8.295 | 1.00 | 37.69 | 6 |
| N | HIS | A | 3 | 34.252 | 32.781 | 9.324 | 1.00 | 38.35 | 7 |
| C | HIS | A | 3 | 37.241 | 36.534 | 8.359 | 1.00 | 36.69 | 6 |
| O | HIS | A | 3 | 37.175 | 36.922 | 7.190 | 1.00 | 37.23 | 8 |
| N | PHE | A | 4 | 36.755 | 37.250 | 9.362 | 1.00 | 35.95 | 7 |
| CA | PHE | A | 4 | 36.197 | 38.584 | 9.192 | 1.00 | 35.56 | 6 |
| CB | PHE | A | 4 | 34.794 | 38.632 | 8.633 | 1.00 | 31.76 | 6 |
| C | PHE | A | 4 | 33.678 | 38.069 | 9.458 | 1.00 | 31.43 | 6 |
| C | PHE | A | 4 | 33.244 | 36.770 | 9.253 | 1.00 | 27.02 | 6 |
| C | PHE | A | 4 | 33.035 | 38.840 | 10.416 | 1.00 | 28.56 | 6 |
| CE | PHE | A | 4 | 32.212 | 36.241 | 10.000 | 1.00 | 28.21 | 6 |
| CE | PHE | A | 4 | 31.998 | 38.315 | 11.163 | 1.00 | 29.67 | 6 |
| CZ | PHE | A | 4 | 31.585 | 37.014 | 10.957 | 1.00 | 27.52 | 6 |
| C | PHE | A | 4 | 36.327 | 39.324 | 10.527 | 1.00 | 36.35 | 6 |
| O | PHE | A | 4 | 36.487 | 38.691 | 11.571 | 1.00 | 35.69 | 8 |
| N | ASP | A | 4 | 36.400 | 40.648 | 10.472 | 1.00 | 37.94 | 7 |
| CA | ASP | A | 4 | 36.552 | 41.437 | 11.690 | 1.00 | 39.82 | 6 |
| CB | ASP | A | 4 | 36.910 | 42.886 | 11.349 | 1.00 | 45.32 | 6 |
| C | ASP | A | 4 | 37.632 | 43.576 | 12.491 | 1.00 | 49.18 | 6 |
| O | ASP | A | 4 | 38.498 | 42.932 | 13.121 | 1.00 | 53.55 | 8 |
| O | ASP | A | 4 | 37.336 | 44.758 | 12.759 | 1.00 | 51.63 | 8 |
| C | ASP | A | 4 | 35.290 | 41.390 | 12.541 | 1.00 | 39.52 | 6 |
| O | ASP | A | 4 | 34.238 | 41.888 | 12.140 | 1.00 | 39.80 | 8 |
| N | THR | A | 4 | 35.393 | 40.807 | 13.732 | 1.00 | 39.36 | 7 |
| CA | THR | A | 4 | 34.259 | 40.695 | 14.639 | 1.00 | 39.57 | 6 |
| CB | THR | A | 4 | 34.194 | 39.280 | 15.254 | 1.00 | 37.93 | 6 |
| O | THR | A | 4 | 35.410 | 39.020 | 15.962 | 1.00 | 39.07 | 8 |
| C | THR | A | 4 | 34.012 | 38.226 | 14.175 | 1.00 | 37.57 | 6 |
| C | THR | A | 4 | 34.270 | 41.724 | 15.760 | 1.00 | 39.78 | 6 |
| O | THR | A | 4 | 33.585 | 41.562 | 16.774 | 1.00 | 40.41 | 8 |
| N | SER | A | 4 | 34.935 | 42.853 | 15.568 | 1.00 | 40.48 | 7 |
| CA | SER | A | 4 | 35.051 | 43.916 | 16.548 | 1.00 | 40.85 | 6 |
| CB | SER | A | 4 | 35.893 | 45.067 | 15.972 | 1.00 | 43.88 | 6 |
| O | SER | A | 4 | 37.275 | 44.779 | 16.102 | 1.00 | 49.24 | 8 |
| C | SER | A | 4 | 33.727 | 44.489 | 17.029 | 1.00 | 40.22 | 6 |
| O | SER | A | 4 | 33.536 | 44.709 | 18.226 | 1.00 | 40.13 | 8 |
| N | ALA | A | 4 | 32.799 | 44.744 | 16.116 | 1.00 | 39.96 | 7 |
| CA | ALA | A | 4 | 31.495 | 45.299 | 16.440 | 1.00 | 38.98 | 6 |
| CB | ALA | A | 4 | 30.998 | 46.115 | 15.247 | 1.00 | 39.66 | 6 |
| C | ALA | A | 4 | 30.449 | 44.245 | 16.774 | 1.00 | 38.40 | 6 |
| O | ALA | A | 4 | 29.325 | 44.570 | 17.164 | 1.00 | 39.15 | 8 |
| N | TYR | A | 4 | 30.798 | 42.979 | 16.611 | 1.00 | 37.11 | 7 |
| CA | TYR | A | 4 | 29.870 | 41.881 | 16.810 | 1.00 | 35.72 | 6 |
| CB | TYR | A | 4 | 30.317 | 40.698 | 15.938 | 1.00 | 35.08 | 6 |
| C | TYR | A | 4 | 30.085 | 40.940 | 14.460 | 1.00 | 34.28 | 6 |

| | | | | | | | | |
|---|---|---|---|---|---|---|---|---|
| C | TYR | A | 4 | 30.900 | 41.793 | 13.731 | 1.00 | 34.32 | 6 |
| CE | TYR | A | 4 | 30.682 | 42.017 | 12.383 | 1.00 | 34.43 | 6 |
| C | TYR | A | 4 | 29.040 | 40.311 | 13.795 | 1.00 | 34.03 | 6 |
| CE | TYR | A | 4 | 28.815 | 40.526 | 12.449 | 1.00 | 33.57 | 6 |
| CZ | TYR | A | 4 | 29.640 | 41.376 | 11.747 | 1.00 | 33.72 | 6 |
| O | TYR | A | 4 | 29.419 | 41.594 | 10.407 | 1.00 | 33.46 | 8 |
| C | TYR | A | 4 | 29.708 | 41.468 | 18.261 | 1.00 | 35.53 | 6 |
| O | TYR | A | 4 | 30.648 | 41.428 | 19.049 | 1.00 | 35.26 | 8 |
| N | ALA | A | 4 | 28.470 | 41.112 | 18.607 | 1.00 | 35.46 | 7 |
| CA | ALA | A | 4 | 28.129 | 40.652 | 19.946 | 1.00 | 34.81 | 6 |
| CB | ALA | A | 4 | 26.634 | 40.786 | 20.186 | 1.00 | 36.41 | 6 |
| C | ALA | A | 4 | 28.579 | 39.208 | 20.146 | 1.00 | 34.10 | 6 |
| O | ALA | A | 4 | 28.883 | 38.792 | 21.263 | 1.00 | 34.60 | 8 |
| N | THR | A | 4 | 28.586 | 38.435 | 19.067 | 1.00 | 32.65 | 7 |
| CA | THR | A | 4 | 29.063 | 37.056 | 19.106 | 1.00 | 31.17 | 6 |
| CB | THR | A | 4 | 27.988 | 36.038 | 18.717 | 1.00 | 29.80 | 6 |
| O | THR | A | 4 | 26.858 | 36.202 | 19.587 | 1.00 | 29.18 | 8 |
| C | THR | A | 4 | 28.527 | 34.620 | 18.850 | 1.00 | 26.37 | 6 |
| C | THR | A | 4 | 30.286 | 36.962 | 18.197 | 1.00 | 31.21 | 6 |
| O | THR | A | 4 | 30.245 | 37.331 | 17.024 | 1.00 | 31.46 | 8 |
| N | LYS | A | 4 | 31.396 | 36.508 | 18.768 | 1.00 | 31.20 | 7 |
| CA | LYS | A | 4 | 32.657 | 36.423 | 18.050 | 1.00 | 31.32 | 6 |
| CB | LYS | A | 4 | 33.717 | 37.235 | 18.819 | 1.00 | 34.11 | 6 |
| C | LYS | A | 4 | 33.374 | 38.702 | 19.005 | 1.00 | 34.97 | 6 |
| C | LYS | A | 4 | 33.873 | 39.244 | 20.333 | 1.00 | 35.60 | 6 |
| CE | LYS | A | 4 | 33.865 | 40.764 | 20.339 | 1.00 | 35.32 | 6 |
| NZ | LYS | A | 4 | 32.586 | 41.311 | 20.865 | 1.00 | 34.62 | 7 |
| C | LYS | A | 4 | 33.163 | 35.005 | 17.861 | 1.00 | 30.79 | 6 |
| O | LYS | A | 4 | 34.296 | 34.813 | 17.414 | 1.00 | 31.29 | 8 |
| N | PHE | A | 4 | 32.331 | 34.024 | 18.189 | 1.00 | 30.23 | 7 |
| CA | PHE | A | 4 | 32.746 | 32.631 | 18.067 | 1.00 | 29.90 | 6 |
| CB | PHE | A | 4 | 32.956 | 32.036 | 19.465 | 1.00 | 26.81 | 6 |
| C | PHE | A | 4 | 31.749 | 32.146 | 20.352 | 1.00 | 23.68 | 6 |
| C | PHE | A | 4 | 30.814 | 31.127 | 20.404 | 1.00 | 22.70 | 6 |
| C | PHE | A | 4 | 31.550 | 33.273 | 21.135 | 1.00 | 23.53 | 6 |
| CE | PHE | A | 4 | 29.701 | 31.226 | 21.220 | 1.00 | 22.77 | 6 |
| CE | PHE | A | 4 | 30.437 | 33.379 | 21.946 | 1.00 | 21.85 | 6 |
| CZ | PHE | A | 4 | 29.516 | 32.352 | 21.996 | 1.00 | 22.46 | 6 |
| C | PHE | A | 4 | 31.739 | 31.794 | 17.292 | 1.00 | 30.06 | 6 |
| O | PHE | A | 4 | 30.587 | 32.180 | 17.108 | 1.00 | 30.44 | 8 |
| N | ALA | A | 5 | 32.186 | 30.619 | 16.864 | 1.00 | 30.06 | 7 |
| CA | ALA | A | 5 | 31.347 | 29.682 | 16.135 | 1.00 | 29.97 | 6 |
| CB | ALA | A | 5 | 31.022 | 30.226 | 14.749 | 1.00 | 30.60 | 6 |
| C | ALA | A | 5 | 32.021 | 28.317 | 16.010 | 1.00 | 29.72 | 6 |
| O | ALA | A | 5 | 33.199 | 28.141 | 16.314 | 1.00 | 29.34 | 8 |
| N | GLY | A | 5 | 31.240 | 27.343 | 15.560 | 1.00 | 29.39 | 7 |
| CA | GLY | A | 5 | 31.771 | 25.999 | 15.301 | 1.00 | 29.28 | 6 |
| C | GLY | A | 5 | 32.187 | 26.026 | 13.820 | 1.00 | 29.28 | 6 |
| O | GLY | A | 5 | 31.333 | 26.008 | 12.933 | 1.00 | 28.28 | 8 |
| N | LEU | A | 5 | 33.484 | 26.171 | 13.579 | 1.00 | 29.22 | 7 |
| CA | LEU | A | 5 | 33.978 | 26.271 | 12.212 | 1.00 | 30.02 | 6 |
| CB | LEU | A | 5 | 34.980 | 27.425 | 12.103 | 1.00 | 28.78 | 6 |
| C | LEU | A | 5 | 34.413 | 28.821 | 12.389 | 1.00 | 28.71 | 6 |
| C | LEU | A | 5 | 35.511 | 29.750 | 12.886 | 1.00 | 27.15 | 6 |
| C | LEU | A | 5 | 33.731 | 29.388 | 11.153 | 1.00 | 25.21 | 6 |
| C | LEU | A | 5 | 34.605 | 24.969 | 11.736 | 1.00 | 30.75 | 6 |
| O | LEU | A | 5 | 35.148 | 24.207 | 12.533 | 1.00 | 31.22 | 8 |
| N | VAL | A | 5 | 34.488 | 24.708 | 10.437 | 1.00 | 31.59 | 7 |
| CA | VAL | A | 5 | 35.117 | 23.509 | 9.866 | 1.00 | 32.60 | 6 |
| CB | VAL | A | 5 | 34.479 | 23.078 | 8.547 | 1.00 | 30.09 | 6 |
| C | VAL | A | 5 | 35.310 | 22.034 | 7.817 | 1.00 | 29.51 | 6 |
| C | VAL | A | 5 | 33.080 | 22.523 | 8.810 | 1.00 | 26.99 | 6 |
| C | VAL | A | 5 | 36.599 | 23.850 | 9.731 | 1.00 | 34.05 | 6 |
| O | VAL | A | 5 | 36.949 | 24.879 | 9.153 | 1.00 | 33.97 | 8 |

Figure 1 - 3

| | | | | | | | | |
|---|---|---|---|---|---|---|---|---|
| N | LYS | A | 5 | 37.449 | 23.043 | 10.349 | 1.00 | 36.41 | 7 |
| CA | LYS | A | 5 | 38.878 | 23.314 | 10.391 | 1.00 | 38.50 | 6 |
| CB | LYS | A | 5 | 39.363 | 23.117 | 11.840 | 1.00 | 38.42 | 6 |
| C | LYS | A | 5 | 38.814 | 24.167 | 12.794 | 1.00 | 40.28 | 6 |
| C | LYS | A | 5 | 38.770 | 23.668 | 14.228 | 1.00 | 42.84 | 6 |
| CE | LYS | A | 5 | 37.350 | 23.437 | 14.705 | 1.00 | 43.44 | 6 |
| NZ | LYS | A | 5 | 36.653 | 24.697 | 15.081 | 1.00 | 44.14 | 7 |
| C | LYS | A | 5 | 39.718 | 22.478 | 9.444 | 1.00 | 40.42 | 6 |
| O | LYS | A | 5 | 39.596 | 21.260 | 9.337 | 1.00 | 40.62 | 8 |
| N | ASP | A | 5 | 40.664 | 23.147 | 8.783 | 1.00 | 42.10 | 7 |
| CA | ASP | A | 5 | 41.617 | 22.514 | 7.881 | 1.00 | 43.84 | 6 |
| CB | ASP | A | 5 | 42.512 | 21.555 | 8.678 | 1.00 | 47.61 | 6 |
| C | ASP | A | 5 | 43.289 | 22.268 | 9.771 | 1.00 | 50.56 | 6 |
| O | ASP | A | 5 | 43.952 | 23.279 | 9.459 | 1.00 | 52.38 | 8 |
| O | ASP | A | 5 | 43.187 | 21.836 | 10.940 | 1.00 | 52.15 | 8 |
| C | ASP | A | 5 | 40.941 | 21.788 | 6.727 | 1.00 | 44.21 | 6 |
| O | ASP | A | 5 | 41.227 | 20.626 | 6.428 | 1.00 | 44.58 | 8 |
| N | PHE | A | 5 | 40.050 | 22.488 | 6.037 | 1.00 | 43.94 | 7 |
| CA | PHE | A | 5 | 39.275 | 21.914 | 4.945 | 1.00 | 44.27 | 6 |
| CB | PHE | A | 5 | 37.963 | 22.698 | 4.825 | 1.00 | 38.90 | 6 |
| C | PHE | A | 5 | 37.060 | 22.308 | 3.696 | 1.00 | 34.96 | 6 |
| C | PHE | A | 5 | 36.432 | 21.075 | 3.672 | 1.00 | 32.24 | 6 |
| C | PHE | A | 5 | 36.827 | 23.193 | 2.653 | 1.00 | 33.21 | 6 |
| CE | PHE | A | 5 | 35.597 | 20.725 | 2.629 | 1.00 | 31.61 | 6 |
| CE | PHE | A | 5 | 35.992 | 22.848 | 1.607 | 1.00 | 32.75 | 6 |
| CZ | PHE | A | 5 | 35.377 | 21.612 | 1.595 | 1.00 | 32.24 | 6 |
| C | PHE | A | 5 | 40.028 | 21.868 | 3.627 | 1.00 | 45.76 | 6 |
| O | PHE | A | 5 | 40.511 | 22.875 | 3.115 | 1.00 | 45.77 | 8 |
| N | ASN | A | 5 | 40.109 | 20.672 | 3.051 | 1.00 | 47.93 | 7 |
| CA | ASN | A | 5 | 40.764 | 20.458 | 1.769 | 1.00 | 50.19 | 6 |
| CB | ASN | A | 5 | 42.108 | 19.750 | 1.930 | 1.00 | 55.16 | 6 |
| C | ASN | A | 5 | 42.893 | 19.657 | 0.637 | 1.00 | 59.33 | 6 |
| O | ASN | A | 5 | 43.373 | 18.585 | 0.266 | 1.00 | 61.85 | 8 |
| N | ASN | A | 5 | 43.038 | 20.776 | -0.065 | 1.00 | 60.64 | 7 |
| C | ASN | A | 5 | 39.860 | 19.647 | 0.842 | 1.00 | 50.97 | 6 |
| O | ASN | A | 5 | 39.380 | 18.573 | 1.203 | 1.00 | 51.24 | 8 |
| N | CYS | A | 5 | 39.606 | 20.198 | -0.338 | 1.00 | 51.32 | 7 |
| CA | CYS | A | 5 | 38.762 | 19.529 | -1.322 | 1.00 | 52.14 | 6 |
| CB | CYS | A | 5 | 37.365 | 20.144 | -1.347 | 1.00 | 52.43 | 6 |
| SG | CYS | A | 5 | 37.309 | 21.830 | -1.997 | 1.00 | 50.96 | 1 |
| C | CYS | A | 5 | 39.408 | 19.600 | -2.699 | 1.00 | 52.89 | 6 |
| O | CYS | A | 5 | 38.805 | 19.251 | -3.709 | 1.00 | 52.44 | 8 |
| N | GLU | A | 5 | 40.689 | 19.951 | -2.722 | 1.00 | 54.30 | 7 |
| CA | GLU | A | 5 | 41.479 | 20.027 | -3.943 | 1.00 | 56.17 | 6 |
| CB | GLU | A | 5 | 42.919 | 20.418 | -3.604 | 1.00 | 60.28 | 6 |
| C | GLU | A | 5 | 43.697 | 21.045 | -4.743 | 1.00 | 65.46 | 6 |
| C | GLU | A | 5 | 43.878 | 22.543 | -4.612 | 1.00 | 68.19 | 6 |
| O | GLU | A | 5 | 44.798 | 23.084 | -5.266 | 1.00 | 69.51 | 8 |
| O | GLU | A | 5 | 43.111 | 23.192 | -3.872 | 1.00 | 69.64 | 8 |
| C | GLU | A | 5 | 41.457 | 18.714 | -4.717 | 1.00 | 56.61 | 6 |
| O | GLU | A | 5 | 41.277 | 18.697 | -5.936 | 1.00 | 56.60 | 8 |
| N | ASP | A | 6 | 41.571 | 17.594 | -4.013 | 1.00 | 57.07 | 7 |
| CA | ASP | A | 6 | 41.491 | 16.269 | -4.601 | 1.00 | 57.64 | 6 |
| CB | ASP | A | 6 | 41.873 | 15.183 | -3.599 | 1.00 | 62.92 | 6 |
| C | ASP | A | 6 | 41.772 | 15.563 | -2.141 | 1.00 | 66.58 | 6 |
| O | ASP | A | 6 | 40.916 | 14.989 | -1.431 | 1.00 | 68.82 | 8 |
| O | ASP | A | 6 | 42.559 | 16.417 | -1.677 | 1.00 | 68.78 | 8 |
| C | ASP | A | 6 | 40.111 | 15.977 | -5.186 | 1.00 | 56.94 | 6 |
| O | ASP | A | 6 | 40.014 | 15.332 | -6.232 | 1.00 | 56.79 | 8 |
| N | ILE | A | 6 | 39.049 | 16.432 | -4.531 | 1.00 | 56.25 | 7 |
| CA | ILE | A | 6 | 37.691 | 16.200 | -4.995 | 1.00 | 55.48 | 6 |
| CB | ILE | A | 6 | 36.685 | 16.184 | -3.824 | 1.00 | 54.74 | 6 |
| C | ILE | A | 6 | 35.366 | 15.567 | -4.270 | 1.00 | 53.87 | 6 |
| C | ILE | A | 6 | 37.242 | 15.462 | -2.600 | 1.00 | 54.58 | 6 |
| C | ILE | A | 6 | 37.567 | 13.998 | -2.774 | 1.00 | 54.63 | 6 |
| C | ILE | A | 6 | 37.223 | 17.225 | -6.020 | 1.00 | 55.26 | 6 |
| O | ILE | A | 6 | 36.583 | 16.871 | -7.013 | 1.00 | 54.72 | 8 |
| N | ILE | A | 6 | 37.389 | 18.509 | -5.720 | 1.00 | 55.58 | 7 |
| CA | ILE | A | 6 | 36.959 | 19.594 | -6.587 | 1.00 | 56.21 | 6 |
| CB | ILE | A | 6 | 35.885 | 20.502 | -5.963 | 1.00 | 54.72 | 6 |
| C | ILE | A | 6 | 35.379 | 21.516 | -6.985 | 1.00 | 53.62 | 6 |
| C | ILE | A | 6 | 34.697 | 19.717 | -5.404 | 1.00 | 54.25 | 6 |
| C | ILE | A | 6 | 34.399 | 20.027 | -3.952 | 1.00 | 53.74 | 6 |
| C | ILE | A | 6 | 38.151 | 20.477 | -6.962 | 1.00 | 57.36 | 6 |
| O | ILE | A | 6 | 38.886 | 20.940 | -6.089 | 1.00 | 56.79 | 8 |
| N | SER | A | 6 | 38.297 | 20.751 | -8.254 | 1.00 | 59.16 | 7 |
| CA | SER | A | 6 | 39.409 | 21.565 | -8.732 | 1.00 | 61.00 | 6 |
| CB | SER | A | 6 | 39.496 | 21.520 | -10.258 | 1.00 | 61.46 | 6 |
| O | SER | A | 6 | 38.215 | 21.648 | -10.849 | 1.00 | 63.02 | 8 |
| C | SER | A | 6 | 39.286 | 23.007 | -8.261 | 1.00 | 62.26 | 6 |
| O | SER | A | 6 | 38.203 | 23.459 | -7.890 | 1.00 | 62.61 | 8 |
| N | ARG | A | 6 | 40.389 | 23.749 | -8.340 | 1.00 | 63.24 | 7 |
| CA | ARG | A | 6 | 40.391 | 25.163 | -7.975 | 1.00 | 64.33 | 6 |
| CB | ARG | A | 6 | 41.798 | 25.733 | -7.862 | 1.00 | 70.36 | 6 |
| C | ARG | A | 6 | 42.847 | 24.781 | -7.312 | 1.00 | 75.55 | 6 |
| C | ARG | A | 6 | 43.965 | 24.570 | -8.322 | 1.00 | 79.64 | 6 |
| N | ARG | A | 6 | 44.571 | 23.249 | -8.210 | 1.00 | 83.48 | 7 |
| CZ | ARG | A | 6 | 45.874 | 23.006 | -8.289 | 1.00 | 85.63 | 6 |
| N | ARG | A | 6 | 46.737 | 23.996 | -8.481 | 1.00 | 87.20 | 7 |
| N | ARG | A | 6 | 46.327 | 21.764 | -8.173 | 1.00 | 86.70 | 7 |
| C | ARG | A | 6 | 39.578 | 25.952 | -9.003 | 1.00 | 63.68 | 6 |
| O | ARG | A | 6 | 38.912 | 26.929 | -8.665 | 1.00 | 63.91 | 8 |
| N | LYS | A | 6 | 39.621 | 25.512 | -10.259 | 1.00 | 62.41 | 7 |
| CA | LYS | A | 6 | 38.838 | 26.122 | -11.323 | 1.00 | 61.01 | 6 |
| CB | LYS | A | 6 | 39.078 | 25.442 | -12.667 | 1.00 | 64.05 | 6 |
| C | LYS | A | 6 | 40.473 | 25.584 | -13.247 | 1.00 | 67.89 | 6 |
| C | LYS | A | 6 | 40.692 | 24.601 | -14.390 | 1.00 | 70.27 | 6 |
| CE | LYS | A | 6 | 42.115 | 24.069 | -14.405 | 1.00 | 72.41 | 6 |
| NZ | LYS | A | 6 | 42.174 | 22.613 | -14.094 | 1.00 | 73.35 | 7 |
| C | LYS | A | 6 | 37.355 | 25.952 | -10.959 | 1.00 | 59.05 | 6 |
| O | LYS | A | 6 | 36.623 | 26.977 | -10.893 | 1.00 | 59.16 | 8 |
| N | GLU | A | 6 | 36.933 | 24.768 | -10.663 | 1.00 | 56.50 | 7 |
| CA | GLU | A | 6 | 35.560 | 24.458 | -10.303 | 1.00 | 54.00 | 6 |
| CB | GLU | A | 6 | 35.351 | 22.937 | -10.348 | 1.00 | 53.27 | 6 |
| C | GLU | A | 6 | 35.135 | 22.410 | -11.759 | 1.00 | 52.23 | 6 |
| C | GLU | A | 6 | 33.753 | 22.724 | -12.296 | 1.00 | 51.74 | 6 |
| O | GLU | A | 6 | 33.652 | 23.202 | -13.444 | 1.00 | 49.51 | 8 |
| O | GLU | A | 6 | 32.764 | 22.494 | -11.571 | 1.00 | 52.67 | 8 |
| C | GLU | A | 6 | 35.113 | 25.008 | -8.961 | 1.00 | 52.28 | 6 |
| O | GLU | A | 6 | 33.929 | 25.285 | -8.749 | 1.00 | 51.71 | 8 |
| N | GLN | A | 6 | 36.032 | 25.227 | -8.034 | 1.00 | 50.86 | 7 |
| CA | GLN | A | 6 | 35.780 | 25.773 | -6.715 | 1.00 | 49.27 | 6 |
| CB | GLN | A | 6 | 37.107 | 25.821 | -5.948 | 1.00 | 49.56 | 6 |
| C | GLN | A | 6 | 37.061 | 25.384 | -4.497 | 1.00 | 50.72 | 6 |
| C | GLN | A | 6 | 38.460 | 25.262 | -3.918 | 1.00 | 51.56 | 6 |
| O | GLN | A | 6 | 39.130 | 26.269 | -3.682 | 1.00 | 51.87 | 8 |
| N | GLN | A | 6 | 38.908 | 24.031 | -3.700 | 1.00 | 50.91 | 7 |
| C | GLN | A | 6 | 35.184 | 27.173 | -6.731 | 1.00 | 48.26 | 6 |
| O | GLN | A | 6 | 34.447 | 27.566 | -5.825 | 1.00 | 48.39 | 8 |
| N | ARG | A | 6 | 35.475 | 27.960 | -7.756 | 1.00 | 47.26 | 7 |
| CA | ARG | A | 6 | 35.017 | 29.320 | -7.939 | 1.00 | 45.38 | 6 |
| CB | ARG | A | 6 | 35.835 | 29.966 | -9.074 | 1.00 | 52.16 | 6 |
| C | ARG | A | 6 | 35.884 | 31.480 | -9.005 | 1.00 | 59.18 | 6 |
| C | ARG | A | 6 | 35.460 | 32.120 | -10.317 | 1.00 | 65.00 | 6 |
| N | ARG | A | 6 | 34.851 | 33.429 | -10.120 | 1.00 | 70.09 | 7 |
| CZ | ARG | A | 6 | 35.477 | 34.531 | -9.730 | 1.00 | 72.67 | 6 |
| N | ARG | A | 6 | 36.780 | 34.518 | -9.476 | 1.00 | 73.94 | 7 |
| N | ARG | A | 6 | 34.797 | 35.664 | -9.589 | 1.00 | 74.21 | 7 |

Figure 1-4

| | | | | | | | | |
|---|---|---|---|---|---|---|---|---|
| C | ARG | A | 6 | 33.541 | 29.463 | -8.272 | 1.00 | 42.38 | 6 |
| O | ARG | A | 6 | 32.974 | 30.555 | -8.163 | 1.00 | 42.43 | 8 |
| N | LYS | A | 6 | 32.895 | 28.387 | -8.698 | 1.00 | 38.98 | 7 |
| CA | LYS | A | 6 | 31.489 | 28.391 | -9.047 | 1.00 | 36.08 | 6 |
| CB | LYS | A | 6 | 31.233 | 27.425 | -10.211 | 1.00 | 38.25 | 6 |
| C | LYS | A | 6 | 32.187 | 27.547 | -11.385 | 1.00 | 41.26 | 6 |
| C | LYS | A | 6 | 31.832 | 26.533 | -12.467 | 1.00 | 43.21 | 6 |
| CE | LYS | A | 6 | 32.688 | 26.729 | -13.707 | 1.00 | 45.12 | 6 |
| NZ | LYS | A | 6 | 32.841 | 25.473 | -14.491 | 1.00 | 44.54 | 7 |
| C | LYS | A | 6 | 30.595 | 27.970 | -7.885 | 1.00 | 33.41 | 6 |
| O | LYS | A | 6 | 29.393 | 27.786 | -8.094 | 1.00 | 32.34 | 8 |
| N | MET | A | 7 | 31.148 | 27.782 | -6.690 | 1.00 | 31.31 | 7 |
| CA | MET | A | 7 | 30.352 | 27.276 | -5.584 | 1.00 | 30.21 | 6 |
| CB | MET | A | 7 | 30.475 | 25.744 | -5.527 | 1.00 | 32.32 | 6 |
| C | MET | A | 7 | 31.857 | 25.194 | -5.822 | 1.00 | 35.12 | 6 |
| SD | MET | A | 7 | 31.957 | 23.402 | -5.704 | 1.00 | 36.02 | 1 |
| CE | MET | A | 7 | 31.529 | 22.901 | -7.367 | 1.00 | 34.53 | 6 |
| C | MET | A | 7 | 30.684 | 27.848 | -4.215 | 1.00 | 28.31 | 6 |
| O | MET | A | 7 | 31.832 | 27.922 | -3.787 | 1.00 | 28.11 | 8 |
| N | ASP | A | 7 | 29.624 | 28.234 | -3.503 | 1.00 | 25.95 | 7 |
| CA | ASP | A | 7 | 29.766 | 28.751 | -2.143 | 1.00 | 23.65 | 6 |
| CB | ASP | A | 7 | 28.413 | 29.222 | -1.616 | 1.00 | 20.66 | 6 |
| C | ASP | A | 7 | 28.479 | 29.865 | -0.246 | 1.00 | 22.27 | 6 |
| O | ASP | A | 7 | 28.312 | 29.143 | 0.762 | 1.00 | 21.88 | 8 |
| O | ASP | A | 7 | 28.718 | 31.089 | -0.170 | 1.00 | 21.04 | 8 |
| C | ASP | A | 7 | 30.326 | 27.629 | -1.273 | 1.00 | 22.62 | 6 |
| O | ASP | A | 7 | 30.144 | 26.453 | -1.603 | 1.00 | 22.32 | 8 |
| N | ALA | A | 7 | 30.882 | 27.953 | -0.115 | 1.00 | 21.68 | 7 |
| CA | ALA | A | 7 | 31.389 | 26.979 | 0.831 | 1.00 | 21.95 | 6 |
| CB | ALA | A | 7 | 31.922 | 27.690 | 2.079 | 1.00 | 19.90 | 6 |
| C | ALA | A | 7 | 30.380 | 25.920 | 1.251 | 1.00 | 22.22 | 6 |
| O | ALA | A | 7 | 30.796 | 24.777 | 1.483 | 1.00 | 22.29 | 8 |
| N | PHE | A | 7 | 29.093 | 26.236 | 1.373 | 1.00 | 22.19 | 7 |
| CA | PHE | A | 7 | 28.095 | 25.239 | 1.753 | 1.00 | 22.22 | 6 |
| CB | PHE | A | 7 | 26.728 | 25.848 | 2.038 | 1.00 | 20.07 | 6 |
| C | PHE | A | 7 | 25.717 | 25.891 | 0.936 | 1.00 | 17.46 | 6 |
| C | PHE | A | 7 | 24.749 | 24.907 | 0.811 | 1.00 | 18.74 | 6 |
| C | PHE | A | 7 | 25.726 | 26.918 | 0.006 | 1.00 | 17.25 | 6 |
| CE | PHE | A | 7 | 23.818 | 24.946 | -0.210 | 1.00 | 18.48 | 6 |
| CE | PHE | A | 7 | 24.806 | 26.962 | -1.024 | 1.00 | 12.10 | 6 |
| CZ | PHE | A | 7 | 23.842 | 25.981 | -1.126 | 1.00 | 15.15 | 6 |
| C | PHE | A | 7 | 28.014 | 24.132 | 0.705 | 1.00 | 22.32 | 6 |
| O | PHE | A | 7 | 27.900 | 22.953 | 1.064 | 1.00 | 22.55 | 8 |
| N | ILE | A | 7 | 28.084 | 24.484 | -0.574 | 1.00 | 22.33 | 7 |
| CA | ILE | A | 7 | 28.084 | 23.492 | -1.645 | 1.00 | 22.84 | 6 |
| CB | ILE | A | 7 | 27.881 | 24.146 | -3.022 | 1.00 | 23.95 | 6 |
| C | ILE | A | 7 | 28.144 | 23.175 | -4.164 | 1.00 | 24.20 | 6 |
| C | ILE | A | 7 | 26.451 | 24.694 | -3.121 | 1.00 | 21.72 | 6 |
| C | ILE | A | 7 | 26.260 | 25.703 | -4.232 | 1.00 | 20.39 | 6 |
| C | ILE | A | 7 | 29.365 | 22.667 | -1.611 | 1.00 | 22.04 | 6 |
| O | ILE | A | 7 | 29.318 | 21.448 | -1.777 | 1.00 | 20.83 | 8 |
| N | GLN | A | 7 | 30.501 | 23.312 | -1.364 | 1.00 | 22.64 | 7 |
| CA | GLN | A | 7 | 31.777 | 22.612 | -1.257 | 1.00 | 23.44 | 6 |
| CB | GLN | A | 7 | 32.923 | 23.597 | -1.047 | 1.00 | 25.82 | 6 |
| C | GLN | A | 7 | 33.158 | 24.544 | -2.211 | 1.00 | 29.28 | 6 |
| C | GLN | A | 7 | 34.326 | 25.483 | -1.984 | 1.00 | 31.36 | 6 |
| O | GLN | A | 7 | 35.184 | 25.241 | -1.131 | 1.00 | 33.44 | 8 |
| N | GLN | A | 7 | 34.369 | 26.565 | -2.755 | 1.00 | 28.85 | 7 |
| C | GLN | A | 7 | 31.730 | 21.592 | -0.122 | 1.00 | 23.75 | 6 |
| O | GLN | A | 7 | 32.095 | 20.428 | -0.314 | 1.00 | 24.15 | 8 |
| N | TYR | A | 7 | 31.209 | 21.984 | 1.038 | 1.00 | 23.05 | 7 |
| CA | TYR | A | 7 | 31.025 | 21.063 | 2.151 | 1.00 | 23.66 | 6 |
| CB | TYR | A | 7 | 30.436 | 21.773 | 3.365 | 1.00 | 23.91 | 6 |
| C | TYR | A | 7 | 31.303 | 22.775 | 4.083 | 1.00 | 24.75 | 6 |
| C | TYR | A | 7 | 30.779 | 23.481 | 5.163 | 1.00 | 25.10 | 6 |
| CE | TYR | A | 7 | 31.538 | 24.408 | 5.853 | 1.00 | 25.02 | 6 |
| C | TYR | A | 7 | 32.615 | 23.038 | 3.717 | 1.00 | 25.66 | 6 |
| CE | TYR | A | 7 | 33.382 | 23.970 | 4.390 | 1.00 | 25.67 | 6 |
| CZ | TYR | A | 7 | 32.835 | 24.651 | 5.457 | 1.00 | 25.21 | 6 |
| O | TYR | A | 7 | 33.592 | 25.576 | 6.133 | 1.00 | 25.47 | 8 |
| C | TYR | A | 7 | 30.106 | 19.904 | 1.768 | 1.00 | 23.62 | 6 |
| O | TYR | A | 7 | 30.406 | 18.741 | 2.037 | 1.00 | 23.40 | 8 |
| N | GLY | A | 7 | 28.986 | 20.218 | 1.124 | 1.00 | 22.96 | 7 |
| CA | GLY | A | 7 | 28.018 | 19.230 | 0.696 | 1.00 | 23.75 | 6 |
| C | GLY | A | 7 | 28.588 | 18.158 | -0.218 | 1.00 | 24.27 | 6 |
| O | GLY | A | 7 | 28.290 | 16.977 | -0.034 | 1.00 | 23.78 | 8 |
| N | ILE | A | 7 | 29.369 | 18.551 | -1.219 | 1.00 | 25.10 | 7 |
| CA | ILE | A | 7 | 29.975 | 17.602 | -2.144 | 1.00 | 25.73 | 6 |
| CB | ILE | A | 7 | 30.674 | 18.315 | -3.316 | 1.00 | 27.05 | 6 |
| C | ILE | A | 7 | 31.383 | 17.316 | -4.222 | 1.00 | 27.14 | 6 |
| C | ILE | A | 7 | 29.645 | 19.119 | -4.117 | 1.00 | 27.25 | 6 |
| C | ILE | A | 7 | 30.230 | 20.052 | -5.152 | 1.00 | 29.01 | 6 |
| C | ILE | A | 7 | 30.945 | 16.669 | -1.430 | 1.00 | 25.57 | 6 |
| O | ILE | A | 7 | 30.797 | 15.447 | -1.504 | 1.00 | 24.87 | 8 |
| N | VAL | A | 7 | 31.896 | 17.231 | -0.691 | 1.00 | 25.62 | 7 |
| CA | VAL | A | 7 | 32.878 | 16.438 | 0.045 | 1.00 | 25.35 | 6 |
| CB | VAL | A | 7 | 33.812 | 17.327 | 0.881 | 1.00 | 22.69 | 6 |
| C | VAL | A | 7 | 34.663 | 16.522 | 1.851 | 1.00 | 21.61 | 6 |
| C | VAL | A | 7 | 34.714 | 18.139 | -0.045 | 1.00 | 22.34 | 6 |
| C | VAL | A | 7 | 32.199 | 15.387 | 0.909 | 1.00 | 26.06 | 6 |
| O | VAL | A | 7 | 32.502 | 14.198 | 0.786 | 1.00 | 27.16 | 8 |
| N | ALA | A | 8 | 31.232 | 15.783 | 1.731 | 1.00 | 26.43 | 7 |
| CA | ALA | A | 8 | 30.483 | 14.846 | 2.558 | 1.00 | 26.69 | 6 |
| CB | ALA | A | 8 | 29.549 | 15.590 | 3.500 | 1.00 | 25.12 | 6 |
| C | ALA | A | 8 | 29.689 | 13.857 | 1.711 | 1.00 | 27.31 | 6 |
| O | ALA | A | 8 | 29.503 | 12.707 | 2.112 | 1.00 | 26.33 | 8 |
| N | GLY | A | 8 | 29.198 | 14.295 | 0.555 | 1.00 | 28.24 | 7 |
| CA | GLY | A | 8 | 28.478 | 13.434 | -0.370 | 1.00 | 29.83 | 6 |
| C | GLY | A | 8 | 29.401 | 12.376 | -0.965 | 1.00 | 31.54 | 6 |
| O | GLY | A | 8 | 29.058 | 11.195 | -1.014 | 1.00 | 32.46 | 8 |
| N | VAL | A | 8 | 30.606 | 12.785 | -1.357 | 1.00 | 32.13 | 7 |
| CA | VAL | A | 8 | 31.593 | 11.855 | -1.897 | 1.00 | 32.49 | 6 |
| CB | VAL | A | 8 | 32.849 | 12.576 | -2.405 | 1.00 | 32.48 | 6 |
| C | VAL | A | 8 | 33.927 | 11.590 | -2.836 | 1.00 | 29.55 | 6 |
| C | VAL | A | 8 | 32.485 | 13.493 | -3.570 | 1.00 | 30.84 | 6 |
| C | VAL | A | 8 | 31.945 | 10.798 | -0.859 | 1.00 | 33.38 | 6 |
| O | VAL | A | 8 | 31.960 | 9.607 | -1.179 | 1.00 | 34.11 | 8 |
| N | GLN | A | 8 | 32.121 | 11.195 | 0.397 | 1.00 | 33.20 | 7 |
| CA | GLN | A | 8 | 32.353 | 10.260 | 1.485 | 1.00 | 33.16 | 6 |
| CB | GLN | A | 8 | 32.487 | 10.995 | 2.822 | 1.00 | 33.36 | 6 |
| C | GLN | A | 8 | 33.776 | 11.775 | 3.007 | 1.00 | 34.15 | 6 |
| C | GLN | A | 8 | 33.891 | 12.385 | 4.389 | 1.00 | 35.18 | 6 |
| O | GLN | A | 8 | 33.162 | 12.014 | 5.309 | 1.00 | 35.45 | 8 |
| N | GLN | A | 8 | 34.810 | 13.330 | 4.554 | 1.00 | 35.50 | 7 |
| C | GLN | A | 8 | 31.240 | 9.224 | 1.602 | 1.00 | 33.48 | 6 |
| O | GLN | A | 8 | 31.521 | 8.034 | 1.758 | 1.00 | 33.91 | 8 |
| N | ALA | A | 8 | 29.982 | 9.655 | 1.539 | 1.00 | 33.54 | 7 |
| CA | ALA | A | 8 | 28.854 | 8.740 | 1.660 | 1.00 | 33.80 | 6 |
| CB | ALA | A | 8 | 27.554 | 9.509 | 1.828 | 1.00 | 32.23 | 6 |
| C | ALA | A | 8 | 28.767 | 7.777 | 0.484 | 1.00 | 34.48 | 6 |
| O | ALA | A | 8 | 28.464 | 6.596 | 0.673 | 1.00 | 34.17 | 8 |
| N | MET | A | 8 | 29.032 | 8.262 | -0.724 | 1.00 | 35.38 | 7 |
| CA | MET | A | 8 | 29.047 | 7.401 | -1.902 | 1.00 | 36.89 | 6 |
| CB | MET | A | 8 | 29.234 | 8.228 | -3.172 | 1.00 | 39.17 | 6 |
| C | MET | A | 8 | 27.977 | 8.960 | -3.621 | 1.00 | 41.02 | 6 |
| SD | MET | A | 8 | 26.540 | 7.880 | -3.753 | 1.00 | 43.01 | 1 |
| CE | MET | A | 8 | 26.317 | 7.818 | -5.528 | 1.00 | 43.92 | 6 |
| C | MET | A | 8 | 30.132 | 6.340 | -1.757 | 1.00 | 37.28 | 6 |

Figure 1 - 5

| | | | | | | | | | | | | | | | | | |
|---|---|---|---|---|---|---|---|---|---|---|---|---|---|---|---|---|---|
| O | MET | A | 8 | 29.873 | 5.147 | -1.919 | 1.00 | 37.28 | 8 | C | GLU | A | 9 | 23.353 | 4.138 | -20.431 | 1.00 | 70.30 | 6 |
| N | GLN | A | 8 | 31.338 | 6.765 | -1.397 | 1.00 | 37.87 | 7 | O | GLU | A | 9 | 22.552 | 5.077 | -20.630 | 1.00 | 70.81 | 8 |
| CA | GLN | A | 8 | 32.462 | 5.860 | -1.192 | 1.00 | 38.47 | 6 | O | GLU | A | 9 | 24.484 | 4.092 | -20.959 | 1.00 | 72.24 | 8 |
| CB | GLN | A | 8 | 33.741 | 6.661 | -0.925 | 1.00 | 39.65 | 6 | C | GLU | A | 9 | 22.261 | 2.275 | -16.722 | 1.00 | 60.55 | 6 |
| C | GLN | A | 8 | 34.320 | 7.292 | -2.182 | 1.00 | 41.26 | 6 | O | GLU | A | 9 | 21.246 | 2.969 | -16.829 | 1.00 | 60.93 | 8 |
| C | GLN | A | 8 | 35.553 | 8.126 | -1.924 | 1.00 | 44.46 | 6 | N | GLU | A | 9 | 22.187 | 1.025 | -16.283 | 1.00 | 60.08 | 7 |
| O | GLN | A | 8 | 35.965 | 8.328 | -0.781 | 1.00 | 48.85 | 8 | CA | GLU | A | 9 | 20.972 | 0.362 | -15.864 | 1.00 | 59.62 | 6 |
| N | GLN | A | 8 | 36.170 | 8.625 | -2.991 | 1.00 | 45.09 | 7 | CB | GLU | A | 9 | 21.143 | -1.161 | -15.975 | 1.00 | 65.14 | 6 |
| C | GLN | A | 8 | 32.195 | 4.862 | -0.077 | 1.00 | 38.33 | 6 | C | GLU | A | 9 | 20.576 | -1.748 | -17.254 | 1.00 | 70.30 | 6 |
| O | GLN | A | 8 | 32.309 | 3.653 | -0.293 | 1.00 | 38.79 | 8 | C | GLU | A | 9 | 21.426 | -2.860 | -17.834 | 1.00 | 73.39 | 6 |
| N | ASP | A | 8 | 31.705 | 5.316 | 1.071 | 1.00 | 38.25 | 7 | O | GLU | A | 9 | 21.214 | -4.032 | -17.458 | 1.00 | 74.84 | 8 |
| CA | ASP | A | 8 | 31.356 | 4.431 | 2.171 | 1.00 | 38.61 | 6 | O | GLU | A | 9 | 22.302 | -2.564 | -18.674 | 1.00 | 74.99 | 8 |
| CB | ASP | A | 8 | 30.800 | 5.221 | 3.364 | 1.00 | 35.92 | 6 | C | GLU | A | 9 | 20.570 | 0.709 | -14.432 | 1.00 | 57.78 | 6 |
| C | ASP | A | 8 | 30.769 | 4.381 | 4.627 | 1.00 | 34.86 | 6 | O | GLU | A | 9 | 19.505 | 0.300 | -13.964 | 1.00 | 58.25 | 8 |
| O | ASP | A | 8 | 31.730 | 4.836 | 4.836 | 1.00 | 38.15 | 8 | N | ASN | A | 9 | 21.403 | 1.442 | -13.708 | 1.00 | 55.25 | 7 |
| O | ASP | A | 8 | 29.807 | 4.473 | 5.413 | 1.00 | 32.47 | 8 | CA | ASN | A | 9 | 21.154 | 1.857 | -12.345 | 1.00 | 52.48 | 6 |
| C | ASP | A | 8 | 30.338 | 3.362 | 1.785 | 1.00 | 39.15 | 6 | CB | ASN | A | 9 | 22.436 | 1.692 | -11.509 | 1.00 | 52.33 | 6 |
| O | ASP | A | 8 | 30.418 | 2.228 | 2.261 | 1.00 | 39.15 | 8 | C | ASN | A | 9 | 22.256 | 0.836 | -10.279 | 1.00 | 52.34 | 6 |
| N | SER | A | 8 | 29.341 | 3.717 | 0.987 | 1.00 | 40.00 | 7 | O | ASN | A | 9 | 21.147 | 0.414 | -9.952 | 1.00 | 53.95 | 8 |
| CA | SER | A | 8 | 28.268 | 2.824 | 0.605 | 1.00 | 40.96 | 6 | N | ASN | A | 9 | 23.355 | 0.564 | -9.584 | 1.00 | 52.48 | 7 |
| CB | SER | A | 8 | 27.186 | 3.609 | -0.151 | 1.00 | 37.71 | 6 | C | ASN | A | 9 | 20.747 | 3.320 | -12.209 | 1.00 | 50.29 | 6 |
| O | SER | A | 8 | 27.641 | 3.995 | -1.435 | 1.00 | 34.05 | 8 | O | ASN | A | 9 | 19.918 | 3.684 | -11.376 | 1.00 | 49.91 | 8 |
| C | SER | A | 8 | 28.687 | 1.626 | -0.235 | 1.00 | 42.86 | 6 | N | ALA | A | 9 | 21.390 | 4.190 | -12.974 | 1.00 | 48.07 | 7 |
| O | SER | A | 8 | 28.158 | 0.529 | -0.031 | 1.00 | 42.42 | 8 | CA | ALA | A | 9 | 21.232 | 5.632 | -12.898 | 1.00 | 46.01 | 6 |
| N | GLY | A | 8 | 29.572 | 1.835 | -1.203 | 1.00 | 44.78 | 7 | CB | ALA | A | 9 | 21.670 | 6.263 | -14.219 | 1.00 | 45.08 | 6 |
| CA | GLY | A | 8 | 29.933 | 0.745 | -2.114 | 1.00 | 47.74 | 6 | C | ALA | A | 9 | 19.837 | 6.108 | -12.535 | 1.00 | 44.36 | 6 |
| C | GLY | A | 8 | 28.791 | 0.593 | -3.124 | 1.00 | 49.79 | 6 | O | ALA | A | 9 | 19.606 | 6.801 | -11.545 | 1.00 | 43.66 | 8 |
| O | GLY | A | 8 | 28.100 | -0.420 | -3.181 | 1.00 | 50.71 | 8 | N | THR | A | 9 | 18.847 | 5.727 | -13.317 | 1.00 | 42.87 | 7 |
| N | LEU | A | 9 | 28.528 | 1.689 | -3.826 | 1.00 | 51.03 | 7 | CA | THR | A | 9 | 17.439 | 6.032 | -13.183 | 1.00 | 41.55 | 6 |
| CA | LEU | A | 9 | 27.506 | 1.717 | -4.861 | 1.00 | 52.32 | 6 | CB | THR | A | 9 | 16.725 | 5.210 | -14.293 | 1.00 | 41.55 | 6 |
| CB | LEU | A | 9 | 26.528 | 2.868 | -4.677 | 1.00 | 54.13 | 6 | O | THR | A | 9 | 16.719 | 6.004 | -15.494 | 1.00 | 40.58 | 8 |
| C | LEU | A | 9 | 25.057 | 2.570 | -4.394 | 1.00 | 54.85 | 6 | C | THR | A | 9 | 15.307 | 4.783 | -13.985 | 1.00 | 41.61 | 6 |
| C | LEU | A | 9 | 24.486 | 1.519 | -5.334 | 1.00 | 54.50 | 6 | C | THR | A | 9 | 16.812 | 5.788 | -11.826 | 1.00 | 40.49 | 6 |
| C | LEU | A | 9 | 24.866 | 2.145 | -2.943 | 1.00 | 55.70 | 6 | O | THR | A | 9 | 15.785 | 6.415 | -11.520 | 1.00 | 40.45 | 8 |
| C | LEU | A | 9 | 28.206 | 1.842 | -6.216 | 1.00 | 53.14 | 6 | N | ARG | A | 9 | 17.337 | 4.908 | -10.983 | 1.00 | 39.59 | 7 |
| O | LEU | A | 9 | 29.081 | 2.691 | -6.384 | 1.00 | 52.83 | 8 | CA | ARG | A | 9 | 16.774 | 4.614 | -9.680 | 1.00 | 38.37 | 6 |
| N | GLU | A | 9 | 27.909 | 0.911 | -7.112 | 1.00 | 54.36 | 7 | CB | ARG | A | 9 | 16.709 | 3.094 | -9.462 | 1.00 | 38.52 | 6 |
| CA | GLU | A | 9 | 28.436 | 1.005 | -8.474 | 1.00 | 55.52 | 6 | C | ARG | A | 9 | 15.974 | 2.321 | -10.544 | 1.00 | 37.03 | 6 |
| CB | GLU | A | 9 | 28.912 | -0.344 | -8.989 | 1.00 | 60.57 | 6 | C | ARG | A | 9 | 14.479 | 2.597 | -10.499 | 1.00 | 37.03 | 6 |
| C | GLU | A | 9 | 30.077 | -0.937 | -8.213 | 1.00 | 66.39 | 6 | N | ARG | A | 9 | 13.865 | 2.041 | -9.300 | 1.00 | 38.20 | 7 |
| C | GLU | A | 9 | 31.198 | -1.433 | -9.104 | 1.00 | 70.22 | 6 | CZ | ARG | A | 9 | 12.707 | 2.430 | -8.785 | 1.00 | 38.63 | 6 |
| O | GLU | A | 9 | 30.912 | -2.114 | -10.113 | 1.00 | 71.43 | 8 | N | ARG | A | 9 | 12.002 | 3.397 | -9.357 | 1.00 | 38.37 | 7 |
| O | GLU | A | 9 | 32.375 | -1.147 | -8.797 | 1.00 | 72.65 | 8 | N | ARG | A | 9 | 12.248 | 1.845 | -7.686 | 1.00 | 38.97 | 7 |
| C | GLU | A | 9 | 27.323 | 1.595 | -9.339 | 1.00 | 54.98 | 6 | C | ARG | A | 9 | 17.523 | 5.238 | -8.512 | 1.00 | 37.78 | 6 |
| O | GLU | A | 9 | 26.219 | 1.047 | -9.355 | 1.00 | 54.62 | 8 | O | ARG | A | 9 | 17.180 | 4.972 | -7.356 | 1.00 | 38.19 | 8 |
| N | ILE | A | 9 | 27.578 | 2.756 | -9.933 | 1.00 | 54.70 | 7 | N | ILE | A | 1 | 18.586 | 5.988 | -8.777 | 1.00 | 37.13 | 7 |
| CA | ILE | A | 9 | 26.552 | 3.400 | -10.753 | 1.00 | 54.44 | 6 | CA | ILE | A | 1 | 19.341 | 6.642 | -7.716 | 1.00 | 36.46 | 6 |
| CB | ILE | A | 9 | 26.540 | 4.926 | -10.595 | 1.00 | 53.38 | 6 | CB | ILE | A | 1 | 20.835 | 6.276 | -7.700 | 1.00 | 38.03 | 6 |
| C | ILE | A | 9 | 25.665 | 5.601 | -11.642 | 1.00 | 52.58 | 6 | C | ILE | A | 1 | 21.468 | 6.737 | -6.389 | 1.00 | 36.28 | 6 |
| C | ILE | A | 9 | 26.039 | 5.304 | -9.195 | 1.00 | 53.52 | 6 | C | ILE | A | 1 | 21.072 | 4.776 | -7.890 | 1.00 | 37.64 | 6 |
| C | ILE | A | 9 | 27.133 | 5.719 | -8.239 | 1.00 | 53.86 | 6 | C | ILE | A | 1 | 22.387 | 4.447 | -8.564 | 1.00 | 38.13 | 6 |
| C | ILE | A | 9 | 26.728 | 2.992 | -12.212 | 1.00 | 54.48 | 6 | C | ILE | A | 1 | 19.222 | 8.160 | -7.839 | 1.00 | 35.71 | 6 |
| O | ILE | A | 9 | 27.718 | 3.308 | -12.864 | 1.00 | 53.82 | 8 | O | ILE | A | 1 | 19.502 | 8.713 | -8.904 | 1.00 | 35.52 | 8 |
| N | THR | A | 9 | 25.758 | 2.226 | -12.868 | 1.00 | 55.02 | 7 | N | GLY | A | 1 | 18.822 | 8.819 | -6.756 | 1.00 | 34.95 | 7 |
| CA | THR | A | 9 | 25.753 | 1.743 | -14.070 | 1.00 | 56.18 | 6 | CA | GLY | A | 1 | 18.705 | 10.273 | -6.771 | 1.00 | 34.19 | 6 |
| CB | THR | A | 9 | 25.556 | 0.214 | -14.128 | 1.00 | 53.64 | 6 | C | GLY | A | 1 | 19.233 | 10.914 | -5.493 | 1.00 | 33.40 | 6 |
| O | THR | A | 9 | 24.276 | -0.107 | -13.563 | 1.00 | 51.69 | 8 | O | GLY | A | 1 | 20.044 | 10.319 | -4.781 | 1.00 | 34.11 | 8 |
| C | THR | A | 9 | 26.639 | -0.524 | -13.365 | 1.00 | 51.89 | 6 | N | ALA | A | 1 | 18.740 | 12.115 | -5.193 | 1.00 | 31.57 | 7 |
| C | THR | A | 9 | 24.612 | 2.378 | -14.854 | 1.00 | 57.86 | 6 | CA | ALA | A | 1 | 19.184 | 12.858 | -4.025 | 1.00 | 29.34 | 6 |
| O | THR | A | 9 | 23.657 | 2.897 | -14.274 | 1.00 | 57.93 | 8 | CB | ALA | A | 1 | 20.373 | 13.728 | -4.437 | 1.00 | 30.70 | 6 |
| N | GLU | A | 9 | 24.672 | 2.301 | -16.180 | 1.00 | 59.43 | 7 | C | ALA | A | 1 | 18.123 | 13.747 | -3.390 | 1.00 | 28.20 | 6 |
| CA | GLU | A | 9 | 23.635 | 2.847 | -17.050 | 1.00 | 60.73 | 6 | O | ALA | A | 1 | 17.177 | 14.224 | -4.008 | 1.00 | 28.29 | 8 |
| CB | GLU | A | 9 | 23.989 | 2.595 | -18.517 | 1.00 | 64.29 | 6 | N | ALA | A | 1 | 18.293 | 13.983 | -2.093 | 1.00 | 26.43 | 7 |
| C | GLU | A | 9 | 22.926 | 3.011 | -19.515 | 1.00 | 67.99 | 6 | CA | ALA | A | 1 | 17.403 | 14.814 | -1.294 | 1.00 | 23.90 | 6 |

Figure 1-6

| | | | | | | | | |
|---|---|---|---|---|---|---|---|---|
| CB | ALA | A | 1 | 16.330 | 13.994 | -0.604 | 1.00 | 20.94 | 6 |
| C | ALA | A | 1 | 18.266 | 15.578 | -0.290 | 1.00 | 23.06 | 6 |
| O | ALA | A | 1 | 18.438 | 15.176 | 0.858 | 1.00 | 22.58 | 8 |
| N | ILE | A | 1 | 18.951 | 16.600 | -0.799 | 1.00 | 22.65 | 7 |
| CA | ILE | A | 1 | 19.890 | 17.384 | -0.008 | 1.00 | 22.42 | 6 |
| CB | ILE | A | 1 | 21.308 | 17.361 | -0.609 | 1.00 | 19.34 | 6 |
| C | ILE | A | 1 | 22.263 | 18.211 | 0.218 | 1.00 | 19.61 | 6 |
| C | ILE | A | 1 | 21.846 | 15.931 | -0.727 | 1.00 | 19.04 | 6 |
| C | ILE | A | 1 | 22.912 | 15.769 | -1.789 | 1.00 | 14.64 | 6 |
| C | ILE | A | 1 | 19.430 | 18.837 | 0.103 | 1.00 | 22.33 | 6 |
| O | ILE | A | 1 | 19.185 | 19.485 | -0.912 | 1.00 | 22.91 | 8 |
| N | GLY | A | 1 | 19.398 | 19.363 | 1.321 | 1.00 | 21.49 | 7 |
| CA | GLY | A | 1 | 18.983 | 20.732 | 1.546 | 1.00 | 21.32 | 6 |
| C | GLY | A | 1 | 19.985 | 21.571 | 2.326 | 1.00 | 21.77 | 6 |
| O | GLY | A | 1 | 21.116 | 21.201 | 2.619 | 1.00 | 20.74 | 8 |
| N | SER | A | 1 | 19.526 | 22.767 | 2.663 | 1.00 | 22.27 | 7 |
| CA | SER | A | 1 | 20.263 | 23.779 | 3.400 | 1.00 | 22.50 | 6 |
| CB | SER | A | 1 | 21.306 | 24.448 | 2.511 | 1.00 | 22.72 | 6 |
| O | SER | A | 1 | 22.078 | 25.395 | 3.224 | 1.00 | 21.91 | 8 |
| C | SER | A | 1 | 19.248 | 24.811 | 3.895 | 1.00 | 22.77 | 6 |
| O | SER | A | 1 | 18.261 | 25.058 | 3.198 | 1.00 | 22.73 | 8 |
| N | GLY | A | 1 | 19.473 | 25.393 | 5.062 | 1.00 | 22.84 | 7 |
| CA | GLY | A | 1 | 18.557 | 26.368 | 5.619 | 1.00 | 23.14 | 6 |
| C | GLY | A | 1 | 18.683 | 27.762 | 5.036 | 1.00 | 23.90 | 6 |
| O | GLY | A | 1 | 17.665 | 28.437 | 4.846 | 1.00 | 23.26 | 8 |
| N | ILE | A | 1 | 19.904 | 28.234 | 4.800 | 1.00 | 24.27 | 7 |
| CA | ILE | A | 1 | 20.130 | 29.582 | 4.284 | 1.00 | 25.21 | 6 |
| CB | ILE | A | 1 | 20.904 | 30.424 | 5.317 | 1.00 | 28.84 | 6 |
| C | ILE | A | 1 | 21.399 | 31.746 | 4.750 | 1.00 | 29.40 | 6 |
| C | ILE | A | 1 | 20.025 | 30.718 | 6.544 | 1.00 | 30.94 | 6 |
| C | ILE | A | 1 | 20.804 | 31.053 | 7.796 | 1.00 | 32.04 | 6 |
| C | ILE | A | 1 | 20.839 | 29.580 | 2.938 | 1.00 | 25.28 | 6 |
| O | ILE | A | 1 | 20.712 | 30.527 | 2.153 | 1.00 | 25.17 | 8 |
| N | GLY | A | 1 | 21.587 | 28.527 | 2.623 | 1.00 | 25.28 | 7 |
| CA | GLY | A | 1 | 22.284 | 28.453 | 1.345 | 1.00 | 25.24 | 6 |
| C | GLY | A | 1 | 23.457 | 29.418 | 1.274 | 1.00 | 25.63 | 6 |
| O | GLY | A | 1 | 24.083 | 29.755 | 2.279 | 1.00 | 25.92 | 8 |
| N | GLY | A | 1 | 23.862 | 29.789 | 0.062 | 1.00 | 25.45 | 7 |
| CA | GLY | A | 1 | 25.084 | 30.496 | -0.218 | 1.00 | 26.20 | 6 |
| C | GLY | A | 1 | 25.213 | 31.934 | 0.223 | 1.00 | 27.33 | 6 |
| O | GLY | A | 1 | 25.522 | 32.817 | -0.585 | 1.00 | 27.71 | 8 |
| N | LEU | A | 1 | 25.181 | 32.186 | 1.526 | 1.00 | 27.58 | 7 |
| CA | LEU | A | 1 | 25.252 | 33.513 | 2.104 | 1.00 | 26.89 | 6 |
| CB | LEU | A | 1 | 25.045 | 33.438 | 3.622 | 1.00 | 30.54 | 6 |
| C | LEU | A | 1 | 23.844 | 34.161 | 4.225 | 1.00 | 33.04 | 6 |
| C | LEU | A | 1 | 23.965 | 34.212 | 5.744 | 1.00 | 34.23 | 6 |
| C | LEU | A | 1 | 23.678 | 35.565 | 3.670 | 1.00 | 31.51 | 6 |
| C | LEU | A | 1 | 26.579 | 34.203 | 1.822 | 1.00 | 25.55 | 6 |
| O | LEU | A | 1 | 26.623 | 35.387 | 1.493 | 1.00 | 24.44 | 8 |
| N | GLY | A | 1 | 27.668 | 33.453 | 1.966 | 1.00 | 24.93 | 7 |
| CA | GLY | A | 1 | 29.006 | 33.973 | 1.717 | 1.00 | 24.16 | 6 |
| C | GLY | A | 1 | 29.109 | 34.602 | 0.333 | 1.00 | 23.21 | 6 |
| O | GLY | A | 1 | 29.471 | 35.771 | 0.215 | 1.00 | 22.61 | 8 |
| N | LEU | A | 1 | 28.675 | 33.879 | -0.696 | 1.00 | 23.12 | 7 |
| CA | LEU | A | 1 | 28.747 | 34.359 | -2.069 | 1.00 | 23.32 | 6 |
| CB | LEU | A | 1 | 28.713 | 33.180 | -3.045 | 1.00 | 21.08 | 6 |
| C | LEU | A | 1 | 30.015 | 32.880 | -3.794 | 1.00 | 22.62 | 6 |
| C | LEU | A | 1 | 31.248 | 33.029 | -2.917 | 1.00 | 21.29 | 6 |
| C | LEU | A | 1 | 29.986 | 31.481 | -4.396 | 1.00 | 19.43 | 6 |
| C | LEU | A | 1 | 27.719 | 35.426 | -2.403 | 1.00 | 23.44 | 6 |
| O | LEU | A | 1 | 27.980 | 36.253 | -3.288 | 1.00 | 23.38 | 8 |
| N | ILE | A | 1 | 26.586 | 35.477 | -1.707 | 1.00 | 22.94 | 7 |
| CA | ILE | A | 1 | 25.596 | 36.524 | -1.959 | 1.00 | 22.61 | 6 |
| CB | ILE | A | 1 | 24.235 | 36.235 | -1.314 | 1.00 | 22.78 | 6 |

| | | | | | | | | |
|---|---|---|---|---|---|---|---|---|
| C | ILE | A | 1 | 23.320 | 37.452 | -1.351 | 1.00 | 20.68 | 6 |
| C | ILE | A | 1 | 23.558 | 35.053 | -2.019 | 1.00 | 21.17 | 6 |
| C | ILE | A | 1 | 22.467 | 34.395 | -1.206 | 1.00 | 20.81 | 6 |
| C | ILE | A | 1 | 26.148 | 37.861 | -1.461 | 1.00 | 22.38 | 6 |
| O | ILE | A | 1 | 25.969 | 38.896 | -2.103 | 1.00 | 21.79 | 8 |
| N | GLU | A | 1 | 26.848 | 37.329 | -0.332 | 1.00 | 22.40 | 7 |
| CA | GLU | A | 1 | 27.490 | 39.019 | 0.209 | 1.00 | 23.90 | 6 |
| CB | GLU | A | 1 | 28.076 | 38.737 | 1.590 | 1.00 | 23.43 | 6 |
| C | GLU | A | 1 | 27.029 | 38.487 | 2.666 | 1.00 | 24.28 | 6 |
| C | GLU | A | 1 | 27.682 | 38.221 | 4.010 | 1.00 | 26.12 | 6 |
| O | GLU | A | 1 | 27.217 | 37.322 | 4.736 | 1.00 | 24.90 | 8 |
| O | GLU | A | 1 | 28.671 | 38.918 | 4.318 | 1.00 | 28.72 | 8 |
| C | GLU | A | 1 | 28.575 | 39.538 | -0.727 | 1.00 | 24.96 | 6 |
| O | GLU | A | 1 | 28.586 | 40.724 | -1.050 | 1.00 | 25.66 | 8 |
| N | GLU | A | 1 | 29.464 | 38.665 | -1.189 | 1.00 | 26.22 | 7 |
| CA | GLU | A | 1 | 30.525 | 39.052 | -2.107 | 1.00 | 27.40 | 6 |
| CB | GLU | A | 1 | 31.361 | 37.838 | -2.520 | 1.00 | 29.69 | 6 |
| C | GLU | A | 1 | 32.500 | 38.186 | -3.466 | 1.00 | 36.82 | 6 |
| C | GLU | A | 1 | 33.298 | 36.974 | -3.901 | 1.00 | 39.85 | 6 |
| O | GLU | A | 1 | 34.033 | 36.420 | -3.058 | 1.00 | 42.55 | 8 |
| O | GLU | A | 1 | 33.191 | 36.575 | -5.079 | 1.00 | 43.21 | 8 |
| C | GLU | A | 1 | 29.968 | 39.727 | -3.358 | 1.00 | 27.74 | 6 |
| O | GLU | A | 1 | 30.345 | 40.847 | -3.698 | 1.00 | 27.49 | 8 |
| N | ASN | A | 1 | 29.038 | 39.051 | -4.026 | 1.00 | 27.54 | 7 |
| CA | ASN | A | 1 | 28.397 | 39.569 | -5.223 | 1.00 | 27.47 | 6 |
| CB | ASN | A | 1 | 27.450 | 38.524 | -5.823 | 1.00 | 25.94 | 6 |
| C | ASN | A | 1 | 28.191 | 37.404 | -6.525 | 1.00 | 24.69 | 6 |
| O | ASN | A | 1 | 28.773 | 37.602 | -7.591 | 1.00 | 25.98 | 8 |
| N | ASN | A | 1 | 28.168 | 36.214 | -5.940 | 1.00 | 22.87 | 7 |
| C | ASN | A | 1 | 27.639 | 40.862 | -4.958 | 1.00 | 27.92 | 6 |
| O | ASN | A | 1 | 27.674 | 41.763 | -5.801 | 1.00 | 27.84 | 8 |
| N | HIS | A | 1 | 26.965 | 40.976 | -3.811 | 1.00 | 28.73 | 7 |
| CA | HIS | A | 1 | 26.266 | 42.219 | -3.503 | 1.00 | 29.88 | 6 |
| CB | HIS | A | 1 | 25.334 | 42.129 | -2.295 | 1.00 | 26.18 | 6 |
| C | HIS | A | 1 | 24.463 | 43.353 | -2.216 | 1.00 | 23.31 | 6 |
| C | HIS | A | 1 | 24.431 | 44.382 | -1.343 | 1.00 | 22.00 | 6 |
| N | HIS | A | 1 | 23.484 | 43.614 | -3.151 | 1.00 | 23.32 | 7 |
| CE | HIS | A | 1 | 22.881 | 44.750 | -2.852 | 1.00 | 23.34 | 6 |
| N | HIS | A | 1 | 23.438 | 45.235 | -1.755 | 1.00 | 23.46 | 7 |
| C | HIS | A | 1 | 27.290 | 43.339 | -3.321 | 1.00 | 31.26 | 6 |
| O | HIS | A | 1 | 27.141 | 44.417 | -3.898 | 1.00 | 31.42 | 8 |
| N | THR | A | 1 | 28.382 | 43.048 | -2.620 | 1.00 | 32.61 | 7 |
| CA | THR | A | 1 | 29.466 | 44.011 | -2.448 | 1.00 | 33.99 | 6 |
| CB | THR | A | 1 | 30.580 | 43.428 | -1.562 | 1.00 | 34.40 | 6 |
| O | THR | A | 1 | 30.011 | 43.087 | -0.288 | 1.00 | 33.02 | 8 |
| C | THR | A | 1 | 31.707 | 44.425 | -1.345 | 1.00 | 35.33 | 6 |
| C | THR | A | 1 | 30.018 | 44.464 | -3.792 | 1.00 | 34.89 | 6 |
| O | THR | A | 1 | 30.148 | 45.668 | -4.033 | 1.00 | 35.35 | 8 |
| N | SER | A | 1 | 30.289 | 43.527 | -4.695 | 1.00 | 35.14 | 7 |
| CA | SER | A | 1 | 30.726 | 43.862 | -6.047 | 1.00 | 35.99 | 6 |
| CB | SER | A | 1 | 30.916 | 42.588 | -6.870 | 1.00 | 35.21 | 6 |
| O | SER | A | 1 | 31.858 | 41.733 | -6.236 | 1.00 | 37.30 | 8 |
| C | SER | A | 1 | 29.734 | 44.807 | -6.711 | 1.00 | 37.29 | 6 |
| O | SER | A | 1 | 30.092 | 45.918 | -7.100 | 1.00 | 37.19 | 8 |
| N | LEU | A | 1 | 28.464 | 44.426 | -6.777 | 1.00 | 38.61 | 7 |
| CA | LEU | A | 1 | 27.411 | 45.250 | -7.350 | 1.00 | 40.26 | 6 |
| CB | LEU | A | 1 | 26.054 | 44.565 | -7.172 | 1.00 | 39.02 | 6 |
| C | LEU | A | 1 | 24.786 | 45.386 | -7.405 | 1.00 | 37.46 | 6 |
| C | LEU | A | 1 | 24.538 | 45.621 | -8.887 | 1.00 | 35.37 | 6 |
| C | LEU | A | 1 | 23.583 | 44.700 | -6.770 | 1.00 | 34.67 | 6 |
| C | LEU | A | 1 | 27.377 | 46.657 | -6.775 | 1.00 | 42.20 | 6 |
| O | LEU | A | 1 | 27.267 | 47.624 | -7.535 | 1.00 | 42.75 | 8 |
| N | MET | A | 1 | 27.473 | 46.815 | -5.461 | 1.00 | 44.22 | 7 |
| CA | MET | A | 1 | 27.448 | 48.124 | -4.826 | 1.00 | 46.59 | 6 |

Figure 1 - 7

| | | | | | | | | |
|---|---|---|---|---|---|---|---|---|
| CB | MET | A | 1 | 27.435 | 47.984 | -3.301 | 1.00 | 52.03 | 6 |
| C | MET | A | 1 | 26.067 | 48.225 | -2.680 | 1.00 | 57.93 | 6 |
| SD | MET | A | 1 | 26.084 | 48.049 | -0.886 | 1.00 | 64.29 | 1 |
| CE | MET | A | 1 | 26.407 | 49.739 | -0.383 | 1.00 | 64.73 | 6 |
| C | MET | A | 1 | 28.613 | 49.012 | -5.246 | 1.00 | 47.07 | 6 |
| O | MET | A | 1 | 28.443 | 50.220 | -5.426 | 1.00 | 47.31 | 8 |
| N | ASN | A | 1 | 29.799 | 48.433 | -5.396 | 1.00 | 46.74 | 7 |
| CA | ASN | A | 1 | 30.983 | 49.177 | -5.779 | 1.00 | 46.35 | 6 |
| CB | ASN | A | 1 | 32.214 | 48.573 | -5.088 | 1.00 | 45.88 | 6 |
| C | ASN | A | 1 | 32.174 | 48.660 | -3.581 | 1.00 | 45.33 | 6 |
| O | ASN | A | 1 | 32.794 | 47.836 | -2.904 | 1.00 | 46.65 | 8 |
| N | ASN | A | 1 | 31.462 | 49.639 | -3.037 | 1.00 | 44.11 | 7 |
| C | ASN | A | 1 | 31.255 | 49.202 | -7.277 | 1.00 | 45.75 | 6 |
| O | ASN | A | 1 | 32.177 | 49.917 | -7.685 | 1.00 | 46.59 | 8 |
| N | GLY | A | 1 | 30.574 | 48.383 | -8.072 | 1.00 | 44.74 | 7 |
| CA | GLY | A | 1 | 30.922 | 48.253 | -9.474 | 1.00 | 43.33 | 6 |
| C | GLY | A | 1 | 29.781 | 48.197 | -10.464 | 1.00 | 42.25 | 6 |
| O | GLY | A | 1 | 30.035 | 48.292 | -11.671 | 1.00 | 42.48 | 8 |
| N | GLY | A | 1 | 28.543 | 48.053 | -10.006 | 1.00 | 41.17 | 7 |
| CA | GLY | A | 1 | 27.409 | 47.945 | -10.932 | 1.00 | 39.64 | 6 |
| C | GLY | A | 1 | 27.225 | 46.464 | -11.262 | 1.00 | 38.72 | 6 |
| O | GLY | A | 1 | 28.002 | 45.627 | -10.801 | 1.00 | 38.34 | 8 |
| N | PRO | A | 1 | 26.237 | 46.137 | -12.085 | 1.00 | 38.22 | 7 |
| C | PRO | A | 1 | 25.259 | 47.111 | -12.633 | 1.00 | 37.72 | 6 |
| CA | PRO | A | 1 | 25.895 | 44.772 | -12.416 | 1.00 | 38.34 | 6 |
| CB | PRO | A | 1 | 24.527 | 44.880 | -13.095 | 1.00 | 38.14 | 6 |
| C | PRO | A | 1 | 24.423 | 46.282 | -13.571 | 1.00 | 37.58 | 6 |
| C | PRO | A | 1 | 26.854 | 43.988 | -13.281 | 1.00 | 39.14 | 6 |
| O | PRO | A | 1 | 26.795 | 42.750 | -13.297 | 1.00 | 38.94 | 8 |
| N | ARG | A | 1 | 27.801 | 44.631 | -13.949 | 1.00 | 40.36 | 7 |
| CA | ARG | A | 1 | 28.785 | 43.959 | -14.785 | 1.00 | 41.09 | 6 |
| CB | ARG | A | 1 | 29.455 | 44.970 | -15.724 | 1.00 | 46.18 | 6 |
| C | ARG | A | 1 | 28.562 | 45.416 | -16.872 | 1.00 | 50.28 | 6 |
| C | ARG | A | 1 | 29.350 | 45.527 | -18.166 | 1.00 | 53.24 | 6 |
| N | ARG | A | 1 | 28.796 | 46.521 | -19.076 | 1.00 | 55.29 | 7 |
| CZ | ARG | A | 1 | 29.506 | 47.462 | -19.690 | 1.00 | 55.01 | 6 |
| N | ARG | A | 1 | 30.816 | 47.556 | -19.497 | 1.00 | 55.03 | 7 |
| N | ARG | A | 1 | 28.905 | 48.318 | -20.505 | 1.00 | 55.60 | 7 |
| C | ARG | A | 1 | 29.845 | 43.225 | -13.977 | 1.00 | 40.64 | 6 |
| O | ARG | A | 1 | 30.548 | 42.358 | -14.500 | 1.00 | 40.85 | 8 |
| N | LYS | A | 1 | 29.974 | 43.549 | -12.695 | 1.00 | 39.68 | 7 |
| CA | LYS | A | 1 | 30.926 | 42.913 | -11.804 | 1.00 | 39.19 | 6 |
| CB | LYS | A | 1 | 31.481 | 43.917 | -10.789 | 1.00 | 42.97 | 6 |
| C | LYS | A | 1 | 32.320 | 45.016 | -11.425 | 1.00 | 47.77 | 6 |
| C | LYS | A | 1 | 33.497 | 45.393 | -10.539 | 1.00 | 52.40 | 6 |
| CE | LYS | A | 1 | 34.820 | 45.185 | -11.258 | 1.00 | 54.77 | 6 |
| NZ | LYS | A | 1 | 35.931 | 44.909 | -10.304 | 1.00 | 56.71 | 7 |
| C | LYS | A | 1 | 30.302 | 41.719 | -11.086 | 1.00 | 37.56 | 6 |
| O | LYS | A | 1 | 30.981 | 41.025 | -10.330 | 1.00 | 37.63 | 8 |
| N | ILE | A | 1 | 29.011 | 41.485 | -11.305 | 1.00 | 35.54 | 7 |
| CA | ILE | A | 1 | 28.334 | 40.336 | -10.731 | 1.00 | 33.68 | 6 |
| CB | ILE | A | 1 | 26.801 | 40.387 | -10.856 | 1.00 | 32.19 | 6 |
| C | ILE | A | 1 | 26.176 | 39.099 | -10.324 | 1.00 | 29.64 | 6 |
| C | ILE | A | 1 | 26.240 | 41.601 | -10.113 | 1.00 | 30.24 | 6 |
| C | ILE | A | 1 | 24.751 | 41.810 | -10.277 | 1.00 | 29.97 | 6 |
| C | ILE | A | 1 | 28.840 | 39.071 | -11.427 | 1.00 | 32.94 | 6 |
| O | ILE | A | 1 | 28.713 | 38.917 | -12.639 | 1.00 | 33.73 | 8 |
| N | SER | A | 1 | 29.406 | 38.170 | -10.638 | 1.00 | 32.07 | 7 |
| CA | SER | A | 1 | 29.892 | 36.905 | -11.172 | 1.00 | 31.05 | 6 |
| CB | SER | A | 1 | 30.316 | 35.998 | -10.011 | 1.00 | 27.43 | 6 |
| O | SER | A | 1 | 30.212 | 34.634 | -10.380 | 1.00 | 29.41 | 8 |
| C | SER | A | 1 | 28.797 | 36.224 | -11.978 | 1.00 | 30.95 | 6 |
| O | SER | A | 1 | 27.666 | 36.067 | -11.516 | 1.00 | 30.37 | 8 |
| N | PRO | A | 1 | 29.168 | 35.630 | -13.110 | 1.00 | 31.19 | 7 |

| | | | | | | | | |
|---|---|---|---|---|---|---|---|---|
| C | PRO | A | 1 | 30.522 | 35.725 | -13.712 | 1.00 | 30.70 | 6 |
| CA | PRO | A | 1 | 28.262 | 34.851 | -13.934 | 1.00 | 30.42 | 6 |
| CB | PRO | A | 1 | 29.075 | 34.511 | -15.176 | 1.00 | 30.53 | 6 |
| C | PRO | A | 1 | 30.497 | 34.659 | -14.773 | 1.00 | 30.46 | 6 |
| C | PRO | A | 1 | 27.747 | 33.598 | -13.247 | 1.00 | 29.81 | 6 |
| O | PRO | A | 1 | 26.717 | 33.040 | -13.634 | 1.00 | 30.42 | 8 |
| N | PHE | A | 1 | 28.418 | 33.122 | -12.205 | 1.00 | 29.31 | 7 |
| CA | PHE | A | 1 | 27.966 | 31.998 | -11.409 | 1.00 | 28.57 | 6 |
| CB | PHE | A | 1 | 29.165 | 31.134 | -10.994 | 1.00 | 32.50 | 6 |
| C | PHE | A | 1 | 30.000 | 30.707 | -12.171 | 1.00 | 35.29 | 6 |
| C | PHE | A | 1 | 31.285 | 31.197 | -12.336 | 1.00 | 36.91 | 6 |
| C | PHE | A | 1 | 29.496 | 29.828 | -13.114 | 1.00 | 36.02 | 6 |
| CE | PHE | A | 1 | 32.054 | 30.816 | -13.420 | 1.00 | 36.75 | 6 |
| CE | PHE | A | 1 | 30.259 | 29.444 | -14.200 | 1.00 | 37.47 | 6 |
| CZ | PHE | A | 1 | 31.539 | 29.939 | -14.352 | 1.00 | 37.10 | 6 |
| C | PHE | A | 1 | 27.152 | 32.407 | -10.189 | 1.00 | 27.24 | 6 |
| O | PHE | A | 1 | 26.811 | 31.525 | -9.391 | 1.00 | 26.69 | 8 |
| N | PHE | A | 1 | 26.728 | 33.662 | -10.062 | 1.00 | 26.22 | 7 |
| CA | PHE | A | 1 | 25.921 | 34.075 | -8.923 | 1.00 | 26.42 | 6 |
| CB | PHE | A | 1 | 25.261 | 35.452 | -9.115 | 1.00 | 28.07 | 6 |
| C | PHE | A | 1 | 24.327 | 35.782 | -7.976 | 1.00 | 29.48 | 6 |
| C | PHE | A | 1 | 24.822 | 36.022 | -6.707 | 1.00 | 30.09 | 6 |
| C | PHE | A | 1 | 22.957 | 35.816 | -8.173 | 1.00 | 30.82 | 6 |
| CE | PHE | A | 1 | 23.971 | 36.306 | -5.657 | 1.00 | 31.10 | 6 |
| CE | PHE | A | 1 | 22.102 | 36.097 | -7.126 | 1.00 | 32.04 | 6 |
| CZ | PHE | A | 1 | 22.608 | 36.346 | -5.865 | 1.00 | 31.21 | 6 |
| C | PHE | A | 1 | 24.866 | 33.039 | -8.545 | 1.00 | 25.76 | 6 |
| O | PHE | A | 1 | 24.956 | 32.446 | -7.469 | 1.00 | 25.97 | 8 |
| N | VAL | A | 1 | 23.859 | 32.828 | -9.381 | 1.00 | 25.35 | 7 |
| CA | VAL | A | 1 | 22.756 | 31.927 | -9.077 | 1.00 | 24.82 | 6 |
| CB | VAL | A | 1 | 21.736 | 31.901 | -10.235 | 1.00 | 22.95 | 6 |
| C | VAL | A | 1 | 20.575 | 30.962 | -9.955 | 1.00 | 24.37 | 6 |
| C | VAL | A | 1 | 21.217 | 33.306 | -10.508 | 1.00 | 22.82 | 6 |
| C | VAL | A | 1 | 23.164 | 30.517 | -8.695 | 1.00 | 25.43 | 6 |
| O | VAL | A | 1 | 22.904 | 30.055 | -7.578 | 1.00 | 26.10 | 8 |
| N | PRO | A | 1 | 23.845 | 29.785 | -9.572 | 1.00 | 25.98 | 7 |
| C | PRO | A | 1 | 24.205 | 30.252 | -10.939 | 1.00 | 25.42 | 6 |
| CA | PRO | A | 1 | 24.246 | 28.412 | -9.343 | 1.00 | 25.35 | 6 |
| CB | PRO | A | 1 | 24.917 | 27.980 | -10.644 | 1.00 | 25.44 | 6 |
| C | PRO | A | 1 | 24.556 | 28.987 | -11.666 | 1.00 | 25.60 | 6 |
| C | PRO | A | 1 | 25.181 | 28.166 | -8.174 | 1.00 | 25.15 | 6 |
| O | PRO | A | 1 | 25.336 | 27.030 | -7.712 | 1.00 | 24.38 | 8 |
| N | SER | A | 1 | 25.873 | 29.189 | -7.698 | 1.00 | 25.35 | 7 |
| CA | SER | A | 1 | 26.777 | 29.098 | -6.572 | 1.00 | 25.73 | 6 |
| CB | SER | A | 1 | 27.891 | 30.138 | -6.762 | 1.00 | 25.82 | 6 |
| O | SER | A | 1 | 27.404 | 31.448 | -6.544 | 1.00 | 27.24 | 8 |
| C | SER | A | 1 | 26.093 | 29.358 | -5.237 | 1.00 | 26.25 | 6 |
| O | SER | A | 1 | 26.650 | 29.026 | -4.187 | 1.00 | 26.94 | 8 |
| N | THR | A | 1 | 24.906 | 29.957 | -5.255 | 1.00 | 26.36 | 7 |
| CA | THR | A | 1 | 24.197 | 30.272 | -4.027 | 1.00 | 26.23 | 6 |
| CB | THR | A | 1 | 23.792 | 31.770 | -4.031 | 1.00 | 24.90 | 6 |
| O | THR | A | 1 | 22.987 | 32.023 | -5.189 | 1.00 | 25.09 | 8 |
| C | THR | A | 1 | 25.015 | 32.666 | -4.056 | 1.00 | 25.45 | 6 |
| C | THR | A | 1 | 22.938 | 29.480 | -3.728 | 1.00 | 25.83 | 6 |
| O | THR | A | 1 | 22.611 | 29.341 | -2.541 | 1.00 | 26.06 | 8 |
| N | ILE | A | 1 | 22.171 | 29.075 | -4.734 | 1.00 | 25.78 | 7 |
| CA | ILE | A | 1 | 20.862 | 28.480 | -4.459 | 1.00 | 25.48 | 6 |
| CB | ILE | A | 1 | 19.937 | 28.542 | -5.682 | 1.00 | 28.32 | 6 |
| C | ILE | A | 1 | 19.648 | 30.010 | -5.995 | 1.00 | 28.81 | 6 |
| C | ILE | A | 1 | 20.538 | 27.838 | -6.894 | 1.00 | 29.07 | 6 |
| C | ILE | A | 1 | 19.614 | 27.762 | -8.092 | 1.00 | 31.74 | 6 |
| C | ILE | A | 1 | 20.950 | 27.095 | -3.849 | 1.00 | 25.16 | 6 |
| O | ILE | A | 1 | 21.805 | 26.258 | -4.121 | 1.00 | 25.27 | 8 |
| N | VAL | A | 1 | 20.018 | 26.835 | -2.945 | 1.00 | 25.11 | 7 |

Figure 1-8

| | | | | | | | | |
|---|---|---|---|---|---|---|---|---|
| CA | VAL | A | 1 | 19.895 | 25.653 | -2.121 | 1.00 | 25.35 | 6 |
| CB | VAL | A | 1 | 18.603 | 25.780 | -1.273 | 1.00 | 27.33 | 6 |
| C | VAL | A | 1 | 18.095 | 24.469 | -0.709 | 1.00 | 29.41 | 6 |
| C | VAL | A | 1 | 18.866 | 26.764 | -0.133 | 1.00 | 28.85 | 6 |
| C | VAL | A | 1 | 19.959 | 24.312 | -2.815 | 1.00 | 25.00 | 6 |
| O | VAL | A | 1 | 20.571 | 23.385 | -2.257 | 1.00 | 24.69 | 8 |
| N | ASN | A | 1 | 19.368 | 24.140 | -3.991 | 1.00 | 24.21 | 7 |
| CA | ASN | A | 1 | 19.357 | 22.841 | -4.651 | 1.00 | 24.07 | 6 |
| CB | ASN | A | 1 | 18.105 | 22.748 | -5.540 | 1.00 | 22.14 | 6 |
| C | ASN | A | 1 | 18.226 | 23.637 | -6.762 | 1.00 | 22.88 | 6 |
| O | ASN | A | 1 | 18.291 | 24.859 | -6.633 | 1.00 | 22.25 | 8 |
| N | ASN | A | 1 | 18.316 | 23.019 | -7.933 | 1.00 | 22.17 | 7 |
| C | ASN | A | 1 | 20.613 | 22.517 | -5.443 | 1.00 | 24.43 | 6 |
| O | ASN | A | 1 | 20.701 | 21.419 | -6.008 | 1.00 | 23.79 | 8 |
| N | MET | A | 1 | 21.630 | 23.371 | -5.435 | 1.00 | 25.03 | 7 |
| CA | MET | A | 1 | 22.850 | 23.139 | -6.196 | 1.00 | 26.58 | 6 |
| CB | MET | A | 1 | 23.547 | 24.458 | -6.529 | 1.00 | 27.98 | 6 |
| C | MET | A | 1 | 22.821 | 25.227 | -7.629 | 1.00 | 32.05 | 6 |
| SD | MET | A | 1 | 22.346 | 24.205 | -9.040 | 1.00 | 35.93 | 1 |
| CE | MET | A | 1 | 23.951 | 23.688 | -9.643 | 1.00 | 36.90 | 6 |
| C | MET | A | 1 | 23.777 | 22.099 | -5.593 | 1.00 | 27.33 | 6 |
| O | MET | A | 1 | 24.655 | 21.602 | -6.317 | 1.00 | 28.18 | 8 |
| N | VAL | A | 1 | 23.598 | 21.699 | -4.337 | 1.00 | 27.13 | 7 |
| CA | VAL | A | 1 | 24.425 | 20.637 | -3.771 | 1.00 | 27.35 | 6 |
| CB | VAL | A | 1 | 24.341 | 20.475 | -2.251 | 1.00 | 27.90 | 6 |
| C | VAL | A | 1 | 25.268 | 19.352 | -1.785 | 1.00 | 25.87 | 6 |
| C | VAL | A | 1 | 24.698 | 21.767 | -1.536 | 1.00 | 25.87 | 6 |
| C | VAL | A | 1 | 23.973 | 19.328 | -4.435 | 1.00 | 27.41 | 6 |
| O | VAL | A | 1 | 24.783 | 18.507 | -4.856 | 1.00 | 28.08 | 8 |
| N | ALA | A | 1 | 22.658 | 19.158 | -4.561 | 1.00 | 27.02 | 7 |
| CA | ALA | A | 1 | 22.079 | 17.988 | -5.214 | 1.00 | 26.49 | 6 |
| CB | ALA | A | 1 | 20.598 | 17.856 | -4.897 | 1.00 | 21.24 | 6 |
| C | ALA | A | 1 | 22.302 | 18.059 | -6.723 | 1.00 | 26.51 | 6 |
| O | ALA | A | 1 | 22.549 | 17.048 | -7.378 | 1.00 | 25.54 | 8 |
| N | GLY | A | 1 | 22.291 | 19.270 | -7.275 | 1.00 | 27.35 | 7 |
| CA | GLY | A | 1 | 22.623 | 19.479 | -8.678 | 1.00 | 28.51 | 6 |
| C | GLY | A | 1 | 24.041 | 18.991 | -8.970 | 1.00 | 29.26 | 6 |
| O | GLY | A | 1 | 24.238 | 18.218 | -9.905 | 1.00 | 29.73 | 8 |
| N | HIS | A | 1 | 25.018 | 19.404 | -8.172 | 1.00 | 30.44 | 7 |
| CA | HIS | A | 1 | 26.403 | 19.012 | -8.362 | 1.00 | 31.50 | 6 |
| CB | HIS | A | 1 | 27.347 | 19.828 | -7.458 | 1.00 | 31.18 | 6 |
| C | HIS | A | 1 | 27.723 | 21.121 | -8.124 | 1.00 | 30.77 | 6 |
| C | HIS | A | 1 | 28.449 | 21.359 | -9.242 | 1.00 | 29.89 | 6 |
| N | HIS | A | 1 | 27.298 | 22.347 | -7.668 | 1.00 | 31.84 | 7 |
| CE | HIS | A | 1 | 27.765 | 23.293 | -8.467 | 1.00 | 31.24 | 6 |
| C | HIS | A | 1 | 28.464 | 22.719 | -9.430 | 1.00 | 28.66 | 7 |
| C | HIS | A | 1 | 26.666 | 17.528 | -8.173 | 1.00 | 32.17 | 6 |
| O | HIS | A | 1 | 27.415 | 16.950 | -8.967 | 1.00 | 31.93 | 8 |
| N | LEU | A | 1 | 26.070 | 16.905 | -7.163 | 1.00 | 33.38 | 7 |
| CA | LEU | A | 1 | 26.284 | 15.480 | -6.932 | 1.00 | 34.08 | 6 |
| CB | LEU | A | 1 | 25.766 | 15.068 | -5.555 | 1.00 | 33.94 | 6 |
| C | LEU | A | 1 | 26.696 | 15.347 | -4.370 | 1.00 | 35.38 | 6 |
| C | LEU | A | 1 | 26.024 | 14.968 | -3.059 | 1.00 | 33.09 | 6 |
| C | LEU | A | 1 | 28.019 | 14.607 | -4.510 | 1.00 | 35.02 | 6 |
| C | LEU | A | 1 | 25.667 | 14.626 | -8.032 | 1.00 | 34.56 | 6 |
| O | LEU | A | 1 | 26.298 | 13.669 | -8.492 | 1.00 | 34.56 | 8 |
| N | THR | A | 1 | 24.459 | 14.963 | -8.475 | 1.00 | 34.57 | 7 |
| CA | THR | A | 1 | 23.785 | 14.223 | -9.532 | 1.00 | 34.15 | 6 |
| CB | THR | A | 1 | 22.420 | 14.826 | -9.914 | 1.00 | 29.47 | 6 |
| O | THR | A | 1 | 22.582 | 16.220 | -10.197 | 1.00 | 26.25 | 8 |
| C | THR | A | 1 | 21.395 | 14.651 | -8.809 | 1.00 | 24.88 | 6 |
| C | THR | A | 1 | 24.646 | 14.159 | -10.792 | 1.00 | 35.65 | 6 |
| O | THR | A | 1 | 24.850 | 13.081 | -11.350 | 1.00 | 35.92 | 8 |
| N | ILE | A | 1 | 25.147 | 15.306 | -11.241 | 1.00 | 36.68 | 7 |

| | | | | | | | | |
|---|---|---|---|---|---|---|---|---|
| CA | ILE | A | 1 | 26.035 | 15.369 | -12.394 | 1.00 | 37.59 | 6 |
| CB | ILE | A | 1 | 26.478 | 16.811 | -12.704 | 1.00 | 38.89 | 6 |
| C | ILE | A | 1 | 27.394 | 16.854 | -13.919 | 1.00 | 37.93 | 6 |
| C | ILE | A | 1 | 25.266 | 17.723 | -12.924 | 1.00 | 38.70 | 6 |
| C | ILE | A | 1 | 25.565 | 19.186 | -12.670 | 1.00 | 37.99 | 6 |
| C | ILE | A | 1 | 27.283 | 14.521 | -12.164 | 1.00 | 37.99 | 6 |
| O | ILE | A | 1 | 27.627 | 13.656 | -12.966 | 1.00 | 38.29 | 8 |
| N | MET | A | 1 | 27.967 | 14.762 | -11.053 | 1.00 | 37.90 | 7 |
| CA | MET | A | 1 | 29.175 | 14.047 | -10.686 | 1.00 | 38.24 | 6 |
| CB | MET | A | 1 | 29.616 | 14.468 | -9.277 | 1.00 | 39.44 | 6 |
| C | MET | A | 1 | 30.324 | 15.813 | -9.239 | 1.00 | 40.87 | 6 |
| SD | MET | A | 1 | 30.886 | 16.247 | -7.581 | 1.00 | 42.12 | 1 |
| CE | MET | A | 1 | 32.332 | 15.198 | -7.440 | 1.00 | 41.22 | 6 |
| C | MET | A | 1 | 29.056 | 12.531 | -10.747 | 1.00 | 37.94 | 6 |
| O | MET | A | 1 | 29.979 | 11.880 | -11.247 | 1.00 | 38.17 | 8 |
| N | TYR | A | 1 | 27.984 | 11.945 | -10.223 | 1.00 | 37.10 | 7 |
| CA | TYR | A | 1 | 27.818 | 10.501 | -10.220 | 1.00 | 36.19 | 6 |
| CB | TYR | A | 1 | 27.350 | 10.040 | -8.822 | 1.00 | 36.32 | 6 |
| C | TYR | A | 1 | 28.508 | 10.115 | -7.843 | 1.00 | 36.68 | 6 |
| C | TYR | A | 1 | 28.715 | 11.251 | -7.073 | 1.00 | 36.50 | 6 |
| CE | TYR | A | 1 | 29.778 | 11.325 | -6.193 | 1.00 | 36.74 | 6 |
| C | TYR | A | 1 | 29.399 | 9.058 | -7.720 | 1.00 | 36.65 | 6 |
| CE | TYR | A | 1 | 30.463 | 9.127 | -6.840 | 1.00 | 36.77 | 6 |
| CZ | TYR | A | 1 | 30.647 | 10.262 | -6.080 | 1.00 | 36.77 | 6 |
| O | TYR | A | 1 | 31.705 | 10.334 | -5.205 | 1.00 | 37.18 | 8 |
| C | TYR | A | 1 | 26.857 | 9.974 | -11.272 | 1.00 | 35.61 | 6 |
| O | TYR | A | 1 | 26.628 | 8.761 | -11.334 | 1.00 | 35.78 | 8 |
| N | GLY | A | 1 | 26.245 | 10.850 | -12.060 | 1.00 | 34.65 | 7 |
| CA | GLY | A | 1 | 25.277 | 10.432 | -13.063 | 1.00 | 33.62 | 6 |
| C | GLY | A | 1 | 23.987 | 9.912 | -12.443 | 1.00 | 33.64 | 6 |
| O | GLY | A | 1 | 23.404 | 8.949 | -12.947 | 1.00 | 32.91 | 8 |
| N | LEU | A | 1 | 23.524 | 10.555 | -11.371 | 1.00 | 33.89 | 7 |
| CA | LEU | A | 1 | 22.277 | 10.155 | -10.718 | 1.00 | 34.12 | 6 |
| CB | LEU | A | 1 | 22.255 | 10.578 | -9.253 | 1.00 | 34.78 | 6 |
| C | LEU | A | 1 | 23.480 | 10.255 | -8.399 | 1.00 | 36.43 | 6 |
| C | LEU | A | 1 | 23.386 | 10.932 | -7.038 | 1.00 | 36.23 | 6 |
| C | LEU | A | 1 | 23.656 | 8.753 | -8.225 | 1.00 | 36.82 | 6 |
| C | LEU | A | 1 | 21.095 | 10.757 | -11.474 | 1.00 | 34.20 | 6 |
| O | LEU | A | 1 | 20.954 | 11.976 | -11.573 | 1.00 | 34.71 | 8 |
| N | ARG | A | 1 | 20.275 | 9.896 | -12.067 | 1.00 | 34.03 | 7 |
| CA | ARG | A | 1 | 19.162 | 10.333 | -12.899 | 1.00 | 33.73 | 6 |
| CB | ARG | A | 1 | 19.212 | 9.617 | -14.255 | 1.00 | 37.33 | 6 |
| C | ARG | A | 1 | 20.590 | 9.564 | -14.892 | 1.00 | 39.93 | 6 |
| C | ARG | A | 1 | 20.559 | 9.681 | -16.405 | 1.00 | 45.40 | 6 |
| N | ARG | A | 1 | 19.555 | 8.819 | -17.010 | 1.00 | 50.00 | 7 |
| CZ | ARG | A | 1 | 18.668 | 9.187 | -17.925 | 1.00 | 52.17 | 6 |
| N | ARG | A | 1 | 18.637 | 10.432 | -18.380 | 1.00 | 53.86 | 7 |
| N | ARG | A | 1 | 17.795 | 8.302 | -18.391 | 1.00 | 53.95 | 7 |
| C | ARG | A | 1 | 17.811 | 10.130 | -12.228 | 1.00 | 32.95 | 6 |
| O | ARG | A | 1 | 16.766 | 10.388 | -12.826 | 1.00 | 32.75 | 8 |
| N | GLY | A | 1 | 17.824 | 9.688 | -10.975 | 1.00 | 32.29 | 7 |
| CA | GLY | A | 1 | 16.593 | 9.481 | -10.221 | 1.00 | 31.31 | 6 |
| C | GLY | A | 1 | 16.101 | 10.809 | -9.649 | 1.00 | 30.98 | 6 |
| O | GLY | A | 1 | 16.608 | 11.880 | -9.981 | 1.00 | 30.61 | 8 |
| N | PRO | A | 1 | 15.096 | 10.737 | -8.780 | 1.00 | 30.29 | 7 |
| C | PRO | A | 1 | 14.456 | 9.478 | -8.332 | 1.00 | 30.09 | 6 |
| CA | PRO | A | 1 | 14.509 | 11.909 | -8.166 | 1.00 | 29.57 | 6 |
| CB | PRO | A | 1 | 13.519 | 11.360 | -7.154 | 1.00 | 29.77 | 6 |
| C | PRO | A | 1 | 13.355 | 9.915 | -7.418 | 1.00 | 29.79 | 6 |
| C | PRO | A | 1 | 15.533 | 12.807 | -7.488 | 1.00 | 29.38 | 6 |
| O | PRO | A | 1 | 16.450 | 12.336 | -6.817 | 1.00 | 28.41 | 8 |
| N | SER | A | 1 | 15.356 | 14.118 | -7.629 | 1.00 | 28.94 | 7 |
| CA | SER | A | 1 | 16.250 | 15.094 | -7.023 | 1.00 | 27.53 | 6 |
| CB | SER | A | 1 | 17.149 | 15.708 | -8.103 | 1.00 | 29.57 | 6 |

Figure 1-9

| | | | | | | | | |
|---|---|---|---|---|---|---|---|---|
| O | SER | A | 1 | 18.098 | 16.586 | -7.525 | 1.00 | 33.35 | 8 |
| C | SER | A | 1 | 15.482 | 16.210 | -6.329 | 1.00 | 26.68 | 6 |
| O | SER | A | 1 | 14.883 | 17.041 | -7.016 | 1.00 | 26.03 | 8 |
| N | ILE | A | 1 | 15.474 | 16.244 | -4.995 | 1.00 | 26.03 | 7 |
| CA | ILE | A | 1 | 14.787 | 17.320 | -4.297 | 1.00 | 25.17 | 6 |
| CB | ILE | A | 1 | 13.482 | 16.951 | -3.579 | 1.00 | 24.96 | 6 |
| C | ILE | A | 1 | 12.331 | 16.776 | -4.559 | 1.00 | 22.35 | 6 |
| C | ILE | A | 1 | 13.650 | 15.714 | -2.691 | 1.00 | 22.54 | 6 |
| C | ILE | A | 1 | 12.588 | 15.627 | -1.610 | 1.00 | 19.83 | 6 |
| C | ILE | A | 1 | 15.709 | 17.968 | -3.259 | 1.00 | 25.23 | 6 |
| O | ILE | A | 1 | 16.762 | 17.455 | -2.899 | 1.00 | 24.97 | 8 |
| N | SER | A | 1 | 15.272 | 19.131 | -2.791 | 1.00 | 23.95 | 7 |
| CA | SER | A | 1 | 15.975 | 19.891 | -1.776 | 1.00 | 23.50 | 6 |
| CB | SER | A | 1 | 16.846 | 20.992 | -2.374 | 1.00 | 22.64 | 6 |
| O | SER | A | 1 | 17.886 | 20.488 | -3.183 | 1.00 | 24.55 | 8 |
| C | SER | A | 1 | 14.954 | 20.529 | -0.830 | 1.00 | 22.76 | 6 |
| O | SER | A | 1 | 14.203 | 21.410 | -1.268 | 1.00 | 22.27 | 8 |
| N | ILE | A | 1 | 14.925 | 20.083 | 0.422 | 1.00 | 21.99 | 7 |
| CA | ILE | A | 1 | 13.988 | 20.677 | 1.379 | 1.00 | 21.74 | 6 |
| CB | ILE | A | 1 | 13.273 | 19.657 | 2.271 | 1.00 | 19.43 | 6 |
| C | ILE | A | 1 | 12.340 | 20.363 | 3.253 | 1.00 | 18.21 | 6 |
| C | ILE | A | 1 | 12.485 | 18.630 | 1.394 | 1.00 | 16.47 | 6 |
| C | ILE | A | 1 | 11.801 | 17.553 | 2.125 | 1.00 | 15.37 | 6 |
| C | ILE | A | 1 | 14.732 | 21.721 | 2.212 | 1.00 | 21.86 | 6 |
| O | ILE | A | 1 | 15.832 | 21.490 | 2.710 | 1.00 | 22.41 | 8 |
| N | ALA | A | 1 | 14.136 | 22.904 | 2.305 | 1.00 | 21.42 | 7 |
| CA | ALA | A | 1 | 14.730 | 24.012 | 3.047 | 1.00 | 20.33 | 6 |
| CB | ALA | A | 1 | 15.008 | 25.172 | 2.105 | 1.00 | 16.53 | 6 |
| C | ALA | A | 1 | 13.798 | 24.428 | 4.180 | 1.00 | 19.82 | 6 |
| O | ALA | A | 1 | 12.924 | 25.278 | 4.015 | 1.00 | 18.81 | 8 |
| N | THR | A | 1 | 13.981 | 23.797 | 5.336 | 1.00 | 19.95 | 7 |
| CA | THR | A | 1 | 13.149 | 24.098 | 6.499 | 1.00 | 20.29 | 6 |
| CB | THR | A | 1 | 12.256 | 22.902 | 6.879 | 1.00 | 18.29 | 6 |
| O | THR | A | 1 | 13.009 | 21.692 | 6.725 | 1.00 | 17.31 | 8 |
| C | THR | A | 1 | 11.023 | 22.835 | 5.992 | 1.00 | 13.32 | 6 |
| C | THR | A | 1 | 14.011 | 24.514 | 7.684 | 1.00 | 20.40 | 6 |
| O | THR | A | 1 | 13.897 | 23.945 | 8.770 | 1.00 | 20.37 | 8 |
| N | ALA | A | 1 | 14.905 | 25.476 | 7.453 | 1.00 | 20.45 | 7 |
| CA | ALA | A | 1 | 15.764 | 25.976 | 8.530 | 1.00 | 21.02 | 6 |
| CB | ALA | A | 1 | 14.946 | 26.878 | 9.445 | 1.00 | 18.59 | 6 |
| C | ALA | A | 1 | 16.387 | 24.821 | 9.297 | 1.00 | 21.40 | 6 |
| O | ALA | A | 1 | 16.920 | 23.888 | 8.690 | 1.00 | 21.38 | 8 |
| N | CYS | A | 1 | 16.226 | 24.780 | 10.615 | 1.00 | 22.02 | 7 |
| CA | CYS | A | 1 | 16.747 | 23.748 | 11.482 | 1.00 | 22.36 | 6 |
| CB | CYS | A | 1 | 16.442 | 24.074 | 12.957 | 1.00 | 21.11 | 6 |
| SG | CYS | A | 1 | 16.391 | 25.832 | 13.348 | 1.00 | 19.89 | 1 |
| C | CYS | A | 1 | 16.234 | 22.335 | 11.252 | 1.00 | 23.18 | 6 |
| O | CYS | A | 1 | 16.802 | 21.406 | 11.841 | 1.00 | 24.80 | 8 |
| N | THR | A | 1 | 15.163 | 22.137 | 10.504 | 1.00 | 23.36 | 7 |
| CA | THR | A | 1 | 14.602 | 20.807 | 10.288 | 1.00 | 22.40 | 6 |
| CB | THR | A | 1 | 13.067 | 20.868 | 10.439 | 1.00 | 23.80 | 6 |
| O | THR | A | 1 | 12.757 | 21.679 | 11.585 | 1.00 | 24.52 | 8 |
| C | THR | A | 1 | 12.460 | 19.491 | 10.627 | 1.00 | 22.84 | 6 |
| C | THR | A | 1 | 14.989 | 20.237 | 8.938 | 1.00 | 21.06 | 6 |
| O | THR | A | 1 | 14.718 | 19.075 | 8.628 | 1.00 | 22.39 | 8 |
| N | SER | A | 1 | 15.715 | 21.009 | 8.140 | 1.00 | 20.00 | 7 |
| CA | SER | A | 1 | 16.110 | 20.631 | 6.795 | 1.00 | 19.25 | 6 |
| CB | SER | A | 1 | 17.141 | 21.618 | 6.239 | 1.00 | 17.46 | 6 |
| O | SER | A | 1 | 16.582 | 22.893 | 6.014 | 1.00 | 17.15 | 8 |
| C | SER | A | 1 | 16.684 | 19.224 | 6.707 | 1.00 | 19.87 | 6 |
| O | SER | A | 1 | 16.217 | 18.389 | 5.928 | 1.00 | 19.12 | 8 |
| N | GLY | A | 1 | 17.724 | 18.954 | 7.490 | 1.00 | 20.89 | 7 |
| CA | GLY | A | 1 | 18.379 | 17.655 | 7.493 | 1.00 | 22.58 | 6 |
| C | GLY | A | 1 | 17.412 | 16.513 | 7.766 | 1.00 | 24.06 | 6 |
| O | GLY | A | 1 | 17.502 | 15.461 | 7.132 | 1.00 | 24.80 | 8 |
| N | VAL | A | 1 | 16.529 | 16.677 | 8.744 | 1.00 | 25.23 | 7 |
| CA | VAL | A | 1 | 15.568 | 15.639 | 9.104 | 1.00 | 26.31 | 6 |
| CB | VAL | A | 1 | 14.954 | 15.935 | 10.485 | 1.00 | 26.54 | 6 |
| C | VAL | A | 1 | 13.631 | 15.222 | 10.713 | 1.00 | 28.08 | 6 |
| C | VAL | A | 1 | 15.946 | 15.553 | 11.579 | 1.00 | 25.33 | 6 |
| C | VAL | A | 1 | 14.485 | 15.475 | 8.048 | 1.00 | 26.62 | 6 |
| O | VAL | A | 1 | 14.045 | 14.351 | 7.792 | 1.00 | 27.98 | 8 |
| N | HIS | A | 1 | 14.039 | 16.570 | 7.442 | 1.00 | 26.00 | 7 |
| CA | HIS | A | 1 | 12.999 | 16.512 | 6.424 | 1.00 | 24.82 | 6 |
| CB | HIS | A | 1 | 12.453 | 17.908 | 6.120 | 1.00 | 23.96 | 6 |
| C | HIS | A | 1 | 11.405 | 18.394 | 7.069 | 1.00 | 23.62 | 6 |
| C | HIS | A | 1 | 10.606 | 17.745 | 7.947 | 1.00 | 22.84 | 6 |
| N | HIS | A | 1 | 11.084 | 19.733 | 7.180 | 1.00 | 22.53 | 7 |
| CE | HIS | A | 1 | 10.136 | 19.880 | 8.085 | 1.00 | 21.95 | 6 |
| N | HIS | A | 1 | 9.828 | 18.691 | 8.571 | 1.00 | 22.11 | 7 |
| C | HIS | A | 1 | 13.505 | 15.866 | 5.138 | 1.00 | 24.05 | 6 |
| O | HIS | A | 1 | 12.780 | 15.110 | 4.489 | 1.00 | 23.48 | 8 |
| N | ASN | A | 1 | 14.738 | 16.191 | 4.760 | 1.00 | 23.02 | 7 |
| CA | ASN | A | 1 | 15.337 | 15.637 | 3.551 | 1.00 | 22.46 | 6 |
| CB | ASN | A | 1 | 16.657 | 16.341 | 3.249 | 1.00 | 20.13 | 6 |
| C | ASN | A | 1 | 16.509 | 17.666 | 2.535 | 1.00 | 19.01 | 6 |
| O | ASN | A | 1 | 16.753 | 18.736 | 3.102 | 1.00 | 20.03 | 8 |
| N | ASN | A | 1 | 16.117 | 17.630 | 1.268 | 1.00 | 14.76 | 7 |
| C | ASN | A | 1 | 15.532 | 14.131 | 3.684 | 1.00 | 22.99 | 6 |
| O | ASN | A | 1 | 15.091 | 13.358 | 2.832 | 1.00 | 23.06 | 8 |
| N | ILE | A | 1 | 16.123 | 13.691 | 4.791 | 1.00 | 23.65 | 7 |
| CA | ILE | A | 1 | 16.336 | 12.273 | 5.057 | 1.00 | 24.37 | 6 |
| CB | ILE | A | 1 | 17.089 | 12.047 | 6.382 | 1.00 | 23.70 | 6 |
| C | ILE | A | 1 | 17.092 | 10.579 | 6.787 | 1.00 | 22.39 | 6 |
| C | ILE | A | 1 | 18.523 | 12.568 | 6.258 | 1.00 | 22.09 | 6 |
| C | ILE | A | 1 | 19.263 | 12.683 | 7.570 | 1.00 | 23.14 | 6 |
| C | ILE | A | 1 | 15.023 | 11.497 | 5.061 | 1.00 | 24.26 | 6 |
| O | ILE | A | 1 | 14.932 | 10.445 | 4.427 | 1.00 | 23.49 | 8 |
| N | GLY | A | 1 | 14.012 | 11.997 | 5.762 | 1.00 | 24.58 | 7 |
| CA | GLY | A | 1 | 12.713 | 11.349 | 5.812 | 1.00 | 25.44 | 6 |
| C | GLY | A | 1 | 11.980 | 11.315 | 4.479 | 1.00 | 25.99 | 6 |
| O | GLY | A | 1 | 11.320 | 10.312 | 4.179 | 1.00 | 26.63 | 8 |
| N | HIS | A | 1 | 12.080 | 12.365 | 3.659 | 1.00 | 25.24 | 7 |
| CA | HIS | A | 1 | 11.370 | 12.367 | 2.374 | 1.00 | 25.23 | 6 |
| CB | HIS | A | 1 | 10.991 | 13.778 | 1.924 | 1.00 | 22.39 | 6 |
| C | HIS | A | 1 | 9.705 | 14.164 | 2.612 | 1.00 | 19.50 | 6 |
| C | HIS | A | 1 | 8.432 | 13.773 | 2.381 | 1.00 | 18.58 | 6 |
| N | HIS | A | 1 | 9.662 | 14.997 | 3.705 | 1.00 | 19.92 | 7 |
| CE | HIS | A | 1 | 8.411 | 15.125 | 4.108 | 1.00 | 18.51 | 6 |
| N | HIS | A | 1 | 7.645 | 14.391 | 3.321 | 1.00 | 18.63 | 7 |
| C | HIS | A | 1 | 12.110 | 11.526 | 1.352 | 1.00 | 25.82 | 6 |
| O | HIS | A | 1 | 11.508 | 10.936 | 0.451 | 1.00 | 25.77 | 8 |
| N | ALA | A | 1 | 13.415 | 11.347 | 1.551 | 1.00 | 26.62 | 7 |
| CA | ALA | A | 1 | 14.201 | 10.450 | 0.711 | 1.00 | 27.35 | 6 |
| CB | ALA | A | 1 | 15.678 | 10.562 | 1.039 | 1.00 | 27.03 | 6 |
| C | ALA | A | 1 | 13.708 | 9.019 | 0.957 | 1.00 | 27.92 | 6 |
| O | ALA | A | 1 | 13.531 | 8.234 | 0.027 | 1.00 | 28.61 | 8 |
| N | ALA | A | 1 | 13.412 | 8.701 | 2.216 | 1.00 | 27.72 | 7 |
| CA | ALA | A | 1 | 12.864 | 7.411 | 2.605 | 1.00 | 28.34 | 6 |
| CB | ALA | A | 1 | 12.932 | 7.219 | 4.111 | 1.00 | 24.59 | 6 |
| C | ALA | A | 1 | 11.434 | 7.241 | 2.103 | 1.00 | 28.66 | 6 |
| O | ALA | A | 1 | 11.083 | 6.159 | 1.626 | 1.00 | 29.30 | 8 |
| N | ARG | A | 1 | 10.626 | 8.298 | 2.173 | 1.00 | 28.76 | 7 |
| CA | ARG | A | 1 | 9.262 | 8.225 | 1.648 | 1.00 | 28.61 | 6 |
| CB | ARG | A | 1 | 8.456 | 9.488 | 1.913 | 1.00 | 24.10 | 6 |
| C | ARG | A | 1 | 8.154 | 9.789 | 3.365 | 1.00 | 23.11 | 6 |
| C | ARG | A | 1 | 7.081 | 8.881 | 3.938 | 1.00 | 24.33 | 6 |
| N | ARG | A | 1 | 6.449 | 9.447 | 5.126 | 1.00 | 24.09 | 7 |

Figure 1 - 10

| | | | | | | | | |
|---|---|---|---|---|---|---|---|---|
| CZ | ARG | A | 1 | 6.668 | 9.071 | 6.379 | 1.00 | 25.51 | 6 |
| N | ARG | A | 1 | 7.531 | 8.100 | 6.653 | 1.00 | 25.70 | 7 |
| N | ARG | A | 1 | 6.027 | 9.664 | 7.383 | 1.00 | 22.96 | 7 |
| C | ARG | A | 1 | 9.337 | 7.947 | 0.146 | 1.00 | 29.05 | 6 |
| O | ARG | A | 1 | 8.764 | 6.963 | -0.322 | 1.00 | 28.83 | 8 |
| N | ILE | A | 1 | 10.175 | 8.700 | -0.571 | 1.00 | 29.97 | 7 |
| CA | ILE | A | 1 | 10.412 | 8.435 | -1.987 | 1.00 | 30.60 | 6 |
| CB | ILE | A | 1 | 11.472 | 9.361 | -2.602 | 1.00 | 29.35 | 6 |
| C | ILE | A | 1 | 11.847 | 8.928 | -4.014 | 1.00 | 26.83 | 6 |
| C | ILE | A | 1 | 10.983 | 10.815 | -2.636 | 1.00 | 30.12 | 6 |
| C | ILE | A | 1 | 12.070 | 11.813 | -2.989 | 1.00 | 30.42 | 6 |
| C | ILE | A | 1 | 10.797 | 6.975 | -2.206 | 1.00 | 31.59 | 6 |
| O | ILE | A | 1 | 10.158 | 6.295 | -3.013 | 1.00 | 31.73 | 8 |
| N | ILE | A | 1 | 11.810 | 6.481 | -1.498 | 1.00 | 32.37 | 7 |
| CA | ILE | A | 1 | 12.236 | 5.092 | -1.645 | 1.00 | 33.03 | 6 |
| CB | ILE | A | 1 | 13.463 | 4.776 | -0.770 | 1.00 | 32.09 | 6 |
| C | ILE | A | 1 | 13.683 | 3.280 | -0.605 | 1.00 | 32.34 | 6 |
| C | ILE | A | 1 | 14.690 | 5.435 | -1.408 | 1.00 | 29.55 | 6 |
| C | ILE | A | 1 | 15.962 | 5.310 | -0.614 | 1.00 | 26.75 | 6 |
| C | ILE | A | 1 | 11.111 | 4.111 | -1.362 | 1.00 | 33.89 | 6 |
| O | ILE | A | 1 | 10.851 | 3.228 | -2.183 | 1.00 | 34.76 | 8 |
| N | ALA | A | 1 | 10.379 | 4.296 | -0.271 | 1.00 | 33.88 | 7 |
| CA | ALA | A | 1 | 9.267 | 3.434 | 0.091 | 1.00 | 35.05 | 6 |
| CB | ALA | A | 1 | 8.764 | 3.815 | 1.479 | 1.00 | 30.13 | 6 |
| C | ALA | A | 1 | 8.117 | 3.463 | -0.908 | 1.00 | 36.72 | 6 |
| O | ALA | A | 1 | 7.360 | 2.491 | -1.009 | 1.00 | 37.70 | 8 |
| N | TYR | A | 1 | 7.950 | 4.554 | -1.642 | 1.00 | 37.34 | 7 |
| CA | TYR | A | 1 | 6.910 | 4.689 | -2.645 | 1.00 | 37.89 | 6 |
| CB | TYR | A | 1 | 6.661 | 6.171 | -2.943 | 1.00 | 37.46 | 6 |
| C | TYR | A | 1 | 5.438 | 6.430 | -3.794 | 1.00 | 36.91 | 6 |
| C | TYR | A | 1 | 4.191 | 6.618 | -3.212 | 1.00 | 36.65 | 6 |
| CE | TYR | A | 1 | 3.070 | 6.854 | -3.986 | 1.00 | 36.32 | 6 |
| C | TYR | A | 1 | 5.532 | 6.486 | -5.177 | 1.00 | 36.28 | 6 |
| CE | TYR | A | 1 | 4.418 | 6.719 | -5.958 | 1.00 | 36.59 | 6 |
| CZ | TYR | A | 1 | 3.191 | 6.904 | -5.358 | 1.00 | 36.47 | 6 |
| O | TYR | A | 1 | 2.083 | 7.139 | -6.138 | 1.00 | 36.39 | 8 |
| C | TYR | A | 1 | 7.244 | 3.953 | -3.937 | 1.00 | 38.42 | 6 |
| O | TYR | A | 1 | 6.336 | 3.537 | -4.662 | 1.00 | 39.08 | 8 |
| N | GLY | A | 1 | 8.529 | 3.812 | -4.248 | 1.00 | 38.49 | 7 |
| CA | GLY | A | 1 | 8.947 | 3.118 | -5.455 | 1.00 | 38.13 | 6 |
| C | GLY | A | 1 | 9.594 | 4.021 | -6.490 | 1.00 | 37.94 | 6 |
| O | GLY | A | 1 | 10.048 | 3.537 | -7.533 | 1.00 | 38.16 | 8 |
| N | ASP | A | 1 | 9.750 | 5.307 | -6.180 | 1.00 | 36.86 | 7 |
| CA | ASP | A | 1 | 10.333 | 6.258 | -7.116 | 1.00 | 35.48 | 6 |
| CB | ASP | A | 1 | 9.949 | 7.697 | -6.736 | 1.00 | 34.24 | 6 |
| C | ASP | A | 1 | 8.548 | 8.026 | -7.227 | 1.00 | 32.91 | 6 |
| O | ASP | A | 1 | 7.848 | 8.814 | -6.560 | 1.00 | 32.83 | 8 |
| O | ASP | A | 1 | 8.162 | 7.483 | -8.284 | 1.00 | 30.59 | 8 |
| C | ASP | A | 1 | 11.844 | 6.145 | -7.234 | 1.00 | 34.86 | 6 |
| O | ASP | A | 1 | 12.424 | 6.574 | -8.234 | 1.00 | 34.50 | 8 |
| N | ALA | A | 1 | 12.484 | 5.581 | -6.218 | 1.00 | 34.49 | 7 |
| CA | ALA | A | 1 | 13.930 | 5.407 | -6.227 | 1.00 | 34.21 | 6 |
| CB | ALA | A | 1 | 14.610 | 6.650 | -5.671 | 1.00 | 31.32 | 6 |
| C | ALA | A | 1 | 14.312 | 4.177 | -5.410 | 1.00 | 34.14 | 6 |
| O | ALA | A | 1 | 13.507 | 3.693 | -4.613 | 1.00 | 34.34 | 8 |
| N | ASP | A | 1 | 15.526 | 3.683 | -5.622 | 1.00 | 34.11 | 7 |
| CA | ASP | A | 1 | 16.005 | 2.533 | -4.857 | 1.00 | 34.81 | 6 |
| CB | ASP | A | 1 | 16.571 | 1.432 | -5.746 | 1.00 | 36.28 | 6 |
| C | ASP | A | 1 | 15.495 | 0.778 | -6.598 | 1.00 | 36.55 | 6 |
| O | ASP | A | 1 | 15.795 | 0.428 | -7.758 | 1.00 | 37.03 | 8 |
| O | ASP | A | 1 | 14.356 | 0.633 | -6.106 | 1.00 | 36.08 | 8 |
| C | ASP | A | 1 | 17.044 | 3.035 | -3.854 | 1.00 | 34.37 | 6 |
| O | ASP | A | 1 | 17.037 | 2.673 | -2.684 | 1.00 | 34.29 | 8 |
| N | VAL | A | 1 | 17.900 | 3.937 | -4.321 | 1.00 | 34.24 | 7 |

| | | | | | | | | |
|---|---|---|---|---|---|---|---|---|
| CA | VAL | A | 1 | 18.917 | 4.578 | -3.508 | 1.00 | 33.83 | 6 |
| CB | VAL | A | 1 | 20.345 | 4.287 | -4.011 | 1.00 | 35.53 | 6 |
| C | VAL | A | 1 | 21.388 | 4.950 | -3.114 | 1.00 | 36.35 | 6 |
| C | VAL | A | 1 | 20.639 | 2.798 | -4.108 | 1.00 | 35.37 | 6 |
| C | VAL | A | 1 | 18.733 | 6.096 | -3.518 | 1.00 | 33.19 | 6 |
| O | VAL | A | 1 | 18.432 | 6.683 | -4.555 | 1.00 | 33.44 | 8 |
| N | MET | A | 1 | 18.951 | 6.739 | -2.378 | 1.00 | 32.55 | 7 |
| CA | MET | A | 1 | 18.937 | 8.186 | -2.263 | 1.00 | 31.13 | 6 |
| CB | MET | A | 1 | 17.660 | 8.727 | -1.631 | 1.00 | 29.51 | 6 |
| C | MET | A | 1 | 16.342 | 8.551 | -2.341 | 1.00 | 29.70 | 6 |
| SD | MET | A | 1 | 16.246 | 9.357 | -3.946 | 1.00 | 29.08 | 1 |
| CE | MET | A | 1 | 15.597 | 10.961 | -3.486 | 1.00 | 31.20 | 6 |
| C | MET | A | 1 | 20.109 | 8.666 | -1.395 | 1.00 | 30.44 | 6 |
| O | MET | A | 1 | 20.302 | 8.170 | -0.284 | 1.00 | 29.87 | 8 |
| N | VAL | A | 1 | 20.857 | 9.642 | -1.890 | 1.00 | 29.52 | 7 |
| CA | VAL | A | 1 | 21.815 | 10.382 | -1.073 | 1.00 | 28.81 | 6 |
| CB | VAL | A | 1 | 22.956 | 11.026 | -1.865 | 1.00 | 30.53 | 6 |
| C | VAL | A | 1 | 24.149 | 11.320 | -0.962 | 1.00 | 29.68 | 6 |
| C | VAL | A | 1 | 23.391 | 10.162 | -3.041 | 1.00 | 32.18 | 6 |
| C | VAL | A | 1 | 21.003 | 11.492 | -0.394 | 1.00 | 28.25 | 6 |
| O | VAL | A | 1 | 20.334 | 12.247 | -1.103 | 1.00 | 28.36 | 8 |
| N | ALA | A | 1 | 21.009 | 11.563 | 0.927 | 1.00 | 28.00 | 7 |
| CA | ALA | A | 1 | 20.229 | 12.580 | 1.623 | 1.00 | 27.92 | 6 |
| CB | ALA | A | 1 | 19.000 | 11.963 | 2.275 | 1.00 | 24.93 | 6 |
| C | ALA | A | 1 | 21.058 | 13.294 | 2.684 | 1.00 | 28.72 | 6 |
| O | ALA | A | 1 | 22.054 | 12.756 | 3.172 | 1.00 | 30.05 | 8 |
| N | GLY | A | 1 | 20.628 | 14.502 | 3.037 | 1.00 | 27.99 | 7 |
| CA | GLY | A | 1 | 21.336 | 15.263 | 4.055 | 1.00 | 27.29 | 6 |
| C | GLY | A | 1 | 21.168 | 16.765 | 3.879 | 1.00 | 26.54 | 6 |
| O | GLY | A | 1 | 20.284 | 17.256 | 3.181 | 1.00 | 26.98 | 8 |
| N | GLY | A | 1 | 22.058 | 17.494 | 4.543 | 1.00 | 25.00 | 7 |
| CA | GLY | A | 1 | 22.044 | 18.947 | 4.497 | 1.00 | 23.84 | 6 |
| C | GLY | A | 1 | 23.474 | 19.468 | 4.611 | 1.00 | 23.62 | 6 |
| O | GLY | A | 1 | 24.391 | 18.762 | 5.026 | 1.00 | 23.67 | 8 |
| N | ALA | A | 1 | 23.636 | 20.717 | 4.211 | 1.00 | 22.65 | 7 |
| CA | ALA | A | 1 | 24.920 | 21.397 | 4.285 | 1.00 | 22.01 | 6 |
| CB | ALA | A | 1 | 25.707 | 21.264 | 3.001 | 1.00 | 20.15 | 6 |
| C | ALA | A | 1 | 24.631 | 22.862 | 4.618 | 1.00 | 21.60 | 6 |
| O | ALA | A | 1 | 23.618 | 23.403 | 4.182 | 1.00 | 21.84 | 8 |
| N | GLU | A | 1 | 25.487 | 23.458 | 5.429 | 1.00 | 20.83 | 7 |
| CA | GLU | A | 1 | 25.319 | 24.851 | 5.816 | 1.00 | 19.89 | 6 |
| CB | GLU | A | 1 | 24.426 | 24.977 | 7.049 | 1.00 | 18.28 | 6 |
| C | GLU | A | 1 | 23.831 | 26.355 | 7.291 | 1.00 | 18.28 | 6 |
| C | GLU | A | 1 | 22.489 | 26.516 | 6.598 | 1.00 | 18.67 | 6 |
| O | GLU | A | 1 | 21.572 | 25.707 | 6.865 | 1.00 | 19.58 | 8 |
| O | GLU | A | 1 | 22.362 | 27.441 | 5.773 | 1.00 | 16.71 | 8 |
| C | GLU | A | 1 | 26.686 | 25.469 | 6.094 | 1.00 | 19.29 | 6 |
| O | GLU | A | 1 | 27.621 | 24.801 | 6.521 | 1.00 | 18.97 | 8 |
| N | LYS | A | 1 | 26.786 | 26.757 | 5.833 | 1.00 | 19.94 | 7 |
| CA | LYS | A | 1 | 27.969 | 27.550 | 6.134 | 1.00 | 20.57 | 6 |
| CB | LYS | A | 1 | 29.088 | 27.407 | 5.117 | 1.00 | 23.02 | 6 |
| C | LYS | A | 1 | 30.476 | 27.636 | 5.704 | 1.00 | 21.33 | 6 |
| C | LYS | A | 1 | 30.817 | 29.119 | 5.749 | 1.00 | 20.79 | 6 |
| CE | LYS | A | 1 | 32.283 | 29.325 | 6.102 | 1.00 | 18.62 | 6 |
| NZ | LYS | A | 1 | 32.453 | 30.430 | 7.087 | 1.00 | 22.09 | 7 |
| C | LYS | A | 1 | 27.477 | 28.996 | 6.252 | 1.00 | 21.04 | 6 |
| O | LYS | A | 1 | 27.588 | 29.801 | 5.335 | 1.00 | 21.85 | 8 |
| N | ALA | A | 1 | 26.826 | 29.254 | 7.380 | 1.00 | 21.26 | 7 |
| CA | ALA | A | 1 | 26.207 | 30.540 | 7.651 | 1.00 | 22.03 | 6 |
| CB | ALA | A | 1 | 24.777 | 30.350 | 8.145 | 1.00 | 17.02 | 6 |
| C | ALA | A | 1 | 27.006 | 31.365 | 8.643 | 1.00 | 23.37 | 6 |
| O | ALA | A | 1 | 26.490 | 32.344 | 9.197 | 1.00 | 25.73 | 8 |
| N | SER | A | 1 | 28.278 | 31.032 | 8.842 | 1.00 | 23.12 | 7 |
| CA | SER | A | 1 | 29.124 | 31.824 | 9.733 | 1.00 | 23.49 | 6 |

Figure 1 - 11

| | | | | | | | | |
|---|---|---|---|---|---|---|---|---|
| CB | SER | A | 1 | 30.187 | 30.978 | 10.425 | 1.00 | 22.54 | 6 |
| O | SER | A | 1 | 30.945 | 30.242 | 9.481 | 1.00 | 25.70 | 8 |
| C | SER | A | 1 | 29.753 | 32.948 | 8.915 | 1.00 | 23.53 | 6 |
| O | SER | A | 1 | 30.941 | 32.962 | 8.617 | 1.00 | 24.01 | 8 |
| N | THR | A | 1 | 28.929 | 33.890 | 8.475 | 1.00 | 23.83 | 7 |
| CA | THR | A | 1 | 29.327 | 35.046 | 7.696 | 1.00 | 23.35 | 6 |
| CB | THR | A | 1 | 28.751 | 35.080 | 6.270 | 1.00 | 22.12 | 6 |
| O | THR | A | 1 | 27.347 | 35.382 | 6.337 | 1.00 | 21.97 | 8 |
| C | THR | A | 1 | 28.954 | 33.781 | 5.510 | 1.00 | 16.87 | 6 |
| C | THR | A | 1 | 28.827 | 36.288 | 8.434 | 1.00 | 23.72 | 6 |
| O | THR | A | 1 | 27.950 | 36.195 | 9.293 | 1.00 | 24.19 | 8 |
| N | PRO | A | 1 | 29.316 | 37.457 | 8.053 | 1.00 | 24.41 | 7 |
| C | PRO | A | 1 | 30.360 | 37.644 | 7.012 | 1.00 | 24.34 | 6 |
| CA | PRO | A | 1 | 28.891 | 38.718 | 8.633 | 1.00 | 25.09 | 6 |
| CB | PRO | A | 1 | 29.459 | 39.754 | 7.663 | 1.00 | 25.21 | 6 |
| C | PRO | A | 1 | 30.683 | 39.111 | 7.107 | 1.00 | 24.81 | 6 |
| C | PRO | A | 1 | 27.385 | 38.854 | 8.766 | 1.00 | 26.19 | 6 |
| O | PRO | A | 1 | 26.860 | 39.216 | 9.820 | 1.00 | 26.80 | 8 |
| N | LEU | A | 1 | 26.649 | 38.559 | 7.699 | 1.00 | 26.66 | 7 |
| CA | LEU | A | 1 | 25.198 | 38.611 | 7.668 | 1.00 | 26.40 | 6 |
| CB | LEU | A | 1 | 24.707 | 38.491 | 6.223 | 1.00 | 27.52 | 6 |
| C | LEU | A | 1 | 23.511 | 39.326 | 5.775 | 1.00 | 28.54 | 6 |
| C | LEU | A | 1 | 23.621 | 40.777 | 6.217 | 1.00 | 27.00 | 6 |
| C | LEU | A | 1 | 23.355 | 39.254 | 4.261 | 1.00 | 28.22 | 6 |
| C | LEU | A | 1 | 24.573 | 37.516 | 8.524 | 1.00 | 26.06 | 6 |
| O | LEU | A | 1 | 23.518 | 37.713 | 9.128 | 1.00 | 25.03 | 8 |
| N | GLY | A | 1 | 25.215 | 36.352 | 8.563 | 1.00 | 26.14 | 7 |
| CA | GLY | A | 1 | 24.746 | 35.221 | 9.342 | 1.00 | 26.26 | 6 |
| C | GLY | A | 1 | 24.916 | 35.436 | 10.841 | 1.00 | 26.88 | 6 |
| O | GLY | A | 1 | 23.988 | 35.190 | 11.616 | 1.00 | 26.92 | 8 |
| N | VAL | A | 1 | 26.104 | 35.869 | 11.257 | 1.00 | 27.33 | 7 |
| CA | VAL | A | 1 | 26.345 | 36.126 | 12.680 | 1.00 | 28.17 | 6 |
| CB | VAL | A | 1 | 27.834 | 36.302 | 13.000 | 1.00 | 29.36 | 6 |
| C | VAL | A | 1 | 28.057 | 36.503 | 14.492 | 1.00 | 30.77 | 6 |
| C | VAL | A | 1 | 28.629 | 35.096 | 12.516 | 1.00 | 29.20 | 6 |
| C | VAL | A | 1 | 25.536 | 37.351 | 13.100 | 1.00 | 27.85 | 6 |
| O | VAL | A | 1 | 24.751 | 37.307 | 14.046 | 1.00 | 27.96 | 8 |
| N | GLY | A | 2 | 25.652 | 38.425 | 12.326 | 1.00 | 27.37 | 7 |
| CA | GLY | A | 2 | 24.911 | 39.646 | 12.580 | 1.00 | 27.30 | 6 |
| C | GLY | A | 2 | 23.403 | 39.455 | 12.607 | 1.00 | 27.03 | 6 |
| O | GLY | A | 2 | 22.738 | 39.970 | 13.505 | 1.00 | 27.08 | 8 |
| N | GLY | A | 2 | 22.838 | 38.762 | 11.627 | 1.00 | 26.23 | 7 |
| CA | GLY | A | 2 | 21.413 | 38.550 | 11.495 | 1.00 | 24.79 | 6 |
| C | GLY | A | 2 | 20.776 | 37.836 | 12.672 | 1.00 | 24.76 | 6 |
| O | GLY | A | 2 | 19.736 | 38.245 | 13.187 | 1.00 | 25.40 | 8 |
| N | PHE | A | 2 | 21.406 | 36.755 | 13.116 | 1.00 | 24.57 | 7 |
| CA | PHE | A | 2 | 20.938 | 35.996 | 14.269 | 1.00 | 24.30 | 6 |
| CB | PHE | A | 2 | 21.573 | 34.611 | 14.314 | 1.00 | 22.09 | 6 |
| C | PHE | A | 2 | 20.910 | 33.583 | 13.445 | 1.00 | 21.81 | 6 |
| C | PHE | A | 2 | 21.598 | 33.006 | 12.390 | 1.00 | 22.56 | 6 |
| C | PHE | A | 2 | 19.605 | 33.183 | 13.683 | 1.00 | 21.56 | 6 |
| CE | PHE | A | 2 | 20.998 | 32.056 | 11.585 | 1.00 | 20.56 | 6 |
| CE | PHE | A | 2 | 18.998 | 32.232 | 12.885 | 1.00 | 21.92 | 6 |
| CZ | PHE | A | 2 | 19.699 | 31.668 | 11.835 | 1.00 | 20.90 | 6 |
| C | PHE | A | 2 | 21.280 | 36.791 | 15.531 | 1.00 | 24.51 | 6 |
| O | PHE | A | 2 | 20.522 | 36.827 | 16.493 | 1.00 | 23.72 | 8 |
| N | GLY | A | 2 | 22.385 | 37.529 | 15.481 | 1.00 | 25.54 | 7 |
| CA | GLY | A | 2 | 22.787 | 38.466 | 16.513 | 1.00 | 27.69 | 6 |
| C | GLY | A | 2 | 21.755 | 39.569 | 16.716 | 1.00 | 29.46 | 6 |
| O | GLY | A | 2 | 21.429 | 39.940 | 17.845 | 1.00 | 30.10 | 8 |
| N | ALA | A | 2 | 21.197 | 40.082 | 15.625 | 1.00 | 30.15 | 7 |
| CA | ALA | A | 2 | 20.195 | 41.129 | 15.617 | 1.00 | 30.95 | 6 |
| CB | ALA | A | 2 | 19.958 | 41.606 | 14.186 | 1.00 | 31.39 | 6 |
| C | ALA | A | 2 | 18.870 | 40.715 | 16.238 | 1.00 | 32.05 | 6 |
| O | ALA | A | 2 | 18.132 | 41.553 | 16.760 | 1.00 | 32.29 | 8 |
| N | ALA | A | 2 | 18.560 | 39.424 | 16.211 | 1.00 | 32.49 | 7 |
| CA | ALA | A | 2 | 17.363 | 38.876 | 16.825 | 1.00 | 33.33 | 6 |
| CB | ALA | A | 2 | 16.872 | 37.674 | 16.026 | 1.00 | 31.09 | 6 |
| C | ALA | A | 2 | 17.627 | 38.463 | 18.270 | 1.00 | 33.90 | 6 |
| O | ALA | A | 2 | 16.754 | 37.938 | 18.963 | 1.00 | 33.39 | 8 |
| N | ARG | A | 2 | 18.869 | 38.611 | 18.722 | 1.00 | 34.28 | 7 |
| CA | ARG | A | 2 | 19.287 | 38.270 | 20.070 | 1.00 | 34.97 | 6 |
| CB | ARG | A | 2 | 18.524 | 39.123 | 21.090 | 1.00 | 38.59 | 6 |
| C | ARG | A | 2 | 18.886 | 40.600 | 21.079 | 1.00 | 41.47 | 6 |
| C | ARG | A | 2 | 18.409 | 41.314 | 22.337 | 1.00 | 43.64 | 6 |
| N | ARG | A | 2 | 18.620 | 40.498 | 23.526 | 1.00 | 46.60 | 7 |
| CZ | ARG | A | 2 | 17.676 | 40.032 | 24.333 | 1.00 | 46.43 | 6 |
| N | ARG | A | 2 | 18.031 | 39.291 | 25.377 | 1.00 | 45.04 | 7 |
| N | ARG | A | 2 | 16.394 | 40.294 | 24.113 | 1.00 | 45.74 | 7 |
| C | ARG | A | 2 | 19.102 | 36.788 | 20.376 | 1.00 | 34.33 | 6 |
| O | ARG | A | 2 | 18.837 | 36.404 | 21.515 | 1.00 | 35.01 | 8 |
| N | ALA | A | 2 | 19.323 | 35.933 | 19.386 | 1.00 | 33.04 | 7 |
| CA | ALA | A | 2 | 19.103 | 34.501 | 19.508 | 1.00 | 32.04 | 6 |
| CB | ALA | A | 2 | 18.494 | 33.973 | 18.211 | 1.00 | 31.13 | 6 |
| C | ALA | A | 2 | 20.396 | 33.748 | 19.798 | 1.00 | 31.06 | 6 |
| O | ALA | A | 2 | 20.383 | 32.573 | 20.149 | 1.00 | 30.34 | 8 |
| N | LEU | A | 2 | 21.513 | 34.438 | 19.625 | 1.00 | 31.25 | 7 |
| CA | LEU | A | 2 | 22.835 | 33.865 | 19.813 | 1.00 | 31.96 | 6 |
| CB | LEU | A | 2 | 23.775 | 34.494 | 18.780 | 1.00 | 30.13 | 6 |
| C | LEU | A | 2 | 24.331 | 33.694 | 17.612 | 1.00 | 29.17 | 6 |
| C | LEU | A | 2 | 23.350 | 32.683 | 17.050 | 1.00 | 22.09 | 6 |
| C | LEU | A | 2 | 24.784 | 34.649 | 16.505 | 1.00 | 28.52 | 6 |
| C | LEU | A | 2 | 23.417 | 34.124 | 21.197 | 1.00 | 32.46 | 6 |
| O | LEU | A | 2 | 23.197 | 35.180 | 21.784 | 1.00 | 31.50 | 8 |
| N | SER | A | 2 | 24.209 | 33.171 | 21.687 | 1.00 | 33.80 | 7 |
| CA | SER | A | 2 | 24.908 | 33.342 | 22.955 | 1.00 | 34.47 | 6 |
| CB | SER | A | 2 | 25.572 | 32.045 | 23.409 | 1.00 | 33.50 | 6 |
| O | SER | A | 2 | 26.593 | 32.316 | 24.358 | 1.00 | 29.58 | 8 |
| C | SER | A | 2 | 25.975 | 34.425 | 22.784 | 1.00 | 35.41 | 6 |
| O | SER | A | 2 | 26.492 | 34.604 | 21.680 | 1.00 | 35.11 | 8 |
| N | THR | A | 2 | 26.305 | 35.132 | 23.859 | 1.00 | 36.45 | 7 |
| CA | THR | A | 2 | 27.279 | 36.231 | 23.762 | 1.00 | 37.19 | 6 |
| CB | THR | A | 2 | 26.537 | 37.561 | 23.962 | 1.00 | 39.54 | 6 |
| O | THR | A | 2 | 25.655 | 37.753 | 22.832 | 1.00 | 41.74 | 8 |
| C | THR | A | 2 | 27.416 | 38.794 | 24.035 | 1.00 | 42.95 | 6 |
| C | THR | A | 2 | 28.441 | 36.006 | 24.708 | 1.00 | 36.70 | 6 |
| O | THR | A | 2 | 29.285 | 36.866 | 24.973 | 1.00 | 36.29 | 8 |
| N | ARG | A | 2 | 28.636 | 34.756 | 25.133 | 1.00 | 36.20 | 7 |
| CA | ARG | A | 2 | 29.705 | 34.383 | 26.051 | 1.00 | 36.03 | 6 |
| CB | ARG | A | 2 | 29.360 | 33.028 | 26.690 | 1.00 | 35.31 | 6 |
| C | ARG | A | 2 | 30.100 | 32.742 | 27.985 | 1.00 | 37.08 | 6 |
| C | ARG | A | 2 | 29.729 | 31.380 | 28.553 | 1.00 | 40.22 | 6 |
| N | ARG | A | 2 | 28.718 | 31.483 | 29.599 | 1.00 | 44.00 | 7 |
| CZ | ARG | A | 2 | 27.407 | 31.439 | 29.399 | 1.00 | 47.44 | 6 |
| N | ARG | A | 2 | 26.904 | 31.286 | 28.179 | 1.00 | 48.14 | 7 |
| N | ARG | A | 2 | 26.581 | 31.547 | 30.433 | 1.00 | 48.31 | 7 |
| C | ARG | A | 2 | 31.085 | 34.338 | 25.417 | 1.00 | 36.15 | 6 |
| O | ARG | A | 2 | 31.717 | 33.282 | 25.333 | 1.00 | 34.44 | 8 |
| N | ASN | A | 2 | 31.642 | 35.480 | 25.025 | 1.00 | 37.86 | 7 |
| CA | ASN | A | 2 | 32.943 | 35.576 | 24.394 | 1.00 | 40.94 | 6 |
| CB | ASN | A | 2 | 33.150 | 36.977 | 23.797 | 1.00 | 43.10 | 6 |
| C | ASN | A | 2 | 32.132 | 37.323 | 22.732 | 1.00 | 45.64 | 6 |
| O | ASN | A | 2 | 32.199 | 36.833 | 21.602 | 1.00 | 48.03 | 8 |
| N | ASN | A | 2 | 31.175 | 38.174 | 23.082 | 1.00 | 44.97 | 7 |
| C | ASN | A | 2 | 34.118 | 35.264 | 25.307 | 1.00 | 42.95 | 6 |
| O | ASN | A | 2 | 35.199 | 34.931 | 24.811 | 1.00 | 43.48 | 8 |
| N | ASP | A | 2 | 33.952 | 35.353 | 26.622 | 1.00 | 45.18 | 7 |
| CA | ASP | A | 2 | 35.028 | 35.065 | 27.564 | 1.00 | 47.07 | 6 |

Figure 1 - 12

| | | | | | | | | |
|---|---|---|---|---|---|---|---|---|
| CB | ASP | A | 2 | 34.667 | 35.501 | 28.983 | 1.00 | 53.38 | 6 |
| C | ASP | A | 2 | 33.371 | 34.900 | 29.487 | 1.00 | 58.02 | 6 |
| O | ASP | A | 2 | 32.291 | 35.360 | 29.058 | 1.00 | 61.40 | 8 |
| O | ASP | A | 2 | 33.426 | 33.965 | 30.313 | 1.00 | 60.57 | 8 |
| C | ASP | A | 2 | 35.396 | 33.585 | 27.518 | 1.00 | 46.62 | 6 |
| O | ASP | A | 2 | 36.563 | 33.215 | 27.634 | 1.00 | 46.96 | 8 |
| N | ASN | A | 2 | 34.396 | 32.737 | 27.314 | 1.00 | 45.83 | 7 |
| CA | ASN | A | 2 | 34.589 | 31.298 | 27.205 | 1.00 | 44.67 | 6 |
| CB | ASN | A | 2 | 34.307 | 30.646 | 28.555 | 1.00 | 47.32 | 6 |
| C | ASN | A | 2 | 34.731 | 29.206 | 28.693 | 1.00 | 49.19 | 6 |
| O | ASN | A | 2 | 34.710 | 28.665 | 29.804 | 1.00 | 51.07 | 8 |
| N | ASN | A | 2 | 35.110 | 28.548 | 27.605 | 1.00 | 50.01 | 7 |
| C | ASN | A | 2 | 33.702 | 30.716 | 26.111 | 1.00 | 43.18 | 6 |
| O | ASN | A | 2 | 32.596 | 30.231 | 26.353 | 1.00 | 43.11 | 8 |
| N | PRO | A | 2 | 34.198 | 30.724 | 24.877 | 1.00 | 41.75 | 7 |
| C | PRO | A | 2 | 35.503 | 31.329 | 24.497 | 1.00 | 41.44 | 6 |
| CA | PRO | A | 2 | 33.490 | 30.210 | 23.722 | 1.00 | 40.67 | 6 |
| CB | PRO | A | 2 | 34.468 | 30.398 | 22.564 | 1.00 | 40.80 | 6 |
| C | PRO | A | 2 | 35.391 | 31.478 | 23.004 | 1.00 | 41.02 | 6 |
| C | PRO | A | 2 | 33.042 | 28.763 | 23.813 | 1.00 | 39.35 | 6 |
| O | PRO | A | 2 | 31.944 | 28.425 | 23.353 | 1.00 | 38.82 | 8 |
| N | GLN | A | 2 | 33.830 | 27.891 | 24.419 | 1.00 | 37.99 | 7 |
| CA | GLN | A | 2 | 33.509 | 26.472 | 24.546 | 1.00 | 36.26 | 6 |
| CB | GLN | A | 2 | 34.772 | 25.643 | 24.816 | 1.00 | 39.69 | 6 |
| C | GLN | A | 2 | 35.799 | 25.668 | 23.704 | 1.00 | 44.96 | 6 |
| C | GLN | A | 2 | 37.042 | 26.454 | 24.073 | 1.00 | 48.84 | 6 |
| O | GLN | A | 2 | 36.960 | 27.544 | 24.642 | 1.00 | 49.73 | 8 |
| N | GLN | A | 2 | 38.202 | 25.894 | 23.745 | 1.00 | 51.41 | 7 |
| C | GLN | A | 2 | 32.499 | 26.138 | 25.669 | 1.00 | 34.32 | 6 |
| O | GLN | A | 2 | 32.096 | 24.976 | 25.739 | 1.00 | 32.80 | 8 |
| N | ALA | A | 2 | 32.114 | 27.094 | 26.466 | 1.00 | 33.94 | 7 |
| CA | ALA | A | 2 | 31.137 | 26.852 | 27.521 | 1.00 | 33.57 | 6 |
| CB | ALA | A | 2 | 31.693 | 27.300 | 28.365 | 1.00 | 33.35 | 6 |
| C | ALA | A | 2 | 29.837 | 27.588 | 27.213 | 1.00 | 33.31 | 6 |
| O | ALA | A | 2 | 28.850 | 27.491 | 27.940 | 1.00 | 33.64 | 8 |
| N | ALA | A | 2 | 29.847 | 28.327 | 26.111 | 1.00 | 32.94 | 7 |
| CA | ALA | A | 2 | 28.700 | 29.104 | 25.669 | 1.00 | 32.57 | 6 |
| CB | ALA | A | 2 | 29.084 | 29.939 | 24.455 | 1.00 | 33.89 | 6 |
| C | ALA | A | 2 | 27.498 | 28.226 | 25.350 | 1.00 | 32.18 | 6 |
| O | ALA | A | 2 | 26.384 | 28.515 | 25.790 | 1.00 | 32.82 | 8 |
| N | SER | A | 2 | 27.716 | 27.171 | 24.574 | 1.00 | 31.80 | 7 |
| CA | SER | A | 2 | 26.628 | 26.259 | 24.222 | 1.00 | 31.73 | 6 |
| CB | SER | A | 2 | 26.971 | 25.487 | 22.951 | 1.00 | 30.83 | 6 |
| O | SER | A | 2 | 25.928 | 24.593 | 22.607 | 1.00 | 29.99 | 8 |
| C | SER | A | 2 | 26.380 | 25.328 | 25.402 | 1.00 | 31.43 | 6 |
| O | SER | A | 2 | 27.148 | 24.394 | 25.621 | 1.00 | 31.37 | 8 |
| N | ARG | A | 2 | 25.322 | 25.591 | 26.158 | 1.00 | 32.04 | 7 |
| CA | ARG | A | 2 | 25.007 | 24.798 | 27.343 | 1.00 | 33.31 | 6 |
| CB | ARG | A | 2 | 25.527 | 25.523 | 28.594 | 1.00 | 29.80 | 6 |
| C | ARG | A | 2 | 25.136 | 26.984 | 28.718 | 1.00 | 32.62 | 6 |
| C | ARG | A | 2 | 25.444 | 27.558 | 30.100 | 1.00 | 36.23 | 6 |
| N | ARG | A | 2 | 26.876 | 27.614 | 30.337 | 1.00 | 38.08 | 7 |
| CZ | ARG | A | 2 | 27.584 | 26.968 | 31.248 | 1.00 | 38.88 | 6 |
| N | ARG | A | 2 | 27.022 | 26.152 | 32.126 | 1.00 | 39.67 | 7 |
| N | ARG | A | 2 | 28.900 | 27.145 | 31.292 | 1.00 | 39.59 | 7 |
| C | ARG | A | 2 | 23.517 | 24.530 | 27.476 | 1.00 | 34.27 | 6 |
| O | ARG | A | 2 | 22.812 | 25.153 | 28.273 | 1.00 | 34.34 | 8 |
| N | PRO | A | 2 | 23.011 | 23.604 | 26.668 | 1.00 | 34.77 | 7 |
| C | PRO | A | 2 | 23.759 | 22.798 | 25.680 | 1.00 | 34.63 | 6 |
| CA | PRO | A | 2 | 21.596 | 23.290 | 26.663 | 1.00 | 35.68 | 6 |
| CB | PRO | A | 2 | 21.414 | 22.259 | 25.563 | 1.00 | 34.95 | 6 |
| C | PRO | A | 2 | 22.771 | 21.759 | 25.235 | 1.00 | 35.12 | 6 |
| C | PRO | A | 2 | 21.117 | 22.787 | 28.008 | 1.00 | 36.80 | 6 |
| O | PRO | A | 2 | 21.718 | 21.928 | 28.647 | 1.00 | 36.75 | 8 |

| | | | | | | | | |
|---|---|---|---|---|---|---|---|---|
| N | TRP | A | 2 | 20.006 | 23.348 | 28.471 | 1.00 | 38.16 | 7 |
| CA | TRP | A | 2 | 19.340 | 23.015 | 29.712 | 1.00 | 39.63 | 6 |
| CB | TRP | A | 2 | 19.102 | 21.506 | 29.803 | 1.00 | 35.31 | 6 |
| C | TRP | A | 2 | 18.105 | 20.982 | 28.812 | 1.00 | 33.04 | 6 |
| C | TRP | A | 2 | 18.371 | 20.039 | 27.765 | 1.00 | 32.01 | 6 |
| CE | TRP | A | 2 | 17.161 | 19.826 | 27.079 | 1.00 | 31.00 | 6 |
| CE | TRP | A | 2 | 19.518 | 19.357 | 27.344 | 1.00 | 32.03 | 6 |
| C | TRP | A | 2 | 16.781 | 21.294 | 28.719 | 1.00 | 30.50 | 6 |
| N | TRP | A | 2 | 16.206 | 20.601 | 27.681 | 1.00 | 29.81 | 7 |
| CZ | TRP | A | 2 | 17.062 | 18.957 | 25.994 | 1.00 | 32.45 | 6 |
| CZ | TRP | A | 2 | 19.420 | 18.496 | 26.268 | 1.00 | 34.32 | 6 |
| C | TRP | A | 2 | 18.199 | 18.306 | 25.607 | 1.00 | 34.41 | 6 |
| C | TRP | A | 2 | 20.014 | 23.518 | 30.980 | 1.00 | 41.79 | 6 |
| O | TRP | A | 2 | 19.477 | 23.335 | 32.077 | 1.00 | 42.19 | 8 |
| N | ASP | A | 2 | 21.147 | 24.190 | 30.865 | 1.00 | 43.09 | 7 |
| CA | ASP | A | 2 | 21.818 | 24.835 | 31.980 | 1.00 | 44.52 | 6 |
| CB | ASP | A | 2 | 23.278 | 25.103 | 31.631 | 1.00 | 43.42 | 6 |
| C | ASP | A | 2 | 24.118 | 25.502 | 32.825 | 1.00 | 43.46 | 6 |
| O | ASP | A | 2 | 24.475 | 26.697 | 32.926 | 1.00 | 42.68 | 8 |
| O | ASP | A | 2 | 24.445 | 24.622 | 33.647 | 1.00 | 42.29 | 8 |
| C | ASP | A | 2 | 21.084 | 26.137 | 32.293 | 1.00 | 45.89 | 6 |
| O | ASP | A | 2 | 20.438 | 26.712 | 31.414 | 1.00 | 46.28 | 8 |
| N | LYS | A | 2 | 21.191 | 26.613 | 33.526 | 1.00 | 46.55 | 7 |
| CA | LYS | A | 2 | 20.516 | 27.826 | 33.956 | 1.00 | 46.61 | 6 |
| CB | LYS | A | 2 | 20.543 | 27.916 | 35.490 | 1.00 | 49.39 | 6 |
| C | LYS | A | 2 | 21.936 | 28.097 | 36.070 | 1.00 | 51.89 | 6 |
| C | LYS | A | 2 | 21.944 | 29.115 | 37.199 | 1.00 | 54.74 | 6 |
| CE | LYS | A | 2 | 22.163 | 30.525 | 36.679 | 1.00 | 56.43 | 6 |
| NZ | LYS | A | 2 | 23.250 | 31.225 | 37.419 | 1.00 | 57.67 | 7 |
| C | LYS | A | 2 | 21.084 | 29.104 | 33.361 | 1.00 | 46.01 | 6 |
| O | LYS | A | 2 | 20.356 | 30.093 | 33.235 | 1.00 | 45.69 | 8 |
| N | GLU | A | 2 | 22.357 | 29.115 | 32.989 | 1.00 | 45.88 | 7 |
| CA | GLU | A | 2 | 23.003 | 30.286 | 32.424 | 1.00 | 45.19 | 6 |
| CB | GLU | A | 2 | 24.486 | 30.296 | 32.810 | 1.00 | 49.81 | 6 |
| C | GLU | A | 2 | 24.786 | 30.476 | 34.291 | 1.00 | 55.39 | 6 |
| C | GLU | A | 2 | 26.292 | 30.404 | 34.508 | 1.00 | 58.82 | 6 |
| O | GLU | A | 2 | 26.965 | 31.416 | 34.221 | 1.00 | 61.25 | 8 |
| O | GLU | A | 2 | 26.780 | 29.338 | 34.934 | 1.00 | 61.03 | 8 |
| C | GLU | A | 2 | 22.903 | 30.411 | 30.910 | 1.00 | 43.34 | 6 |
| O | GLU | A | 2 | 23.571 | 31.282 | 30.338 | 1.00 | 43.47 | 8 |
| N | ARG | A | 2 | 22.109 | 29.591 | 30.240 | 1.00 | 41.68 | 7 |
| CA | ARG | A | 2 | 21.890 | 29.686 | 28.809 | 1.00 | 39.75 | 6 |
| CB | ARG | A | 2 | 20.645 | 28.904 | 28.382 | 1.00 | 39.29 | 6 |
| C | ARG | A | 2 | 20.740 | 27.401 | 28.338 | 1.00 | 38.54 | 6 |
| C | ARG | A | 2 | 19.370 | 26.750 | 28.281 | 1.00 | 40.21 | 6 |
| N | ARG | A | 2 | 18.358 | 27.433 | 29.063 | 1.00 | 45.53 | 7 |
| CZ | ARG | A | 2 | 17.272 | 26.884 | 29.592 | 1.00 | 49.23 | 6 |
| N | ARG | A | 2 | 17.009 | 25.593 | 29.440 | 1.00 | 50.93 | 7 |
| N | ARG | A | 2 | 16.428 | 27.637 | 30.289 | 1.00 | 51.50 | 7 |
| C | ARG | A | 2 | 21.617 | 31.124 | 28.362 | 1.00 | 38.38 | 6 |
| O | ARG | A | 2 | 20.788 | 31.790 | 28.984 | 1.00 | 38.95 | 8 |
| N | ASP | A | 2 | 22.224 | 31.545 | 27.262 | 1.00 | 36.70 | 7 |
| CA | ASP | A | 2 | 21.954 | 32.878 | 26.731 | 1.00 | 35.08 | 6 |
| CB | ASP | A | 2 | 23.014 | 33.878 | 27.184 | 1.00 | 33.06 | 6 |
| C | ASP | A | 2 | 24.383 | 33.649 | 26.586 | 1.00 | 31.30 | 6 |
| O | ASP | A | 2 | 24.752 | 32.483 | 26.343 | 1.00 | 31.19 | 8 |
| O | ASP | A | 2 | 25.108 | 34.639 | 26.356 | 1.00 | 34.92 | 8 |
| C | ASP | A | 2 | 21.817 | 32.864 | 25.211 | 1.00 | 34.13 | 6 |
| O | ASP | A | 2 | 21.991 | 33.908 | 24.576 | 1.00 | 34.59 | 8 |
| N | GLY | A | 2 | 21.480 | 31.719 | 24.622 | 1.00 | 32.88 | 7 |
| CA | GLY | A | 2 | 21.288 | 31.637 | 23.180 | 1.00 | 31.77 | 6 |
| C | GLY | A | 2 | 22.078 | 30.521 | 22.513 | 1.00 | 30.48 | 6 |
| O | GLY | A | 2 | 23.036 | 29.997 | 23.082 | 1.00 | 31.75 | 8 |
| N | PHE | A | 2 | 21.690 | 30.148 | 21.293 | 1.00 | 28.57 | 7 |

Figure 1-13

| | | | | | | | | |
|---|---|---|---|---|---|---|---|---|
| CA | PHE | A | 2 | 22.371 | 29.067 | 20.587 | 1.00 | 25.74 | 6 |
| CB | PHE | A | 2 | 21.471 | 28.412 | 19.546 | 1.00 | 25.79 | 6 |
| C | PHE | A | 2 | 21.216 | 29.119 | 18.254 | 1.00 | 24.95 | 6 |
| C | PHE | A | 2 | 22.114 | 29.029 | 17.203 | 1.00 | 24.19 | 6 |
| C | PHE | A | 2 | 20.068 | 29.376 | 18.077 | 1.00 | 23.27 | 6 |
| CE | PHE | A | 2 | 21.878 | 29.680 | 16.007 | 1.00 | 25.52 | 6 |
| CE | PHE | A | 2 | 19.825 | 30.531 | 16.884 | 1.00 | 24.37 | 6 |
| CZ | PHE | A | 2 | 20.731 | 30.434 | 15.848 | 1.00 | 25.52 | 6 |
| C | PHE | A | 2 | 23.710 | 29.499 | 20.011 | 1.00 | 23.85 | 6 |
| O | PHE | A | 2 | 24.058 | 30.676 | 19.954 | 1.00 | 22.69 | 8 |
| N | VAL | A | 2 | 24.512 | 28.501 | 19.649 | 1.00 | 23.40 | 7 |
| CA | VAL | A | 2 | 25.827 | 28.727 | 19.061 | 1.00 | 23.14 | 6 |
| CB | VAL | A | 2 | 26.963 | 28.060 | 19.845 | 1.00 | 21.81 | 6 |
| C | VAL | A | 2 | 28.308 | 28.317 | 19.177 | 1.00 | 21.07 | 6 |
| C | VAL | A | 2 | 27.009 | 28.565 | 21.282 | 1.00 | 26.15 | 6 |
| C | VAL | A | 2 | 25.815 | 28.227 | 17.615 | 1.00 | 22.86 | 6 |
| O | VAL | A | 2 | 25.369 | 27.121 | 17.331 | 1.00 | 21.50 | 8 |
| N | LEU | A | 2 | 26.245 | 29.082 | 16.701 | 1.00 | 23.86 | 7 |
| CA | LEU | A | 2 | 26.240 | 28.798 | 15.274 | 1.00 | 23.88 | 6 |
| CB | LEU | A | 2 | 26.346 | 30.119 | 14.519 | 1.00 | 29.61 | 6 |
| C | LEU | A | 2 | 25.871 | 30.274 | 13.085 | 1.00 | 33.44 | 6 |
| C | LEU | A | 2 | 24.777 | 29.293 | 12.696 | 1.00 | 35.45 | 6 |
| C | LEU | A | 2 | 25.382 | 31.707 | 12.865 | 1.00 | 34.21 | 6 |
| C | LEU | A | 2 | 27.377 | 27.868 | 14.868 | 1.00 | 25.05 | 6 |
| O | LEU | A | 2 | 28.507 | 28.038 | 15.327 | 1.00 | 25.49 | 8 |
| N | GLY | A | 2 | 27.086 | 26.903 | 14.001 | 1.00 | 24.15 | 7 |
| CA | GLY | A | 2 | 28.085 | 25.959 | 13.531 | 1.00 | 24.11 | 6 |
| C | GLY | A | 2 | 27.960 | 25.662 | 12.042 | 1.00 | 24.67 | 6 |
| O | GLY | A | 2 | 26.880 | 25.754 | 11.456 | 1.00 | 25.37 | 8 |
| N | ASP | A | 2 | 29.069 | 25.277 | 11.419 | 1.00 | 24.44 | 7 |
| CA | ASP | A | 2 | 29.110 | 24.945 | 10.007 | 1.00 | 23.88 | 6 |
| CB | ASP | A | 2 | 30.222 | 25.682 | 9.261 | 1.00 | 23.99 | 6 |
| C | ASP | A | 2 | 30.213 | 27.180 | 9.450 | 1.00 | 24.50 | 6 |
| O | ASP | A | 2 | 29.125 | 27.786 | 9.377 | 1.00 | 29.71 | 8 |
| O | ASP | A | 2 | 31.298 | 27.752 | 9.676 | 1.00 | 25.78 | 8 |
| C | ASP | A | 2 | 29.361 | 23.450 | 9.804 | 1.00 | 23.41 | 6 |
| O | ASP | A | 2 | 29.973 | 22.805 | 10.654 | 1.00 | 23.79 | 8 |
| N | GLY | A | 2 | 28.949 | 22.941 | 8.644 | 1.00 | 22.27 | 7 |
| CA | GLY | A | 2 | 29.191 | 21.541 | 8.336 | 1.00 | 21.31 | 6 |
| C | GLY | A | 2 | 28.186 | 20.948 | 7.363 | 1.00 | 20.58 | 6 |
| O | GLY | A | 2 | 27.441 | 21.636 | 6.671 | 1.00 | 20.04 | 8 |
| N | ALA | A | 2 | 28.193 | 19.621 | 7.305 | 1.00 | 20.48 | 7 |
| CA | ALA | A | 2 | 27.344 | 18.872 | 6.393 | 1.00 | 21.61 | 6 |
| CB | ALA | A | 2 | 27.762 | 19.108 | 4.948 | 1.00 | 20.78 | 6 |
| C | ALA | A | 2 | 27.433 | 17.380 | 6.706 | 1.00 | 21.99 | 6 |
| O | ALA | A | 2 | 28.522 | 16.846 | 6.890 | 1.00 | 22.37 | 8 |
| N | GLY | A | 2 | 26.278 | 16.745 | 6.779 | 1.00 | 22.26 | 7 |
| CA | GLY | A | 2 | 26.193 | 15.310 | 7.029 | 1.00 | 23.98 | 6 |
| C | GLY | A | 2 | 25.442 | 14.711 | 5.837 | 1.00 | 25.43 | 6 |
| O | GLY | A | 2 | 24.558 | 15.374 | 5.292 | 1.00 | 25.88 | 8 |
| N | MET | A | 2 | 25.809 | 13.502 | 5.442 | 1.00 | 26.56 | 7 |
| CA | MET | A | 2 | 25.162 | 12.884 | 4.284 | 1.00 | 27.91 | 6 |
| CB | MET | A | 2 | 25.987 | 13.213 | 3.041 | 1.00 | 27.89 | 6 |
| C | MET | A | 2 | 25.234 | 13.503 | 1.769 | 1.00 | 30.30 | 6 |
| SD | MET | A | 2 | 24.418 | 15.099 | 1.678 | 1.00 | 31.13 | 1 |
| CE | MET | A | 2 | 25.677 | 16.204 | 2.299 | 1.00 | 32.90 | 6 |
| C | MET | A | 2 | 25.054 | 11.381 | 4.482 | 1.00 | 29.36 | 6 |
| O | MET | A | 2 | 26.020 | 10.774 | 4.952 | 1.00 | 30.39 | 8 |
| N | LEU | A | 2 | 23.891 | 10.802 | 4.184 | 1.00 | 29.56 | 7 |
| CA | LEU | A | 2 | 23.748 | 9.362 | 4.290 | 1.00 | 30.24 | 6 |
| CB | LEU | A | 2 | 22.869 | 8.838 | 5.406 | 1.00 | 30.18 | 6 |
| C | LEU | A | 2 | 22.076 | 9.717 | 6.348 | 1.00 | 29.17 | 6 |
| C | LEU | A | 2 | 21.017 | 8.902 | 7.084 | 1.00 | 29.29 | 6 |
| C | LEU | A | 2 | 22.986 | 10.389 | 7.364 | 1.00 | 30.62 | 6 |

| | | | | | | | | |
|---|---|---|---|---|---|---|---|---|
| C | LEU | A | 2 | 23.205 | 8.789 | 2.973 | 1.00 | 31.47 | 6 |
| O | LEU | A | 2 | 22.504 | 9.447 | 2.213 | 1.00 | 32.20 | 8 |
| N | VAL | A | 2 | 23.559 | 7.529 | 2.753 | 1.00 | 31.86 | 7 |
| CA | VAL | A | 2 | 23.031 | 6.776 | 1.629 | 1.00 | 32.03 | 6 |
| CB | VAL | A | 2 | 24.033 | 5.825 | 0.970 | 1.00 | 31.99 | 6 |
| C | VAL | A | 2 | 23.378 | 5.082 | -0.190 | 1.00 | 33.53 | 6 |
| C | VAL | A | 2 | 25.261 | 6.577 | 0.485 | 1.00 | 31.64 | 6 |
| C | VAL | A | 2 | 21.851 | 5.964 | 2.178 | 1.00 | 32.37 | 6 |
| O | VAL | A | 2 | 22.003 | 5.194 | 3.124 | 1.00 | 32.10 | 8 |
| N | LEU | A | 2 | 20.675 | 6.234 | 1.633 | 1.00 | 32.90 | 7 |
| CA | LEU | A | 2 | 19.473 | 5.506 | 2.023 | 1.00 | 32.91 | 6 |
| CB | LEU | A | 2 | 18.307 | 6.453 | 2.270 | 1.00 | 32.52 | 6 |
| C | LEU | A | 2 | 18.303 | 7.271 | 3.561 | 1.00 | 31.91 | 6 |
| C | LEU | A | 2 | 17.139 | 8.254 | 3.566 | 1.00 | 32.20 | 6 |
| C | LEU | A | 2 | 18.230 | 6.365 | 4.779 | 1.00 | 33.24 | 6 |
| C | LEU | A | 2 | 19.146 | 4.547 | 0.882 | 1.00 | 33.63 | 6 |
| O | LEU | A | 2 | 19.229 | 4.984 | -0.271 | 1.00 | 33.36 | 8 |
| N | GLU | A | 2 | 18.806 | 3.297 | 1.169 | 1.00 | 35.24 | 7 |
| CA | GLU | A | 2 | 18.428 | 2.403 | 0.074 | 1.00 | 37.02 | 6 |
| CB | GLU | A | 2 | 19.635 | 1.854 | -0.663 | 1.00 | 39.18 | 6 |
| C | GLU | A | 2 | 20.444 | 0.775 | 0.026 | 1.00 | 41.57 | 6 |
| C | GLU | A | 2 | 21.610 | 0.335 | -0.845 | 1.00 | 43.33 | 6 |
| O | GLU | A | 2 | 22.733 | 0.832 | -0.631 | 1.00 | 42.15 | 8 |
| O | GLU | A | 2 | 21.393 | -0.501 | -1.748 | 1.00 | 46.02 | 8 |
| C | GLU | A | 2 | 17.490 | 1.295 | 0.538 | 1.00 | 37.80 | 6 |
| O | GLU | A | 2 | 17.315 | 1.048 | 1.729 | 1.00 | 37.74 | 8 |
| N | GLU | A | 2 | 16.774 | 0.747 | -0.440 | 1.00 | 38.04 | 7 |
| CA | GLU | A | 2 | 15.789 | -0.298 | -0.182 | 1.00 | 38.80 | 6 |
| CB | GLU | A | 2 | 14.981 | -0.568 | -1.450 | 1.00 | 38.06 | 6 |
| C | GLU | A | 2 | 13.782 | -1.481 | -1.233 | 1.00 | 33.93 | 6 |
| C | GLU | A | 2 | 14.167 | -2.937 | -1.445 | 1.00 | 33.44 | 6 |
| O | GLU | A | 2 | 15.034 | -3.194 | -2.308 | 1.00 | 31.55 | 8 |
| O | GLU | A | 2 | 13.612 | -3.797 | -0.734 | 1.00 | 31.76 | 8 |
| C | GLU | A | 2 | 16.475 | -1.555 | 0.338 | 1.00 | 39.50 | 6 |
| O | GLU | A | 2 | 17.517 | -1.974 | -0.159 | 1.00 | 38.79 | 8 |
| N | TYR | A | 2 | 15.880 | -2.163 | 1.355 | 1.00 | 41.62 | 7 |
| CA | TYR | A | 2 | 16.427 | -3.344 | 1.999 | 1.00 | 44.09 | 6 |
| CB | TYR | A | 2 | 15.416 | -3.907 | 3.007 | 1.00 | 47.05 | 6 |
| C | TYR | A | 2 | 15.966 | -5.062 | 3.815 | 1.00 | 51.46 | 6 |
| C | TYR | A | 2 | 17.060 | -4.900 | 4.653 | 1.00 | 53.28 | 6 |
| CE | TYR | A | 2 | 17.559 | -5.961 | 5.385 | 1.00 | 55.01 | 6 |
| C | TYR | A | 2 | 15.386 | -6.320 | 3.726 | 1.00 | 53.44 | 6 |
| CE | TYR | A | 2 | 15.880 | -7.387 | 4.453 | 1.00 | 55.01 | 6 |
| CZ | TYR | A | 2 | 16.965 | -7.200 | 5.281 | 1.00 | 55.79 | 6 |
| O | TYR | A | 2 | 17.458 | -8.260 | 6.005 | 1.00 | 56.98 | 8 |
| C | TYR | A | 2 | 16.892 | -4.439 | 1.056 | 1.00 | 44.36 | 6 |
| O | TYR | A | 2 | 18.074 | -4.800 | 1.067 | 1.00 | 43.99 | 8 |
| N | GLU | A | 2 | 16.001 | -4.973 | 0.230 | 1.00 | 44.51 | 7 |
| CA | GLU | A | 2 | 16.327 | -6.045 | -0.699 | 1.00 | 45.08 | 6 |
| CB | GLU | A | 2 | 15.054 | -6.560 | -1.380 | 1.00 | 46.87 | 6 |
| C | GLU | A | 2 | 14.085 | -7.234 | -0.421 | 1.00 | 49.42 | 6 |
| C | GLU | A | 2 | 14.666 | -8.461 | 0.254 | 1.00 | 50.74 | 6 |
| O | GLU | A | 2 | 14.917 | -9.469 | -0.439 | 1.00 | 52.14 | 8 |
| O | GLU | A | 2 | 14.879 | -8.424 | 1.483 | 1.00 | 51.57 | 8 |
| C | GLU | A | 2 | 17.379 | -5.678 | -1.732 | 1.00 | 45.15 | 6 |
| O | GLU | A | 2 | 18.145 | -6.545 | -2.162 | 1.00 | 45.06 | 8 |
| N | HIS | A | 2 | 17.454 | -4.415 | -2.130 | 1.00 | 45.19 | 7 |
| CA | HIS | A | 2 | 18.467 | -3.936 | -3.055 | 1.00 | 45.66 | 6 |
| CB | HIS | A | 2 | 18.143 | -2.502 | -3.484 | 1.00 | 40.61 | 6 |
| C | HIS | A | 2 | 19.076 | -1.926 | -4.501 | 1.00 | 35.46 | 6 |
| C | HIS | A | 2 | 18.978 | -1.839 | -5.848 | 1.00 | 33.88 | 6 |
| N | HIS | A | 2 | 20.277 | -1.340 | -4.168 | 1.00 | 34.67 | 7 |
| CE | HIS | A | 2 | 20.886 | -0.926 | -5.264 | 1.00 | 33.14 | 6 |
| N | HIS | A | 2 | 20.119 | -1.219 | -6.298 | 1.00 | 33.39 | 7 |

Figure 1 - 14

| | | | | | | | | |
|---|---|---|---|---|---|---|---|---|
| C | HIS | A | 2 | 19.852 | -3.972 | -2.410 | 1.00 47.38 | 6 |
| O | HIS | A | 2 | 20.841 | -4.346 | -3.035 | 1.00 47.01 | 8 |
| N | ALA | A | 2 | 19.918 | -3.568 | -1.146 | 1.00 49.48 | 7 |
| CA | ALA | A | 2 | 21.156 | -3.512 | -0.387 | 1.00 51.58 | 6 |
| CB | ALA | A | 2 | 20.957 | -2.642 | 0.850 | 1.00 50.94 | 6 |
| C | ALA | A | 2 | 21.672 | -4.883 | 0.025 | 1.00 53.16 | 6 |
| O | ALA | A | 2 | 22.872 | -5.150 | -0.033 | 1.00 53.00 | 8 |
| N | LYS | A | 2 | 20.762 | -5.756 | 0.439 | 1.00 55.23 | 7 |
| CA | LYS | A | 2 | 21.119 | -7.119 | 0.829 | 1.00 57.65 | 6 |
| CB | LYS | A | 2 | 19.908 | -7.816 | 1.441 | 1.00 60.63 | 6 |
| C | LYS | A | 2 | 20.032 | -9.315 | 1.639 | 1.00 65.05 | 6 |
| C | LYS | A | 2 | 18.678 | -9.947 | 1.929 | 1.00 67.78 | 6 |
| CE | LYS | A | 2 | 18.832 | - | 2.540 | 1.00 69.75 | 6 |
| NZ | LYS | A | 2 | 17.937 | - | 3.715 | 1.00 71.19 | 7 |
| C | LYS | A | 2 | 21.651 | -7.883 | -0.379 | 1.00 58.57 | 6 |
| O | LYS | A | 2 | 22.648 | -8.601 | -0.295 | 1.00 59.09 | 8 |
| N | LYS | A | 2 | 21.013 | -7.719 | -1.532 | 1.00 59.06 | 7 |
| CA | LYS | A | 2 | 21.396 | -8.367 | -2.775 | 1.00 59.54 | 6 |
| CB | LYS | A | 2 | 20.417 | -7.977 | -3.889 | 1.00 61.74 | 6 |
| C | LYS | A | 2 | 20.739 | -8.548 | -5.257 | 1.00 64.55 | 6 |
| C | LYS | A | 2 | 19.526 | -8.538 | -6.174 | 1.00 67.02 | 6 |
| CE | LYS | A | 2 | 18.684 | -9.790 | -5.989 | 1.00 67.96 | 6 |
| NZ | LYS | A | 2 | 17.562 | -9.562 | -5.037 | 1.00 69.74 | 7 |
| C | LYS | A | 2 | 22.823 | -8.063 | -3.209 | 1.00 59.47 | 6 |
| O | LYS | A | 2 | 23.481 | -8.928 | -3.797 | 1.00 59.77 | 8 |
| N | ARG | A | 2 | 23.316 | -6.854 | -2.971 | 1.00 59.19 | 7 |
| CA | ARG | A | 2 | 24.684 | -6.494 | -3.318 | 1.00 58.96 | 6 |
| CB | ARG | A | 2 | 24.750 | -5.060 | -3.845 | 1.00 64.49 | 6 |
| C | ARG | A | 2 | 24.662 | -4.964 | -5.361 | 1.00 70.34 | 6 |
| C | ARG | A | 2 | 23.628 | -3.938 | -5.797 | 1.00 75.18 | 6 |
| N | ARG | A | 2 | 22.590 | -4.519 | -6.639 | 1.00 79.23 | 7 |
| CZ | ARG | A | 2 | 21.967 | -3.901 | -7.633 | 1.00 81.69 | 6 |
| N | ARG | A | 2 | 22.262 | -2.646 | -7.948 | 1.00 83.33 | 7 |
| N | ARG | A | 2 | 21.033 | -4.539 | -8.329 | 1.00 82.48 | 7 |
| C | ARG | A | 2 | 25.622 | -6.683 | -2.129 | 1.00 57.70 | 6 |
| O | ARG | A | 2 | 26.843 | -6.647 | -2.276 | 1.00 57.09 | 8 |
| N | GLY | A | 2 | 25.063 | -6.888 | -0.942 | 1.00 56.76 | 7 |
| CA | GLY | A | 2 | 25.818 | -7.122 | 0.271 | 1.00 55.73 | 6 |
| C | GLY | A | 2 | 26.477 | -5.887 | 0.860 | 1.00 55.04 | 6 |
| O | GLY | A | 2 | 27.669 | -5.896 | 1.171 | 1.00 55.17 | 8 |
| N | ALA | A | 2 | 25.704 | -4.826 | 1.051 | 1.00 54.08 | 7 |
| CA | ALA | A | 2 | 26.217 | -3.573 | 1.579 | 1.00 52.80 | 6 |
| CB | ALA | A | 2 | 25.297 | -2.438 | 1.128 | 1.00 52.47 | 6 |
| C | ALA | A | 2 | 26.349 | -3.532 | 3.095 | 1.00 51.83 | 6 |
| O | ALA | A | 2 | 25.664 | -4.236 | 3.829 | 1.00 51.72 | 8 |
| N | LYS | A | 2 | 27.193 | -2.616 | 3.565 | 1.00 51.12 | 7 |
| CA | LYS | A | 2 | 27.295 | -2.288 | 4.982 | 1.00 50.26 | 6 |
| CB | LYS | A | 2 | 28.369 | -1.226 | 5.205 | 1.00 53.24 | 6 |
| C | LYS | A | 2 | 29.768 | -1.712 | 5.519 | 1.00 56.48 | 6 |
| C | LYS | A | 2 | 30.667 | -0.551 | 5.931 | 1.00 58.30 | 6 |
| CE | LYS | A | 2 | 31.652 | -0.193 | 4.830 | 1.00 60.07 | 6 |
| NZ | LYS | A | 2 | 32.926 | -0.955 | 4.954 | 1.00 60.39 | 7 |
| C | LYS | A | 2 | 25.952 | -1.720 | 5.445 | 1.00 48.90 | 6 |
| O | LYS | A | 2 | 25.615 | -0.610 | 5.024 | 1.00 49.32 | 8 |
| N | ILE | A | 2 | 25.198 | -2.448 | 6.257 | 1.00 47.08 | 7 |
| CA | ILE | A | 2 | 23.908 | -1.931 | 6.720 | 1.00 45.16 | 6 |
| CB | ILE | A | 2 | 22.789 | -2.978 | 6.630 | 1.00 47.32 | 6 |
| C | ILE | A | 2 | 21.571 | -2.590 | 7.459 | 1.00 48.62 | 6 |
| C | ILE | A | 2 | 22.379 | -3.171 | 5.165 | 1.00 48.61 | 6 |
| C | ILE | A | 2 | 21.380 | -4.277 | 4.914 | 1.00 49.33 | 6 |
| O | ILE | A | 2 | 24.061 | -1.379 | 8.132 | 1.00 43.27 | 6 |
| O | ILE | A | 2 | 24.130 | -2.120 | 9.109 | 1.00 43.57 | 8 |
| N | TYR | A | 2 | 24.085 | -0.055 | 8.243 | 1.00 40.91 | 7 |
| CA | TYR | A | 2 | 24.251 | 0.633 | 9.510 | 1.00 38.29 | 6 |

| | | | | | | | | |
|---|---|---|---|---|---|---|---|---|
| CB | TYR | A | 2 | 24.564 | 2.118 | 9.276 | 1.00 36.36 | 6 |
| C | TYR | A | 2 | 25.973 | 2.410 | 8.826 | 1.00 33.88 | 6 |
| C | TYR | A | 2 | 26.265 | 2.576 | 7.480 | 1.00 33.29 | 6 |
| CE | TYR | A | 2 | 27.553 | 2.850 | 7.058 | 1.00 33.19 | 6 |
| C | TYR | A | 2 | 27.007 | 2.532 | 9.744 | 1.00 32.95 | 6 |
| CE | TYR | A | 2 | 28.298 | 2.805 | 9.331 | 1.00 32.34 | 6 |
| CZ | TYR | A | 2 | 28.562 | 2.963 | 7.990 | 1.00 32.93 | 6 |
| O | TYR | A | 2 | 29.843 | 3.235 | 7.572 | 1.00 33.91 | 8 |
| C | TYR | A | 2 | 23.010 | 0.588 | 10.393 | 1.00 37.77 | 6 |
| O | TYR | A | 2 | 23.112 | 0.610 | 11.619 | 1.00 37.81 | 8 |
| N | ALA | A | 2 | 21.839 | 0.629 | 9.769 | 1.00 37.28 | 7 |
| CA | ALA | A | 2 | 20.581 | 0.637 | 10.500 | 1.00 36.62 | 6 |
| CB | ALA | A | 2 | 20.556 | 1.758 | 11.528 | 1.00 37.87 | 6 |
| C | ALA | A | 2 | 19.407 | 0.791 | 9.536 | 1.00 36.09 | 6 |
| O | ALA | A | 2 | 19.578 | 0.861 | 8.320 | 1.00 35.78 | 8 |
| N | GLU | A | 2 | 18.214 | 0.845 | 10.109 | 1.00 35.82 | 7 |
| CA | GLU | A | 2 | 16.988 | 0.971 | 9.338 | 1.00 35.66 | 6 |
| CB | GLU | A | 2 | 16.120 | -0.270 | 9.577 | 1.00 37.13 | 6 |
| C | GLU | A | 2 | 14.914 | -0.407 | 8.670 | 1.00 40.33 | 6 |
| C | GLU | A | 2 | 14.032 | -1.593 | 8.998 | 1.00 41.53 | 6 |
| O | GLU | A | 2 | 12.858 | -1.611 | 8.569 | 1.00 42.20 | 8 |
| O | GLU | A | 2 | 14.495 | -2.527 | 9.684 | 1.00 44.11 | 8 |
| C | GLU | A | 2 | 16.206 | 2.219 | 9.719 | 1.00 35.25 | 6 |
| O | GLU | A | 2 | 16.047 | 2.517 | 10.903 | 1.00 35.55 | 8 |
| N | LEU | A | 2 | 15.720 | 2.940 | 8.714 | 1.00 35.26 | 7 |
| CA | LEU | A | 2 | 14.875 | 4.109 | 8.973 | 1.00 35.14 | 6 |
| CB | LEU | A | 2 | 14.941 | 5.121 | 7.842 | 1.00 37.51 | 6 |
| C | LEU | A | 2 | 14.734 | 6.596 | 8.200 | 1.00 38.88 | 6 |
| C | LEU | A | 2 | 14.959 | 7.476 | 6.980 | 1.00 39.79 | 6 |
| C | LEU | A | 2 | 13.347 | 6.835 | 8.775 | 1.00 39.55 | 6 |
| C | LEU | A | 2 | 13.459 | 3.548 | 9.133 | 1.00 34.67 | 6 |
| O | LEU | A | 2 | 12.973 | 2.920 | 8.188 | 1.00 34.29 | 8 |
| N | VAL | A | 2 | 12.895 | 3.592 | 10.335 | 1.00 34.72 | 7 |
| CA | VAL | A | 2 | 11.617 | 2.935 | 10.582 | 1.00 34.44 | 6 |
| CB | VAL | A | 2 | 11.705 | 1.917 | 11.743 | 1.00 34.57 | 6 |
| C | VAL | A | 2 | 12.615 | 0.751 | 11.386 | 1.00 34.70 | 6 |
| C | VAL | A | 2 | 12.178 | 2.591 | 13.021 | 1.00 33.08 | 6 |
| C | VAL | A | 2 | 10.470 | 3.886 | 10.886 | 1.00 34.39 | 6 |
| O | VAL | A | 2 | 9.314 | 3.451 | 10.859 | 1.00 34.63 | 8 |
| N | GLY | A | 2 | 10.762 | 5.143 | 11.202 | 1.00 33.88 | 7 |
| CA | GLY | A | 2 | 9.705 | 6.096 | 11.517 | 1.00 33.36 | 6 |
| C | GLY | A | 2 | 10.056 | 7.521 | 11.115 | 1.00 33.06 | 6 |
| O | GLY | A | 2 | 11.207 | 7.948 | 11.198 | 1.00 32.88 | 8 |
| N | PHE | A | 2 | 9.045 | 8.266 | 10.676 | 1.00 32.28 | 7 |
| CA | PHE | A | 2 | 9.210 | 9.662 | 10.292 | 1.00 31.30 | 6 |
| CB | PHE | A | 2 | 9.510 | 9.826 | 8.806 | 1.00 28.59 | 6 |
| C | PHE | A | 2 | 9.670 | 11.243 | 8.332 | 1.00 26.83 | 6 |
| C | PHE | A | 2 | 10.350 | 12.190 | 9.078 | 1.00 25.03 | 6 |
| C | PHE | A | 2 | 9.142 | 11.628 | 7.107 | 1.00 26.91 | 6 |
| CE | PHE | A | 2 | 10.483 | 13.492 | 8.636 | 1.00 23.91 | 6 |
| CE | PHE | A | 2 | 9.283 | 12.923 | 6.648 | 1.00 27.39 | 6 |
| CZ | PHE | A | 2 | 9.956 | 13.857 | 7.415 | 1.00 25.55 | 6 |
| C | PHE | A | 2 | 7.959 | 10.450 | 10.674 | 1.00 30.86 | 6 |
| O | PHE | A | 2 | 6.861 | 10.129 | 10.222 | 1.00 31.29 | 8 |
| N | GLY | A | 2 | 8.133 | 11.468 | 11.508 | 1.00 30.72 | 7 |
| CA | GLY | A | 2 | 7.022 | 12.288 | 11.963 | 1.00 30.39 | 6 |
| C | GLY | A | 2 | 7.260 | 13.770 | 11.707 | 1.00 30.81 | 6 |
| O | GLY | A | 2 | 8.373 | 14.278 | 11.829 | 1.00 30.69 | 8 |
| N | MET | A | 2 | 6.197 | 14.471 | 11.324 | 1.00 30.70 | 7 |
| CA | MET | A | 2 | 6.247 | 15.891 | 11.031 | 1.00 30.12 | 6 |
| CB | MET | A | 2 | 6.123 | 16.172 | 9.536 | 1.00 29.88 | 6 |
| C | MET | A | 2 | 7.226 | 15.696 | 8.618 | 1.00 29.92 | 6 |
| SD | MET | A | 2 | 6.633 | 15.492 | 6.924 | 1.00 34.18 | 1 |
| CE | MET | A | 2 | 6.376 | 17.202 | 6.467 | 1.00 37.05 | 6 |

Figure 1 - 15

| | | | | | | | | | | | | | | | | | |
|---|---|---|---|---|---|---|---|---|---|---|---|---|---|---|---|---|---|
| C | MET | A | 2 | 5.090 | 16.631 | 11.707 | 1.00 | 29.62 | 6 | N | SER | A | 2 | 9.879 | 31.662 | 18.196 | 1.00 | 46.47 | 7 |
| O | MET | A | 2 | 3.994 | 16.089 | 11.829 | 1.00 | 29.55 | 8 | CA | SER | A | 2 | 9.714 | 31.026 | 19.495 | 1.00 | 47.43 | 6 |
| N | SER | A | 2 | 5.320 | 17.892 | 12.046 | 1.00 | 29.54 | 7 | CB | SER | A | 2 | 9.270 | 32.058 | 20.538 | 1.00 | 49.71 | 6 |
| CA | SER | A | 2 | 4.278 | 18.725 | 12.629 | 1.00 | 29.53 | 6 | O | SER | A | 2 | 10.284 | 33.013 | 20.790 | 1.00 | 52.26 | 8 |
| CB | SER | A | 2 | 4.122 | 18.390 | 14.119 | 1.00 | 30.34 | 6 | C | SER | A | 2 | 8.701 | 29.888 | 19.459 | 1.00 | 47.25 | 6 |
| O | SER | A | 2 | 5.115 | 19.081 | 14.866 | 1.00 | 29.32 | 8 | O | SER | A | 2 | 7.660 | 29.962 | 18.811 | 1.00 | 47.41 | 8 |
| C | SER | A | 2 | 4.615 | 20.207 | 12.499 | 1.00 | 29.31 | 6 | N | PRO | A | 2 | 8.982 | 28.840 | 20.221 | 1.00 | 46.81 | 7 |
| O | SER | A | 2 | 5.715 | 20.579 | 12.098 | 1.00 | 28.62 | 8 | C | PRO | A | 2 | 10.212 | 28.661 | 21.033 | 1.00 | 46.92 | 6 |
| N | SER | A | 2 | 3.671 | 21.054 | 12.890 | 1.00 | 29.86 | 7 | CA | PRO | A | 2 | 8.101 | 27.693 | 20.357 | 1.00 | 46.66 | 6 |
| CA | SER | A | 2 | 3.872 | 22.489 | 12.941 | 1.00 | 30.22 | 6 | CB | PRO | A | 2 | 9.087 | 26.562 | 20.623 | 1.00 | 46.56 | 6 |
| CB | SER | A | 2 | 3.231 | 23.285 | 11.817 | 1.00 | 27.32 | 6 | C | PRO | A | 2 | 10.210 | 27.194 | 21.365 | 1.00 | 46.64 | 6 |
| O | SER | A | 2 | 3.053 | 22.555 | 10.628 | 1.00 | 25.45 | 8 | C | PRO | A | 2 | 7.137 | 27.868 | 21.518 | 1.00 | 46.77 | 6 |
| C | SER | A | 2 | 3.324 | 22.997 | 14.282 | 1.00 | 31.35 | 6 | O | PRO | A | 2 | 7.342 | 28.716 | 22.390 | 1.00 | 46.67 | 8 |
| O | SER | A | 2 | 2.380 | 22.420 | 14.814 | 1.00 | 32.24 | 8 | N | PRO | A | 2 | 6.072 | 27.078 | 21.539 | 1.00 | 47.01 | 7 |
| N | ASP | A | 2 | 3.914 | 24.073 | 14.780 | 1.00 | 31.85 | 7 | C | PRO | A | 2 | 5.770 | 26.011 | 20.560 | 1.00 | 46.89 | 6 |
| CA | ASP | A | 2 | 3.515 | 24.660 | 16.043 | 1.00 | 32.92 | 6 | CA | PRO | A | 2 | 5.129 | 27.090 | 22.643 | 1.00 | 47.40 | 6 |
| CB | ASP | A | 2 | 4.679 | 25.459 | 16.645 | 1.00 | 28.71 | 6 | CB | PRO | A | 2 | 3.973 | 26.227 | 22.173 | 1.00 | 47.06 | 6 |
| C | ASP | A | 2 | 5.764 | 24.604 | 17.259 | 1.00 | 25.31 | 6 | C | PRO | A | 2 | 4.400 | 25.537 | 20.935 | 1.00 | 47.05 | 6 |
| O | ASP | A | 2 | 5.563 | 23.380 | 17.390 | 1.00 | 23.22 | 8 | C | PRO | A | 2 | 5.789 | 26.528 | 23.889 | 1.00 | 47.82 | 6 |
| O | ASP | A | 2 | 6.818 | 25.182 | 17.601 | 1.00 | 20.63 | 8 | O | PRO | A | 2 | 6.397 | 25.453 | 23.831 | 1.00 | 47.54 | 8 |
| C | ASP | A | 2 | 2.342 | 25.623 | 15.912 | 1.00 | 34.31 | 6 | N | GLU | A | 2 | 5.619 | 27.172 | 25.038 | 1.00 | 48.53 | 7 |
| O | ASP | A | 2 | 1.535 | 25.753 | 16.831 | 1.00 | 35.57 | 8 | CA | GLU | A | 2 | 6.188 | 26.696 | 26.299 | 1.00 | 49.69 | 6 |
| N | ALA | A | 2 | 2.280 | 26.342 | 14.796 | 1.00 | 35.24 | 7 | CB | GLU | A | 2 | 5.816 | 27.643 | 27.441 | 1.00 | 55.27 | 6 |
| CA | ALA | A | 2 | 1.222 | 27.322 | 14.562 | 1.00 | 35.36 | 6 | C | GLU | A | 2 | 6.199 | 29.094 | 27.188 | 1.00 | 61.22 | 6 |
| CB | ALA | A | 2 | -0.098 | 26.614 | 14.305 | 1.00 | 36.57 | 6 | C | GLU | A | 2 | 6.819 | 29.771 | 28.392 | 1.00 | 64.76 | 6 |
| C | ALA | A | 2 | 1.139 | 28.258 | 15.764 | 1.00 | 36.24 | 6 | O | GLU | A | 2 | 6.115 | 30.546 | 29.075 | 1.00 | 66.47 | 8 |
| O | ALA | A | 2 | 0.082 | 28.434 | 16.366 | 1.00 | 36.52 | 8 | O | GLU | A | 2 | 8.016 | 29.536 | 28.665 | 1.00 | 67.96 | 8 |
| N | TYR | A | 2 | 2.274 | 28.851 | 16.119 | 1.00 | 36.71 | 7 | C | GLU | A | 2 | 5.772 | 25.262 | 26.599 | 1.00 | 48.73 | 6 |
| CA | TYR | A | 2 | 2.392 | 29.675 | 17.311 | 1.00 | 37.36 | 6 | O | GLU | A | 2 | 6.514 | 24.447 | 27.146 | 1.00 | 48.71 | 8 |
| CB | TYR | A | 2 | 3.032 | 28.830 | 18.431 | 1.00 | 39.14 | 6 | N | ASN | A | 2 | 4.570 | 24.890 | 26.211 | 1.00 | 47.71 | 7 |
| C | TYR | A | 2 | 3.145 | 29.584 | 19.738 | 1.00 | 42.32 | 6 | CA | ASN | A | 2 | 3.976 | 23.584 | 26.207 | 1.00 | 46.85 | 6 |
| C | TYR | A | 2 | 2.036 | 29.771 | 20.552 | 1.00 | 43.82 | 6 | CB | ASN | A | 2 | 2.691 | 23.692 | 25.349 | 1.00 | 52.48 | 6 |
| CE | TYR | A | 2 | 2.134 | 30.479 | 21.735 | 1.00 | 45.38 | 6 | C | ASN | A | 2 | 1.620 | 22.697 | 25.717 | 1.00 | 56.08 | 6 |
| C | TYR | A | 2 | 4.355 | 30.135 | 20.138 | 1.00 | 43.48 | 6 | O | ASN | A | 2 | 0.462 | 23.077 | 25.906 | 1.00 | 59.18 | 8 |
| CE | TYR | A | 2 | 4.463 | 30.845 | 21.317 | 1.00 | 44.72 | 6 | N | ASN | A | 2 | 1.980 | 21.424 | 25.817 | 1.00 | 58.91 | 7 |
| CZ | TYR | A | 2 | 3.348 | 31.013 | 22.110 | 1.00 | 46.22 | 6 | C | ASN | A | 2 | 4.824 | 22.498 | 25.550 | 1.00 | 45.13 | 6 |
| O | TYR | A | 2 | 3.449 | 31.720 | 23.288 | 1.00 | 47.70 | 8 | O | ASN | A | 2 | 4.848 | 21.351 | 25.996 | 1.00 | 45.12 | 8 |
| C | TYR | A | 2 | 3.179 | 30.949 | 17.058 | 1.00 | 37.20 | 6 | N | GLY | A | 2 | 5.368 | 22.805 | 24.372 | 1.00 | 42.77 | 7 |
| O | TYR | A | 2 | 2.594 | 32.032 | 16.980 | 1.00 | 37.11 | 8 | CA | GLY | A | 2 | 6.118 | 21.853 | 23.566 | 1.00 | 39.23 | 6 |
| N | HIS | A | 2 | 4.497 | 30.850 | 16.925 | 1.00 | 37.26 | 7 | C | GLY | A | 2 | 5.180 | 21.002 | 22.712 | 1.00 | 36.81 | 6 |
| CA | HIS | A | 2 | 5.335 | 32.021 | 16.677 | 1.00 | 38.24 | 6 | O | GLY | A | 2 | 5.537 | 19.931 | 22.223 | 1.00 | 35.93 | 8 |
| CB | HIS | A | 2 | 6.002 | 32.471 | 17.973 | 1.00 | 39.44 | 6 | N | ALA | A | 2 | 3.965 | 21.483 | 22.501 | 1.00 | 35.24 | 7 |
| C | HIS | A | 2 | 6.665 | 33.811 | 17.927 | 1.00 | 42.02 | 6 | CA | ALA | A | 2 | 2.909 | 20.820 | 21.771 | 1.00 | 34.29 | 6 |
| C | HIS | A | 2 | 6.167 | 35.060 | 18.087 | 1.00 | 42.79 | 6 | CB | ALA | A | 2 | 1.708 | 21.768 | 21.662 | 1.00 | 35.14 | 6 |
| N | HIS | A | 2 | 8.017 | 33.965 | 17.701 | 1.00 | 43.00 | 7 | C | ALA | A | 2 | 3.247 | 20.299 | 20.385 | 1.00 | 33.82 | 6 |
| CE | HIS | A | 2 | 8.325 | 35.248 | 17.719 | 1.00 | 43.48 | 6 | O | ALA | A | 2 | 2.782 | 19.215 | 20.012 | 1.00 | 34.26 | 8 |
| N | HIS | A | 2 | 7.220 | 35.934 | 17.952 | 1.00 | 45.06 | 7 | N | GLY | A | 2 | 3.941 | 21.079 | 19.564 | 1.00 | 32.88 | 7 |
| C | HIS | A | 2 | 6.369 | 31.723 | 15.598 | 1.00 | 38.89 | 6 | CA | GLY | A | 2 | 4.288 | 20.642 | 18.215 | 1.00 | 31.65 | 6 |
| O | HIS | A | 2 | 6.782 | 30.572 | 15.436 | 1.00 | 38.24 | 8 | C | GLY | A | 2 | 5.373 | 19.573 | 18.254 | 1.00 | 31.06 | 6 |
| N | MET | A | 2 | 6.834 | 32.751 | 14.889 | 1.00 | 39.98 | 7 | O | GLY | A | 2 | 5.369 | 18.638 | 17.452 | 1.00 | 30.38 | 8 |
| CA | MET | A | 2 | 7.789 | 32.553 | 13.806 | 1.00 | 41.79 | 6 | N | ALA | A | 2 | 6.303 | 19.714 | 19.193 | 1.00 | 30.57 | 7 |
| CB | MET | A | 2 | 7.939 | 33.779 | 12.915 | 1.00 | 42.46 | 6 | CA | ALA | A | 2 | 7.395 | 18.760 | 19.358 | 1.00 | 30.90 | 6 |
| C | MET | A | 2 | 7.913 | 35.144 | 13.565 | 1.00 | 46.63 | 6 | CB | ALA | A | 2 | 8.396 | 19.291 | 20.373 | 1.00 | 30.84 | 6 |
| SD | MET | A | 2 | 8.464 | 36.456 | 12.453 | 1.00 | 50.85 | 1 | C | ALA | A | 2 | 6.855 | 17.397 | 19.775 | 1.00 | 31.12 | 6 |
| CE | MET | A | 2 | 6.904 | 37.197 | 11.990 | 1.00 | 51.20 | 6 | O | ALA | A | 2 | 7.261 | 16.360 | 19.251 | 1.00 | 31.20 | 8 |
| C | MET | A | 2 | 9.150 | 32.063 | 14.283 | 1.00 | 42.80 | 6 | N | ALA | A | 2 | 5.874 | 17.393 | 20.672 | 1.00 | 31.97 | 7 |
| O | MET | A | 2 | 9.819 | 31.352 | 13.521 | 1.00 | 42.73 | 8 | CA | ALA | A | 2 | 5.196 | 16.175 | 21.094 | 1.00 | 32.35 | 6 |
| N | THR | A | 2 | 9.576 | 32.410 | 15.491 | 1.00 | 43.60 | 7 | CB | ALA | A | 2 | 4.149 | 16.497 | 22.151 | 1.00 | 31.67 | 6 |
| CA | THR | A | 2 | 10.871 | 31.967 | 15.991 | 1.00 | 44.83 | 6 | C | ALA | A | 2 | 4.525 | 15.497 | 19.904 | 1.00 | 33.17 | 6 |
| CB | THR | A | 2 | 11.855 | 33.144 | 16.144 | 1.00 | 43.66 | 6 | O | ALA | A | 2 | 4.686 | 14.299 | 19.674 | 1.00 | 33.02 | 8 |
| O | THR | A | 2 | 11.143 | 34.316 | 16.565 | 1.00 | 45.26 | 8 | N | LEU | A | 2 | 3.786 | 16.282 | 19.123 | 1.00 | 33.96 | 7 |
| C | THR | A | 2 | 12.558 | 33.422 | 14.824 | 1.00 | 41.25 | 6 | CA | LEU | A | 2 | 3.090 | 15.788 | 17.944 | 1.00 | 34.35 | 6 |
| C | THR | A | 2 | 10.775 | 31.228 | 17.318 | 1.00 | 45.67 | 6 | CB | LEU | A | 2 | 2.396 | 16.953 | 17.234 | 1.00 | 38.10 | 6 |
| O | THR | A | 2 | 11.515 | 30.267 | 17.539 | 1.00 | 46.17 | 8 | C | LEU | A | 2 | 0.910 | 16.799 | 16.906 | 1.00 | 41.16 | 6 |

Figure 1 - 16

| | | | | | | | | |
|---|---|---|---|---|---|---|---|---|
| C | LEU | A | 2 | 0.415 | 18.015 | 16.133 | 1.00 | 40.11 | 6 |
| C | LEU | A | 2 | 0.639 | 15.522 | 16.125 | 1.00 | 41.11 | 6 |
| C | LEU | A | 2 | 4.007 | 15.066 | 16.966 | 1.00 | 34.13 | 6 |
| O | LEU | A | 2 | 3.695 | 13.968 | 16.499 | 1.00 | 33.81 | 8 |
| N | ALA | A | 2 | 5.152 | 15.667 | 16.648 | 1.00 | 33.82 | 7 |
| CA | ALA | A | 2 | 6.119 | 15.068 | 15.736 | 1.00 | 33.23 | 6 |
| CB | ALA | A | 2 | 7.212 | 16.070 | 15.395 | 1.00 | 32.79 | 6 |
| C | ALA | A | 2 | 6.713 | 13.783 | 16.305 | 1.00 | 32.82 | 6 |
| O | ALA | A | 2 | 6.930 | 12.826 | 15.555 | 1.00 | 31.82 | 8 |
| N | MET | A | 2 | 6.969 | 13.751 | 17.614 | 1.00 | 32.44 | 7 |
| CA | MET | A | 2 | 7.455 | 12.516 | 18.239 | 1.00 | 32.54 | 6 |
| CB | MET | A | 2 | 7.999 | 12.771 | 19.636 | 1.00 | 32.06 | 6 |
| C | MET | A | 2 | 9.285 | 13.590 | 19.637 | 1.00 | 30.75 | 6 |
| SD | MET | A | 2 | 10.047 | 13.718 | 21.262 | 1.00 | 31.85 | 1 |
| CE | MET | A | 2 | 9.278 | 15.202 | 21.899 | 1.00 | 24.03 | 6 |
| C | MET | A | 2 | 6.317 | 11.502 | 18.214 | 1.00 | 32.99 | 6 |
| O | MET | A | 2 | 6.464 | 10.387 | 17.711 | 1.00 | 33.07 | 8 |
| N | ALA | A | 2 | 5.123 | 11.934 | 18.613 | 1.00 | 33.83 | 7 |
| CA | ALA | A | 2 | 3.931 | 11.100 | 18.540 | 1.00 | 34.86 | 6 |
| CB | ALA | A | 2 | 2.696 | 11.897 | 18.938 | 1.00 | 36.22 | 6 |
| C | ALA | A | 2 | 3.739 | 10.514 | 17.145 | 1.00 | 35.40 | 6 |
| O | ALA | A | 2 | 3.541 | 9.302 | 17.030 | 1.00 | 36.47 | 8 |
| N | ASN | A | 2 | 3.817 | 11.328 | 16.094 | 1.00 | 35.07 | 7 |
| CA | ASN | A | 2 | 3.628 | 10.851 | 14.733 | 1.00 | 34.90 | 6 |
| CB | ASN | A | 2 | 3.547 | 12.010 | 13.730 | 1.00 | 36.26 | 6 |
| C | ASN | A | 2 | 2.252 | 12.789 | 13.851 | 1.00 | 38.25 | 6 |
| O | ASN | A | 2 | 1.213 | 12.236 | 14.216 | 1.00 | 38.80 | 8 |
| N | ASN | A | 2 | 2.304 | 14.081 | 13.551 | 1.00 | 37.08 | 7 |
| C | ASN | A | 2 | 4.695 | 9.867 | 14.279 | 1.00 | 34.23 | 6 |
| O | ASN | A | 2 | 4.368 | 8.877 | 13.619 | 1.00 | 34.76 | 8 |
| N | ALA | A | 2 | 5.960 | 10.112 | 14.603 | 1.00 | 33.99 | 7 |
| CA | ALA | A | 2 | 7.040 | 9.208 | 14.218 | 1.00 | 33.42 | 6 |
| CB | ALA | A | 2 | 8.390 | 9.816 | 14.556 | 1.00 | 32.45 | 6 |
| C | ALA | A | 2 | 6.871 | 7.856 | 14.905 | 1.00 | 33.89 | 6 |
| O | ALA | A | 2 | 7.067 | 6.797 | 14.309 | 1.00 | 33.23 | 8 |
| N | LEU | A | 2 | 6.505 | 7.889 | 16.183 | 1.00 | 34.57 | 7 |
| CA | LEU | A | 2 | 6.198 | 6.693 | 16.953 | 1.00 | 35.73 | 6 |
| CB | LEU | A | 2 | 5.749 | 7.072 | 18.366 | 1.00 | 36.10 | 6 |
| C | LEU | A | 2 | 6.828 | 7.524 | 19.350 | 1.00 | 36.96 | 6 |
| C | LEU | A | 2 | 6.202 | 7.916 | 20.681 | 1.00 | 36.30 | 6 |
| C | LEU | A | 2 | 7.876 | 6.440 | 19.560 | 1.00 | 38.05 | 6 |
| C | LEU | A | 2 | 5.109 | 5.871 | 16.271 | 1.00 | 36.49 | 6 |
| O | LEU | A | 2 | 5.281 | 4.682 | 16.001 | 1.00 | 36.03 | 8 |
| N | ARG | A | 2 | 3.990 | 6.518 | 15.949 | 1.00 | 37.50 | 7 |
| CA | ARG | A | 2 | 2.879 | 5.857 | 15.266 | 1.00 | 38.38 | 6 |
| CB | ARG | A | 2 | 1.704 | 6.321 | 15.124 | 1.00 | 43.58 | 6 |
| C | ARG | A | 2 | 0.688 | 6.482 | 14.048 | 1.00 | 49.95 | 6 |
| C | ARG | A | 2 | -0.490 | 7.442 | 14.066 | 1.00 | 55.15 | 6 |
| N | ARG | A | 2 | -0.190 | 8.707 | 13.408 | 1.00 | 60.73 | 7 |
| CZ | ARG | A | 2 | -0.955 | 9.791 | 13.453 | 1.00 | 63.18 | 6 |
| N | ARG | A | 2 | -2.094 | 9.789 | 14.131 | 1.00 | 64.89 | 7 |
| N | ARG | A | 2 | -0.582 | 10.893 | 12.814 | 1.00 | 65.39 | 7 |
| C | ARG | A | 2 | 3.324 | 5.309 | 13.917 | 1.00 | 38.17 | 6 |
| O | ARG | A | 2 | 3.049 | 4.160 | 13.573 | 1.00 | 38.25 | 8 |
| N | ASP | A | 2 | 4.130 | 6.070 | 13.186 | 1.00 | 37.94 | 7 |
| CA | ASP | A | 2 | 4.700 | 5.669 | 11.916 | 1.00 | 38.16 | 6 |
| CB | ASP | A | 2 | 5.501 | 6.838 | 11.323 | 1.00 | 36.55 | 6 |
| C | ASP | A | 2 | 5.773 | 6.631 | 9.846 | 1.00 | 34.77 | 6 |
| O | ASP | A | 2 | 6.910 | 6.897 | 9.411 | 1.00 | 32.57 | 6 |
| O | ASP | A | 2 | 4.847 | 6.193 | 9.132 | 1.00 | 37.98 | 8 |
| C | ASP | A | 2 | 5.590 | 4.436 | 11.994 | 1.00 | 39.31 | 6 |
| O | ASP | A | 2 | 5.689 | 3.699 | 11.009 | 1.00 | 39.50 | 8 |
| N | ALA | A | 2 | 6.259 | 4.207 | 13.118 | 1.00 | 40.45 | 7 |
| CA | ALA | A | 2 | 7.114 | 3.043 | 13.301 | 1.00 | 41.61 | 6 |

| | | | | | | | | |
|---|---|---|---|---|---|---|---|---|
| CB | ALA | A | 2 | 8.334 | 3.400 | 14.135 | 1.00 | 42.87 | 6 |
| C | ALA | A | 2 | 6.335 | 1.908 | 13.964 | 1.00 | 42.62 | 6 |
| O | ALA | A | 2 | 6.650 | 0.731 | 13.796 | 1.00 | 43.14 | 8 |
| N | GLY | A | 2 | 5.304 | 2.271 | 14.719 | 1.00 | 43.20 | 7 |
| CA | GLY | A | 2 | 4.452 | 1.297 | 15.387 | 1.00 | 43.62 | 6 |
| C | GLY | A | 2 | 5.114 | 0.739 | 16.638 | 1.00 | 43.92 | 6 |
| O | GLY | A | 2 | 5.107 | -0.466 | 16.884 | 1.00 | 44.21 | 8 |
| N | ILE | A | 2 | 5.771 | 1.613 | 17.390 | 1.00 | 43.72 | 7 |
| CA | ILE | A | 2 | 6.425 | 1.245 | 18.635 | 1.00 | 43.55 | 6 |
| CB | ILE | A | 2 | 7.958 | 1.199 | 18.545 | 1.00 | 42.75 | 6 |
| C | ILE | A | 2 | 8.444 | -0.071 | 17.859 | 1.00 | 41.52 | 6 |
| C | ILE | A | 2 | 8.506 | 2.431 | 17.820 | 1.00 | 42.54 | 6 |
| C | ILE | A | 2 | 9.940 | 2.759 | 18.178 | 1.00 | 43.11 | 6 |
| C | ILE | A | 2 | 6.023 | 2.261 | 19.704 | 1.00 | 43.86 | 6 |
| O | ILE | A | 2 | 5.637 | 3.378 | 19.357 | 1.00 | 43.43 | 8 |
| N | GLU | A | 2 | 6.097 | 1.867 | 20.968 | 1.00 | 45.03 | 7 |
| CA | GLU | A | 2 | 5.758 | 2.805 | 22.040 | 1.00 | 46.66 | 6 |
| CB | GLU | A | 2 | 5.132 | 2.074 | 23.223 | 1.00 | 53.41 | 6 |
| C | GLU | A | 2 | 3.772 | 1.466 | 22.905 | 1.00 | 60.11 | 6 |
| C | GLU | A | 2 | 2.955 | 1.176 | 24.149 | 1.00 | 64.17 | 6 |
| O | GLU | A | 2 | 2.576 | 0.003 | 24.354 | 1.00 | 66.12 | 8 |
| O | GLU | A | 2 | 2.690 | 2.121 | 24.922 | 1.00 | 66.54 | 8 |
| C | GLU | A | 2 | 7.005 | 3.582 | 22.436 | 1.00 | 46.19 | 6 |
| O | GLU | A | 2 | 8.121 | 3.206 | 22.071 | 1.00 | 45.77 | 8 |
| N | ALA | A | 2 | 6.845 | 4.639 | 23.220 | 1.00 | 46.33 | 7 |
| CA | ALA | A | 2 | 7.948 | 5.479 | 23.657 | 1.00 | 46.88 | 6 |
| CB | ALA | A | 2 | 7.386 | 6.701 | 24.387 | 1.00 | 45.93 | 6 |
| C | ALA | A | 2 | 8.978 | 4.794 | 24.538 | 1.00 | 47.23 | 6 |
| O | ALA | A | 2 | 10.126 | 5.249 | 24.609 | 1.00 | 47.89 | 8 |
| N | SER | A | 2 | 8.656 | 3.686 | 25.190 | 1.00 | 47.44 | 7 |
| CA | SER | A | 2 | 9.558 | 2.956 | 26.061 | 1.00 | 47.10 | 6 |
| CB | SER | A | 2 | 8.742 | 2.180 | 27.106 | 1.00 | 48.58 | 6 |
| O | SER | A | 2 | 8.071 | 1.092 | 26.492 | 1.00 | 49.60 | 8 |
| C | SER | A | 2 | 10.487 | 1.993 | 25.337 | 1.00 | 46.51 | 6 |
| O | SER | A | 2 | 11.244 | 1.248 | 25.965 | 1.00 | 47.13 | 8 |
| N | GLN | A | 2 | 10.457 | 1.987 | 24.013 | 1.00 | 45.51 | 7 |
| CA | GLN | A | 2 | 11.310 | 1.141 | 23.192 | 1.00 | 43.84 | 6 |
| CB | GLN | A | 2 | 10.514 | 0.498 | 22.058 | 1.00 | 45.59 | 6 |
| C | GLN | A | 2 | 9.657 | -0.671 | 22.514 | 1.00 | 48.22 | 6 |
| C | GLN | A | 2 | 8.571 | -1.048 | 21.531 | 1.00 | 50.32 | 6 |
| O | GLN | A | 2 | 8.830 | -1.682 | 20.506 | 1.00 | 51.41 | 8 |
| N | GLN | A | 2 | 7.336 | -0.664 | 21.837 | 1.00 | 51.31 | 7 |
| C | GLN | A | 2 | 12.472 | 1.979 | 22.658 | 1.00 | 42.12 | 6 |
| O | GLN | A | 2 | 13.417 | 1.474 | 22.059 | 1.00 | 41.78 | 8 |
| N | ILE | A | 2 | 12.397 | 3.283 | 22.904 | 1.00 | 40.51 | 7 |
| CA | ILE | A | 2 | 13.436 | 4.222 | 22.523 | 1.00 | 39.86 | 6 |
| CB | ILE | A | 2 | 12.873 | 5.622 | 22.207 | 1.00 | 40.19 | 6 |
| C | ILE | A | 2 | 13.992 | 6.609 | 21.897 | 1.00 | 39.47 | 6 |
| C | ILE | A | 2 | 11.861 | 5.567 | 21.063 | 1.00 | 40.86 | 6 |
| C | ILE | A | 2 | 12.417 | 5.221 | 19.702 | 1.00 | 40.33 | 6 |
| C | ILE | A | 2 | 14.466 | 4.359 | 23.644 | 1.00 | 39.12 | 6 |
| O | ILE | A | 2 | 14.144 | 4.781 | 24.753 | 1.00 | 39.07 | 8 |
| N | GLY | A | 2 | 15.712 | 4.023 | 23.335 | 1.00 | 38.94 | 7 |
| CA | GLY | A | 2 | 16.789 | 4.127 | 24.309 | 1.00 | 38.40 | 6 |
| C | GLY | A | 2 | 17.317 | 5.557 | 24.385 | 1.00 | 38.27 | 6 |
| O | GLY | A | 2 | 17.438 | 6.113 | 25.478 | 1.00 | 39.05 | 8 |
| N | TYR | A | 2 | 17.608 | 6.152 | 23.231 | 1.00 | 37.49 | 7 |
| CA | TYR | A | 2 | 18.231 | 7.471 | 23.206 | 1.00 | 36.85 | 6 |
| CB | TYR | A | 2 | 19.714 | 7.308 | 22.877 | 1.00 | 36.62 | 6 |
| C | TYR | A | 2 | 20.474 | 8.536 | 22.443 | 1.00 | 36.28 | 6 |
| C | TYR | A | 2 | 21.036 | 8.603 | 21.173 | 1.00 | 36.11 | 6 |
| CE | TYR | A | 2 | 21.745 | 9.715 | 20.759 | 1.00 | 35.70 | 6 |
| C | TYR | A | 2 | 20.650 | 9.621 | 23.290 | 1.00 | 36.10 | 6 |
| CE | TYR | A | 2 | 21.362 | 10.736 | 22.887 | 1.00 | 36.03 | 6 |

Figure 1 - 17

| | | | | | | | | |
|---|---|---|---|---|---|---|---|---|
| CZ | TYR | A | 2 | 21.905 | 10.777 | 21.621 | 1.00 | 35.72 | 6 |
| O | TYR | A | 2 | 22.617 | 11.885 | 21.218 | 1.00 | 35.48 | 8 |
| C | TYR | A | 2 | 17.576 | 8.447 | 22.237 | 1.00 | 36.52 | 6 |
| O | TYR | A | 2 | 17.242 | 8.145 | 21.096 | 1.00 | 35.93 | 8 |
| N | VAL | A | 3 | 17.430 | 9.680 | 22.716 | 1.00 | 35.99 | 7 |
| CA | VAL | A | 3 | 16.887 | 10.788 | 21.955 | 1.00 | 35.60 | 6 |
| CB | VAL | A | 3 | 15.694 | 11.455 | 22.668 | 1.00 | 37.52 | 6 |
| C | VAL | A | 3 | 15.134 | 12.606 | 21.839 | 1.00 | 38.08 | 6 |
| C | VAL | A | 3 | 14.592 | 10.451 | 22.970 | 1.00 | 39.63 | 6 |
| C | VAL | A | 3 | 17.958 | 11.856 | 21.725 | 1.00 | 34.43 | 6 |
| O | VAL | A | 3 | 18.409 | 12.496 | 22.675 | 1.00 | 33.82 | 8 |
| N | ASN | A | 3 | 18.389 | 12.018 | 20.480 | 1.00 | 34.00 | 7 |
| CA | ASN | A | 3 | 19.251 | 13.152 | 20.122 | 1.00 | 32.94 | 6 |
| CB | ASN | A | 3 | 19.999 | 12.918 | 18.828 | 1.00 | 33.36 | 6 |
| C | ASN | A | 3 | 21.046 | 13.957 | 18.499 | 1.00 | 35.05 | 6 |
| O | ASN | A | 3 | 22.239 | 13.747 | 18.730 | 1.00 | 36.83 | 8 |
| N | ASN | A | 3 | 20.620 | 15.086 | 17.946 | 1.00 | 35.26 | 7 |
| C | ASN | A | 3 | 18.307 | 14.355 | 20.032 | 1.00 | 32.21 | 6 |
| O | ASN | A | 3 | 17.477 | 14.448 | 19.130 | 1.00 | 31.53 | 8 |
| N | ALA | A | 3 | 18.392 | 15.219 | 21.029 | 1.00 | 31.54 | 7 |
| CA | ALA | A | 3 | 17.516 | 16.366 | 21.148 | 1.00 | 31.65 | 6 |
| CB | ALA | A | 3 | 17.630 | 16.910 | 22.576 | 1.00 | 27.55 | 6 |
| C | ALA | A | 3 | 17.819 | 17.498 | 20.183 | 1.00 | 31.57 | 6 |
| O | ALA | A | 3 | 18.915 | 17.585 | 19.637 | 1.00 | 31.93 | 8 |
| N | HIS | A | 3 | 16.837 | 18.396 | 20.037 | 1.00 | 31.47 | 7 |
| CA | HIS | A | 3 | 17.066 | 19.582 | 19.205 | 1.00 | 31.50 | 6 |
| CB | HIS | A | 3 | 15.774 | 20.293 | 18.825 | 1.00 | 30.71 | 6 |
| C | HIS | A | 3 | 16.012 | 21.492 | 17.954 | 1.00 | 30.47 | 6 |
| C | HIS | A | 3 | 16.639 | 21.804 | 16.758 | 1.00 | 30.33 | 6 |
| N | HIS | A | 3 | 15.623 | 22.765 | 18.306 | 1.00 | 31.27 | 7 |
| CE | HIS | A | 3 | 15.990 | 23.610 | 17.361 | 1.00 | 31.78 | 6 |
| N | HIS | A | 3 | 16.610 | 22.932 | 16.411 | 1.00 | 32.01 | 7 |
| C | HIS | A | 3 | 18.023 | 20.467 | 20.012 | 1.00 | 31.54 | 6 |
| O | HIS | A | 3 | 19.076 | 20.889 | 19.544 | 1.00 | 31.65 | 8 |
| N | GLY | A | 3 | 17.751 | 20.594 | 21.304 | 1.00 | 31.96 | 7 |
| CA | GLY | A | 3 | 18.569 | 21.240 | 22.298 | 1.00 | 32.18 | 6 |
| C | GLY | A | 3 | 19.554 | 22.282 | 21.817 | 1.00 | 32.16 | 6 |
| O | GLY | A | 3 | 20.765 | 22.041 | 21.787 | 1.00 | 32.53 | 8 |
| N | THR | A | 3 | 19.075 | 23.478 | 21.485 | 1.00 | 32.26 | 7 |
| CA | THR | A | 3 | 19.942 | 24.526 | 20.965 | 1.00 | 31.80 | 6 |
| CB | THR | A | 3 | 19.195 | 25.393 | 19.926 | 1.00 | 30.30 | 6 |
| O | THR | A | 3 | 17.971 | 25.868 | 20.489 | 1.00 | 33.79 | 8 |
| C | THR | A | 3 | 18.916 | 24.563 | 18.686 | 1.00 | 29.22 | 6 |
| C | THR | A | 3 | 20.567 | 25.441 | 21.994 | 1.00 | 31.72 | 6 |
| O | THR | A | 3 | 21.445 | 26.225 | 21.621 | 1.00 | 31.84 | 8 |
| N | SER | A | 3 | 20.178 | 25.357 | 23.253 | 1.00 | 31.92 | 7 |
| CA | SER | A | 3 | 20.743 | 26.174 | 24.316 | 1.00 | 32.75 | 6 |
| CB | SER | A | 3 | 22.254 | 26.359 | 24.195 | 1.00 | 33.63 | 6 |
| O | SER | A | 3 | 22.778 | 26.944 | 25.377 | 1.00 | 35.52 | 8 |
| C | SER | A | 3 | 20.038 | 27.524 | 24.425 | 1.00 | 32.80 | 6 |
| O | SER | A | 3 | 20.605 | 28.532 | 24.845 | 1.00 | 31.92 | 8 |
| N | THR | A | 3 | 18.762 | 27.525 | 24.054 | 1.00 | 33.61 | 7 |
| CA | THR | A | 3 | 17.931 | 28.718 | 24.172 | 1.00 | 34.81 | 6 |
| CB | THR | A | 3 | 17.073 | 28.985 | 22.928 | 1.00 | 32.66 | 6 |
| O | THR | A | 3 | 16.429 | 27.765 | 22.530 | 1.00 | 30.74 | 8 |
| C | THR | A | 3 | 17.926 | 29.510 | 21.786 | 1.00 | 31.00 | 6 |
| C | THR | A | 3 | 17.010 | 28.512 | 25.372 | 1.00 | 35.97 | 6 |
| O | THR | A | 3 | 16.467 | 27.421 | 25.556 | 1.00 | 36.42 | 8 |
| N | PRO | A | 3 | 16.873 | 29.534 | 26.198 | 1.00 | 37.08 | 7 |
| C | PRO | A | 3 | 17.498 | 30.869 | 26.036 | 1.00 | 37.65 | 6 |
| CA | PRO | A | 3 | 15.980 | 29.484 | 27.343 | 1.00 | 37.87 | 6 |
| CB | PRO | A | 3 | 15.850 | 30.942 | 27.764 | 1.00 | 37.78 | 6 |
| C | PRO | A | 3 | 17.111 | 31.587 | 27.303 | 1.00 | 37.64 | 6 |
| C | PRO | A | 3 | 14.643 | 28.864 | 26.977 | 1.00 | 38.58 | 6 |
| O | PRO | A | 3 | 14.346 | 27.732 | 27.366 | 1.00 | 39.90 | 8 |
| N | ALA | A | 3 | 13.863 | 29.551 | 26.149 | 1.00 | 38.58 | 7 |
| CA | ALA | A | 3 | 12.543 | 29.093 | 25.745 | 1.00 | 38.47 | 6 |
| CB | ALA | A | 3 | 11.890 | 30.148 | 24.855 | 1.00 | 38.42 | 6 |
| C | ALA | A | 3 | 12.517 | 27.741 | 25.053 | 1.00 | 38.11 | 6 |
| O | ALA | A | 3 | 11.657 | 26.908 | 25.367 | 1.00 | 38.32 | 8 |
| N | GLY | A | 3 | 13.404 | 27.502 | 24.096 | 1.00 | 37.82 | 7 |
| CA | GLY | A | 3 | 13.418 | 26.268 | 23.333 | 1.00 | 37.36 | 6 |
| C | GLY | A | 3 | 13.765 | 25.021 | 24.125 | 1.00 | 37.41 | 6 |
| O | GLY | A | 3 | 13.141 | 23.971 | 23.945 | 1.00 | 36.65 | 8 |
| N | ASP | A | 3 | 14.746 | 25.106 | 25.018 | 1.00 | 38.18 | 7 |
| CA | ASP | A | 3 | 15.180 | 23.961 | 25.811 | 1.00 | 39.15 | 6 |
| CB | ASP | A | 3 | 16.465 | 24.288 | 26.575 | 1.00 | 40.44 | 6 |
| C | ASP | A | 3 | 17.674 | 24.427 | 25.673 | 1.00 | 41.01 | 6 |
| O | ASP | A | 3 | 18.777 | 24.687 | 26.198 | 1.00 | 41.45 | 8 |
| O | ASP | A | 3 | 17.544 | 24.277 | 24.441 | 1.00 | 42.11 | 8 |
| C | ASP | A | 3 | 14.107 | 23.470 | 26.771 | 1.00 | 39.31 | 6 |
| O | ASP | A | 3 | 13.965 | 22.262 | 26.962 | 1.00 | 38.78 | 8 |
| N | LYS | A | 3 | 13.337 | 24.384 | 27.349 | 1.00 | 40.33 | 7 |
| CA | LYS | A | 3 | 12.248 | 24.038 | 28.249 | 1.00 | 41.37 | 6 |
| CB | LYS | A | 3 | 11.679 | 25.294 | 28.915 | 1.00 | 44.75 | 6 |
| C | LYS | A | 3 | 12.447 | 25.786 | 30.127 | 1.00 | 48.79 | 6 |
| C | LYS | A | 3 | 11.955 | 27.158 | 30.569 | 1.00 | 52.90 | 6 |
| CE | LYS | A | 3 | 10.808 | 27.035 | 31.558 | 1.00 | 55.82 | 6 |
| NZ | LYS | A | 3 | 10.052 | 28.310 | 31.699 | 1.00 | 58.57 | 7 |
| C | LYS | A | 3 | 11.112 | 23.325 | 27.521 | 1.00 | 41.30 | 6 |
| O | LYS | A | 3 | 10.542 | 22.359 | 28.027 | 1.00 | 41.76 | 8 |
| N | ALA | A | 3 | 10.750 | 23.834 | 26.346 | 1.00 | 41.14 | 7 |
| CA | ALA | A | 3 | 9.661 | 23.270 | 25.558 | 1.00 | 40.10 | 6 |
| CB | ALA | A | 3 | 9.430 | 24.095 | 24.301 | 1.00 | 40.50 | 6 |
| C | ALA | A | 3 | 9.938 | 21.816 | 25.199 | 1.00 | 39.44 | 6 |
| O | ALA | A | 3 | 9.110 | 20.941 | 25.449 | 1.00 | 39.45 | 8 |
| N | GLU | A | 3 | 11.117 | 21.553 | 24.642 | 1.00 | 38.86 | 7 |
| CA | GLU | A | 3 | 11.517 | 20.199 | 24.292 | 1.00 | 38.43 | 6 |
| CB | GLU | A | 3 | 12.908 | 20.174 | 23.650 | 1.00 | 36.45 | 6 |
| C | GLU | A | 3 | 13.346 | 18.771 | 23.264 | 1.00 | 35.26 | 6 |
| C | GLU | A | 3 | 14.539 | 18.724 | 22.340 | 1.00 | 35.78 | 6 |
| O | GLU | A | 3 | 15.309 | 19.704 | 22.269 | 1.00 | 34.04 | 8 |
| O | GLU | A | 3 | 14.707 | 17.674 | 21.682 | 1.00 | 37.46 | 8 |
| C | GLU | A | 3 | 11.497 | 19.289 | 25.515 | 1.00 | 38.96 | 6 |
| O | GLU | A | 3 | 10.886 | 18.220 | 25.473 | 1.00 | 39.10 | 8 |
| N | ALA | A | 3 | 12.102 | 19.724 | 26.616 | 1.00 | 39.64 | 7 |
| CA | ALA | A | 3 | 12.042 | 18.983 | 27.874 | 1.00 | 41.27 | 6 |
| CB | ALA | A | 3 | 12.591 | 19.831 | 29.012 | 1.00 | 40.83 | 6 |
| C | ALA | A | 3 | 10.607 | 18.555 | 28.169 | 1.00 | 42.20 | 6 |
| O | ALA | A | 3 | 10.283 | 17.373 | 28.253 | 1.00 | 41.83 | 8 |
| N | GLN | A | 3 | 9.708 | 19.528 | 28.245 | 1.00 | 43.58 | 7 |
| CA | GLN | A | 3 | 8.289 | 19.330 | 28.467 | 1.00 | 45.33 | 6 |
| CB | GLN | A | 3 | 7.590 | 20.697 | 28.418 | 1.00 | 46.77 | 6 |
| C | GLN | A | 3 | 6.134 | 20.675 | 28.840 | 1.00 | 50.69 | 6 |
| C | GLN | A | 3 | 5.951 | 20.383 | 30.316 | 1.00 | 51.91 | 6 |
| O | GLN | A | 3 | 6.100 | 21.270 | 31.156 | 1.00 | 52.38 | 8 |
| N | GLN | A | 3 | 5.631 | 19.132 | 30.630 | 1.00 | 51.50 | 7 |
| C | GLN | A | 3 | 7.630 | 18.385 | 27.473 | 1.00 | 46.33 | 6 |
| O | GLN | A | 3 | 6.745 | 17.607 | 27.844 | 1.00 | 46.33 | 8 |
| N | ALA | A | 3 | 8.046 | 18.411 | 26.211 | 1.00 | 46.88 | 7 |
| CA | ALA | A | 3 | 7.518 | 17.538 | 25.178 | 1.00 | 47.24 | 6 |
| CB | ALA | A | 3 | 7.923 | 18.062 | 23.803 | 1.00 | 50.24 | 6 |
| C | ALA | A | 3 | 7.967 | 16.090 | 25.329 | 1.00 | 47.27 | 6 |
| O | ALA | A | 3 | 7.269 | 15.181 | 24.874 | 1.00 | 47.41 | 8 |
| N | VAL | A | 3 | 9.123 | 15.858 | 25.938 | 1.00 | 47.41 | 7 |
| CA | VAL | A | 3 | 9.631 | 14.508 | 26.168 | 1.00 | 47.69 | 6 |
| CB | VAL | A | 3 | 11.153 | 14.496 | 26.378 | 1.00 | 46.76 | 6 |
| C | VAL | A | 3 | 11.660 | 13.139 | 26.846 | 1.00 | 45.38 | 6 |

Figure 1 - 18

| | | | | | | | | |
|---|---|---|---|---|---|---|---|---|
| C | VAL | A | 3 | 11.856 | 14.898 | 25.087 | 1.00 | 46.70 | 6 |
| C | VAL | A | 3 | 8.919 | 13.883 | 27.364 | 1.00 | 47.82 | 6 |
| O | VAL | A | 3 | 8.604 | 12.693 | 27.365 | 1.00 | 47.71 | 8 |
| N | LYS | A | 3 | 8.585 | 14.714 | 28.349 | 1.00 | 48.07 | 7 |
| CA | LYS | A | 3 | 7.799 | 14.263 | 29.494 | 1.00 | 48.68 | 6 |
| CB | LYS | A | 3 | 7.654 | 15.386 | 30.523 | 1.00 | 48.79 | 6 |
| C | LYS | A | 3 | 8.880 | 15.539 | 31.412 | 1.00 | 49.95 | 6 |
| C | LYS | A | 3 | 8.716 | 16.660 | 32.425 | 1.00 | 51.90 | 6 |
| CE | LYS | A | 3 | 9.831 | 16.618 | 33.459 | 1.00 | 53.93 | 6 |
| NZ | LYS | A | 3 | 9.808 | 17.806 | 34.357 | 1.00 | 55.89 | 7 |
| C | LYS | A | 3 | 6.439 | 13.762 | 29.024 | 1.00 | 49.02 | 6 |
| O | LYS | A | 3 | 6.044 | 12.632 | 29.302 | 1.00 | 49.46 | 8 |
| N | THR | A | 3 | 5.771 | 14.551 | 28.192 | 1.00 | 48.90 | 7 |
| CA | THR | A | 3 | 4.469 | 14.237 | 27.636 | 1.00 | 49.03 | 6 |
| CB | THR | A | 3 | 3.972 | 15.427 | 26.782 | 1.00 | 48.10 | 6 |
| O | THR | A | 3 | 4.097 | 16.635 | 27.549 | 1.00 | 47.21 | 8 |
| C | THR | A | 3 | 2.522 | 15.250 | 26.372 | 1.00 | 46.85 | 6 |
| C | THR | A | 3 | 4.411 | 12.968 | 26.804 | 1.00 | 49.57 | 6 |
| O | THR | A | 3 | 3.380 | 12.285 | 26.804 | 1.00 | 50.05 | 8 |
| N | ILE | A | 3 | 5.462 | 12.637 | 26.068 | 1.00 | 50.18 | 7 |
| CA | ILE | A | 3 | 5.470 | 11.469 | 25.198 | 1.00 | 50.51 | 6 |
| CB | ILE | A | 3 | 6.342 | 11.746 | 23.954 | 1.00 | 50.53 | 6 |
| C | ILE | A | 3 | 6.438 | 10.528 | 23.051 | 1.00 | 50.20 | 6 |
| C | ILE | A | 3 | 5.800 | 12.953 | 23.183 | 1.00 | 51.45 | 6 |
| C | ILE | A | 3 | 4.379 | 12.325 | 22.680 | 1.00 | 51.49 | 6 |
| C | ILE | A | 3 | 5.936 | 10.194 | 25.830 | 1.00 | 50.83 | 6 |
| O | ILE | A | 3 | 5.339 | 9.134 | 25.668 | 1.00 | 50.86 | 8 |
| N | PHE | A | 3 | 7.014 | 10.262 | 26.651 | 1.00 | 51.33 | 7 |
| CA | PHE | A | 3 | 7.560 | 9.065 | 27.288 | 1.00 | 52.19 | 6 |
| CB | PHE | A | 3 | 9.074 | 9.195 | 27.452 | 1.00 | 52.50 | 6 |
| C | PHE | A | 3 | 9.821 | 9.238 | 26.147 | 1.00 | 53.33 | 6 |
| C | PHE | A | 3 | 9.830 | 10.383 | 25.370 | 1.00 | 53.36 | 6 |
| C | PHE | A | 3 | 10.525 | 8.132 | 25.702 | 1.00 | 53.23 | 6 |
| CE | PHE | A | 3 | 10.516 | 10.426 | 24.173 | 1.00 | 53.94 | 6 |
| CE | PHE | A | 3 | 11.217 | 8.168 | 24.507 | 1.00 | 54.53 | 6 |
| CZ | PHE | A | 3 | 11.213 | 9.316 | 23.740 | 1.00 | 54.18 | 6 |
| C | PHE | A | 3 | 6.871 | 8.762 | 28.610 | 1.00 | 52.24 | 6 |
| O | PHE | A | 3 | 6.695 | 7.597 | 28.973 | 1.00 | 51.99 | 8 |
| N | GLY | A | 3 | 6.444 | 9.798 | 29.320 | 1.00 | 52.78 | 7 |
| CA | GLY | A | 3 | 5.693 | 9.654 | 30.551 | 1.00 | 53.77 | 6 |
| C | GLY | A | 3 | 6.446 | 9.986 | 31.687 | 1.00 | 54.34 | 6 |
| O | GLY | A | 3 | 7.227 | 9.630 | 32.388 | 1.00 | 54.23 | 8 |
| N | GLU | A | 3 | 6.205 | 7.690 | 31.888 | 1.00 | 54.80 | 7 |
| CA | GLU | A | 3 | 6.838 | 6.949 | 32.975 | 1.00 | 55.28 | 6 |
| CB | GLU | A | 3 | 5.960 | 5.789 | 33.443 | 1.00 | 58.98 | 6 |
| C | GLU | A | 3 | 4.949 | 6.181 | 34.517 | 1.00 | 62.90 | 6 |
| C | GLU | A | 3 | 3.537 | 6.208 | 33.959 | 1.00 | 65.17 | 6 |
| O | GLU | A | 3 | 3.089 | 7.295 | 33.536 | 1.00 | 67.07 | 6 |
| O | GLU | A | 3 | 2.888 | 5.142 | 33.934 | 1.00 | 65.23 | 8 |
| C | GLU | A | 3 | 8.228 | 6.464 | 32.591 | 1.00 | 54.50 | 6 |
| O | GLU | A | 3 | 9.043 | 6.116 | 33.445 | 1.00 | 54.82 | 8 |
| N | ALA | A | 3 | 8.521 | 6.463 | 31.294 | 1.00 | 53.52 | 7 |
| CA | ALA | A | 3 | 9.823 | 6.062 | 30.782 | 1.00 | 52.63 | 6 |
| CB | ALA | A | 3 | 9.689 | 5.365 | 29.440 | 1.00 | 50.42 | 6 |
| C | ALA | A | 3 | 10.734 | 7.284 | 30.676 | 1.00 | 52.26 | 6 |
| O | ALA | A | 3 | 11.926 | 7.171 | 30.394 | 1.00 | 51.59 | 8 |
| N | ALA | A | 3 | 10.210 | 8.471 | 30.953 | 1.00 | 52.74 | 7 |
| CA | ALA | A | 3 | 10.943 | 9.724 | 30.925 | 1.00 | 54.05 | 6 |
| CB | ALA | A | 3 | 10.102 | 10.838 | 31.539 | 1.00 | 53.68 | 6 |
| C | ALA | A | 3 | 12.291 | 9.648 | 31.629 | 1.00 | 55.13 | 6 |
| O | ALA | A | 3 | 13.320 | 9.986 | 31.034 | 1.00 | 55.60 | 8 |
| N | SER | A | 3 | 12.327 | 9.160 | 32.867 | 1.00 | 55.54 | 7 |
| CA | SER | A | 3 | 13.573 | 9.002 | 33.606 | 1.00 | 55.99 | 6 |
| CB | SER | A | 3 | 13.306 | 8.859 | 35.105 | 1.00 | 57.01 | 6 |

| | | | | | | | | |
|---|---|---|---|---|---|---|---|---|
| O | SER | A | 3 | 12.171 | 8.052 | 35.359 | 1.00 | 57.76 | 8 |
| C | SER | A | 3 | 14.399 | 7.821 | 33.107 | 1.00 | 56.08 | 6 |
| O | SER | A | 3 | 15.603 | 7.733 | 33.355 | 1.00 | 56.24 | 8 |
| N | ARG | A | 3 | 13.781 | 6.902 | 32.386 | 1.00 | 56.22 | 7 |
| CA | ARG | A | 3 | 14.416 | 5.726 | 31.814 | 1.00 | 56.26 | 6 |
| CB | ARG | A | 3 | 13.344 | 4.651 | 31.647 | 1.00 | 61.19 | 6 |
| C | ARG | A | 3 | 13.701 | 3.372 | 30.920 | 1.00 | 66.66 | 6 |
| C | ARG | A | 3 | 12.447 | 2.526 | 30.737 | 1.00 | 71.39 | 6 |
| N | ARG | A | 3 | 12.695 | 1.230 | 30.126 | 1.00 | 75.06 | 7 |
| CZ | ARG | A | 3 | 11.756 | 0.312 | 29.913 | 1.00 | 77.16 | 6 |
| N | ARG | A | 3 | 10.497 | 0.540 | 30.262 | 1.00 | 78.29 | 7 |
| N | ARG | A | 3 | 12.073 | -0.845 | 29.347 | 1.00 | 78.92 | 7 |
| C | ARG | A | 3 | 15.110 | 6.023 | 30.491 | 1.00 | 55.03 | 6 |
| O | ARG | A | 3 | 16.028 | 5.296 | 30.105 | 1.00 | 55.13 | 8 |
| N | VAL | A | 3 | 14.705 | 7.077 | 29.789 | 1.00 | 53.57 | 7 |
| CA | VAL | A | 3 | 15.284 | 7.424 | 28.496 | 1.00 | 51.50 | 6 |
| CB | VAL | A | 3 | 14.174 | 7.860 | 27.515 | 1.00 | 51.84 | 6 |
| C | VAL | A | 3 | 13.523 | 9.165 | 27.947 | 1.00 | 51.31 | 6 |
| C | VAL | A | 3 | 14.710 | 7.972 | 26.095 | 1.00 | 51.08 | 6 |
| C | VAL | A | 3 | 16.377 | 8.479 | 28.545 | 1.00 | 49.96 | 6 |
| O | VAL | A | 3 | 16.278 | 9.497 | 29.227 | 1.00 | 50.25 | 8 |
| N | LEU | A | 3 | 17.436 | 8.250 | 27.770 | 1.00 | 48.09 | 7 |
| CA | LEU | A | 3 | 18.567 | 9.163 | 27.688 | 1.00 | 45.94 | 6 |
| CB | LEU | A | 3 | 19.875 | 8.398 | 27.483 | 1.00 | 43.63 | 6 |
| C | LEU | A | 3 | 20.080 | 7.094 | 28.254 | 1.00 | 43.75 | 6 |
| C | LEU | A | 3 | 21.455 | 6.510 | 27.955 | 1.00 | 41.34 | 6 |
| C | LEU | A | 3 | 19.912 | 7.299 | 29.751 | 1.00 | 42.51 | 6 |
| C | LEU | A | 3 | 18.397 | 10.313 | 26.566 | 1.00 | 44.92 | 6 |
| O | LEU | A | 3 | 18.184 | 9.849 | 25.402 | 1.00 | 44.57 | 8 |
| N | VAL | A | 3 | 18.446 | 11.460 | 26.934 | 1.00 | 43.75 | 7 |
| CA | VAL | A | 3 | 18.292 | 12.568 | 26.006 | 1.00 | 42.60 | 6 |
| CB | VAL | A | 3 | 17.056 | 13.434 | 26.333 | 1.00 | 42.79 | 6 |
| C | VAL | A | 3 | 16.914 | 14.564 | 25.318 | 1.00 | 43.51 | 6 |
| C | VAL | A | 3 | 15.771 | 12.628 | 26.391 | 1.00 | 41.10 | 6 |
| C | VAL | A | 3 | 19.511 | 13.487 | 26.057 | 1.00 | 41.36 | 6 |
| O | VAL | A | 3 | 19.660 | 14.195 | 27.055 | 1.00 | 41.26 | 8 |
| N | SER | A | 3 | 20.277 | 13.602 | 24.978 | 1.00 | 40.10 | 7 |
| CA | SER | A | 3 | 21.417 | 14.515 | 24.995 | 1.00 | 38.23 | 6 |
| CB | SER | A | 3 | 22.726 | 13.733 | 25.111 | 1.00 | 38.48 | 6 |
| O | SER | A | 3 | 23.125 | 13.209 | 23.860 | 1.00 | 37.54 | 8 |
| C | SER | A | 3 | 21.462 | 15.432 | 23.779 | 1.00 | 37.10 | 6 |
| O | SER | A | 3 | 20.980 | 15.110 | 22.696 | 1.00 | 36.20 | 8 |
| N | SER | A | 3 | 22.080 | 16.597 | 23.971 | 1.00 | 36.01 | 7 |
| CA | SER | A | 3 | 22.287 | 17.541 | 22.882 | 1.00 | 34.31 | 6 |
| CB | SER | A | 3 | 21.798 | 18.939 | 23.261 | 1.00 | 34.82 | 6 |
| O | SER | A | 3 | 22.083 | 19.885 | 22.245 | 1.00 | 31.05 | 8 |
| C | SER | A | 3 | 23.762 | 17.580 | 22.501 | 1.00 | 33.61 | 6 |
| O | SER | A | 3 | 24.597 | 18.118 | 23.233 | 1.00 | 33.03 | 8 |
| N | THR | A | 3 | 24.072 | 17.129 | 21.284 | 1.00 | 32.62 | 7 |
| CA | THR | A | 3 | 25.437 | 17.172 | 20.775 | 1.00 | 32.08 | 6 |
| CB | THR | A | 3 | 25.726 | 16.101 | 19.712 | 1.00 | 33.01 | 6 |
| O | THR | A | 3 | 24.747 | 16.143 | 18.667 | 1.00 | 34.86 | 8 |
| C | THR | A | 3 | 25.711 | 14.716 | 20.347 | 1.00 | 32.74 | 6 |
| C | THR | A | 3 | 25.793 | 18.553 | 20.240 | 1.00 | 31.64 | 6 |
| O | THR | A | 3 | 26.924 | 18.826 | 19.840 | 1.00 | 31.14 | 8 |
| N | LYS | A | 3 | 24.856 | 19.491 | 20.300 | 1.00 | 31.31 | 7 |
| CA | LYS | A | 3 | 25.010 | 20.881 | 19.939 | 1.00 | 31.62 | 6 |
| CB | LYS | A | 3 | 23.654 | 21.553 | 19.710 | 1.00 | 29.29 | 6 |
| C | LYS | A | 3 | 22.892 | 21.070 | 18.485 | 1.00 | 26.40 | 6 |
| C | LYS | A | 3 | 21.836 | 22.083 | 18.071 | 1.00 | 26.12 | 6 |
| CE | LYS | A | 3 | 21.019 | 21.625 | 16.880 | 1.00 | 19.32 | 6 |
| NZ | LYS | A | 3 | 20.357 | 20.315 | 17.079 | 1.00 | 19.99 | 7 |
| C | LYS | A | 3 | 25.777 | 21.650 | 21.017 | 1.00 | 32.18 | 6 |
| O | LYS | A | 3 | 26.227 | 22.774 | 20.790 | 1.00 | 31.78 | 8 |

Figure 1 - 19

| | | | | | | | | | |
|---|---|---|---|---|---|---|---|---|---|
| N | SER | A | 3 | 26.013 | 21.033 | 22.170 | 1.00 | 32.16 | 7 |
| CA | SER | A | 3 | 26.870 | 21.550 | 23.217 | 1.00 | 32.60 | 6 |
| CB | SER | A | 3 | 26.670 | 20.797 | 24.533 | 1.00 | 33.17 | 6 |
| O | SER | A | 3 | 26.705 | 19.395 | 24.356 | 1.00 | 33.68 | 8 |
| C | SER | A | 3 | 28.342 | 21.501 | 22.812 | 1.00 | 32.18 | 6 |
| O | SER | A | 3 | 29.145 | 22.294 | 23.305 | 1.00 | 32.58 | 8 |
| N | MET | A | 3 | 28.707 | 20.593 | 21.918 | 1.00 | 31.37 | 7 |
| CA | MET | A | 3 | 30.066 | 20.471 | 21.421 | 1.00 | 30.45 | 6 |
| CB | MET | A | 3 | 30.467 | 18.989 | 21.389 | 1.00 | 29.91 | 6 |
| C | MET | A | 3 | 30.627 | 18.359 | 22.763 | 1.00 | 30.11 | 6 |
| SD | MET | A | 3 | 30.676 | 16.559 | 22.727 | 1.00 | 27.38 | 1 |
| CE | MET | A | 3 | 28.930 | 16.174 | 22.612 | 1.00 | 28.29 | 6 |
| C | MET | A | 3 | 30.209 | 21.045 | 20.013 | 1.00 | 29.74 | 6 |
| O | MET | A | 3 | 31.181 | 21.695 | 19.643 | 1.00 | 30.42 | 8 |
| N | THR | A | 3 | 29.206 | 20.776 | 19.194 | 1.00 | 28.53 | 7 |
| CA | THR | A | 3 | 29.221 | 21.052 | 17.764 | 1.00 | 26.82 | 6 |
| CB | THR | A | 3 | 28.529 | 19.849 | 17.084 | 1.00 | 25.06 | 6 |
| O | THR | A | 3 | 29.276 | 19.446 | 15.930 | 1.00 | 30.10 | 8 |
| C | THR | A | 3 | 27.090 | 20.114 | 16.701 | 1.00 | 18.67 | 6 |
| C | THR | A | 3 | 28.614 | 22.391 | 17.399 | 1.00 | 26.37 | 6 |
| O | THR | A | 3 | 29.054 | 23.058 | 16.457 | 1.00 | 26.07 | 8 |
| N | GLY | A | 3 | 27.618 | 22.819 | 18.170 | 1.00 | 25.19 | 7 |
| CA | GLY | A | 3 | 26.920 | 24.078 | 17.903 | 1.00 | 23.14 | 6 |
| C | GLY | A | 3 | 25.703 | 23.739 | 17.033 | 1.00 | 22.02 | 6 |
| O | GLY | A | 3 | 25.454 | 22.562 | 16.775 | 1.00 | 20.89 | 8 |
| N | HIS | A | 3 | 24.951 | 24.734 | 16.597 | 1.00 | 21.15 | 7 |
| CA | HIS | A | 3 | 23.784 | 24.482 | 15.756 | 1.00 | 21.64 | 6 |
| CB | HIS | A | 3 | 22.651 | 25.433 | 16.132 | 1.00 | 22.64 | 6 |
| C | HIS | A | 3 | 21.345 | 25.179 | 15.448 | 1.00 | 22.18 | 6 |
| C | HIS | A | 3 | 20.906 | 24.174 | 14.655 | 1.00 | 22.76 | 6 |
| N | HIS | A | 3 | 20.290 | 26.062 | 15.559 | 1.00 | 21.82 | 7 |
| CE | HIS | A | 3 | 19.267 | 25.608 | 14.868 | 1.00 | 22.80 | 6 |
| N | HIS | A | 3 | 19.610 | 24.462 | 14.307 | 1.00 | 22.54 | 7 |
| C | HIS | A | 3 | 24.154 | 24.629 | 14.285 | 1.00 | 21.46 | 6 |
| O | HIS | A | 3 | 24.436 | 25.735 | 13.825 | 1.00 | 20.69 | 8 |
| N | LEU | A | 3 | 24.046 | 23.547 | 13.518 | 1.00 | 21.57 | 7 |
| CA | LEU | A | 3 | 24.414 | 23.543 | 12.110 | 1.00 | 21.84 | 6 |
| CB | LEU | A | 3 | 25.023 | 22.217 | 11.684 | 1.00 | 23.76 | 6 |
| C | LEU | A | 3 | 26.176 | 21.514 | 12.363 | 1.00 | 26.89 | 6 |
| C | LEU | A | 3 | 27.099 | 20.895 | 11.311 | 1.00 | 23.94 | 6 |
| C | LEU | A | 3 | 26.984 | 22.392 | 13.303 | 1.00 | 26.29 | 6 |
| C | LEU | A | 3 | 23.230 | 23.833 | 11.187 | 1.00 | 21.61 | 6 |
| O | LEU | A | 3 | 23.245 | 23.478 | 10.007 | 1.00 | 20.96 | 8 |
| N | LEU | A | 3 | 22.196 | 24.471 | 11.711 | 1.00 | 21.90 | 7 |
| CA | LEU | A | 3 | 21.000 | 24.829 | 10.971 | 1.00 | 20.97 | 6 |
| CB | LEU | A | 3 | 21.256 | 26.146 | 10.227 | 1.00 | 25.02 | 6 |
| C | LEU | A | 3 | 21.228 | 27.387 | 11.132 | 1.00 | 29.21 | 6 |
| C | LEU | A | 3 | 21.823 | 28.592 | 10.425 | 1.00 | 31.78 | 6 |
| C | LEU | A | 3 | 19.805 | 27.671 | 11.588 | 1.00 | 31.03 | 6 |
| C | LEU | A | 3 | 20.517 | 23.723 | 10.053 | 1.00 | 20.08 | 6 |
| O | LEU | A | 3 | 20.109 | 22.668 | 10.547 | 1.00 | 19.70 | 8 |
| N | GLY | A | 3 | 20.685 | 23.857 | 8.743 | 1.00 | 18.85 | 7 |
| CA | GLY | A | 3 | 20.189 | 22.912 | 7.767 | 1.00 | 17.73 | 6 |
| C | GLY | A | 3 | 20.916 | 21.583 | 7.708 | 1.00 | 17.85 | 6 |
| O | GLY | A | 3 | 20.420 | 20.628 | 7.105 | 1.00 | 18.50 | 8 |
| N | ALA | A | 3 | 22.098 | 21.491 | 8.305 | 1.00 | 16.95 | 7 |
| CA | ALA | A | 3 | 22.859 | 20.258 | 8.366 | 1.00 | 16.12 | 6 |
| CB | ALA | A | 3 | 24.336 | 20.533 | 8.116 | 1.00 | 14.89 | 6 |
| C | ALA | A | 3 | 22.706 | 19.597 | 9.734 | 1.00 | 16.19 | 6 |
| O | ALA | A | 3 | 23.205 | 18.491 | 9.940 | 1.00 | 16.13 | 8 |
| N | ALA | A | 3 | 22.053 | 20.282 | 10.670 | 1.00 | 16.51 | 7 |
| CA | ALA | A | 3 | 21.914 | 19.783 | 12.032 | 1.00 | 17.53 | 6 |
| CB | ALA | A | 3 | 21.234 | 20.798 | 12.943 | 1.00 | 14.26 | 6 |
| C | ALA | A | 3 | 21.200 | 18.444 | 12.097 | 1.00 | 17.49 | 6 |
| O | ALA | A | 3 | 21.709 | 17.524 | 12.734 | 1.00 | 18.70 | 8 |
| N | GLY | A | 3 | 20.093 | 18.284 | 11.392 | 1.00 | 18.49 | 7 |
| CA | GLY | A | 3 | 19.346 | 17.044 | 11.340 | 1.00 | 18.89 | 6 |
| C | GLY | A | 3 | 20.085 | 15.914 | 10.641 | 1.00 | 19.95 | 6 |
| O | GLY | A | 3 | 19.804 | 14.742 | 10.908 | 1.00 | 20.23 | 8 |
| N | ALA | A | 3 | 20.979 | 16.235 | 9.714 | 1.00 | 20.89 | 7 |
| CA | ALA | A | 3 | 21.739 | 15.234 | 8.980 | 1.00 | 22.22 | 6 |
| CB | ALA | A | 3 | 22.286 | 15.830 | 7.690 | 1.00 | 20.29 | 6 |
| C | ALA | A | 3 | 22.879 | 14.657 | 9.815 | 1.00 | 23.42 | 6 |
| O | ALA | A | 3 | 22.993 | 13.436 | 9.944 | 1.00 | 22.82 | 8 |
| N | VAL | A | 3 | 23.692 | 15.528 | 10.413 | 1.00 | 23.70 | 7 |
| CA | VAL | A | 3 | 24.804 | 15.087 | 11.243 | 1.00 | 24.94 | 6 |
| CB | VAL | A | 3 | 25.732 | 16.231 | 11.691 | 1.00 | 24.96 | 6 |
| C | VAL | A | 3 | 26.375 | 16.906 | 10.489 | 1.00 | 24.13 | 6 |
| C | VAL | A | 3 | 25.004 | 17.259 | 12.543 | 1.00 | 24.96 | 6 |
| C | VAL | A | 3 | 24.313 | 14.344 | 12.482 | 1.00 | 25.74 | 6 |
| O | VAL | A | 3 | 24.898 | 13.344 | 12.896 | 1.00 | 25.66 | 8 |
| N | GLU | A | 3 | 23.217 | 14.813 | 13.064 | 1.00 | 26.47 | 7 |
| CA | GLU | A | 3 | 22.620 | 14.235 | 14.251 | 1.00 | 27.57 | 6 |
| CB | GLU | A | 3 | 21.656 | 15.256 | 14.879 | 1.00 | 24.46 | 6 |
| C | GLU | A | 3 | 22.395 | 16.436 | 15.485 | 1.00 | 22.46 | 6 |
| C | GLU | A | 3 | 21.493 | 17.567 | 15.920 | 1.00 | 21.93 | 6 |
| O | GLU | A | 3 | 20.285 | 17.356 | 16.143 | 1.00 | 25.13 | 8 |
| O | GLU | A | 3 | 22.008 | 18.695 | 16.057 | 1.00 | 23.51 | 8 |
| C | GLU | A | 3 | 21.897 | 12.920 | 14.010 | 1.00 | 28.69 | 6 |
| O | GLU | A | 3 | 21.691 | 12.158 | 14.960 | 1.00 | 29.70 | 8 |
| N | SER | A | 3 | 21.511 | 12.638 | 12.770 | 1.00 | 28.70 | 7 |
| CA | SER | A | 3 | 20.966 | 11.335 | 12.408 | 1.00 | 28.87 | 6 |
| CB | SER | A | 3 | 20.299 | 11.349 | 11.037 | 1.00 | 29.67 | 6 |
| O | SER | A | 3 | 19.060 | 12.029 | 11.055 | 1.00 | 30.09 | 8 |
| C | SER | A | 3 | 22.102 | 10.311 | 12.417 | 1.00 | 28.45 | 6 |
| O | SER | A | 3 | 21.917 | 9.172 | 12.834 | 1.00 | 29.17 | 8 |
| N | ILE | A | 3 | 23.279 | 10.741 | 11.973 | 1.00 | 28.01 | 7 |
| CA | ILE | A | 3 | 24.466 | 9.891 | 11.972 | 1.00 | 28.28 | 6 |
| CB | ILE | A | 3 | 25.635 | 10.555 | 11.223 | 1.00 | 27.00 | 6 |
| C | ILE | A | 3 | 26.906 | 9.724 | 11.315 | 1.00 | 24.00 | 6 |
| C | ILE | A | 3 | 25.237 | 10.769 | 9.761 | 1.00 | 25.93 | 6 |
| C | ILE | A | 3 | 26.150 | 11.648 | 8.942 | 1.00 | 25.92 | 6 |
| C | ILE | A | 3 | 24.857 | 9.551 | 13.407 | 1.00 | 28.54 | 6 |
| O | ILE | A | 3 | 24.990 | 8.374 | 13.750 | 1.00 | 29.30 | 8 |
| N | TYR | A | 3 | 24.886 | 10.547 | 14.288 | 1.00 | 27.81 | 7 |
| CA | TYR | A | 3 | 25.154 | 10.328 | 15.705 | 1.00 | 27.86 | 6 |
| CB | TYR | A | 3 | 25.121 | 11.625 | 16.505 | 1.00 | 25.65 | 6 |
| C | TYR | A | 3 | 25.927 | 12.780 | 15.961 | 1.00 | 23.07 | 6 |
| C | TYR | A | 3 | 25.562 | 14.087 | 16.265 | 1.00 | 21.60 | 6 |
| CE | TYR | A | 3 | 26.286 | 15.162 | 15.788 | 1.00 | 21.08 | 6 |
| C | TYR | A | 3 | 27.047 | 12.591 | 15.162 | 1.00 | 22.29 | 6 |
| CE | TYR | A | 3 | 27.769 | 13.657 | 14.670 | 1.00 | 22.16 | 6 |
| CZ | TYR | A | 3 | 27.385 | 14.942 | 14.990 | 1.00 | 21.49 | 6 |
| O | TYR | A | 3 | 28.109 | 16.006 | 14.503 | 1.00 | 22.00 | 8 |
| C | TYR | A | 3 | 24.163 | 9.331 | 16.298 | 1.00 | 28.50 | 6 |
| O | TYR | A | 3 | 24.562 | 8.399 | 16.999 | 1.00 | 29.32 | 8 |
| N | SER | A | 3 | 22.883 | 9.476 | 15.971 | 1.00 | 28.28 | 7 |
| CA | SER | A | 3 | 21.853 | 8.550 | 16.415 | 1.00 | 28.66 | 6 |
| CB | SER | A | 3 | 20.471 | 9.074 | 16.017 | 1.00 | 26.37 | 6 |
| O | SER | A | 3 | 20.239 | 10.351 | 16.586 | 1.00 | 24.94 | 8 |
| C | SER | A | 3 | 22.059 | 7.145 | 15.858 | 1.00 | 29.49 | 6 |
| O | SER | A | 3 | 21.716 | 6.164 | 16.523 | 1.00 | 29.71 | 8 |
| N | ILE | A | 3 | 22.581 | 7.026 | 14.644 | 1.00 | 29.91 | 7 |
| CA | ILE | A | 3 | 22.871 | 5.731 | 14.041 | 1.00 | 30.85 | 6 |
| CB | ILE | A | 3 | 23.042 | 5.854 | 12.518 | 1.00 | 29.44 | 6 |
| C | ILE | A | 3 | 23.695 | 4.632 | 11.898 | 1.00 | 24.70 | 6 |
| C | ILE | A | 3 | 21.671 | 6.100 | 11.866 | 1.00 | 30.99 | 6 |
| C | ILE | A | 3 | 21.746 | 6.717 | 10.487 | 1.00 | 31.70 | 6 |

Figure 1 - 20

| | | | | | | | | |
|---|---|---|---|---|---|---|---|---|
| C | ILE | A | 3 | 24.097 | 5.109 | 14.695 | 1.00 | 32.09 | 6 |
| O | ILE | A | 3 | 24.031 | 3.988 | 15.209 | 1.00 | 33.13 | 8 |
| N | LEU | A | 3 | 25.190 | 5.860 | 14.785 | 1.00 | 32.34 | 7 |
| CA | LEU | A | 3 | 26.426 | 5.390 | 15.399 | 1.00 | 32.59 | 6 |
| CB | LEU | A | 3 | 27.530 | 6.448 | 15.295 | 1.00 | 29.08 | 6 |
| C | LEU | A | 3 | 27.995 | 6.776 | 13.872 | 1.00 | 28.35 | 6 |
| C | LEU | A | 3 | 28.988 | 7.929 | 13.381 | 1.00 | 25.33 | 6 |
| C | LEU | A | 3 | 28.590 | 5.552 | 13.191 | 1.00 | 25.41 | 6 |
| C | LEU | A | 3 | 26.230 | 4.952 | 16.840 | 1.00 | 33.29 | 6 |
| O | LEU | A | 3 | 26.799 | 3.947 | 17.275 | 1.00 | 32.95 | 8 |
| N | ALA | A | 3 | 25.381 | 5.648 | 17.590 | 1.00 | 34.07 | 7 |
| CA | ALA | A | 3 | 25.047 | 5.296 | 18.959 | 1.00 | 35.50 | 6 |
| CB | ALA | A | 3 | 24.015 | 6.269 | 19.512 | 1.00 | 32.60 | 6 |
| C | ALA | A | 3 | 24.517 | 3.866 | 19.051 | 1.00 | 36.95 | 6 |
| O | ALA | A | 3 | 24.828 | 3.138 | 19.996 | 1.00 | 37.29 | 8 |
| N | LEU | A | 3 | 23.718 | 3.445 | 18.076 | 1.00 | 38.32 | 7 |
| CA | LEU | A | 3 | 23.214 | 2.088 | 17.983 | 1.00 | 39.35 | 6 |
| CB | LEU | A | 3 | 22.126 | 1.997 | 16.905 | 1.00 | 38.88 | 6 |
| C | LEU | A | 3 | 20.818 | 2.741 | 17.183 | 1.00 | 39.57 | 6 |
| C | LEU | A | 3 | 19.876 | 2.632 | 15.997 | 1.00 | 38.00 | 6 |
| C | LEU | A | 3 | 20.150 | 2.219 | 18.451 | 1.00 | 37.64 | 6 |
| C | LEU | A | 3 | 24.309 | 1.071 | 17.680 | 1.00 | 40.04 | 6 |
| O | LEU | A | 3 | 24.264 | -0.056 | 18.179 | 1.00 | 40.72 | 8 |
| N | ARG | A | 3 | 25.284 | 1.444 | 16.859 | 1.00 | 39.72 | 7 |
| CA | ARG | A | 3 | 26.374 | 0.555 | 16.489 | 1.00 | 39.68 | 6 |
| CB | ARG | A | 3 | 27.145 | 1.143 | 15.299 | 1.00 | 38.11 | 6 |
| C | ARG | A | 3 | 28.395 | 0.374 | 14.912 | 1.00 | 36.96 | 6 |
| C | ARG | A | 3 | 29.233 | 1.118 | 13.887 | 1.00 | 35.78 | 6 |
| N | ARG | A | 3 | 30.059 | 2.153 | 14.494 | 1.00 | 36.32 | 7 |
| CZ | ARG | A | 3 | 31.013 | 2.835 | 13.874 | 1.00 | 35.89 | 6 |
| N | ARG | A | 3 | 31.282 | 2.612 | 12.595 | 1.00 | 35.44 | 7 |
| N | ARG | A | 3 | 31.700 | 3.756 | 14.537 | 1.00 | 37.40 | 7 |
| C | ARG | A | 3 | 27.347 | 0.292 | 17.632 | 1.00 | 40.11 | 6 |
| O | ARG | A | 3 | 27.841 | -0.823 | 17.798 | 1.00 | 40.63 | 8 |
| N | ASP | A | 3 | 27.683 | 1.330 | 18.381 | 1.00 | 39.98 | 7 |
| CA | ASP | A | 3 | 28.670 | 1.282 | 19.440 | 1.00 | 40.06 | 6 |
| CB | ASP | A | 3 | 29.519 | 2.566 | 19.359 | 1.00 | 39.64 | 6 |
| C | ASP | A | 3 | 30.451 | 2.630 | 18.176 | 1.00 | 40.62 | 6 |
| O | ASP | A | 3 | 30.287 | 1.857 | 17.211 | 1.00 | 42.45 | 8 |
| O | ASP | A | 3 | 31.377 | 3.472 | 18.203 | 1.00 | 42.37 | 8 |
| C | ASP | A | 3 | 28.094 | 1.233 | 20.843 | 1.00 | 40.44 | 6 |
| O | ASP | A | 3 | 28.839 | 1.293 | 21.827 | 1.00 | 40.41 | 8 |
| N | GLN | A | 3 | 26.775 | 1.261 | 20.977 | 1.00 | 40.68 | 7 |
| CA | GLN | A | 3 | 26.120 | 1.289 | 22.279 | 1.00 | 41.07 | 6 |
| CB | GLN | A | 3 | 26.060 | -0.110 | 22.889 | 1.00 | 41.34 | 6 |
| C | GLN | A | 3 | 25.441 | -1.157 | 21.980 | 1.00 | 43.02 | 6 |
| C | GLN | A | 3 | 23.932 | -1.101 | 21.920 | 1.00 | 43.88 | 6 |
| O | GLN | A | 3 | 23.254 | -0.919 | 22.930 | 1.00 | 43.71 | 8 |
| N | GLN | A | 3 | 23.379 | -1.258 | 20.720 | 1.00 | 45.09 | 7 |
| C | GLN | A | 3 | 26.773 | 2.285 | 23.235 | 1.00 | 40.94 | 6 |
| O | GLN | A | 3 | 26.900 | 2.032 | 24.433 | 1.00 | 41.47 | 8 |
| N | ALA | A | 3 | 26.982 | 3.509 | 22.772 | 1.00 | 40.54 | 7 |
| CA | ALA | A | 3 | 27.526 | 4.607 | 23.550 | 1.00 | 40.25 | 6 |
| CB | ALA | A | 3 | 29.003 | 4.811 | 23.267 | 1.00 | 39.67 | 6 |
| C | ALA | A | 3 | 26.733 | 5.869 | 23.207 | 1.00 | 40.54 | 6 |
| O | ALA | A | 3 | 26.398 | 6.083 | 22.041 | 1.00 | 40.55 | 8 |
| N | VAL | A | 3 | 26.400 | 6.655 | 24.220 | 1.00 | 40.29 | 7 |
| CA | VAL | A | 3 | 25.621 | 7.873 | 24.018 | 1.00 | 40.33 | 6 |
| CB | VAL | A | 3 | 24.326 | 7.849 | 24.847 | 1.00 | 41.69 | 6 |
| C | VAL | A | 3 | 23.693 | 9.228 | 24.973 | 1.00 | 44.15 | 6 |
| C | VAL | A | 3 | 23.316 | 6.886 | 24.230 | 1.00 | 42.65 | 6 |
| C | VAL | A | 3 | 26.461 | 9.099 | 24.356 | 1.00 | 39.55 | 6 |
| O | VAL | A | 3 | 26.954 | 9.232 | 25.472 | 1.00 | 39.88 | 8 |
| N | PRO | A | 3 | 26.593 | 10.004 | 23.392 | 1.00 | 38.67 | 7 |
| C | PRO | A | 3 | 25.982 | 9.912 | 22.044 | 1.00 | 38.43 | 6 |
| CA | PRO | A | 3 | 27.341 | 11.232 | 23.561 | 1.00 | 37.39 | 6 |
| CB | PRO | A | 3 | 27.373 | 11.879 | 22.188 | 1.00 | 37.81 | 6 |
| C | PRO | A | 3 | 26.699 | 10.959 | 21.245 | 1.00 | 38.10 | 6 |
| C | PRO | A | 3 | 26.686 | 12.149 | 24.582 | 1.00 | 36.31 | 6 |
| O | PRO | A | 3 | 25.463 | 12.195 | 24.703 | 1.00 | 36.61 | 8 |
| N | PRO | A | 3 | 27.502 | 12.397 | 25.314 | 1.00 | 34.96 | 7 |
| C | PRO | A | 3 | 28.985 | 12.873 | 25.229 | 1.00 | 34.65 | 6 |
| CA | PRO | A | 3 | 27.030 | 13.776 | 26.355 | 1.00 | 34.12 | 6 |
| CB | PRO | A | 3 | 28.269 | 13.948 | 27.243 | 1.00 | 34.16 | 6 |
| C | PRO | A | 3 | 29.419 | 13.827 | 26.307 | 1.00 | 34.54 | 6 |
| C | PRO | A | 3 | 26.562 | 15.158 | 25.945 | 1.00 | 33.33 | 6 |
| O | PRO | A | 3 | 26.823 | 15.673 | 24.864 | 1.00 | 32.70 | 8 |
| N | THR | A | 3 | 25.873 | 15.790 | 26.892 | 1.00 | 33.07 | 7 |
| CA | THR | A | 3 | 25.505 | 17.193 | 26.785 | 1.00 | 33.34 | 6 |
| CB | THR | A | 3 | 24.125 | 17.525 | 27.365 | 1.00 | 32.36 | 6 |
| O | THR | A | 3 | 23.125 | 16.690 | 26.775 | 1.00 | 34.77 | 8 |
| C | THR | A | 3 | 23.787 | 18.987 | 27.116 | 1.00 | 30.68 | 6 |
| C | THR | A | 3 | 26.572 | 17.928 | 27.607 | 1.00 | 33.64 | 6 |
| O | THR | A | 3 | 26.393 | 17.987 | 28.824 | 1.00 | 34.29 | 8 |
| N | ILE | A | 3 | 27.709 | 18.280 | 27.019 | 1.00 | 33.67 | 7 |
| CA | ILE | A | 3 | 28.753 | 18.913 | 27.829 | 1.00 | 34.08 | 6 |
| CB | ILE | A | 3 | 30.091 | 19.062 | 27.090 | 1.00 | 31.83 | 6 |
| C | ILE | A | 3 | 30.542 | 17.710 | 26.551 | 1.00 | 31.40 | 6 |
| C | ILE | A | 3 | 30.011 | 20.091 | 25.963 | 1.00 | 31.66 | 6 |
| C | ILE | A | 3 | 31.348 | 20.624 | 25.497 | 1.00 | 27.91 | 6 |
| C | ILE | A | 3 | 28.267 | 20.259 | 28.343 | 1.00 | 34.65 | 6 |
| O | ILE | A | 3 | 27.273 | 20.813 | 27.877 | 1.00 | 34.80 | 8 |
| N | ASN | A | 3 | 28.953 | 20.806 | 29.338 | 1.00 | 35.52 | 7 |
| CA | ASN | A | 3 | 28.678 | 22.085 | 29.954 | 1.00 | 36.17 | 6 |
| CB | ASN | A | 3 | 28.564 | 23.192 | 28.895 | 1.00 | 37.53 | 6 |
| C | ASN | A | 3 | 29.853 | 23.478 | 28.157 | 1.00 | 39.33 | 6 |
| O | ASN | A | 3 | 30.942 | 23.435 | 28.729 | 1.00 | 41.49 | 8 |
| N | ASN | A | 3 | 29.725 | 23.759 | 26.865 | 1.00 | 38.26 | 7 |
| C | ASN | A | 3 | 27.438 | 22.141 | 30.834 | 1.00 | 37.42 | 6 |
| O | ASN | A | 3 | 27.059 | 23.240 | 31.267 | 1.00 | 36.65 | 8 |
| N | LEU | A | 3 | 26.805 | 21.021 | 31.152 | 1.00 | 39.20 | 7 |
| CA | LEU | A | 3 | 25.583 | 21.032 | 31.951 | 1.00 | 41.87 | 6 |
| CB | LEU | A | 3 | 24.686 | 19.861 | 31.559 | 1.00 | 39.97 | 6 |
| C | LEU | A | 3 | 23.296 | 19.758 | 32.183 | 1.00 | 39.36 | 6 |
| C | LEU | A | 3 | 22.575 | 21.095 | 32.216 | 1.00 | 39.37 | 6 |
| C | LEU | A | 3 | 22.457 | 18.727 | 31.438 | 1.00 | 37.75 | 6 |
| C | LEU | A | 3 | 25.891 | 21.037 | 33.443 | 1.00 | 44.02 | 6 |
| O | LEU | A | 3 | 25.739 | 20.048 | 34.153 | 1.00 | 43.56 | 8 |
| N | ASP | A | 3 | 26.281 | 22.205 | 33.940 | 1.00 | 46.66 | 7 |
| CA | ASP | A | 3 | 26.700 | 22.407 | 35.311 | 1.00 | 49.49 | 6 |
| CB | ASP | A | 3 | 27.590 | 23.656 | 35.391 | 1.00 | 50.43 | 6 |
| C | ASP | A | 3 | 28.868 | 23.531 | 34.591 | 1.00 | 50.97 | 6 |
| O | ASP | A | 3 | 29.356 | 24.568 | 34.092 | 1.00 | 52.47 | 8 |
| O | ASP | A | 3 | 29.393 | 22.406 | 34.463 | 1.00 | 51.53 | 8 |
| C | ASP | A | 3 | 25.533 | 22.583 | 36.271 | 1.00 | 51.39 | 6 |
| O | ASP | A | 3 | 25.652 | 22.273 | 37.457 | 1.00 | 52.19 | 8 |
| N | ASN | A | 3 | 24.415 | 23.097 | 35.773 | 1.00 | 52.98 | 7 |
| CA | ASN | A | 3 | 23.240 | 23.333 | 36.597 | 1.00 | 54.38 | 6 |
| CB | ASN | A | 3 | 23.354 | 24.718 | 37.246 | 1.00 | 55.67 | 6 |
| C | ASN | A | 3 | 23.817 | 24.718 | 38.683 | 1.00 | 56.56 | 6 |
| O | ASN | A | 3 | 23.364 | 23.912 | 39.498 | 1.00 | 58.64 | 8 |
| N | ASN | A | 3 | 24.732 | 25.628 | 39.001 | 1.00 | 54.49 | 7 |
| C | ASN | A | 3 | 21.945 | 23.281 | 35.796 | 1.00 | 55.65 | 6 |
| O | ASN | A | 3 | 21.533 | 24.272 | 35.192 | 1.00 | 55.61 | 8 |
| N | PRO | A | 3 | 21.269 | 22.139 | 35.827 | 1.00 | 56.99 | 7 |
| C | PRO | A | 3 | 21.700 | 20.916 | 36.544 | 1.00 | 56.97 | 6 |
| CA | PRO | A | 3 | 20.000 | 21.961 | 35.149 | 1.00 | 58.36 | 6 |
| CB | PRO | A | 3 | 19.505 | 20.603 | 35.633 | 1.00 | 57.72 | 6 |

Figure 1-21

| | | | | | | | | |
|---|---|---|---|---|---|---|---|---|
| C | PRO | A | 3 | 20.703 | 19.878 | 36.120 | 1.00 | 57.10 | 6 |
| C | PRO | A | 3 | 18.996 | 23.049 | 35.491 | 1.00 | 60.26 | 6 |
| O | PRO | A | 3 | 19.009 | 23.592 | 36.597 | 1.00 | 60.43 | 8 |
| N | ASP | A | 3 | 18.120 | 23.370 | 34.544 | 1.00 | 62.72 | 7 |
| CA | ASP | A | 3 | 17.091 | 24.389 | 34.766 | 1.00 | 65.42 | 6 |
| CB | ASP | A | 3 | 16.358 | 24.680 | 33.461 | 1.00 | 65.96 | 6 |
| C | ASP | A | 3 | 15.930 | 26.125 | 33.310 | 1.00 | 66.13 | 6 |
| O | ASP | A | 3 | 16.724 | 27.026 | 33.650 | 1.00 | 66.02 | 8 |
| O | ASP | A | 3 | 14.791 | 26.358 | 32.850 | 1.00 | 66.29 | 8 |
| C | ASP | A | 3 | 16.146 | 23.894 | 35.856 | 1.00 | 67.55 | 6 |
| O | ASP | A | 3 | 16.062 | 22.683 | 36.086 | 1.00 | 67.61 | 8 |
| N | GLU | A | 3 | 15.435 | 24.785 | 36.534 | 1.00 | 69.63 | 7 |
| CA | GLU | A | 3 | 14.574 | 24.425 | 37.650 | 1.00 | 71.91 | 6 |
| CB | GLU | A | 3 | 13.891 | 25.670 | 38.236 | 1.00 | 75.55 | 6 |
| C | GLU | A | 3 | 12.875 | 26.305 | 37.311 | 1.00 | 80.01 | 6 |
| C | GLU | A | 3 | 11.769 | 27.059 | 38.015 | 1.00 | 82.31 | 6 |
| O | GLU | A | 3 | 10.586 | 26.784 | 37.716 | 1.00 | 83.41 | 8 |
| O | GLU | A | 3 | 12.072 | 27.930 | 38.856 | 1.00 | 83.82 | 8 |
| C | GLU | A | 3 | 13.522 | 23.369 | 37.350 | 1.00 | 72.78 | 6 |
| O | GLU | A | 3 | 13.282 | 22.501 | 38.198 | 1.00 | 73.13 | 8 |
| N | GLY | A | 3 | 12.857 | 23.430 | 36.204 | 1.00 | 73.37 | 7 |
| CA | GLY | A | 3 | 11.854 | 22.436 | 35.831 | 1.00 | 73.98 | 6 |
| C | GLY | A | 3 | 12.445 | 21.469 | 34.805 | 1.00 | 74.22 | 6 |
| O | GLY | A | 3 | 11.937 | 21.288 | 33.703 | 1.00 | 74.73 | 8 |
| N | CYS | A | 3 | 13.556 | 20.859 | 35.182 | 1.00 | 74.04 | 7 |
| CA | CYS | A | 3 | 14.279 | 19.887 | 34.372 | 1.00 | 73.35 | 6 |
| CB | CYS | A | 3 | 15.607 | 20.434 | 33.873 | 1.00 | 74.61 | 6 |
| SG | CYS | A | 3 | 15.467 | 21.537 | 32.442 | 1.00 | 75.82 | 1 |
| C | CYS | A | 3 | 14.457 | 18.656 | 35.264 | 1.00 | 72.43 | 6 |
| O | CYS | A | 3 | 14.589 | 18.836 | 36.482 | 1.00 | 72.96 | 8 |
| N | ASP | A | 3 | 14.240 | 17.458 | 34.736 | 1.00 | 70.74 | 7 |
| CA | ASP | A | 3 | 14.193 | 16.275 | 35.592 | 1.00 | 68.42 | 6 |
| CB | ASP | A | 3 | 12.750 | 16.087 | 36.082 | 1.00 | 73.06 | 6 |
| C | ASP | A | 3 | 12.572 | 16.349 | 37.563 | 1.00 | 76.10 | 6 |
| O | ASP | A | 3 | 12.705 | 17.519 | 37.983 | 1.00 | 77.34 | 8 |
| O | ASP | A | 3 | 12.283 | 15.389 | 38.308 | 1.00 | 77.87 | 8 |
| C | ASP | A | 3 | 14.644 | 15.011 | 34.878 | 1.00 | 65.39 | 6 |
| O | ASP | A | 3 | 14.655 | 13.929 | 35.468 | 1.00 | 65.66 | 8 |
| N | LEU | A | 3 | 14.976 | 15.137 | 33.600 | 1.00 | 61.63 | 7 |
| CA | LEU | A | 3 | 15.371 | 13.988 | 32.798 | 1.00 | 57.08 | 6 |
| CB | LEU | A | 3 | 14.923 | 14.189 | 31.345 | 1.00 | 55.81 | 6 |
| C | LEU | A | 3 | 13.488 | 14.681 | 31.137 | 1.00 | 54.21 | 6 |
| C | LEU | A | 3 | 13.376 | 15.503 | 29.863 | 1.00 | 53.80 | 6 |
| C | LEU | A | 3 | 12.523 | 13.506 | 31.107 | 1.00 | 53.91 | 6 |
| C | LEU | A | 3 | 16.876 | 13.755 | 32.832 | 1.00 | 53.93 | 6 |
| O | LEU | A | 3 | 17.651 | 14.633 | 33.214 | 1.00 | 53.81 | 8 |
| N | ASP | A | 3 | 17.279 | 12.559 | 32.412 | 1.00 | 50.75 | 7 |
| CA | ASP | A | 3 | 18.700 | 12.234 | 32.329 | 1.00 | 47.57 | 6 |
| CB | ASP | A | 3 | 18.957 | 10.737 | 32.446 | 1.00 | 47.56 | 6 |
| C | ASP | A | 3 | 20.434 | 10.393 | 32.426 | 1.00 | 47.70 | 6 |
| O | ASP | A | 3 | 20.789 | 9.300 | 31.938 | 1.00 | 48.81 | 8 |
| O | ASP | A | 3 | 21.250 | 11.214 | 32.895 | 1.00 | 48.47 | 8 |
| C | ASP | A | 3 | 19.226 | 12.766 | 30.995 | 1.00 | 45.22 | 6 |
| O | ASP | A | 3 | 19.021 | 12.170 | 29.939 | 1.00 | 43.88 | 8 |
| N | PHE | A | 3 | 19.926 | 13.893 | 31.053 | 1.00 | 43.38 | 7 |
| CA | PHE | A | 3 | 20.451 | 14.559 | 29.873 | 1.00 | 42.15 | 6 |
| CB | PHE | A | 3 | 20.418 | 16.078 | 30.088 | 1.00 | 41.31 | 6 |
| C | PHE | A | 3 | 19.057 | 16.688 | 30.234 | 1.00 | 42.33 | 6 |
| C | PHE | A | 3 | 18.735 | 17.421 | 31.366 | 1.00 | 42.04 | 6 |
| C | PHE | A | 3 | 18.092 | 16.544 | 29.250 | 1.00 | 42.50 | 6 |
| CE | PHE | A | 3 | 17.486 | 17.992 | 31.515 | 1.00 | 41.44 | 6 |
| CE | PHE | A | 3 | 16.842 | 17.111 | 29.391 | 1.00 | 42.67 | 6 |
| CZ | PHE | A | 3 | 16.538 | 17.837 | 30.526 | 1.00 | 42.42 | 6 |
| C | PHE | A | 3 | 21.871 | 14.141 | 29.516 | 1.00 | 41.29 | 6 |

| | | | | | | | | |
|---|---|---|---|---|---|---|---|---|
| O | PHE | A | 3 | 22.597 | 14.874 | 28.844 | 1.00 | 40.83 | 8 |
| N | VAL | A | 3 | 22.307 | 12.972 | 29.970 | 1.00 | 40.72 | 7 |
| CA | VAL | A | 3 | 23.650 | 12.448 | 29.776 | 1.00 | 40.16 | 6 |
| CB | VAL | A | 3 | 23.891 | 11.815 | 28.403 | 1.00 | 38.09 | 6 |
| C | VAL | A | 3 | 25.173 | 10.990 | 28.427 | 1.00 | 36.99 | 6 |
| C | VAL | A | 3 | 22.727 | 10.932 | 27.974 | 1.00 | 38.10 | 6 |
| C | VAL | A | 3 | 24.659 | 13.563 | 30.056 | 1.00 | 40.38 | 6 |
| O | VAL | A | 3 | 25.385 | 14.035 | 29.186 | 1.00 | 40.38 | 8 |
| N | PRO | A | 3 | 24.700 | 14.009 | 31.313 | 1.00 | 40.78 | 7 |
| C | PRO | A | 3 | 23.800 | 13.524 | 32.404 | 1.00 | 40.85 | 6 |
| CA | PRO | A | 3 | 25.309 | 15.254 | 31.696 | 1.00 | 40.90 | 6 |
| CB | PRO | A | 3 | 25.114 | 15.342 | 33.216 | 1.00 | 40.96 | 6 |
| C | PRO | A | 3 | 24.428 | 14.100 | 33.638 | 1.00 | 40.79 | 6 |
| C | PRO | A | 3 | 26.734 | 15.593 | 31.358 | 1.00 | 41.19 | 6 |
| O | PRO | A | 3 | 26.904 | 16.768 | 30.971 | 1.00 | 42.24 | 8 |
| N | HIS | A | 3 | 27.780 | 14.807 | 31.590 | 1.00 | 40.96 | 7 |
| CA | HIS | A | 3 | 29.125 | 15.321 | 31.308 | 1.00 | 40.86 | 6 |
| CB | HIS | A | 3 | 29.855 | 15.671 | 32.615 | 1.00 | 40.66 | 6 |
| C | HIS | A | 3 | 29.399 | 16.966 | 33.216 | 1.00 | 40.73 | 6 |
| C | HIS | A | 3 | 29.717 | 18.252 | 32.951 | 1.00 | 41.56 | 6 |
| N | HIS | A | 3 | 28.427 | 17.004 | 34.194 | 1.00 | 41.70 | 7 |
| CE | HIS | A | 3 | 28.196 | 18.257 | 34.535 | 1.00 | 40.82 | 6 |
| N | HIS | A | 3 | 28.964 | 19.035 | 33.793 | 1.00 | 42.13 | 7 |
| C | HIS | A | 3 | 29.998 | 14.402 | 30.476 | 1.00 | 40.86 | 6 |
| O | HIS | A | 3 | 30.871 | 14.875 | 29.743 | 1.00 | 39.80 | 8 |
| N | GLU | A | 3 | 29.799 | 13.098 | 30.610 | 1.00 | 41.82 | 7 |
| CA | GLU | A | 3 | 30.603 | 12.134 | 29.866 | 1.00 | 42.65 | 6 |
| CB | GLU | A | 3 | 31.560 | 11.395 | 30.800 | 1.00 | 48.00 | 6 |
| C | GLU | A | 3 | 33.025 | 11.769 | 30.651 | 1.00 | 54.38 | 6 |
| C | GLU | A | 3 | 33.949 | 10.601 | 30.938 | 1.00 | 58.70 | 6 |
| O | GLU | A | 3 | 34.307 | 10.398 | 32.118 | 1.00 | 62.14 | 8 |
| O | GLU | A | 3 | 34.320 | 9.878 | 29.990 | 1.00 | 60.16 | 8 |
| C | GLU | A | 3 | 29.690 | 11.143 | 29.152 | 1.00 | 41.91 | 6 |
| O | GLU | A | 3 | 28.533 | 10.976 | 29.536 | 1.00 | 41.07 | 8 |
| N | ALA | A | 3 | 30.220 | 10.524 | 28.105 | 1.00 | 41.81 | 7 |
| CA | ALA | A | 3 | 29.453 | 9.543 | 27.348 | 1.00 | 41.61 | 6 |
| CB | ALA | A | 3 | 30.301 | 8.960 | 26.230 | 1.00 | 41.62 | 6 |
| C | ALA | A | 3 | 28.964 | 8.436 | 28.276 | 1.00 | 41.80 | 6 |
| O | ALA | A | 3 | 29.691 | 8.012 | 29.176 | 1.00 | 41.92 | 8 |
| N | ARG | A | 3 | 27.726 | 7.999 | 28.069 | 1.00 | 41.60 | 7 |
| CA | ARG | A | 3 | 27.181 | 6.905 | 28.866 | 1.00 | 40.84 | 6 |
| CB | ARG | A | 3 | 25.735 | 7.170 | 29.277 | 1.00 | 40.27 | 6 |
| C | ARG | A | 3 | 25.176 | 6.134 | 30.241 | 1.00 | 39.78 | 6 |
| C | ARG | A | 3 | 25.303 | 6.599 | 31.683 | 1.00 | 38.06 | 6 |
| N | ARG | A | 3 | 24.282 | 7.589 | 32.015 | 1.00 | 38.84 | 7 |
| CZ | ARG | A | 3 | 24.534 | 8.880 | 32.190 | 1.00 | 41.57 | 6 |
| N | ARG | A | 3 | 25.771 | 9.349 | 32.071 | 1.00 | 43.04 | 7 |
| N | ARG | A | 3 | 23.545 | 9.711 | 32.490 | 1.00 | 42.78 | 7 |
| C | ARG | A | 3 | 27.280 | 5.603 | 28.078 | 1.00 | 40.36 | 6 |
| O | ARG | A | 3 | 27.220 | 5.612 | 26.850 | 1.00 | 40.45 | 8 |
| N | GLN | A | 3 | 27.494 | 4.502 | 28.783 | 1.00 | 40.51 | 7 |
| CA | GLN | A | 3 | 27.539 | 3.181 | 28.159 | 1.00 | 39.98 | 6 |
| CB | GLN | A | 3 | 28.581 | 2.309 | 28.851 | 1.00 | 41.17 | 6 |
| C | GLN | A | 3 | 28.564 | 0.840 | 28.470 | 1.00 | 42.05 | 6 |
| C | GLN | A | 3 | 29.364 | 0.558 | 27.216 | 1.00 | 41.53 | 6 |
| O | GLN | A | 3 | 28.850 | -0.009 | 26.251 | 1.00 | 44.79 | 8 |
| N | GLN | A | 3 | 30.629 | 0.959 | 27.223 | 1.00 | 40.43 | 7 |
| C | GLN | A | 3 | 26.151 | 2.558 | 28.260 | 1.00 | 39.51 | 6 |
| O | GLN | A | 3 | 25.491 | 2.744 | 29.287 | 1.00 | 39.97 | 8 |
| N | VAL | A | 3 | 25.644 | 1.971 | 27.185 | 1.00 | 39.03 | 7 |
| CA | VAL | A | 3 | 24.332 | 1.327 | 27.199 | 1.00 | 38.60 | 6 |
| CB | VAL | A | 3 | 23.234 | 2.055 | 26.417 | 1.00 | 37.27 | 6 |
| C | VAL | A | 3 | 22.917 | 3.429 | 27.001 | 1.00 | 37.12 | 6 |
| C | VAL | A | 3 | 23.579 | 2.190 | 24.942 | 1.00 | 34.97 | 6 |

Figure 1 - 22

| | | | | | | | | |
|---|---|---|---|---|---|---|---|---|
| C | VAL | A | 3 | 24.491 | -0.100 | 26.668 | 1.00 | 38.94 | 6 |
| O | VAL | A | 3 | 25.540 | -0.387 | 26.081 | 1.00 | 38.81 | 8 |
| N | SER | A | 3 | 23.501 | -0.967 | 26.865 | 1.00 | 39.38 | 7 |
| CA | SER | A | 3 | 23.663 | -2.356 | 26.464 | 1.00 | 40.73 | 6 |
| CB | SER | A | 3 | 23.649 | -3.252 | 27.720 | 1.00 | 40.55 | 6 |
| O | SER | A | 3 | 23.861 | -4.601 | 27.327 | 1.00 | 42.48 | 8 |
| C | SER | A | 3 | 22.681 | -2.919 | 25.456 | 1.00 | 41.20 | 6 |
| O | SER | A | 3 | 23.144 | -3.476 | 24.447 | 1.00 | 41.74 | 8 |
| N | GLY | A | 3 | 21.377 | -2.851 | 25.636 | 1.00 | 41.13 | 7 |
| CA | GLY | A | 3 | 20.429 | -3.435 | 24.741 | 1.00 | 42.12 | 6 |
| C | GLY | A | 3 | 19.550 | -2.401 | 24.054 | 1.00 | 42.75 | 6 |
| O | GLY | A | 3 | 18.326 | -2.538 | 24.022 | 1.00 | 42.94 | 8 |
| N | MET | A | 3 | 20.167 | -1.367 | 23.500 | 1.00 | 43.16 | 7 |
| CA | MET | A | 3 | 19.440 | -0.299 | 22.822 | 1.00 | 43.71 | 6 |
| CB | MET | A | 3 | 20.230 | 1.004 | 22.944 | 1.00 | 43.69 | 6 |
| C | MET | A | 3 | 19.642 | 2.207 | 22.232 | 1.00 | 43.01 | 6 |
| SD | MET | A | 3 | 20.366 | 3.767 | 22.774 | 1.00 | 43.68 | 1 |
| CE | MET | A | 3 | 21.976 | 3.688 | 21.993 | 1.00 | 42.01 | 6 |
| C | MET | A | 3 | 19.192 | -0.651 | 21.361 | 1.00 | 44.30 | 6 |
| O | MET | A | 3 | 20.141 | -0.930 | 20.627 | 1.00 | 44.01 | 8 |
| N | GLU | A | 3 | 17.931 | -0.626 | 20.941 | 1.00 | 45.44 | 7 |
| CA | GLU | A | 3 | 17.587 | -0.949 | 19.560 | 1.00 | 46.71 | 6 |
| CB | GLU | A | 3 | 16.583 | -2.106 | 19.526 | 1.00 | 43.38 | 6 |
| C | GLU | A | 3 | 16.984 | -3.255 | 18.615 | 1.00 | 57.87 | 6 |
| C | GLU | A | 3 | 16.009 | -4.416 | 18.694 | 1.00 | 61.10 | 6 |
| O | GLU | A | 3 | 16.263 | -5.350 | 19.485 | 1.00 | 63.46 | 8 |
| O | GLU | A | 3 | 14.991 | -4.392 | 17.973 | 1.00 | 61.67 | 8 |
| C | GLU | A | 3 | 17.025 | 0.239 | 18.789 | 1.00 | 46.35 | 6 |
| O | GLU | A | 3 | 17.177 | 0.304 | 17.565 | 1.00 | 46.24 | 8 |
| N | TYR | A | 3 | 16.373 | 1.173 | 19.474 | 1.00 | 45.47 | 7 |
| CA | TYR | A | 3 | 15.785 | 2.334 | 18.820 | 1.00 | 44.72 | 6 |
| CB | TYR | A | 3 | 14.269 | 2.389 | 19.063 | 1.00 | 45.79 | 6 |
| C | TYR | A | 3 | 13.494 | 1.272 | 18.401 | 1.00 | 47.57 | 6 |
| C | TYR | A | 3 | 13.104 | 0.157 | 19.132 | 1.00 | 48.71 | 6 |
| CE | TYR | A | 3 | 12.420 | -0.886 | 18.535 | 1.00 | 49.56 | 6 |
| C | TYR | A | 3 | 13.182 | 1.313 | 17.051 | 1.00 | 48.28 | 6 |
| CE | TYR | A | 3 | 12.496 | 0.277 | 16.445 | 1.00 | 49.38 | 6 |
| CZ | TYR | A | 3 | 12.119 | -0.819 | 17.192 | 1.00 | 50.16 | 6 |
| O | TYR | A | 3 | 11.437 | -1.855 | 16.597 | 1.00 | 51.10 | 8 |
| C | TYR | A | 3 | 16.390 | 3.650 | 19.294 | 1.00 | 43.38 | 6 |
| O | TYR | A | 3 | 16.662 | 3.827 | 20.482 | 1.00 | 43.12 | 8 |
| N | THR | A | 3 | 16.541 | 4.606 | 18.381 | 1.00 | 41.59 | 7 |
| CA | THR | A | 3 | 16.920 | 5.968 | 18.718 | 1.00 | 39.98 | 6 |
| CB | THR | A | 3 | 18.373 | 6.345 | 18.388 | 1.00 | 40.58 | 6 |
| O | THR | A | 3 | 18.696 | 5.961 | 17.044 | 1.00 | 38.16 | 8 |
| C | THR | A | 3 | 19.360 | 5.709 | 19.354 | 1.00 | 41.15 | 6 |
| C | THR | A | 3 | 16.008 | 6.965 | 17.995 | 1.00 | 38.98 | 6 |
| O | THR | A | 3 | 15.540 | 6.724 | 16.887 | 1.00 | 38.49 | 8 |
| N | LEU | A | 3 | 15.788 | 8.107 | 18.626 | 1.00 | 38.40 | 7 |
| CA | LEU | A | 3 | 14.951 | 9.179 | 18.101 | 1.00 | 37.48 | 6 |
| CB | LEU | A | 3 | 13.862 | 9.461 | 19.134 | 1.00 | 40.89 | 6 |
| C | LEU | A | 3 | 12.706 | 10.398 | 18.820 | 1.00 | 43.96 | 6 |
| C | LEU | A | 3 | 11.655 | 9.721 | 17.955 | 1.00 | 45.59 | 6 |
| C | LEU | A | 3 | 12.058 | 10.894 | 20.110 | 1.00 | 45.23 | 6 |
| C | LEU | A | 3 | 15.778 | 10.431 | 17.835 | 1.00 | 36.55 | 6 |
| O | LEU | A | 3 | 16.477 | 10.888 | 18.745 | 1.00 | 36.35 | 8 |
| N | CYS | A | 3 | 15.754 | 10.970 | 16.616 | 1.00 | 35.33 | 7 |
| CA | CYS | A | 3 | 16.465 | 12.209 | 16.319 | 1.00 | 34.09 | 6 |
| CB | CYS | A | 3 | 17.441 | 12.103 | 15.146 | 1.00 | 30.99 | 6 |
| SG | CYS | A | 3 | 18.186 | 13.714 | 14.750 | 1.00 | 29.61 | 1 |
| C | CYS | A | 3 | 15.483 | 13.347 | 16.038 | 1.00 | 33.67 | 6 |
| O | CYS | A | 3 | 14.700 | 13.305 | 15.093 | 1.00 | 34.22 | 8 |
| N | ASN | A | 3 | 15.558 | 14.388 | 16.852 | 1.00 | 33.84 | 7 |
| CA | ASN | A | 3 | 14.661 | 15.523 | 16.801 | 1.00 | 33.60 | 6 |

| | | | | | | | | |
|---|---|---|---|---|---|---|---|---|
| CB | ASN | A | 3 | 14.226 | 15.790 | 18.260 | 1.00 | 36.16 | 6 |
| C | ASN | A | 3 | 13.048 | 14.951 | 18.697 | 1.00 | 39.16 | 6 |
| O | ASN | A | 3 | 12.375 | 14.313 | 17.887 | 1.00 | 41.53 | 8 |
| N | ASN | A | 3 | 12.774 | 14.966 | 19.997 | 1.00 | 39.24 | 7 |
| C | ASN | A | 3 | 15.191 | 16.827 | 16.233 | 1.00 | 32.97 | 6 |
| O | ASN | A | 3 | 16.246 | 17.325 | 16.617 | 1.00 | 32.75 | 8 |
| N | SER | A | 3 | 14.373 | 17.483 | 15.413 | 1.00 | 32.66 | 7 |
| CA | SER | A | 3 | 14.676 | 18.793 | 14.851 | 1.00 | 31.74 | 6 |
| CB | SER | A | 3 | 15.200 | 18.682 | 13.422 | 1.00 | 31.39 | 6 |
| O | SER | A | 3 | 16.598 | 18.874 | 13.359 | 1.00 | 31.26 | 8 |
| C | SER | A | 3 | 13.416 | 19.656 | 14.860 | 1.00 | 31.57 | 6 |
| O | SER | A | 3 | 12.435 | 19.319 | 14.194 | 1.00 | 31.75 | 8 |
| N | PHE | A | 3 | 13.415 | 20.722 | 15.649 | 1.00 | 30.83 | 7 |
| CA | PHE | A | 3 | 12.270 | 21.619 | 15.761 | 1.00 | 31.51 | 6 |
| CB | PHE | A | 3 | 11.712 | 21.643 | 17.185 | 1.00 | 31.46 | 6 |
| C | PHE | A | 3 | 11.529 | 20.317 | 17.862 | 1.00 | 32.87 | 6 |
| C | PHE | A | 3 | 12.125 | 20.065 | 19.087 | 1.00 | 33.75 | 6 |
| C | PHE | A | 3 | 10.774 | 19.310 | 17.280 | 1.00 | 33.53 | 6 |
| CE | PHE | A | 3 | 11.976 | 18.843 | 19.714 | 1.00 | 33.89 | 6 |
| CE | PHE | A | 3 | 10.633 | 18.082 | 17.894 | 1.00 | 35.78 | 6 |
| CZ | PHE | A | 3 | 11.227 | 17.850 | 19.119 | 1.00 | 33.73 | 6 |
| C | PHE | A | 3 | 12.688 | 23.029 | 15.347 | 1.00 | 31.43 | 6 |
| O | PHE | A | 3 | 13.279 | 23.753 | 16.150 | 1.00 | 31.64 | 8 |
| N | GLY | A | 3 | 12.398 | 23.442 | 14.116 | 1.00 | 31.34 | 7 |
| CA | GLY | A | 3 | 12.972 | 24.648 | 13.571 | 1.00 | 30.81 | 6 |
| C | GLY | A | 3 | 12.146 | 25.906 | 13.465 | 1.00 | 30.77 | 6 |
| O | GLY | A | 3 | 10.939 | 25.956 | 13.680 | 1.00 | 29.83 | 8 |
| N | PHE | A | 4 | 12.847 | 26.982 | 13.095 | 1.00 | 31.24 | 7 |
| CA | PHE | A | 4 | 12.239 | 28.297 | 12.897 | 1.00 | 31.72 | 6 |
| CB | PHE | A | 4 | 13.280 | 29.283 | 12.373 | 1.00 | 35.13 | 6 |
| C | PHE | A | 4 | 14.430 | 29.453 | 13.330 | 1.00 | 37.25 | 6 |
| C | PHE | A | 4 | 15.692 | 28.998 | 13.002 | 1.00 | 39.09 | 6 |
| C | PHE | A | 4 | 14.245 | 30.067 | 14.558 | 1.00 | 38.34 | 6 |
| CE | PHE | A | 4 | 16.752 | 29.147 | 13.876 | 1.00 | 38.52 | 6 |
| CE | PHE | A | 4 | 15.299 | 30.220 | 15.436 | 1.00 | 38.09 | 6 |
| CZ | PHE | A | 4 | 16.555 | 29.759 | 15.095 | 1.00 | 37.29 | 6 |
| C | PHE | A | 4 | 11.042 | 28.155 | 11.971 | 1.00 | 30.64 | 6 |
| O | PHE | A | 4 | 11.052 | 27.334 | 11.054 | 1.00 | 30.82 | 8 |
| N | GLY | A | 4 | 9.976 | 28.894 | 12.261 | 1.00 | 29.80 | 7 |
| CA | GLY | A | 4 | 8.742 | 28.810 | 11.489 | 1.00 | 28.76 | 6 |
| C | GLY | A | 4 | 7.805 | 27.760 | 12.082 | 1.00 | 27.97 | 6 |
| O | GLY | A | 4 | 6.727 | 27.488 | 11.554 | 1.00 | 28.67 | 8 |
| N | GLY | A | 4 | 8.217 | 27.113 | 13.162 | 1.00 | 26.86 | 7 |
| CA | GLY | A | 4 | 7.475 | 26.074 | 13.835 | 1.00 | 26.12 | 6 |
| C | GLY | A | 4 | 7.370 | 24.786 | 13.036 | 1.00 | 26.70 | 6 |
| O | GLY | A | 4 | 6.376 | 24.071 | 13.171 | 1.00 | 27.71 | 8 |
| N | THR | A | 4 | 8.377 | 24.450 | 12.237 | 1.00 | 25.43 | 7 |
| CA | THR | A | 4 | 8.323 | 23.222 | 11.440 | 1.00 | 24.02 | 6 |
| CB | THR | A | 4 | 8.749 | 23.499 | 9.993 | 1.00 | 21.80 | 6 |
| O | THR | A | 4 | 8.766 | 22.279 | 9.243 | 1.00 | 19.29 | 8 |
| C | THR | A | 4 | 10.113 | 24.167 | 9.915 | 1.00 | 20.36 | 6 |
| C | THR | A | 4 | 9.131 | 22.138 | 12.134 | 1.00 | 24.60 | 6 |
| O | THR | A | 4 | 10.324 | 22.291 | 12.401 | 1.00 | 24.92 | 8 |
| N | ASN | A | 4 | 8.455 | 21.061 | 12.542 | 1.00 | 24.70 | 7 |
| CA | ASN | A | 4 | 9.067 | 20.005 | 13.322 | 1.00 | 24.60 | 6 |
| CB | ASN | A | 4 | 8.250 | 19.701 | 14.591 | 1.00 | 23.50 | 6 |
| C | ASN | A | 4 | 7.907 | 20.924 | 15.404 | 1.00 | 23.01 | 6 |
| O | ASN | A | 4 | 8.801 | 21.625 | 15.878 | 1.00 | 26.17 | 8 |
| N | ASN | A | 4 | 6.616 | 21.179 | 15.556 | 1.00 | 22.16 | 7 |
| C | ASN | A | 4 | 9.204 | 18.667 | 12.604 | 1.00 | 24.49 | 6 |
| O | ASN | A | 4 | 8.407 | 18.309 | 11.745 | 1.00 | 24.10 | 8 |
| N | GLY | A | 4 | 10.187 | 17.896 | 13.071 | 1.00 | 24.98 | 7 |
| CA | GLY | A | 4 | 10.420 | 16.572 | 12.516 | 1.00 | 26.39 | 6 |
| C | GLY | A | 4 | 11.169 | 15.675 | 13.491 | 1.00 | 26.58 | 6 |

Figure 1 - 23

| | | | | | | | | |
|---|---|---|---|---|---|---|---|---|
| O | GLY | A | 4 | 11.944 | 16.126 | 14.327 | 1.00 | 27.32 | 8 |
| N | SER | A | 4 | 10.927 | 14.377 | 13.367 | 1.00 | 27.36 | 7 |
| CA | SER | A | 4 | 11.586 | 13.366 | 14.170 | 1.00 | 28.27 | 6 |
| CB | SER | A | 4 | 10.743 | 12.925 | 15.365 | 1.00 | 28.64 | 6 |
| O | SER | A | 4 | 10.364 | 13.975 | 16.224 | 1.00 | 26.79 | 8 |
| C | SER | A | 4 | 11.856 | 12.135 | 13.302 | 1.00 | 28.72 | 6 |
| O | SER | A | 4 | 11.003 | 11.766 | 12.495 | 1.00 | 29.31 | 8 |
| N | LEU | A | 4 | 13.016 | 11.523 | 13.484 | 1.00 | 28.57 | 7 |
| CA | LEU | A | 4 | 13.348 | 10.304 | 12.751 | 1.00 | 28.67 | 6 |
| CB | LEU | A | 4 | 14.534 | 10.504 | 11.819 | 1.00 | 26.79 | 6 |
| C | LEU | A | 4 | 14.245 | 11.209 | 10.488 | 1.00 | 28.09 | 6 |
| C | LEU | A | 4 | 15.526 | 11.739 | 9.863 | 1.00 | 26.35 | 6 |
| C | LEU | A | 4 | 13.529 | 10.278 | 9.521 | 1.00 | 26.42 | 6 |
| C | LEU | A | 4 | 13.600 | 9.198 | 13.777 | 1.00 | 29.89 | 6 |
| O | LEU | A | 4 | 14.008 | 9.492 | 14.906 | 1.00 | 30.25 | 8 |
| N | ILE | A | 4 | 13.195 | 7.972 | 13.474 | 1.00 | 30.42 | 7 |
| CA | ILE | A | 4 | 13.409 | 6.837 | 14.359 | 1.00 | 31.78 | 6 |
| CB | ILE | A | 4 | 12.123 | 6.165 | 14.866 | 1.00 | 30.94 | 6 |
| C | ILE | A | 4 | 12.444 | 4.865 | 15.599 | 1.00 | 32.61 | 6 |
| C | ILE | A | 4 | 11.340 | 7.091 | 15.798 | 1.00 | 30.59 | 6 |
| C | ILE | A | 4 | 10.007 | 6.541 | 16.250 | 1.00 | 32.84 | 6 |
| C | ILE | A | 4 | 14.260 | 5.794 | 13.630 | 1.00 | 33.11 | 6 |
| O | ILE | A | 4 | 13.939 | 5.388 | 12.516 | 1.00 | 32.58 | 8 |
| N | PHE | A | 4 | 15.342 | 5.376 | 14.279 | 1.00 | 34.56 | 7 |
| CA | PHE | A | 4 | 16.240 | 4.388 | 13.690 | 1.00 | 36.29 | 6 |
| CB | PHE | A | 4 | 17.655 | 4.958 | 13.596 | 1.00 | 36.33 | 6 |
| C | PHE | A | 4 | 17.792 | 6.083 | 12.608 | 1.00 | 36.69 | 6 |
| C | PHE | A | 4 | 17.659 | 7.400 | 13.015 | 1.00 | 36.61 | 6 |
| C | PHE | A | 4 | 18.034 | 5.823 | 11.268 | 1.00 | 36.58 | 6 |
| CE | PHE | A | 4 | 17.780 | 8.437 | 12.109 | 1.00 | 36.25 | 6 |
| CE | PHE | A | 4 | 18.160 | 6.856 | 10.360 | 1.00 | 35.22 | 6 |
| CZ | PHE | A | 4 | 18.036 | 8.164 | 10.780 | 1.00 | 34.67 | 6 |
| C | PHE | A | 4 | 16.212 | 3.087 | 14.484 | 1.00 | 37.64 | 6 |
| O | PHE | A | 4 | 15.945 | 3.087 | 15.685 | 1.00 | 37.30 | 8 |
| N | LYS | A | 4 | 16.428 | 1.970 | 13.796 | 1.00 | 39.20 | 7 |
| CA | LYS | A | 4 | 16.389 | 0.662 | 14.445 | 1.00 | 41.08 | 6 |
| CB | LYS | A | 4 | 15.108 | -0.070 | 14.064 | 1.00 | 43.25 | 6 |
| C | LYS | A | 4 | 15.203 | -1.551 | 13.771 | 1.00 | 45.80 | 6 |
| C | LYS | A | 4 | 14.079 | -2.339 | 14.425 | 1.00 | 49.50 | 6 |
| CE | LYS | A | 4 | 13.749 | -3.586 | 13.620 | 1.00 | 51.82 | 6 |
| NZ | LYS | A | 4 | 14.971 | -4.355 | 13.251 | 1.00 | 54.38 | 7 |
| C | LYS | A | 4 | 17.644 | -0.138 | 14.115 | 1.00 | 42.37 | 6 |
| O | LYS | A | 4 | 18.085 | -0.196 | 12.970 | 1.00 | 41.82 | 8 |
| N | LYS | A | 4 | 18.215 | -0.759 | 15.142 | 1.00 | 44.35 | 7 |
| CA | LYS | A | 4 | 19.416 | -1.569 | 14.990 | 1.00 | 46.87 | 6 |
| CB | LYS | A | 4 | 20.013 | -1.879 | 16.366 | 1.00 | 49.16 | 6 |
| C | LYS | A | 4 | 21.527 | -1.964 | 16.399 | 1.00 | 52.66 | 6 |
| C | LYS | A | 4 | 22.016 | -3.371 | 16.089 | 1.00 | 54.95 | 6 |
| CE | LYS | A | 4 | 23.498 | -3.518 | 16.391 | 1.00 | 56.19 | 6 |
| NZ | LYS | A | 4 | 24.349 | -3.018 | 15.277 | 1.00 | 56.91 | 7 |
| C | LYS | A | 4 | 19.104 | -2.876 | 14.269 | 1.00 | 48.27 | 6 |
| O | LYS | A | 4 | 18.169 | -3.580 | 14.652 | 1.00 | 48.31 | 8 |
| N | ILE | A | 4 | 19.868 | -3.191 | 13.230 | 1.00 | 50.03 | 7 |
| CA | ILE | A | 4 | 19.704 | -4.461 | 12.522 | 1.00 | 51.93 | 6 |
| CB | ILE | A | 4 | 19.304 | -4.278 | 11.053 | 1.00 | 53.55 | 6 |
| C | ILE | A | 4 | 19.778 | -5.421 | 10.163 | 1.00 | 54.48 | 6 |
| C | ILE | A | 4 | 17.777 | -4.145 | 10.945 | 1.00 | 53.27 | 6 |
| C | ILE | A | 4 | 17.291 | -3.765 | 9.564 | 1.00 | 54.97 | 6 |
| C | ILE | A | 4 | 20.994 | -5.269 | 12.659 | 1.00 | 52.78 | 6 |
| O | ILE | A | 4 | 21.398 | -5.522 | 13.816 | 1.00 | 54.07 | 8 |
| O1 | WAT | W | 5 | 21.478 | 17.601 | 19.536 | 1.00 | 19.73 | 8 |
| O1 | WAT | W | 5 | 21.076 | 20.754 | -2.535 | 1.00 | 16.84 | 8 |
| O1 | WAT | W | 5 | 26.737 | 32.257 | 19.752 | 1.00 | 20.81 | 8 |
| O1 | WAT | W | 5 | 28.234 | 30.811 | 2.839 | 1.00 | 19.99 | 8 |

| | | | | | | | | |
|---|---|---|---|---|---|---|---|---|
| O1 | WAT | W | 5 | 24.648 | 28.103 | 4.390 | 1.00 | 24.17 | 8 |
| O1 | WAT | W | 5 | 24.853 | 18.181 | 17.061 | 1.00 | 21.49 | 8 |
| O1 | WAT | W | 5 | 15.266 | 27.397 | 5.435 | 1.00 | 23.74 | 8 |
| O1 | WAT | W | 5 | 29.879 | 26.729 | 23.056 | 1.00 | 27.80 | 8 |
| O1 | WAT | W | 5 | 8.228 | 26.466 | 7.960 | 1.00 | 28.01 | 8 |
| O1 | WAT | W | 5 | 25.350 | -0.832 | -1.565 | 1.00 | 33.85 | 8 |
| O1 | WAT | W | 5 | 23.401 | 42.296 | 15.101 | 1.00 | 39.31 | 8 |
| O1 | WAT | W | 5 | 22.521 | 37.586 | 20.198 | 1.00 | 39.72 | 8 |
| O1 | WAT | W | 5 | 35.693 | 38.967 | -9.343 | 1.00 | 45.45 | 8 |
| O1 | WAT | W | 5 | 8.464 | 1.674 | 8.701 | 1.00 | 48.55 | 8 |
| O1 | WAT | W | 5 | 14.310 | 29.899 | 19.439 | 1.00 | 43.00 | 8 |
| O1 | WAT | W | 5 | 10.440 | 4.010 | 6.351 | 1.00 | 41.78 | 8 |
| O1 | WAT | W | 5 | 9.624 | 13.271 | 34.855 | 1.00 | 46.76 | 8 |
| O1 | WAT | W | 5 | 31.169 | 43.463 | 9.374 | 1.00 | 48.95 | 8 |
| O1 | WAT | W | 5 | 37.224 | 13.856 | 2.117 | 1.00 | 48.60 | 8 |
| O1 | WAT | W | 5 | 0.645 | 16.105 | 12.588 | 1.00 | 51.59 | 8 |
| O1 | WAT | W | 5 | 1.627 | 11.628 | 29.727 | 1.00 | 42.16 | 8 |
| O1 | WAT | W | 5 | 13.937 | 1.427 | 26.436 | 1.00 | 51.44 | 8 |
| O1 | WAT | W | 5 | 30.994 | 42.927 | 5.494 | 1.00 | 51.60 | 8 |
| O1 | WAT | W | 5 | 31.903 | 36.386 | 2.731 | 1.00 | 52.75 | 8 |
| O1 | WAT | W | 5 | 8.997 | 5.935 | -10.232 | 1.00 | 49.23 | 8 |
| O1 | WAT | W | 5 | 41.291 | 24.980 | -1.863 | 1.00 | 52.73 | 8 |
| O1 | WAT | W | 5 | 4.756 | 26.898 | 30.457 | 1.00 | 58.53 | 8 |
| O1 | WAT | W | 5 | 11.584 | 26.160 | 17.142 | 1.00 | 53.90 | 8 |
| O1 | WAT | W | 5 | 33.094 | 30.228 | 32.080 | 1.00 | 57.62 | 8 |
| O1 | WAT | W | 5 | 5.401 | -7.420 | 13.608 | 1.00 | 57.30 | 8 |
| O1 | WAT | W | 5 | -0.837 | 26.774 | 18.246 | 1.00 | 50.00 | 8 |
| Wr | by | O | v | 5.10.3 | | | | | |
| M | Oct | 2 | 0 | 1997 | | | | | |
| 1 0 | 1 00 | 1. | 9 | 90.00 | 90.00 | | | | |
| 1 0 | 0 00 | 0. | 0. | | | | | | |
| 0 0 | 1 00 | 0. | 0. | | | | | | |
| 0 0 | 0 00 | 1. | 0. | | | | | | |
| 1 0 | - | - | 0. | | | | | | |
| 0 0 | 1 00 | - | 0. | | | | | | |
| 0 0 | 0 00 | 1. | 0. | | | | | | |
| 1 | CB | L | B | 2 | -5.685 | 3.199 | - | 0.00 | 0. |
| 2 | CG | L | B | 2 | -5.545 | 4.098 | - | 0.00 | 0. |
| 3 | CD | L | B | 2 | -4.260 | 3.812 | - | 0.00 | 0. |
| 4 | CE | L | B | 2 | -3.315 | 5.000 | - | 0.00 | 0. |
| 5 | NZ | L | B | 2 | -2.850 | 5.406 | - | 0.00 | 0. |
| 6 | C | L | B | 2 | -6.109 | 5.140 | - | 0.00 | 0. |
| 7 | O | L | B | 2 | -7.335 | 5.109 | - | 0.00 | 0. |
| 8 | N | L | B | 2 | -5.524 | 2.911 | - | 0.00 | 0. |
| 9 | CA | L | B | 2 | -5.318 | 3.855 | - | 0.00 | 0. |
| N | ARG | B | 3 | -5.409 | 6.268 | -1.248 | 0.00 | 0.00 | 7 |
| CA | ARG | B | 3 | -6.048 | 7.556 | -1.019 | 0.00 | 0.00 | 6 |
| CB | ARG | B | 3 | -5.523 | 8.164 | 0.286 | 0.00 | 0.00 | 6 |
| C | ARG | B | 3 | -6.160 | 7.568 | 1.531 | 0.00 | 0.00 | 6 |
| C | ARG | B | 3 | -5.244 | 7.692 | 2.736 | 0.00 | 0.00 | 6 |
| N | ARG | B | 3 | -5.086 | 9.074 | 3.168 | 0.00 | 0.00 | 7 |
| CZ | ARG | B | 3 | -5.833 | 9.683 | 4.077 | 0.00 | 0.00 | 6 |
| N | ARG | B | 3 | -6.834 | 9.048 | 4.674 | 0.00 | 0.00 | 7 |
| N | ARG | B | 3 | -5.580 | 10.947 | 4.395 | 0.00 | 0.00 | 7 |
| C | ARG | B | 3 | -5.845 | 8.535 | -2.167 | 0.00 | 0.00 | 6 |
| O | ARG | B | 3 | -4.724 | 8.919 | -2.498 | 0.00 | 0.00 | 8 |
| N | ARG | B | 4 | -6.958 | 8.957 | -2.759 | 0.00 | 0.00 | 7 |
| CA | ARG | B | 4 | -6.949 | 9.879 | -3.884 | 0.00 | 0.00 | 6 |
| CB | ARG | B | 4 | -8.191 | 9.657 | -4.753 | 0.00 | 0.00 | 6 |
| C | ARG | B | 4 | -8.287 | 8.262 | -5.351 | 0.00 | 0.00 | 6 |
| C | ARG | B | 4 | -9.716 | 7.922 | -5.750 | 0.00 | 0.00 | 6 |
| N | ARG | B | 4 | -10.353 | 9.005 | -6.482 | 0.00 | 0.00 | 7 |
| CZ | ARG | B | 4 | -11.372 | 8.909 | -7.320 | 0.00 | 0.00 | 6 |
| N | ARG | B | 4 | -11.938 | 7.739 | -7.583 | 0.00 | 0.00 | 7 |

Figure 1 - 24

| | | | | | | | | | |
|---|---|---|---|---|---|---|---|---|---|
| N | ARG | B | 4 | -11.838 | 10.004 | -7.911 | 0.00 | 0.00 | 7 |
| C | ARG | B | 4 | -6.886 | 11.333 | -3.435 | 0.00 | 0.00 | 6 |
| O | ARG | B | 4 | -7.460 | 11.712 | -2.416 | 0.00 | 0.00 | 8 |
| N | VAL | B | 5 | -6.150 | 12.141 | -4.194 | 0.00 | 0.00 | 7 |
| CA | VAL | B | 5 | -5.980 | 13.555 | -3.891 | 0.00 | 0.00 | 6 |
| CB | VAL | B | 5 | -4.499 | 13.967 | -3.796 | 0.00 | 0.00 | 6 |
| C | VAL | B | 5 | -4.375 | 15.410 | -3.320 | 0.00 | 0.00 | 6 |
| C | VAL | B | 5 | -3.712 | 13.046 | -2.877 | 0.00 | 0.00 | 6 |
| C | VAL | B | 5 | -6.649 | 14.423 | -4.953 | 0.00 | 0.00 | 6 |
| O | VAL | B | 5 | -6.439 | 14.236 | -6.151 | 0.00 | 0.00 | 8 |
| N | VAL | B | 6 | -7.458 | 15.377 | -4.506 | 0.00 | 0.00 | 7 |
| CA | VAL | B | 6 | -8.162 | 16.289 | -5.394 | 0.00 | 0.00 | 6 |
| CB | VAL | B | 6 | -9.689 | 16.096 | -5.351 | 0.00 | 0.00 | 6 |
| C | VAL | B | 6 | -10.108 | 14.791 | -6.013 | 0.00 | 0.00 | 6 |
| C | VAL | B | 6 | -10.207 | 16.146 | -3.921 | 0.00 | 0.00 | 6 |
| C | VAL | B | 6 | -7.835 | 17.739 | -5.044 | 0.00 | 0.00 | 6 |
| O | VAL | B | 6 | -7.351 | 18.031 | -3.954 | 0.00 | 0.00 | 8 |
| N | VAL | B | 7 | -8.082 | 18.647 | -5.981 | 0.00 | 0.00 | 7 |
| CA | VAL | B | 7 | -7.829 | 20.072 | -5.781 | 0.00 | 0.00 | 6 |
| CB | VAL | B | 7 | -7.171 | 20.707 | -7.016 | 0.00 | 0.00 | 6 |
| C | VAL | B | 7 | -6.746 | 22.142 | -6.736 | 0.00 | 0.00 | 6 |
| C | VAL | B | 7 | -5.973 | 19.884 | -7.474 | 0.00 | 0.00 | 6 |
| C | VAL | B | 7 | -9.141 | 20.780 | -5.464 | 0.00 | 0.00 | 6 |
| O | VAL | B | 7 | -10.056 | 20.800 | -6.287 | 0.00 | 0.00 | 8 |
| N | THR | B | 8 | -9.248 | 21.344 | -4.264 | 0.00 | 0.00 | 7 |
| CA | THR | B | 8 | -10.464 | 22.008 | -3.833 | 0.00 | 0.00 | 6 |
| CB | THR | B | 8 | -10.960 | 21.391 | -2.496 | 0.00 | 0.00 | 6 |
| O | THR | B | 8 | -10.012 | 21.721 | -1.470 | 0.00 | 0.00 | 8 |
| C | THR | B | 8 | -11.126 | 19.888 | -2.579 | 0.00 | 0.00 | 6 |
| C | THR | B | 8 | -10.367 | 23.504 | -3.600 | 0.00 | 0.00 | 6 |
| O | THR | B | 8 | -11.293 | 24.068 | -3.004 | 0.00 | 0.00 | 8 |
| N | GLY | B | 9 | -9.286 | 24.153 | -4.005 | 0.00 | 0.00 | 7 |
| CA | GLY | B | 9 | -9.144 | 25.589 | -3.757 | 0.00 | 0.00 | 6 |
| C | GLY | B | 9 | -7.950 | 26.136 | -4.528 | 0.00 | 0.00 | 6 |
| O | GLY | B | 9 | -6.886 | 25.518 | -4.564 | 0.00 | 0.00 | 8 |
| N | LEU | B | 1 | -8.152 | 27.280 | -5.174 | 0.00 | 0.00 | 7 |
| CA | LEU | B | 1 | -7.105 | 27.900 | -5.976 | 0.00 | 0.00 | 6 |
| CB | LEU | B | 1 | -7.446 | 27.838 | -7.465 | 0.00 | 0.00 | 6 |
| C | LEU | B | 1 | -7.764 | 26.482 | -8.091 | 0.00 | 0.00 | 6 |
| C | LEU | B | 1 | -8.238 | 26.644 | -9.528 | 0.00 | 0.00 | 6 |
| C | LEU | B | 1 | -6.558 | 25.554 | -8.027 | 0.00 | 0.00 | 6 |
| C | LEU | B | 1 | -6.897 | 29.350 | -5.557 | 0.00 | 0.00 | 6 |
| O | LEU | B | 1 | -7.841 | 30.024 | -5.142 | 0.00 | 0.00 | 8 |
| N | GLY | B | 1 | -5.664 | 29.823 | -5.668 | 0.00 | 0.00 | 7 |
| CA | GLY | B | 1 | -5.349 | 31.207 | -5.306 | 0.00 | 0.00 | 6 |
| C | GLY | B | 1 | -4.062 | 31.628 | -6.007 | 0.00 | 0.00 | 6 |
| O | GLY | B | 1 | -3.216 | 30.774 | -6.284 | 0.00 | 0.00 | 8 |
| N | MET | B | 1 | -3.931 | 32.914 | -6.317 | 0.00 | 0.00 | 7 |
| CA | MET | B | 1 | -2.727 | 33.388 | -6.974 | 0.00 | 0.00 | 6 |
| CB | MET | B | 1 | -2.490 | 32.625 | -8.282 | 0.00 | 0.00 | 6 |
| C | MET | B | 1 | -2.990 | 33.281 | -9.554 | 0.00 | 0.00 | 6 |
| SD | MET | B | 1 | -2.427 | 32.418 | -11.033 | 0.00 | 0.00 | 1 |
| CE | MET | B | 1 | -3.853 | 31.394 | -11.381 | 0.00 | 0.00 | 6 |
| C | MET | B | 1 | -2.670 | 34.885 | -7.258 | 0.00 | 0.00 | 6 |
| O | MET | B | 1 | -3.628 | 35.626 | -7.402 | 0.00 | 0.00 | 8 |
| N | LEU | B | 1 | -1.423 | 35.318 | -7.387 | 0.00 | 0.00 | 7 |
| CA | LEU | B | 1 | -1.019 | 36.658 | -7.762 | 0.00 | 0.00 | 6 |
| CB | LEU | B | 1 | -0.345 | 37.416 | -6.630 | 0.00 | 0.00 | 6 |
| C | LEU | B | 1 | -1.225 | 37.783 | -5.431 | 0.00 | 0.00 | 6 |
| C | LEU | B | 1 | -0.386 | 37.931 | -4.173 | 0.00 | 0.00 | 6 |
| C | LEU | B | 1 | -2.012 | 39.053 | -5.721 | 0.00 | 0.00 | 6 |
| C | LEU | B | 1 | -0.049 | 36.455 | -8.933 | 0.00 | 0.00 | 6 |
| O | LEU | B | 1 | 0.878 | 35.652 | -8.823 | 0.00 | 0.00 | 8 |
| N | SER | B | 1 | -0.290 | 37.142 | -10.034 | 0.00 | 0.00 | 7 |

| | | | | | | | | | |
|---|---|---|---|---|---|---|---|---|---|
| CA | SER | B | 1 | 0.573 | 37.004 | -11.205 | 0.00 | 0.00 | 6 |
| CB | SER | B | 1 | -0.015 | 35.962 | -12.155 | 0.00 | 0.00 | 6 |
| O | SER | B | 1 | -0.875 | 36.553 | -13.112 | 0.00 | 0.00 | 8 |
| C | SER | B | 1 | 0.707 | 38.350 | -11.895 | 0.00 | 0.00 | 6 |
| O | SER | B | 1 | -0.036 | 39.287 | -11.612 | 0.00 | 0.00 | 8 |
| N | PRO | B | 1 | 1.592 | 38.431 | -12.880 | 0.00 | 0.00 | 7 |
| C | PRO | B | 1 | 2.528 | 37.351 | -13.288 | 0.00 | 0.00 | 6 |
| CA | PRO | B | 1 | 1.796 | 39.632 | -13.665 | 0.00 | 0.00 | 6 |
| CB | PRO | B | 1 | 3.008 | 39.317 | -14.535 | 0.00 | 0.00 | 6 |
| C | PRO | B | 1 | 3.661 | 38.139 | -13.902 | 0.00 | 0.00 | 6 |
| C | PRO | B | 1 | 0.602 | 40.043 | -14.509 | 0.00 | 0.00 | 6 |
| O | PRO | B | 1 | 0.561 | 41.209 | -14.924 | 0.00 | 0.00 | 8 |
| N | VAL | B | 1 | -0.355 | 39.168 | -14.817 | 0.00 | 0.00 | 7 |
| CA | VAL | B | 1 | -1.521 | 39.561 | -15.592 | 0.00 | 0.00 | 6 |
| CB | VAL | B | 1 | -1.781 | 38.692 | -16.836 | 0.00 | 0.00 | 6 |
| C | VAL | B | 1 | -0.708 | 38.926 | -17.890 | 0.00 | 0.00 | 6 |
| C | VAL | B | 1 | -1.882 | 37.219 | -16.477 | 0.00 | 0.00 | 6 |
| C | VAL | B | 1 | -2.799 | 39.600 | -14.761 | 0.00 | 0.00 | 6 |
| O | VAL | B | 1 | -3.883 | 39.725 | -15.340 | 0.00 | 0.00 | 8 |
| N | GLY | B | 1 | -2.703 | 39.502 | -13.440 | 0.00 | 0.00 | 7 |
| CA | GLY | B | 1 | -3.904 | 39.542 | -12.612 | 0.00 | 0.00 | 6 |
| C | GLY | B | 1 | -3.619 | 39.258 | -11.146 | 0.00 | 0.00 | 6 |
| O | GLY | B | 1 | -2.708 | 38.499 | -10.817 | 0.00 | 0.00 | 8 |
| N | ASN | B | 1 | -4.419 | 39.856 | -10.269 | 0.00 | 0.00 | 7 |
| CA | ASN | B | 1 | -4.271 | 39.693 | -8.833 | 0.00 | 0.00 | 6 |
| CB | ASN | B | 1 | -4.557 | 41.013 | -8.113 | 0.00 | 0.00 | 6 |
| C | ASN | B | 1 | -3.346 | 41.910 | -7.977 | 0.00 | 0.00 | 6 |
| O | ASN | B | 1 | -2.706 | 42.284 | -8.961 | 0.00 | 0.00 | 8 |
| N | ASN | B | 1 | -3.014 | 42.291 | -6.748 | 0.00 | 0.00 | 7 |
| C | ASN | B | 1 | -5.170 | 38.603 | -8.269 | 0.00 | 0.00 | 6 |
| O | ASN | B | 1 | -5.198 | 38.386 | -7.058 | 0.00 | 0.00 | 8 |
| N | THR | B | 1 | -5.984 | 37.976 | -9.104 | 0.00 | 0.00 | 7 |
| CA | THR | B | 1 | -6.834 | 36.866 | -8.721 | 0.00 | 0.00 | 6 |
| CB | THR | B | 1 | -8.337 | 37.195 | -8.653 | 0.00 | 0.00 | 6 |
| O | THR | B | 1 | -8.753 | 37.727 | -9.920 | 0.00 | 0.00 | 8 |
| C | THR | B | 1 | -8.673 | 38.174 | -7.548 | 0.00 | 0.00 | 6 |
| C | THR | B | 1 | -6.685 | 35.733 | -9.743 | 0.00 | 0.00 | 6 |
| O | THR | B | 1 | -6.175 | 35.946 | -10.840 | 0.00 | 0.00 | 8 |
| N | VAL | B | 2 | -7.245 | 34.576 | -9.417 | 0.00 | 0.00 | 7 |
| CA | VAL | B | 2 | -7.206 | 33.430 | -10.309 | 0.00 | 0.00 | 6 |
| CB | VAL | B | 2 | -7.775 | 32.172 | -9.621 | 0.00 | 0.00 | 6 |
| C | VAL | B | 2 | -7.815 | 30.979 | -10.564 | 0.00 | 0.00 | 6 |
| C | VAL | B | 2 | -6.945 | 31.826 | -8.392 | 0.00 | 0.00 | 6 |
| C | VAL | B | 2 | -7.959 | 33.676 | -11.609 | 0.00 | 0.00 | 6 |
| O | VAL | B | 2 | -7.390 | 33.528 | -12.694 | 0.00 | 0.00 | 8 |
| N | GLU | B | 2 | -9.235 | 34.032 | -11.517 | 0.00 | 0.00 | 7 |
| CA | GLU | B | 2 | -10.064 | 34.260 | -12.692 | 0.00 | 0.00 | 6 |
| CB | GLU | B | 2 | -11.531 | 34.440 | -12.281 | 0.00 | 0.00 | 6 |
| C | GLU | B | 2 | -12.137 | 33.233 | -11.590 | 0.00 | 0.00 | 6 |
| C | GLU | B | 2 | -12.288 | 32.006 | -12.464 | 0.00 | 0.00 | 6 |
| O | GLU | B | 2 | -12.184 | 32.123 | -13.703 | 0.00 | 0.00 | 8 |
| O | GLU | B | 2 | -12.522 | 30.903 | -11.919 | 0.00 | 0.00 | 8 |
| C | GLU | B | 2 | -9.599 | 35.406 | -13.571 | 0.00 | 0.00 | 6 |
| O | GLU | B | 2 | -9.489 | 35.218 | -14.789 | 0.00 | 0.00 | 8 |
| N | SER | B | 2 | -9.214 | 36.545 | -13.005 | 0.00 | 0.00 | 7 |
| CA | SER | B | 2 | -8.706 | 37.658 | -13.805 | 0.00 | 0.00 | 6 |
| CB | SER | B | 2 | -8.514 | 38.913 | -12.967 | 0.00 | 0.00 | 6 |
| O | SER | B | 2 | -7.593 | 38.724 | -11.911 | 0.00 | 0.00 | 8 |
| C | SER | B | 2 | -7.429 | 37.252 | -14.529 | 0.00 | 0.00 | 6 |
| O | SER | B | 2 | -7.234 | 37.591 | -15.698 | 0.00 | 0.00 | 8 |
| N | THR | B | 2 | -6.555 | 36.509 | -13.854 | 0.00 | 0.00 | 7 |
| CA | THR | B | 2 | -5.319 | 36.021 | -14.459 | 0.00 | 0.00 | 6 |
| CB | THR | B | 2 | -4.442 | 35.270 | -13.444 | 0.00 | 0.00 | 6 |
| O | THR | B | 2 | -3.761 | 36.220 | -12.614 | 0.00 | 0.00 | 8 |

Figure 1 - 25

| | | | | | | | | |
|---|---|---|---|---|---|---|---|---|
| C | THR | B | 2 | -3.400 | 34.381 | -14.101 | 0.00 | 0.00 | 6 |
| C | THR | B | 2 | -5.685 | 35.070 | -15.601 | 0.00 | 0.00 | 6 |
| O | THR | B | 2 | -5.100 | 35.126 | -16.681 | 0.00 | 0.00 | 8 |
| N | TRP | B | 2 | -6.625 | 34.166 | -15.337 | 0.00 | 0.00 | 7 |
| CA | TRP | B | 2 | -7.069 | 33.187 | -16.324 | 0.00 | 0.00 | 6 |
| CB | TRP | B | 2 | -8.124 | 32.257 | -15.721 | 0.00 | 0.00 | 6 |
| C | TRP | B | 2 | -8.554 | 31.131 | -16.610 | 0.00 | 0.00 | 6 |
| C | TRP | B | 2 | -7.715 | 30.225 | -17.335 | 0.00 | 0.00 | 6 |
| CE | TRP | B | 2 | -8.556 | 29.338 | -18.035 | 0.00 | 0.00 | 6 |
| CE | TRP | B | 2 | -6.330 | 30.079 | -17.462 | 0.00 | 0.00 | 6 |
| C | TRP | B | 2 | -9.839 | 30.763 | -16.892 | 0.00 | 0.00 | 6 |
| N | TRP | B | 2 | -9.849 | 29.686 | -17.746 | 0.00 | 0.00 | 7 |
| CZ | TRP | B | 2 | -8.062 | 28.322 | -18.849 | 0.00 | 0.00 | 6 |
| CZ | TRP | B | 2 | -5.840 | 29.069 | -18.269 | 0.00 | 0.00 | 6 |
| C | TRP | B | 2 | -6.704 | 28.201 | -18.952 | 0.00 | 0.00 | 6 |
| C | TRP | B | 2 | -7.583 | 33.858 | -17.592 | 0.00 | 0.00 | 6 |
| O | TRP | B | 2 | -7.160 | 33.508 | -18.694 | 0.00 | 0.00 | 8 |
| N | LYS | B | 2 | -8.470 | 34.834 | -17.456 | 0.00 | 0.00 | 7 |
| CA | LYS | B | 2 | -9.042 | 35.564 | -18.576 | 0.00 | 0.00 | 6 |
| CB | LYS | B | 2 | -10.109 | 36.555 | -18.097 | 0.00 | 0.00 | 6 |
| C | LYS | B | 2 | -11.283 | 35.913 | -17.377 | 0.00 | 0.00 | 6 |
| C | LYS | B | 2 | -12.370 | 36.937 | -17.083 | 0.00 | 0.00 | 6 |
| CE | LYS | B | 2 | -13.606 | 36.274 | -16.497 | 0.00 | 0.00 | 6 |
| NZ | LYS | B | 2 | -14.851 | 36.738 | -17.170 | 0.00 | 0.00 | 7 |
| C | LYS | B | 2 | -8.001 | 36.320 | -19.393 | 0.00 | 0.00 | 6 |
| O | LYS | B | 2 | -8.069 | 36.331 | -20.626 | 0.00 | 0.00 | 8 |
| N | ALA | B | 2 | -7.024 | 36.927 | -18.727 | 0.00 | 0.00 | 7 |
| CA | ALA | B | 2 | -5.956 | 37.637 | -19.422 | 0.00 | 0.00 | 6 |
| CB | ALA | B | 2 | -5.089 | 38.401 | -18.433 | 0.00 | 0.00 | 6 |
| C | ALA | B | 2 | -5.117 | 36.686 | -20.267 | 0.00 | 0.00 | 6 |
| O | ALA | B | 2 | -4.735 | 37.036 | -21.390 | 0.00 | 0.00 | 8 |
| N | LEU | B | 2 | -4.852 | 35.485 | -19.765 | 0.00 | 0.00 | 7 |
| CA | LEU | B | 2 | -4.074 | 34.491 | -20.487 | 0.00 | 0.00 | 6 |
| CB | LEU | B | 2 | -3.722 | 33.310 | -19.585 | 0.00 | 0.00 | 6 |
| C | LEU | B | 2 | -2.629 | 33.472 | -18.534 | 0.00 | 0.00 | 6 |
| C | LEU | B | 2 | -2.164 | 32.095 | -18.065 | 0.00 | 0.00 | 6 |
| C | LEU | B | 2 | -1.441 | 34.278 | -19.038 | 0.00 | 0.00 | 6 |
| C | LEU | B | 2 | -4.782 | 33.983 | -21.736 | 0.00 | 0.00 | 6 |
| O | LEU | B | 2 | -4.157 | 33.830 | -22.788 | 0.00 | 0.00 | 8 |
| N | LEU | B | 2 | -6.090 | 33.756 | -21.655 | 0.00 | 0.00 | 7 |
| CA | LEU | B | 2 | -6.862 | 33.296 | -22.804 | 0.00 | 0.00 | 6 |
| CB | LEU | B | 2 | -8.251 | 32.826 | -22.371 | 0.00 | 0.00 | 6 |
| C | LEU | B | 2 | -8.328 | 31.592 | -21.467 | 0.00 | 0.00 | 6 |
| C | LEU | B | 2 | -9.775 | 31.260 | -21.133 | 0.00 | 0.00 | 6 |
| C | LEU | B | 2 | -7.647 | 30.388 | -22.099 | 0.00 | 0.00 | 6 |
| C | LEU | B | 2 | -6.965 | 34.357 | -23.891 | 0.00 | 0.00 | 6 |
| O | LEU | B | 2 | -6.998 | 34.023 | -25.078 | 0.00 | 0.00 | 8 |
| N | ALA | B | 2 | -6.884 | 35.636 | -23.540 | 0.00 | 0.00 | 7 |
| CA | ALA | B | 2 | -6.886 | 36.733 | -24.490 | 0.00 | 0.00 | 6 |
| CB | ALA | B | 2 | -7.539 | 37.965 | -23.870 | 0.00 | 0.00 | 6 |
| C | ALA | B | 2 | -5.491 | 37.096 | -24.980 | 0.00 | 0.00 | 6 |
| O | ALA | B | 2 | -5.332 | 38.055 | -25.741 | 0.00 | 0.00 | 8 |
| N | GLY | B | 3 | -4.463 | 36.382 | -24.544 | 0.00 | 0.00 | 7 |
| CA | GLY | B | 3 | -3.096 | 36.619 | -24.953 | 0.00 | 0.00 | 6 |
| C | GLY | B | 3 | -2.487 | 37.912 | -24.446 | 0.00 | 0.00 | 6 |
| O | GLY | B | 3 | -1.571 | 38.445 | -25.078 | 0.00 | 0.00 | 8 |
| N | GLN | B | 3 | -2.918 | 38.388 | -23.283 | 0.00 | 0.00 | 7 |
| CA | GLN | B | 3 | -2.359 | 39.598 | -22.699 | 0.00 | 0.00 | 6 |
| CB | GLN | B | 3 | -3.312 | 40.181 | -21.654 | 0.00 | 0.00 | 6 |
| C | GLN | B | 3 | -4.566 | 40.798 | -22.243 | 0.00 | 0.00 | 6 |
| C | GLN | B | 3 | -5.525 | 41.358 | -21.215 | 0.00 | 0.00 | 6 |
| O | GLN | B | 3 | -5.143 | 41.723 | -20.103 | 0.00 | 0.00 | 8 |
| N | GLN | B | 3 | -6.801 | 41.435 | -21.588 | 0.00 | 0.00 | 7 |
| C | GLN | B | 3 | -0.990 | 39.329 | -22.078 | 0.00 | 0.00 | 6 |
| O | GLN | B | 3 | -0.765 | 38.310 | -21.429 | 0.00 | 0.00 | 8 |
| N | SER | B | 3 | -0.062 | 40.251 | -22.307 | 0.00 | 0.00 | 7 |
| CA | SER | B | 3 | 1.278 | 40.169 | -21.739 | 0.00 | 0.00 | 6 |
| CB | SER | B | 3 | 2.294 | 40.807 | -22.679 | 0.00 | 0.00 | 6 |
| O | SER | B | 3 | 3.597 | 40.331 | -22.140 | 0.00 | 0.00 | 8 |
| C | SER | B | 3 | 1.274 | 40.874 | -20.336 | 0.00 | 0.00 | 6 |
| O | SER | B | 3 | 0.493 | 41.811 | -20.191 | 0.00 | 0.00 | 8 |
| N | GLY | B | 3 | 2.110 | 40.424 | -19.459 | 0.00 | 0.00 | 7 |
| CA | GLY | B | 3 | 2.170 | 41.044 | -18.135 | 0.00 | 0.00 | 6 |
| C | GLY | B | 3 | 3.536 | 41.687 | -17.921 | 0.00 | 0.00 | 6 |
| O | GLY | B | 3 | 3.897 | 42.130 | -16.835 | 0.00 | 0.00 | 8 |
| N | ILE | B | 3 | 4.303 | 41.749 | -19.000 | 0.00 | 0.00 | 7 |
| CA | ILE | B | 3 | 5.671 | 42.238 | -18.997 | 0.00 | 0.00 | 6 |
| CB | ILE | B | 3 | 6.473 | 41.482 | -20.089 | 0.00 | 0.00 | 6 |
| C | ILE | B | 3 | 7.954 | 41.783 | -19.950 | 0.00 | 0.00 | 6 |
| C | ILE | B | 3 | 6.125 | 40.003 | -19.990 | 0.00 | 0.00 | 6 |
| C | ILE | B | 3 | 7.148 | 38.944 | -20.253 | 0.00 | 0.00 | 6 |
| C | ILE | B | 3 | 5.778 | 43.741 | -19.184 | 0.00 | 0.00 | 6 |
| O | ILE | B | 3 | 5.345 | 44.318 | -20.180 | 0.00 | 0.00 | 8 |
| N | SER | B | 3 | 6.393 | 44.396 | -18.204 | 0.00 | 0.00 | 7 |
| CA | SER | B | 3 | 6.552 | 45.837 | -18.154 | 0.00 | 0.00 | 6 |
| CB | SER | B | 3 | 5.698 | 46.401 | -17.008 | 0.00 | 0.00 | 6 |
| O | SER | B | 3 | 4.422 | 46.810 | -17.454 | 0.00 | 0.00 | 8 |
| C | SER | B | 3 | 7.998 | 46.253 | -17.896 | 0.00 | 0.00 | 6 |
| O | SER | B | 3 | 8.837 | 45.419 | -17.558 | 0.00 | 0.00 | 8 |
| N | LEU | B | 3 | 8.270 | 47.548 | -18.011 | 0.00 | 0.00 | 7 |
| CA | LEU | B | 3 | 9.597 | 48.088 | -17.731 | 0.00 | 0.00 | 6 |
| CB | LEU | B | 3 | 9.788 | 49.454 | -18.383 | 0.00 | 0.00 | 6 |
| C | LEU | B | 3 | 10.093 | 49.512 | -19.878 | 0.00 | 0.00 | 6 |
| C | LEU | B | 3 | 10.049 | 50.952 | -20.370 | 0.00 | 0.00 | 6 |
| C | LEU | B | 3 | 11.445 | 48.888 | -20.193 | 0.00 | 0.00 | 6 |
| C | LEU | B | 3 | 9.778 | 48.224 | -16.219 | 0.00 | 0.00 | 6 |
| O | LEU | B | 3 | 8.828 | 48.607 | -15.534 | 0.00 | 0.00 | 8 |
| N | ILE | B | 3 | 10.960 | 47.910 | -15.704 | 0.00 | 0.00 | 7 |
| CA | ILE | B | 3 | 11.197 | 48.024 | -14.264 | 0.00 | 0.00 | 6 |
| CB | ILE | B | 3 | 12.471 | 47.285 | -13.832 | 0.00 | 0.00 | 6 |
| C | ILE | B | 3 | 12.855 | 47.610 | -12.395 | 0.00 | 0.00 | 6 |
| C | ILE | B | 3 | 12.293 | 45.770 | -13.991 | 0.00 | 0.00 | 6 |
| C | ILE | B | 3 | 13.596 | 45.010 | -14.122 | 0.00 | 0.00 | 6 |
| C | ILE | B | 3 | 11.289 | 49.497 | -13.874 | 0.00 | 0.00 | 6 |
| O | ILE | B | 3 | 11.972 | 50.271 | -14.546 | 0.00 | 0.00 | 8 |
| N | ASP | B | 3 | 10.643 | 49.871 | -12.772 | 0.00 | 0.00 | 7 |
| CA | ASP | B | 3 | 10.675 | 51.259 | -12.331 | 0.00 | 0.00 | 6 |
| CB | ASP | B | 3 | 9.336 | 51.943 | -12.629 | 0.00 | 0.00 | 6 |
| C | ASP | B | 3 | 8.143 | 51.205 | -12.064 | 0.00 | 0.00 | 6 |
| O | ASP | B | 3 | 7.473 | 51.744 | -11.160 | 0.00 | 0.00 | 8 |
| O | ASP | B | 3 | 7.855 | 50.079 | -12.525 | 0.00 | 0.00 | 8 |
| C | ASP | B | 3 | 11.031 | 51.429 | -10.863 | 0.00 | 0.00 | 6 |
| O | ASP | B | 3 | 11.153 | 52.575 | -10.414 | 0.00 | 0.00 | 8 |
| N | HIS | B | 3 | 11.266 | 50.348 | -10.127 | 0.00 | 0.00 | 7 |
| CA | HIS | B | 3 | 11.539 | 50.473 | -8.696 | 0.00 | 0.00 | 6 |
| CB | HIS | B | 3 | 10.808 | 49.400 | -7.893 | 0.00 | 0.00 | 6 |
| C | HIS | B | 3 | 11.110 | 48.005 | -8.342 | 0.00 | 0.00 | 6 |
| C | HIS | B | 3 | 10.636 | 47.274 | -9.377 | 0.00 | 0.00 | 6 |
| N | HIS | B | 3 | 12.022 | 47.210 | -7.684 | 0.00 | 0.00 | 7 |
| CE | HIS | B | 3 | 12.091 | 46.042 | -8.295 | 0.00 | 0.00 | 6 |
| N | HIS | B | 3 | 11.264 | 46.052 | -9.324 | 0.00 | 0.00 | 7 |
| C | HIS | B | 3 | 13.020 | 50.517 | -8.359 | 0.00 | 0.00 | 6 |
| O | HIS | B | 3 | 13.389 | 50.654 | -7.190 | 0.00 | 0.00 | 8 |
| N | PHE | B | 3 | 13.883 | 50.454 | -9.362 | 0.00 | 0.00 | 7 |
| CA | PHE | B | 4 | 15.318 | 50.638 | -9.192 | 0.00 | 0.00 | 6 |
| CB | PHE | B | 4 | 16.061 | 49.447 | -8.633 | 0.00 | 0.00 | 6 |
| C | PHE | B | 4 | 16.131 | 48.199 | -9.458 | 0.00 | 0.00 | 6 |
| C | PHE | B | 4 | 15.223 | 47.174 | -9.253 | 0.00 | 0.00 | 6 |

| | | | | | | | | |
|---|---|---|---|---|---|---|---|---|
| C | PHE | B | 4 | 17.120 | 48.028 | -10.416 | 0.00 | 0.00 | 6 |
| CE | PHE | B | 4 | 15.281 | 46.015 | -10.000 | 0.00 | 0.00 | 6 |
| CE | PHE | B | 4 | 17.184 | 46.867 | -11.163 | 0.00 | 0.00 | 6 |
| CZ | PHE | B | 4 | 16.264 | 45.859 | -10.957 | 0.00 | 0.00 | 6 |
| C | PHE | B | 4 | 15.393 | 51.121 | -10.527 | 0.00 | 0.00 | 6 |
| O | PHE | B | 4 | 15.265 | 50.943 | -11.571 | 0.00 | 0.00 | 8 |
| N | ASP | B | 4 | 17.003 | 51.846 | -10.472 | 0.00 | 0.00 | 7 |
| CA | ASP | B | 4 | 17.611 | 52.372 | -11.690 | 0.00 | 0.00 | 6 |
| CB | ASP | B | 4 | 18.687 | 53.406 | -11.349 | 0.00 | 0.00 | 6 |
| C | ASP | B | 4 | 18.923 | 54.376 | -12.491 | 0.00 | 0.00 | 6 |
| O | ASP | B | 4 | 17.932 | 54.804 | -13.121 | 0.00 | 0.00 | 8 |
| O | ASP | B | 4 | 20.095 | 54.711 | -12.759 | 0.00 | 0.00 | 8 |
| C | ASP | B | 4 | 18.201 | 51.255 | -12.541 | 0.00 | 0.00 | 6 |
| O | ASP | B | 4 | 19.158 | 50.593 | -12.140 | 0.00 | 0.00 | 8 |
| N | THR | B | 4 | 17.644 | 51.053 | -13.732 | 0.00 | 0.00 | 7 |
| CA | THR | B | 4 | 18.114 | 50.015 | -14.639 | 0.00 | 0.00 | 6 |
| CB | THR | B | 4 | 16.921 | 49.251 | -15.254 | 0.00 | 0.00 | 6 |
| O | THR | B | 4 | 16.088 | 50.174 | -15.962 | 0.00 | 0.00 | 8 |
| C | THR | B | 4 | 16.100 | 48.566 | -14.175 | 0.00 | 0.00 | 6 |
| C | THR | B | 4 | 19.000 | 50.539 | -15.760 | 0.00 | 0.00 | 6 |
| O | THR | B | 4 | 19.202 | 49.864 | -16.774 | 0.00 | 0.00 | 8 |
| N | SER | B | 4 | 19.645 | 51.679 | -15.568 | 0.00 | 0.00 | 7 |
| CA | SER | B | 4 | 20.508 | 52.311 | -16.548 | 0.00 | 0.00 | 6 |
| CB | SER | B | 4 | 21.084 | 53.616 | -15.972 | 0.00 | 0.00 | 6 |
| O | SER | B | 4 | 20.143 | 54.668 | -16.102 | 0.00 | 0.00 | 8 |
| C | SER | B | 4 | 21.666 | 51.451 | -17.029 | 0.00 | 0.00 | 6 |
| O | SER | B | 4 | 21.952 | 51.395 | -18.226 | 0.00 | 0.00 | 8 |
| N | ALA | B | 4 | 22.351 | 50.775 | -16.116 | 0.00 | 0.00 | 7 |
| CA | ALA | B | 4 | 23.483 | 49.923 | -16.440 | 0.00 | 0.00 | 6 |
| CB | ALA | B | 4 | 24.439 | 49.900 | -15.247 | 0.00 | 0.00 | 6 |
| C | ALA | B | 4 | 23.094 | 48.490 | -16.774 | 0.00 | 0.00 | 6 |
| O | ALA | B | 4 | 23.937 | 47.679 | -17.164 | 0.00 | 0.00 | 8 |
| N | TYR | B | 4 | 21.823 | 48.159 | -16.611 | 0.00 | 0.00 | 7 |
| CA | TYR | B | 4 | 21.336 | 46.806 | -16.810 | 0.00 | 0.00 | 6 |
| CB | TYR | B | 4 | 20.088 | 46.602 | -15.938 | 0.00 | 0.00 | 6 |
| C | TYR | B | 4 | 20.413 | 46.522 | -14.460 | 0.00 | 0.00 | 6 |
| C | TYR | B | 4 | 20.745 | 47.655 | -13.731 | 0.00 | 0.00 | 6 |
| CE | TYR | B | 4 | 21.048 | 47.578 | -12.383 | 0.00 | 0.00 | 6 |
| C | TYR | B | 4 | 20.391 | 45.303 | -13.795 | 0.00 | 0.00 | 6 |
| CE | TYR | B | 4 | 20.690 | 45.216 | -12.449 | 0.00 | 0.00 | 6 |
| CZ | TYR | B | 4 | 21.014 | 46.355 | -11.747 | 0.00 | 0.00 | 6 |
| O | TYR | B | 4 | 21.313 | 46.273 | -10.407 | 0.00 | 0.00 | 8 |
| C | TYR | B | 4 | 21.059 | 46.459 | -18.261 | 0.00 | 0.00 | 6 |
| O | TYR | B | 4 | 20.554 | 47.253 | -19.049 | 0.00 | 0.00 | 8 |
| N | ALA | B | 4 | 21.370 | 45.209 | -18.607 | 0.00 | 0.00 | 7 |
| CA | ALA | B | 4 | 21.142 | 44.684 | -19.946 | 0.00 | 0.00 | 6 |
| CB | ALA | B | 4 | 22.005 | 43.456 | -20.186 | 0.00 | 0.00 | 6 |
| C | ALA | B | 4 | 19.666 | 44.352 | -20.146 | 0.00 | 0.00 | 6 |
| O | ALA | B | 4 | 19.154 | 44.407 | -21.263 | 0.00 | 0.00 | 8 |
| N | THR | B | 4 | 18.993 | 43.971 | -19.067 | 0.00 | 0.00 | 7 |
| CA | THR | B | 4 | 17.560 | 43.695 | -19.106 | 0.00 | 0.00 | 6 |
| CB | THR | B | 4 | 17.216 | 42.255 | -18.717 | 0.00 | 0.00 | 6 |
| O | THR | B | 4 | 17.923 | 41.358 | -19.587 | 0.00 | 0.00 | 8 |
| C | THR | B | 4 | 15.719 | 42.013 | -18.850 | 0.00 | 0.00 | 6 |
| C | THR | B | 4 | 16.868 | 44.707 | -18.197 | 0.00 | 0.00 | 6 |
| O | THR | B | 4 | 17.208 | 44.856 | -17.024 | 0.00 | 0.00 | 8 |
| N | LYS | B | 4 | 15.919 | 45.441 | -18.768 | 0.00 | 0.00 | 7 |
| CA | LYS | B | 4 | 15.215 | 46.491 | -18.050 | 0.00 | 0.00 | 6 |
| CB | LYS | B | 4 | 15.389 | 47.815 | -18.819 | 0.00 | 0.00 | 6 |
| C | LYS | B | 4 | 16.831 | 48.251 | -19.005 | 0.00 | 0.00 | 6 |
| C | LYS | B | 4 | 17.050 | 48.954 | -20.333 | 0.00 | 0.00 | 6 |
| CE | LYS | B | 4 | 18.371 | 49.707 | -20.339 | 0.00 | 0.00 | 6 |
| NZ | LYS | B | 4 | 19.484 | 48.873 | -20.865 | 0.00 | 0.00 | 7 |
| C | LYS | B | 4 | 13.734 | 46.220 | -17.861 | 0.00 | 0.00 | 6 |
| O | LYS | B | 4 | 13.002 | 47.106 | -17.414 | 0.00 | 0.00 | 8 |
| N | PHE | B | 4 | 13.301 | 45.009 | -18.189 | 0.00 | 0.00 | 7 |
| CA | PHE | B | 4 | 11.887 | 44.672 | -18.067 | 0.00 | 0.00 | 6 |
| CB | PHE | B | 4 | 11.267 | 44.557 | -19.465 | 0.00 | 0.00 | 6 |
| C | PHE | B | 4 | 11.965 | 43.566 | -20.352 | 0.00 | 0.00 | 6 |
| C | PHE | B | 4 | 11.550 | 42.247 | -20.404 | 0.00 | 0.00 | 6 |
| C | PHE | B | 4 | 13.041 | 43.957 | -21.135 | 0.00 | 0.00 | 6 |
| CE | PHE | B | 4 | 12.192 | 41.332 | -21.220 | 0.00 | 0.00 | 6 |
| CE | PHE | B | 4 | 13.689 | 43.046 | -21.946 | 0.00 | 0.00 | 6 |
| CZ | PHE | B | 4 | 13.260 | 41.735 | -21.996 | 0.00 | 0.00 | 6 |
| C | PHE | B | 4 | 11.666 | 43.382 | -17.292 | 0.00 | 0.00 | 6 |
| O | PHE | B | 4 | 12.576 | 42.577 | -17.108 | 0.00 | 0.00 | 8 |
| N | ALA | B | 5 | 10.424 | 43.181 | -16.864 | 0.00 | 0.00 | 7 |
| CA | ALA | B | 5 | 10.032 | 41.986 | -16.135 | 0.00 | 0.00 | 6 |
| CB | ALA | B | 5 | 10.666 | 41.977 | -14.749 | 0.00 | 0.00 | 6 |
| C | ALA | B | 5 | 8.513 | 41.888 | -16.010 | 0.00 | 0.00 | 6 |
| O | ALA | B | 5 | 7.772 | 42.820 | -16.314 | 0.00 | 0.00 | 8 |
| N | GLY | B | 5 | 8.060 | 40.724 | -15.560 | 0.00 | 0.00 | 7 |
| CA | GLY | B | 5 | 6.631 | 40.512 | -15.301 | 0.00 | 0.00 | 6 |
| C | GLY | B | 5 | 6.446 | 40.886 | -13.820 | 0.00 | 0.00 | 6 |
| O | GLY | B | 5 | 6.858 | 40.138 | -12.933 | 0.00 | 0.00 | 8 |
| N | LEU | B | 5 | 5.924 | 42.082 | -13.579 | 0.00 | 0.00 | 7 |
| CA | LEU | B | 5 | 5.763 | 42.560 | -12.212 | 0.00 | 0.00 | 6 |
| CB | LEU | B | 5 | 6.262 | 44.005 | -12.103 | 0.00 | 0.00 | 6 |
| C | LEU | B | 5 | 7.754 | 44.212 | -12.389 | 0.00 | 0.00 | 6 |
| C | LEU | B | 5 | 8.010 | 45.627 | -12.886 | 0.00 | 0.00 | 6 |
| C | LEU | B | 5 | 8.586 | 43.905 | -11.153 | 0.00 | 0.00 | 6 |
| C | LEU | B | 5 | 4.322 | 42.452 | -11.736 | 0.00 | 0.00 | 6 |
| O | LEU | B | 5 | 3.391 | 42.541 | -12.533 | 0.00 | 0.00 | 8 |
| N | VAL | B | 5 | 4.155 | 42.220 | -10.437 | 0.00 | 0.00 | 7 |
| CA | VAL | B | 5 | 2.802 | 42.166 | -9.866 | 0.00 | 0.00 | 6 |
| CB | VAL | B | 5 | 2.748 | 41.398 | -8.547 | 0.00 | 0.00 | 6 |
| C | VAL | B | 5 | 1.428 | 41.596 | -7.817 | 0.00 | 0.00 | 6 |
| C | VAL | B | 5 | 2.966 | 39.909 | -8.810 | 0.00 | 0.00 | 6 |
| C | VAL | B | 5 | 2.356 | 43.620 | -9.731 | 0.00 | 0.00 | 6 |
| O | VAL | B | 5 | 3.072 | 44.437 | -9.153 | 0.00 | 0.00 | 8 |
| N | LYS | B | 5 | 1.232 | 43.952 | -10.349 | 0.00 | 0.00 | 7 |
| CA | LYS | B | 5 | 0.753 | 45.325 | -10.391 | 0.00 | 0.00 | 6 |
| CB | LYS | B | 5 | 0.339 | 45.647 | -11.840 | 0.00 | 0.00 | 6 |
| C | LYS | B | 5 | 1.523 | 45.696 | -12.794 | 0.00 | 0.00 | 6 |
| C | LYS | B | 5 | 1.113 | 45.408 | -14.228 | 0.00 | 0.00 | 6 |
| CE | LYS | B | 5 | 1.623 | 44.063 | -14.705 | 0.00 | 0.00 | 6 |
| NZ | LYS | B | 5 | 3.062 | 44.089 | -15.081 | 0.00 | 0.00 | 7 |
| C | LYS | B | 5 | -0.391 | 45.635 | -9.444 | 0.00 | 0.00 | 6 |
| O | LYS | B | 5 | -1.385 | 44.920 | -9.337 | 0.00 | 0.00 | 8 |
| N | ASP | B | 5 | -0.285 | 46.789 | -8.783 | 0.00 | 0.00 | 7 |
| CA | ASP | B | 5 | -1.310 | 47.298 | -7.881 | 0.00 | 0.00 | 6 |
| CB | ASP | B | 5 | -2.588 | 47.593 | -8.678 | 0.00 | 0.00 | 6 |
| C | ASP | B | 5 | -2.359 | 48.623 | -9.771 | 0.00 | 0.00 | 6 |
| O | ASP | B | 5 | -1.815 | 49.702 | -9.459 | 0.00 | 0.00 | 8 |
| O | ASP | B | 5 | -2.682 | 48.318 | -10.940 | 0.00 | 0.00 | 8 |
| C | ASP | B | 5 | -1.600 | 46.349 | -6.727 | 0.00 | 0.00 | 6 |
| O | ASP | B | 5 | -2.750 | 46.016 | -6.428 | 0.00 | 0.00 | 8 |
| N | PHE | B | 5 | -0.549 | 45.928 | -6.037 | 0.00 | 0.00 | 7 |
| CA | PHE | B | 5 | -0.658 | 44.970 | -4.945 | 0.00 | 0.00 | 6 |
| CB | PHE | B | 5 | 0.677 | 44.225 | -4.825 | 0.00 | 0.00 | 6 |
| C | PHE | B | 5 | 0.791 | 43.249 | -3.696 | 0.00 | 0.00 | 6 |
| C | PHE | B | 5 | 0.037 | 42.088 | -3.672 | 0.00 | 0.00 | 6 |
| C | PHE | B | 5 | 1.674 | 43.489 | -2.653 | 0.00 | 0.00 | 6 |
| CE | PHE | B | 5 | 0.151 | 41.190 | -2.629 | 0.00 | 0.00 | 6 |
| CE | PHE | B | 5 | 1.792 | 42.594 | -1.607 | 0.00 | 0.00 | 6 |
| CZ | PHE | B | 5 | 1.029 | 41.443 | -1.595 | 0.00 | 0.00 | 6 |
| C | PHE | B | 5 | -1.074 | 45.599 | -3.627 | 0.00 | 0.00 | 6 |
| O | PHE | B | 5 | -0.444 | 46.521 | -3.115 | 0.00 | 0.00 | 8 |

Figure 1 - 27

| | | | | | | | | |
|---|---|---|---|---|---|---|---|---|
| N | ASN | B | 5 | -2.151 | 45.071 | -3.051 | 0.00 | 0.00 | 7 |
| CA | ASN | B | 5 | -2.663 | 45.532 | -1.769 | 0.00 | 0.00 | 6 |
| CB | ASN | B | 5 | -3.948 | 46.342 | -1.930 | 0.00 | 0.00 | 6 |
| C | ASN | B | 5 | -4.421 | 46.975 | -0.637 | 0.00 | 0.00 | 6 |
| O | ASN | B | 5 | -5.590 | 46.855 | -0.266 | 0.00 | 0.00 | 8 |
| N | ASN | B | 5 | -3.525 | 47.660 | 0.065 | 0.00 | 0.00 | 7 |
| C | ASN | B | 5 | -2.914 | 44.343 | -0.842 | 0.00 | 0.00 | 6 |
| O | ASN | B | 5 | -3.604 | 43.391 | -1.203 | 0.00 | 0.00 | 8 |
| N | CYS | B | 5 | -2.309 | 44.399 | 0.338 | 0.00 | 0.00 | 7 |
| CA | CYS | B | 5 | -2.467 | 43.334 | 1.322 | 0.00 | 0.00 | 6 |
| CB | CYS | B | 5 | -1.236 | 42.431 | 1.347 | 0.00 | 0.00 | 6 |
| SG | CYS | B | 5 | 0.252 | 43.226 | 1.997 | 0.00 | 0.00 | 1 |
| C | CYS | B | 5 | -2.728 | 43.929 | 2.699 | 0.00 | 0.00 | 6 |
| O | CYS | B | 5 | -2.729 | 43.232 | 3.709 | 0.00 | 0.00 | 8 |
| N | GLU | B | 5 | -3.065 | 45.214 | 2.722 | 0.00 | 0.00 | 7 |
| CA | GLU | B | 5 | -3.394 | 45.936 | 3.943 | 0.00 | 0.00 | 6 |
| CB | GLU | B | 5 | -3.775 | 47.378 | 3.604 | 0.00 | 0.00 | 6 |
| C | GLU | B | 5 | -3.621 | 48.366 | 4.743 | 0.00 | 0.00 | 6 |
| C | GLU | B | 5 | -2.414 | 49.271 | 4.612 | 0.00 | 0.00 | 6 |
| O | GLU | B | 5 | -2.406 | 50.339 | 5.266 | 0.00 | 0.00 | 8 |
| O | GLU | B | 5 | -1.469 | 48.932 | 3.872 | 0.00 | 0.00 | 8 |
| C | GLU | B | 5 | -4.520 | 45.260 | 4.717 | 0.00 | 0.00 | 6 |
| O | GLU | B | 5 | -4.445 | 45.096 | 5.936 | 0.00 | 0.00 | 8 |
| N | ASP | B | 6 | -5.547 | 44.799 | 4.013 | 0.00 | 0.00 | 7 |
| CA | ASP | B | 6 | -6.654 | 44.067 | 4.601 | 0.00 | 0.00 | 6 |
| CB | ASP | B | 6 | -7.786 | 43.855 | 3.599 | 0.00 | 0.00 | 6 |
| C | ASP | B | 6 | -7.406 | 43.958 | 2.141 | 0.00 | 0.00 | 6 |
| O | ASP | B | 6 | -7.476 | 42.929 | 1.431 | 0.00 | 0.00 | 8 |
| O | ASP | B | 6 | -7.060 | 45.066 | 1.677 | 0.00 | 0.00 | 8 |
| C | ASP | B | 6 | -6.217 | 42.726 | 5.186 | 0.00 | 0.00 | 6 |
| O | ASP | B | 6 | -6.727 | 42.320 | 6.232 | 0.00 | 0.00 | 8 |
| N | ILE | B | 6 | -5.292 | 42.034 | 4.531 | 0.00 | 0.00 | 7 |
| CA | ILE | B | 6 | -4.814 | 40.742 | 4.995 | 0.00 | 0.00 | 6 |
| CB | ILE | B | 6 | -4.325 | 39.863 | 3.824 | 0.00 | 0.00 | 6 |
| C | ILE | B | 6 | -4.200 | 38.412 | 4.270 | 0.00 | 0.00 | 6 |
| C | ILE | B | 6 | -5.229 | 39.984 | 2.600 | 0.00 | 0.00 | 6 |
| C | ILE | B | 6 | -6.659 | 39.533 | 2.774 | 0.00 | 0.00 | 6 |
| C | ILE | B | 6 | -3.692 | 40.849 | 6.020 | 0.00 | 0.00 | 6 |
| O | ILE | B | 6 | -3.679 | 40.118 | 7.013 | 0.00 | 0.00 | 8 |
| N | ILE | B | 6 | -2.663 | 41.635 | 5.720 | 0.00 | 0.00 | 7 |
| CA | ILE | B | 6 | -1.509 | 41.805 | 6.587 | 0.00 | 0.00 | 6 |
| CB | ILE | B | 6 | -0.185 | 41.329 | 5.963 | 0.00 | 0.00 | 6 |
| C | ILE | B | 6 | 0.946 | 41.398 | 6.985 | 0.00 | 0.00 | 6 |
| C | ILE | B | 6 | -0.271 | 39.907 | 5.404 | 0.00 | 0.00 | 6 |
| C | ILE | B | 6 | 0.146 | 39.804 | 3.952 | 0.00 | 0.00 | 6 |
| C | ILE | B | 6 | -1.340 | 43.279 | 6.962 | 0.00 | 0.00 | 6 |
| O | ILE | B | 6 | -1.307 | 44.147 | 6.089 | 0.00 | 0.00 | 8 |
| N | SER | B | 6 | -1.176 | 43.542 | 8.254 | 0.00 | 0.00 | 7 |
| CA | SER | B | 6 | -1.027 | 44.913 | 8.732 | 0.00 | 0.00 | 6 |
| CB | SER | B | 6 | -1.109 | 44.966 | 10.258 | 0.00 | 0.00 | 6 |
| O | SER | B | 6 | -0.358 | 43.920 | 10.849 | 0.00 | 0.00 | 8 |
| C | SER | B | 6 | 0.284 | 45.527 | 8.261 | 0.00 | 0.00 | 6 |
| O | SER | B | 6 | 1.217 | 44.815 | 7.890 | 0.00 | 0.00 | 8 |
| N | ARG | B | 6 | 0.375 | 46.853 | 8.340 | 0.00 | 0.00 | 7 |
| CA | ARG | B | 6 | 1.598 | 47.562 | 7.975 | 0.00 | 0.00 | 6 |
| CB | ARG | B | 6 | 1.389 | 49.065 | 7.862 | 0.00 | 0.00 | 6 |
| C | ARG | B | 6 | 0.040 | 49.498 | 7.312 | 0.00 | 0.00 | 6 |
| C | ARG | B | 6 | -0.702 | 50.361 | 8.322 | 0.00 | 0.00 | 6 |
| N | ARG | B | 6 | -2.149 | 50.225 | 8.210 | 0.00 | 0.00 | 7 |
| CZ | ARG | B | 6 | -3.011 | 51.232 | 8.289 | 0.00 | 0.00 | 6 |
| N | ARG | B | 6 | -2.585 | 52.474 | 8.481 | 0.00 | 0.00 | 7 |
| N | ARG | B | 6 | -4.313 | 51.003 | 8.173 | 0.00 | 0.00 | 7 |
| C | ARG | B | 6 | 2.688 | 47.252 | 9.003 | 0.00 | 0.00 | 6 |
| O | ARG | B | 6 | 3.867 | 47.164 | 8.665 | 0.00 | 0.00 | 8 |
| N | LYS | B | 6 | 2.286 | 47.070 | 10.259 | 0.00 | 0.00 | 7 |
| CA | LYS | B | 6 | 3.206 | 46.697 | 11.323 | 0.00 | 0.00 | 6 |
| CB | LYS | B | 6 | 2.497 | 46.565 | 12.667 | 0.00 | 0.00 | 6 |
| C | LYS | B | 6 | 1.922 | 47.814 | 13.247 | 0.00 | 0.00 | 6 |
| C | LYS | B | 6 | 0.962 | 47.542 | 14.390 | 0.00 | 0.00 | 6 |
| CE | LYS | B | 6 | -0.211 | 48.508 | 14.405 | 0.00 | 0.00 | 6 |
| NZ | LYS | B | 6 | -1.501 | 47.832 | 14.094 | 0.00 | 0.00 | 7 |
| C | LYS | B | 6 | 3.836 | 45.348 | 10.959 | 0.00 | 0.00 | 6 |
| O | LYS | B | 6 | 5.053 | 45.206 | 10.893 | 0.00 | 0.00 | 8 |
| N | GLU | B | 6 | 2.985 | 44.370 | 10.663 | 0.00 | 0.00 | 7 |
| CA | GLU | B | 6 | 3.403 | 43.026 | 10.303 | 0.00 | 0.00 | 6 |
| CB | GLU | B | 6 | 2.191 | 42.084 | 10.348 | 0.00 | 0.00 | 6 |
| C | GLU | B | 6 | 1.842 | 41.634 | 11.759 | 0.00 | 0.00 | 6 |
| C | GLU | B | 6 | 2.805 | 40.594 | 12.296 | 0.00 | 0.00 | 6 |
| O | GLU | B | 6 | 3.270 | 40.746 | 13.444 | 0.00 | 0.00 | 8 |
| O | GLU | B | 6 | 3.100 | 39.622 | 11.571 | 0.00 | 0.00 | 8 |
| C | GLU | B | 6 | 4.103 | 42.913 | 8.961 | 0.00 | 0.00 | 6 |
| O | GLU | B | 6 | 4.935 | 42.026 | 8.749 | 0.00 | 0.00 | 8 |
| N | GLN | B | 6 | 3.833 | 43.819 | 8.034 | 0.00 | 0.00 | 7 |
| CA | GLN | B | 6 | 4.432 | 43.873 | 6.715 | 0.00 | 0.00 | 6 |
| CB | GLN | B | 6 | 3.810 | 45.047 | 5.948 | 0.00 | 0.00 | 6 |
| C | GLN | B | 6 | 3.455 | 44.788 | 4.497 | 0.00 | 0.00 | 6 |
| C | GLN | B | 6 | 2.649 | 45.939 | 3.918 | 0.00 | 0.00 | 6 |
| O | GLN | B | 6 | 3.186 | 47.022 | 3.682 | 0.00 | 0.00 | 8 |
| N | GLN | B | 6 | 1.359 | 45.711 | 3.700 | 0.00 | 0.00 | 7 |
| C | GLN | B | 6 | 5.942 | 44.057 | 6.731 | 0.00 | 0.00 | 6 |
| O | GLN | B | 6 | 6.651 | 43.615 | 5.825 | 0.00 | 0.00 | 8 |
| N | ARG | B | 6 | 6.479 | 44.703 | 7.756 | 0.00 | 0.00 | 7 |
| CA | ARG | B | 6 | 7.885 | 44.986 | 7.939 | 0.00 | 0.00 | 6 |
| CB | ARG | B | 6 | 8.036 | 46.018 | 9.074 | 0.00 | 0.00 | 6 |
| C | ARG | B | 6 | 9.323 | 46.817 | 9.005 | 0.00 | 0.00 | 6 |
| C | ARG | B | 6 | 10.089 | 46.770 | 10.317 | 0.00 | 0.00 | 6 |
| N | ARG | B | 6 | 11.527 | 46.897 | 10.120 | 0.00 | 0.00 | 7 |
| CZ | ARG | B | 6 | 12.168 | 47.990 | 9.730 | 0.00 | 0.00 | 6 |
| N | ARG | B | 6 | 11.506 | 49.112 | 9.476 | 0.00 | 0.00 | 7 |
| N | ARG | B | 6 | 13.490 | 47.967 | 9.589 | 0.00 | 0.00 | 7 |
| C | ARG | B | 6 | 8.747 | 43.779 | 8.272 | 0.00 | 0.00 | 6 |
| O | ARG | B | 6 | 9.976 | 43.834 | 8.163 | 0.00 | 0.00 | 8 |
| N | LYS | B | 6 | 8.138 | 42.682 | 8.698 | 0.00 | 0.00 | 7 |
| CA | LYS | B | 6 | 8.845 | 41.466 | 9.047 | 0.00 | 0.00 | 6 |
| CB | LYS | B | 6 | 8.136 | 40.762 | 10.211 | 0.00 | 0.00 | 6 |
| C | LYS | B | 6 | 7.765 | 41.649 | 11.385 | 0.00 | 0.00 | 6 |
| C | LYS | B | 6 | 7.064 | 40.835 | 12.467 | 0.00 | 0.00 | 6 |
| CE | LYS | B | 6 | 6.806 | 41.674 | 13.707 | 0.00 | 0.00 | 6 |
| NZ | LYS | B | 6 | 5.642 | 41.179 | 14.491 | 0.00 | 0.00 | 7 |
| C | LYS | B | 6 | 8.927 | 40.481 | 7.885 | 0.00 | 0.00 | 6 |
| O | LYS | B | 6 | 9.369 | 39.348 | 8.094 | 0.00 | 0.00 | 8 |
| N | MET | B | 7 | 8.488 | 40.866 | 6.690 | 0.00 | 0.00 | 7 |
| CA | MET | B | 7 | 8.447 | 39.924 | 5.584 | 0.00 | 0.00 | 6 |
| CB | MET | B | 7 | 7.059 | 39.264 | 5.527 | 0.00 | 0.00 | 6 |
| C | MET | B | 7 | 5.892 | 40.186 | 5.822 | 0.00 | 0.00 | 6 |
| SD | MET | B | 7 | 4.290 | 39.377 | 5.704 | 0.00 | 0.00 | 1 |
| CE | MET | B | 7 | 4.070 | 38.756 | 7.367 | 0.00 | 0.00 | 6 |
| C | MET | B | 7 | 8.777 | 40.497 | 4.215 | 0.00 | 0.00 | 6 |
| O | MET | B | 7 | 8.267 | 41.528 | 3.787 | 0.00 | 0.00 | 8 |
| N | ASP | B | 7 | 9.641 | 39.772 | 3.503 | 0.00 | 0.00 | 7 |
| CA | ASP | B | 7 | 10.018 | 40.153 | 2.143 | 0.00 | 0.00 | 6 |
| CB | ASP | B | 7 | 11.102 | 39.217 | 1.616 | 0.00 | 0.00 | 6 |
| C | ASP | B | 7 | 11.626 | 39.596 | 0.246 | 0.00 | 0.00 | 6 |
| O | ASP | B | 7 | 11.084 | 39.090 | -0.762 | 0.00 | 0.00 | 8 |
| O | ASP | B | 7 | 12.566 | 40.415 | 0.170 | 0.00 | 0.00 | 8 |
| C | ASP | B | 7 | 8.766 | 40.077 | 1.273 | 0.00 | 0.00 | 6 |
| O | ASP | B | 7 | 7.838 | 39.332 | 1.603 | 0.00 | 0.00 | 8 |
| N | ALA | B | 7 | 8.768 | 40.721 | 0.115 | 0.00 | 0.00 | 7 |

Figure 1 - 28

| | | | | | | | | |
|---|---|---|---|---|---|---|---|---|
| CA | ALA | B | 7 | 7.671 | 40.673 | -0.831 | 0.00 | 0.00 | 6 |
| CB | ALA | B | 7 | 8.021 | 41.490 | -2.079 | 0.00 | 0.00 | 6 |
| C | ALA | B | 7 | 7.259 | 39.269 | -1.251 | 0.00 | 0.00 | 6 |
| O | ALA | B | 7 | 6.061 | 39.058 | -1.483 | 0.00 | 0.00 | 8 |
| N | PHE | B | 7 | 8.176 | 38.313 | -1.373 | 0.00 | 0.00 | 7 |
| CA | PHE | B | 7 | 7.811 | 36.950 | -1.753 | 0.00 | 0.00 | 6 |
| CB | PHE | B | 7 | 9.022 | 36.071 | -2.038 | 0.00 | 0.00 | 6 |
| C | PHE | B | 7 | 9.565 | 35.217 | -0.936 | 0.00 | 0.00 | 6 |
| C | PHE | B | 7 | 9.197 | 33.886 | -0.811 | 0.00 | 0.00 | 6 |
| C | PHE | B | 7 | 10.450 | 35.738 | -0.006 | 0.00 | 0.00 | 6 |
| CE | PHE | B | 7 | 9.696 | 33.100 | 0.210 | 0.00 | 0.00 | 6 |
| CE | PHE | B | 7 | 10.948 | 34.963 | 1.024 | 0.00 | 0.00 | 6 |
| CZ | PHE | B | 7 | 10.580 | 33.638 | 1.126 | 0.00 | 0.00 | 6 |
| C | PHE | B | 7 | 6.893 | 36.327 | -0.705 | 0.00 | 0.00 | 6 |
| O | PHE | B | 7 | 5.933 | 35.641 | -1.064 | 0.00 | 0.00 | 8 |
| N | ILE | B | 7 | 7.163 | 36.563 | 0.574 | 0.00 | 0.00 | 7 |
| CA | ILE | B | 7 | 6.304 | 36.067 | 1.645 | 0.00 | 0.00 | 6 |
| CB | ILE | B | 7 | 6.972 | 36.219 | 3.022 | 0.00 | 0.00 | 6 |
| C | ILE | B | 7 | 6.000 | 35.961 | 4.164 | 0.00 | 0.00 | 6 |
| C | ILE | B | 7 | 8.162 | 35.254 | 3.121 | 0.00 | 0.00 | 6 |
| C | ILE | B | 7 | 9.131 | 35.593 | 4.232 | 0.00 | 0.00 | 6 |
| C | ILE | B | 7 | 4.949 | 36.764 | 1.611 | 0.00 | 0.00 | 6 |
| O | ILE | B | 7 | 3.917 | 36.114 | 1.777 | 0.00 | 0.00 | 8 |
| N | GLN | B | 7 | 4.940 | 38.071 | 1.364 | 0.00 | 0.00 | 7 |
| CA | GLN | B | 7 | 3.695 | 38.826 | 1.257 | 0.00 | 0.00 | 6 |
| CB | GLN | B | 7 | 3.976 | 40.311 | 1.047 | 0.00 | 0.00 | 6 |
| C | GLN | B | 7 | 4.678 | 40.988 | 2.211 | 0.00 | 0.00 | 6 |
| C | GLN | B | 7 | 4.908 | 42.469 | 1.984 | 0.00 | 0.00 | 6 |
| O | GLN | B | 7 | 4.269 | 43.091 | 1.131 | 0.00 | 0.00 | 8 |
| N | GLN | B | 7 | 5.823 | 43.047 | 2.755 | 0.00 | 0.00 | 7 |
| C | GLN | B | 7 | 2.836 | 38.275 | 0.122 | 0.00 | 0.00 | 6 |
| O | GLN | B | 7 | 1.645 | 38.009 | 0.314 | 0.00 | 0.00 | 8 |
| N | TYR | B | 7 | 3.435 | 38.020 | -1.038 | 0.00 | 0.00 | 7 |
| CA | TYR | B | 7 | 2.730 | 37.400 | -2.151 | 0.00 | 0.00 | 6 |
| CB | TYR | B | 7 | 3.639 | 37.244 | -3.365 | 0.00 | 0.00 | 6 |
| C | TYR | B | 7 | 4.073 | 38.496 | -4.083 | 0.00 | 0.00 | 6 |
| C | TYR | B | 7 | 4.947 | 38.395 | -5.163 | 0.00 | 0.00 | 6 |
| CE | TYR | B | 7 | 5.370 | 39.516 | -5.853 | 0.00 | 0.00 | 6 |
| C | TYR | B | 7 | 3.645 | 39.764 | -3.717 | 0.00 | 0.00 | 6 |
| CE | TYR | B | 7 | 4.069 | 40.894 | -4.390 | 0.00 | 0.00 | 6 |
| CZ | TYR | B | 7 | 4.932 | 40.761 | -5.457 | 0.00 | 0.00 | 6 |
| O | TYR | B | 7 | 5.355 | 41.879 | -6.133 | 0.00 | 0.00 | 8 |
| C | TYR | B | 7 | 2.186 | 36.024 | -1.768 | 0.00 | 0.00 | 6 |
| O | TYR | B | 7 | 1.028 | 35.703 | -2.037 | 0.00 | 0.00 | 8 |
| N | GLY | B | 7 | 3.017 | 35.211 | -1.124 | 0.00 | 0.00 | 7 |
| CA | GLY | B | 7 | 2.646 | 33.879 | -0.696 | 0.00 | 0.00 | 6 |
| C | GLY | B | 7 | 1.432 | 33.837 | 0.218 | 0.00 | 0.00 | 6 |
| O | GLY | B | 7 | 0.559 | 32.988 | 0.034 | 0.00 | 0.00 | 8 |
| N | ILE | B | 7 | 1.382 | 34.710 | 1.219 | 0.00 | 0.00 | 7 |
| CA | ILE | B | 7 | 0.258 | 34.760 | 2.144 | 0.00 | 0.00 | 6 |
| CB | ILE | B | 7 | 0.526 | 35.722 | 3.316 | 0.00 | 0.00 | 6 |
| C | ILE | B | 7 | -0.694 | 35.837 | 4.222 | 0.00 | 0.00 | 6 |
| C | ILE | B | 7 | 1.736 | 35.233 | 4.117 | 0.00 | 0.00 | 6 |
| C | ILE | B | 7 | 2.252 | 36.206 | 5.152 | 0.00 | 0.00 | 6 |
| C | ILE | B | 7 | -1.035 | 35.134 | 1.430 | 0.00 | 0.00 | 6 |
| O | ILE | B | 7 | -2.020 | 34.395 | 1.504 | 0.00 | 0.00 | 8 |
| N | VAL | B | 7 | -1.024 | 36.238 | 0.691 | 0.00 | 0.00 | 7 |
| CA | VAL | B | 7 | -2.202 | 36.692 | -0.045 | 0.00 | 0.00 | 6 |
| CB | VAL | B | 7 | -1.899 | 37.946 | -0.881 | 0.00 | 0.00 | 6 |
| C | VAL | B | 7 | -3.022 | 38.280 | -1.851 | 0.00 | 0.00 | 6 |
| C | VAL | B | 7 | -1.647 | 39.133 | 0.045 | 0.00 | 0.00 | 6 |
| C | VAL | B | 7 | -2.773 | 35.579 | -0.909 | 0.00 | 0.00 | 6 |
| O | VAL | B | 7 | -3.954 | 35.247 | -0.786 | 0.00 | 0.00 | 8 |
| N | ALA | B | 8 | -1.946 | 34.939 | -1.731 | 0.00 | 0.00 | 7 |
| CA | ALA | B | 8 | -2.383 | 33.822 | -2.558 | 0.00 | 0.00 | 6 |
| CB | ALA | B | 8 | -1.272 | 33.385 | -3.500 | 0.00 | 0.00 | 6 |
| C | ALA | B | 8 | -2.843 | 32.640 | -1.711 | 0.00 | 0.00 | 6 |
| O | ALA | B | 8 | -3.746 | 31.904 | -2.112 | 0.00 | 0.00 | 8 |
| N | GLY | B | 8 | -2.218 | 32.434 | -0.555 | 0.00 | 0.00 | 7 |
| CA | GLY | B | 8 | -2.604 | 31.380 | 0.370 | 0.00 | 0.00 | 6 |
| C | GLY | B | 8 | -3.981 | 31.650 | 0.965 | 0.00 | 0.00 | 6 |
| O | GLY | B | 8 | -4.833 | 30.763 | 1.014 | 0.00 | 0.00 | 8 |
| N | VAL | B | 8 | -4.230 | 32.898 | 1.357 | 0.00 | 0.00 | 7 |
| CA | VAL | B | 8 | -5.528 | 33.288 | 1.897 | 0.00 | 0.00 | 6 |
| CB | VAL | B | 8 | -5.532 | 34.736 | 2.405 | 0.00 | 0.00 | 6 |
| C | VAL | B | 8 | -6.925 | 35.177 | 2.836 | 0.00 | 0.00 | 6 |
| C | VAL | B | 8 | -4.556 | 34.880 | 3.570 | 0.00 | 0.00 | 6 |
| C | VAL | B | 8 | -6.620 | 33.064 | 0.859 | 0.00 | 0.00 | 6 |
| O | VAL | B | 8 | -7.659 | 32.482 | 1.179 | 0.00 | 0.00 | 8 |
| N | GLN | B | 8 | -6.364 | 33.415 | -0.397 | 0.00 | 0.00 | 7 |
| CA | GLN | B | 8 | -7.290 | 33.149 | -1.485 | 0.00 | 0.00 | 6 |
| CB | GLN | B | 8 | -6.721 | 33.632 | -2.822 | 0.00 | 0.00 | 6 |
| C | GLN | B | 8 | -6.689 | 35.138 | -3.007 | 0.00 | 0.00 | 6 |
| C | GLN | B | 8 | -6.219 | 35.543 | -4.389 | 0.00 | 0.00 | 6 |
| O | GLN | B | 8 | -6.176 | 34.726 | -5.309 | 0.00 | 0.00 | 8 |
| N | GLN | B | 8 | -5.860 | 36.811 | -4.554 | 0.00 | 0.00 | 7 |
| C | GLN | B | 8 | -7.631 | 31.667 | -1.602 | 0.00 | 0.00 | 6 |
| O | GLN | B | 8 | -8.802 | 31.315 | -1.758 | 0.00 | 0.00 | 8 |
| N | ALA | B | 8 | -6.629 | 30.793 | -1.539 | 0.00 | 0.00 | 7 |
| CA | ALA | B | 8 | -6.857 | 29.358 | -1.660 | 0.00 | 0.00 | 6 |
| CB | ALA | B | 8 | -5.541 | 28.617 | -1.828 | 0.00 | 0.00 | 6 |
| C | ALA | B | 8 | -7.647 | 28.802 | -0.484 | 0.00 | 0.00 | 6 |
| O | ALA | B | 8 | -8.519 | 27.949 | -0.673 | 0.00 | 0.00 | 8 |
| N | MET | B | 8 | -7.360 | 29.274 | 0.724 | 0.00 | 0.00 | 7 |
| CA | MET | B | 8 | -8.113 | 28.856 | 1.902 | 0.00 | 0.00 | 6 |
| CB | MET | B | 8 | -7.490 | 29.432 | 3.172 | 0.00 | 0.00 | 6 |
| C | MET | B | 8 | -6.228 | 28.709 | 3.621 | 0.00 | 0.00 | 6 |
| SD | MET | B | 8 | -6.445 | 26.925 | 3.753 | 0.00 | 0.00 | 1 |
| CE | MET | B | 8 | -6.387 | 26.701 | 5.528 | 0.00 | 0.00 | 6 |
| C | MET | B | 8 | -9.574 | 29.266 | 1.757 | 0.00 | 0.00 | 6 |
| O | MET | B | 8 | -10.478 | 28.445 | 1.919 | 0.00 | 0.00 | 8 |
| N | GLN | B | 8 | -9.809 | 30.522 | 1.397 | 0.00 | 0.00 | 7 |
| CA | GLN | B | 8 | -11.155 | 31.043 | 1.192 | 0.00 | 0.00 | 6 |
| CB | GLN | B | 8 | -11.101 | 32.552 | 0.925 | 0.00 | 0.00 | 6 |
| C | GLN | B | 8 | -10.844 | 33.369 | 2.182 | 0.00 | 0.00 | 6 |
| C | GLN | B | 8 | -10.738 | 34.853 | 1.924 | 0.00 | 0.00 | 6 |
| O | GLN | B | 8 | -10.769 | 35.311 | 0.781 | 0.00 | 0.00 | 8 |
| N | GLN | B | 8 | -10.614 | 35.637 | 2.991 | 0.00 | 0.00 | 7 |
| C | GLN | B | 8 | -11.886 | 30.313 | 0.077 | 0.00 | 0.00 | 6 |
| O | GLN | B | 8 | -12.990 | 29.807 | 0.293 | 0.00 | 0.00 | 8 |
| N | ASP | B | 8 | -11.248 | 30.116 | -1.071 | 0.00 | 0.00 | 7 |
| CA | ASP | B | 8 | -11.840 | 29.371 | -2.171 | 0.00 | 0.00 | 6 |
| CB | ASP | B | 8 | -10.878 | 29.284 | -3.364 | 0.00 | 0.00 | 6 |
| C | ASP | B | 8 | -11.590 | 28.837 | -4.627 | 0.00 | 0.00 | 6 |
| O | ASP | B | 8 | -12.739 | 29.283 | -4.836 | 0.00 | 0.00 | 8 |
| O | ASP | B | 8 | -11.029 | 28.050 | -5.413 | 0.00 | 0.00 | 8 |
| C | ASP | B | 8 | -12.257 | 27.955 | -1.785 | 0.00 | 0.00 | 6 |
| O | ASP | B | 8 | -13.279 | 27.457 | -2.261 | 0.00 | 0.00 | 8 |
| N | SER | B | 8 | -11.451 | 27.269 | -0.987 | 0.00 | 0.00 | 7 |
| CA | SER | B | 8 | -11.687 | 25.893 | -0.605 | 0.00 | 0.00 | 6 |
| CB | SER | B | 8 | -10.467 | 25.349 | 0.151 | 0.00 | 0.00 | 6 |
| O | SER | B | 8 | -10.360 | 25.936 | 1.435 | 0.00 | 0.00 | 8 |
| C | SER | B | 8 | -12.934 | 25.657 | 0.235 | 0.00 | 0.00 | 6 |
| O | SER | B | 8 | -13.620 | 24.651 | 0.031 | 0.00 | 0.00 | 8 |
| N | GLY | B | 8 | -13.196 | 26.528 | 1.203 | 0.00 | 0.00 | 7 |
| CA | GLY | B | 8 | -14.320 | 26.296 | 2.114 | 0.00 | 0.00 | 6 |
| C | GLY | B | 8 | -13.881 | 25.231 | 3.124 | 0.00 | 0.00 | 6 |
| O | GLY | B | 8 | -14.413 | 24.126 | 3.181 | 0.00 | 0.00 | 8 |

Figure 1 - 29

| | | | | | | | | |
|---|---|---|---|---|---|---|---|---|
| N | LEU | B | 9 | -12.800 | 25.551 | 3.826 | 0.00 | 0.00 | 7 |
| CA | LEU | B | 9 | -12.265 | 24.680 | 4.861 | 0.00 | 0.00 | 6 |
| CB | LEU | B | 9 | -10.779 | 24.409 | 4.677 | 0.00 | 0.00 | 6 |
| C | LEU | B | 9 | -10.302 | 22.986 | 4.394 | 0.00 | 0.00 | 6 |
| C | LEU | B | 9 | -10.926 | 21.966 | 5.334 | 0.00 | 0.00 | 6 |
| C | LEU | B | 9 | -10.574 | 22.608 | 2.943 | 0.00 | 0.00 | 6 |
| C | LEU | B | 9 | -12.507 | 25.349 | 6.216 | 0.00 | 0.00 | 6 |
| O | LEU | B | 9 | -12.209 | 26.531 | 6.384 | 0.00 | 0.00 | 8 |
| N | GLU | B | 9 | -13.164 | 24.627 | 7.112 | 0.00 | 0.00 | 7 |
| CA | GLU | B | 9 | -13.346 | 25.130 | 8.474 | 0.00 | 0.00 | 6 |
| CB | GLU | B | 9 | -14.753 | 24.868 | 8.989 | 0.00 | 0.00 | 6 |
| C | GLU | B | 9 | -15.849 | 25.580 | 8.213 | 0.00 | 0.00 | 6 |
| C | GLU | B | 9 | -16.839 | 26.303 | 9.104 | 0.00 | 0.00 | 6 |
| O | GLU | B | 9 | -17.285 | 25.715 | 10.113 | 0.00 | 0.00 | 8 |
| O | GLU | B | 9 | -17.179 | 27.465 | 8.797 | 0.00 | 0.00 | 8 |
| C | GLU | B | 9 | -12.279 | 24.461 | 9.339 | 0.00 | 0.00 | 6 |
| O | GLU | B | 9 | -12.201 | 23.231 | 9.355 | 0.00 | 0.00 | 8 |
| N | ILE | B | 9 | -11.401 | 25.263 | 9.933 | 0.00 | 0.00 | 7 |
| CA | ILE | B | 9 | -10.330 | 24.696 | 10.753 | 0.00 | 0.00 | 6 |
| CB | ILE | B | 9 | -9.003 | 25.449 | 10.595 | 0.00 | 0.00 | 6 |
| C | ILE | B | 9 | -7.980 | 25.028 | 11.642 | 0.00 | 0.00 | 6 |
| C | ILE | B | 9 | -8.425 | 25.204 | 9.195 | 0.00 | 0.00 | 6 |
| C | ILE | B | 9 | -8.612 | 26.358 | 8.239 | 0.00 | 0.00 | 6 |
| C | ILE | B | 9 | -10.771 | 24.645 | 12.212 | 0.00 | 0.00 | 6 |
| O | ILE | B | 9 | -10.993 | 25.660 | 12.864 | 0.00 | 0.00 | 8 |
| N | THR | B | 9 | -10.950 | 23.422 | 12.698 | 0.00 | 0.00 | 7 |
| CA | THR | B | 9 | -11.365 | 23.176 | 14.070 | 0.00 | 0.00 | 6 |
| CB | THR | B | 9 | -12.591 | 22.241 | 14.128 | 0.00 | 0.00 | 6 |
| O | THR | B | 9 | -12.229 | 20.972 | 13.563 | 0.00 | 0.00 | 8 |
| C | THR | B | 9 | -13.772 | 22.810 | 13.365 | 0.00 | 0.00 | 6 |
| C | THR | B | 9 | -10.245 | 22.505 | 14.854 | 0.00 | 0.00 | 6 |
| O | THR | B | 9 | -9.318 | 21.938 | 14.274 | 0.00 | 0.00 | 8 |
| N | GLU | B | 9 | -10.342 | 22.519 | 16.180 | 0.00 | 0.00 | 7 |
| CA | GLU | B | 9 | -9.350 | 21.894 | 17.050 | 0.00 | 0.00 | 6 |
| CB | GLU | B | 9 | -9.745 | 22.075 | 18.517 | 0.00 | 0.00 | 6 |
| C | GLU | B | 9 | -8.854 | 21.362 | 19.515 | 0.00 | 0.00 | 6 |
| C | GLU | B | 9 | -8.091 | 22.295 | 20.431 | 0.00 | 0.00 | 6 |
| O | GLU | B | 9 | -6.877 | 22.071 | 20.630 | 0.00 | 0.00 | 8 |
| O | GLU | B | 9 | -8.696 | 23.252 | 20.959 | 0.00 | 0.00 | 8 |
| C | GLU | B | 9 | -9.159 | 20.418 | 16.722 | 0.00 | 0.00 | 6 |
| O | GLU | B | 9 | -8.050 | 19.886 | 16.829 | 0.00 | 0.00 | 8 |
| N | GLU | B | 9 | -10.204 | 19.729 | 16.283 | 0.00 | 0.00 | 7 |
| CA | GLU | B | 9 | -10.171 | 18.345 | 15.864 | 0.00 | 0.00 | 6 |
| CB | GLU | B | 9 | -11.575 | 17.732 | 15.975 | 0.00 | 0.00 | 6 |
| C | GLU | B | 9 | -11.800 | 16.947 | 17.254 | 0.00 | 0.00 | 6 |
| C | GLU | B | 9 | -13.188 | 17.128 | 17.834 | 0.00 | 0.00 | 6 |
| O | GLU | B | 9 | -14.097 | 16.358 | 17.458 | 0.00 | 0.00 | 8 |
| O | GLU | B | 9 | -13.370 | 18.034 | 18.674 | 0.00 | 0.00 | 8 |
| C | GLU | B | 9 | -9.670 | 18.170 | 14.432 | 0.00 | 0.00 | 6 |
| O | GLU | B | 9 | -9.491 | 17.043 | 13.964 | 0.00 | 0.00 | 8 |
| N | ASN | B | 9 | -9.451 | 19.258 | 13.708 | 0.00 | 0.00 | 7 |
| CA | ASN | B | 9 | -8.967 | 19.250 | 12.345 | 0.00 | 0.00 | 6 |
| CB | ASN | B | 9 | -9.751 | 20.278 | 11.509 | 0.00 | 0.00 | 6 |
| C | ASN | B | 9 | -10.403 | 19.694 | 10.279 | 0.00 | 0.00 | 6 |
| O | ASN | B | 9 | -10.214 | 18.522 | 9.952 | 0.00 | 0.00 | 8 |
| N | ASN | B | 9 | -11.188 | 20.509 | 9.584 | 0.00 | 0.00 | 7 |
| C | ASN | B | 9 | -7.497 | 19.629 | 12.209 | 0.00 | 0.00 | 6 |
| O | ASN | B | 9 | -6.767 | 19.093 | 11.376 | 0.00 | 0.00 | 8 |
| N | ALA | B | 9 | -7.065 | 20.621 | 12.974 | 0.00 | 0.00 | 7 |
| CA | ALA | B | 9 | -5.737 | 21.205 | 12.898 | 0.00 | 0.00 | 6 |
| CB | ALA | B | 9 | -5.410 | 21.900 | 14.219 | 0.00 | 0.00 | 6 |
| C | ALA | B | 9 | -4.627 | 20.235 | 12.535 | 0.00 | 0.00 | 6 |
| O | ALA | B | 9 | -3.912 | 20.381 | 11.545 | 0.00 | 0.00 | 8 |
| N | THR | B | 9 | -4.462 | 19.187 | 13.317 | 0.00 | 0.00 | 7 |
| CA | THR | B | 9 | -3.494 | 18.120 | 13.183 | 0.00 | 0.00 | 6 |
| CB | THR | B | 9 | -3.849 | 17.091 | 14.293 | 0.00 | 0.00 | 6 |
| O | THR | B | 9 | -3.158 | 17.483 | 15.494 | 0.00 | 0.00 | 8 |
| C | THR | B | 9 | -3.510 | 15.649 | 13.985 | 0.00 | 0.00 | 6 |
| C | THR | B | 9 | -3.392 | 17.455 | 11.826 | 0.00 | 0.00 | 6 |
| O | THR | B | 9 | -2.336 | 16.879 | 11.520 | 0.00 | 0.00 | 8 |
| N | ARG | B | 9 | -4.417 | 17.469 | 10.983 | 0.00 | 0.00 | 7 |
| CA | ARG | B | 9 | -4.390 | 16.835 | 9.680 | 0.00 | 0.00 | 6 |
| CB | ARG | B | 9 | -5.674 | 16.018 | 9.462 | 0.00 | 0.00 | 6 |
| C | ARG | B | 9 | -5.976 | 14.996 | 10.544 | 0.00 | 0.00 | 6 |
| C | ARG | B | 9 | -4.989 | 13.839 | 10.499 | 0.00 | 0.00 | 6 |
| N | ARG | B | 9 | -5.164 | 13.029 | 9.300 | 0.00 | 0.00 | 7 |
| CZ | ARG | B | 9 | -4.248 | 12.221 | 8.785 | 0.00 | 0.00 | 6 |
| N | ARG | B | 9 | -3.058 | 12.093 | 9.357 | 0.00 | 0.00 | 7 |
| N | ARG | B | 9 | -4.525 | 11.530 | 7.686 | 0.00 | 0.00 | 7 |
| C | ARG | B | 9 | -4.224 | 17.795 | 8.512 | 0.00 | 0.00 | 6 |
| O | ARG | B | 9 | -4.283 | 17.365 | 7.356 | 0.00 | 0.00 | 8 |
| N | ILE | B | 1 | -4.106 | 19.091 | 8.777 | 0.00 | 0.00 | 7 |
| CA | ILE | B | 1 | -3.917 | 20.072 | 7.716 | 0.00 | 0.00 | 6 |
| CB | ILE | B | 1 | -4.981 | 21.183 | 7.700 | 0.00 | 0.00 | 6 |
| C | ILE | B | 1 | -4.898 | 21.961 | 6.389 | 0.00 | 0.00 | 6 |
| C | ILE | B | 1 | -6.399 | 20.638 | 7.890 | 0.00 | 0.00 | 6 |
| C | ILE | B | 1 | -7.341 | 21.612 | 8.564 | 0.00 | 0.00 | 6 |
| C | ILE | B | 1 | -2.543 | 20.728 | 7.839 | 0.00 | 0.00 | 6 |
| O | ILE | B | 1 | -2.204 | 21.247 | 8.904 | 0.00 | 0.00 | 8 |
| N | GLY | B | 1 | -1.772 | 20.711 | 6.756 | 0.00 | 0.00 | 7 |
| CA | GLY | B | 1 | -0.455 | 21.336 | 6.771 | 0.00 | 0.00 | 6 |
| C | GLY | B | 1 | -0.164 | 22.114 | 5.493 | 0.00 | 0.00 | 6 |
| O | GLY | B | 1 | -1.084 | 22.519 | 4.781 | 0.00 | 0.00 | 8 |
| N | ALA | B | 1 | 1.123 | 22.287 | 5.193 | 0.00 | 0.00 | 7 |
| CA | ALA | B | 1 | 1.544 | 23.043 | 4.025 | 0.00 | 0.00 | 6 |
| CB | ALA | B | 1 | 1.703 | 24.508 | 4.437 | 0.00 | 0.00 | 6 |
| C | ALA | B | 1 | 2.945 | 22.569 | 3.390 | 0.00 | 0.00 | 6 |
| O | ALA | B | 1 | 3.731 | 21.988 | 4.008 | 0.00 | 0.00 | 8 |
| N | ALA | B | 1 | 2.964 | 22.834 | 2.093 | 0.00 | 0.00 | 7 |
| CA | ALA | B | 1 | 4.129 | 22.478 | 1.294 | 0.00 | 0.00 | 6 |
| CB | ALA | B | 1 | 3.955 | 21.139 | 0.604 | 0.00 | 0.00 | 6 |
| C | ALA | B | 1 | 4.359 | 23.608 | 0.290 | 0.00 | 0.00 | 6 |
| O | ALA | B | 1 | 3.925 | 23.556 | -0.858 | 0.00 | 0.00 | 8 |
| N | ILE | B | 1 | 4.901 | 24.712 | 0.799 | 0.00 | 0.00 | 7 |
| CA | ILE | B | 1 | 5.111 | 25.917 | 0.008 | 0.00 | 0.00 | 6 |
| CB | ILE | B | 1 | 4.382 | 27.134 | 0.609 | 0.00 | 0.00 | 6 |
| C | ILE | B | 1 | 4.641 | 28.386 | -0.218 | 0.00 | 0.00 | 6 |
| C | ILE | B | 1 | 2.875 | 26.885 | 0.727 | 0.00 | 0.00 | 6 |
| C | ILE | B | 1 | 2.201 | 27.727 | 1.789 | 0.00 | 0.00 | 6 |
| C | ILE | B | 1 | 6.599 | 26.245 | -0.103 | 0.00 | 0.00 | 6 |
| O | ILE | B | 1 | 7.283 | 26.357 | 0.912 | 0.00 | 0.00 | 8 |
| N | GLY | B | 1 | 7.071 | 26.480 | -1.321 | 0.00 | 0.00 | 7 |
| CA | GLY | B | 1 | 8.464 | 26.805 | -1.546 | 0.00 | 0.00 | 6 |
| C | GLY | B | 1 | 8.689 | 28.092 | -2.326 | 0.00 | 0.00 | 6 |
| O | GLY | B | 1 | 7.803 | 28.887 | -2.619 | 0.00 | 0.00 | 8 |
| N | SER | B | 1 | 9.955 | 28.293 | -2.663 | 0.00 | 0.00 | 7 |
| CA | SER | B | 1 | 10.463 | 29.437 | -3.400 | 0.00 | 0.00 | 6 |
| CB | SER | B | 1 | 10.521 | 30.675 | -2.511 | 0.00 | 0.00 | 6 |
| O | SER | B | 1 | 10.955 | 31.817 | -3.224 | 0.00 | 0.00 | 8 |
| C | SER | B | 1 | 11.864 | 29.074 | -3.895 | 0.00 | 0.00 | 6 |
| O | SER | B | 1 | 12.571 | 28.343 | -3.198 | 0.00 | 0.00 | 8 |
| N | GLY | B | 1 | 12.255 | 29.560 | -5.062 | 0.00 | 0.00 | 7 |
| CA | GLY | B | 1 | 13.558 | 29.254 | -5.619 | 0.00 | 0.00 | 6 |
| C | GLY | B | 1 | 14.702 | 30.060 | -5.036 | 0.00 | 0.00 | 6 |
| O | GLY | B | 1 | 15.795 | 29.516 | -4.846 | 0.00 | 0.00 | 8 |
| N | ILE | B | 1 | 14.500 | 31.353 | -4.800 | 0.00 | 0.00 | 7 |
| CA | ILE | B | 1 | 15.555 | 32.223 | -4.284 | 0.00 | 0.00 | 6 |
| CB | ILE | B | 1 | 15.897 | 33.314 | -5.317 | 0.00 | 0.00 | 6 |

Figure 1 - 30

| | | | | | | | | | |
|---|---|---|---|---|---|---|---|---|---|
| C | ILE | B | 1 | 16.794 | 34.404 | -4.750 | 0.00 | 0.00 | 6 |
| C | ILE | B | 1 | 16.591 | 32.700 | -6.544 | 0.00 | 0.00 | 6 |
| C | ILE | B | 1 | 16.491 | 33.542 | -7.796 | 0.00 | 0.00 | 6 |
| C | ILE | B | 1 | 15.199 | 32.836 | -2.938 | 0.00 | 0.00 | 6 |
| O | ILE | B | 1 | 16.082 | 33.200 | -2.153 | 0.00 | 0.00 | 8 |
| N | GLY | B | 1 | 13.913 | 32.958 | -2.623 | 0.00 | 0.00 | 7 |
| CA | GLY | B | 1 | 13.500 | 33.524 | -1.345 | 0.00 | 0.00 | 6 |
| C | GLY | B | 1 | 13.749 | 35.023 | -1.274 | 0.00 | 0.00 | 6 |
| O | GLY | B | 1 | 13.728 | 35.733 | -2.279 | 0.00 | 0.00 | 8 |
| N | GLY | B | 1 | 13.868 | 35.559 | -0.062 | 0.00 | 0.00 | 7 |
| CA | GLY | B | 1 | 13.870 | 36.971 | 0.218 | 0.00 | 0.00 | 6 |
| C | GLY | B | 1 | 15.050 | 37.802 | -0.223 | 0.00 | 0.00 | 6 |
| O | GLY | B | 1 | 15.661 | 38.511 | 0.585 | 0.00 | 0.00 | 8 |
| N | LEU | B | 1 | 15.285 | 37.900 | -1.526 | 0.00 | 0.00 | 7 |
| CA | LEU | B | 1 | 16.398 | 38.625 | -2.104 | 0.00 | 0.00 | 6 |
| CB | LEU | B | 1 | 16.437 | 38.408 | -3.622 | 0.00 | 0.00 | 6 |
| C | LEU | B | 1 | 17.663 | 37.729 | -4.225 | 0.00 | 0.00 | 6 |
| C | LEU | B | 1 | 17.647 | 37.859 | -5.744 | 0.00 | 0.00 | 6 |
| C | LEU | B | 1 | 18.962 | 38.287 | -3.670 | 0.00 | 0.00 | 6 |
| C | LEU | B | 1 | 16.332 | 40.119 | -1.822 | 0.00 | 0.00 | 6 |
| O | LEU | B | 1 | 17.336 | 40.749 | -1.493 | 0.00 | 0.00 | 8 |
| N | GLY | B | 1 | 15.138 | 40.687 | -1.966 | 0.00 | 0.00 | 7 |
| CA | GLY | B | 1 | 14.920 | 42.106 | -1.717 | 0.00 | 0.00 | 6 |
| C | GLY | B | 1 | 15.413 | 42.510 | -0.333 | 0.00 | 0.00 | 6 |
| O | GLY | B | 1 | 16.245 | 43.408 | -0.215 | 0.00 | 0.00 | 8 |
| N | LEU | B | 1 | 15.004 | 41.772 | 0.696 | 0.00 | 0.00 | 7 |
| CA | LEU | B | 1 | 15.384 | 42.075 | 2.069 | 0.00 | 0.00 | 6 |
| CB | LEU | B | 1 | 14.380 | 41.456 | 3.045 | 0.00 | 0.00 | 6 |
| C | LEU | B | 1 | 13.469 | 42.434 | 3.794 | 0.00 | 0.00 | 6 |
| C | LEU | B | 1 | 12.982 | 43.576 | 2.917 | 0.00 | 0.00 | 6 |
| C | LEU | B | 1 | 12.272 | 41.709 | 4.396 | 0.00 | 0.00 | 6 |
| C | LEU | B | 1 | 16.822 | 41.718 | 2.403 | 0.00 | 0.00 | 6 |
| O | LEU | B | 1 | 17.408 | 42.358 | 3.288 | 0.00 | 0.00 | 8 |
| N | ILE | B | 1 | 17.433 | 40.762 | 1.707 | 0.00 | 0.00 | 7 |
| CA | ILE | B | 1 | 18.834 | 40.428 | 1.959 | 0.00 | 0.00 | 6 |
| CB | ILE | B | 1 | 19.264 | 39.105 | 1.314 | 0.00 | 0.00 | 6 |
| C | ILE | B | 1 | 20.776 | 38.921 | 1.351 | 0.00 | 0.00 | 6 |
| C | ILE | B | 1 | 18.579 | 37.928 | 2.019 | 0.00 | 0.00 | 6 |
| C | ILE | B | 1 | 18.555 | 36.654 | 1.206 | 0.00 | 0.00 | 6 |
| C | ILE | B | 1 | 19.716 | 41.575 | 1.461 | 0.00 | 0.00 | 6 |
| O | ILE | B | 1 | 20.702 | 41.937 | 2.103 | 0.00 | 0.00 | 8 |
| N | GLU | B | 1 | 19.338 | 42.165 | 0.332 | 0.00 | 0.00 | 7 |
| CA | GLU | B | 1 | 20.048 | 43.316 | -0.209 | 0.00 | 0.00 | 6 |
| CB | GLU | B | 1 | 19.511 | 43.682 | -1.590 | 0.00 | 0.00 | 6 |
| C | GLU | B | 1 | 19.818 | 42.650 | -2.666 | 0.00 | 0.00 | 6 |
| C | GLU | B | 1 | 19.261 | 43.083 | -4.010 | 0.00 | 0.00 | 6 |
| O | GLU | B | 1 | 18.715 | 42.231 | -4.736 | 0.00 | 0.00 | 8 |
| O | GLU | B | 1 | 19.370 | 44.288 | -4.318 | 0.00 | 0.00 | 8 |
| C | GLU | B | 1 | 19.955 | 44.515 | 0.727 | 0.00 | 0.00 | 6 |
| O | GLU | B | 1 | 20.977 | 45.118 | 1.050 | 0.00 | 0.00 | 8 |
| N | GLU | B | 1 | 18.755 | 44.849 | 1.189 | 0.00 | 0.00 | 7 |
| CA | GLU | B | 1 | 18.559 | 45.961 | 2.107 | 0.00 | 0.00 | 6 |
| CB | GLU | B | 1 | 17.090 | 46.078 | 2.520 | 0.00 | 0.00 | 6 |
| C | GLU | B | 1 | 16.822 | 47.239 | 3.466 | 0.00 | 0.00 | 6 |
| C | GLU | B | 1 | 15.373 | 47.324 | 3.901 | 0.00 | 0.00 | 6 |
| O | GLU | B | 1 | 14.526 | 47.683 | 3.058 | 0.00 | 0.00 | 8 |
| O | GLU | B | 1 | 15.081 | 47.032 | 5.079 | 0.00 | 0.00 | 8 |
| C | GLU | B | 1 | 19.422 | 45.816 | 3.358 | 0.00 | 0.00 | 6 |
| O | GLU | B | 1 | 20.204 | 46.703 | 3.698 | 0.00 | 0.00 | 8 |
| N | ASN | B | 1 | 19.302 | 44.673 | 4.026 | 0.00 | 0.00 | 7 |
| CA | ASN | B | 1 | 20.071 | 44.377 | 5.223 | 0.00 | 0.00 | 6 |
| CB | ASN | B | 1 | 19.640 | 43.034 | 5.823 | 0.00 | 0.00 | 6 |
| C | ASN | B | 1 | 18.299 | 43.116 | 6.525 | 0.00 | 0.00 | 6 |
| O | ASN | B | 1 | 18.180 | 43.719 | 7.591 | 0.00 | 0.00 | 8 |

| | | | | | | | | | |
|---|---|---|---|---|---|---|---|---|---|
| N | ASN | B | 1 | 17.280 | 42.501 | 5.940 | 0.00 | 0.00 | 7 |
| C | ASN | B | 1 | 21.570 | 44.367 | 4.958 | 0.00 | 0.00 | 6 |
| O | ASN | B | 1 | 22.333 | 44.848 | 5.801 | 0.00 | 0.00 | 8 |
| N | HIS | B | 1 | 22.005 | 43.840 | 3.811 | 0.00 | 0.00 | 7 |
| CA | HIS | B | 1 | 23.431 | 43.856 | 3.503 | 0.00 | 0.00 | 6 |
| CB | HIS | B | 1 | 23.819 | 43.004 | 2.295 | 0.00 | 0.00 | 6 |
| C | HIS | B | 1 | 25.315 | 42.861 | 2.216 | 0.00 | 0.00 | 6 |
| C | HIS | B | 1 | 26.222 | 43.348 | 1.343 | 0.00 | 0.00 | 6 |
| N | HIS | B | 1 | 26.030 | 42.144 | 3.151 | 0.00 | 0.00 | 7 |
| CE | HIS | B | 1 | 27.316 | 42.190 | 2.852 | 0.00 | 0.00 | 6 |
| N | HIS | B | 1 | 27.457 | 42.915 | 1.755 | 0.00 | 0.00 | 7 |
| C | HIS | B | 1 | 23.889 | 45.303 | 3.321 | 0.00 | 0.00 | 6 |
| O | HIS | B | 1 | 24.898 | 45.713 | 3.898 | 0.00 | 0.00 | 8 |
| N | THR | B | 1 | 23.091 | 46.103 | 2.620 | 0.00 | 0.00 | 7 |
| CA | THR | B | 1 | 23.383 | 47.523 | 2.448 | 0.00 | 0.00 | 6 |
| CB | THR | B | 1 | 22.322 | 48.196 | 1.562 | 0.00 | 0.00 | 6 |
| O | THR | B | 1 | 22.311 | 47.533 | 0.288 | 0.00 | 0.00 | 8 |
| C | THR | B | 1 | 22.621 | 49.671 | 1.345 | 0.00 | 0.00 | 6 |
| C | THR | B | 1 | 23.500 | 48.228 | 3.792 | 0.00 | 0.00 | 6 |
| O | THR | B | 1 | 24.478 | 48.942 | 4.033 | 0.00 | 0.00 | 8 |
| N | SER | B | 1 | 22.553 | 47.994 | 4.695 | 0.00 | 0.00 | 7 |
| CA | SER | B | 1 | 22.625 | 48.540 | 6.047 | 0.00 | 0.00 | 6 |
| CB | SER | B | 1 | 21.426 | 48.068 | 6.870 | 0.00 | 0.00 | 6 |
| O | SER | B | 1 | 20.215 | 48.456 | 6.236 | 0.00 | 0.00 | 8 |
| C | SER | B | 1 | 23.939 | 48.154 | 6.711 | 0.00 | 0.00 | 6 |
| O | SER | B | 1 | 24.722 | 49.019 | 7.100 | 0.00 | 0.00 | 8 |
| N | LEU | B | 1 | 24.244 | 46.863 | 6.777 | 0.00 | 0.00 | 7 |
| CA | LEU | B | 1 | 25.484 | 46.363 | 7.350 | 0.00 | 0.00 | 6 |
| CB | LEU | B | 1 | 25.569 | 44.846 | 7.172 | 0.00 | 0.00 | 6 |
| C | LEU | B | 1 | 26.914 | 44.158 | 7.405 | 0.00 | 0.00 | 6 |
| C | LEU | B | 1 | 27.242 | 44.061 | 8.887 | 0.00 | 0.00 | 6 |
| C | LEU | B | 1 | 26.922 | 42.773 | 6.770 | 0.00 | 0.00 | 6 |
| C | LEU | B | 1 | 26.720 | 47.037 | 6.775 | 0.00 | 0.00 | 6 |
| O | LEU | B | 1 | 27.612 | 47.426 | 7.535 | 0.00 | 0.00 | 8 |
| N | MET | B | 1 | 26.808 | 47.199 | 5.461 | 0.00 | 0.00 | 7 |
| CA | MET | B | 1 | 27.955 | 47.832 | 4.826 | 0.00 | 0.00 | 6 |
| CB | MET | B | 1 | 27.840 | 47.751 | 3.301 | 0.00 | 0.00 | 6 |
| C | MET | B | 1 | 28.732 | 46.686 | 2.680 | 0.00 | 0.00 | 6 |
| SD | MET | B | 1 | 28.571 | 46.613 | 0.886 | 0.00 | 0.00 | 1 |
| CE | MET | B | 1 | 29.873 | 47.738 | 0.383 | 0.00 | 0.00 | 6 |
| C | MET | B | 1 | 28.141 | 49.285 | 5.246 | 0.00 | 0.00 | 6 |
| O | MET | B | 1 | 29.272 | 49.742 | 5.426 | 0.00 | 0.00 | 8 |
| N | ASN | B | 1 | 27.047 | 50.023 | 5.396 | 0.00 | 0.00 | 7 |
| CA | ASN | B | 1 | 27.099 | 51.420 | 5.779 | 0.00 | 0.00 | 6 |
| CB | ASN | B | 1 | 25.961 | 52.184 | 5.088 | 0.00 | 0.00 | 6 |
| C | ASN | B | 1 | 26.056 | 52.193 | 3.581 | 0.00 | 0.00 | 6 |
| O | ASN | B | 1 | 25.032 | 52.318 | 2.904 | 0.00 | 0.00 | 8 |
| N | ASN | B | 1 | 27.260 | 52.066 | 3.037 | 0.00 | 0.00 | 7 |
| C | ASN | B | 1 | 26.985 | 51.668 | 7.277 | 0.00 | 0.00 | 6 |
| O | ASN | B | 1 | 27.143 | 52.824 | 7.685 | 0.00 | 0.00 | 8 |
| N | GLY | B | 1 | 26.616 | 50.669 | 8.072 | 0.00 | 0.00 | 7 |
| CA | GLY | B | 1 | 26.330 | 50.906 | 9.474 | 0.00 | 0.00 | 6 |
| C | GLY | B | 1 | 26.852 | 49.890 | 10.464 | 0.00 | 0.00 | 6 |
| O | GLY | B | 1 | 26.807 | 50.157 | 11.671 | 0.00 | 0.00 | 8 |
| N | GLY | B | 1 | 27.346 | 48.745 | 10.006 | 0.00 | 0.00 | 7 |
| CA | GLY | B | 1 | 27.819 | 47.709 | 10.932 | 0.00 | 0.00 | 6 |
| C | GLY | B | 1 | 26.629 | 46.810 | 11.262 | 0.00 | 0.00 | 6 |
| O | GLY | B | 1 | 25.515 | 47.064 | 10.801 | 0.00 | 0.00 | 8 |
| N | PRO | B | 1 | 26.840 | 45.791 | 12.085 | 0.00 | 0.00 | 7 |
| C | PRO | B | 1 | 28.172 | 45.431 | 12.638 | 0.00 | 0.00 | 6 |
| CA | PRO | B | 1 | 25.828 | 44.812 | 12.416 | 0.00 | 0.00 | 6 |
| CB | PRO | B | 1 | 26.606 | 43.681 | 13.095 | 0.00 | 0.00 | 6 |
| C | PRO | B | 1 | 27.872 | 44.292 | 13.571 | 0.00 | 0.00 | 6 |
| C | PRO | B | 1 | 24.670 | 45.251 | 13.281 | 0.00 | 0.00 | 6 |

Figure 1 - 31

| | | | | | | | | |
|---|---|---|---|---|---|---|---|---|
| O | PRO | B | 1 | 23.627 | 44.581 | 13.297 | 0.00 | 0.00 | 8 |
| N | ARG | B | 1 | 24.753 | 46.392 | 13.949 | 0.00 | 0.00 | 7 |
| CA | ARG | B | 1 | 23.680 | 46.909 | 14.785 | 0.00 | 0.00 | 6 |
| CB | ARG | B | 1 | 24.220 | 47.994 | 15.724 | 0.00 | 0.00 | 6 |
| C | ARG | B | 1 | 25.053 | 47.444 | 16.872 | 0.00 | 0.00 | 6 |
| C | ARG | B | 1 | 24.755 | 48.182 | 18.166 | 0.00 | 0.00 | 6 |
| N | ARG | B | 1 | 25.893 | 48.199 | 19.076 | 0.00 | 0.00 | 7 |
| CZ | ARG | B | 1 | 26.353 | 49.285 | 19.690 | 0.00 | 0.00 | 6 |
| N | ARG | B | 1 | 25.780 | 50.466 | 19.497 | 0.00 | 0.00 | 7 |
| N | ARG | B | 1 | 27.395 | 49.192 | 20.505 | 0.00 | 0.00 | 7 |
| C | ARG | B | 1 | 22.514 | 47.460 | 13.977 | 0.00 | 0.00 | 6 |
| O | ARG | B | 1 | 21.412 | 47.635 | 14.500 | 0.00 | 0.00 | 8 |
| N | LYS | B | 1 | 22.730 | 47.733 | 12.695 | 0.00 | 0.00 | 7 |
| CA | LYS | B | 1 | 21.703 | 48.240 | 11.804 | 0.00 | 0.00 | 6 |
| CB | LYS | B | 1 | 22.295 | 49.222 | 10.789 | 0.00 | 0.00 | 6 |
| C | LYS | B | 1 | 22.827 | 50.498 | 11.425 | 0.00 | 0.00 | 6 |
| C | LYS | B | 1 | 22.565 | 51.706 | 10.539 | 0.00 | 0.00 | 6 |
| CE | LYS | B | 1 | 21.724 | 52.748 | 11.258 | 0.00 | 0.00 | 6 |
| NZ | LYS | B | 1 | 20.929 | 53.572 | 10.304 | 0.00 | 0.00 | 7 |
| C | LYS | B | 1 | 20.981 | 47.102 | 11.086 | 0.00 | 0.00 | 6 |
| O | LYS | B | 1 | 20.040 | 47.343 | 10.330 | 0.00 | 0.00 | 8 |
| N | ILE | B | 1 | 21.424 | 45.867 | 11.305 | 0.00 | 0.00 | 7 |
| CA | ILE | B | 1 | 20.767 | 44.706 | 10.731 | 0.00 | 0.00 | 6 |
| CB | ILE | B | 1 | 21.578 | 43.404 | 10.856 | 0.00 | 0.00 | 6 |
| C | ILE | B | 1 | 20.775 | 42.219 | 10.324 | 0.00 | 0.00 | 6 |
| C | ILE | B | 1 | 22.910 | 43.525 | 10.113 | 0.00 | 0.00 | 6 |
| C | ILE | B | 1 | 23.835 | 42.340 | 10.277 | 0.00 | 0.00 | 6 |
| C | ILE | B | 1 | 19.419 | 44.512 | 11.427 | 0.00 | 0.00 | 6 |
| O | ILE | B | 1 | 19.349 | 44.325 | 12.639 | 0.00 | 0.00 | 8 |
| N | SER | B | 1 | 18.355 | 44.552 | 10.638 | 0.00 | 0.00 | 7 |
| CA | SER | B | 1 | 17.017 | 44.340 | 11.172 | 0.00 | 0.00 | 6 |
| CB | SER | B | 1 | 16.019 | 44.254 | 10.011 | 0.00 | 0.00 | 6 |
| O | SER | B | 1 | 14.890 | 43.482 | 10.380 | 0.00 | 0.00 | 8 |
| C | SER | B | 1 | 16.975 | 43.051 | 11.978 | 0.00 | 0.00 | 6 |
| O | SER | B | 1 | 17.404 | 41.993 | 11.516 | 0.00 | 0.00 | 8 |
| N | PRO | B | 1 | 16.275 | 43.076 | 13.110 | 0.00 | 0.00 | 7 |
| C | PRO | B | 1 | 15.680 | 44.296 | 13.712 | 0.00 | 0.00 | 6 |
| CA | PRO | B | 1 | 16.053 | 41.902 | 13.934 | 0.00 | 0.00 | 6 |
| CB | PRO | B | 1 | 15.352 | 42.436 | 15.176 | 0.00 | 0.00 | 6 |
| C | PRO | B | 1 | 14.769 | 43.742 | 14.773 | 0.00 | 0.00 | 6 |
| C | PRO | B | 1 | 15.225 | 40.829 | 13.247 | 0.00 | 0.00 | 6 |
| O | PRO | B | 1 | 15.257 | 39.658 | 13.634 | 0.00 | 0.00 | 8 |
| N | PHE | B | 1 | 14.478 | 41.172 | 12.205 | 0.00 | 0.00 | 7 |
| CA | PHE | B | 1 | 13.730 | 40.219 | 11.409 | 0.00 | 0.00 | 6 |
| CB | PHE | B | 1 | 12.382 | 40.825 | 10.994 | 0.00 | 0.00 | 6 |
| C | PHE | B | 1 | 11.595 | 41.335 | 12.171 | 0.00 | 0.00 | 6 |
| C | PHE | B | 1 | 11.377 | 42.693 | 12.336 | 0.00 | 0.00 | 6 |
| C | PHE | B | 1 | 11.086 | 40.459 | 13.114 | 0.00 | 0.00 | 6 |
| CE | PHE | B | 1 | 10.663 | 43.168 | 13.420 | 0.00 | 0.00 | 6 |
| CE | PHE | B | 1 | 10.372 | 40.928 | 14.200 | 0.00 | 0.00 | 6 |
| CZ | PHE | B | 1 | 10.161 | 42.284 | 14.352 | 0.00 | 0.00 | 6 |
| C | PHE | B | 1 | 14.491 | 39.718 | 10.189 | 0.00 | 0.00 | 6 |
| O | PHE | B | 1 | 13.898 | 38.982 | 9.391 | 0.00 | 0.00 | 8 |
| N | PHE | B | 1 | 15.790 | 39.978 | 10.062 | 0.00 | 0.00 | 7 |
| CA | PHE | B | 1 | 16.551 | 39.486 | 8.923 | 0.00 | 0.00 | 6 |
| CB | PHE | B | 1 | 18.074 | 39.603 | 9.115 | 0.00 | 0.00 | 6 |
| C | PHE | B | 1 | 18.826 | 38.959 | 7.976 | 0.00 | 0.00 | 6 |
| C | PHE | B | 1 | 18.787 | 39.507 | 6.707 | 0.00 | 0.00 | 6 |
| C | PHE | B | 1 | 19.541 | 37.789 | 8.173 | 0.00 | 0.00 | 6 |
| CE | PHE | B | 1 | 19.458 | 38.912 | 5.657 | 0.00 | 0.00 | 6 |
| CE | PHE | B | 1 | 20.212 | 37.189 | 7.126 | 0.00 | 0.00 | 6 |
| CZ | PHE | B | 1 | 20.174 | 37.752 | 5.865 | 0.00 | 0.00 | 6 |
| C | PHE | B | 1 | 16.181 | 38.054 | 8.545 | 0.00 | 0.00 | 6 |
| O | PHE | B | 1 | 15.623 | 37.836 | 7.469 | 0.00 | 0.00 | 8 |

| | | | | | | | | |
|---|---|---|---|---|---|---|---|---|
| N | VAL | B | 1 | 16.502 | 37.077 | 9.381 | 0.00 | 0.00 | 7 |
| CA | VAL | B | 1 | 16.273 | 35.671 | 9.077 | 0.00 | 0.00 | 6 |
| CB | VAL | B | 1 | 16.761 | 34.775 | 10.235 | 0.00 | 0.00 | 6 |
| C | VAL | B | 1 | 16.528 | 33.300 | 9.955 | 0.00 | 0.00 | 6 |
| C | VAL | B | 1 | 18.237 | 35.028 | 10.508 | 0.00 | 0.00 | 6 |
| C | VAL | B | 1 | 14.848 | 35.319 | 8.695 | 0.00 | 0.00 | 6 |
| O | VAL | B | 1 | 14.578 | 34.863 | 7.578 | 0.00 | 0.00 | 8 |
| N | PRO | B | 1 | 13.874 | 35.543 | 9.572 | 0.00 | 0.00 | 7 |
| C | PRO | B | 1 | 14.098 | 36.089 | 10.939 | 0.00 | 0.00 | 6 |
| CA | PRO | B | 1 | 12.484 | 35.204 | 9.343 | 0.00 | 0.00 | 6 |
| CB | PRO | B | 1 | 11.775 | 35.569 | 10.644 | 0.00 | 0.00 | 6 |
| C | PRO | B | 1 | 12.327 | 35.760 | 11.666 | 0.00 | 0.00 | 6 |
| C | PRO | B | 1 | 11.804 | 35.891 | 8.174 | 0.00 | 0.00 | 6 |
| O | PRO | B | 1 | 10.742 | 35.457 | 7.712 | 0.00 | 0.00 | 8 |
| N | SER | B | 1 | 12.344 | 37.001 | 7.698 | 0.00 | 0.00 | 7 |
| CA | SER | B | 1 | 11.813 | 37.739 | 6.572 | 0.00 | 0.00 | 6 |
| CB | SER | B | 1 | 12.157 | 39.223 | 6.762 | 0.00 | 0.00 | 6 |
| O | SER | B | 1 | 13.534 | 39.457 | 6.544 | 0.00 | 0.00 | 8 |
| C | SER | B | 1 | 12.380 | 37.276 | 5.237 | 0.00 | 0.00 | 6 |
| O | SER | B | 1 | 11.814 | 37.593 | 4.187 | 0.00 | 0.00 | 8 |
| N | THR | B | 1 | 13.492 | 36.548 | 5.255 | 0.00 | 0.00 | 7 |
| CA | THR | B | 1 | 14.119 | 36.091 | 4.027 | 0.00 | 0.00 | 6 |
| CB | THR | B | 1 | 15.619 | 36.489 | 4.031 | 0.00 | 0.00 | 6 |
| O | THR | B | 1 | 16.341 | 35.919 | 5.189 | 0.00 | 0.00 | 8 |
| C | THR | B | 1 | 15.784 | 37.996 | 4.056 | 0.00 | 0.00 | 6 |
| C | THR | B | 1 | 14.063 | 34.605 | 3.728 | 0.00 | 0.00 | 6 |
| O | THR | B | 1 | 14.106 | 34.252 | 2.541 | 0.00 | 0.00 | 8 |
| N | ILE | B | 1 | 14.096 | 33.738 | 4.734 | 0.00 | 0.00 | 7 |
| CA | ILE | B | 1 | 14.235 | 32.307 | 4.459 | 0.00 | 0.00 | 6 |
| CB | ILE | B | 1 | 14.751 | 31.537 | 5.682 | 0.00 | 0.00 | 6 |
| C | ILE | B | 1 | 16.167 | 32.021 | 5.995 | 0.00 | 0.00 | 6 |
| C | ILE | B | 1 | 13.841 | 31.706 | 6.894 | 0.00 | 0.00 | 6 |
| C | ILE | B | 1 | 14.237 | 30.867 | 8.092 | 0.00 | 0.00 | 6 |
| C | ILE | B | 1 | 12.991 | 31.691 | 3.849 | 0.00 | 0.00 | 6 |
| O | ILE | B | 1 | 11.839 | 32.013 | 4.121 | 0.00 | 0.00 | 8 |
| N | VAL | B | 1 | 13.232 | 30.753 | 2.945 | 0.00 | 0.00 | 7 |
| CA | VAL | B | 1 | 12.270 | 30.056 | 2.121 | 0.00 | 0.00 | 6 |
| CB | VAL | B | 1 | 13.026 | 29.000 | 1.273 | 0.00 | 0.00 | 6 |
| C | VAL | B | 1 | 12.144 | 27.905 | 0.709 | 0.00 | 0.00 | 6 |
| C | VAL | B | 1 | 13.746 | 29.720 | 0.133 | 0.00 | 0.00 | 6 |
| C | VAL | B | 1 | 11.076 | 29.441 | 2.815 | 0.00 | 0.00 | 6 |
| O | VAL | B | 1 | 9.968 | 29.507 | 2.257 | 0.00 | 0.00 | 8 |
| N | ASN | B | 1 | 11.223 | 28.843 | 3.991 | 0.00 | 0.00 | 7 |
| CA | ASN | B | 1 | 10.104 | 28.184 | 4.651 | 0.00 | 0.00 | 6 |
| CB | ASN | B | 1 | 10.649 | 27.054 | 5.540 | 0.00 | 0.00 | 6 |
| C | ASN | B | 1 | 11.359 | 27.603 | 6.762 | 0.00 | 0.00 | 6 |
| O | ASN | B | 1 | 12.384 | 28.270 | 6.633 | 0.00 | 0.00 | 8 |
| N | ASN | B | 1 | 10.778 | 27.372 | 7.933 | 0.00 | 0.00 | 7 |
| C | ASN | B | 1 | 9.195 | 29.110 | 5.443 | 0.00 | 0.00 | 6 |
| O | ASN | B | 1 | 8.200 | 28.637 | 6.008 | 0.00 | 0.00 | 8 |
| N | MET | B | 1 | 9.426 | 30.418 | 5.435 | 0.00 | 0.00 | 7 |
| CA | MET | B | 1 | 8.615 | 31.358 | 6.196 | 0.00 | 0.00 | 6 |
| CB | MET | B | 1 | 9.409 | 32.622 | 6.529 | 0.00 | 0.00 | 6 |
| C | MET | B | 1 | 10.438 | 32.377 | 7.629 | 0.00 | 0.00 | 6 |
| SD | MET | B | 1 | 9.791 | 31.455 | 9.040 | 0.00 | 0.00 | 1 |
| CE | MET | B | 1 | 8.541 | 32.587 | 9.643 | 0.00 | 0.00 | 6 |
| C | MET | B | 1 | 7.251 | 31.641 | 5.593 | 0.00 | 0.00 | 6 |
| O | MET | B | 1 | 6.382 | 32.153 | 6.317 | 0.00 | 0.00 | 8 |
| N | VAL | B | 1 | 6.994 | 31.286 | 4.337 | 0.00 | 0.00 | 7 |
| CA | VAL | B | 1 | 5.661 | 31.471 | 3.771 | 0.00 | 0.00 | 6 |
| CB | VAL | B | 1 | 5.563 | 31.317 | 2.251 | 0.00 | 0.00 | 6 |
| C | VAL | B | 1 | 4.127 | 31.559 | 1.785 | 0.00 | 0.00 | 6 |
| C | VAL | B | 1 | 6.503 | 32.273 | 1.536 | 0.00 | 0.00 | 6 |
| C | VAL | B | 1 | 4.753 | 30.425 | 4.435 | 0.00 | 0.00 | 6 |

Figure 1 - 32

| | | | | | | | | | |
|---|---|---|---|---|---|---|---|---|---|
| O | VAL | B | 1 | 3.637 | 30.717 | 4.856 | 0.00 | 0.00 | 8 |
| N | ALA | B | 1 | 5.264 | 29.202 | 4.561 | 0.00 | 0.00 | 7 |
| CA | ALA | B | 1 | 4.540 | 28.115 | 5.214 | 0.00 | 0.00 | 6 |
| CB | ALA | B | 1 | 5.166 | 26.767 | 4.897 | 0.00 | 0.00 | 6 |
| C | ALA | B | 1 | 4.490 | 28.344 | 6.723 | 0.00 | 0.00 | 6 |
| O | ALA | B | 1 | 3.491 | 28.053 | 7.378 | 0.00 | 0.00 | 8 |
| N | GLY | B | 1 | 5.544 | 28.940 | 7.275 | 0.00 | 0.00 | 7 |
| CA | GLY | B | 1 | 5.559 | 29.332 | 8.678 | 0.00 | 0.00 | 6 |
| C | GLY | B | 1 | 4.428 | 30.316 | 8.970 | 0.00 | 0.00 | 6 |
| O | GLY | B | 1 | 3.660 | 30.100 | 9.905 | 0.00 | 0.00 | 8 |
| N | HIS | B | 1 | 4.297 | 31.369 | 8.172 | 0.00 | 0.00 | 7 |
| CA | HIS | B | 1 | 3.265 | 32.372 | 8.362 | 0.00 | 0.00 | 6 |
| CB | HIS | B | 1 | 3.500 | 33.598 | 7.458 | 0.00 | 0.00 | 6 |
| C | HIS | B | 1 | 4.431 | 34.570 | 8.124 | 0.00 | 0.00 | 6 |
| C | HIS | B | 1 | 4.275 | 35.318 | 9.242 | 0.00 | 0.00 | 6 |
| N | HIS | B | 1 | 5.706 | 34.815 | 7.668 | 0.00 | 0.00 | 7 |
| CE | HIS | B | 1 | 6.292 | 35.692 | 8.467 | 0.00 | 0.00 | 6 |
| N | HIS | B | 1 | 5.445 | 36.011 | 9.430 | 0.00 | 0.00 | 7 |
| C | HIS | B | 1 | 1.848 | 31.858 | 8.173 | 0.00 | 0.00 | 6 |
| O | HIS | B | 1 | 0.973 | 32.218 | 8.967 | 0.00 | 0.00 | 8 |
| N | LEU | B | 1 | 1.607 | 31.030 | 7.163 | 0.00 | 0.00 | 7 |
| CA | LEU | B | 1 | 0.266 | 30.503 | 6.932 | 0.00 | 0.00 | 6 |
| CB | LEU | B | 1 | 0.168 | 29.849 | 5.555 | 0.00 | 0.00 | 6 |
| C | LEU | B | 1 | -0.056 | 30.793 | 4.370 | 0.00 | 0.00 | 6 |
| C | LEU | B | 1 | -0.048 | 30.022 | 3.059 | 0.00 | 0.00 | 6 |
| C | LEU | B | 1 | -1.358 | 31.569 | 4.510 | 0.00 | 0.00 | 6 |
| C | LEU | B | 1 | -0.166 | 29.542 | 8.032 | 0.00 | 0.00 | 6 |
| O | LEU | B | 1 | -1.310 | 29.610 | 8.492 | 0.00 | 0.00 | 8 |
| N | THR | B | 1 | 0.730 | 28.664 | 8.475 | 0.00 | 0.00 | 7 |
| CA | THR | B | 1 | 0.426 | 27.711 | 9.532 | 0.00 | 0.00 | 6 |
| CB | THR | B | 1 | 1.631 | 26.830 | 9.914 | 0.00 | 0.00 | 6 |
| O | THR | B | 1 | 2.757 | 27.667 | 10.197 | 0.00 | 0.00 | 8 |
| C | THR | B | 1 | 1.992 | 25.855 | 8.809 | 0.00 | 0.00 | 6 |
| C | THR | B | 1 | -0.059 | 28.425 | 10.792 | 0.00 | 0.00 | 6 |
| O | THR | B | 1 | -1.095 | 28.062 | 11.350 | 0.00 | 0.00 | 8 |
| N | ILE | B | 1 | 0.684 | 29.432 | 11.241 | 0.00 | 0.00 | 7 |
| CA | ILE | B | 1 | 0.294 | 30.233 | 12.394 | 0.00 | 0.00 | 6 |
| CB | ILE | B | 1 | 1.322 | 31.337 | 12.704 | 0.00 | 0.00 | 6 |
| C | ILE | B | 1 | 0.901 | 32.152 | 13.919 | 0.00 | 0.00 | 6 |
| C | ILE | B | 1 | 2.717 | 30.744 | 12.924 | 0.00 | 0.00 | 6 |
| C | ILE | B | 1 | 3.835 | 31.734 | 12.670 | 0.00 | 0.00 | 6 |
| C | ILE | B | 1 | -1.064 | 30.889 | 12.164 | 0.00 | 0.00 | 6 |
| O | ILE | B | 1 | -1.985 | 30.755 | 12.966 | 0.00 | 0.00 | 8 |
| N | MET | B | 1 | -1.198 | 31.602 | 11.053 | 0.00 | 0.00 | 7 |
| CA | MET | B | 1 | -2.421 | 32.291 | 10.686 | 0.00 | 0.00 | 6 |
| CB | MET | B | 1 | -2.277 | 32.883 | 9.277 | 0.00 | 0.00 | 6 |
| C | MET | B | 1 | -1.466 | 34.169 | 9.239 | 0.00 | 0.00 | 6 |
| SD | MET | B | 1 | -1.371 | 34.872 | 7.581 | 0.00 | 0.00 | 1 |
| CE | MET | B | 1 | -3.003 | 35.600 | 7.440 | 0.00 | 0.00 | 6 |
| C | MET | B | 1 | -3.674 | 31.430 | 10.747 | 0.00 | 0.00 | 6 |
| O | MET | B | 1 | -4.699 | 31.904 | 11.247 | 0.00 | 0.00 | 8 |
| N | TYR | B | 1 | -3.646 | 30.208 | 10.223 | 0.00 | 0.00 | 7 |
| CA | TYR | B | 1 | -4.813 | 29.343 | 10.220 | 0.00 | 0.00 | 6 |
| CB | TYR | B | 1 | -4.979 | 28.707 | 8.822 | 0.00 | 0.00 | 6 |
| C | TYR | B | 1 | -5.493 | 29.747 | 7.843 | 0.00 | 0.00 | 6 |
| C | TYR | B | 1 | -4.612 | 30.494 | 7.073 | 0.00 | 0.00 | 6 |
| CE | TYR | B | 1 | -5.080 | 31.452 | 6.193 | 0.00 | 0.00 | 6 |
| C | TYR | B | 1 | -6.854 | 29.990 | 7.720 | 0.00 | 0.00 | 6 |
| CE | TYR | B | 1 | -7.326 | 30.946 | 6.840 | 0.00 | 0.00 | 6 |
| CZ | TYR | B | 1 | -6.435 | 31.673 | 6.080 | 0.00 | 0.00 | 6 |
| O | TYR | B | 1 | -6.902 | 32.625 | 5.205 | 0.00 | 0.00 | 8 |
| C | TYR | B | 1 | -4.789 | 28.247 | 11.272 | 0.00 | 0.00 | 6 |
| O | TYR | B | 1 | -5.725 | 27.442 | 11.334 | 0.00 | 0.00 | 8 |
| N | GLY | B | 1 | -3.724 | 28.155 | 12.060 | 0.00 | 0.00 | 7 |
| CA | GLY | B | 1 | -3.602 | 27.108 | 13.063 | 0.00 | 0.00 | 6 |
| C | GLY | B | 1 | -3.408 | 25.731 | 12.443 | 0.00 | 0.00 | 6 |
| O | GLY | B | 1 | -3.950 | 24.744 | 12.947 | 0.00 | 0.00 | 8 |
| N | LEU | B | 1 | -2.623 | 25.649 | 11.371 | 0.00 | 0.00 | 7 |
| CA | LEU | B | 1 | -2.343 | 24.371 | 10.718 | 0.00 | 0.00 | 6 |
| CB | LEU | B | 1 | -1.965 | 24.563 | 9.253 | 0.00 | 0.00 | 6 |
| C | LEU | B | 1 | -2.858 | 25.463 | 8.399 | 0.00 | 0.00 | 6 |
| C | LEU | B | 1 | -2.224 | 25.720 | 7.038 | 0.00 | 0.00 | 6 |
| C | LEU | B | 1 | -4.246 | 24.864 | 8.225 | 0.00 | 0.00 | 6 |
| C | LEU | B | 1 | -1.230 | 23.648 | 11.474 | 0.00 | 0.00 | 6 |
| O | LEU | B | 1 | -0.104 | 24.136 | 11.573 | 0.00 | 0.00 | 8 |
| N | ARG | B | 1 | -1.566 | 22.508 | 12.067 | 0.00 | 0.00 | 7 |
| CA | ARG | B | 1 | -0.631 | 21.762 | 12.899 | 0.00 | 0.00 | 6 |
| CB | ARG | B | 1 | -1.276 | 21.448 | 14.255 | 0.00 | 0.00 | 6 |
| C | ARG | B | 1 | -2.011 | 22.615 | 14.892 | 0.00 | 0.00 | 6 |
| C | ARG | B | 1 | -1.894 | 22.647 | 16.405 | 0.00 | 0.00 | 6 |
| N | ARG | B | 1 | -2.138 | 21.346 | 17.010 | 0.00 | 0.00 | 7 |
| CZ | ARG | B | 1 | -1.376 | 20.762 | 17.925 | 0.00 | 0.00 | 6 |
| N | ARG | B | 1 | -0.282 | 21.358 | 18.380 | 0.00 | 0.00 | 7 |
| N | ARG | B | 1 | -1.706 | 19.564 | 18.391 | 0.00 | 0.00 | 7 |
| C | ARG | B | 1 | -0.131 | 20.491 | 12.228 | 0.00 | 0.00 | 6 |
| O | ARG | B | 1 | 0.615 | 19.715 | 12.826 | 0.00 | 0.00 | 8 |
| N | GLY | B | 1 | -0.521 | 20.281 | 10.975 | 0.00 | 0.00 | 7 |
| CA | GLY | B | 1 | -0.085 | 19.111 | 10.221 | 0.00 | 0.00 | 6 |
| C | GLY | B | 1 | 1.312 | 19.349 | 9.649 | 0.00 | 0.00 | 6 |
| O | GLY | B | 1 | 1.986 | 20.324 | 9.981 | 0.00 | 0.00 | 8 |
| N | PRO | B | 1 | 1.752 | 18.443 | 8.780 | 0.00 | 0.00 | 7 |
| C | PRO | B | 1 | 0.931 | 17.259 | 8.332 | 0.00 | 0.00 | 6 |
| CA | PRO | B | 1 | 3.060 | 18.520 | 8.166 | 0.00 | 0.00 | 6 |
| CB | PRO | B | 1 | 3.030 | 17.388 | 7.154 | 0.00 | 0.00 | 6 |
| C | PRO | B | 1 | 1.910 | 16.524 | 7.418 | 0.00 | 0.00 | 6 |
| C | PRO | B | 1 | 3.326 | 19.856 | 7.488 | 0.00 | 0.00 | 6 |
| O | PRO | B | 1 | 2.459 | 20.415 | 6.817 | 0.00 | 0.00 | 8 |
| N | SER | B | 1 | 4.550 | 20.358 | 7.629 | 0.00 | 0.00 | 7 |
| CA | SER | B | 1 | 4.948 | 21.620 | 7.023 | 0.00 | 0.00 | 6 |
| CB | SER | B | 1 | 5.030 | 22.706 | 8.103 | 0.00 | 0.00 | 6 |
| O | SER | B | 1 | 5.316 | 23.967 | 7.525 | 0.00 | 0.00 | 8 |
| C | SER | B | 1 | 6.298 | 21.513 | 6.329 | 0.00 | 0.00 | 6 |
| O | SER | B | 1 | 7.318 | 21.410 | 7.016 | 0.00 | 0.00 | 8 |
| N | ILE | B | 1 | 6.332 | 21.523 | 4.995 | 0.00 | 0.00 | 7 |
| CA | ILE | B | 1 | 7.607 | 21.466 | 4.297 | 0.00 | 0.00 | 6 |
| CB | ILE | B | 1 | 7.940 | 20.151 | 3.579 | 0.00 | 0.00 | 6 |
| C | ILE | B | 1 | 8.364 | 19.067 | 4.559 | 0.00 | 0.00 | 6 |
| C | ILE | B | 1 | 6.785 | 19.678 | 2.691 | 0.00 | 0.00 | 6 |
| C | ILE | B | 1 | 7.240 | 18.715 | 1.610 | 0.00 | 0.00 | 6 |
| C | ILE | B | 1 | 7.707 | 22.588 | 3.259 | 0.00 | 0.00 | 6 |
| O | ILE | B | 1 | 6.736 | 23.244 | 2.899 | 0.00 | 0.00 | 8 |
| N | SER | B | 1 | 8.933 | 22.791 | 2.791 | 0.00 | 0.00 | 7 |
| CA | SER | B | 1 | 9.240 | 23.780 | 1.776 | 0.00 | 0.00 | 6 |
| CB | SER | B | 1 | 9.758 | 25.085 | 2.374 | 0.00 | 0.00 | 6 |
| O | SER | B | 1 | 8.801 | 25.734 | 3.183 | 0.00 | 0.00 | 8 |
| C | SER | B | 1 | 10.302 | 23.215 | 0.830 | 0.00 | 0.00 | 6 |
| O | SER | B | 1 | 11.438 | 23.009 | 1.268 | 0.00 | 0.00 | 8 |
| N | ILE | B | 1 | 9.931 | 22.967 | -0.422 | 0.00 | 0.00 | 7 |
| CA | ILE | B | 1 | 10.914 | 22.452 | -1.379 | 0.00 | 0.00 | 6 |
| CB | ILE | B | 1 | 10.388 | 21.323 | -2.271 | 0.00 | 0.00 | 6 |
| C | ILE | B | 1 | 11.465 | 20.868 | -3.253 | 0.00 | 0.00 | 6 |
| C | ILE | B | 1 | 9.935 | 20.152 | -1.394 | 0.00 | 0.00 | 6 |
| C | ILE | B | 1 | 9.301 | 18.996 | -2.125 | 0.00 | 0.00 | 6 |
| C | ILE | B | 1 | 11.446 | 23.618 | -2.212 | 0.00 | 0.00 | 6 |
| O | ILE | B | 1 | 10.696 | 24.455 | -2.710 | 0.00 | 0.00 | 8 |
| N | ALA | B | 1 | 12.768 | 23.693 | -2.305 | 0.00 | 0.00 | 7 |
| CA | ALA | B | 1 | 13.431 | 24.762 | -3.047 | 0.00 | 0.00 | 6 |
| CB | ALA | B | 1 | 14.296 | 25.583 | -2.105 | 0.00 | 0.00 | 6 |

Figure 1 - 33

| | | | | | | | | |
|---|---|---|---|---|---|---|---|---|
| C | ALA | B | 1 | 14.257 | 24.163 | -4.180 | 0.00 | 0.00 | 6 |
| O | ALA | B | 1 | 15.430 | 23.831 | -4.015 | 0.00 | 0.00 | 8 |
| N | THR | B | 1 | 13.619 | 24.005 | -5.336 | 0.00 | 0.00 | 7 |
| CA | THR | B | 1 | 14.295 | 23.435 | -6.499 | 0.00 | 0.00 | 6 |
| CB | THR | B | 1 | 13.706 | 22.064 | -6.879 | 0.00 | 0.00 | 6 |
| O | THR | B | 1 | 12.282 | 22.111 | -6.725 | 0.00 | 0.00 | 8 |
| C | THR | B | 1 | 14.265 | 20.963 | -5.992 | 0.00 | 0.00 | 6 |
| C | THR | B | 1 | 14.225 | 24.390 | -7.684 | 0.00 | 0.00 | 6 |
| O | THR | B | 1 | 13.789 | 24.006 | -8.770 | 0.00 | 0.00 | 8 |
| N | ALA | B | 1 | 14.611 | 25.645 | -7.453 | 0.00 | 0.00 | 7 |
| CA | ALA | B | 1 | 14.614 | 26.639 | -8.530 | 0.00 | 0.00 | 6 |
| CB | ALA | B | 1 | 15.804 | 26.381 | -9.445 | 0.00 | 0.00 | 6 |
| C | ALA | B | 1 | 13.303 | 26.601 | -9.297 | 0.00 | 0.00 | 6 |
| O | ALA | B | 1 | 13.228 | 26.596 | -8.690 | 0.00 | 0.00 | 8 |
| N | CYS | B | 1 | 13.347 | 26.441 | -10.615 | 0.00 | 0.00 | 7 |
| CA | CYS | B | 1 | 12.193 | 26.376 | -11.482 | 0.00 | 0.00 | 6 |
| CB | CYS | B | 1 | 12.628 | 26.275 | -12.957 | 0.00 | 0.00 | 6 |
| SG | CYS | B | 1 | 14.176 | 27.109 | -13.348 | 0.00 | 0.00 | 1 |
| C | CYS | B | 1 | 11.226 | 25.225 | -11.252 | 0.00 | 0.00 | 6 |
| O | CYS | B | 1 | 10.137 | 25.253 | -11.841 | 0.00 | 0.00 | 8 |
| N | THR | B | 1 | 11.590 | 24.199 | -10.504 | 0.00 | 0.00 | 7 |
| CA | THR | B | 1 | 10.719 | 23.048 | -10.288 | 0.00 | 0.00 | 6 |
| CB | THR | B | 1 | 11.539 | 21.749 | -10.439 | 0.00 | 0.00 | 6 |
| O | THR | B | 1 | 12.396 | 21.886 | -11.585 | 0.00 | 0.00 | 8 |
| C | THR | B | 1 | 10.650 | 20.535 | -10.627 | 0.00 | 0.00 | 6 |
| C | THR | B | 1 | 10.032 | 23.098 | -8.938 | 0.00 | 0.00 | 6 |
| O | THR | B | 1 | 9.161 | 22.283 | -8.628 | 0.00 | 0.00 | 8 |
| N | SER | B | 1 | 10.337 | 24.113 | -8.140 | 0.00 | 0.00 | 7 |
| CA | SER | B | 1 | 9.812 | 24.266 | -6.795 | 0.00 | 0.00 | 6 |
| CB | SER | B | 1 | 10.152 | 25.653 | -6.239 | 0.00 | 0.00 | 6 |
| O | SER | B | 1 | 11.536 | 25.806 | -6.014 | 0.00 | 0.00 | 8 |
| C | SER | B | 1 | 8.307 | 24.060 | -6.707 | 0.00 | 0.00 | 6 |
| O | SER | B | 1 | 7.817 | 23.238 | -5.928 | 0.00 | 0.00 | 8 |
| N | GLY | B | 1 | 7.553 | 24.825 | -7.490 | 0.00 | 0.00 | 7 |
| CA | GLY | B | 1 | 6.101 | 24.743 | -7.493 | 0.00 | 0.00 | 6 |
| C | GLY | B | 1 | 5.595 | 23.335 | -7.766 | 0.00 | 0.00 | 6 |
| O | GLY | B | 1 | 4.639 | 22.887 | -7.132 | 0.00 | 0.00 | 8 |
| N | VAL | B | 1 | 6.179 | 22.652 | -8.744 | 0.00 | 0.00 | 7 |
| CA | VAL | B | 1 | 5.760 | 21.301 | -9.104 | 0.00 | 0.00 | 6 |
| CB | VAL | B | 1 | 6.323 | 20.917 | -10.485 | 0.00 | 0.00 | 6 |
| C | VAL | B | 1 | 6.367 | 19.415 | -10.713 | 0.00 | 0.00 | 6 |
| C | VAL | B | 1 | 5.496 | 21.585 | -11.579 | 0.00 | 0.00 | 6 |
| C | VAL | B | 1 | 6.160 | 20.281 | -8.048 | 0.00 | 0.00 | 6 |
| O | VAL | B | 1 | 5.406 | 19.338 | -7.792 | 0.00 | 0.00 | 8 |
| N | HIS | B | 1 | 7.331 | 20.442 | -7.442 | 0.00 | 0.00 | 7 |
| CA | HIS | B | 1 | 7.801 | 19.513 | -6.424 | 0.00 | 0.00 | 6 |
| CB | HIS | B | 1 | 9.283 | 19.738 | -6.120 | 0.00 | 0.00 | 6 |
| C | HIS | B | 1 | 10.227 | 19.073 | -7.069 | 0.00 | 0.00 | 6 |
| C | HIS | B | 1 | 10.065 | 18.056 | -7.947 | 0.00 | 0.00 | 6 |
| N | HIS | B | 1 | 11.548 | 19.464 | -7.180 | 0.00 | 0.00 | 7 |
| CE | HIS | B | 1 | 12.149 | 18.717 | -8.085 | 0.00 | 0.00 | 6 |
| N | HIS | B | 1 | 11.273 | 17.856 | -8.571 | 0.00 | 0.00 | 7 |
| C | HIS | B | 1 | 6.988 | 19.628 | -5.138 | 0.00 | 0.00 | 6 |
| O | HIS | B | 1 | 6.696 | 18.622 | -4.489 | 0.00 | 0.00 | 8 |
| N | ASN | B | 1 | 6.653 | 20.858 | -4.760 | 0.00 | 0.00 | 7 |
| CA | ASN | B | 1 | 5.874 | 21.100 | -3.551 | 0.00 | 0.00 | 6 |
| CB | ASN | B | 1 | 5.824 | 22.595 | -3.249 | 0.00 | 0.00 | 6 |
| C | ASN | B | 1 | 7.045 | 23.130 | -2.535 | 0.00 | 0.00 | 6 |
| O | ASN | B | 1 | 7.850 | 23.876 | -3.102 | 0.00 | 0.00 | 8 |
| N | ASN | B | 1 | 7.210 | 22.772 | -1.268 | 0.00 | 0.00 | 7 |
| C | ASN | B | 1 | 4.472 | 20.516 | -3.684 | 0.00 | 0.00 | 6 |
| O | ASN | B | 1 | 4.023 | 19.748 | -2.832 | 0.00 | 0.00 | 8 |
| N | ILE | B | 1 | 3.796 | 20.808 | -4.791 | 0.00 | 0.00 | 7 |
| CA | ILE | B | 1 | 2.461 | 20.283 | -5.057 | 0.00 | 0.00 | 6 |

| | | | | | | | | |
|---|---|---|---|---|---|---|---|---|
| CB | ILE | B | 1 | 1.889 | 20.822 | -6.382 | 0.00 | 0.00 | 6 |
| C | ILE | B | 1 | 0.616 | 20.091 | -6.787 | 0.00 | 0.00 | 6 |
| C | ILE | B | 1 | 1.623 | 22.325 | -6.258 | 0.00 | 0.00 | 6 |
| C | ILE | B | 1 | 1.353 | 23.023 | -7.570 | 0.00 | 0.00 | 6 |
| C | ILE | B | 1 | 2.446 | 19.758 | -5.061 | 0.00 | 0.00 | 6 |
| O | ILE | B | 1 | 1.580 | 18.154 | -4.427 | 0.00 | 0.00 | 8 |
| N | GLY | B | 1 | 3.384 | 18.133 | -5.762 | 0.00 | 0.00 | 7 |
| CA | GLY | B | 1 | 3.472 | 16.684 | -5.812 | 0.00 | 0.00 | 6 |
| C | GLY | B | 1 | 3.309 | 16.032 | -4.479 | 0.00 | 0.00 | 6 |
| O | GLY | B | 1 | 3.271 | 14.959 | -4.179 | 0.00 | 0.00 | 8 |
| N | HIS | B | 1 | 4.669 | 16.644 | -3.659 | 0.00 | 0.00 | 7 |
| CA | HIS | B | 1 | 5.026 | 16.030 | -2.374 | 0.00 | 0.00 | 6 |
| CB | HIS | B | 1 | 6.437 | 16.407 | -1.924 | 0.00 | 0.00 | 6 |
| C | HIS | B | 1 | 7.414 | 15.486 | -2.612 | 0.00 | 0.00 | 6 |
| C | HIS | B | 1 | 7.712 | 14.188 | -2.381 | 0.00 | 0.00 | 6 |
| N | HIS | B | 1 | 8.157 | 15.865 | -3.705 | 0.00 | 0.00 | 7 |
| CE | HIS | B | 1 | 8.893 | 14.846 | -4.108 | 0.00 | 0.00 | 6 |
| N | HIS | B | 1 | 8.641 | 13.816 | -3.321 | 0.00 | 0.00 | 7 |
| C | HIS | B | 1 | 3.927 | 16.250 | -1.352 | 0.00 | 0.00 | 6 |
| O | HIS | B | 1 | 3.717 | 15.434 | -0.451 | 0.00 | 0.00 | 8 |
| N | ALA | B | 1 | 3.120 | 17.291 | -1.551 | 0.00 | 0.00 | 7 |
| CA | ALA | B | 1 | 1.950 | 17.523 | -0.711 | 0.00 | 0.00 | 6 |
| CB | ALA | B | 1 | 1.309 | 18.858 | -1.039 | 0.00 | 0.00 | 6 |
| C | ALA | B | 1 | 0.957 | 16.381 | -0.957 | 0.00 | 0.00 | 6 |
| O | ALA | B | 1 | 0.366 | 15.835 | -0.027 | 0.00 | 0.00 | 8 |
| N | ALA | B | 1 | 0.830 | 15.965 | -2.216 | 0.00 | 0.00 | 7 |
| CA | ALA | B | 1 | -0.014 | 14.846 | -2.605 | 0.00 | 0.00 | 6 |
| CB | ALA | B | 1 | -0.214 | 14.809 | -4.111 | 0.00 | 0.00 | 6 |
| C | ALA | B | 1 | 0.554 | 13.522 | -2.103 | 0.00 | 0.00 | 6 |
| O | ALA | B | 1 | -0.207 | 12.678 | -1.626 | 0.00 | 0.00 | 8 |
| N | ARG | B | 1 | 1.874 | 13.351 | -2.173 | 0.00 | 0.00 | 7 |
| CA | ARG | B | 1 | 2.492 | 12.133 | -1.648 | 0.00 | 0.00 | 6 |
| CB | ARG | B | 1 | 3.989 | 12.067 | -1.913 | 0.00 | 0.00 | 6 |
| C | ARG | B | 1 | 4.401 | 11.956 | -3.365 | 0.00 | 0.00 | 6 |
| C | ARG | B | 1 | 4.151 | 10.572 | -3.938 | 0.00 | 0.00 | 6 |
| N | ARG | B | 1 | 4.957 | 10.308 | -5.126 | 0.00 | 0.00 | 7 |
| CZ | ARG | B | 1 | 4.522 | 10.309 | -6.379 | 0.00 | 0.00 | 6 |
| N | ARG | B | 1 | 3.249 | 10.571 | -6.653 | 0.00 | 0.00 | 7 |
| N | ARG | B | 1 | 5.356 | 10.051 | -7.383 | 0.00 | 0.00 | 7 |
| C | ARG | B | 1 | 2.214 | 12.059 | -0.146 | 0.00 | 0.00 | 6 |
| O | ARG | B | 1 | 1.649 | 11.071 | 0.322 | 0.00 | 0.00 | 8 |
| N | ILE | B | 1 | 2.447 | 13.162 | 0.571 | 0.00 | 0.00 | 7 |
| CA | ILE | B | 1 | 2.099 | 13.235 | 1.987 | 0.00 | 0.00 | 6 |
| CB | ILE | B | 1 | 2.372 | 14.616 | 2.602 | 0.00 | 0.00 | 6 |
| C | ILE | B | 1 | 1.809 | 14.724 | 4.014 | 0.00 | 0.00 | 6 |
| C | ILE | B | 1 | 3.875 | 14.919 | 2.636 | 0.00 | 0.00 | 6 |
| C | ILE | B | 1 | 4.196 | 16.360 | 2.989 | 0.00 | 0.00 | 6 |
| C | ILE | B | 1 | 0.643 | 12.838 | 2.206 | 0.00 | 0.00 | 6 |
| O | ILE | B | 1 | 0.373 | 11.945 | 3.013 | 0.00 | 0.00 | 8 |
| N | ILE | B | 1 | -0.292 | 13.468 | 1.498 | 0.00 | 0.00 | 7 |
| CA | ILE | B | 1 | -1.708 | 13.143 | 1.645 | 0.00 | 0.00 | 6 |
| CB | ILE | B | 1 | -2.595 | 14.047 | 0.770 | 0.00 | 0.00 | 6 |
| C | ILE | B | 1 | -4.000 | 13.490 | 0.605 | 0.00 | 0.00 | 6 |
| C | ILE | B | 1 | -2.638 | 15.440 | 1.408 | 0.00 | 0.00 | 6 |
| C | ILE | B | 1 | -3.382 | 16.479 | 0.614 | 0.00 | 0.00 | 6 |
| C | ILE | B | 1 | -1.995 | 11.678 | 1.362 | 0.00 | 0.00 | 6 |
| O | ILE | B | 1 | -2.629 | 11.012 | 2.183 | 0.00 | 0.00 | 8 |
| N | ALA | B | 1 | -1.469 | 11.137 | 0.271 | 0.00 | 0.00 | 7 |
| CA | ALA | B | 1 | -1.659 | 9.743 | -0.091 | 0.00 | 0.00 | 6 |
| CB | ALA | B | 1 | -1.078 | 9.497 | -1.479 | 0.00 | 0.00 | 6 |
| C | ALA | B | 1 | -1.059 | 8.761 | 0.903 | 0.00 | 0.00 | 6 |
| O | ALA | B | 1 | -1.522 | 7.620 | 1.009 | 0.00 | 0.00 | 8 |
| N | TYR | B | 1 | -0.031 | 9.162 | 1.642 | 0.00 | 0.00 | 7 |
| CA | TYR | B | 1 | 0.606 | 8.329 | 2.645 | 0.00 | 0.00 | 6 |

Figure 1 - 34

| | | | | | | | | |
|---|---|---|---|---|---|---|---|---|
| CB | TYR | B | 1 | 2.014 | 8.854 | 2.943 | 0.00 | 0.00 | 6 |
| C | TYR | B | 1 | 2.850 | 7.925 | 3.794 | 0.00 | 0.00 | 6 |
| C | TYR | B | 1 | 3.636 | 6.939 | 3.212 | 0.00 | 0.00 | 6 |
| CE | TYR | B | 1 | 4.401 | 6.086 | 3.986 | 0.00 | 0.00 | 6 |
| C | TYR | B | 1 | 2.852 | 8.034 | 5.177 | 0.00 | 0.00 | 6 |
| CE | TYR | B | 1 | 3.610 | 7.186 | 5.953 | 0.00 | 0.00 | 6 |
| CZ | TYR | B | 1 | 4.384 | 6.216 | 5.358 | 0.00 | 0.00 | 6 |
| O | TYR | B | 1 | 5.142 | 5.374 | 6.138 | 0.00 | 0.00 | 8 |
| C | TYR | B | 1 | -0.198 | 8.250 | 3.937 | 0.00 | 0.00 | 6 |
| O | TYR | B | 1 | -0.104 | 7.256 | 4.662 | 0.00 | 0.00 | 8 |
| N | GLY | B | 1 | -0.963 | 9.293 | 4.248 | 0.00 | 0.00 | 7 |
| CA | GLY | B | 1 | -1.773 | 9.308 | 5.455 | 0.00 | 0.00 | 6 |
| C | GLY | B | 1 | -1.314 | 10.320 | 6.490 | 0.00 | 0.00 | 6 |
| O | GLY | B | 1 | -1.960 | 10.471 | 7.533 | 0.00 | 0.00 | 8 |
| N | ASP | B | 1 | -0.278 | 11.098 | 6.180 | 0.00 | 0.00 | 7 |
| CA | ASP | B | 1 | 0.254 | 12.078 | 7.116 | 0.00 | 0.00 | 6 |
| CB | ASP | B | 1 | 1.692 | 12.465 | 6.736 | 0.00 | 0.00 | 6 |
| C | ASP | B | 1 | 2.678 | 11.416 | 7.227 | 0.00 | 0.00 | 6 |
| O | ASP | B | 1 | 3.710 | 11.204 | 6.560 | 0.00 | 0.00 | 8 |
| O | ASP | B | 1 | 2.400 | 10.811 | 8.284 | 0.00 | 0.00 | 8 |
| C | ASP | B | 1 | -0.599 | 13.330 | 7.234 | 0.00 | 0.00 | 6 |
| O | ASP | B | 1 | -0.518 | 14.047 | 8.234 | 0.00 | 0.00 | 8 |
| N | ALA | B | 1 | -1.408 | 13.603 | 6.218 | 0.00 | 0.00 | 7 |
| CA | ALA | B | 1 | -2.282 | 14.768 | 6.227 | 0.00 | 0.00 | 6 |
| CB | ALA | B | 1 | -1.545 | 15.978 | 5.671 | 0.00 | 0.00 | 6 |
| C | ALA | B | 1 | -3.538 | 14.484 | 5.410 | 0.00 | 0.00 | 6 |
| O | ALA | B | 1 | -3.555 | 13.544 | 4.613 | 0.00 | 0.00 | 8 |
| N | ASP | B | 1 | -4.573 | 15.288 | 5.622 | 0.00 | 0.00 | 7 |
| CA | ASP | B | 1 | -5.808 | 15.128 | 4.857 | 0.00 | 0.00 | 6 |
| CB | ASP | B | 1 | -7.045 | 15.068 | 5.746 | 0.00 | 0.00 | 6 |
| C | ASP | B | 1 | -7.073 | 13.809 | 6.598 | 0.00 | 0.00 | 6 |
| O | ASP | B | 1 | -7.526 | 13.894 | 7.758 | 0.00 | 0.00 | 8 |
| O | ASP | B | 1 | -6.629 | 12.750 | 6.106 | 0.00 | 0.00 | 8 |
| C | ASP | B | 1 | -5.893 | 16.279 | 3.854 | 0.00 | 0.00 | 6 |
| O | ASP | B | 1 | -6.203 | 16.091 | 2.684 | 0.00 | 0.00 | 8 |
| N | VAL | B | 1 | -5.540 | 17.471 | 4.321 | 0.00 | 0.00 | 7 |
| CA | VAL | B | 1 | -5.493 | 18.672 | 3.508 | 0.00 | 0.00 | 6 |
| CB | VAL | B | 1 | -6.459 | 19.763 | 4.011 | 0.00 | 0.00 | 6 |
| C | VAL | B | 1 | -6.406 | 20.998 | 3.114 | 0.00 | 0.00 | 6 |
| C | VAL | B | 1 | -7.895 | 19.274 | 4.108 | 0.00 | 0.00 | 6 |
| C | VAL | B | 1 | -4.086 | 19.272 | 3.518 | 0.00 | 0.00 | 6 |
| O | VAL | B | 1 | -3.427 | 19.305 | 4.555 | 0.00 | 0.00 | 8 |
| N | MET | B | 1 | -3.639 | 19.782 | 2.378 | 0.00 | 0.00 | 7 |
| CA | MET | B | 1 | -2.378 | 20.493 | 2.263 | 0.00 | 0.00 | 6 |
| CB | MET | B | 1 | -1.271 | 19.658 | 1.631 | 0.00 | 0.00 | 6 |
| C | MET | B | 1 | -0.765 | 18.428 | 2.341 | 0.00 | 0.00 | 6 |
| SD | MET | B | 1 | -0.019 | 18.748 | 3.946 | 0.00 | 0.00 | 1 |
| CE | MET | B | 1 | 1.695 | 18.988 | 3.486 | 0.00 | 0.00 | 6 |
| C | MET | B | 1 | -2.549 | 21.748 | 1.395 | 0.00 | 0.00 | 6 |
| O | MET | B | 1 | -3.075 | 21.667 | 0.284 | 0.00 | 0.00 | 8 |
| N | VAL | B | 1 | -2.077 | 22.884 | 1.890 | 0.00 | 0.00 | 7 |
| CA | VAL | B | 1 | -1.916 | 24.084 | 1.073 | 0.00 | 0.00 | 6 |
| CB | VAL | B | 1 | -1.928 | 25.394 | 1.865 | 0.00 | 0.00 | 6 |
| C | VAL | B | 1 | -2.270 | 26.574 | 0.962 | 0.00 | 0.00 | 6 |
| C | VAL | B | 1 | -2.894 | 25.339 | 3.041 | 0.00 | 0.00 | 6 |
| C | VAL | B | 1 | -0.548 | 23.935 | 0.394 | 0.00 | 0.00 | 6 |
| O | VAL | B | 1 | 0.440 | 23.733 | 1.103 | 0.00 | 0.00 | 8 |
| N | ALA | B | 1 | -0.490 | 23.976 | -0.927 | 0.00 | 0.00 | 7 |
| CA | ALA | B | 1 | 0.781 | 23.809 | -1.623 | 0.00 | 0.00 | 6 |
| CB | ALA | B | 1 | 0.861 | 22.436 | -2.275 | 0.00 | 0.00 | 6 |
| C | ALA | B | 1 | 0.985 | 24.883 | -2.684 | 0.00 | 0.00 | 6 |
| O | ALA | B | 1 | 0.021 | 25.477 | -3.172 | 0.00 | 0.00 | 8 |
| N | GLY | B | 1 | 2.246 | 25.115 | -3.037 | 0.00 | 0.00 | 7 |
| CA | GLY | B | 1 | 2.551 | 26.109 | -4.055 | 0.00 | 0.00 | 6 |
| C | GLY | B | 1 | 3.936 | 26.714 | -3.879 | 0.00 | 0.00 | 6 |
| O | GLY | B | 1 | 4.803 | 26.194 | -3.181 | 0.00 | 0.00 | 8 |
| N | GLY | B | 1 | 4.122 | 27.849 | -4.543 | 0.00 | 0.00 | 7 |
| CA | GLY | B | 1 | 5.387 | 28.564 | -4.497 | 0.00 | 0.00 | 6 |
| C | GLY | B | 1 | 5.124 | 30.062 | -4.611 | 0.00 | 0.00 | 6 |
| O | GLY | B | 1 | 4.054 | 30.504 | -5.026 | 0.00 | 0.00 | 8 |
| N | ALA | B | 1 | 6.124 | 30.827 | -4.211 | 0.00 | 0.00 | 7 |
| CA | ALA | B | 1 | 6.071 | 32.279 | -4.285 | 0.00 | 0.00 | 6 |
| CB | ALA | B | 1 | 5.563 | 32.894 | -3.001 | 0.00 | 0.00 | 6 |
| C | ALA | B | 1 | 7.484 | 32.761 | -4.618 | 0.00 | 0.00 | 6 |
| O | ALA | B | 1 | 8.460 | 32.155 | -4.182 | 0.00 | 0.00 | 8 |
| N | GLU | B | 1 | 7.573 | 33.801 | -5.429 | 0.00 | 0.00 | 7 |
| CA | GLU | B | 1 | 8.863 | 34.352 | -5.816 | 0.00 | 0.00 | 6 |
| CB | GLU | B | 1 | 9.419 | 33.641 | -7.049 | 0.00 | 0.00 | 6 |
| C | GLU | B | 1 | 10.909 | 33.815 | -7.291 | 0.00 | 0.00 | 6 |
| C | GLU | B | 1 | 11.720 | 32.733 | -6.598 | 0.00 | 0.00 | 6 |
| O | GLU | B | 1 | 11.478 | 31.534 | -6.865 | 0.00 | 0.00 | 8 |
| O | GLU | B | 1 | 12.584 | 33.096 | -5.773 | 0.00 | 0.00 | 8 |
| C | GLU | B | 1 | 8.715 | 35.844 | -6.094 | 0.00 | 0.00 | 6 |
| O | GLU | B | 1 | 7.669 | 36.320 | -6.521 | 0.00 | 0.00 | 8 |
| N | LYS | B | 1 | 9.780 | 36.575 | -5.833 | 0.00 | 0.00 | 7 |
| CA | LYS | B | 1 | 9.876 | 37.996 | -6.134 | 0.00 | 0.00 | 6 |
| CB | LYS | B | 1 | 9.192 | 38.894 | -5.117 | 0.00 | 0.00 | 6 |
| C | LYS | B | 1 | 8.697 | 40.210 | -5.704 | 0.00 | 0.00 | 6 |
| C | LYS | B | 1 | 9.810 | 41.247 | -5.749 | 0.00 | 0.00 | 6 |
| CE | LYS | B | 1 | 9.256 | 42.620 | -6.102 | 0.00 | 0.00 | 6 |
| NZ | LYS | B | 1 | 10.128 | 43.319 | -7.087 | 0.00 | 0.00 | 7 |
| C | LYS | B | 1 | 11.374 | 38.293 | -6.252 | 0.00 | 0.00 | 6 |
| O | LYS | B | 1 | 12.016 | 38.792 | -5.335 | 0.00 | 0.00 | 8 |
| N | ALA | B | 1 | 11.923 | 37.858 | -7.380 | 0.00 | 0.00 | 7 |
| CA | ALA | B | 1 | 13.346 | 37.965 | -7.651 | 0.00 | 0.00 | 6 |
| CB | ALA | B | 1 | 13.896 | 36.631 | -8.145 | 0.00 | 0.00 | 6 |
| C | ALA | B | 1 | 13.661 | 39.069 | -8.643 | 0.00 | 0.00 | 6 |
| O | ALA | B | 1 | 14.767 | 39.112 | -9.197 | 0.00 | 0.00 | 8 |
| N | SER | B | 1 | 12.736 | 40.004 | -8.842 | 0.00 | 0.00 | 7 |
| CA | SER | B | 1 | 12.999 | 41.133 | -9.733 | 0.00 | 0.00 | 6 |
| CB | SER | B | 1 | 11.735 | 41.630 | -10.425 | 0.00 | 0.00 | 6 |
| O | SER | B | 1 | 10.719 | 41.919 | -9.481 | 0.00 | 0.00 | 8 |
| C | SER | B | 1 | 13.658 | 42.240 | -8.915 | 0.00 | 0.00 | 6 |
| O | SER | B | 1 | 13.077 | 43.275 | -8.617 | 0.00 | 0.00 | 8 |
| N | THR | B | 1 | 14.886 | 41.997 | -8.475 | 0.00 | 0.00 | 7 |
| CA | THR | B | 1 | 15.688 | 42.920 | -7.696 | 0.00 | 0.00 | 6 |
| CB | THR | B | 1 | 16.006 | 42.438 | -6.270 | 0.00 | 0.00 | 6 |
| O | THR | B | 1 | 16.969 | 41.373 | -6.337 | 0.00 | 0.00 | 8 |
| C | THR | B | 1 | 14.779 | 41.964 | -5.510 | 0.00 | 0.00 | 6 |
| C | THR | B | 1 | 17.014 | 43.108 | -8.434 | 0.00 | 0.00 | 6 |
| O | THR | B | 1 | 17.372 | 42.301 | -9.293 | 0.00 | 0.00 | 8 |
| N | PRO | B | 1 | 17.783 | 44.116 | -8.053 | 0.00 | 0.00 | 7 |
| C | PRO | B | 1 | 17.422 | 45.113 | -7.012 | 0.00 | 0.00 | 6 |
| CA | PRO | B | 1 | 19.086 | 44.378 | -8.633 | 0.00 | 0.00 | 6 |
| CB | PRO | B | 1 | 19.700 | 45.388 | -7.663 | 0.00 | 0.00 | 6 |
| C | PRO | B | 1 | 18.531 | 46.126 | -7.107 | 0.00 | 0.00 | 6 |
| C | PRO | B | 1 | 19.957 | 43.142 | -8.766 | 0.00 | 0.00 | 6 |
| O | PRO | B | 1 | 20.533 | 42.868 | -9.820 | 0.00 | 0.00 | 8 |
| N | LEU | B | 1 | 20.070 | 42.357 | -7.699 | 0.00 | 0.00 | 7 |
| CA | LEU | B | 1 | 20.840 | 41.126 | -7.668 | 0.00 | 0.00 | 6 |
| CB | LEU | B | 1 | 20.982 | 40.641 | -6.223 | 0.00 | 0.00 | 6 |
| C | LEU | B | 1 | 22.303 | 40.023 | -5.775 | 0.00 | 0.00 | 6 |
| C | LEU | B | 1 | 23.505 | 40.843 | -6.217 | 0.00 | 0.00 | 6 |
| C | LEU | B | 1 | 22.319 | 39.852 | -4.261 | 0.00 | 0.00 | 6 |
| C | LEU | B | 1 | 20.204 | 40.037 | -8.524 | 0.00 | 0.00 | 6 |
| O | LEU | B | 1 | 20.902 | 39.222 | -9.128 | 0.00 | 0.00 | 8 |
| N | GLY | B | 1 | 18.875 | 40.011 | -8.563 | 0.00 | 0.00 | 7 |
| CA | GLY | B | 1 | 18.130 | 39.040 | -9.342 | 0.00 | 0.00 | 6 |

Figure 1 - 35

| C | GLY | B | 1 | 18.231 | 39.294 | -10.841 | 0.00 | 0.00 | 6 |
|---|---|---|---|---|---|---|---|---|---|
| O | GLY | B | 1 | 18.482 | 38.368 | -11.616 | 0.00 | 0.00 | 8 |
| N | VAL | B | 1 | 18.012 | 40.540 | -11.257 | 0.00 | 0.00 | 7 |
| CA | VAL | B | 1 | 18.114 | 40.877 | -12.680 | 0.00 | 0.00 | 6 |
| CB | VAL | B | 1 | 17.522 | 42.254 | -13.000 | 0.00 | 0.00 | 6 |
| C | VAL | B | 1 | 17.535 | 42.548 | -14.492 | 0.00 | 0.00 | 6 |
| C | VAL | B | 1 | 16.080 | 42.340 | -12.516 | 0.00 | 0.00 | 6 |
| C | VAL | B | 1 | 19.580 | 40.788 | -13.100 | 0.00 | 0.00 | 6 |
| O | VAL | B | 1 | 19.934 | 40.087 | -14.046 | 0.00 | 0.00 | 8 |
| N | GLY | B | 2 | 20.452 | 41.426 | -12.326 | 0.00 | 0.00 | 7 |
| CA | GLY | B | 2 | 21.890 | 41.395 | -12.580 | 0.00 | 0.00 | 6 |
| C | GLY | B | 2 | 22.468 | 39.993 | -12.607 | 0.00 | 0.00 | 6 |
| O | GLY | B | 2 | 23.247 | 39.675 | -13.505 | 0.00 | 0.00 | 8 |
| N | GLY | B | 2 | 22.151 | 39.157 | -11.627 | 0.00 | 0.00 | 7 |
| CA | GLY | B | 2 | 22.680 | 37.817 | -11.495 | 0.00 | 0.00 | 6 |
| C | GLY | B | 2 | 22.380 | 36.909 | -12.672 | 0.00 | 0.00 | 6 |
| O | GLY | B | 2 | 23.254 | 36.212 | -13.187 | 0.00 | 0.00 | 8 |
| N | PHE | B | 2 | 21.128 | 36.914 | -13.116 | 0.00 | 0.00 | 7 |
| CA | PHE | B | 2 | 20.705 | 36.129 | -14.269 | 0.00 | 0.00 | 6 |
| CB | PHE | B | 2 | 19.188 | 35.986 | -14.314 | 0.00 | 0.00 | 6 |
| C | PHE | B | 2 | 18.629 | 34.898 | -13.445 | 0.00 | 0.00 | 6 |
| C | PHE | B | 2 | 17.786 | 35.206 | -12.390 | 0.00 | 0.00 | 6 |
| C | PHE | B | 2 | 18.935 | 33.568 | -13.683 | 0.00 | 0.00 | 6 |
| CE | PHE | B | 2 | 17.263 | 34.211 | -11.585 | 0.00 | 0.00 | 6 |
| CE | PHE | B | 2 | 18.415 | 32.567 | -12.885 | 0.00 | 0.00 | 6 |
| CZ | PHE | B | 2 | 17.576 | 32.892 | -11.835 | 0.00 | 0.00 | 6 |
| C | PHE | B | 2 | 21.222 | 36.822 | -15.531 | 0.00 | 0.00 | 6 |
| O | PHE | B | 2 | 21.633 | 36.184 | -16.493 | 0.00 | 0.00 | 8 |
| N | GLY | B | 2 | 21.309 | 38.148 | -15.481 | 0.00 | 0.00 | 7 |
| CA | GLY | B | 2 | 21.920 | 38.965 | -16.513 | 0.00 | 0.00 | 6 |
| C | GLY | B | 2 | 23.391 | 38.623 | -16.716 | 0.00 | 0.00 | 6 |
| O | GLY | B | 2 | 23.875 | 38.526 | -17.845 | 0.00 | 0.00 | 8 |
| N | ALA | B | 2 | 24.114 | 38.396 | -15.625 | 0.00 | 0.00 | 7 |
| CA | ALA | B | 2 | 25.522 | 38.052 | -15.617 | 0.00 | 0.00 | 6 |
| CB | ALA | B | 2 | 26.053 | 38.085 | -14.186 | 0.00 | 0.00 | 6 |
| C | ALA | B | 2 | 25.826 | 36.697 | -16.238 | 0.00 | 0.00 | 6 |
| O | ALA | B | 2 | 26.920 | 36.477 | -16.760 | 0.00 | 0.00 | 8 |
| N | ALA | B | 2 | 24.863 | 35.783 | -16.211 | 0.00 | 0.00 | 7 |
| CA | ALA | B | 2 | 24.986 | 34.472 | -16.825 | 0.00 | 0.00 | 6 |
| CB | ALA | B | 2 | 24.191 | 33.446 | -16.026 | 0.00 | 0.00 | 6 |
| C | ALA | B | 2 | 24.497 | 34.494 | -18.270 | 0.00 | 0.00 | 6 |
| O | ALA | B | 2 | 24.478 | 33.476 | -18.963 | 0.00 | 0.00 | 8 |
| N | ARG | B | 2 | 24.004 | 35.644 | -18.722 | 0.00 | 0.00 | 7 |
| CA | ARG | B | 2 | 23.499 | 35.835 | -20.070 | 0.00 | 0.00 | 6 |
| CB | ARG | B | 2 | 24.620 | 35.601 | -21.090 | 0.00 | 0.00 | 6 |
| C | ARG | B | 2 | 25.718 | 36.653 | -21.079 | 0.00 | 0.00 | 6 |
| C | ARG | B | 2 | 26.575 | 36.597 | -22.337 | 0.00 | 0.00 | 6 |
| N | ARG | B | 2 | 25.762 | 36.371 | -23.526 | 0.00 | 0.00 | 7 |
| CZ | ARG | B | 2 | 25.831 | 35.321 | -24.333 | 0.00 | 0.00 | 6 |
| N | ARG | B | 2 | 25.011 | 35.258 | -25.377 | 0.00 | 0.00 | 7 |
| N | ARG | B | 2 | 26.699 | 34.341 | -24.113 | 0.00 | 0.00 | 7 |
| C | ARG | B | 2 | 22.308 | 34.934 | -20.376 | 0.00 | 0.00 | 6 |
| O | ARG | B | 2 | 22.108 | 34.513 | -21.515 | 0.00 | 0.00 | 8 |
| N | ALA | B | 2 | 21.458 | 34.698 | -19.386 | 0.00 | 0.00 | 7 |
| CA | ALA | B | 2 | 20.327 | 33.792 | -19.508 | 0.00 | 0.00 | 6 |
| CB | ALA | B | 2 | 20.175 | 33.000 | -18.211 | 0.00 | 0.00 | 6 |
| C | ALA | B | 2 | 19.029 | 34.535 | -19.798 | 0.00 | 0.00 | 6 |
| O | ALA | B | 2 | 18.018 | 33.936 | -20.149 | 0.00 | 0.00 | 8 |
| N | LEU | B | 2 | 19.068 | 35.847 | -19.625 | 0.00 | 0.00 | 7 |
| CA | LEU | B | 2 | 17.911 | 36.706 | -19.813 | 0.00 | 0.00 | 6 |
| CB | LEU | B | 2 | 17.986 | 37.834 | -18.780 | 0.00 | 0.00 | 6 |
| C | LEU | B | 2 | 17.015 | 37.916 | -17.612 | 0.00 | 0.00 | 6 |
| C | LEU | B | 2 | 16.630 | 36.561 | -17.050 | 0.00 | 0.00 | 6 |
| C | LEU | B | 2 | 17.615 | 38.786 | -16.505 | 0.00 | 0.00 | 6 |

| C | LEU | B | 2 | 17.844 | 37.339 | -21.197 | 0.00 | 0.00 | 6 |
|---|---|---|---|---|---|---|---|---|---|
| O | LEU | B | 2 | 18.863 | 37.677 | -21.784 | 0.00 | 0.00 | 8 |
| N | SER | B | 2 | 16.623 | 37.549 | -21.687 | 0.00 | 0.00 | 7 |
| CA | SER | B | 2 | 16.421 | 38.239 | -22.955 | 0.00 | 0.00 | 6 |
| CB | SER | B | 2 | 14.966 | 38.166 | -23.409 | 0.00 | 0.00 | 6 |
| O | SER | B | 2 | 14.690 | 39.185 | -24.358 | 0.00 | 0.00 | 8 |
| C | SER | B | 2 | 16.826 | 39.705 | -22.784 | 0.00 | 0.00 | 6 |
| O | SER | B | 2 | 16.722 | 40.242 | -21.680 | 0.00 | 0.00 | 8 |
| N | THR | B | 2 | 17.273 | 40.344 | -23.859 | 0.00 | 0.00 | 7 |
| CA | THR | B | 2 | 17.738 | 41.737 | -23.762 | 0.00 | 0.00 | 6 |
| CB | THR | B | 2 | 19.260 | 41.759 | -23.962 | 0.00 | 0.00 | 6 |
| O | THR | B | 2 | 19.868 | 41.092 | -22.832 | 0.00 | 0.00 | 8 |
| C | THR | B | 2 | 19.889 | 43.137 | -24.035 | 0.00 | 0.00 | 6 |
| C | THR | B | 2 | 16.962 | 42.631 | -24.708 | 0.00 | 0.00 | 6 |
| O | THR | B | 2 | 17.285 | 43.792 | -24.973 | 0.00 | 0.00 | 8 |
| N | ARG | B | 2 | 15.782 | 42.175 | -25.133 | 0.00 | 0.00 | 7 |
| CA | ARG | B | 2 | 14.924 | 42.914 | -26.051 | 0.00 | 0.00 | 6 |
| CB | ARG | B | 2 | 13.923 | 41.938 | -26.690 | 0.00 | 0.00 | 6 |
| C | ARG | B | 2 | 13.305 | 42.435 | -27.985 | 0.00 | 0.00 | 6 |
| C | ARG | B | 2 | 12.311 | 41.433 | -28.553 | 0.00 | 0.00 | 6 |
| N | ARG | B | 2 | 12.906 | 40.609 | -29.599 | 0.00 | 0.00 | 7 |
| CZ | ARG | B | 2 | 13.523 | 39.451 | -29.399 | 0.00 | 0.00 | 6 |
| N | ARG | B | 2 | 13.642 | 38.939 | -28.179 | 0.00 | 0.00 | 7 |
| N | ARG | B | 2 | 14.030 | 38.790 | -30.433 | 0.00 | 0.00 | 7 |
| C | ARG | B | 2 | 14.195 | 44.087 | -25.417 | 0.00 | 0.00 | 6 |
| O | ARG | B | 2 | 12.965 | 44.106 | -25.333 | 0.00 | 0.00 | 8 |
| N | ASN | B | 2 | 14.906 | 45.140 | -25.025 | 0.00 | 0.00 | 7 |
| CA | ASN | B | 2 | 14.339 | 46.315 | -24.394 | 0.00 | 0.00 | 6 |
| CB | ASN | B | 2 | 15.448 | 47.195 | -23.797 | 0.00 | 0.00 | 6 |
| C | ASN | B | 2 | 16.257 | 46.486 | -22.732 | 0.00 | 0.00 | 6 |
| O | ASN | B | 2 | 15.799 | 46.299 | -21.602 | 0.00 | 0.00 | 8 |
| N | ASN | B | 2 | 17.473 | 46.083 | -23.082 | 0.00 | 0.00 | 7 |
| C | ASN | B | 2 | 13.481 | 47.176 | -25.307 | 0.00 | 0.00 | 6 |
| O | ASN | B | 2 | 12.652 | 47.946 | -24.811 | 0.00 | 0.00 | 8 |
| N | ASP | B | 2 | 13.641 | 47.077 | -26.622 | 0.00 | 0.00 | 7 |
| CA | ASP | B | 2 | 12.853 | 47.865 | -27.564 | 0.00 | 0.00 | 6 |
| CB | ASP | B | 2 | 13.411 | 47.770 | -28.983 | 0.00 | 0.00 | 6 |
| C | ASP | B | 2 | 13.639 | 46.347 | -29.487 | 0.00 | 0.00 | 6 |
| O | ASP | B | 2 | 14.477 | 45.642 | -29.058 | 0.00 | 0.00 | 8 |
| O | ASP | B | 2 | 12.702 | 45.927 | -30.313 | 0.00 | 0.00 | 8 |
| C | ASP | B | 2 | 11.388 | 47.443 | -27.518 | 0.00 | 0.00 | 6 |
| O | ASP | B | 2 | 10.484 | 48.269 | -27.634 | 0.00 | 0.00 | 8 |
| N | ASN | B | 2 | 11.153 | 46.153 | -27.314 | 0.00 | 0.00 | 7 |
| CA | ASN | B | 2 | 9.811 | 45.601 | -27.205 | 0.00 | 0.00 | 6 |
| CB | ASN | B | 2 | 9.387 | 45.031 | -28.555 | 0.00 | 0.00 | 6 |
| C | ASN | B | 2 | 7.928 | 44.678 | -28.693 | 0.00 | 0.00 | 6 |
| O | ASN | B | 2 | 7.470 | 44.389 | -29.804 | 0.00 | 0.00 | 8 |
| N | ASN | B | 2 | 7.168 | 44.677 | -27.605 | 0.00 | 0.00 | 7 |
| C | ASN | B | 2 | 9.750 | 44.542 | -26.111 | 0.00 | 0.00 | 6 |
| O | ASN | B | 2 | 9.883 | 43.342 | -26.353 | 0.00 | 0.00 | 8 |
| N | PRO | B | 2 | 9.509 | 44.976 | -24.877 | 0.00 | 0.00 | 7 |
| C | PRO | B | 2 | 9.381 | 46.408 | -24.497 | 0.00 | 0.00 | 6 |
| CA | PRO | B | 2 | 9.418 | 44.106 | -23.722 | 0.00 | 0.00 | 6 |
| CB | PRO | B | 2 | 9.092 | 45.047 | -22.564 | 0.00 | 0.00 | 6 |
| C | PRO | B | 2 | 9.566 | 46.386 | -23.004 | 0.00 | 0.00 | 6 |
| C | PRO | B | 2 | 8.389 | 42.994 | -23.813 | 0.00 | 0.00 | 6 |
| O | PRO | B | 2 | 8.645 | 41.874 | -23.353 | 0.00 | 0.00 | 8 |
| N | GLN | B | 2 | 7.231 | 43.236 | -24.419 | 0.00 | 0.00 | 7 |
| CA | GLN | B | 2 | 6.171 | 42.253 | -24.546 | 0.00 | 0.00 | 6 |
| CB | GLN | B | 2 | 4.822 | 42.932 | -24.816 | 0.00 | 0.00 | 6 |
| C | GLN | B | 2 | 4.330 | 43.835 | -23.704 | 0.00 | 0.00 | 6 |
| C | GLN | B | 2 | 4.389 | 45.304 | -24.073 | 0.00 | 0.00 | 6 |
| O | GLN | B | 2 | 5.374 | 45.778 | -24.642 | 0.00 | 0.00 | 8 |
| N | GLN | B | 2 | 3.324 | 46.029 | -23.745 | 0.00 | 0.00 | 7 |

Figure 1 - 36

| | | | | | | | | | | | | | | | | |
|---|---|---|---|---|---|---|---|---|---|---|---|---|---|---|---|---|
| C | GLN | B | 2 | 6.387 | 41.211 | -25.635 | 0.00 | 0.00 | 6 | NZ | LYS | B | 2 | 15.416 | 35.744 | -37.419 | 0.00 | 0.00 | 7 |
| O | GLN | B | 2 | 5.582 | 40.281 | -25.739 | 0.00 | 0.00 | 8 | C | LYS | B | 2 | 14.662 | 32.808 | -33.361 | 0.00 | 0.00 | 6 |
| N | ALA | B | 2 | 7.407 | 41.356 | -26.466 | 0.00 | 0.00 | 7 | O | LYS | B | 2 | 15.883 | 32.672 | -33.235 | 0.00 | 0.00 | 8 |
| CA | ALA | B | 2 | 7.686 | 40.389 | -27.521 | 0.00 | 0.00 | 6 | N | GLU | B | 2 | 14.035 | 33.916 | -32.989 | 0.00 | 0.00 | 7 |
| CB | ALA | B | 2 | 7.796 | 41.094 | -28.865 | 0.00 | 0.00 | 6 | CA | GLU | B | 2 | 14.726 | 35.061 | -32.424 | 0.00 | 0.00 | 6 |
| C | ALA | B | 2 | 8.973 | 39.631 | -27.213 | 0.00 | 0.00 | 6 | CB | GLU | B | 2 | 13.994 | 36.350 | -32.810 | 0.00 | 0.00 | 6 |
| O | ALA | B | 2 | 9.383 | 38.727 | -27.940 | 0.00 | 0.00 | 8 | C | GLU | B | 2 | 13.999 | 36.700 | -34.291 | 0.00 | 0.00 | 6 |
| N | ALA | B | 2 | 9.608 | 40.009 | -26.111 | 0.00 | 0.00 | 7 | C | GLU | B | 2 | 13.184 | 37.968 | -34.508 | 0.00 | 0.00 | 6 |
| CA | ALA | B | 2 | 10.855 | 39.404 | -25.669 | 0.00 | 0.00 | 6 | O | GLU | B | 2 | 13.724 | 39.057 | -34.221 | 0.00 | 0.00 | 8 |
| CB | ALA | B | 2 | 11.386 | 40.154 | -24.455 | 0.00 | 0.00 | 6 | O | GLU | B | 2 | 12.017 | 37.858 | -34.934 | 0.00 | 0.00 | 8 |
| C | ALA | B | 2 | 10.695 | 37.924 | -25.350 | 0.00 | 0.00 | 6 | C | GLU | B | 2 | 14.885 | 35.037 | -30.910 | 0.00 | 0.00 | 6 |
| O | ALA | B | 2 | 11.503 | 37.104 | -25.790 | 0.00 | 0.00 | 8 | O | GLU | B | 2 | 15.305 | 36.051 | -30.338 | 0.00 | 0.00 | 8 |
| N | SER | B | 2 | 9.673 | 37.586 | -24.574 | 0.00 | 0.00 | 7 | N | ARG | B | 2 | 14.572 | 33.939 | -30.240 | 0.00 | 0.00 | 7 |
| CA | SER | B | 2 | 9.427 | 36.187 | -24.222 | 0.00 | 0.00 | 6 | CA | ARG | B | 2 | 14.764 | 33.797 | -28.809 | 0.00 | 0.00 | 6 |
| CB | SER | B | 2 | 8.587 | 36.099 | -22.951 | 0.00 | 0.00 | 6 | CB | ARG | B | 2 | 14.709 | 32.328 | -28.382 | 0.00 | 0.00 | 6 |
| O | SER | B | 2 | 8.334 | 34.748 | -22.607 | 0.00 | 0.00 | 8 | C | ARG | B | 2 | 13.360 | 31.659 | -28.338 | 0.00 | 0.00 | 6 |
| C | SER | B | 2 | 8.745 | 35.507 | -25.402 | 0.00 | 0.00 | 6 | C | ARG | B | 2 | 13.481 | 30.147 | -28.281 | 0.00 | 0.00 | 6 |
| O | SER | B | 2 | 7.552 | 35.705 | -25.621 | 0.00 | 0.00 | 8 | N | ARG | B | 2 | 14.578 | 29.612 | -29.063 | 0.00 | 0.00 | 7 |
| N | ARG | B | 2 | 9.501 | 34.722 | -26.158 | 0.00 | 0.00 | 7 | CZ | ARG | B | 2 | 14.646 | 28.397 | -29.592 | 0.00 | 0.00 | 6 |
| CA | ARG | B | 2 | 8.972 | 34.053 | -27.343 | 0.00 | 0.00 | 6 | N | ARG | B | 2 | 13.659 | 27.524 | -29.440 | 0.00 | 0.00 | 7 |
| CB | ARG | B | 2 | 9.340 | 34.866 | -28.594 | 0.00 | 0.00 | 6 | N | ARG | B | 2 | 15.720 | 28.042 | -30.289 | 0.00 | 0.00 | 7 |
| C | ARG | B | 2 | 10.801 | 35.257 | -28.718 | 0.00 | 0.00 | 6 | C | ARG | B | 2 | 16.145 | 34.280 | -28.362 | 0.00 | 0.00 | 6 |
| C | ARG | B | 2 | 11.144 | 35.811 | -30.100 | 0.00 | 0.00 | 6 | O | ARG | B | 2 | 17.137 | 33.895 | -28.984 | 0.00 | 0.00 | 8 |
| N | ARG | B | 2 | 10.476 | 37.079 | -30.337 | 0.00 | 0.00 | 7 | N | ASP | B | 2 | 16.207 | 35.016 | -27.262 | 0.00 | 0.00 | 7 |
| CZ | ARG | B | 2 | 9.563 | 37.369 | -31.248 | 0.00 | 0.00 | 6 | CA | ASP | B | 2 | 17.496 | 35.449 | -26.731 | 0.00 | 0.00 | 6 |
| N | ARG | B | 2 | 9.137 | 36.474 | -32.126 | 0.00 | 0.00 | 7 | CB | ASP | B | 2 | 17.832 | 36.867 | -27.184 | 0.00 | 0.00 | 6 |
| N | ARG | B | 2 | 9.058 | 38.597 | -31.292 | 0.00 | 0.00 | 7 | C | ASP | B | 2 | 16.949 | 37.938 | -26.586 | 0.00 | 0.00 | 6 |
| C | ARG | B | 2 | 9.485 | 32.628 | -27.476 | 0.00 | 0.00 | 6 | O | ASP | B | 2 | 15.755 | 37.674 | -26.343 | 0.00 | 0.00 | 8 |
| O | ARG | B | 2 | 10.377 | 32.329 | -28.273 | 0.00 | 0.00 | 8 | O | ASP | B | 2 | 17.444 | 39.061 | -26.356 | 0.00 | 0.00 | 8 |
| N | PRO | B | 2 | 8.936 | 31.727 | -26.668 | 0.00 | 0.00 | 7 | C | ASP | B | 2 | 17.552 | 35.323 | -25.211 | 0.00 | 0.00 | 6 |
| C | PRO | B | 2 | 7.864 | 31.972 | -25.680 | 0.00 | 0.00 | 6 | O | ASP | B | 2 | 18.370 | 35.996 | -24.576 | 0.00 | 0.00 | 8 |
| CA | PRO | B | 2 | 9.371 | 30.345 | -26.663 | 0.00 | 0.00 | 6 | N | GLY | B | 2 | 16.729 | 34.459 | -24.622 | 0.00 | 0.00 | 7 |
| CB | PRO | B | 2 | 8.570 | 29.672 | -25.563 | 0.00 | 0.00 | 6 | CA | GLY | B | 2 | 16.754 | 34.252 | -23.180 | 0.00 | 0.00 | 6 |
| C | PRO | B | 2 | 7.458 | 30.597 | -25.235 | 0.00 | 0.00 | 6 | C | GLY | B | 2 | 15.393 | 34.378 | -22.513 | 0.00 | 0.00 | 6 |
| C | PRO | B | 2 | 9.175 | 29.678 | -28.008 | 0.00 | 0.00 | 6 | O | GLY | B | 2 | 14.460 | 34.946 | -23.082 | 0.00 | 0.00 | 8 |
| O | PRO | B | 2 | 8.131 | 29.769 | -28.647 | 0.00 | 0.00 | 8 | N | PHE | B | 2 | 15.264 | 33.856 | -21.293 | 0.00 | 0.00 | 7 |
| N | TRP | B | 2 | 10.216 | 28.997 | -28.471 | 0.00 | 0.00 | 7 | CA | PHE | B | 2 | 13.987 | 33.905 | -20.587 | 0.00 | 0.00 | 6 |
| CA | TRP | B | 2 | 10.261 | 28.253 | -29.712 | 0.00 | 0.00 | 6 | CB | PHE | B | 2 | 13.870 | 32.798 | -19.546 | 0.00 | 0.00 | 6 |
| CB | TRP | B | 2 | 9.073 | 27.293 | -29.803 | 0.00 | 0.00 | 6 | C | PHE | B | 2 | 14.610 | 32.931 | -18.254 | 0.00 | 0.00 | 6 |
| C | TRP | B | 2 | 9.118 | 26.167 | -28.812 | 0.00 | 0.00 | 6 | C | PHE | B | 2 | 14.083 | 33.664 | -17.203 | 0.00 | 0.00 | 6 |
| C | TRP | B | 2 | 8.168 | 25.926 | -27.765 | 0.00 | 0.00 | 6 | C | PHE | B | 2 | 15.840 | 32.315 | -18.077 | 0.00 | 0.00 | 6 |
| CE | TRP | B | 2 | 8.589 | 24.772 | -27.079 | 0.00 | 0.00 | 6 | CE | PHE | B | 2 | 14.765 | 33.785 | -16.007 | 0.00 | 0.00 | 6 |
| CE | TRP | B | 2 | 7.004 | 26.579 | -27.344 | 0.00 | 0.00 | 6 | CE | PHE | B | 2 | 16.528 | 32.432 | -16.884 | 0.00 | 0.00 | 6 |
| C | TRP | B | 2 | 10.050 | 25.177 | -28.719 | 0.00 | 0.00 | 6 | CZ | PHE | B | 2 | 15.991 | 33.169 | -15.848 | 0.00 | 0.00 | 6 |
| N | TRP | B | 2 | 9.737 | 24.332 | -27.681 | 0.00 | 0.00 | 7 | C | PHE | B | 2 | 13.692 | 35.281 | -20.011 | 0.00 | 0.00 | 6 |
| CZ | TRP | B | 2 | 7.886 | 24.252 | -25.994 | 0.00 | 0.00 | 6 | O | PHE | B | 2 | 14.537 | 36.171 | -19.954 | 0.00 | 0.00 | 8 |
| CZ | TRP | B | 2 | 6.308 | 26.064 | -26.268 | 0.00 | 0.00 | 6 | N | VAL | B | 2 | 12.427 | 35.476 | -19.649 | 0.00 | 0.00 | 7 |
| C | TRP | B | 2 | 6.753 | 24.911 | -25.607 | 0.00 | 0.00 | 6 | CA | VAL | B | 2 | 11.965 | 36.728 | -19.061 | 0.00 | 0.00 | 6 |
| C | TRP | B | 2 | 10.360 | 29.088 | -30.980 | 0.00 | 0.00 | 6 | CB | VAL | B | 2 | 10.819 | 37.378 | -19.845 | 0.00 | 0.00 | 6 |
| O | TRP | B | 2 | 10.470 | 28.532 | -32.077 | 0.00 | 0.00 | 8 | C | VAL | B | 2 | 10.370 | 38.672 | -19.177 | 0.00 | 0.00 | 6 |
| N | ASP | B | 2 | 10.375 | 30.406 | -30.865 | 0.00 | 0.00 | 7 | C | VAL | B | 2 | 11.234 | 37.671 | -21.282 | 0.00 | 0.00 | 6 |
| CA | ASP | B | 2 | 10.598 | 31.309 | -31.980 | 0.00 | 0.00 | 6 | C | VAL | B | 2 | 11.538 | 36.468 | -17.615 | 0.00 | 0.00 | 6 |
| CB | ASP | B | 2 | 10.100 | 32.708 | -31.631 | 0.00 | 0.00 | 6 | O | VAL | B | 2 | 10.803 | 35.529 | -17.331 | 0.00 | 0.00 | 8 |
| C | ASP | B | 2 | 10.026 | 33.634 | -32.825 | 0.00 | 0.00 | 6 | N | LEU | B | 2 | 12.064 | 37.268 | -16.701 | 0.00 | 0.00 | 7 |
| O | ASP | B | 2 | 10.882 | 34.541 | -32.926 | 0.00 | 0.00 | 8 | CA | LEU | B | 2 | 11.820 | 37.122 | -15.274 | 0.00 | 0.00 | 6 |
| O | ASP | B | 2 | 9.100 | 33.478 | -33.647 | 0.00 | 0.00 | 8 | CB | LEU | B | 2 | 12.911 | 37.874 | -14.519 | 0.00 | 0.00 | 6 |
| C | ASP | B | 2 | 12.093 | 31.324 | -32.293 | 0.00 | 0.00 | 6 | C | LEU | B | 2 | 13.283 | 37.540 | -13.085 | 0.00 | 0.00 | 6 |
| O | ASP | B | 2 | 12.914 | 31.053 | -31.414 | 0.00 | 0.00 | 8 | C | LEU | B | 2 | 12.981 | 36.102 | -12.696 | 0.00 | 0.00 | 6 |
| N | LYS | B | 2 | 12.451 | 31.655 | -33.526 | 0.00 | 0.00 | 7 | C | LEU | B | 2 | 14.769 | 37.833 | -12.865 | 0.00 | 0.00 | 6 |
| CA | LYS | B | 2 | 13.839 | 31.677 | -33.956 | 0.00 | 0.00 | 6 | C | LEU | B | 2 | 10.446 | 37.641 | -14.868 | 0.00 | 0.00 | 6 |
| CB | LYS | B | 2 | 13.904 | 31.745 | -35.490 | 0.00 | 0.00 | 6 | O | LEU | B | 2 | 10.029 | 38.705 | -15.327 | 0.00 | 0.00 | 8 |
| C | LYS | B | 2 | 13.364 | 33.042 | -36.070 | 0.00 | 0.00 | 6 | N | GLY | B | 2 | 9.756 | 36.907 | -14.001 | 0.00 | 0.00 | 7 |
| C | LYS | B | 2 | 14.242 | 33.558 | -37.199 | 0.00 | 0.00 | 6 | CA | GLY | B | 2 | 8.439 | 37.300 | -13.531 | 0.00 | 0.00 | 6 |
| CE | LYS | B | 2 | 15.353 | 34.452 | -36.679 | 0.00 | 0.00 | 6 | C | GLY | B | 2 | 8.245 | 37.044 | -12.042 | 0.00 | 0.00 | 6 |

Figure 1 - 37

| | | | | | | | | |
|---|---|---|---|---|---|---|---|---|
| O | GLY | B | 2 | 8.864 | 36.154 | -11.456 | 0.00 | 0.00 | 8 |
| N | ASP | B | 2 | 7.357 | 37.812 | -11.419 | 0.00 | 0.00 | 7 |
| CA | ASP | B | 2 | 7.049 | 37.681 | -10.007 | 0.00 | 0.00 | 6 |
| CB | ASP | B | 2 | 7.131 | 39.013 | -9.261 | 0.00 | 0.00 | 6 |
| C | ASP | B | 2 | 8.433 | 39.754 | -9.450 | 0.00 | 0.00 | 6 |
| O | ASP | B | 2 | 9.502 | 39.115 | -9.377 | 0.00 | 0.00 | 8 |
| O | ASP | B | 2 | 8.386 | 40.980 | -9.676 | 0.00 | 0.00 | 8 |
| C | ASP | B | 2 | 5.629 | 37.151 | -9.804 | 0.00 | 0.00 | 6 |
| O | ASP | B | 2 | 4.764 | 37.359 | -10.654 | 0.00 | 0.00 | 8 |
| N | GLY | B | 2 | 5.394 | 36.540 | -8.644 | 0.00 | 0.00 | 7 |
| CA | GLY | B | 2 | 4.060 | 36.050 | -8.336 | 0.00 | 0.00 | 6 |
| C | GLY | B | 2 | 4.049 | 34.883 | -7.363 | 0.00 | 0.00 | 6 |
| O | GLY | B | 2 | 5.018 | 34.582 | -6.671 | 0.00 | 0.00 | 8 |
| N | ALA | B | 2 | 2.897 | 34.226 | -7.305 | 0.00 | 0.00 | 7 |
| CA | ALA | B | 2 | 2.672 | 33.116 | -6.393 | 0.00 | 0.00 | 6 |
| CB | ALA | B | 2 | 2.668 | 33.596 | -4.948 | 0.00 | 0.00 | 6 |
| C | ALA | B | 2 | 1.336 | 32.447 | -6.706 | 0.00 | 0.00 | 6 |
| O | ALA | B | 2 | 0.329 | 33.123 | -6.890 | 0.00 | 0.00 | 8 |
| N | GLY | B | 2 | 1.363 | 31.129 | -6.779 | 0.00 | 0.00 | 7 |
| CA | GLY | B | 2 | 0.163 | 30.338 | -7.029 | 0.00 | 0.00 | 6 |
| C | GLY | B | 2 | 0.020 | 29.388 | -5.837 | 0.00 | 0.00 | 6 |
| O | GLY | B | 2 | 1.036 | 28.954 | -5.292 | 0.00 | 0.00 | 8 |
| N | MET | B | 2 | -1.211 | 29.102 | -5.442 | 0.00 | 0.00 | 7 |
| CA | MET | B | 2 | -1.422 | 28.233 | -4.284 | 0.00 | 0.00 | 6 |
| CB | MET | B | 2 | -1.550 | 29.112 | -3.041 | 0.00 | 0.00 | 6 |
| C | MET | B | 2 | -0.922 | 28.605 | -1.769 | 0.00 | 0.00 | 6 |
| SD | MET | B | 2 | 0.868 | 28.696 | -1.678 | 0.00 | 0.00 | 1 |
| CE | MET | B | 2 | 1.196 | 30.339 | -2.299 | 0.00 | 0.00 | 6 |
| C | MET | B | 2 | -2.670 | 27.388 | -4.482 | 0.00 | 0.00 | 6 |
| O | MET | B | 2 | -3.679 | 27.921 | -4.952 | 0.00 | 0.00 | 8 |
| N | LEU | B | 2 | -2.590 | 26.091 | -4.184 | 0.00 | 0.00 | 7 |
| CA | LEU | B | 2 | -3.766 | 25.247 | -4.290 | 0.00 | 0.00 | 6 |
| CB | LEU | B | 2 | -3.780 | 24.224 | -5.406 | 0.00 | 0.00 | 6 |
| C | LEU | B | 2 | -2.622 | 23.976 | -6.348 | 0.00 | 0.00 | 6 |
| C | LEU | B | 2 | -2.799 | 22.652 | -7.084 | 0.00 | 0.00 | 6 |
| C | LEU | B | 2 | -2.495 | 25.100 | -7.364 | 0.00 | 0.00 | 6 |
| C | LEU | B | 2 | -3.990 | 24.490 | -2.973 | 0.00 | 0.00 | 6 |
| O | LEU | B | 2 | -3.070 | 24.212 | -2.213 | 0.00 | 0.00 | 8 |
| N | VAL | B | 2 | -5.258 | 24.167 | -2.753 | 0.00 | 0.00 | 7 |
| CA | VAL | B | 2 | -5.647 | 23.333 | -1.629 | 0.00 | 0.00 | 6 |
| CB | VAL | B | 2 | -6.971 | 23.726 | -0.970 | 0.00 | 0.00 | 6 |
| C | VAL | B | 2 | -7.287 | 22.787 | 0.190 | 0.00 | 0.00 | 6 |
| C | VAL | B | 2 | -6.934 | 25.165 | -0.485 | 0.00 | 0.00 | 6 |
| C | VAL | B | 2 | -5.760 | 21.906 | -2.178 | 0.00 | 0.00 | 6 |
| O | VAL | B | 2 | -6.503 | 21.652 | -3.124 | 0.00 | 0.00 | 8 |
| N | LEU | B | 2 | -4.938 | 21.022 | -1.633 | 0.00 | 0.00 | 7 |
| CA | LEU | B | 2 | -4.968 | 19.617 | -2.023 | 0.00 | 0.00 | 6 |
| CB | LEU | B | 2 | -3.564 | 19.081 | -2.270 | 0.00 | 0.00 | 6 |
| C | LEU | B | 2 | -2.854 | 19.486 | -3.561 | 0.00 | 0.00 | 6 |
| C | LEU | B | 2 | -1.421 | 18.970 | -3.566 | 0.00 | 0.00 | 6 |
| C | LEU | B | 2 | -3.602 | 18.970 | -4.779 | 0.00 | 0.00 | 6 |
| C | LEU | B | 2 | -5.635 | 18.855 | -0.882 | 0.00 | 0.00 | 6 |
| O | LEU | B | 2 | -5.298 | 19.145 | 0.271 | 0.00 | 0.00 | 8 |
| N | GLU | B | 2 | -6.547 | 17.935 | -1.169 | 0.00 | 0.00 | 7 |
| CA | GLU | B | 2 | -7.132 | 17.161 | -0.074 | 0.00 | 0.00 | 6 |
| CB | GLU | B | 2 | -8.211 | 17.932 | 0.663 | 0.00 | 0.00 | 6 |
| C | GLU | B | 2 | -9.550 | 18.093 | -0.026 | 0.00 | 0.00 | 6 |
| C | GLU | B | 2 | -10.514 | 18.883 | 0.845 | 0.00 | 0.00 | 6 |
| O | GLU | B | 2 | -10.645 | 20.104 | 0.631 | 0.00 | 0.00 | 8 |
| O | GLU | B | 2 | -11.130 | 18.277 | 1.748 | 0.00 | 0.00 | 8 |
| C | GLU | B | 2 | -7.623 | 15.795 | -0.538 | 0.00 | 0.00 | 6 |
| O | GLU | B | 2 | -7.749 | 15.519 | -1.729 | 0.00 | 0.00 | 8 |
| N | GLU | B | 2 | -7.740 | 14.901 | 0.440 | 0.00 | 0.00 | 7 |
| CA | GLU | B | 2 | -8.152 | 13.525 | 0.182 | 0.00 | 0.00 | 6 |
| CB | GLU | B | 2 | -7.982 | 12.690 | 1.450 | 0.00 | 0.00 | 6 |
| C | GLU | B | 2 | -8.173 | 11.195 | 1.233 | 0.00 | 0.00 | 6 |
| C | GLU | B | 2 | -9.627 | 10.801 | 1.445 | 0.00 | 0.00 | 6 |
| O | GLU | B | 2 | -10.283 | 11.423 | 2.308 | 0.00 | 0.00 | 8 |
| O | GLU | B | 2 | -10.094 | 9.890 | 0.734 | 0.00 | 0.00 | 8 |
| C | GLU | B | 2 | -9.584 | 13.491 | -0.338 | 0.00 | 0.00 | 6 |
| O | GLU | B | 2 | -10.468 | 14.184 | 0.159 | 0.00 | 0.00 | 8 |
| N | TYR | B | 2 | -9.813 | 12.671 | -1.355 | 0.00 | 0.00 | 7 |
| CA | TYR | B | 2 | -11.109 | 12.554 | -1.999 | 0.00 | 0.00 | 6 |
| CB | TYR | B | 2 | -11.091 | 11.397 | -3.007 | 0.00 | 0.00 | 6 |
| C | TYR | B | 2 | -12.367 | 11.296 | -3.815 | 0.00 | 0.00 | 6 |
| C | TYR | B | 2 | -12.773 | 12.324 | -4.653 | 0.00 | 0.00 | 6 |
| CE | TYR | B | 2 | -13.942 | 12.226 | -5.385 | 0.00 | 0.00 | 6 |
| C | TYR | B | 2 | -13.166 | 10.165 | -3.726 | 0.00 | 0.00 | 6 |
| CE | TYR | B | 2 | -14.337 | 10.059 | -4.453 | 0.00 | 0.00 | 6 |
| CZ | TYR | B | 2 | -14.718 | 11.092 | -5.281 | 0.00 | 0.00 | 6 |
| O | TYR | B | 2 | -15.882 | 10.989 | -6.005 | 0.00 | 0.00 | 8 |
| C | TYR | B | 2 | -12.290 | 12.410 | -1.056 | 0.00 | 0.00 | 6 |
| O | TYR | B | 2 | -13.194 | 13.253 | -1.067 | 0.00 | 0.00 | 8 |
| N | GLU | B | 2 | -12.307 | 11.371 | -0.230 | 0.00 | 0.00 | 7 |
| CA | GLU | B | 2 | -13.398 | 11.118 | 0.699 | 0.00 | 0.00 | 6 |
| CB | GLU | B | 2 | -13.208 | 9.758 | 1.380 | 0.00 | 0.00 | 6 |
| C | GLU | B | 2 | -13.307 | 8.581 | 0.421 | 0.00 | 0.00 | 6 |
| C | GLU | B | 2 | -14.660 | 8.471 | -0.254 | 0.00 | 0.00 | 6 |
| O | GLU | B | 2 | -15.659 | 8.185 | 0.439 | 0.00 | 0.00 | 8 |
| O | GLU | B | 2 | -14.735 | 8.674 | -1.483 | 0.00 | 0.00 | 8 |
| C | GLU | B | 2 | -13.606 | 12.212 | 1.732 | 0.00 | 0.00 | 6 |
| O | GLU | B | 2 | -14.740 | 12.442 | 2.162 | 0.00 | 0.00 | 8 |
| N | HIS | B | 2 | -12.550 | 12.909 | 2.130 | 0.00 | 0.00 | 7 |
| CA | HIS | B | 2 | -12.642 | 14.026 | 3.055 | 0.00 | 0.00 | 6 |
| CB | HIS | B | 2 | -11.238 | 14.462 | 3.484 | 0.00 | 0.00 | 6 |
| C | HIS | B | 2 | -11.205 | 15.558 | 4.501 | 0.00 | 0.00 | 6 |
| C | HIS | B | 2 | -11.081 | 15.517 | 5.848 | 0.00 | 0.00 | 6 |
| N | HIS | B | 2 | -11.298 | 16.891 | 4.168 | 0.00 | 0.00 | 7 |
| CE | HIS | B | 2 | -11.244 | 17.626 | 5.264 | 0.00 | 0.00 | 6 |
| N | HIS | B | 2 | -11.114 | 16.815 | 6.298 | 0.00 | 0.00 | 7 |
| C | HIS | B | 2 | -13.365 | 15.207 | 2.410 | 0.00 | 0.00 | 6 |
| O | HIS | B | 2 | -14.184 | 15.877 | 3.035 | 0.00 | 0.00 | 8 |
| N | ALA | B | 2 | -13.048 | 15.466 | 1.146 | 0.00 | 0.00 | 7 |
| CA | ALA | B | 2 | -13.619 | 16.566 | 0.387 | 0.00 | 0.00 | 6 |
| CB | ALA | B | 2 | -12.766 | 16.829 | -0.850 | 0.00 | 0.00 | 6 |
| C | ALA | B | 2 | -15.064 | 16.328 | -0.025 | 0.00 | 0.00 | 6 |
| O | ALA | B | 2 | -15.895 | 17.233 | 0.033 | 0.00 | 0.00 | 8 |
| N | LYS | B | 2 | -15.365 | 15.103 | -0.439 | 0.00 | 0.00 | 7 |
| CA | LYS | B | 2 | -16.724 | 14.731 | -0.829 | 0.00 | 0.00 | 6 |
| CB | LYS | B | 2 | -16.722 | 13.333 | -1.441 | 0.00 | 0.00 | 6 |
| C | LYS | B | 2 | -18.083 | 12.691 | -1.639 | 0.00 | 0.00 | 6 |
| C | LYS | B | 2 | -17.953 | 11.203 | -1.929 | 0.00 | 0.00 | 6 |
| CE | LYS | B | 2 | -19.228 | 10.644 | -2.540 | 0.00 | 0.00 | 6 |
| NZ | LYS | B | 2 | -18.946 | 9.774 | -3.715 | 0.00 | 0.00 | 7 |
| C | LYS | B | 2 | -17.652 | 14.809 | 0.379 | 0.00 | 0.00 | 6 |
| O | LYS | B | 2 | -18.772 | 15.314 | 0.295 | 0.00 | 0.00 | 8 |
| N | LYS | B | 2 | -17.191 | 14.339 | 1.532 | 0.00 | 0.00 | 7 |
| CA | LYS | B | 2 | -17.943 | 14.347 | 2.775 | 0.00 | 0.00 | 6 |
| CB | LYS | B | 2 | -17.116 | 13.694 | 3.889 | 0.00 | 0.00 | 6 |
| C | LYS | B | 2 | -17.772 | 13.688 | 5.257 | 0.00 | 0.00 | 6 |
| C | LYS | B | 2 | -17.156 | 12.642 | 6.174 | 0.00 | 0.00 | 6 |
| CE | LYS | B | 2 | -17.820 | 11.287 | 5.989 | 0.00 | 0.00 | 6 |
| NZ | LYS | B | 2 | -17.061 | 10.429 | 5.037 | 0.00 | 0.00 | 7 |
| C | LYS | B | 2 | -18.394 | 15.735 | 3.209 | 0.00 | 0.00 | 6 |
| O | LYS | B | 2 | -19.472 | 15.872 | 3.797 | 0.00 | 0.00 | 8 |
| N | ARG | B | 2 | -17.593 | 16.766 | 2.971 | 0.00 | 0.00 | 7 |
| CA | ARG | B | 2 | -17.965 | 18.131 | 3.318 | 0.00 | 0.00 | 6 |
| CB | ARG | B | 2 | -16.756 | 18.905 | 3.845 | 0.00 | 0.00 | 6 |

Figure 1 - 38

| | | | | | | | |
|---|---|---|---|---|---|---|---|
| C | ARG | B | 2 | -16.629 | 18.877 | 5.361 | 0.00 | 0.00 | 6 |
| C | ARG | B | 2 | -15.223 | 18.495 | 5.797 | 0.00 | 0.00 | 6 |
| N | ARG | B | 2 | -15.208 | 17.305 | 6.639 | 0.00 | 0.00 | 7 |
| CZ | ARG | B | 2 | -14.361 | 17.075 | 7.633 | 0.00 | 0.00 | 6 |
| N | ARG | B | 2 | -13.421 | 17.958 | 7.948 | 0.00 | 0.00 | 7 |
| N | ARG | B | 2 | -14.446 | 15.947 | 8.329 | 0.00 | 0.00 | 7 |
| C | ARG | B | 2 | -18.598 | 18.349 | 2.129 | 0.00 | 0.00 | 6 |
| O | ARG | B | 2 | -19.177 | 19.924 | 2.276 | 0.00 | 0.00 | 8 |
| N | GLY | B | 2 | -18.496 | 18.262 | 0.942 | 0.00 | 0.00 | 7 |
| CA | GLY | B | 2 | -19.076 | 18.799 | -0.271 | 0.00 | 0.00 | 6 |
| C | GLY | B | 2 | -18.336 | 19.987 | -0.860 | 0.00 | 0.00 | 6 |
| O | GLY | B | 2 | -18.940 | 21.015 | -1.171 | 0.00 | 0.00 | 8 |
| N | ALA | B | 2 | -17.031 | 19.848 | -1.051 | 0.00 | 0.00 | 7 |
| CA | ALA | B | 2 | -16.202 | 20.919 | -1.579 | 0.00 | 0.00 | 6 |
| CB | ALA | B | 2 | -14.759 | 20.689 | -1.128 | 0.00 | 0.00 | 6 |
| C | ALA | B | 2 | -16.233 | 21.053 | -3.095 | 0.00 | 0.00 | 6 |
| O | ALA | B | 2 | -16.500 | 20.108 | -3.829 | 0.00 | 0.00 | 8 |
| N | LYS | B | 2 | -15.861 | 22.242 | -3.565 | 0.00 | 0.00 | 7 |
| CA | LYS | B | 2 | -15.628 | 22.494 | -4.982 | 0.00 | 0.00 | 6 |
| CB | LYS | B | 2 | -15.246 | 23.955 | -5.205 | 0.00 | 0.00 | 6 |
| C | LYS | B | 2 | -16.366 | 24.924 | -5.519 | 0.00 | 0.00 | 6 |
| C | LYS | B | 2 | -15.810 | 26.283 | -5.931 | 0.00 | 0.00 | 6 |
| CE | LYS | B | 2 | -15.992 | 27.315 | -4.830 | 0.00 | 0.00 | 6 |
| NZ | LYS | B | 2 | -17.289 | 28.037 | -4.954 | 0.00 | 0.00 | 7 |
| C | LYS | B | 2 | -14.465 | 21.615 | -5.445 | 0.00 | 0.00 | 6 |
| O | LYS | B | 2 | -13.335 | 21.878 | -5.024 | 0.00 | 0.00 | 8 |
| N | ILE | B | 2 | -14.719 | 20.598 | -6.257 | 0.00 | 0.00 | 7 |
| CA | ILE | B | 2 | -13.626 | 19.739 | -6.720 | 0.00 | 0.00 | 6 |
| CB | ILE | B | 2 | -13.973 | 18.247 | -6.630 | 0.00 | 0.00 | 6 |
| C | ILE | B | 2 | -13.028 | 17.386 | -7.459 | 0.00 | 0.00 | 6 |
| C | ILE | B | 2 | -13.935 | 17.795 | -5.165 | 0.00 | 0.00 | 6 |
| C | ILE | B | 2 | -14.394 | 16.377 | -4.914 | 0.00 | 0.00 | 6 |
| C | ILE | B | 2 | -13.224 | 20.148 | -8.132 | 0.00 | 0.00 | 6 |
| O | ILE | B | 2 | -13.901 | 19.837 | -9.109 | 0.00 | 0.00 | 8 |
| N | TYR | B | 2 | -12.090 | 20.830 | -8.243 | 0.00 | 0.00 | 7 |
| CA | TYR | B | 2 | -11.577 | 21.318 | -9.510 | 0.00 | 0.00 | 6 |
| CB | TYR | B | 2 | -10.447 | 22.332 | -9.276 | 0.00 | 0.00 | 6 |
| C | TYR | B | 2 | -10.899 | 23.698 | -8.826 | 0.00 | 0.00 | 6 |
| C | TYR | B | 2 | -10.901 | 24.034 | -7.480 | 0.00 | 0.00 | 6 |
| CE | TYR | B | 2 | -11.308 | 25.286 | -7.058 | 0.00 | 0.00 | 6 |
| C | TYR | B | 2 | -11.310 | 24.654 | -9.744 | 0.00 | 0.00 | 6 |
| CE | TYR | B | 2 | -11.719 | 25.909 | -9.331 | 0.00 | 0.00 | 6 |
| CZ | TYR | B | 2 | -11.714 | 26.217 | -7.990 | 0.00 | 0.00 | 6 |
| O | TYR | B | 2 | -12.119 | 27.462 | -7.572 | 0.00 | 0.00 | 8 |
| C | TYR | B | 2 | -10.996 | 20.221 | -10.393 | 0.00 | 0.00 | 6 |
| O | TYR | B | 2 | -11.028 | 20.320 | -11.619 | 0.00 | 0.00 | 8 |
| N | ALA | B | 2 | -10.375 | 19.227 | -9.769 | 0.00 | 0.00 | 7 |
| CA | ALA | B | 2 | -9.739 | 18.142 | -10.500 | 0.00 | 0.00 | 6 |
| CB | ALA | B | 2 | -8.755 | 18.680 | -11.528 | 0.00 | 0.00 | 6 |
| C | ALA | B | 2 | -9.018 | 17.202 | -9.536 | 0.00 | 0.00 | 6 |
| O | ALA | B | 2 | -9.043 | 17.385 | -8.320 | 0.00 | 0.00 | 8 |
| N | GLU | B | 2 | -8.375 | 16.196 | -10.109 | 0.00 | 0.00 | 7 |
| CA | GLU | B | 2 | -7.653 | 15.197 | -9.338 | 0.00 | 0.00 | 6 |
| CB | GLU | B | 2 | -8.294 | 13.825 | -9.577 | 0.00 | 0.00 | 6 |
| C | GLU | B | 2 | -7.809 | 12.712 | -8.670 | 0.00 | 0.00 | 6 |
| C | GLU | B | 2 | -8.396 | 11.355 | -8.998 | 0.00 | 0.00 | 6 |
| O | GLU | B | 2 | -7.824 | 10.329 | -8.569 | 0.00 | 0.00 | 8 |
| O | GLU | B | 2 | -9.436 | 11.289 | -9.684 | 0.00 | 0.00 | 8 |
| C | GLU | B | 2 | -6.181 | 15.144 | -9.719 | 0.00 | 0.00 | 6 |
| O | GLU | B | 2 | -5.844 | 15.155 | -10.903 | 0.00 | 0.00 | 8 |
| N | LEU | B | 2 | -5.314 | 15.083 | -8.714 | 0.00 | 0.00 | 7 |
| CA | LEU | B | 2 | -3.879 | 14.936 | -8.973 | 0.00 | 0.00 | 6 |
| CB | LEU | B | 2 | -3.035 | 15.499 | -7.842 | 0.00 | 0.00 | 6 |
| C | LEU | B | 2 | -1.655 | 16.057 | -8.200 | 0.00 | 0.00 | 6 |
| C | LEU | B | 2 | -1.005 | 16.692 | -6.980 | 0.00 | 0.00 | 6 |
| C | LEU | B | 2 | -0.754 | 14.976 | -8.775 | 0.00 | 0.00 | 6 |
| C | LEU | B | 2 | -3.657 | 13.429 | -9.133 | 0.00 | 0.00 | 6 |
| O | LEU | B | 2 | -3.958 | 12.694 | -8.188 | 0.00 | 0.00 | 8 |
| N | VAL | B | 2 | -3.337 | 12.963 | -10.335 | 0.00 | 0.00 | 7 |
| CA | VAL | B | 2 | -3.267 | 11.527 | -10.582 | 0.00 | 0.00 | 6 |
| CB | VAL | B | 2 | -4.193 | 11.094 | -11.743 | 0.00 | 0.00 | 6 |
| C | VAL | B | 2 | -5.657 | 11.300 | -11.386 | 0.00 | 0.00 | 6 |
| C | VAL | B | 2 | -3.845 | 11.841 | -13.021 | 0.00 | 0.00 | 6 |
| C | VAL | B | 2 | -1.870 | 11.009 | -10.886 | 0.00 | 0.00 | 6 |
| O | VAL | B | 2 | -1.669 | 9.791 | -10.859 | 0.00 | 0.00 | 8 |
| N | GLY | B | 2 | -0.927 | 11.891 | -11.202 | 0.00 | 0.00 | 7 |
| CA | GLY | B | 2 | 0.427 | 11.452 | -11.517 | 0.00 | 0.00 | 6 |
| C | GLY | B | 2 | 1.485 | 12.468 | -11.115 | 0.00 | 0.00 | 6 |
| O | GLY | B | 2 | 1.280 | 13.678 | -11.198 | 0.00 | 0.00 | 8 |
| N | PHE | B | 2 | 2.636 | 11.965 | -10.676 | 0.00 | 0.00 | 7 |
| CA | PHE | B | 2 | 3.762 | 12.806 | -10.292 | 0.00 | 0.00 | 6 |
| CB | PHE | B | 2 | 3.755 | 13.148 | -8.806 | 0.00 | 0.00 | 6 |
| C | PHE | B | 2 | 4.902 | 13.995 | -8.332 | 0.00 | 0.00 | 6 |
| C | PHE | B | 2 | 5.382 | 15.057 | -9.078 | 0.00 | 0.00 | 6 |
| C | PHE | B | 2 | 5.499 | 13.730 | -7.107 | 0.00 | 0.00 | 6 |
| CE | PHE | B | 2 | 6.443 | 15.824 | -8.636 | 0.00 | 0.00 | 6 |
| CE | PHE | B | 2 | 6.550 | 14.500 | -6.648 | 0.00 | 0.00 | 6 |
| CZ | PHE | B | 2 | 7.023 | 15.550 | -7.415 | 0.00 | 0.00 | 6 |
| C | PHE | B | 2 | 5.070 | 12.117 | -10.674 | 0.00 | 0.00 | 6 |
| O | PHE | B | 2 | 5.341 | 11.005 | -10.222 | 0.00 | 0.00 | 8 |
| N | GLY | B | 2 | 5.865 | 12.776 | -11.508 | 0.00 | 0.00 | 7 |
| CA | GLY | B | 2 | 7.131 | 12.224 | -11.963 | 0.00 | 0.00 | 6 |
| C | GLY | B | 2 | 8.295 | 13.171 | -11.707 | 0.00 | 0.00 | 6 |
| O | GLY | B | 2 | 8.178 | 14.389 | -11.829 | 0.00 | 0.00 | 8 |
| N | MET | B | 2 | 9.434 | 12.601 | -11.324 | 0.00 | 0.00 | 7 |
| CA | MET | B | 2 | 10.638 | 13.354 | -11.031 | 0.00 | 0.00 | 6 |
| CB | MET | B | 2 | 10.944 | 13.387 | -9.536 | 0.00 | 0.00 | 6 |
| C | MET | B | 2 | 9.980 | 14.105 | -8.618 | 0.00 | 0.00 | 6 |
| SD | MET | B | 2 | 10.100 | 13.489 | -6.924 | 0.00 | 0.00 | 1 |
| CE | MET | B | 2 | 11.710 | 14.122 | -6.467 | 0.00 | 0.00 | 6 |
| C | MET | B | 2 | 11.858 | 12.722 | -11.707 | 0.00 | 0.00 | 6 |
| O | MET | B | 2 | 11.936 | 11.502 | -11.829 | 0.00 | 0.00 | 8 |
| N | SER | B | 2 | 12.835 | 13.552 | -12.046 | 0.00 | 0.00 | 7 |
| CA | SER | B | 2 | 14.077 | 13.066 | -12.629 | 0.00 | 0.00 | 6 |
| CB | SER | B | 2 | 13.865 | 12.763 | -14.119 | 0.00 | 0.00 | 6 |
| O | SER | B | 2 | 13.967 | 13.968 | -14.866 | 0.00 | 0.00 | 8 |
| C | SER | B | 2 | 15.192 | 14.099 | -12.499 | 0.00 | 0.00 | 6 |
| O | SER | B | 2 | 14.964 | 15.237 | -12.098 | 0.00 | 0.00 | 8 |
| N | SER | B | 2 | 16.398 | 13.704 | -12.890 | 0.00 | 0.00 | 7 |
| CA | SER | B | 2 | 17.540 | 14.596 | -12.941 | 0.00 | 0.00 | 6 |
| CB | SER | B | 2 | 18.550 | 14.439 | -11.817 | 0.00 | 0.00 | 6 |
| O | SER | B | 2 | 18.007 | 13.920 | -10.628 | 0.00 | 0.00 | 8 |
| C | SER | B | 2 | 18.354 | 14.375 | -14.282 | 0.00 | 0.00 | 6 |
| O | SER | B | 2 | 18.226 | 13.269 | -14.814 | 0.00 | 0.00 | 8 |
| N | ASP | B | 2 | 18.891 | 15.424 | -14.780 | 0.00 | 0.00 | 7 |
| CA | ASP | B | 2 | 19.598 | 15.372 | -16.043 | 0.00 | 0.00 | 6 |
| CB | ASP | B | 2 | 19.708 | 16.779 | -16.645 | 0.00 | 0.00 | 6 |
| C | ASP | B | 2 | 18.425 | 17.292 | -17.259 | 0.00 | 0.00 | 6 |
| O | ASP | B | 2 | 17.466 | 16.505 | -17.390 | 0.00 | 0.00 | 8 |
| O | ASP | B | 2 | 18.399 | 18.493 | -17.601 | 0.00 | 0.00 | 8 |
| C | ASP | B | 2 | 21.019 | 14.838 | -15.912 | 0.00 | 0.00 | 6 |
| O | ASP | B | 2 | 21.535 | 14.204 | -16.831 | 0.00 | 0.00 | 8 |
| N | ALA | B | 2 | 21.673 | 15.143 | -14.796 | 0.00 | 0.00 | 7 |
| CA | ALA | B | 2 | 23.050 | 14.717 | -14.562 | 0.00 | 0.00 | 6 |
| CB | ALA | B | 2 | 23.097 | 13.220 | -14.305 | 0.00 | 0.00 | 6 |
| C | ALA | B | 2 | 23.902 | 15.113 | -15.764 | 0.00 | 0.00 | 6 |
| O | ALA | B | 2 | 24.583 | 14.286 | -16.366 | 0.00 | 0.00 | 8 |
| N | TYR | B | 2 | 23.848 | 16.393 | -16.119 | 0.00 | 0.00 | 7 |

Figure 1 - 39

| | | | | | | | | |
|---|---|---|---|---|---|---|---|---|
| CA | TYR | B | 2 | 24.503 | 16.907 | -17.311 | 0.00 | 0.00 | 6 |
| CB | TYR | B | 2 | 23.451 | 17.038 | -18.431 | 0.00 | 0.00 | 6 |
| C | TYR | B | 2 | 24.048 | 17.513 | -19.738 | 0.00 | 0.00 | 6 |
| C | TYR | B | 2 | 24.764 | 16.646 | -20.552 | 0.00 | 0.00 | 6 |
| CE | TYR | B | 2 | 25.328 | 17.085 | -21.735 | 0.00 | 0.00 | 6 |
| C | TYR | B | 2 | 23.920 | 18.336 | -20.138 | 0.00 | 0.00 | 6 |
| CE | TYR | B | 2 | 24.481 | 19.285 | -21.317 | 0.00 | 0.00 | 6 |
| CZ | TYR | B | 2 | 25.184 | 18.403 | -22.110 | 0.00 | 0.00 | 6 |
| O | TYR | B | 2 | 25.745 | 18.844 | -23.288 | 0.00 | 0.00 | 8 |
| C | TYR | B | 2 | 25.213 | 18.225 | -17.058 | 0.00 | 0.00 | 6 |
| O | TYR | B | 2 | 26.443 | 18.260 | -16.980 | 0.00 | 0.00 | 8 |
| N | HIS | B | 2 | 24.468 | 19.317 | -16.925 | 0.00 | 0.00 | 7 |
| CA | HIS | B | 2 | 25.063 | 20.628 | -16.677 | 0.00 | 0.00 | 6 |
| CB | HIS | B | 2 | 25.120 | 21.431 | -17.973 | 0.00 | 0.00 | 6 |
| C | HIS | B | 2 | 25.949 | 22.675 | -17.927 | 0.00 | 0.00 | 6 |
| C | HIS | B | 2 | 27.279 | 22.868 | -18.087 | 0.00 | 0.00 | 6 |
| N | HIS | B | 2 | 25.406 | 23.923 | -17.701 | 0.00 | 0.00 | 7 |
| CE | HIS | B | 2 | 26.363 | 24.831 | -17.719 | 0.00 | 0.00 | 6 |
| N | HIS | B | 2 | 27.510 | 24.217 | -17.952 | 0.00 | 0.00 | 7 |
| C | HIS | B | 2 | 24.288 | 21.375 | -15.598 | 0.00 | 0.00 | 6 |
| O | HIS | B | 2 | 23.085 | 21.157 | -15.436 | 0.00 | 0.00 | 8 |
| N | MET | B | 2 | 24.946 | 22.292 | -14.889 | 0.00 | 0.00 | 7 |
| CA | MET | B | 2 | 24.297 | 23.020 | -13.806 | 0.00 | 0.00 | 6 |
| CB | MET | B | 2 | 25.284 | 23.763 | -12.915 | 0.00 | 0.00 | 6 |
| C | MET | B | 2 | 26.479 | 24.423 | -13.565 | 0.00 | 0.00 | 6 |
| SD | MET | B | 2 | 27.340 | 25.556 | -12.453 | 0.00 | 0.00 | 1 |
| CE | MET | B | 2 | 28.762 | 24.575 | -11.990 | 0.00 | 0.00 | 6 |
| C | MET | B | 2 | 23.192 | 23.954 | -14.283 | 0.00 | 0.00 | 6 |
| O | MET | B | 2 | 22.242 | 24.177 | -13.521 | 0.00 | 0.00 | 8 |
| N | THR | B | 2 | 23.280 | 24.496 | -15.491 | 0.00 | 0.00 | 7 |
| CA | THR | B | 2 | 22.249 | 25.396 | -15.991 | 0.00 | 0.00 | 6 |
| CB | THR | B | 2 | 22.776 | 26.836 | -16.144 | 0.00 | 0.00 | 6 |
| O | THR | B | 2 | 24.147 | 26.806 | -16.565 | 0.00 | 0.00 | 8 |
| C | THR | B | 2 | 22.665 | 27.584 | -14.824 | 0.00 | 0.00 | 6 |
| C | THR | B | 2 | 21.657 | 24.943 | -17.318 | 0.00 | 0.00 | 6 |
| O | THR | B | 2 | 20.454 | 25.103 | -17.539 | 0.00 | 0.00 | 8 |
| N | SER | B | 2 | 22.480 | 24.384 | -18.196 | 0.00 | 0.00 | 7 |
| CA | SER | B | 2 | 22.012 | 23.923 | -19.495 | 0.00 | 0.00 | 6 |
| CB | SER | B | 2 | 23.128 | 24.054 | -20.538 | 0.00 | 0.00 | 6 |
| O | SER | B | 2 | 23.448 | 25.410 | -20.790 | 0.00 | 0.00 | 8 |
| C | SER | B | 2 | 21.533 | 22.477 | -19.459 | 0.00 | 0.00 | 6 |
| O | SER | B | 2 | 22.118 | 21.612 | -18.811 | 0.00 | 0.00 | 8 |
| N | PRO | B | 2 | 20.485 | 22.196 | -20.221 | 0.00 | 0.00 | 7 |
| C | PRO | B | 2 | 19.715 | 23.172 | -21.033 | 0.00 | 0.00 | 6 |
| CA | PRO | B | 2 | 19.932 | 20.860 | -20.357 | 0.00 | 0.00 | 6 |
| CB | PRO | B | 2 | 18.460 | 21.148 | -20.623 | 0.00 | 0.00 | 6 |
| C | PRO | B | 2 | 18.445 | 22.437 | -21.365 | 0.00 | 0.00 | 6 |
| C | PRO | B | 2 | 20.565 | 20.112 | -21.518 | 0.00 | 0.00 | 6 |
| O | PRO | B | 2 | 21.197 | 20.714 | -22.390 | 0.00 | 0.00 | 8 |
| N | PRO | B | 2 | 20.414 | 18.795 | -21.539 | 0.00 | 0.00 | 7 |
| C | PRO | B | 2 | 19.641 | 18.000 | -20.560 | 0.00 | 0.00 | 6 |
| CA | PRO | B | 2 | 20.896 | 17.984 | -22.643 | 0.00 | 0.00 | 6 |
| CB | PRO | B | 2 | 20.726 | 16.551 | -22.173 | 0.00 | 0.00 | 6 |
| C | PRO | B | 2 | 19.915 | 16.576 | -20.935 | 0.00 | 0.00 | 6 |
| C | PRO | B | 2 | 20.079 | 18.275 | -23.889 | 0.00 | 0.00 | 6 |
| O | PRO | B | 2 | 18.844 | 18.264 | -23.831 | 0.00 | 0.00 | 8 |
| N | GLU | B | 2 | 20.721 | 18.449 | -25.038 | 0.00 | 0.00 | 7 |
| CA | GLU | B | 2 | 20.025 | 18.704 | -26.299 | 0.00 | 0.00 | 6 |
| CB | GLU | B | 2 | 21.031 | 18.855 | -27.441 | 0.00 | 0.00 | 6 |
| C | GLU | B | 2 | 22.096 | 19.912 | -27.188 | 0.00 | 0.00 | 6 |
| C | GLU | B | 2 | 22.372 | 20.788 | -28.392 | 0.00 | 0.00 | 6 |
| O | GLU | B | 2 | 23.395 | 20.565 | -29.075 | 0.00 | 0.00 | 8 |
| O | GLU | B | 2 | 21.570 | 21.707 | -28.665 | 0.00 | 0.00 | 8 |
| C | GLU | B | 2 | 18.991 | 17.627 | -26.599 | 0.00 | 0.00 | 6 |
| O | GLU | B | 2 | 17.914 | 17.862 | -27.146 | 0.00 | 0.00 | 8 |
| N | ASN | B | 2 | 19.270 | 16.400 | -26.211 | 0.00 | 0.00 | 7 |
| CA | ASN | B | 2 | 18.435 | 15.232 | -26.207 | 0.00 | 0.00 | 6 |
| CB | ASN | B | 2 | 19.172 | 14.173 | -25.349 | 0.00 | 0.00 | 6 |
| C | ASN | B | 2 | 18.345 | 12.748 | -25.717 | 0.00 | 0.00 | 6 |
| O | ASN | B | 2 | 19.753 | 11.936 | -25.906 | 0.00 | 0.00 | 8 |
| N | ASN | B | 2 | 17.563 | 12.424 | -25.817 | 0.00 | 0.00 | 7 |
| C | ASN | B | 2 | 17.071 | 15.424 | -25.550 | 0.00 | 0.00 | 6 |
| O | ASN | B | 2 | 16.066 | 14.871 | -25.996 | 0.00 | 0.00 | 8 |
| N | GLY | B | 2 | 17.065 | 16.049 | -24.372 | 0.00 | 0.00 | 7 |
| CA | GLY | B | 2 | 15.866 | 16.222 | -23.566 | 0.00 | 0.00 | 6 |
| C | GLY | B | 2 | 15.598 | 14.984 | -22.712 | 0.00 | 0.00 | 6 |
| O | GLY | B | 2 | 14.492 | 14.758 | -22.223 | 0.00 | 0.00 | 8 |
| N | ALA | B | 2 | 16.622 | 14.173 | -22.501 | 0.00 | 0.00 | 7 |
| CA | ALA | B | 2 | 16.575 | 12.927 | -21.771 | 0.00 | 0.00 | 6 |
| CB | ALA | B | 2 | 17.997 | 12.361 | -21.662 | 0.00 | 0.00 | 6 |
| C | ALA | B | 2 | 15.955 | 12.959 | -20.385 | 0.00 | 0.00 | 6 |
| O | ALA | B | 2 | 15.249 | 12.014 | -20.012 | 0.00 | 0.00 | 8 |
| N | GLY | B | 2 | 16.284 | 13.950 | -19.564 | 0.00 | 0.00 | 7 |
| CA | GLY | B | 2 | 15.732 | 14.032 | -18.215 | 0.00 | 0.00 | 6 |
| C | GLY | B | 2 | 14.264 | 14.437 | -18.254 | 0.00 | 0.00 | 6 |
| O | GLY | B | 2 | 13.456 | 13.967 | -17.452 | 0.00 | 0.00 | 8 |
| N | ALA | B | 2 | 13.921 | 15.313 | -19.193 | 0.00 | 0.00 | 7 |
| CA | ALA | B | 2 | 12.549 | 15.782 | -19.358 | 0.00 | 0.00 | 6 |
| CB | ALA | B | 2 | 12.508 | 16.914 | -20.373 | 0.00 | 0.00 | 6 |
| C | ALA | B | 2 | 11.638 | 14.633 | -19.775 | 0.00 | 0.00 | 6 |
| O | ALA | B | 2 | 10.537 | 14.466 | -19.251 | 0.00 | 0.00 | 8 |
| N | ALA | B | 2 | 12.125 | 13.781 | -20.672 | 0.00 | 0.00 | 7 |
| CA | ALA | B | 2 | 11.409 | 12.585 | -21.094 | 0.00 | 0.00 | 6 |
| CB | ALA | B | 2 | 12.212 | 11.839 | -22.151 | 0.00 | 0.00 | 6 |
| C | ALA | B | 2 | 11.158 | 11.665 | -19.904 | 0.00 | 0.00 | 6 |
| O | ALA | B | 2 | 10.040 | 11.206 | -19.674 | 0.00 | 0.00 | 8 |
| N | LEU | B | 2 | 12.207 | 11.418 | -19.123 | 0.00 | 0.00 | 7 |
| CA | LEU | B | 2 | 12.127 | 10.568 | -17.944 | 0.00 | 0.00 | 6 |
| CB | LEU | B | 2 | 13.483 | 10.549 | -17.234 | 0.00 | 0.00 | 6 |
| C | LEU | B | 2 | 14.093 | 9.186 | -16.906 | 0.00 | 0.00 | 6 |
| C | LEU | B | 2 | 15.393 | 9.365 | -16.133 | 0.00 | 0.00 | 6 |
| C | LEU | B | 2 | 13.122 | 8.312 | -16.125 | 0.00 | 0.00 | 6 |
| C | LEU | B | 2 | 11.044 | 11.001 | -16.966 | 0.00 | 0.00 | 6 |
| O | LEU | B | 2 | 10.249 | 10.182 | -16.499 | 0.00 | 0.00 | 8 |
| N | ALA | B | 2 | 10.992 | 12.293 | -16.648 | 0.00 | 0.00 | 7 |
| CA | ALA | B | 2 | 9.989 | 12.831 | -15.736 | 0.00 | 0.00 | 6 |
| CB | ALA | B | 2 | 10.311 | 14.279 | -15.395 | 0.00 | 0.00 | 6 |
| C | ALA | B | 2 | 8.580 | 12.703 | -16.305 | 0.00 | 0.00 | 6 |
| O | ALA | B | 2 | 7.642 | 12.413 | -15.555 | 0.00 | 0.00 | 8 |
| N | MET | B | 2 | 8.424 | 12.909 | -17.614 | 0.00 | 0.00 | 7 |
| CA | MET | B | 2 | 7.111 | 12.712 | -18.239 | 0.00 | 0.00 | 6 |
| CB | MET | B | 2 | 7.060 | 13.311 | -19.636 | 0.00 | 0.00 | 6 |
| C | MET | B | 2 | 7.126 | 14.834 | -20.677 | 0.00 | 0.00 | 6 |
| SD | MET | B | 2 | 6.856 | 15.558 | -21.262 | 0.00 | 0.00 | 1 |
| CE | MET | B | 2 | 8.526 | 15.634 | -21.899 | 0.00 | 0.00 | 6 |
| C | MET | B | 2 | 6.802 | 11.220 | -18.214 | 0.00 | 0.00 | 6 |
| O | MET | B | 2 | 5.763 | 10.790 | -17.711 | 0.00 | 0.00 | 8 |
| N | ALA | B | 2 | 7.773 | 10.402 | -18.613 | 0.00 | 0.00 | 7 |
| CA | ALA | B | 2 | 7.647 | 8.952 | -18.540 | 0.00 | 0.00 | 6 |
| CB | ALA | B | 2 | 8.954 | 8.281 | -18.938 | 0.00 | 0.00 | 6 |
| C | ALA | B | 2 | 7.235 | 8.493 | -17.145 | 0.00 | 0.00 | 6 |
| O | ALA | B | 2 | 6.285 | 7.716 | -17.030 | 0.00 | 0.00 | 8 |
| N | ASN | B | 2 | 7.901 | 8.968 | -16.094 | 0.00 | 0.00 | 7 |
| CA | ASN | B | 2 | 7.583 | 8.566 | -14.733 | 0.00 | 0.00 | 6 |
| CB | ASN | B | 2 | 8.627 | 9.075 | -13.730 | 0.00 | 0.00 | 6 |
| C | ASN | B | 2 | 9.949 | 8.343 | -13.851 | 0.00 | 0.00 | 6 |
| O | ASN | B | 2 | 9.990 | 7.167 | -14.216 | 0.00 | 0.00 | 8 |
| N | ASN | B | 2 | 11.042 | 9.034 | -13.551 | 0.00 | 0.00 | 7 |

Figure 1 - 40

| | | | | | | | | | | | | | | | | | |
|---|---|---|---|---|---|---|---|---|---|---|---|---|---|---|---|---|---|
| C | ASN | B | 2 | 6.197 | 8.998 | -14.279 | 0.00 | 0.00 | 6 | O | ALA | B | 2 | -0.518 | 11.392 | -24.609 | 0.00 | 0.00 | 8 |
| O | ASN | B | 2 | 5.503 | 8.220 | -13.619 | 0.00 | 0.00 | 8 | N | SER | B | 2 | -1.137 | 9.337 | -25.190 | 0.00 | 0.00 | 7 |
| N | ALA | B | 2 | 5.777 | 10.216 | -14.603 | 0.00 | 0.00 | 7 | CA | SER | B | 2 | -2.220 | 9.753 | -26.061 | 0.00 | 0.00 | 6 |
| CA | ALA | B | 2 | 4.454 | 10.699 | -14.218 | 0.00 | 0.00 | 6 | CB | SER | B | 2 | -2.484 | 8.658 | -27.106 | 0.00 | 0.00 | 6 |
| CB | ALA | B | 2 | 4.306 | 12.172 | -14.556 | 0.00 | 0.00 | 6 | O | SER | B | 2 | -3.091 | 7.533 | -26.492 | 0.00 | 0.00 | 8 |
| C | ALA | B | 2 | 3.368 | 9.877 | -14.905 | 0.00 | 0.00 | 6 | C | SER | B | 2 | -3.518 | 10.076 | -25.337 | 0.00 | 0.00 | 6 |
| O | ALA | B | 2 | 2.352 | 9.517 | -14.309 | 0.00 | 0.00 | 8 | O | SER | B | 2 | -4.542 | 10.359 | -25.965 | 0.00 | 0.00 | 8 |
| N | LEU | B | 2 | 3.579 | 9.576 | -16.183 | 0.00 | 0.00 | 7 | N | GLN | B | 2 | -3.509 | 10.047 | -24.013 | 0.00 | 0.00 | 7 |
| CA | LEU | B | 2 | 2.697 | 8.712 | -16.953 | 0.00 | 0.00 | 6 | CA | GLN | B | 2 | -4.668 | 10.363 | -23.192 | 0.00 | 0.00 | 6 |
| CB | LEU | B | 2 | 3.249 | 8.513 | -18.366 | 0.00 | 0.00 | 6 | CB | GLN | B | 2 | -4.827 | 9.353 | -22.058 | 0.00 | 0.00 | 6 |
| C | LEU | B | 2 | 3.101 | 9.673 | -19.350 | 0.00 | 0.00 | 6 | C | GLN | B | 2 | -5.411 | 8.026 | -22.514 | 0.00 | 0.00 | 6 |
| C | LEU | B | 2 | 3.754 | 9.327 | -20.681 | 0.00 | 0.00 | 6 | C | GLN | B | 2 | -5.194 | 6.897 | -21.531 | 0.00 | 0.00 | 6 |
| C | LEU | B | 2 | 1.639 | 10.039 | -19.560 | 0.00 | 0.00 | 6 | O | GLN | B | 2 | -5.872 | 6.804 | -20.506 | 0.00 | 0.00 | 8 |
| C | LEU | B | 2 | 2.529 | 7.358 | -16.271 | 0.00 | 0.00 | 6 | N | GLN | B | 2 | -4.244 | 6.019 | -21.837 | 0.00 | 0.00 | 7 |
| O | LEU | B | 2 | 1.414 | 6.913 | -16.001 | 0.00 | 0.00 | 8 | C | GLN | B | 2 | -4.523 | 11.789 | -22.658 | 0.00 | 0.00 | 6 |
| N | ARG | B | 2 | 3.649 | 6.713 | -15.949 | 0.00 | 0.00 | 7 | O | GLN | B | 2 | -5.433 | 12.355 | -22.059 | 0.00 | 0.00 | 8 |
| CA | ARG | B | 2 | 3.632 | 5.420 | -15.266 | 0.00 | 0.00 | 6 | N | ILE | B | 2 | -3.356 | 12.376 | -22.904 | 0.00 | 0.00 | 7 |
| CB | ARG | B | 2 | 5.055 | 4.885 | -15.124 | 0.00 | 0.00 | 6 | CA | ILE | B | 2 | -3.062 | 13.745 | -22.523 | 0.00 | 0.00 | 6 |
| C | ARG | B | 2 | 5.269 | 3.835 | -14.048 | 0.00 | 0.00 | 6 | CB | ILE | B | 2 | -1.568 | 13.957 | -22.207 | 0.00 | 0.00 | 6 |
| C | ARG | B | 2 | 6.689 | 3.295 | -14.066 | 0.00 | 0.00 | 6 | C | ILE | B | 2 | -1.273 | 15.420 | -21.897 | 0.00 | 0.00 | 6 |
| N | ARG | B | 2 | 7.635 | 4.187 | -13.408 | 0.00 | 0.00 | 7 | C | ILE | B | 2 | -1.110 | 13.054 | -21.063 | 0.00 | 0.00 | 6 |
| CZ | ARG | B | 2 | 8.956 | 4.067 | -13.453 | 0.00 | 0.00 | 6 | C | ILE | B | 2 | -1.688 | 13.362 | -19.702 | 0.00 | 0.00 | 6 |
| N | ARG | B | 2 | 9.524 | 3.079 | -14.131 | 0.00 | 0.00 | 7 | C | ILE | B | 2 | -3.459 | 14.705 | -23.644 | 0.00 | 0.00 | 6 |
| N | ARG | B | 2 | 9.724 | 4.941 | -12.814 | 0.00 | 0.00 | 7 | O | ILE | B | 2 | -2.932 | 14.637 | -24.753 | 0.00 | 0.00 | 8 |
| C | ARG | B | 2 | 2.935 | 5.532 | -13.917 | 0.00 | 0.00 | 6 | N | GLY | B | 2 | -4.373 | 15.617 | -23.335 | 0.00 | 0.00 | 7 |
| O | ARG | B | 2 | 2.078 | 4.719 | -13.573 | 0.00 | 0.00 | 8 | CA | GLY | B | 2 | -4.821 | 16.601 | -24.309 | 0.00 | 0.00 | 6 |
| N | ASP | B | 2 | 3.191 | 6.610 | -13.186 | 0.00 | 0.00 | 7 | C | GLY | B | 2 | -3.847 | 17.773 | -24.385 | 0.00 | 0.00 | 6 |
| CA | ASP | B | 2 | 2.559 | 6.904 | -11.916 | 0.00 | 0.00 | 6 | O | GLY | B | 2 | -3.426 | 18.156 | -25.478 | 0.00 | 0.00 | 8 |
| CB | ASP | B | 2 | 3.171 | 8.182 | -11.323 | 0.00 | 0.00 | 6 | N | TYR | B | 2 | -3.477 | 18.323 | -23.231 | 0.00 | 0.00 | 7 |
| C | ASP | B | 2 | 2.856 | 8.314 | -9.846 | 0.00 | 0.00 | 6 | CA | TYR | B | 2 | -2.646 | 19.522 | -23.206 | 0.00 | 0.00 | 6 |
| O | ASP | B | 2 | 2.518 | 9.432 | -9.411 | 0.00 | 0.00 | 8 | CB | TYR | B | 2 | -3.529 | 20.725 | -22.877 | 0.00 | 0.00 | 6 |
| O | ASP | B | 2 | 2.940 | 7.293 | -9.132 | 0.00 | 0.00 | 8 | C | TYR | B | 2 | -2.845 | 21.997 | -22.443 | 0.00 | 0.00 | 6 |
| C | ASP | B | 2 | 1.046 | 7.058 | -11.994 | 0.00 | 0.00 | 6 | C | TYR | B | 2 | -3.068 | 22.517 | -21.173 | 0.00 | 0.00 | 6 |
| O | ASP | B | 2 | 0.359 | 6.775 | -11.009 | 0.00 | 0.00 | 8 | CE | TYR | B | 2 | -2.459 | 23.687 | -20.759 | 0.00 | 0.00 | 6 |
| N | ALA | B | 2 | 0.513 | 7.523 | -13.118 | 0.00 | 0.00 | 7 | C | TYR | B | 2 | -1.993 | 22.692 | -23.290 | 0.00 | 0.00 | 6 |
| CA | ALA | B | 2 | -0.922 | 7.681 | -13.301 | 0.00 | 0.00 | 6 | CE | TYR | B | 2 | -1.384 | 23.866 | -22.887 | 0.00 | 0.00 | 6 |
| CB | ALA | B | 2 | -1.223 | 8.916 | -14.135 | 0.00 | 0.00 | 6 | CZ | TYR | B | 2 | -1.620 | 24.357 | -21.621 | 0.00 | 0.00 | 6 |
| C | ALA | B | 2 | -1.516 | 6.439 | -13.964 | 0.00 | 0.00 | 6 | O | TYR | B | 2 | -1.016 | 25.527 | -21.218 | 0.00 | 0.00 | 8 |
| O | ALA | B | 2 | -2.692 | 6.123 | -13.796 | 0.00 | 0.00 | 8 | C | TYR | B | 2 | -1.473 | 19.443 | -22.237 | 0.00 | 0.00 | 6 |
| N | GLY | B | 2 | -0.686 | 5.728 | -14.719 | 0.00 | 0.00 | 7 | O | TYR | B | 2 | -1.568 | 19.003 | -21.096 | 0.00 | 0.00 | 8 |
| CA | GLY | B | 2 | -1.103 | 4.503 | -15.387 | 0.00 | 0.00 | 6 | N | VAL | B | 3 | -0.332 | 19.933 | -22.716 | 0.00 | 0.00 | 7 |
| C | GLY | B | 2 | -1.918 | 4.797 | -16.638 | 0.00 | 0.00 | 6 | CA | VAL | B | 3 | 0.899 | 20.017 | -21.955 | 0.00 | 0.00 | 6 |
| O | GLY | B | 2 | -2.958 | 4.188 | -16.884 | 0.00 | 0.00 | 8 | CB | VAL | B | 3 | 2.073 | 19.317 | -22.668 | 0.00 | 0.00 | 6 |
| N | ILE | B | 2 | -1.489 | 5.803 | -17.390 | 0.00 | 0.00 | 7 | C | VAL | B | 3 | 3.350 | 19.407 | -21.839 | 0.00 | 0.00 | 6 |
| CA | ILE | B | 2 | -2.135 | 6.185 | -18.635 | 0.00 | 0.00 | 6 | C | VAL | B | 3 | 1.754 | 17.860 | -22.970 | 0.00 | 0.00 | 6 |
| CB | ILE | B | 2 | -2.941 | 7.490 | -18.545 | 0.00 | 0.00 | 6 | C | VAL | B | 3 | 1.288 | 21.478 | -21.725 | 0.00 | 0.00 | 6 |
| C | ILE | B | 2 | -4.284 | 7.276 | -17.859 | 0.00 | 0.00 | 6 | O | VAL | B | 3 | 1.617 | 22.189 | -22.675 | 0.00 | 0.00 | 8 |
| C | ILE | B | 2 | -2.148 | 8.580 | -17.820 | 0.00 | 0.00 | 6 | N | ASN | B | 3 | 1.213 | 21.932 | -20.480 | 0.00 | 0.00 | 7 |
| C | ILE | B | 2 | -2.581 | 9.986 | -18.178 | 0.00 | 0.00 | 6 | CA | ASN | B | 3 | 1.764 | 23.246 | -20.122 | 0.00 | 0.00 | 6 |
| C | ILE | B | 2 | -1.054 | 6.345 | -19.704 | 0.00 | 0.00 | 6 | CB | ASN | B | 3 | 1.188 | 23.777 | -18.828 | 0.00 | 0.00 | 6 |
| O | ILE | B | 2 | 0.106 | 6.569 | -19.357 | 0.00 | 0.00 | 8 | C | ASN | B | 3 | 1.564 | 25.203 | -18.499 | 0.00 | 0.00 | 6 |
| N | GLU | B | 2 | -1.433 | 6.212 | -20.968 | 0.00 | 0.00 | 7 | O | ASN | B | 3 | 0.786 | 26.131 | -18.730 | 0.00 | 0.00 | 8 |
| CA | GLU | B | 2 | -0.451 | 6.387 | -22.040 | 0.00 | 0.00 | 6 | N | ASN | B | 3 | 2.755 | 25.399 | -17.946 | 0.00 | 0.00 | 7 |
| CB | GLU | B | 2 | -0.771 | 5.479 | -23.223 | 0.00 | 0.00 | 6 | C | ASN | B | 3 | 3.278 | 23.030 | -20.032 | 0.00 | 0.00 | 6 |
| C | GLU | B | 2 | -0.617 | 3.998 | -22.905 | 0.00 | 0.00 | 6 | O | ASN | B | 3 | 3.774 | 22.358 | -19.130 | 0.00 | 0.00 | 8 |
| C | GLU | B | 2 | -0.460 | 3.145 | -24.149 | 0.00 | 0.00 | 6 | N | ALA | B | 3 | 3.984 | 23.535 | -21.029 | 0.00 | 0.00 | 7 |
| O | GLU | B | 2 | -1.287 | 2.230 | -24.354 | 0.00 | 0.00 | 8 | CA | ALA | B | 3 | 5.415 | 23.350 | -21.148 | 0.00 | 0.00 | 6 |
| O | GLU | B | 2 | 0.491 | 3.388 | -24.922 | 0.00 | 0.00 | 8 | CB | ALA | B | 3 | 5.829 | 23.721 | -22.576 | 0.00 | 0.00 | 6 |
| C | GLU | B | 2 | -0.401 | 7.855 | -22.436 | 0.00 | 0.00 | 6 | C | ALA | B | 3 | 6.244 | 24.179 | -20.183 | 0.00 | 0.00 | 6 |
| O | GLU | B | 2 | -1.285 | 8.634 | -22.071 | 0.00 | 0.00 | 8 | O | ALA | B | 3 | 5.771 | 25.171 | -19.637 | 0.00 | 0.00 | 8 |
| N | ALA | B | 2 | 0.594 | 8.245 | -23.220 | 0.00 | 0.00 | 7 | N | HIS | B | 3 | 7.513 | 23.777 | -20.037 | 0.00 | 0.00 | 7 |
| CA | ALA | B | 2 | 0.770 | 9.620 | -23.657 | 0.00 | 0.00 | 6 | CA | HIS | B | 3 | 8.425 | 24.569 | -19.205 | 0.00 | 0.00 | 6 |
| CB | ALA | B | 2 | 2.109 | 9.745 | -24.387 | 0.00 | 0.00 | 6 | CB | HIS | B | 3 | 9.687 | 23.805 | -18.825 | 0.00 | 0.00 | 6 |
| C | ALA | B | 2 | -0.338 | 10.170 | -24.538 | 0.00 | 0.00 | 6 | C | HIS | B | 3 | 10.607 | 24.611 | -17.954 | 0.00 | 0.00 | 6 |

Figure 1 - 41

| | | | | | | | | | | | | | | | | | |
|---|---|---|---|---|---|---|---|---|---|---|---|---|---|---|---|---|---|
| C | HIS | B | 3 | 10.390 | 25.210 | -16.758 | 0.00 | 0.00 | 6 | CA | ALA | B | 3 | 15.321 | 19.999 | -25.558 | 0.00 | 0.00 | 6 |
| N | HIS | B | 3 | 11.903 | 24.910 | -18.306 | 0.00 | 0.00 | 7 | CB | ALA | B | 3 | 16.151 | 20.211 | -24.301 | 0.00 | 0.00 | 6 |
| CE | HIS | B | 3 | 12.452 | 25.651 | -17.361 | 0.00 | 0.00 | 6 | C | ALA | B | 3 | 13.924 | 19.512 | -25.199 | 0.00 | 0.00 | 6 |
| N | HIS | B | 3 | 11.555 | 25.349 | -16.411 | 0.00 | 0.00 | 7 | O | ALA | B | 3 | 13.580 | 18.357 | -25.449 | 0.00 | 0.00 | 8 |
| C | HIS | B | 3 | 8.713 | 25.840 | -20.012 | 0.00 | 0.00 | 6 | N | GLU | B | 3 | 13.106 | 20.401 | -24.642 | 0.00 | 0.00 | 7 |
| O | HIS | B | 3 | 8.552 | 26.963 | -19.544 | 0.00 | 0.00 | 8 | CA | GLU | B | 3 | 11.734 | 20.071 | -24.292 | 0.00 | 0.00 | 6 |
| N | GLY | B | 3 | 8.959 | 25.668 | -21.304 | 0.00 | 0.00 | 7 | CB | GLU | B | 3 | 11.017 | 21.263 | -23.650 | 0.00 | 0.00 | 6 |
| CA | GLY | B | 3 | 9.110 | 26.699 | -22.298 | 0.00 | 0.00 | 6 | C | GLU | B | 3 | 9.583 | 20.941 | -23.264 | 0.00 | 0.00 | 6 |
| C | GLY | B | 3 | 9.520 | 28.073 | -21.817 | 0.00 | 0.00 | 6 | C | GLU | B | 3 | 8.946 | 21.951 | -22.340 | 0.00 | 0.00 | 6 |
| O | GLY | B | 3 | 8.705 | 29.001 | -21.787 | 0.00 | 0.00 | 8 | O | GLU | B | 3 | 9.409 | 23.108 | -22.269 | 0.00 | 0.00 | 8 |
| N | THR | B | 3 | 10.795 | 28.256 | -21.485 | 0.00 | 0.00 | 7 | O | GLU | B | 3 | 7.952 | 21.571 | -21.682 | 0.00 | 0.00 | 8 |
| CA | THR | B | 3 | 11.269 | 29.531 | -20.965 | 0.00 | 0.00 | 6 | C | GLU | B | 3 | 10.956 | 19.598 | -25.515 | 0.00 | 0.00 | 6 |
| CB | THR | B | 3 | 12.393 | 29.318 | -19.926 | 0.00 | 0.00 | 6 | O | GLU | B | 3 | 10.335 | 18.535 | -25.473 | 0.00 | 0.00 | 8 |
| O | THR | B | 3 | 13.417 | 28.495 | -20.489 | 0.00 | 0.00 | 8 | N | ALA | B | 3 | 11.030 | 20.340 | -26.616 | 0.00 | 0.00 | 7 |
| C | THR | B | 3 | 11.814 | 28.661 | -18.686 | 0.00 | 0.00 | 6 | CA | ALA | B | 3 | 10.418 | 19.917 | -27.874 | 0.00 | 0.00 | 6 |
| C | THR | B | 3 | 11.749 | 30.530 | -21.994 | 0.00 | 0.00 | 6 | CB | ALA | B | 3 | 10.878 | 20.817 | -29.012 | 0.00 | 0.00 | 6 |
| O | THR | B | 3 | 11.989 | 31.682 | -21.621 | 0.00 | 0.00 | 8 | C | ALA | B | 3 | 10.765 | 18.460 | -28.169 | 0.00 | 0.00 | 6 |
| N | SER | B | 3 | 11.871 | 30.151 | -23.253 | 0.00 | 0.00 | 7 | O | ALA | B | 3 | 9.903 | 17.589 | -28.253 | 0.00 | 0.00 | 8 |
| CA | SER | B | 3 | 12.296 | 31.048 | -24.316 | 0.00 | 0.00 | 6 | N | GLN | B | 3 | 12.057 | 18.168 | -28.245 | 0.00 | 0.00 | 7 |
| CB | SER | B | 3 | 11.700 | 32.449 | -24.195 | 0.00 | 0.00 | 6 | CA | GLN | B | 3 | 12.595 | 16.840 | -28.467 | 0.00 | 0.00 | 6 |
| O | SER | B | 3 | 11.945 | 33.196 | -25.377 | 0.00 | 0.00 | 8 | CB | GLN | B | 3 | 14.128 | 16.919 | -28.418 | 0.00 | 0.00 | 6 |
| C | SER | B | 3 | 13.817 | 31.113 | -24.425 | 0.00 | 0.00 | 6 | C | GLN | B | 3 | 14.837 | 15.647 | -28.840 | 0.00 | 0.00 | 6 |
| O | SER | B | 3 | 14.407 | 32.108 | -24.845 | 0.00 | 0.00 | 8 | C | GLN | B | 3 | 14.676 | 15.342 | -30.316 | 0.00 | 0.00 | 6 |
| N | THR | B | 3 | 14.456 | 30.003 | -24.054 | 0.00 | 0.00 | 7 | O | GLN | B | 3 | 15.369 | 15.914 | -31.156 | 0.00 | 0.00 | 8 |
| CA | THR | B | 3 | 15.905 | 29.895 | -24.172 | 0.00 | 0.00 | 6 | N | GLN | B | 3 | 13.752 | 14.439 | -30.630 | 0.00 | 0.00 | 7 |
| CB | THR | B | 3 | 16.565 | 29.275 | -22.928 | 0.00 | 0.00 | 6 | C | GLN | B | 3 | 12.106 | 15.797 | -27.473 | 0.00 | 0.00 | 6 |
| O | THR | B | 3 | 15.830 | 28.108 | -22.530 | 0.00 | 0.00 | 8 | O | GLN | B | 3 | 11.875 | 14.642 | -27.844 | 0.00 | 0.00 | 8 |
| C | THR | B | 3 | 16.593 | 30.277 | -21.786 | 0.00 | 0.00 | 6 | N | ALA | B | 3 | 11.921 | 16.171 | -26.211 | 0.00 | 0.00 | 7 |
| C | THR | B | 3 | 16.187 | 28.984 | -25.372 | 0.00 | 0.00 | 6 | CA | ALA | B | 3 | 11.429 | 15.277 | -25.178 | 0.00 | 0.00 | 6 |
| O | THR | B | 3 | 15.513 | 27.968 | -25.556 | 0.00 | 0.00 | 8 | CB | ALA | B | 3 | 11.680 | 15.890 | -23.803 | 0.00 | 0.00 | 6 |
| N | PRO | B | 3 | 17.140 | 29.376 | -26.198 | 0.00 | 0.00 | 7 | C | ALA | B | 3 | 9.950 | 14.942 | -25.329 | 0.00 | 0.00 | 6 |
| C | PRO | B | 3 | 17.984 | 30.585 | -26.036 | 0.00 | 0.00 | 6 | O | ALA | B | 3 | 9.512 | 13.883 | -24.874 | 0.00 | 0.00 | 8 |
| CA | PRO | B | 3 | 17.543 | 28.578 | -27.343 | 0.00 | 0.00 | 6 | N | VAL | B | 3 | 9.171 | 15.327 | -25.938 | 0.00 | 0.00 | 7 |
| CB | PRO | B | 3 | 18.871 | 29.194 | -27.764 | 0.00 | 0.00 | 6 | CA | VAL | B | 3 | 7.748 | 15.592 | -26.168 | 0.00 | 0.00 | 6 |
| C | PRO | B | 3 | 18.799 | 30.609 | -27.303 | 0.00 | 0.00 | 6 | CB | VAL | B | 3 | 6.977 | 16.904 | -26.378 | 0.00 | 0.00 | 6 |
| C | PRO | B | 3 | 17.675 | 27.110 | -26.977 | 0.00 | 0.00 | 6 | C | VAL | B | 3 | 5.548 | 16.665 | -26.846 | 0.00 | 0.00 | 6 |
| O | PRO | B | 3 | 16.843 | 26.287 | -27.366 | 0.00 | 0.00 | 8 | C | VAL | B | 3 | 6.973 | 17.714 | -25.087 | 0.00 | 0.00 | 6 |
| N | ALA | B | 3 | 18.660 | 26.778 | -26.149 | 0.00 | 0.00 | 7 | C | VAL | B | 3 | 7.563 | 14.663 | -27.364 | 0.00 | 0.00 | 6 |
| CA | ALA | B | 3 | 18.923 | 25.406 | -25.745 | 0.00 | 0.00 | 6 | O | VAL | B | 3 | 6.690 | 13.795 | -27.365 | 0.00 | 0.00 | 8 |
| CB | ALA | B | 3 | 20.164 | 25.368 | -24.855 | 0.00 | 0.00 | 6 | N | LYS | B | 3 | 8.449 | 14.789 | -28.349 | 0.00 | 0.00 | 7 |
| C | ALA | B | 3 | 17.765 | 24.708 | -25.053 | 0.00 | 0.00 | 6 | CA | LYS | B | 3 | 8.452 | 13.883 | -29.494 | 0.00 | 0.00 | 6 |
| O | ALA | B | 3 | 17.474 | 23.546 | -25.367 | 0.00 | 0.00 | 8 | CB | LYS | B | 3 | 9.497 | 14.318 | -30.523 | 0.00 | 0.00 | 6 |
| N | GLY | B | 3 | 17.115 | 25.356 | -24.096 | 0.00 | 0.00 | 7 | C | LYS | B | 3 | 9.016 | 15.457 | -31.412 | 0.00 | 0.00 | 6 |
| CA | GLY | B | 3 | 16.039 | 24.752 | -23.333 | 0.00 | 0.00 | 6 | C | LYS | B | 3 | 10.069 | 15.875 | -32.425 | 0.00 | 0.00 | 6 |
| C | GLY | B | 3 | 14.786 | 24.429 | -24.125 | 0.00 | 0.00 | 6 | CE | LYS | B | 3 | 9.475 | 16.820 | -33.459 | 0.00 | 0.00 | 6 |
| O | GLY | B | 3 | 14.189 | 23.363 | -23.945 | 0.00 | 0.00 | 8 | NZ | LYS | B | 3 | 10.515 | 17.393 | -34.357 | 0.00 | 0.00 | 7 |
| N | ASP | B | 3 | 14.369 | 25.321 | -25.018 | 0.00 | 0.00 | 7 | C | LYS | B | 3 | 8.698 | 12.454 | -29.024 | 0.00 | 0.00 | 6 |
| CA | ASP | B | 3 | 13.160 | 25.124 | -25.811 | 0.00 | 0.00 | 6 | O | LYS | B | 3 | 7.916 | 11.547 | -29.302 | 0.00 | 0.00 | 8 |
| CB | ASP | B | 3 | 12.801 | 26.400 | -26.575 | 0.00 | 0.00 | 6 | N | THR | B | 3 | 9.715 | 12.270 | -28.192 | 0.00 | 0.00 | 7 |
| C | ASP | B | 3 | 12.317 | 27.517 | -25.673 | 0.00 | 0.00 | 6 | CA | THR | B | 3 | 10.094 | 10.986 | -27.636 | 0.00 | 0.00 | 6 |
| O | ASP | B | 3 | 11.991 | 28.602 | -26.198 | 0.00 | 0.00 | 8 | CB | THR | B | 3 | 11.373 | 11.151 | -26.782 | 0.00 | 0.00 | 6 |
| O | ASP | B | 3 | 12.252 | 27.329 | -24.411 | 0.00 | 0.00 | 8 | O | THR | B | 3 | 12.357 | 11.863 | -27.549 | 0.00 | 0.00 | 8 |
| C | ASP | B | 3 | 13.272 | 23.949 | -26.771 | 0.00 | 0.00 | 6 | C | THR | B | 3 | 11.945 | 9.806 | -26.372 | 0.00 | 0.00 | 6 |
| O | ASP | B | 3 | 12.296 | 23.222 | -26.962 | 0.00 | 0.00 | 8 | C | THR | B | 3 | 9.024 | 10.301 | -26.804 | 0.00 | 0.00 | 6 |
| N | LYS | B | 3 | 14.448 | 23.739 | -27.349 | 0.00 | 0.00 | 7 | O | THR | B | 3 | 8.948 | 9.067 | -26.804 | 0.00 | 0.00 | 8 |
| CA | LYS | B | 3 | 14.693 | 22.623 | -28.249 | 0.00 | 0.00 | 6 | N | ILE | B | 3 | 8.212 | 11.046 | -26.068 | 0.00 | 0.00 | 7 |
| CB | LYS | B | 3 | 16.065 | 22.758 | -28.915 | 0.00 | 0.00 | 6 | CA | ILE | B | 3 | 7.196 | 10.469 | -25.198 | 0.00 | 0.00 | 6 |
| C | LYS | B | 3 | 16.107 | 23.669 | -30.127 | 0.00 | 0.00 | 6 | CB | ILE | B | 3 | 7.000 | 11.363 | -23.954 | 0.00 | 0.00 | 6 |
| C | LYS | B | 3 | 17.541 | 23.929 | -30.569 | 0.00 | 0.00 | 6 | C | ILE | B | 3 | 5.898 | 10.837 | -23.051 | 0.00 | 0.00 | 6 |
| CE | LYS | B | 3 | 18.008 | 22.874 | -31.558 | 0.00 | 0.00 | 6 | C | ILE | B | 3 | 8.317 | 11.497 | -23.183 | 0.00 | 0.00 | 6 |
| NZ | LYS | B | 3 | 19.490 | 22.857 | -31.699 | 0.00 | 0.00 | 7 | C | ILE | B | 3 | 8.916 | 10.202 | -22.680 | 0.00 | 0.00 | 6 |
| C | LYS | B | 3 | 14.643 | 21.283 | -27.521 | 0.00 | 0.00 | 6 | C | ILE | B | 3 | 5.859 | 10.235 | -25.880 | 0.00 | 0.00 | 6 |
| O | LYS | B | 3 | 14.092 | 20.306 | -28.027 | 0.00 | 0.00 | 8 | O | ILE | B | 3 | 5.240 | 9.188 | -25.668 | 0.00 | 0.00 | 8 |
| N | ALA | B | 3 | 15.265 | 21.224 | -26.346 | 0.00 | 0.00 | 7 | N | PHE | B | 3 | 5.379 | 11.203 | -26.651 | 0.00 | 0.00 | 7 |

Figure 1 - 42

| | | | | | | | |
|---|---|---|---|---|---|---|---|
| CA | PHE | B | 3 | 4.069 | 11.077 | -27.288 | 0.00 | 0.00 | 6 |
| CB | PHE | B | 3 | 3.425 | 12.453 | -27.452 | 0.00 | 0.00 | 6 |
| C | PHE | B | 3 | 3.089 | 13.122 | -26.147 | 0.00 | 0.00 | 6 |
| C | PHE | B | 3 | 4.076 | 13.702 | -25.370 | 0.00 | 0.00 | 6 |
| C | PHE | B | 3 | 1.779 | 13.179 | -25.702 | 0.00 | 0.00 | 6 |
| CE | PHE | B | 3 | 3.770 | 14.318 | -24.173 | 0.00 | 0.00 | 6 |
| CE | PHE | B | 3 | 1.464 | 13.796 | -24.507 | 0.00 | 0.00 | 6 |
| CZ | PHE | B | 3 | 2.461 | 14.366 | -23.740 | 0.00 | 0.00 | 6 |
| C | PHE | B | 3 | 4.151 | 10.329 | -28.610 | 0.00 | 0.00 | 6 |
| O | PHE | B | 3 | 3.231 | 9.594 | -28.973 | 0.00 | 0.00 | 8 |
| N | GLY | B | 3 | 5.262 | 10.477 | -29.320 | 0.00 | 0.00 | 7 |
| CA | GLY | B | 3 | 5.513 | 9.754 | -30.551 | 0.00 | 0.00 | 6 |
| C | GLY | B | 3 | 4.558 | 10.072 | -31.687 | 0.00 | 0.00 | 6 |
| O | GLY | B | 3 | 4.725 | 11.071 | -32.388 | 0.00 | 0.00 | 8 |
| N | GLU | B | 3 | 3.556 | 9.216 | -31.888 | 0.00 | 0.00 | 7 |
| CA | GLU | B | 3 | 2.598 | 9.393 | -32.975 | 0.00 | 0.00 | 6 |
| CB | GLU | B | 3 | 2.032 | 8.053 | -33.443 | 0.00 | 0.00 | 6 |
| C | GLU | B | 3 | 2.877 | 7.373 | -34.517 | 0.00 | 0.00 | 6 |
| C | GLU | B | 3 | 3.606 | 6.164 | -33.959 | 0.00 | 0.00 | 6 |
| O | GLU | B | 3 | 4.772 | 6.319 | -33.536 | 0.00 | 0.00 | 8 |
| O | GLU | B | 3 | 3.007 | 5.069 | -33.934 | 0.00 | 0.00 | 8 |
| C | GLU | B | 3 | 1.483 | 10.355 | -32.591 | 0.00 | 0.00 | 6 |
| O | GLU | B | 3 | 0.774 | 10.886 | -33.445 | 0.00 | 0.00 | 8 |
| N | ALA | B | 3 | 1.335 | 10.608 | -31.294 | 0.00 | 0.00 | 7 |
| CA | ALA | B | 3 | 0.337 | 11.535 | -30.782 | 0.00 | 0.00 | 6 |
| CB | ALA | B | 3 | -0.199 | 11.071 | -29.440 | 0.00 | 0.00 | 6 |
| C | ALA | B | 3 | 0.940 | 12.935 | -30.676 | 0.00 | 0.00 | 6 |
| O | ALA | B | 3 | 0.246 | 13.911 | -30.394 | 0.00 | 0.00 | 8 |
| N | ALA | B | 3 | 2.230 | 13.075 | -30.953 | 0.00 | 0.00 | 7 |
| CA | ALA | B | 3 | 2.949 | 14.336 | -30.925 | 0.00 | 0.00 | 6 |
| CB | ALA | B | 3 | 4.334 | 14.165 | -31.539 | 0.00 | 0.00 | 6 |
| C | ALA | B | 3 | 2.209 | 15.465 | -31.629 | 0.00 | 0.00 | 6 |
| O | ALA | B | 3 | 1.987 | 16.526 | -31.034 | 0.00 | 0.00 | 8 |
| N | SER | B | 3 | 1.768 | 15.252 | -32.867 | 0.00 | 0.00 | 7 |
| CA | SER | B | 3 | 1.008 | 16.252 | -33.606 | 0.00 | 0.00 | 6 |
| CB | SER | B | 3 | 1.018 | 15.950 | -35.105 | 0.00 | 0.00 | 6 |
| O | SER | B | 3 | 0.886 | 14.563 | -35.359 | 0.00 | 0.00 | 8 |
| C | SER | B | 3 | -0.427 | 16.377 | -33.107 | 0.00 | 0.00 | 6 |
| O | SER | B | 3 | -1.106 | 17.376 | -33.355 | 0.00 | 0.00 | 8 |
| N | ARG | B | 3 | -0.914 | 15.383 | -32.386 | 0.00 | 0.00 | 7 |
| CA | ARG | B | 3 | -2.250 | 15.345 | -31.814 | 0.00 | 0.00 | 6 |
| CB | ARG | B | 3 | -2.645 | 13.879 | -31.647 | 0.00 | 0.00 | 6 |
| C | ARG | B | 3 | -3.931 | 13.549 | -30.920 | 0.00 | 0.00 | 6 |
| C | ARG | B | 3 | -4.037 | 12.040 | -30.737 | 0.00 | 0.00 | 6 |
| N | ARG | B | 3 | -5.283 | 11.607 | -30.126 | 0.00 | 0.00 | 7 |
| CZ | ARG | B | 3 | -5.609 | 10.334 | -29.913 | 0.00 | 0.00 | 6 |
| N | ARG | B | 3 | -4.782 | 9.358 | -30.262 | 0.00 | 0.00 | 7 |
| N | ARG | B | 3 | -6.769 | 10.031 | -29.347 | 0.00 | 0.00 | 7 |
| C | ARG | B | 3 | -2.340 | 16.094 | -30.491 | 0.00 | 0.00 | 6 |
| O | ARG | B | 3 | -3.429 | 16.526 | -30.105 | 0.00 | 0.00 | 8 |
| N | VAL | B | 3 | -1.225 | 16.271 | -29.789 | 0.00 | 0.00 | 7 |
| CA | VAL | B | 3 | -1.214 | 16.946 | -28.496 | 0.00 | 0.00 | 6 |
| CB | VAL | B | 3 | -0.281 | 16.303 | -27.515 | 0.00 | 0.00 | 6 |
| C | VAL | B | 3 | 1.175 | 16.291 | -27.947 | 0.00 | 0.00 | 6 |
| C | VAL | B | 3 | -0.452 | 16.723 | -26.095 | 0.00 | 0.00 | 6 |
| C | VAL | B | 3 | -0.846 | 18.420 | -28.545 | 0.00 | 0.00 | 6 |
| O | VAL | B | 3 | 0.085 | 18.843 | -29.227 | 0.00 | 0.00 | 8 |
| N | LEU | B | 3 | -1.574 | 19.223 | -27.770 | 0.00 | 0.00 | 7 |
| CA | LEU | B | 3 | -1.349 | 20.659 | -27.688 | 0.00 | 0.00 | 6 |
| CB | LEU | B | 3 | -2.665 | 21.409 | -27.483 | 0.00 | 0.00 | 6 |
| C | LEU | B | 3 | -3.897 | 20.934 | -28.254 | 0.00 | 0.00 | 6 |
| C | LEU | B | 3 | -5.090 | 21.833 | -27.955 | 0.00 | 0.00 | 6 |
| C | LEU | B | 3 | -3.636 | 20.891 | -29.751 | 0.00 | 0.00 | 6 |
| C | LEU | B | 3 | -0.380 | 21.022 | -26.566 | 0.00 | 0.00 | 6 |
| O | LEU | B | 3 | -0.563 | 20.670 | -25.402 | 0.00 | 0.00 | 8 |
| N | VAL | B | 3 | 0.701 | 21.702 | -26.934 | 0.00 | 0.00 | 7 |
| CA | VAL | B | 3 | 1.738 | 22.123 | -26.006 | 0.00 | 0.00 | 6 |
| CB | VAL | B | 3 | 3.106 | 21.485 | -26.333 | 0.00 | 0.00 | 6 |
| C | VAL | B | 3 | 4.155 | 21.927 | -25.318 | 0.00 | 0.00 | 6 |
| C | VAL | B | 3 | 3.050 | 19.970 | -26.391 | 0.00 | 0.00 | 6 |
| C | VAL | B | 3 | 1.924 | 23.638 | -26.057 | 0.00 | 0.00 | 6 |
| O | VAL | B | 3 | 2.463 | 24.121 | -27.055 | 0.00 | 0.00 | 8 |
| N | SER | B | 3 | 1.641 | 24.359 | -24.978 | 0.00 | 0.00 | 7 |
| CA | SER | B | 3 | 1.861 | 25.803 | -24.995 | 0.00 | 0.00 | 6 |
| CB | SER | B | 3 | 0.530 | 26.545 | -25.111 | 0.00 | 0.00 | 6 |
| O | SER | B | 3 | -0.123 | 26.629 | -23.860 | 0.00 | 0.00 | 8 |
| C | SER | B | 3 | 2.633 | 26.300 | -23.779 | 0.00 | 0.00 | 6 |
| O | SER | B | 3 | 2.595 | 25.722 | -22.696 | 0.00 | 0.00 | 8 |
| N | SER | B | 3 | 3.333 | 27.418 | -23.971 | 0.00 | 0.00 | 7 |
| CA | SER | B | 3 | 4.047 | 28.069 | -22.882 | 0.00 | 0.00 | 6 |
| CB | SER | B | 3 | 5.502 | 28.345 | -23.261 | 0.00 | 0.00 | 6 |
| O | SER | B | 3 | 6.179 | 29.065 | -22.245 | 0.00 | 0.00 | 8 |
| C | SER | B | 3 | 3.344 | 29.366 | -22.501 | 0.00 | 0.00 | 6 |
| O | SER | B | 3 | 3.392 | 30.358 | -23.233 | 0.00 | 0.00 | 8 |
| N | THR | B | 3 | 2.798 | 29.409 | -21.284 | 0.00 | 0.00 | 7 |
| CA | THR | B | 3 | 2.153 | 30.613 | -20.775 | 0.00 | 0.00 | 6 |
| CB | THR | B | 3 | 1.081 | 30.328 | -19.712 | 0.00 | 0.00 | 6 |
| O | THR | B | 3 | 1.607 | 29.501 | -18.667 | 0.00 | 0.00 | 8 |
| C | THR | B | 3 | -0.111 | 29.623 | -20.347 | 0.00 | 0.00 | 6 |
| C | THR | B | 3 | 3.171 | 31.612 | -20.240 | 0.00 | 0.00 | 6 |
| O | THR | B | 3 | 2.842 | 32.728 | -19.840 | 0.00 | 0.00 | 8 |
| N | LYS | B | 3 | 4.452 | 31.269 | -20.300 | 0.00 | 0.00 | 7 |
| CA | LYS | B | 3 | 5.579 | 32.098 | -19.939 | 0.00 | 0.00 | 6 |
| CB | LYS | B | 3 | 6.839 | 31.259 | -19.710 | 0.00 | 0.00 | 6 |
| C | LYS | B | 3 | 6.801 | 30.358 | -18.485 | 0.00 | 0.00 | 6 |
| C | LYS | B | 3 | 8.207 | 29.950 | -18.071 | 0.00 | 0.00 | 6 |
| CE | LYS | B | 3 | 8.218 | 29.014 | -16.880 | 0.00 | 0.00 | 6 |
| NZ | LYS | B | 3 | 7.415 | 27.785 | -17.079 | 0.00 | 0.00 | 7 |
| C | LYS | B | 3 | 5.861 | 33.146 | -21.017 | 0.00 | 0.00 | 6 |
| O | LYS | B | 3 | 6.609 | 34.098 | -20.790 | 0.00 | 0.00 | 8 |
| N | SER | B | 3 | 5.209 | 33.042 | -22.170 | 0.00 | 0.00 | 7 |
| CA | SER | B | 3 | 5.228 | 34.043 | -23.217 | 0.00 | 0.00 | 6 |
| CB | SER | B | 3 | 4.676 | 33.493 | -24.533 | 0.00 | 0.00 | 6 |
| O | SER | B | 3 | 3.444 | 32.822 | -24.356 | 0.00 | 0.00 | 8 |
| C | SER | B | 3 | 4.449 | 35.293 | -22.812 | 0.00 | 0.00 | 6 |
| O | SER | B | 3 | 4.735 | 36.385 | -23.305 | 0.00 | 0.00 | 8 |
| N | MET | B | 3 | 3.481 | 35.155 | -21.918 | 0.00 | 0.00 | 7 |
| CA | MET | B | 3 | 2.696 | 36.271 | -21.421 | 0.00 | 0.00 | 6 |
| CB | MET | B | 3 | 1.212 | 35.878 | -21.389 | 0.00 | 0.00 | 6 |
| C | MET | B | 3 | 0.586 | 35.701 | -22.763 | 0.00 | 0.00 | 6 |
| SD | MET | B | 3 | -0.997 | 34.844 | -22.727 | 0.00 | 0.00 | 1 |
| CE | MET | B | 3 | -0.458 | 33.139 | -22.612 | 0.00 | 0.00 | 6 |
| C | MET | B | 3 | 3.121 | 36.682 | -20.013 | 0.00 | 0.00 | 6 |
| O | MET | B | 3 | 3.198 | 37.849 | -19.643 | 0.00 | 0.00 | 8 |
| N | THR | B | 3 | 3.390 | 35.679 | -19.194 | 0.00 | 0.00 | 7 |
| CA | THR | B | 3 | 3.621 | 35.830 | -17.764 | 0.00 | 0.00 | 6 |
| CB | THR | B | 3 | 2.926 | 34.630 | -17.084 | 0.00 | 0.00 | 6 |
| O | THR | B | 3 | 2.203 | 35.075 | -15.930 | 0.00 | 0.00 | 8 |
| C | THR | B | 3 | 3.875 | 33.516 | -16.701 | 0.00 | 0.00 | 6 |
| C | THR | B | 3 | 5.085 | 35.974 | -17.399 | 0.00 | 0.00 | 6 |
| O | THR | B | 3 | 5.442 | 36.689 | -16.457 | 0.00 | 0.00 | 8 |
| N | GLY | B | 3 | 5.953 | 35.326 | -18.170 | 0.00 | 0.00 | 7 |
| CA | GLY | B | 3 | 7.392 | 35.351 | -17.903 | 0.00 | 0.00 | 6 |
| C | GLY | B | 3 | 7.707 | 34.127 | -17.033 | 0.00 | 0.00 | 6 |
| O | GLY | B | 3 | 6.813 | 33.323 | -16.775 | 0.00 | 0.00 | 8 |
| N | HIS | B | 3 | 8.945 | 33.973 | -16.597 | 0.00 | 0.00 | 7 |
| CA | HIS | B | 3 | 9.310 | 32.837 | -15.756 | 0.00 | 0.00 | 6 |
| CB | HIS | B | 3 | 10.700 | 32.331 | -16.132 | 0.00 | 0.00 | 6 |

Figure 1 - 43

| | | | | | | | | |
|---|---|---|---|---|---|---|---|---|
| C | HIS | B | 3 | 11.133 | 31.073 | -15.448 | 0.00 | 0.00 | 6 |
| C | HIS | B | 3 | 10.483 | 30.190 | -14.655 | 0.00 | 0.00 | 6 |
| N | HIS | B | 3 | 12.426 | 30.601 | -15.559 | 0.00 | 0.00 | 7 |
| CE | HIS | B | 3 | 12.544 | 29.488 | -14.868 | 0.00 | 0.00 | 6 |
| N | HIS | B | 3 | 11.380 | 29.212 | -14.307 | 0.00 | 0.00 | 7 |
| C | HIS | B | 3 | 9.253 | 33.231 | -14.285 | 0.00 | 0.00 | 6 |
| O | HIS | B | 3 | 10.070 | 34.028 | -13.825 | 0.00 | 0.00 | 8 |
| N | LEU | B | 3 | 8.370 | 32.596 | -13.518 | 0.00 | 0.00 | 7 |
| CA | LEU | B | 3 | 8.182 | 32.913 | -12.110 | 0.00 | 0.00 | 6 |
| CB | LEU | B | 3 | 6.730 | 32.778 | -11.684 | 0.00 | 0.00 | 6 |
| C | LEU | B | 3 | 5.544 | 33.425 | -12.363 | 0.00 | 0.00 | 6 |
| C | LEU | B | 3 | 4.547 | 33.915 | -11.311 | 0.00 | 0.00 | 6 |
| C | LEU | B | 3 | 5.901 | 34.563 | -13.303 | 0.00 | 0.00 | 6 |
| C | LEU | B | 3 | 9.026 | 32.033 | -11.187 | 0.00 | 0.00 | 6 |
| O | LEU | B | 3 | 8.711 | 31.869 | -10.007 | 0.00 | 0.00 | 8 |
| N | LEU | B | 3 | 10.095 | 31.456 | -11.711 | 0.00 | 0.00 | 7 |
| CA | LEU | B | 3 | 11.003 | 30.600 | -10.971 | 0.00 | 0.00 | 6 |
| CB | LEU | B | 3 | 12.016 | 31.480 | -10.227 | 0.00 | 0.00 | 6 |
| C | LEU | B | 3 | 13.104 | 32.076 | -11.132 | 0.00 | 0.00 | 6 |
| C | LEU | B | 3 | 13.851 | 33.194 | -10.425 | 0.00 | 0.00 | 6 |
| C | LEU | B | 3 | 14.062 | 30.986 | -11.588 | 0.00 | 0.00 | 6 |
| C | LEU | B | 3 | 10.287 | 29.628 | -10.053 | 0.00 | 0.00 | 6 |
| O | LEU | B | 3 | 9.577 | 28.748 | -10.547 | 0.00 | 0.00 | 8 |
| N | GLY | B | 3 | 10.319 | 29.841 | -8.743 | 0.00 | 0.00 | 7 |
| CA | GLY | B | 3 | 9.748 | 28.939 | -7.767 | 0.00 | 0.00 | 6 |
| C | GLY | B | 3 | 8.234 | 28.904 | -7.708 | 0.00 | 0.00 | 6 |
| O | GLY | B | 3 | 7.655 | 27.997 | -7.105 | 0.00 | 0.00 | 8 |
| N | ALA | B | 3 | 7.563 | 29.882 | -8.305 | 0.00 | 0.00 | 7 |
| CA | ALA | B | 3 | 6.115 | 29.924 | -8.366 | 0.00 | 0.00 | 6 |
| CB | ALA | B | 3 | 5.615 | 31.341 | -8.116 | 0.00 | 0.00 | 6 |
| C | ALA | B | 3 | 5.619 | 29.461 | -9.734 | 0.00 | 0.00 | 6 |
| O | ALA | B | 3 | 4.412 | 29.341 | -9.940 | 0.00 | 0.00 | 8 |
| N | ALA | B | 3 | 6.539 | 29.238 | -10.670 | 0.00 | 0.00 | 7 |
| CA | ALA | B | 3 | 6.176 | 28.868 | -12.032 | 0.00 | 0.00 | 6 |
| CB | ALA | B | 3 | 7.395 | 28.787 | -12.943 | 0.00 | 0.00 | 6 |
| C | ALA | B | 3 | 5.373 | 27.580 | -12.097 | 0.00 | 0.00 | 6 |
| O | ALA | B | 3 | 4.322 | 27.561 | -12.734 | 0.00 | 0.00 | 8 |
| N | GLY | B | 3 | 5.788 | 26.542 | -11.392 | 0.00 | 0.00 | 7 |
| CA | GLY | B | 3 | 5.088 | 25.275 | -11.340 | 0.00 | 0.00 | 6 |
| C | GLY | B | 3 | 3.740 | 25.350 | -10.641 | 0.00 | 0.00 | 6 |
| O | GLY | B | 3 | 2.865 | 24.521 | -10.908 | 0.00 | 0.00 | 8 |
| N | ALA | B | 3 | 3.571 | 26.285 | -9.714 | 0.00 | 0.00 | 7 |
| CA | ALA | B | 3 | 2.324 | 26.443 | -8.980 | 0.00 | 0.00 | 6 |
| CB | ALA | B | 3 | 2.567 | 27.214 | -7.690 | 0.00 | 0.00 | 6 |
| C | ALA | B | 3 | 1.254 | 27.141 | -9.815 | 0.00 | 0.00 | 6 |
| O | ALA | B | 3 | 0.137 | 26.634 | -9.944 | 0.00 | 0.00 | 8 |
| N | VAL | B | 3 | 1.602 | 28.281 | -10.413 | 0.00 | 0.00 | 7 |
| CA | VAL | B | 3 | 0.664 | 29.023 | -11.243 | 0.00 | 0.00 | 6 |
| CB | VAL | B | 3 | 1.191 | 30.399 | -11.691 | 0.00 | 0.00 | 6 |
| C | VAL | B | 3 | 1.454 | 31.293 | -10.489 | 0.00 | 0.00 | 6 |
| C | VAL | B | 3 | 2.445 | 30.282 | -12.543 | 0.00 | 0.00 | 6 |
| C | VAL | B | 3 | 0.266 | 28.227 | -12.482 | 0.00 | 0.00 | 6 |
| O | VAL | B | 3 | -0.892 | 28.233 | -12.896 | 0.00 | 0.00 | 8 |
| N | GLU | B | 3 | 1.220 | 27.512 | -13.064 | 0.00 | 0.00 | 7 |
| CA | GLU | B | 3 | 1.018 | 26.706 | -14.251 | 0.00 | 0.00 | 6 |
| CB | GLU | B | 3 | 2.384 | 26.381 | -14.879 | 0.00 | 0.00 | 6 |
| C | GLU | B | 3 | 3.037 | 27.611 | -15.485 | 0.00 | 0.00 | 6 |
| C | GLU | B | 3 | 4.467 | 27.395 | -15.920 | 0.00 | 0.00 | 6 |
| O | GLU | B | 3 | 4.888 | 26.244 | -16.143 | 0.00 | 0.00 | 8 |
| O | GLU | B | 3 | 5.187 | 28.405 | -16.057 | 0.00 | 0.00 | 8 |
| C | GLU | B | 3 | 0.241 | 25.422 | -14.010 | 0.00 | 0.00 | 6 |
| O | GLU | B | 3 | -0.316 | 24.863 | -14.960 | 0.00 | 0.00 | 8 |
| N | SER | B | 3 | 0.190 | 24.947 | -12.770 | 0.00 | 0.00 | 7 |
| CA | SER | B | 3 | -0.666 | 23.823 | -12.408 | 0.00 | 0.00 | 6 |
| CB | SER | B | 3 | -0.321 | 23.253 | -11.037 | 0.00 | 0.00 | 6 |
| O | SER | B | 3 | 0.888 | 22.520 | -11.055 | 0.00 | 0.00 | 8 |
| C | SER | B | 3 | -2.121 | 24.295 | -12.417 | 0.00 | 0.00 | 6 |
| O | SER | B | 3 | -3.015 | 23.566 | -12.834 | 0.00 | 0.00 | 8 |
| N | ILE | B | 3 | -2.337 | 25.530 | -11.973 | 0.00 | 0.00 | 7 |
| CA | ILE | B | 3 | -3.667 | 26.133 | -11.972 | 0.00 | 0.00 | 6 |
| CB | ILE | B | 3 | -3.676 | 27.477 | -11.223 | 0.00 | 0.00 | 6 |
| C | ILE | B | 3 | -5.031 | 28.162 | -11.315 | 0.00 | 0.00 | 6 |
| C | ILE | B | 3 | -3.292 | 27.240 | -9.761 | 0.00 | 0.00 | 6 |
| C | ILE | B | 3 | -2.987 | 28.470 | -8.942 | 0.00 | 0.00 | 6 |
| C | ILE | B | 3 | -4.157 | 26.301 | -13.407 | 0.00 | 0.00 | 6 |
| O | ILE | B | 3 | -5.243 | 25.828 | -13.750 | 0.00 | 0.00 | 8 |
| N | TYR | B | 3 | -3.309 | 26.824 | -14.288 | 0.00 | 0.00 | 7 |
| CA | TYR | B | 3 | -3.633 | 26.947 | -15.705 | 0.00 | 0.00 | 6 |
| CB | TYR | B | 3 | -2.493 | 27.567 | -16.505 | 0.00 | 0.00 | 6 |
| C | TYR | B | 3 | -1.896 | 28.842 | -15.961 | 0.00 | 0.00 | 6 |
| C | TYR | B | 3 | -0.581 | 29.179 | -16.265 | 0.00 | 0.00 | 6 |
| CE | TYR | B | 3 | -0.012 | 30.344 | -15.788 | 0.00 | 0.00 | 6 |
| C | TYR | B | 3 | -2.619 | 29.718 | -15.162 | 0.00 | 0.00 | 6 |
| CE | TYR | B | 3 | -2.057 | 30.876 | -14.670 | 0.00 | 0.00 | 6 |
| CZ | TYR | B | 3 | -0.752 | 31.186 | -14.990 | 0.00 | 0.00 | 6 |
| O | TYR | B | 3 | -0.193 | 32.345 | -14.503 | 0.00 | 0.00 | 8 |
| C | TYR | B | 3 | -4.001 | 25.590 | -16.298 | 0.00 | 0.00 | 6 |
| O | TYR | B | 3 | -5.007 | 25.469 | -16.999 | 0.00 | 0.00 | 8 |
| N | SER | B | 3 | -3.235 | 24.554 | -15.971 | 0.00 | 0.00 | 7 |
| CA | SER | B | 3 | -3.522 | 23.199 | -16.415 | 0.00 | 0.00 | 6 |
| CB | SER | B | 3 | -2.377 | 22.264 | -16.017 | 0.00 | 0.00 | 6 |
| O | SER | B | 3 | -1.155 | 22.702 | -16.586 | 0.00 | 0.00 | 8 |
| C | SER | B | 3 | -4.842 | 22.675 | -15.858 | 0.00 | 0.00 | 6 |
| O | SER | B | 3 | -5.520 | 21.887 | -16.523 | 0.00 | 0.00 | 8 |
| N | ILE | B | 3 | -5.206 | 23.068 | -14.644 | 0.00 | 0.00 | 7 |
| CA | ILE | B | 3 | -6.472 | 22.671 | -14.041 | 0.00 | 0.00 | 6 |
| CB | ILE | B | 3 | -6.451 | 22.881 | -12.518 | 0.00 | 0.00 | 6 |
| C | ILE | B | 3 | -7.836 | 22.836 | -11.898 | 0.00 | 0.00 | 6 |
| C | ILE | B | 3 | -5.553 | 21.817 | -11.866 | 0.00 | 0.00 | 6 |
| C | ILE | B | 3 | -5.056 | 22.190 | -10.487 | 0.00 | 0.00 | 6 |
| C | ILE | B | 3 | -7.624 | 23.422 | -14.695 | 0.00 | 0.00 | 6 |
| O | ILE | B | 3 | -8.562 | 22.804 | -15.209 | 0.00 | 0.00 | 8 |
| N | LEU | B | 3 | -7.520 | 24.744 | -14.785 | 0.00 | 0.00 | 7 |
| CA | LEU | B | 3 | -8.545 | 25.579 | -15.399 | 0.00 | 0.00 | 6 |
| CB | LEU | B | 3 | -8.181 | 27.065 | -15.295 | 0.00 | 0.00 | 6 |
| C | LEU | B | 3 | -8.129 | 27.631 | -13.872 | 0.00 | 0.00 | 6 |
| C | LEU | B | 3 | -7.627 | 29.068 | -13.881 | 0.00 | 0.00 | 6 |
| C | LEU | B | 3 | -9.487 | 27.535 | -13.191 | 0.00 | 0.00 | 6 |
| C | LEU | B | 3 | -8.826 | 25.191 | -16.840 | 0.00 | 0.00 | 6 |
| O | LEU | B | 3 | -9.981 | 25.181 | -17.275 | 0.00 | 0.00 | 8 |
| N | ALA | B | 3 | -7.799 | 24.803 | -17.590 | 0.00 | 0.00 | 7 |
| CA | ALA | B | 3 | -7.937 | 24.338 | -18.959 | 0.00 | 0.00 | 6 |
| CB | ALA | B | 3 | -6.579 | 23.931 | -19.512 | 0.00 | 0.00 | 6 |
| C | ALA | B | 3 | -8.911 | 23.164 | -19.051 | 0.00 | 0.00 | 6 |
| O | ALA | B | 3 | -9.697 | 23.069 | -19.996 | 0.00 | 0.00 | 8 |
| N | LEU | B | 3 | -8.876 | 22.262 | -18.076 | 0.00 | 0.00 | 7 |
| CA | LEU | B | 3 | -9.799 | 21.147 | -17.983 | 0.00 | 0.00 | 6 |
| CB | LEU | B | 3 | -9.334 | 20.159 | -16.905 | 0.00 | 0.00 | 6 |
| C | LEU | B | 3 | -8.035 | 19.398 | -17.188 | 0.00 | 0.00 | 6 |
| C | LEU | B | 3 | -7.659 | 18.528 | -15.997 | 0.00 | 0.00 | 6 |
| C | LEU | B | 3 | -8.154 | 18.559 | -18.451 | 0.00 | 0.00 | 6 |
| C | LEU | B | 3 | -11.227 | 21.586 | -17.680 | 0.00 | 0.00 | 6 |
| O | LEU | B | 3 | -12.181 | 20.984 | -18.179 | 0.00 | 0.00 | 8 |
| N | ARG | B | 3 | -11.392 | 22.617 | -16.859 | 0.00 | 0.00 | 7 |
| CA | ARG | B | 3 | -12.706 | 23.117 | -16.489 | 0.00 | 0.00 | 6 |
| CB | ARG | B | 3 | -12.583 | 24.079 | -15.299 | 0.00 | 0.00 | 6 |
| C | ARG | B | 3 | -13.874 | 24.777 | -14.912 | 0.00 | 0.00 | 6 |
| C | ARG | B | 3 | -13.648 | 25.875 | -13.887 | 0.00 | 0.00 | 6 |

Figure 1 - 44

| | | | | | | | | |
|---|---|---|---|---|---|---|---|---|
| N | ARG | B | 3 | -13.165 | 27.108 | -14.494 | 0.00 | 0.00 | 7 |
| CZ | ARG | B | 3 | -13.051 | 28.275 | -13.874 | 0.00 | 0.00 | 6 |
| N | ARG | B | 3 | -13.379 | 28.396 | -12.595 | 0.00 | 0.00 | 7 |
| N | ARG | B | 3 | -12.597 | 29.330 | -14.537 | 0.00 | 0.00 | 7 |
| C | ARG | B | 3 | -13.421 | 23.328 | -17.632 | 0.00 | 0.00 | 6 |
| O | ARG | B | 3 | -14.633 | 23.698 | -17.798 | 0.00 | 0.00 | 8 |
| N | ASP | B | 3 | -12.690 | 24.638 | -18.381 | 0.00 | 0.00 | 7 |
| CA | ASP | B | 3 | -13.225 | 25.469 | -19.440 | 0.00 | 0.00 | 6 |
| CB | ASP | B | 3 | -12.537 | 26.846 | -19.359 | 0.00 | 0.00 | 6 |
| C | ASP | B | 3 | -12.948 | 27.685 | -18.176 | 0.00 | 0.00 | 6 |
| O | ASP | B | 3 | -13.535 | 27.157 | -17.211 | 0.00 | 0.00 | 8 |
| O | ASP | B | 3 | -12.682 | 28.908 | -18.203 | 0.00 | 0.00 | 8 |
| C | ASP | B | 3 | -12.979 | 24.945 | -20.843 | 0.00 | 0.00 | 6 |
| O | ASP | B | 3 | -13.300 | 25.620 | -21.827 | 0.00 | 0.00 | 8 |
| N | GLN | B | 3 | -12.296 | 23.817 | -20.977 | 0.00 | 0.00 | 7 |
| CA | GLN | B | 3 | -11.944 | 23.263 | -22.279 | 0.00 | 0.00 | 6 |
| CB | GLN | B | 3 | -13.126 | 22.512 | -22.889 | 0.00 | 0.00 | 6 |
| C | GLN | B | 3 | -13.723 | 21.453 | -21.980 | 0.00 | 0.00 | 6 |
| C | GLN | B | 3 | -12.920 | 20.174 | -21.920 | 0.00 | 0.00 | 6 |
| O | GLN | B | 3 | -12.423 | 19.677 | -22.930 | 0.00 | 0.00 | 8 |
| N | GLN | B | 3 | -12.779 | 19.616 | -20.720 | 0.00 | 0.00 | 7 |
| C | GLN | B | 3 | -11.408 | 24.327 | -23.235 | 0.00 | 0.00 | 6 |
| O | GLN | B | 3 | -11.691 | 24.310 | -24.433 | 0.00 | 0.00 | 8 |
| N | ALA | B | 3 | -10.452 | 25.120 | -22.772 | 0.00 | 0.00 | 7 |
| CA | ALA | B | 3 | -9.774 | 26.140 | -23.550 | 0.00 | 0.00 | 6 |
| CB | ALA | B | 3 | -10.335 | 27.521 | -23.267 | 0.00 | 0.00 | 6 |
| C | ALA | B | 3 | -8.284 | 26.084 | -23.207 | 0.00 | 0.00 | 6 |
| O | ALA | B | 3 | -7.931 | 25.901 | -22.041 | 0.00 | 0.00 | 8 |
| N | VAL | B | 3 | -7.437 | 26.189 | -24.220 | 0.00 | 0.00 | 7 |
| CA | VAL | B | 3 | -5.993 | 26.123 | -24.018 | 0.00 | 0.00 | 6 |
| CB | VAL | B | 3 | -5.366 | 24.989 | -24.847 | 0.00 | 0.00 | 6 |
| C | VAL | B | 3 | -3.855 | 25.131 | -24.973 | 0.00 | 0.00 | 6 |
| C | VAL | B | 3 | -5.695 | 23.633 | -24.230 | 0.00 | 0.00 | 6 |
| C | VAL | B | 3 | -5.351 | 27.463 | -24.356 | 0.00 | 0.00 | 6 |
| O | VAL | B | 3 | -5.482 | 27.957 | -25.472 | 0.00 | 0.00 | 8 |
| N | PRO | B | 3 | -4.633 | 28.030 | -23.392 | 0.00 | 0.00 | 7 |
| C | PRO | B | 3 | -4.407 | 27.455 | -22.044 | 0.00 | 0.00 | 6 |
| CA | PRO | B | 3 | -3.944 | 29.292 | -23.561 | 0.00 | 0.00 | 6 |
| CB | PRO | B | 3 | -3.399 | 29.643 | -22.188 | 0.00 | 0.00 | 6 |
| C | PRO | B | 3 | -3.869 | 28.600 | -21.245 | 0.00 | 0.00 | 6 |
| C | PRO | B | 3 | -2.822 | 29.183 | -24.582 | 0.00 | 0.00 | 6 |
| O | PRO | B | 3 | -2.171 | 28.147 | -24.703 | 0.00 | 0.00 | 8 |
| N | PRO | B | 3 | -2.582 | 30.264 | -25.314 | 0.00 | 0.00 | 7 |
| C | PRO | B | 3 | -3.344 | 31.536 | -25.229 | 0.00 | 0.00 | 6 |
| CA | PRO | B | 3 | -1.585 | 30.294 | -26.355 | 0.00 | 0.00 | 6 |
| CB | PRO | B | 3 | -2.056 | 31.453 | -27.243 | 0.00 | 0.00 | 6 |
| C | PRO | B | 3 | -2.735 | 32.389 | -26.307 | 0.00 | 0.00 | 6 |
| C | PRO | B | 3 | -0.154 | 30.580 | -25.945 | 0.00 | 0.00 | 6 |
| O | PRO | B | 3 | 0.162 | 31.064 | -24.864 | 0.00 | 0.00 | 8 |
| N | THR | B | 3 | 0.738 | 30.299 | -26.892 | 0.00 | 0.00 | 7 |
| CA | THR | B | 3 | 2.137 | 30.682 | -26.785 | 0.00 | 0.00 | 6 |
| CB | THR | B | 3 | 3.114 | 29.653 | -27.365 | 0.00 | 0.00 | 6 |
| O | THR | B | 3 | 2.891 | 28.369 | -26.775 | 0.00 | 0.00 | 8 |
| C | THR | B | 3 | 4.549 | 30.091 | -27.116 | 0.00 | 0.00 | 6 |
| C | THR | B | 3 | 2.240 | 31.973 | -27.607 | 0.00 | 0.00 | 6 |
| O | THR | B | 3 | 2.380 | 31.848 | -28.824 | 0.00 | 0.00 | 8 |
| N | ILE | B | 3 | 1.976 | 33.134 | -27.019 | 0.00 | 0.00 | 7 |
| CA | ILE | B | 3 | 2.002 | 34.355 | -27.829 | 0.00 | 0.00 | 6 |
| CB | ILE | B | 3 | 1.463 | 35.588 | -27.090 | 0.00 | 0.00 | 6 |
| C | ILE | B | 3 | 0.066 | 35.303 | -26.551 | 0.00 | 0.00 | 6 |
| C | ILE | B | 3 | 2.394 | 36.033 | -25.963 | 0.00 | 0.00 | 6 |
| C | ILE | B | 3 | 2.187 | 37.458 | -25.497 | 0.00 | 0.00 | 6 |
| C | ILE | B | 3 | 3.411 | 34.607 | -28.343 | 0.00 | 0.00 | 6 |
| O | ILE | B | 3 | 4.388 | 34.023 | -27.877 | 0.00 | 0.00 | 8 |

| | | | | | | | | |
|---|---|---|---|---|---|---|---|---|
| N | ASN | B | 3 | 3.542 | 35.474 | -29.338 | 0.00 | 0.00 | 7 |
| CA | ASN | B | 3 | 4.787 | 35.875 | -29.954 | 0.00 | 0.00 | 6 |
| CB | ASN | B | 3 | 5.803 | 36.330 | -28.895 | 0.00 | 0.00 | 6 |
| C | ASN | B | 3 | 5.406 | 37.590 | -28.157 | 0.00 | 0.00 | 6 |
| O | ASN | B | 3 | 4.824 | 38.511 | -28.729 | 0.00 | 0.00 | 8 |
| N | ASN | B | 3 | 5.713 | 37.619 | -26.865 | 0.00 | 0.00 | 7 |
| C | ASN | B | 3 | 5.455 | 34.830 | -30.834 | 0.00 | 0.00 | 6 |
| O | ASN | B | 3 | 6.597 | 35.051 | -31.267 | 0.00 | 0.00 | 8 |
| N | LEU | B | 3 | 4.802 | 33.721 | -31.152 | 0.00 | 0.00 | 7 |
| CA | LEU | B | 3 | 5.422 | 32.668 | -31.951 | 0.00 | 0.00 | 6 |
| CB | LEU | B | 3 | 4.857 | 31.306 | -31.559 | 0.00 | 0.00 | 6 |
| C | LEU | B | 3 | 5.462 | 30.051 | -32.183 | 0.00 | 0.00 | 6 |
| C | LEU | B | 3 | 6.931 | 30.095 | -32.216 | 0.00 | 0.00 | 6 |
| C | LEU | B | 3 | 4.989 | 28.809 | -31.438 | 0.00 | 0.00 | 6 |
| C | LEU | B | 3 | 5.272 | 32.938 | -33.443 | 0.00 | 0.00 | 6 |
| O | LEU | B | 3 | 4.492 | 32.311 | -34.153 | 0.00 | 0.00 | 8 |
| N | ASP | B | 3 | 6.089 | 33.859 | -33.940 | 0.00 | 0.00 | 7 |
| CA | ASP | B | 3 | 6.054 | 34.323 | -35.311 | 0.00 | 0.00 | 6 |
| CB | ASP | B | 3 | 6.691 | 35.718 | -35.391 | 0.00 | 0.00 | 6 |
| C | ASP | B | 3 | 5.944 | 36.763 | -34.591 | 0.00 | 0.00 | 6 |
| O | ASP | B | 3 | 6.598 | 37.704 | -34.092 | 0.00 | 0.00 | 8 |
| O | ASP | B | 3 | 4.707 | 36.655 | -34.463 | 0.00 | 0.00 | 8 |
| C | ASP | B | 3 | 6.790 | 33.400 | -36.271 | 0.00 | 0.00 | 6 |
| O | ASP | B | 3 | 6.462 | 33.348 | -37.457 | 0.00 | 0.00 | 8 |
| N | ASN | B | 3 | 7.794 | 32.689 | -35.773 | 0.00 | 0.00 | 7 |
| CA | ASN | B | 3 | 8.586 | 31.789 | -36.597 | 0.00 | 0.00 | 6 |
| CB | ASN | B | 3 | 9.729 | 32.580 | -37.246 | 0.00 | 0.00 | 6 |
| C | ASN | B | 3 | 9.497 | 32.981 | -38.683 | 0.00 | 0.00 | 6 |
| O | ASN | B | 3 | 9.025 | 32.186 | -39.498 | 0.00 | 0.00 | 8 |
| N | ASN | B | 3 | 9.828 | 34.229 | -39.001 | 0.00 | 0.00 | 7 |
| C | ASN | B | 3 | 9.189 | 30.642 | -35.796 | 0.00 | 0.00 | 6 |
| O | ASN | B | 3 | 10.253 | 30.781 | -35.192 | 0.00 | 0.00 | 8 |
| N | PRO | B | 3 | 8.538 | 29.485 | -35.827 | 0.00 | 0.00 | 7 |
| C | PRO | B | 3 | 7.263 | 29.247 | -36.544 | 0.00 | 0.00 | 6 |
| CA | PRO | B | 3 | 9.018 | 28.297 | -35.149 | 0.00 | 0.00 | 6 |
| CB | PRO | B | 3 | 8.089 | 27.190 | -35.633 | 0.00 | 0.00 | 6 |
| C | PRO | B | 3 | 6.862 | 27.865 | -36.120 | 0.00 | 0.00 | 6 |
| C | PRO | B | 3 | 10.462 | 27.972 | -35.491 | 0.00 | 0.00 | 6 |
| O | PRO | B | 3 | 10.926 | 28.255 | -36.597 | 0.00 | 0.00 | 8 |
| N | ASP | B | 3 | 11.178 | 27.374 | -34.544 | 0.00 | 0.00 | 7 |
| CA | ASP | B | 3 | 12.575 | 26.992 | -34.766 | 0.00 | 0.00 | 6 |
| CB | ASP | B | 3 | 13.194 | 26.503 | -33.461 | 0.00 | 0.00 | 6 |
| C | ASP | B | 3 | 14.659 | 26.855 | -33.310 | 0.00 | 0.00 | 6 |
| O | ASP | B | 3 | 15.042 | 27.993 | -33.650 | 0.00 | 0.00 | 8 |
| O | ASP | B | 3 | 15.430 | 25.985 | -32.850 | 0.00 | 0.00 | 8 |
| C | ASP | B | 3 | 12.619 | 25.926 | -35.856 | 0.00 | 0.00 | 6 |
| O | ASP | B | 3 | 11.612 | 25.248 | -36.086 | 0.00 | 0.00 | 8 |
| N | GLU | B | 3 | 13.746 | 25.756 | -36.534 | 0.00 | 0.00 | 7 |
| CA | GLU | B | 3 | 13.865 | 24.830 | -37.650 | 0.00 | 0.00 | 6 |
| CB | GLU | B | 3 | 15.284 | 24.861 | -38.236 | 0.00 | 0.00 | 6 |
| C | GLU | B | 3 | 16.342 | 24.299 | -37.311 | 0.00 | 0.00 | 6 |
| C | GLU | B | 3 | 17.548 | 23.718 | -38.015 | 0.00 | 0.00 | 6 |
| O | GLU | B | 3 | 17.901 | 22.556 | -37.716 | 0.00 | 0.00 | 8 |
| O | GLU | B | 3 | 18.151 | 24.415 | -38.856 | 0.00 | 0.00 | 8 |
| C | GLU | B | 3 | 13.476 | 23.391 | -37.350 | 0.00 | 0.00 | 6 |
| O | GLU | B | 3 | 12.844 | 22.749 | -38.198 | 0.00 | 0.00 | 8 |
| N | GLY | B | 3 | 13.861 | 22.846 | -36.204 | 0.00 | 0.00 | 7 |
| CA | GLY | B | 3 | 13.502 | 21.480 | -35.831 | 0.00 | 0.00 | 6 |
| C | GLY | B | 3 | 12.369 | 21.509 | -34.805 | 0.00 | 0.00 | 6 |
| O | GLY | B | 3 | 12.466 | 20.978 | -33.703 | 0.00 | 0.00 | 8 |
| N | CYS | B | 3 | 11.285 | 22.176 | -35.182 | 0.00 | 0.00 | 7 |
| CA | CYS | B | 3 | 10.082 | 22.306 | -34.372 | 0.00 | 0.00 | 6 |
| CB | CYS | B | 3 | 9.892 | 23.730 | -33.873 | 0.00 | 0.00 | 6 |
| SG | CYS | B | 3 | 10.917 | 24.160 | -32.442 | 0.00 | 0.00 | 1 |

Figure 1 - 45

| C | CYS | B | 3 | 8.927 | 21.845 | -35.264 | 0.00 | 0.00 | 6 |
|---|-----|---|---|-------|--------|---------|------|------|---|
| O | CYS | B | 3 | 9.017 | 22.049 | -36.482 | 0.00 | 0.00 | 8 |
| N | ASP | B | 3 | 7.998 | 21.058 | -34.736 | 0.00 | 0.00 | 7 |
| CA | ASP | B | 3 | 6.997 | 20.426 | -35.592 | 0.00 | 0.00 | 6 |
| CB | ASP | B | 3 | 7.556 | 19.082 | -36.082 | 0.00 | 0.00 | 6 |
| C | ASP | B | 3 | 7.871 | 19.058 | -37.563 | 0.00 | 0.00 | 6 |
| O | ASP | B | 3 | 8.818 | 19.759 | -37.983 | 0.00 | 0.00 | 8 |
| O | ASP | B | 3 | 7.184 | 18.328 | -38.308 | 0.00 | 0.00 | 8 |
| C | ASP | B | 3 | 5.677 | 20.184 | -34.878 | 0.00 | 0.00 | 6 |
| O | ASP | B | 3 | 4.734 | 19.653 | -35.468 | 0.00 | 0.00 | 8 |
| N | LEU | B | 3 | 5.620 | 20.535 | -33.600 | 0.00 | 0.00 | 7 |
| CA | LEU | B | 3 | 4.427 | 20.303 | -32.798 | 0.00 | 0.00 | 6 |
| CB | LEU | B | 3 | 4.826 | 20.015 | -31.345 | 0.00 | 0.00 | 6 |
| C | LEU | B | 3 | 5.969 | 19.018 | -31.137 | 0.00 | 0.00 | 6 |
| C | LEU | B | 3 | 6.737 | 19.332 | -29.863 | 0.00 | 0.00 | 6 |
| C | LEU | B | 3 | 5.434 | 17.595 | -31.107 | 0.00 | 0.00 | 6 |
| C | LEU | B | 3 | 3.473 | 21.489 | -32.832 | 0.00 | 0.00 | 6 |
| O | LEU | B | 3 | 3.846 | 22.600 | -33.214 | 0.00 | 0.00 | 8 |
| N | ASP | B | 3 | 2.236 | 21.241 | -32.412 | 0.00 | 0.00 | 7 |
| CA | ASP | B | 3 | 1.244 | 22.309 | -32.329 | 0.00 | 0.00 | 6 |
| CB | ASP | B | 3 | -0.181 | 21.783 | -32.446 | 0.00 | 0.00 | 6 |
| C | ASP | B | 3 | -1.217 | 22.890 | -32.426 | 0.00 | 0.00 | 6 |
| O | ASP | B | 3 | -2.341 | 22.651 | -31.938 | 0.00 | 0.00 | 8 |
| O | ASP | B | 3 | -0.914 | 24.007 | -32.895 | 0.00 | 0.00 | 8 |
| C | ASP | B | 3 | 1.442 | 23.030 | -30.995 | 0.00 | 0.00 | 6 |
| O | ASP | B | 3 | 1.028 | 22.555 | -29.939 | 0.00 | 0.00 | 8 |
| N | PHE | B | 3 | 2.068 | 24.200 | -31.053 | 0.00 | 0.00 | 7 |
| CA | PHE | B | 3 | 2.382 | 24.988 | -29.873 | 0.00 | 0.00 | 6 |
| CB | PHE | B | 3 | 3.714 | 25.719 | -30.088 | 0.00 | 0.00 | 6 |
| C | PHE | B | 3 | 4.923 | 24.845 | -30.234 | 0.00 | 0.00 | 6 |
| C | PHE | B | 3 | 5.719 | 24.932 | -31.366 | 0.00 | 0.00 | 6 |
| C | PHE | B | 3 | 5.281 | 23.937 | -29.250 | 0.00 | 0.00 | 6 |
| CE | PHE | B | 3 | 6.838 | 24.136 | -31.515 | 0.00 | 0.00 | 6 |
| CE | PHE | B | 3 | 6.397 | 23.138 | -29.391 | 0.00 | 0.00 | 6 |
| CZ | PHE | B | 3 | 7.178 | 23.238 | -30.526 | 0.00 | 0.00 | 6 |
| C | PHE | B | 3 | 1.310 | 26.009 | -29.516 | 0.00 | 0.00 | 6 |
| O | PHE | B | 3 | 1.582 | 27.004 | -28.844 | 0.00 | 0.00 | 8 |
| N | VAL | B | 3 | 0.080 | 25.802 | -29.970 | 0.00 | 0.00 | 7 |
| CA | VAL | B | 3 | -1.045 | 26.703 | -29.776 | 0.00 | 0.00 | 6 |
| CB | VAL | B | 3 | -1.714 | 26.595 | -28.403 | 0.00 | 0.00 | 6 |
| C | VAL | B | 3 | -3.069 | 27.293 | -28.427 | 0.00 | 0.00 | 6 |
| C | VAL | B | 3 | -1.897 | 25.146 | -27.974 | 0.00 | 0.00 | 6 |
| C | VAL | B | 3 | -0.584 | 28.134 | -30.056 | 0.00 | 0.00 | 6 |
| O | VAL | B | 3 | -0.538 | 28.999 | -29.186 | 0.00 | 0.00 | 8 |
| N | PRO | B | 3 | -0.218 | 28.392 | -31.313 | 0.00 | 0.00 | 7 |
| C | PRO | B | 3 | -0.189 | 27.370 | -32.404 | 0.00 | 0.00 | 6 |
| CA | PRO | B | 3 | 0.555 | 29.542 | -31.696 | 0.00 | 0.00 | 6 |
| CB | PRO | B | 3 | 0.729 | 29.417 | -33.216 | 0.00 | 0.00 | 6 |
| C | PRO | B | 3 | -0.004 | 28.202 | -33.638 | 0.00 | 0.00 | 6 |
| C | PRO | B | 3 | 0.136 | 30.946 | -31.358 | 0.00 | 0.00 | 6 |
| O | PRO | B | 3 | 1.069 | 31.681 | -30.971 | 0.00 | 0.00 | 8 |
| N | HIS | B | 3 | -1.067 | 31.459 | -31.590 | 0.00 | 0.00 | 7 |
| CA | HIS | B | 3 | -1.295 | 32.881 | -31.308 | 0.00 | 0.00 | 6 |
| CB | HIS | B | 3 | -1.357 | 33.688 | -32.615 | 0.00 | 0.00 | 6 |
| C | HIS | B | 3 | -0.007 | 33.940 | -33.216 | 0.00 | 0.00 | 6 |
| C | HIS | B | 3 | 0.948 | 34.859 | -32.951 | 0.00 | 0.00 | 6 |
| N | HIS | B | 3 | 0.512 | 33.117 | -34.194 | 0.00 | 0.00 | 7 |
| CE | HIS | B | 3 | 1.712 | 33.544 | -34.535 | 0.00 | 0.00 | 6 |
| N | HIS | B | 3 | 2.002 | 34.598 | -33.793 | 0.00 | 0.00 | 7 |
| C | HIS | B | 3 | -2.527 | 33.177 | -30.476 | 0.00 | 0.00 | 6 |
| O | HIS | B | 3 | -2.554 | 34.170 | -29.743 | 0.00 | 0.00 | 8 |
| N | GLU | B | 3 | -3.557 | 32.353 | -30.610 | 0.00 | 0.00 | 7 |
| CA | GLU | B | 3 | -4.794 | 32.567 | -29.866 | 0.00 | 0.00 | 6 |
| CB | GLU | B | 3 | -5.912 | 33.027 | -30.800 | 0.00 | 0.00 | 6 |
| C | GLU | B | 3 | -6.321 | 34.482 | -30.651 | 0.00 | 0.00 | 6 |
| C | GLU | B | 3 | -7.794 | 34.699 | -30.938 | 0.00 | 0.00 | 6 |
| O | GLU | B | 3 | -8.149 | 34.907 | -32.118 | 0.00 | 0.00 | 8 |
| O | GLU | B | 3 | -8.606 | 34.659 | -29.990 | 0.00 | 0.00 | 8 |
| C | GLU | B | 3 | -5.195 | 31.281 | -29.152 | 0.00 | 0.00 | 6 |
| O | GLU | B | 3 | -4.761 | 30.196 | -29.536 | 0.00 | 0.00 | 8 |
| N | ALA | B | 3 | -5.996 | 31.431 | -28.105 | 0.00 | 0.00 | 7 |
| CA | ALA | B | 3 | -6.462 | 30.276 | -27.348 | 0.00 | 0.00 | 6 |
| CB | ALA | B | 3 | -7.391 | 30.719 | -26.230 | 0.00 | 0.00 | 6 |
| C | ALA | B | 3 | -7.177 | 29.299 | -28.276 | 0.00 | 0.00 | 6 |
| O | ALA | B | 3 | -7.907 | 29.717 | -29.176 | 0.00 | 0.00 | 8 |
| N | ARG | B | 3 | -6.936 | 28.009 | -28.069 | 0.00 | 0.00 | 7 |
| CA | ARG | B | 3 | -7.611 | 26.990 | -28.866 | 0.00 | 0.00 | 6 |
| CB | ARG | B | 3 | -6.659 | 25.870 | -29.277 | 0.00 | 0.00 | 6 |
| C | ARG | B | 3 | -7.277 | 24.868 | -30.241 | 0.00 | 0.00 | 6 |
| C | ARG | B | 3 | -6.937 | 25.210 | -31.683 | 0.00 | 0.00 | 6 |
| N | ARG | B | 3 | -5.570 | 24.821 | -32.015 | 0.00 | 0.00 | 7 |
| CZ | ARG | B | 3 | -4.577 | 25.684 | -32.190 | 0.00 | 0.00 | 6 |
| N | ARG | B | 3 | -4.790 | 26.990 | -32.071 | 0.00 | 0.00 | 7 |
| N | ARG | B | 3 | -3.363 | 25.243 | -32.490 | 0.00 | 0.00 | 7 |
| C | ARG | B | 3 | -8.788 | 26.424 | -28.078 | 0.00 | 0.00 | 6 |
| O | ARG | B | 3 | -8.750 | 26.377 | -26.850 | 0.00 | 0.00 | 8 |
| N | GLN | B | 3 | -9.849 | 26.059 | -28.783 | 0.00 | 0.00 | 7 |
| CA | GLN | B | 3 | -11.015 | 25.438 | -28.159 | 0.00 | 0.00 | 6 |
| CB | GLN | B | 3 | -12.291 | 25.904 | -28.851 | 0.00 | 0.00 | 6 |
| C | GLN | B | 3 | -13.555 | 25.155 | -28.470 | 0.00 | 0.00 | 6 |
| C | GLN | B | 3 | -14.199 | 25.707 | -27.216 | 0.00 | 0.00 | 6 |
| O | GLN | B | 3 | -14.433 | 24.978 | -26.251 | 0.00 | 0.00 | 8 |
| N | GLN | B | 3 | -14.484 | 27.003 | -27.223 | 0.00 | 0.00 | 7 |
| C | GLN | B | 3 | -10.861 | 23.924 | -28.260 | 0.00 | 0.00 | 6 |
| O | GLN | B | 3 | -10.370 | 23.446 | -29.287 | 0.00 | 0.00 | 8 |
| N | VAL | B | 3 | -11.116 | 23.192 | -27.185 | 0.00 | 0.00 | 7 |
| CA | VAL | B | 3 | -11.017 | 21.734 | -27.199 | 0.00 | 0.00 | 6 |
| CB | VAL | B | 3 | -9.838 | 21.147 | -26.417 | 0.00 | 0.00 | 6 |
| C | VAL | B | 3 | -8.490 | 21.559 | -27.001 | 0.00 | 0.00 | 6 |
| C | VAL | B | 3 | -9.893 | 21.513 | -24.942 | 0.00 | 0.00 | 6 |
| C | VAL | B | 3 | -12.333 | 21.158 | -26.668 | 0.00 | 0.00 | 6 |
| O | VAL | B | 3 | -13.106 | 21.923 | -26.081 | 0.00 | 0.00 | 8 |
| N | SER | B | 3 | -12.589 | 19.867 | -26.865 | 0.00 | 0.00 | 7 |
| CA | SER | B | 3 | -13.873 | 19.313 | -26.464 | 0.00 | 0.00 | 6 |
| CB | SER | B | 3 | -14.642 | 18.853 | -27.720 | 0.00 | 0.00 | 6 |
| O | SER | B | 3 | -15.916 | 18.362 | -27.327 | 0.00 | 0.00 | 8 |
| C | SER | B | 3 | -13.869 | 18.181 | -25.456 | 0.00 | 0.00 | 6 |
| O | SER | B | 3 | -14.583 | 18.304 | -24.447 | 0.00 | 0.00 | 8 |
| N | GLY | B | 3 | -13.158 | 17.086 | -25.686 | 0.00 | 0.00 | 7 |
| CA | GLY | B | 3 | -13.190 | 15.973 | -24.741 | 0.00 | 0.00 | 6 |
| C | GLY | B | 3 | -11.855 | 15.729 | -24.054 | 0.00 | 0.00 | 6 |
| O | GLY | B | 3 | -11.362 | 14.600 | -24.022 | 0.00 | 0.00 | 8 |
| N | MET | B | 3 | -11.268 | 16.780 | -23.500 | 0.00 | 0.00 | 7 |
| CA | MET | B | 3 | -9.980 | 16.684 | -22.822 | 0.00 | 0.00 | 6 |
| CB | MET | B | 3 | -9.246 | 18.020 | -22.944 | 0.00 | 0.00 | 6 |
| C | MET | B | 3 | -7.910 | 18.112 | -22.232 | 0.00 | 0.00 | 6 |
| SD | MET | B | 3 | -6.921 | 19.519 | -22.774 | 0.00 | 0.00 | 1 |
| CE | MET | B | 3 | -7.795 | 20.874 | -21.993 | 0.00 | 0.00 | 6 |
| C | MET | B | 3 | -10.160 | 16.294 | -21.361 | 0.00 | 0.00 | 6 |
| O | MET | B | 3 | -10.876 | 16.976 | -20.627 | 0.00 | 0.00 | 8 |
| N | GLU | B | 3 | -9.508 | 15.214 | -20.941 | 0.00 | 0.00 | 7 |
| CA | GLU | B | 3 | -9.616 | 14.755 | -19.560 | 0.00 | 0.00 | 6 |
| CB | GLU | B | 3 | -10.116 | 13.307 | -19.526 | 0.00 | 0.00 | 6 |
| C | GLU | B | 3 | -11.311 | 13.080 | -18.615 | 0.00 | 0.00 | 6 |
| C | GLU | B | 3 | -11.829 | 11.655 | -18.694 | 0.00 | 0.00 | 6 |
| O | GLU | B | 3 | -12.765 | 11.408 | -19.485 | 0.00 | 0.00 | 8 |
| O | GLU | B | 3 | -11.300 | 10.785 | -17.973 | 0.00 | 0.00 | 8 |
| C | GLU | B | 3 | -8.306 | 14.862 | -18.789 | 0.00 | 0.00 | 6 |

Figure 1 - 46

| | | | | | | | |
|---|---|---|---|---|---|---|---|
| O | GLU | B | 3 | -8.326 | 15.026 | -17.565 | 0.00 | 0.00 | 8 |
| N | TYR | B | 3 | -7.171 | 14.764 | -19.474 | 0.00 | 0.00 | 7 |
| CA | TYR | B | 3 | -5.872 | 14.836 | -18.820 | 0.00 | 0.00 | 6 |
| CB | TYR | B | 3 | -5.066 | 13.550 | -19.063 | 0.00 | 0.00 | 6 |
| C | TYR | B | 3 | -5.646 | 12.321 | -18.401 | 0.00 | 0.00 | 6 |
| C | TYR | B | 3 | -6.417 | 11.425 | -19.132 | 0.00 | 0.00 | 6 |
| CE | TYR | B | 3 | -6.978 | 10.312 | -18.535 | 0.00 | 0.00 | 6 |
| C | TYR | B | 3 | -5.454 | 12.071 | -17.051 | 0.00 | 0.00 | 6 |
| CE | TYR | B | 3 | -6.009 | 10.959 | -16.445 | 0.00 | 0.00 | 6 |
| CZ | TYR | B | 3 | -6.769 | 10.085 | -17.192 | 0.00 | 0.00 | 6 |
| O | TYR | B | 3 | -7.326 | 8.976 | -16.597 | 0.00 | 0.00 | 8 |
| C | TYR | B | 3 | -5.034 | 16.018 | -19.294 | 0.00 | 0.00 | 6 |
| O | TYR | B | 3 | -5.017 | 16.342 | -20.482 | 0.00 | 0.00 | 8 |
| N | THR | B | 3 | -4.282 | 16.626 | -18.381 | 0.00 | 0.00 | 7 |
| CA | THR | B | 3 | -3.292 | 17.636 | -18.718 | 0.00 | 0.00 | 6 |
| CB | THR | B | 3 | -3.692 | 19.082 | -18.388 | 0.00 | 0.00 | 6 |
| O | THR | B | 3 | -4.186 | 19.170 | -17.044 | 0.00 | 0.00 | 8 |
| C | THR | B | 3 | -4.736 | 19.619 | -19.354 | 0.00 | 0.00 | 6 |
| C | THR | B | 3 | -1.979 | 17.344 | -17.995 | 0.00 | 0.00 | 6 |
| O | THR | B | 3 | -1.947 | 16.819 | -16.887 | 0.00 | 0.00 | 8 |
| N | LEU | B | 3 | -0.873 | 17.725 | -18.626 | 0.00 | 0.00 | 7 |
| CA | LEU | B | 3 | 0.473 | 17.536 | -18.101 | 0.00 | 0.00 | 6 |
| CB | LEU | B | 3 | 1.262 | 16.734 | -19.134 | 0.00 | 0.00 | 6 |
| C | LEU | B | 3 | 2.652 | 16.201 | -18.320 | 0.00 | 0.00 | 6 |
| C | LEU | B | 3 | 2.591 | 14.952 | -17.955 | 0.00 | 0.00 | 6 |
| C | LEU | B | 3 | 3.405 | 15.888 | -20.110 | 0.00 | 0.00 | 6 |
| C | LEU | B | 3 | 1.144 | 18.878 | -17.835 | 0.00 | 0.00 | 6 |
| O | LEU | B | 3 | 1.190 | 19.712 | -18.745 | 0.00 | 0.00 | 8 |
| N | CYS | B | 3 | 1.623 | 19.127 | -16.616 | 0.00 | 0.00 | 7 |
| CA | CYS | B | 3 | 2.341 | 20.362 | -16.319 | 0.00 | 0.00 | 6 |
| CB | CYS | B | 3 | 1.761 | 21.154 | -15.146 | 0.00 | 0.00 | 6 |
| SG | CYS | B | 3 | 2.784 | 22.605 | -14.750 | 0.00 | 0.00 | 1 |
| C | CYS | B | 3 | 3.817 | 20.081 | -16.038 | 0.00 | 0.00 | 6 |
| O | CYS | B | 3 | 4.172 | 19.382 | -15.093 | 0.00 | 0.00 | 8 |
| N | ASN | B | 3 | 4.681 | 20.666 | -16.852 | 0.00 | 0.00 | 7 |
| CA | ASN | B | 3 | 6.113 | 20.457 | -16.801 | 0.00 | 0.00 | 6 |
| CB | ASN | B | 3 | 6.561 | 20.213 | -18.260 | 0.00 | 0.00 | 6 |
| C | ASN | B | 3 | 6.424 | 18.773 | -18.697 | 0.00 | 0.00 | 6 |
| O | ASN | B | 3 | 6.208 | 17.872 | -17.887 | 0.00 | 0.00 | 8 |
| N | ASN | B | 3 | 6.574 | 18.544 | -19.997 | 0.00 | 0.00 | 7 |
| C | ASN | B | 3 | 6.977 | 21.568 | -16.233 | 0.00 | 0.00 | 6 |
| O | ASN | B | 3 | 6.881 | 22.730 | -16.617 | 0.00 | 0.00 | 8 |
| N | SER | B | 3 | 7.954 | 21.187 | -15.413 | 0.00 | 0.00 | 7 |
| CA | SER | B | 3 | 8.937 | 22.105 | -14.851 | 0.00 | 0.00 | 6 |
| CB | SER | B | 3 | 8.579 | 22.503 | -13.422 | 0.00 | 0.00 | 6 |
| O | SER | B | 3 | 8.046 | 23.810 | -13.359 | 0.00 | 0.00 | 8 |
| C | SER | B | 3 | 10.315 | 21.445 | -14.860 | 0.00 | 0.00 | 6 |
| O | SER | B | 3 | 10.513 | 20.427 | -14.194 | 0.00 | 0.00 | 8 |
| N | PHE | B | 3 | 11.238 | 21.977 | -15.649 | 0.00 | 0.00 | 7 |
| CA | PHE | B | 3 | 12.588 | 21.434 | -15.761 | 0.00 | 0.00 | 6 |
| CB | PHE | B | 3 | 12.887 | 20.962 | -17.185 | 0.00 | 0.00 | 6 |
| C | PHE | B | 3 | 11.830 | 20.141 | -17.862 | 0.00 | 0.00 | 6 |
| C | PHE | B | 3 | 11.314 | 20.531 | -19.087 | 0.00 | 0.00 | 6 |
| C | PHE | B | 3 | 11.336 | 18.984 | -17.280 | 0.00 | 0.00 | 6 |
| CE | PHE | B | 3 | 10.330 | 19.791 | -19.714 | 0.00 | 0.00 | 6 |
| CE | PHE | B | 3 | 10.343 | 18.247 | -17.894 | 0.00 | 0.00 | 6 |
| CZ | PHE | B | 3 | 9.845 | 18.646 | -19.119 | 0.00 | 0.00 | 6 |
| C | PHE | B | 3 | 13.600 | 22.501 | -15.347 | 0.00 | 0.00 | 6 |
| O | PHE | B | 3 | 13.931 | 23.374 | -16.150 | 0.00 | 0.00 | 8 |
| N | GLY | B | 3 | 14.102 | 22.456 | -14.116 | 0.00 | 0.00 | 7 |
| CA | GLY | B | 3 | 14.860 | 23.556 | -13.571 | 0.00 | 0.00 | 6 |
| C | GLY | B | 3 | 16.362 | 23.470 | -13.465 | 0.00 | 0.00 | 6 |
| O | GLY | B | 3 | 17.009 | 22.450 | -13.680 | 0.00 | 0.00 | 8 |
| N | PHE | B | 4 | 16.944 | 24.615 | -13.095 | 0.00 | 0.00 | 7 |
| CA | PHE | B | 4 | 18.387 | 24.746 | -12.897 | 0.00 | 0.00 | 6 |
| CB | PHE | B | 4 | 18.720 | 26.141 | -12.373 | 0.00 | 0.00 | 6 |
| C | PHE | B | 4 | 18.292 | 27.221 | -13.330 | 0.00 | 0.00 | 6 |
| C | PHE | B | 4 | 17.267 | 28.087 | -13.002 | 0.00 | 0.00 | 6 |
| C | PHE | B | 4 | 18.916 | 27.368 | -14.558 | 0.00 | 0.00 | 6 |
| CE | PHE | B | 4 | 16.866 | 29.079 | -13.876 | 0.00 | 0.00 | 6 |
| CE | PHE | B | 4 | 18.522 | 28.357 | -15.436 | 0.00 | 0.00 | 6 |
| CZ | PHE | B | 4 | 17.495 | 29.215 | -15.095 | 0.00 | 0.00 | 6 |
| C | PHE | B | 4 | 18.862 | 23.638 | -11.971 | 0.00 | 0.00 | 6 |
| O | PHE | B | 4 | 18.146 | 23.237 | -11.054 | 0.00 | 0.00 | 8 |
| N | GLY | B | 4 | 20.035 | 23.085 | -12.261 | 0.00 | 0.00 | 7 |
| CA | GLY | B | 4 | 20.579 | 21.974 | -11.489 | 0.00 | 0.00 | 6 |
| C | GLY | B | 4 | 20.138 | 20.638 | -12.082 | 0.00 | 0.00 | 6 |
| O | GLY | B | 4 | 20.442 | 19.568 | -11.554 | 0.00 | 0.00 | 8 |
| N | THR | B | 4 | 19.372 | 20.671 | -13.162 | 0.00 | 0.00 | 7 |
| CA | GLY | B | 4 | 18.843 | 19.509 | -13.835 | 0.00 | 0.00 | 6 |
| C | GLY | B | 4 | 17.780 | 18.774 | -13.036 | 0.00 | 0.00 | 6 |
| O | GLY | B | 4 | 17.658 | 17.555 | -13.171 | 0.00 | 0.00 | 8 |
| N | THR | B | 4 | 16.986 | 19.478 | -12.237 | 0.00 | 0.00 | 7 |
| CA | THR | B | 4 | 15.949 | 18.317 | -11.440 | 0.00 | 0.00 | 6 |
| CB | THR | B | 4 | 15.976 | 19.325 | -9.993 | 0.00 | 0.00 | 6 |
| O | THR | B | 4 | 14.911 | 18.730 | -9.243 | 0.00 | 0.00 | 8 |
| C | THR | B | 4 | 15.873 | 20.840 | -9.915 | 0.00 | 0.00 | 6 |
| C | THR | B | 4 | 14.607 | 18.975 | -12.134 | 0.00 | 0.00 | 6 |
| O | THR | B | 4 | 14.143 | 20.085 | -12.401 | 0.00 | 0.00 | 8 |
| N | ASN | B | 4 | 14.012 | 17.851 | -12.542 | 0.00 | 0.00 | 7 |
| CA | ASN | B | 4 | 12.791 | 17.353 | -13.322 | 0.00 | 0.00 | 6 |
| CB | ASN | B | 4 | 12.936 | 16.993 | -14.591 | 0.00 | 0.00 | 6 |
| C | ASN | B | 4 | 14.167 | 17.308 | -15.404 | 0.00 | 0.00 | 6 |
| O | ASN | B | 4 | 14.327 | 18.432 | -15.878 | 0.00 | 0.00 | 8 |
| N | ASN | B | 4 | 15.033 | 16.317 | -15.556 | 0.00 | 0.00 | 7 |
| C | ASN | B | 4 | 11.564 | 17.303 | -12.604 | 0.00 | 0.00 | 6 |
| O | ASN | B | 4 | 11.653 | 16.434 | -11.745 | 0.00 | 0.00 | 8 |
| N | GLY | B | 4 | 10.405 | 17.769 | -13.071 | 0.00 | 0.00 | 7 |
| CA | GLY | B | 4 | 9.142 | 17.309 | -12.516 | 0.00 | 0.00 | 6 |
| C | GLY | B | 4 | 7.990 | 17.509 | -13.491 | 0.00 | 0.00 | 6 |
| O | GLY | B | 4 | 7.993 | 18.405 | -14.327 | 0.00 | 0.00 | 8 |
| N | SER | B | 4 | 6.987 | 16.650 | -13.367 | 0.00 | 0.00 | 7 |
| CA | SER | B | 4 | 5.782 | 16.715 | -14.170 | 0.00 | 0.00 | 6 |
| CB | SER | B | 4 | 5.822 | 15.765 | -15.365 | 0.00 | 0.00 | 6 |
| O | SER | B | 4 | 6.920 | 15.961 | -16.224 | 0.00 | 0.00 | 8 |
| C | SER | B | 4 | 4.581 | 16.334 | -13.302 | 0.00 | 0.00 | 6 |
| O | SER | B | 4 | 4.688 | 15.411 | -12.495 | 0.00 | 0.00 | 8 |
| N | LEU | B | 4 | 3.471 | 17.032 | -13.484 | 0.00 | 0.00 | 7 |
| CA | LEU | B | 4 | 2.249 | 16.710 | -12.751 | 0.00 | 0.00 | 6 |
| CB | LEU | B | 4 | 1.830 | 17.838 | -11.819 | 0.00 | 0.00 | 6 |
| C | LEU | B | 4 | 2.585 | 17.940 | -10.488 | 0.00 | 0.00 | 6 |
| C | LEU | B | 4 | 2.403 | 19.314 | -9.863 | 0.00 | 0.00 | 6 |
| C | LEU | B | 4 | 2.137 | 16.855 | -9.521 | 0.00 | 0.00 | 6 |
| C | LEU | B | 4 | 1.166 | 16.376 | -13.777 | 0.00 | 0.00 | 6 |
| O | LEU | B | 4 | 1.216 | 16.876 | -14.906 | 0.00 | 0.00 | 8 |
| N | ILE | B | 4 | 0.306 | 15.412 | -13.474 | 0.00 | 0.00 | 7 |
| CA | ILE | B | 4 | -0.784 | 15.030 | -14.359 | 0.00 | 0.00 | 6 |
| CB | ILE | B | 4 | -0.723 | 13.580 | -14.866 | 0.00 | 0.00 | 6 |
| C | ILE | B | 4 | -2.009 | 13.208 | -15.599 | 0.00 | 0.00 | 6 |
| C | ILE | B | 4 | 0.471 | 13.365 | -15.798 | 0.00 | 0.00 | 6 |
| C | ILE | B | 4 | 0.661 | 11.935 | -16.250 | 0.00 | 0.00 | 6 |
| C | ILE | B | 4 | -2.112 | 15.245 | -13.630 | 0.00 | 0.00 | 6 |
| O | ILE | B | 4 | -2.303 | 14.764 | -12.516 | 0.00 | 0.00 | 8 |
| N | PHE | B | 4 | -3.015 | 15.973 | -14.279 | 0.00 | 0.00 | 7 |
| CA | PHE | B | 4 | -4.320 | 16.257 | -13.690 | 0.00 | 0.00 | 6 |
| CB | PHE | B | 4 | -4.534 | 17.768 | -13.596 | 0.00 | 0.00 | 6 |
| C | PHE | B | 4 | -3.628 | 18.449 | -12.608 | 0.00 | 0.00 | 6 |
| C | PHE | B | 4 | -2.421 | 18.992 | -13.015 | 0.00 | 0.00 | 6 |

Figure 1 - 47

| C | PHE | B | 4 | -3.974 | 18.529 | -11.268 | 0.00 | 0.00 | 6 |
|---|---|---|---|---|---|---|---|---|---|
| CE | PHE | B | 4 | -1.583 | 19.615 | -12.109 | 0.00 | 0.00 | 6 |
| CE | PHE | B | 4 | -3.142 | 19.154 | -10.360 | 0.00 | 0.00 | 6 |
| CZ | PHE | B | 4 | -1.948 | 19.701 | -10.780 | 0.00 | 0.00 | 6 |
| C | PHE | B | 4 | -5.433 | 15.582 | -14.484 | 0.00 | 0.00 | 6 |
| O | PHE | B | 4 | -5.299 | 15.351 | -15.685 | 0.00 | 0.00 | 8 |
| N | LYS | B | 4 | -6.508 | 15.211 | -13.796 | 0.00 | 0.00 | 7 |
| CA | LYS | B | 4 | -7.621 | 14.523 | -14.445 | 0.00 | 0.00 | 6 |
| CB | LYS | B | 4 | -7.615 | 13.048 | -14.064 | 0.00 | 0.00 | 6 |
| C | LYS | B | 4 | -8.945 | 12.390 | -13.771 | 0.00 | 0.00 | 6 |
| C | LYS | B | 4 | -9.066 | 11.022 | -14.425 | 0.00 | 0.00 | 6 |
| CE | LYS | B | 4 | -9.980 | 10.113 | -13.620 | 0.00 | 0.00 | 6 |
| NZ | LYS | B | 4 | -11.257 | 10.787 | -13.251 | 0.00 | 0.00 | 7 |
| C | LYS | B | 4 | -8.942 | 15.210 | -14.115 | 0.00 | 0.00 | 6 |
| O | LYS | B | 4 | -9.212 | 15.563 | -12.970 | 0.00 | 0.00 | 8 |
| N | LYS | B | 4 | -9.765 | 15.394 | -15.142 | 0.00 | 0.00 | 7 |
| CA | LYS | B | 4 | -11.067 | 16.029 | -14.990 | 0.00 | 0.00 | 6 |
| CB | LYS | B | 4 | -11.634 | 16.391 | -16.366 | 0.00 | 0.00 | 6 |
| C | LYS | B | 4 | -12.465 | 17.660 | -16.399 | 0.00 | 0.00 | 6 |
| C | LYS | B | 4 | -13.928 | 17.380 | -16.089 | 0.00 | 0.00 | 6 |
| CE | LYS | B | 4 | -14.796 | 18.590 | -16.391 | 0.00 | 0.00 | 6 |
| NZ | LYS | B | 4 | -14.788 | 19.577 | -15.277 | 0.00 | 0.00 | 7 |
| C | LYS | B | 4 | -12.043 | 15.106 | -14.269 | 0.00 | 0.00 | 6 |
| O | LYS | B | 4 | -12.185 | 13.944 | -14.652 | 0.00 | 0.00 | 8 |
| N | ILE | B | 4 | -12.698 | 15.610 | -13.230 | 0.00 | 0.00 | 7 |
| CA | ILE | B | 4 | -13.715 | 14.833 | -12.522 | 0.00 | 0.00 | 6 |
| CB | ILE | B | 4 | -13.357 | 14.578 | -11.053 | 0.00 | 0.00 | 6 |
| C | ILE | B | 4 | -14.584 | 14.417 | -10.163 | 0.00 | 0.00 | 6 |
| C | ILE | B | 4 | -12.478 | 13.322 | -10.945 | 0.00 | 0.00 | 6 |
| C | ILE | B | 4 | -11.906 | 13.091 | -9.564 | 0.00 | 0.00 | 6 |
| C | ILE | B | 4 | -15.060 | 15.546 | -12.659 | 0.00 | 0.00 | 6 |
| O | ILE | B | 4 | -15.481 | 15.769 | -13.816 | 0.00 | 0.00 | 8 |
| O1 | WAT | W | 5 | 4.504 | 27.399 | -19.536 | 0.00 | 0.00 | 8 |
| O1 | WAT | W | 5 | 7.437 | 28.629 | 2.535 | 0.00 | 0.00 | 8 |
| O1 | WAT | W | 5 | 14.567 | 39.281 | -19.752 | 0.00 | 0.00 | 8 |
| O1 | WAT | W | 5 | 12.567 | 39.856 | -2.839 | 0.00 | 0.00 | 8 |
| O1 | WAT | W | 5 | 12.015 | 35.396 | -4.390 | 0.00 | 0.00 | 8 |
| O1 | WAT | W | 5 | 3.319 | 30.612 | -17.061 | 0.00 | 0.00 | 8 |
| O1 | WAT | W | 5 | 16.094 | 26.918 | -5.435 | 0.00 | 0.00 | 8 |
| O1 | WAT | W | 5 | 8.209 | 39.238 | -23.056 | 0.00 | 0.00 | 8 |
| O1 | WAT | W | 5 | 13.807 | 20.357 | -7.960 | 0.00 | 0.00 | 8 |
| O1 | WAT | W | 5 | -13.395 | 21.538 | 1.565 | 0.00 | 0.00 | 8 |
| O1 | WAT | W | 5 | 24.930 | 41.412 | -15.101 | 0.00 | 0.00 | 8 |
| O1 | WAT | W | 5 | 21.290 | 38.294 | -20.198 | 0.00 | 0.00 | 8 |
| O1 | WAT | W | 5 | 15.902 | 50.395 | 9.343 | 0.00 | 0.00 | 8 |
| O1 | WAT | W | 5 | -2.782 | 8.166 | -8.701 | 0.00 | 0.00 | 8 |
| O1 | WAT | W | 5 | 19.738 | 27.340 | -19.439 | 0.00 | 0.00 | 8 |
| O1 | WAT | W | 5 | -1.747 | 11.046 | -6.351 | 0.00 | 0.00 | 8 |
| O1 | WAT | W | 5 | 6.680 | 14.967 | -34.855 | 0.00 | 0.00 | 8 |
| O1 | WAT | W | 5 | 22.057 | 48.723 | -9.374 | 0.00 | 0.00 | 8 |
| O1 | WAT | W | 5 | -6.611 | 39.165 | -2.117 | 0.00 | 0.00 | 8 |
| O1 | WAT | W | 5 | 13.624 | 8.609 | -12.588 | 0.00 | 0.00 | 8 |
| O1 | WAT | W | 5 | 9.255 | 7.220 | -29.727 | 0.00 | 0.00 | 8 |
| O1 | WAT | W | 5 | -5.734 | 12.781 | -26.436 | 0.00 | 0.00 | 8 |
| O1 | WAT | W | 5 | 21.680 | 48.304 | -5.494 | 0.00 | 0.00 | 8 |
| O1 | WAT | W | 5 | 15.561 | 45.821 | -2.731 | 0.00 | 0.00 | 8 |
| O1 | WAT | W | 5 | 0.642 | 10.760 | 10.232 | 0.00 | 0.00 | 8 |
| O1 | WAT | W | 5 | 0.990 | 48.249 | 1.863 | 0.00 | 0.00 | 8 |
| O1 | WAT | W | 5 | 20.915 | 17.564 | -30.457 | 0.00 | 0.00 | 8 |
| O1 | WAT | W | 5 | 16.863 | 23.110 | -17.142 | 0.00 | 0.00 | 8 |
| O1 | WAT | W | 5 | 9.631 | 43.771 | -32.080 | 0.00 | 0.00 | 8 |
| O1 | WAT | W | 5 | -9.127 | 0.966 | -13.608 | 0.00 | 0.00 | 8 |
| O1 | WAT | W | 5 | 23.605 | 12.660 | -18.246 | 0.00 | 0.00 | 8 |

Figure 1 - 48

| | | | | | | | | | |
|---|---|---|---|---|---|---|---|---|---|
| N | LYS | A | 2 | 5.691 | -3.942 | 0.967 | 1.00 | 59.01 | N |
| CA | LYS | A | 2 | 6.181 | -2.836 | 1.843 | 1.00 | 59.40 | C |
| C | LYS | A | 2 | 7.698 | -2.690 | 1.729 | 1.00 | 58.26 | C |
| O | LYS | A | 2 | 8.433 | -3.674 | 1.890 | 1.00 | 58.76 | O |
| CB | LYS | A | 2 | 5.769 | -3.035 | 3.298 | 1.00 | 59.99 | C |
| CG | LYS | A | 2 | 6.542 | -2.171 | 4.281 | 1.00 | 60.75 | C |
| CD | LYS | A | 2 | 5.621 | -1.406 | 5.211 | 1.00 | 61.69 | C |
| CE | LYS | A | 2 | 5.333 | -0.004 | 4.701 | 1.00 | 62.26 | C |
| NZ | LYS | A | 2 | 5.569 | 1.027 | 5.757 | 1.00 | 62.54 | N |
| N | ARG | A | 3 | 8.164 | -1.457 | 1.572 | 1.00 | 56.23 | N |
| CA | ARG | A | 3 | 9.587 | -1.211 | 1.400 | 1.00 | 54.46 | C |
| C | ARG | A | 3 | 10.254 | -0.621 | 2.629 | 1.00 | 53.07 | C |
| O | ARG | A | 3 | 9.908 | 0.442 | 3.142 | 1.00 | 53.04 | O |
| CB | ARG | A | 3 | 9.797 | -0.330 | 0.163 | 1.00 | 54.51 | C |
| CG | ARG | A | 3 | 9.528 | -1.088 | -1.137 | 1.00 | 54.53 | C |
| CD | ARG | A | 3 | 9.198 | -0.128 | -2.267 | 1.00 | 54.58 | C |
| NE | ARG | A | 3 | 10.369 | 0.430 | -2.917 | 1.00 | 54.17 | N |
| CZ | ARG | A | 3 | 11.239 | -0.232 | -3.660 | 1.00 | 54.41 | C |
| NH1 | ARG | A | 3 | 11.105 | -1.535 | -3.867 | 1.00 | 54.22 | N |
| NH2 | ARG | A | 3 | 12.268 | 0.409 | -4.208 | 1.00 | 55.03 | N |
| N | ARG | A | 4 | 11.255 | -1.351 | 3.116 | 1.00 | 51.11 | N |
| CA | ARG | A | 4 | 12.014 | -0.957 | 4.293 | 1.00 | 49.31 | C |
| C | ARG | A | 4 | 13.305 | -0.261 | 3.888 | 1.00 | 46.70 | C |
| O | ARG | A | 4 | 14.075 | -0.757 | 3.065 | 1.00 | 45.87 | O |
| CB | ARG | A | 4 | 12.313 | -2.184 | 5.161 | 1.00 | 51.04 | C |
| CG | ARG | A | 4 | 11.082 | -3.026 | 5.462 | 1.00 | 52.54 | C |
| CD | ARG | A | 4 | 11.310 | -4.014 | 6.588 | 1.00 | 54.18 | C |
| NE | ARG | A | 4 | 12.714 | -4.381 | 6.740 | 1.00 | 55.76 | N |
| CZ | ARG | A | 4 | 13.204 | -5.089 | 7.754 | 1.00 | 55.81 | C |
| NH1 | ARG | A | 4 | 12.388 | -5.510 | 8.707 | 1.00 | 56.21 | N |
| NH2 | ARG | A | 4 | 14.499 | -5.363 | 7.792 | 1.00 | 56.00 | N |
| N | VAL | A | 5 | 13.512 | 0.929 | 4.436 | 1.00 | 44.00 | N |
| CA | VAL | A | 5 | 14.691 | 1.721 | 4.082 | 1.00 | 41.65 | C |
| C | VAL | A | 5 | 15.765 | 1.553 | 5.144 | 1.00 | 40.39 | C |
| O | VAL | A | 5 | 15.466 | 1.605 | 6.342 | 1.00 | 40.29 | O |
| CB | VAL | A | 5 | 14.334 | 3.204 | 3.904 | 1.00 | 41.18 | C |
| CG1 | VAL | A | 5 | 15.542 | 4.022 | 3.494 | 1.00 | 40.93 | C |
| CG2 | VAL | A | 5 | 13.215 | 3.337 | 2.878 | 1.00 | 40.99 | C |
| N | VAL | A | 6 | 16.989 | 1.323 | 4.687 | 1.00 | 38.36 | N |
| CA | VAL | A | 6 | 18.127 | 1.134 | 5.579 | 1.00 | 36.46 | C |
| C | VAL | A | 6 | 19.270 | 2.069 | 5.204 | 1.00 | 35.96 | C |
| O | VAL | A | 6 | 19.367 | 2.549 | 4.078 | 1.00 | 34.89 | O |
| CB | VAL | A | 6 | 18.597 | -0.331 | 5.583 | 1.00 | 36.36 | C |
| CG1 | VAL | A | 6 | 17.633 | -1.212 | 6.377 | 1.00 | 35.25 | C |
| CG2 | VAL | A | 6 | 18.774 | -0.883 | 4.176 | 1.00 | 34.82 | C |
| N | VAL | A | 7 | 20.114 | 2.404 | 6.175 | 1.00 | 36.29 | N |
| CA | VAL | A | 7 | 21.209 | 3.359 | 5.973 | 1.00 | 34.89 | C |
| C | VAL | A | 7 | 22.508 | 2.606 | 5.723 | 1.00 | 35.21 | C |
| O | VAL | A | 7 | 23.107 | 2.026 | 6.633 | 1.00 | 34.55 | O |
| CB | VAL | A | 7 | 21.352 | 4.266 | 7.205 | 1.00 | 34.25 | C |
| CG1 | VAL | A | 7 | 22.435 | 5.308 | 6.974 | 1.00 | 34.66 | C |
| CG2 | VAL | A | 7 | 20.030 | 4.915 | 7.568 | 1.00 | 32.51 | C |
| N | THR | A | 8 | 22.947 | 2.600 | 4.468 | 1.00 | 35.16 | N |
| CA | THR | A | 8 | 24.151 | 1.902 | 4.077 | 1.00 | 34.77 | C |
| C | THR | A | 8 | 25.366 | 2.768 | 3.841 | 1.00 | 34.34 | C |
| O | THR | A | 8 | 26.312 | 2.285 | 3.191 | 1.00 | 35.61 | O |
| CB | THR | A | 8 | 23.893 | 1.120 | 2.751 | 1.00 | 35.46 | C |
| OG1 | THR | A | 8 | 23.765 | 2.081 | 1.693 | 1.00 | 35.07 | O |
| CG2 | THR | A | 8 | 22.666 | 0.247 | 2.872 | 1.00 | 34.29 | C |
| N | GLY | A | 9 | 25.403 | 4.010 | 4.292 | 1.00 | 33.53 | N |
| CA | GLY | A | 9 | 26.572 | 4.846 | 4.008 | 1.00 | 32.71 | C |
| C | GLY | A | 9 | 26.496 | 6.173 | 4.745 | 1.00 | 32.55 | C |
| O | GLY | A | 9 | 25.472 | 6.847 | 4.718 | 1.00 | 32.58 | O |

Figure 2-1

| N | LEU | A | 10 | 27.591 | 6.534 | 5.404 | 1.00 | 31.65 | N |
|---|---|---|---|---|---|---|---|---|---|
| CA | LEU | A | 10 | 27.691 | 7.753 | 6.182 | 1.00 | 30.79 | C |
| C | LEU | A | 10 | 28.815 | 8.653 | 5.700 | 1.00 | 30.11 | C |
| O | LEU | A | 10 | 29.837 | 8.168 | 5.209 | 1.00 | 30.41 | O |
| CB | LEU | A | 10 | 27.912 | 7.374 | 7.657 | 1.00 | 31.04 | C |
| CG | LEU | A | 10 | 26.798 | 6.560 | 8.320 | 1.00 | 31.18 | C |
| CD1 | LEU | A | 10 | 27.208 | 6.161 | 9.736 | 1.00 | 31.32 | C |
| CD2 | LEU | A | 10 | 25.488 | 7.329 | 8.323 | 1.00 | 30.03 | C |
| N | GLY | A | 11 | 28.643 | 9.963 | 5.814 | 1.00 | 29.43 | N |
| CA | GLY | A | 11 | 29.679 | 10.911 | 5.372 | 1.00 | 28.90 | C |
| C | GLY | A | 11 | 29.509 | 12.228 | 6.120 | 1.00 | 28.84 | C |
| O | GLY | A | 11 | 28.368 | 12.646 | 6.360 | 1.00 | 27.25 | O |
| N | MET | A | 12 | 30.616 | 12.889 | 6.517 | 1.00 | 29.01 | N |
| CA | MET | A | 12 | 30.376 | 14.128 | 7.269 | 1.00 | 29.71 | C |
| C | MET | A | 12 | 31.538 | 15.041 | 7.553 | 1.00 | 29.99 | C |
| O | MET | A | 12 | 32.635 | 14.675 | 7.959 | 1.00 | 30.04 | O |
| CB | MET | A | 12 | 29.709 | 13.689 | 8.579 | 1.00 | 30.44 | C |
| CG | MET | A | 12 | 30.111 | 14.370 | 9.851 | 1.00 | 31.28 | C |
| SD | MET | A | 12 | 29.114 | 13.787 | 11.236 | 1.00 | 33.04 | S |
| CE | MET | A | 12 | 29.030 | 15.291 | 12.208 | 1.00 | 34.14 | C |
| N | LEU | A | 13 | 31.255 | 16.339 | 7.480 | 1.00 | 29.20 | N |
| CA | LEU | A | 13 | 32.186 | 17.389 | 7.856 | 1.00 | 28.50 | C |
| C | LEU | A | 13 | 31.557 | 18.111 | 9.057 | 1.00 | 28.52 | C |
| O | LEU | A | 13 | 30.355 | 18.378 | 9.039 | 1.00 | 28.74 | O |
| CB | LEU | A | 13 | 32.394 | 18.402 | 6.750 | 1.00 | 28.65 | C |
| CG | LEU | A | 13 | 33.435 | 18.122 | 5.680 | 1.00 | 28.65 | C |
| CD1 | LEU | A | 13 | 33.357 | 19.187 | 4.601 | 1.00 | 28.55 | C |
| CD2 | LEU | A | 13 | 34.829 | 18.057 | 6.293 | 1.00 | 28.84 | C |
| N | SER | A | 14 | 32.344 | 18.403 | 10.070 | 1.00 | 28.97 | N |
| CA | SER | A | 14 | 31.799 | 19.072 | 11.255 | 1.00 | 28.21 | C |
| C | SER | A | 14 | 32.909 | 19.787 | 12.004 | 1.00 | 27.92 | C |
| O | SER | A | 14 | 34.097 | 19.551 | 11.780 | 1.00 | 28.19 | O |
| CB | SER | A | 14 | 31.141 | 18.044 | 12.170 | 1.00 | 28.44 | C |
| OG | SER | A | 14 | 32.052 | 17.670 | 13.191 | 1.00 | 29.39 | O |
| N | PRO | A | 15 | 32.515 | 20.647 | 12.923 | 1.00 | 27.64 | N |
| CA | PRO | A | 15 | 33.437 | 21.428 | 13.717 | 1.00 | 28.13 | C |
| C | PRO | A | 15 | 34.385 | 20.619 | 14.582 | 1.00 | 28.10 | C |
| O | PRO | A | 15 | 35.465 | 21.116 | 14.931 | 1.00 | 26.91 | O |
| CB | PRO | A | 15 | 32.536 | 22.318 | 14.571 | 1.00 | 28.32 | C |
| CG | PRO | A | 15 | 31.220 | 22.323 | 13.885 | 1.00 | 28.67 | C |
| CD | PRO | A | 15 | 31.096 | 20.981 | 13.207 | 1.00 | 27.90 | C |
| N | VAL | A | 16 | 34.019 | 19.402 | 14.975 | 1.00 | 28.38 | N |
| CA | VAL | A | 16 | 34.884 | 18.572 | 15.791 | 1.00 | 28.90 | C |
| C | VAL | A | 16 | 35.607 | 17.534 | 14.941 | 1.00 | 29.97 | C |
| O | VAL | A | 16 | 36.453 | 16.796 | 15.472 | 1.00 | 31.83 | O |
| CB | VAL | A | 16 | 34.157 | 17.879 | 16.955 | 1.00 | 28.71 | C |
| CG1 | VAL | A | 16 | 33.534 | 18.907 | 17.896 | 1.00 | 29.04 | C |
| CG2 | VAL | A | 16 | 33.097 | 16.901 | 16.489 | 1.00 | 28.08 | C |
| N | GLY | A | 17 | 35.307 | 17.450 | 13.648 | 1.00 | 29.27 | N |
| CA | GLY | A | 17 | 35.990 | 16.446 | 12.835 | 1.00 | 30.51 | C |
| C | GLY | A | 17 | 35.651 | 16.531 | 11.360 | 1.00 | 31.65 | C |
| O | GLY | A | 17 | 34.569 | 16.998 | 10.992 | 1.00 | 32.81 | O |
| N | ASN | A | 18 | 36.559 | 16.075 | 10.506 | 1.00 | 31.30 | N |
| CA | ASN | A | 18 | 36.365 | 16.100 | 9.062 | 1.00 | 30.77 | C |
| C | ASN | A | 18 | 35.892 | 14.767 | 8.528 | 1.00 | 29.51 | C |
| O | ASN | A | 18 | 35.733 | 14.560 | 7.319 | 1.00 | 29.78 | O |
| CB | ASN | A | 18 | 37.678 | 16.530 | 8.381 | 1.00 | 32.68 | C |
| CG | ASN | A | 18 | 37.873 | 18.028 | 8.512 | 1.00 | 35.49 | C |
| OD1 | ASN | A | 18 | 36.915 | 18.750 | 8.815 | 1.00 | 37.19 | O |
| ND2 | ASN | A | 18 | 39.081 | 18.526 | 8.303 | 1.00 | 36.58 | N |
| N | THR | A | 19 | 35.804 | 13.749 | 9.379 | 1.00 | 27.98 | N |
| CA | THR | A | 19 | 35.289 | 12.456 | 8.960 | 1.00 | 27.30 | C |
| C | THR | A | 19 | 34.258 | 11.975 | 9.989 | 1.00 | 27.68 | C |

Figure 2-2

| O | THR | A | 19 | 34.070 | 12.579 | 11.046 | 1.00 | 28.33 | O |
|---|---|---|---|---|---|---|---|---|---|
| CB | THR | A | 19 | 36.328 | 11.346 | 8.760 | 1.00 | 25.95 | C |
| OG1 | THR | A | 19 | 36.898 | 10.987 | 10.030 | 1.00 | 26.38 | O |
| CG2 | THR | A | 19 | 37.418 | 11.733 | 7.792 | 1.00 | 23.99 | C |
| N | VAL | A | 20 | 33.560 | 10.909 | 9.640 | 1.00 | 27.75 | N |
| CA | VAL | A | 20 | 32.537 | 10.396 | 10.550 | 1.00 | 28.58 | C |
| C | VAL | A | 20 | 33.159 | 9.898 | 11.840 | 1.00 | 30.09 | C |
| O | VAL | A | 20 | 32.870 | 10.399 | 12.926 | 1.00 | 31.00 | O |
| CB | VAL | A | 20 | 31.737 | 9.270 | 9.872 | 1.00 | 27.71 | C |
| CG1 | VAL | A | 20 | 30.836 | 8.588 | 10.881 | 1.00 | 28.09 | C |
| CG2 | VAL | A | 20 | 30.975 | 9.838 | 8.685 | 1.00 | 26.96 | C |
| N | GLU | A | 21 | 34.033 | 8.897 | 11.735 | 1.00 | 31.53 | N |
| CA | GLU | A | 21 | 34.669 | 8.328 | 12.915 | 1.00 | 32.01 | C |
| C | GLU | A | 21 | 35.385 | 9.347 | 13.770 | 1.00 | 32.56 | C |
| O | GLU | A | 21 | 35.216 | 9.306 | 15.005 | 1.00 | 33.46 | O |
| CB | GLU | A | 21 | 35.592 | 7.178 | 12.500 | 1.00 | 32.25 | C |
| CG | GLU | A | 21 | 34.828 | 6.028 | 11.845 | 1.00 | 32.20 | C |
| CD | GLU | A | 21 | 33.779 | 5.403 | 12.731 | 1.00 | 32.65 | C |
| OE1 | GLU | A | 21 | 33.806 | 5.603 | 13.972 | 1.00 | 33.29 | O |
| OE2 | GLU | A | 21 | 32.893 | 4.693 | 12.198 | 1.00 | 32.86 | O |
| N | SER | A | 22 | 36.124 | 10.300 | 13.198 | 1.00 | 32.24 | N |
| CA | SER | A | 22 | 36.864 | 11.236 | 14.055 | 1.00 | 31.95 | C |
| C | SER | A | 22 | 35.894 | 12.051 | 14.892 | 1.00 | 32.52 | C |
| O | SER | A | 22 | 36.024 | 12.198 | 16.107 | 1.00 | 33.65 | O |
| CB | SER | A | 22 | 37.774 | 12.135 | 13.245 | 1.00 | 32.45 | C |
| OG | SER | A | 22 | 37.164 | 12.619 | 12.073 | 1.00 | 33.99 | O |
| N | THR | A | 23 | 34.883 | 12.592 | 14.222 | 1.00 | 32.30 | N |
| CA | THR | A | 23 | 33.842 | 13.388 | 14.853 | 1.00 | 30.89 | C |
| C | THR | A | 23 | 33.219 | 12.640 | 16.017 | 1.00 | 30.74 | C |
| O | THR | A | 23 | 33.074 | 13.176 | 17.109 | 1.00 | 30.91 | O |
| CB | THR | A | 23 | 32.754 | 13.699 | 13.800 | 1.00 | 30.18 | C |
| OG1 | THR | A | 23 | 33.375 | 14.516 | 12.799 | 1.00 | 30.03 | O |
| CG2 | THR | A | 23 | 31.561 | 14.400 | 14.404 | 1.00 | 29.43 | C |
| N | TRP | A | 24 | 32.834 | 11.394 | 15.770 | 1.00 | 30.66 | N |
| CA | TRP | A | 24 | 32.248 | 10.519 | 16.775 | 1.00 | 31.12 | C |
| C | TRP | A | 24 | 33.139 | 10.322 | 17.989 | 1.00 | 31.58 | C |
| O | TRP | A | 24 | 32.633 | 10.269 | 19.117 | 1.00 | 32.40 | O |
| CB | TRP | A | 24 | 31.898 | 9.174 | 16.126 | 1.00 | 30.43 | C |
| CG | TRP | A | 24 | 31.118 | 8.241 | 16.993 | 1.00 | 29.54 | C |
| CD1 | TRP | A | 24 | 31.407 | 6.936 | 17.273 | 1.00 | 29.43 | C |
| CD2 | TRP | A | 24 | 29.913 | 8.537 | 17.709 | 1.00 | 29.07 | C |
| NE1 | TRP | A | 24 | 30.455 | 6.403 | 18.106 | 1.00 | 29.04 | N |
| CE2 | TRP | A | 24 | 29.526 | 7.366 | 18.388 | 1.00 | 28.68 | C |
| CE3 | TRP | A | 24 | 29.120 | 9.680 | 17.823 | 1.00 | 28.43 | C |
| CZ2 | TRP | A | 24 | 28.382 | 7.304 | 19.175 | 1.00 | 28.30 | C |
| CZ3 | TRP | A | 24 | 27.982 | 9.609 | 18.599 | 1.00 | 28.58 | C |
| CH2 | TRP | A | 24 | 27.623 | 8.433 | 19.274 | 1.00 | 28.30 | C |
| N | LYS | A | 25 | 34.456 | 10.210 | 17.816 | 1.00 | 32.36 | N |
| CA | LYS | A | 25 | 35.365 | 10.069 | 18.950 | 1.00 | 32.47 | C |
| C | LYS | A | 25 | 35.384 | 11.367 | 19.753 | 1.00 | 31.77 | C |
| O | LYS | A | 25 | 35.161 | 11.344 | 20.966 | 1.00 | 32.00 | O |
| CB | LYS | A | 25 | 36.786 | 9.706 | 18.533 | 1.00 | 34.20 | C |
| CG | LYS | A | 25 | 36.856 | 8.568 | 17.532 | 1.00 | 36.79 | C |
| CD | LYS | A | 25 | 38.162 | 7.795 | 17.623 | 1.00 | 38.74 | C |
| CE | LYS | A | 25 | 38.112 | 6.579 | 16.685 | 1.00 | 39.99 | C |
| NZ | LYS | A | 25 | 39.171 | 5.589 | 17.053 | 1.00 | 40.83 | N |
| N | ALA | A | 26 | 35.488 | 12.495 | 19.055 | 1.00 | 30.32 | N |
| CA | ALA | A | 26 | 35.467 | 13.791 | 19.718 | 1.00 | 29.97 | C |
| C | ALA | A | 26 | 34.201 | 14.001 | 20.527 | 1.00 | 30.40 | C |
| O | ALA | A | 26 | 34.274 | 14.526 | 21.654 | 1.00 | 31.66 | O |
| CB | ALA | A | 26 | 35.654 | 14.915 | 18.714 | 1.00 | 30.12 | C |
| N | LEU | A | 27 | 33.043 | 13.626 | 19.995 | 1.00 | 30.16 | N |
| CA | LEU | A | 27 | 31.798 | 13.797 | 20.745 | 1.00 | 30.85 | C |

Figure 2-3

| | | | | | | | | | |
|---|---|---|---|---|---|---|---|---|---|
| C | LEU | A | 27 | 31.799 | 12.936 | 22.006 | 1.00 | 31.50 | C |
| O | LEU | A | 27 | 31.470 | 13.405 | 23.098 | 1.00 | 31.92 | O |
| CB | LEU | A | 27 | 30.585 | 13.468 | 19.896 | 1.00 | 30.80 | C |
| CG | LEU | A | 27 | 30.244 | 14.307 | 18.673 | 1.00 | 30.36 | C |
| CD1 | LEU | A | 27 | 28.797 | 14.053 | 18.270 | 1.00 | 30.28 | C |
| CD2 | LEU | A | 27 | 30.456 | 15.790 | 18.910 | 1.00 | 30.98 | C |
| N | LEU | A | 28 | 32.181 | 11.666 | 21.869 | 1.00 | 31.46 | N |
| CA | LEU | A | 28 | 32.202 | 10.758 | 23.013 | 1.00 | 31.67 | C |
| C | LEU | A | 28 | 33.223 | 11.167 | 24.054 | 1.00 | 32.22 | C |
| O | LEU | A | 28 | 33.013 | 10.970 | 25.258 | 1.00 | 33.37 | O |
| CB | LEU | A | 28 | 32.424 | 9.314 | 22.544 | 1.00 | 30.95 | C |
| CG | LEU | A | 28 | 31.228 | 8.660 | 21.830 | 1.00 | 30.19 | C |
| CD1 | LEU | A | 28 | 31.560 | 7.271 | 21.337 | 1.00 | 28.60 | C |
| CD2 | LEU | A | 28 | 30.002 | 8.622 | 22.744 | 1.00 | 29.86 | C |
| N | ALA | A | 29 | 34.295 | 11.843 | 23.649 | 1.00 | 32.19 | N |
| CA | ALA | A | 29 | 35.302 | 12.346 | 24.565 | 1.00 | 31.97 | C |
| C | ALA | A | 29 | 34.965 | 13.745 | 25.063 | 1.00 | 32.74 | C |
| O | ALA | A | 29 | 35.830 | 14.417 | 25.632 | 1.00 | 33.76 | O |
| CB | ALA | A | 29 | 36.675 | 12.342 | 23.893 | 1.00 | 30.85 | C |
| N | GLY | A | 30 | 33.761 | 14.238 | 24.824 | 1.00 | 32.92 | N |
| CA | GLY | A | 30 | 33.297 | 15.529 | 25.232 | 1.00 | 33.16 | C |
| C | GLY | A | 30 | 34.121 | 16.708 | 24.757 | 1.00 | 34.03 | C |
| O | GLY | A | 30 | 34.194 | 17.728 | 25.454 | 1.00 | 33.69 | O |
| N | GLN | A | 31 | 34.712 | 16.630 | 23.571 | 1.00 | 35.19 | N |
| CA | GLN | A | 31 | 35.478 | 17.738 | 23.014 | 1.00 | 36.06 | C |
| C | GLN | A | 31 | 34.564 | 18.823 | 22.454 | 1.00 | 35.59 | C |
| O | GLN | A | 31 | 33.447 | 18.518 | 22.014 | 1.00 | 36.40 | O |
| CB | GLN | A | 31 | 36.414 | 17.217 | 21.915 | 1.00 | 37.41 | C |
| CG | GLN | A | 31 | 37.802 | 16.866 | 22.389 | 1.00 | 39.45 | C |
| CD | GLN | A | 31 | 38.613 | 16.003 | 21.451 | 1.00 | 40.61 | C |
| OE1 | GLN | A | 31 | 38.690 | 16.219 | 20.241 | 1.00 | 41.07 | O |
| NE2 | GLN | A | 31 | 39.278 | 14.977 | 21.999 | 1.00 | 41.32 | N |
| N | SER | A | 32 | 35.018 | 20.075 | 22.452 | 1.00 | 33.36 | N |
| CA | SER | A | 32 | 34.222 | 21.154 | 21.881 | 1.00 | 32.18 | C |
| C | SER | A | 32 | 34.851 | 21.584 | 20.549 | 1.00 | 32.02 | C |
| O | SER | A | 32 | 36.060 | 21.425 | 20.377 | 1.00 | 32.16 | O |
| CB | SER | A | 32 | 34.092 | 22.344 | 22.816 | 1.00 | 31.37 | C |
| OG | SER | A | 32 | 33.391 | 23.419 | 22.212 | 1.00 | 29.60 | O |
| N | GLY | A | 33 | 34.043 | 22.121 | 19.642 | 1.00 | 30.46 | N |
| CA | GLY | A | 33 | 34.570 | 22.558 | 18.354 | 1.00 | 29.56 | C |
| C | GLY | A | 33 | 34.467 | 24.072 | 18.211 | 1.00 | 28.85 | C |
| O | GLY | A | 33 | 34.791 | 24.628 | 17.163 | 1.00 | 28.54 | O |
| N | ILE | A | 34 | 33.969 | 24.719 | 19.253 | 1.00 | 28.51 | N |
| CA | ILE | A | 34 | 33.770 | 26.156 | 19.246 | 1.00 | 29.03 | C |
| C | ILE | A | 34 | 35.088 | 26.919 | 19.316 | 1.00 | 31.01 | C |
| O | ILE | A | 34 | 36.044 | 26.565 | 20.003 | 1.00 | 31.09 | O |
| CB | ILE | A | 34 | 32.828 | 26.605 | 20.374 | 1.00 | 27.97 | C |
| CG1 | ILE | A | 34 | 31.627 | 25.675 | 20.480 | 1.00 | 27.70 | C |
| CG2 | ILE | A | 34 | 32.375 | 28.046 | 20.158 | 1.00 | 27.56 | C |
| CD1 | ILE | A | 34 | 30.926 | 25.332 | 19.193 | 1.00 | 27.39 | C |
| N | SER | A | 35 | 35.138 | 28.018 | 18.554 | 1.00 | 32.43 | N |
| CA | SER | A | 35 | 36.346 | 28.809 | 18.448 | 1.00 | 33.74 | C |
| C | SER | A | 35 | 36.080 | 30.239 | 18.016 | 1.00 | 33.57 | C |
| O | SER | A | 35 | 34.990 | 30.610 | 17.564 | 1.00 | 33.76 | O |
| CB | SER | A | 35 | 37.304 | 28.154 | 17.427 | 1.00 | 34.84 | C |
| OG | SER | A | 35 | 38.306 | 27.456 | 18.170 | 1.00 | 37.72 | O |
| N | LEU | A | 36 | 37.123 | 31.056 | 18.147 | 1.00 | 33.30 | N |
| CA | LEU | A | 36 | 37.005 | 32.455 | 17.748 | 1.00 | 32.80 | C |
| C | LEU | A | 36 | 37.052 | 32.549 | 16.228 | 1.00 | 32.03 | C |
| O | LEU | A | 36 | 37.848 | 31.904 | 15.555 | 1.00 | 30.53 | O |
| CB | LEU | A | 36 | 38.081 | 33.316 | 18.400 | 1.00 | 33.47 | C |
| CG | LEU | A | 36 | 37.978 | 33.525 | 19.919 | 1.00 | 33.68 | C |
| CD1 | LEU | A | 36 | 39.228 | 34.215 | 20.435 | 1.00 | 34.01 | C |

Figure 2-4

| | | | | | | | | |
|---|---|---|---|---|---|---|---|---|
| CD2 | LEU | A | 36 | 36.741 | 34.337 | 20.280 | 1.00 | 33.48 | C |
| N | ILE | A | 37 | 36.144 | 33.366 | 15.713 | 1.00 | 32.62 | N |
| CA | ILE | A | 37 | 36.052 | 33.595 | 14.266 | 1.00 | 32.27 | C |
| C | ILE | A | 37 | 37.234 | 34.456 | 13.866 | 1.00 | 33.50 | C |
| O | ILE | A | 37 | 37.536 | 35.417 | 14.575 | 1.00 | 34.14 | O |
| CB | ILE | A | 37 | 34.730 | 34.316 | 13.961 | 1.00 | 31.61 | C |
| CG1 | ILE | A | 37 | 33.573 | 33.312 | 13.932 | 1.00 | 30.43 | C |
| CG2 | ILE | A | 37 | 34.812 | 35.106 | 12.666 | 1.00 | 31.81 | C |
| CD1 | ILE | A | 37 | 32.227 | 33.902 | 14.284 | 1.00 | 29.18 | C |
| N | ASP | A | 38 | 37.947 | 34.146 | 12.798 | 1.00 | 36.45 | N |
| CA | ASP | A | 38 | 39.076 | 35.005 | 12.421 | 1.00 | 38.42 | C |
| C | ASP | A | 38 | 39.047 | 35.372 | 10.951 | 1.00 | 38.45 | C |
| O | ASP | A | 38 | 39.881 | 36.176 | 10.520 | 1.00 | 38.84 | O |
| CB | ASP | A | 38 | 40.394 | 34.326 | 12.797 | 1.00 | 40.40 | C |
| CG | ASP | A | 38 | 40.402 | 32.903 | 12.257 | 1.00 | 42.60 | C |
| OD1 | ASP | A | 38 | 40.644 | 32.740 | 11.043 | 1.00 | 43.69 | O |
| OD2 | ASP | A | 38 | 40.106 | 31.982 | 13.045 | 1.00 | 44.53 | O |
| N | HIS | A | 39 | 38.003 | 34.975 | 10.218 | 1.00 | 38.59 | N |
| CA | HIS | A | 39 | 37.926 | 35.284 | 8.792 | 1.00 | 38.54 | C |
| C | HIS | A | 39 | 37.217 | 36.591 | 8.487 | 1.00 | 38.34 | C |
| O | HIS | A | 39 | 37.094 | 36.980 | 7.321 | 1.00 | 38.38 | O |
| CB | HIS | A | 39 | 37.332 | 34.130 | 7.991 | 1.00 | 38.62 | C |
| CG | HIS | A | 39 | 36.023 | 33.615 | 8.480 | 1.00 | 39.30 | C |
| ND1 | HIS | A | 39 | 35.901 | 32.834 | 9.610 | 1.00 | 40.20 | N |
| CD2 | HIS | A | 39 | 34.768 | 33.780 | 7.997 | 1.00 | 39.04 | C |
| CE1 | HIS | A | 39 | 34.625 | 32.533 | 9.798 | 1.00 | 39.85 | C |
| NE2 | HIS | A | 39 | 33.921 | 33.101 | 8.833 | 1.00 | 39.44 | N |
| N | PHE | A | 40 | 36.775 | 37.315 | 9.496 | 1.00 | 38.47 | N |
| CA | PHE | A | 40 | 36.168 | 38.633 | 9.305 | 1.00 | 38.57 | C |
| C | PHE | A | 40 | 36.307 | 39.420 | 10.609 | 1.00 | 39.55 | C |
| O | PHE | A | 40 | 36.427 | 38.804 | 11.671 | 1.00 | 39.71 | O |
| CB | PHE | A | 40 | 34.758 | 38.544 | 8.806 | 1.00 | 37.77 | C |
| CG | PHE | A | 40 | 33.645 | 38.078 | 9.681 | 1.00 | 36.91 | C |
| CD1 | PHE | A | 40 | 33.136 | 36.796 | 9.553 | 1.00 | 36.30 | C |
| CD2 | PHE | A | 40 | 33.023 | 38.931 | 10.582 | 1.00 | 36.50 | C |
| CE1 | PHE | A | 40 | 32.078 | 36.365 | 10.325 | 1.00 | 36.32 | C |
| CE2 | PHE | A | 40 | 31.968 | 38.506 | 11.357 | 1.00 | 36.47 | C |
| CZ | PHE | A | 40 | 31.493 | 37.215 | 11.240 | 1.00 | 36.21 | C |
| N | ASP | A | 41 | 36.441 | 40.735 | 10.523 | 1.00 | 40.59 | N |
| CA | ASP | A | 41 | 36.619 | 41.528 | 11.749 | 1.00 | 42.02 | C |
| C | ASP | A | 41 | 35.370 | 41.430 | 12.610 | 1.00 | 41.11 | C |
| O | ASP | A | 41 | 34.291 | 41.785 | 12.136 | 1.00 | 41.74 | O |
| CB | ASP | A | 41 | 36.952 | 42.972 | 11.390 | 1.00 | 43.80 | C |
| CG | ASP | A | 41 | 37.737 | 43.667 | 12.486 | 1.00 | 45.45 | C |
| OD1 | ASP | A | 41 | 38.750 | 43.090 | 12.935 | 1.00 | 46.51 | O |
| OD2 | ASP | A | 41 | 37.345 | 44.779 | 12.895 | 1.00 | 46.80 | O |
| N | THR | A | 42 | 35.478 | 40.951 | 13.839 | 1.00 | 40.44 | N |
| CA | THR | A | 42 | 34.321 | 40.785 | 14.706 | 1.00 | 40.50 | C |
| C | THR | A | 42 | 34.224 | 41.828 | 15.807 | 1.00 | 40.76 | C |
| O | THR | A | 42 | 33.347 | 41.734 | 16.675 | 1.00 | 40.62 | O |
| CB | THR | A | 42 | 34.295 | 39.379 | 15.352 | 1.00 | 40.02 | C |
| OG1 | THR | A | 42 | 35.528 | 39.130 | 16.028 | 1.00 | 39.27 | O |
| CG2 | THR | A | 42 | 34.100 | 38.290 | 14.308 | 1.00 | 39.67 | C |
| N | SER | A | 43 | 35.051 | 42.859 | 15.744 | 1.00 | 41.65 | N |
| CA | SER | A | 43 | 35.114 | 43.915 | 16.740 | 1.00 | 41.97 | C |
| C | SER | A | 43 | 33.764 | 44.533 | 17.050 | 1.00 | 41.66 | C |
| O | SER | A | 43 | 33.431 | 44.735 | 18.230 | 1.00 | 42.75 | O |
| CB | SER | A | 43 | 36.093 | 45.012 | 16.302 | 1.00 | 42.49 | C |
| OG | SER | A | 43 | 35.789 | 45.413 | 14.971 | 1.00 | 44.87 | O |
| N | ALA | A | 44 | 32.958 | 44.828 | 16.034 | 1.00 | 40.22 | N |
| CA | ALA | A | 44 | 31.642 | 45.406 | 16.288 | 1.00 | 39.07 | C |
| C | ALA | A | 44 | 30.582 | 44.357 | 16.589 | 1.00 | 38.38 | C |
| O | ALA | A | 44 | 29.423 | 44.734 | 16.810 | 1.00 | 39.11 | O |

Figure 2-5

| CB | ALA | A | 44 | 31.208 | 46.211 | 15.064 | 1.00 | 39.04 | C |
|---|---|---|---|---|---|---|---|---|---|
| N | TYR | A | 45 | 30.911 | 43.070 | 16.572 | 1.00 | 36.80 | N |
| CA | TYR | A | 45 | 29.924 | 42.025 | 16.761 | 1.00 | 35.25 | C |
| C | TYR | A | 45 | 29.768 | 41.583 | 18.197 | 1.00 | 34.29 | C |
| O | TYR | A | 45 | 30.735 | 41.526 | 18.958 | 1.00 | 35.60 | O |
| CB | TYR | A | 45 | 30.276 | 40.829 | 15.864 | 1.00 | 35.92 | C |
| CG | TYR | A | 45 | 30.039 | 41.091 | 14.391 | 1.00 | 36.02 | C |
| CD1 | TYR | A | 45 | 30.930 | 41.877 | 13.664 | 1.00 | 36.12 | C |
| CD2 | TYR | A | 45 | 28.944 | 40.551 | 13.727 | 1.00 | 35.78 | C |
| CE1 | TYR | A | 45 | 30.721 | 42.140 | 12.321 | 1.00 | 35.54 | C |
| CE2 | TYR | A | 45 | 28.735 | 40.799 | 12.380 | 1.00 | 35.49 | C |
| CZ | TYR | A | 45 | 29.621 | 41.592 | 11.692 | 1.00 | 35.82 | C |
| OH | TYR | A | 45 | 29.435 | 41.833 | 10.351 | 1.00 | 37.58 | O |
| N | ALA | A | 46 | 28.556 | 41.188 | 18.571 | 1.00 | 32.36 | N |
| CA | ALA | A | 46 | 28.245 | 40.750 | 19.929 | 1.00 | 31.00 | C |
| C | ALA | A | 46 | 28.587 | 39.287 | 20.162 | 1.00 | 30.09 | C |
| O | ALA | A | 46 | 28.536 | 38.763 | 21.281 | 1.00 | 30.77 | O |
| CB | ALA | A | 46 | 26.769 | 41.000 | 20.237 | 1.00 | 29.78 | C |
| N | THR | A | 47 | 28.832 | 38.560 | 19.098 | 1.00 | 29.39 | N |
| CA | THR | A | 47 | 29.274 | 37.171 | 19.162 | 1.00 | 29.14 | C |
| C | THR | A | 47 | 30.518 | 37.099 | 18.273 | 1.00 | 29.84 | C |
| O | THR | A | 47 | 30.500 | 37.554 | 17.120 | 1.00 | 29.99 | O |
| CB | THR | A | 47 | 28.209 | 36.160 | 18.763 | 1.00 | 28.64 | C |
| OG1 | THR | A | 47 | 27.018 | 36.347 | 19.549 | 1.00 | 26.79 | O |
| CG2 | THR | A | 47 | 28.730 | 34.739 | 18.992 | 1.00 | 27.92 | C |
| N | LYS | A | 48 | 31.607 | 36.614 | 18.844 | 1.00 | 30.40 | N |
| CA | LYS | A | 48 | 32.866 | 36.561 | 18.111 | 1.00 | 31.75 | C |
| C | LYS | A | 48 | 33.337 | 35.135 | 17.911 | 1.00 | 31.94 | C |
| O | LYS | A | 48 | 34.499 | 34.911 | 17.538 | 1.00 | 33.23 | O |
| CB | LYS | A | 48 | 33.936 | 37.388 | 18.833 | 1.00 | 33.40 | C |
| CG | LYS | A | 48 | 33.425 | 38.325 | 19.913 | 1.00 | 34.99 | C |
| CD | LYS | A | 48 | 34.435 | 39.384 | 20.296 | 1.00 | 36.14 | C |
| CE | LYS | A | 48 | 34.249 | 40.674 | 19.509 | 1.00 | 36.82 | C |
| NZ | LYS | A | 48 | 33.140 | 41.508 | 20.060 | 1.00 | 37.15 | N |
| N | PHE | A | 49 | 32.433 | 34.182 | 18.140 | 1.00 | 31.02 | N |
| CA | PHE | A | 49 | 32.807 | 32.777 | 18.010 | 1.00 | 30.48 | C |
| C | PHE | A | 49 | 31.747 | 31.913 | 17.344 | 1.00 | 30.81 | C |
| O | PHE | A | 49 | 30.561 | 32.225 | 17.292 | 1.00 | 30.88 | O |
| CB | PHE | A | 49 | 33.110 | 32.226 | 19.413 | 1.00 | 29.09 | C |
| CG | PHE | A | 49 | 31.914 | 32.281 | 20.325 | 1.00 | 28.73 | C |
| CD1 | PHE | A | 49 | 31.032 | 31.225 | 20.409 | 1.00 | 28.37 | C |
| CD2 | PHE | A | 49 | 31.685 | 33.400 | 21.114 | 1.00 | 28.99 | C |
| CE1 | PHE | A | 49 | 29.947 | 31.281 | 21.267 | 1.00 | 29.19 | C |
| CE2 | PHE | A | 49 | 30.593 | 33.466 | 21.957 | 1.00 | 28.39 | C |
| CZ | PHE | A | 49 | 29.720 | 32.401 | 22.041 | 1.00 | 28.17 | C |
| N | ALA | A | 50 | 32.193 | 30.761 | 16.845 | 1.00 | 31.01 | N |
| CA | ALA | A | 50 | 31.329 | 29.803 | 16.187 | 1.00 | 30.91 | C |
| C | ALA | A | 50 | 31.951 | 28.410 | 16.154 | 1.00 | 31.13 | C |
| O | ALA | A | 50 | 33.063 | 28.170 | 16.607 | 1.00 | 31.32 | O |
| CB | ALA | A | 50 | 31.048 | 30.264 | 14.758 | 1.00 | 30.31 | C |
| N | GLY | A | 51 | 31.191 | 27.470 | 15.612 | 1.00 | 31.33 | N |
| CA | GLY | A | 51 | 31.707 | 26.114 | 15.400 | 1.00 | 31.92 | C |
| C | GLY | A | 51 | 32.119 | 26.098 | 13.905 | 1.00 | 32.48 | C |
| O | GLY | A | 51 | 31.249 | 26.054 | 13.042 | 1.00 | 31.41 | O |
| N | LEU | A | 52 | 33.409 | 26.221 | 13.650 | 1.00 | 33.16 | N |
| CA | LEU | A | 52 | 33.924 | 26.250 | 12.289 | 1.00 | 33.73 | C |
| C | LEU | A | 52 | 34.613 | 24.952 | 11.886 | 1.00 | 34.33 | C |
| O | LEU | A | 52 | 35.176 | 24.241 | 12.710 | 1.00 | 34.72 | O |
| CB | LEU | A | 52 | 34.888 | 27.424 | 12.127 | 1.00 | 33.94 | C |
| CG | LEU | A | 52 | 34.364 | 28.806 | 12.525 | 1.00 | 34.26 | C |
| CD1 | LEU | A | 52 | 35.497 | 29.657 | 13.078 | 1.00 | 33.88 | C |
| CD2 | LEU | A | 52 | 33.698 | 29.515 | 11.354 | 1.00 | 33.97 | C |
| N | VAL | A | 53 | 34.539 | 24.625 | 10.602 | 1.00 | 35.38 | N |

Figure 2-6

| | | | | | | | | |
|---|---|---|---|---|---|---|---|---|
| CA | VAL | A | 53 | 35.180 | 23.418 | 10.060 | 1.00 | 36.67 | C |
| C | VAL | A | 53 | 36.657 | 23.748 | 9.883 | 1.00 | 39.49 | C |
| O | VAL | A | 53 | 36.983 | 24.713 | 9.185 | 1.00 | 39.50 | O |
| CB | VAL | A | 53 | 34.492 | 22.991 | 8.765 | 1.00 | 35.64 | C |
| CG1 | VAL | A | 53 | 35.288 | 21.993 | 7.943 | 1.00 | 34.33 | C |
| CG2 | VAL | A | 53 | 33.113 | 22.403 | 9.098 | 1.00 | 34.62 | C |
| N | LYS | A | 54 | 37.535 | 23.040 | 10.588 | 1.00 | 42.77 | N |
| CA | LYS | A | 54 | 38.955 | 23.337 | 10.595 | 1.00 | 46.02 | C |
| C | LYS | A | 54 | 39.807 | 22.528 | 9.634 | 1.00 | 48.60 | C |
| O | LYS | A | 54 | 39.695 | 21.320 | 9.468 | 1.00 | 48.51 | O |
| CB | LYS | A | 54 | 39.498 | 23.184 | 12.031 | 1.00 | 46.00 | C |
| CG | LYS | A | 54 | 38.765 | 24.095 | 13.013 | 1.00 | 46.36 | C |
| CD | LYS | A | 54 | 38.735 | 23.509 | 14.408 | 1.00 | 46.28 | C |
| CE | LYS | A | 54 | 37.330 | 23.395 | 14.954 | 1.00 | 46.49 | C |
| NZ | LYS | A | 54 | 36.792 | 24.669 | 15.488 | 1.00 | 46.54 | N |
| N | ASP | A | 55 | 40.730 | 23.244 | 8.991 | 1.00 | 52.11 | N |
| CA | ASP | A | 55 | 41.654 | 22.694 | 8.012 | 1.00 | 55.06 | C |
| C | ASP | A | 55 | 40.927 | 21.790 | 7.030 | 1.00 | 56.01 | C |
| O | ASP | A | 55 | 41.110 | 20.579 | 6.985 | 1.00 | 56.42 | O |
| CB | ASP | A | 55 | 42.813 | 21.976 | 8.707 | 1.00 | 56.66 | C |
| CG | ASP | A | 55 | 43.718 | 22.953 | 9.441 | 1.00 | 58.45 | C |
| OD1 | ASP | A | 55 | 44.364 | 23.795 | 8.777 | 1.00 | 59.28 | O |
| OD2 | ASP | A | 55 | 43.773 | 22.897 | 10.692 | 1.00 | 59.47 | O |
| N | PHE | A | 56 | 40.060 | 22.409 | 6.230 | 1.00 | 57.29 | N |
| CA | PHE | A | 56 | 39.245 | 21.657 | 5.276 | 1.00 | 58.33 | C |
| C | PHE | A | 56 | 39.919 | 21.613 | 3.915 | 1.00 | 59.60 | C |
| O | PHE | A | 56 | 40.252 | 22.646 | 3.339 | 1.00 | 60.07 | O |
| CB | PHE | A | 56 | 37.845 | 22.257 | 5.201 | 1.00 | 57.68 | C |
| CG | PHE | A | 56 | 37.061 | 21.988 | 3.953 | 1.00 | 56.82 | C |
| CD1 | PHE | A | 56 | 36.509 | 20.746 | 3.707 | 1.00 | 56.49 | C |
| CD2 | PHE | A | 56 | 36.868 | 22.997 | 3.019 | 1.00 | 56.58 | C |
| CE1 | PHE | A | 56 | 35.791 | 20.514 | 2.548 | 1.00 | 56.82 | C |
| CE2 | PHE | A | 56 | 36.143 | 22.774 | 1.868 | 1.00 | 56.36 | C |
| CZ | PHE | A | 56 | 35.602 | 21.526 | 1.630 | 1.00 | 56.45 | C |
| N | ASN | A | 57 | 40.137 | 20.409 | 3.416 | 1.00 | 61.48 | N |
| CA | ASN | A | 57 | 40.716 | 20.206 | 2.094 | 1.00 | 63.34 | C |
| C | ASN | A | 57 | 39.632 | 19.660 | 1.162 | 1.00 | 64.04 | C |
| O | ASN | A | 57 | 38.720 | 18.963 | 1.625 | 1.00 | 64.29 | O |
| CB | ASN | A | 57 | 41.890 | 19.230 | 2.145 | 1.00 | 64.21 | C |
| CG | ASN | A | 57 | 43.104 | 19.746 | 1.398 | 1.00 | 65.21 | C |
| OD1 | ASN | A | 57 | 43.551 | 20.872 | 1.641 | 1.00 | 65.56 | O |
| ND2 | ASN | A | 57 | 43.643 | 18.932 | 0.497 | 1.00 | 65.37 | N |
| N | CYS | A | 58 | 39.697 | 20.028 | -0.111 | 1.00 | 64.22 | N |
| CA | CYS | A | 58 | 38.699 | 19.538 | -1.061 | 1.00 | 64.43 | C |
| C | CYS | A | 58 | 39.324 | 19.389 | -2.440 | 1.00 | 64.92 | C |
| O | CYS | A | 58 | 38.766 | 18.709 | -3.292 | 1.00 | 64.47 | O |
| CB | CYS | A | 58 | 37.460 | 20.414 | -1.089 | 1.00 | 64.20 | C |
| SG | CYS | A | 58 | 37.608 | 22.077 | -1.749 | 1.00 | 63.44 | S |
| N | GLU | A | 59 | 40.546 | 19.874 | -2.582 | 1.00 | 66.16 | N |
| CA | GLU | A | 59 | 41.317 | 19.859 | -3.808 | 1.00 | 67.17 | C |
| C | GLU | A | 59 | 41.375 | 18.503 | -4.492 | 1.00 | 67.32 | C |
| O | GLU | A | 59 | 41.243 | 18.412 | -5.723 | 1.00 | 67.05 | O |
| CB | GLU | A | 59 | 42.735 | 20.381 | -3.532 | 1.00 | 67.79 | C |
| CG | GLU | A | 59 | 43.232 | 21.362 | -4.580 | 1.00 | 69.05 | C |
| CD | GLU | A | 59 | 43.519 | 22.742 | -4.027 | 1.00 | 69.60 | C |
| OE1 | GLU | A | 59 | 44.508 | 23.377 | -4.462 | 1.00 | 70.20 | O |
| OE2 | GLU | A | 59 | 42.755 | 23.220 | -3.164 | 1.00 | 69.62 | O |
| N | ASP | A | 60 | 41.473 | 17.426 | -3.729 | 1.00 | 67.11 | N |
| CA | ASP | A | 60 | 41.451 | 16.077 | -4.254 | 1.00 | 67.51 | C |
| C | ASP | A | 60 | 40.105 | 15.759 | -4.909 | 1.00 | 67.42 | C |
| O | ASP | A | 60 | 40.041 | 15.013 | -5.885 | 1.00 | 67.17 | O |
| CB | ASP | A | 60 | 41.749 | 15.045 | -3.175 | 1.00 | 68.43 | C |
| CG | ASP | A | 60 | 42.080 | 15.567 | -1.798 | 1.00 | 69.14 | C |

Figure 2-7

| OD1 | ASP | A | 60 | 42.745 | 16.618 | -1.651 | 1.00 | 69.37 | O |
|-----|-----|---|----|--------|--------|--------|------|-------|---|
| OD2 | ASP | A | 60 | 41.707 | 14.871 | -0.819 | 1.00 | 69.27 | O |
| N | ILE | A | 61 | 39.022 | 16.292 | -4.357 | 1.00 | 67.60 | N |
| CA | ILE | A | 61 | 37.674 | 16.071 | -4.832 | 1.00 | 67.38 | C |
| C | ILE | A | 61 | 37.180 | 17.149 | -5.787 | 1.00 | 67.54 | C |
| O | ILE | A | 61 | 36.497 | 16.848 | -6.770 | 1.00 | 67.93 | O |
| CB | ILE | A | 61 | 36.667 | 15.988 | -3.664 | 1.00 | 67.40 | C |
| CG1 | ILE | A | 61 | 37.311 | 15.408 | -2.413 | 1.00 | 67.80 | C |
| CG2 | ILE | A | 61 | 35.449 | 15.180 | -4.083 | 1.00 | 67.34 | C |
| CD1 | ILE | A | 61 | 37.777 | 13.973 | -2.513 | 1.00 | 68.03 | C |
| N | ILE | A | 62 | 37.391 | 18.412 | -5.440 | 1.00 | 67.52 | N |
| CA | ILE | A | 62 | 36.982 | 19.529 | -6.274 | 1.00 | 67.98 | C |
| C | ILE | A | 62 | 38.205 | 20.343 | -6.706 | 1.00 | 68.48 | C |
| O | ILE | A | 62 | 38.999 | 20.776 | -5.872 | 1.00 | 68.15 | O |
| CB | ILE | A | 62 | 35.993 | 20.477 | -5.575 | 1.00 | 68.14 | C |
| CG1 | ILE | A | 62 | 34.855 | 19.723 | -4.881 | 1.00 | 67.67 | C |
| CG2 | ILE | A | 62 | 35.412 | 21.476 | -6.575 | 1.00 | 67.87 | C |
| CD1 | ILE | A | 62 | 34.527 | 20.263 | -3.510 | 1.00 | 67.28 | C |
| N | SER | A | 63 | 38.310 | 20.600 | -8.002 | 1.00 | 69.51 | N |
| CA | SER | A | 63 | 39.417 | 21.370 | -8.554 | 1.00 | 70.54 | C |
| C | SER | A | 63 | 39.290 | 22.856 | -8.265 | 1.00 | 70.89 | C |
| O | SER | A | 63 | 38.176 | 23.377 | -8.181 | 1.00 | 71.31 | O |
| CB | SER | A | 63 | 39.443 | 21.182 | -10.081 | 1.00 | 71.01 | C |
| OG | SER | A | 63 | 38.191 | 21.601 | -10.622 | 1.00 | 71.28 | O |
| N | ARG | A | 64 | 40.407 | 23.574 | -8.237 | 1.00 | 71.13 | N |
| CA | ARG | A | 64 | 40.418 | 25.011 | -7.990 | 1.00 | 70.88 | C |
| C | ARG | A | 64 | 39.638 | 25.800 | -9.027 | 1.00 | 69.35 | C |
| O | ARG | A | 64 | 39.069 | 26.861 | -8.737 | 1.00 | 69.23 | O |
| CB | ARG | A | 64 | 41.859 | 25.524 | -7.905 | 1.00 | 72.62 | C |
| CG | ARG | A | 64 | 42.772 | 24.624 | -7.080 | 1.00 | 74.72 | C |
| CD | ARG | A | 64 | 43.816 | 23.964 | -7.969 | 1.00 | 76.13 | C |
| NE | ARG | A | 64 | 44.540 | 22.911 | -7.262 | 1.00 | 77.32 | N |
| CZ | ARG | A | 64 | 45.834 | 22.661 | -7.436 | 1.00 | 78.17 | C |
| NH1 | ARG | A | 64 | 46.546 | 23.383 | -8.294 | 1.00 | 78.63 | N |
| NH2 | ARG | A | 64 | 46.395 | 21.679 | -6.743 | 1.00 | 78.58 | N |
| N | LYS | A | 65 | 39.566 | 25.310 | -10.259 | 1.00 | 67.53 | N |
| CA | LYS | A | 65 | 38.788 | 25.972 | -11.298 | 1.00 | 65.69 | C |
| C | LYS | A | 65 | 37.295 | 25.760 | -11.038 | 1.00 | 63.81 | C |
| O | LYS | A | 65 | 36.479 | 26.601 | -11.405 | 1.00 | 63.43 | O |
| CB | LYS | A | 65 | 39.167 | 25.454 | -12.682 | 1.00 | 66.44 | C |
| CG | LYS | A | 65 | 40.622 | 25.665 | -13.056 | 1.00 | 67.23 | C |
| CD | LYS | A | 65 | 40.858 | 27.006 | -13.722 | 1.00 | 67.48 | C |
| CE | LYS | A | 65 | 41.632 | 26.857 | -15.022 | 1.00 | 67.88 | C |
| NZ | LYS | A | 65 | 41.367 | 27.998 | -15.950 | 1.00 | 67.80 | N |
| N | GLU | A | 66 | 36.945 | 24.645 | -10.402 | 1.00 | 61.40 | N |
| CA | GLU | A | 66 | 35.560 | 24.328 | -10.097 | 1.00 | 59.42 | C |
| C | GLU | A | 66 | 35.121 | 24.864 | -8.741 | 1.00 | 57.68 | C |
| O | GLU | A | 66 | 33.927 | 25.012 | -8.469 | 1.00 | 57.07 | O |
| CB | GLU | A | 66 | 35.341 | 22.812 | -10.174 | 1.00 | 59.70 | C |
| CG | GLU | A | 66 | 35.295 | 22.297 | -11.605 | 1.00 | 60.10 | C |
| CD | GLU | A | 66 | 33.929 | 22.447 | -12.245 | 1.00 | 60.14 | C |
| OE1 | GLU | A | 66 | 33.820 | 23.096 | -13.304 | 1.00 | 59.46 | O |
| OE2 | GLU | A | 66 | 32.952 | 21.907 | -11.682 | 1.00 | 60.54 | O |
| N | GLN | A | 67 | 36.076 | 25.201 | -7.893 | 1.00 | 55.83 | N |
| CA | GLN | A | 67 | 35.842 | 25.754 | -6.574 | 1.00 | 54.78 | C |
| C | GLN | A | 67 | 35.173 | 27.125 | -6.634 | 1.00 | 53.83 | C |
| O | GLN | A | 67 | 34.343 | 27.470 | -5.803 | 1.00 | 53.09 | O |
| CB | GLN | A | 67 | 37.175 | 25.908 | -5.842 | 1.00 | 55.38 | C |
| CG | GLN | A | 67 | 37.455 | 24.916 | -4.738 | 1.00 | 56.07 | C |
| CD | GLN | A | 67 | 38.776 | 25.233 | -4.052 | 1.00 | 56.50 | C |
| OE1 | GLN | A | 67 | 38.931 | 26.290 | -3.447 | 1.00 | 56.45 | O |
| NE2 | GLN | A | 67 | 39.720 | 24.308 | -4.163 | 1.00 | 57.61 | N |
| N | ARG | A | 68 | 35.525 | 27.914 | -7.632 | 1.00 | 53.40 | N |

Figure 2-8

| | | | | | | | | | |
|---|---|---|---|---|---|---|---|---|---|
| CA | ARG | A | 68 | 35.065 | 29.247 | -7.896 | 1.00 | 52.43 | C |
| C | ARG | A | 68 | 33.615 | 29.368 | -8.330 | 1.00 | 49.54 | C |
| O | ARG | A | 68 | 33.100 | 30.491 | -8.400 | 1.00 | 49.30 | O |
| CB | ARG | A | 68 | 35.932 | 29.890 | -9.011 | 1.00 | 55.50 | C |
| CG | ARG | A | 68 | 36.265 | 31.348 | -8.741 | 1.00 | 58.96 | C |
| CD | ARG | A | 68 | 36.100 | 32.210 | -9.982 | 1.00 | 61.92 | C |
| NE | ARG | A | 68 | 35.231 | 33.368 | -9.770 | 1.00 | 64.11 | N |
| CZ | ARG | A | 68 | 35.580 | 34.490 | -9.149 | 1.00 | 64.77 | C |
| NH1 | ARG | A | 68 | 36.802 | 34.633 | -8.651 | 1.00 | 65.05 | N |
| NH2 | ARG | A | 68 | 34.710 | 35.487 | -9.015 | 1.00 | 65.20 | N |
| N | LYS | A | 69 | 32.948 | 28.275 | -8.649 | 1.00 | 45.91 | N |
| CA | LYS | A | 69 | 31.545 | 28.298 | -9.044 | 1.00 | 43.05 | C |
| C | LYS | A | 69 | 30.648 | 27.848 | -7.896 | 1.00 | 40.79 | C |
| O | LYS | A | 69 | 29.514 | 27.405 | -8.079 | 1.00 | 40.97 | O |
| CB | LYS | A | 69 | 31.343 | 27.323 | -10.216 | 1.00 | 42.96 | C |
| CG | LYS | A | 69 | 32.404 | 27.462 | -11.299 | 1.00 | 43.11 | C |
| CD | LYS | A | 69 | 32.480 | 26.204 | -12.151 | 1.00 | 42.58 | C |
| CE | LYS | A | 69 | 31.895 | 26.456 | -13.532 | 1.00 | 42.02 | C |
| NZ | LYS | A | 69 | 32.812 | 25.970 | -14.605 | 1.00 | 41.64 | N |
| N | MET | A | 70 | 31.191 | 27.869 | -6.687 | 1.00 | 37.50 | N |
| CA | MET | A | 70 | 30.633 | 27.175 | -5.555 | 1.00 | 34.98 | C |
| C | MET | A | 70 | 30.758 | 27.902 | -4.223 | 1.00 | 32.38 | C |
| O | MET | A | 70 | 31.871 | 28.210 | -3.798 | 1.00 | 32.03 | O |
| CB | MET | A | 70 | 31.425 | 25.864 | -5.366 | 1.00 | 35.08 | C |
| CG | MET | A | 70 | 30.888 | 24.645 | -6.066 | 1.00 | 35.01 | C |
| SD | MET | A | 70 | 31.957 | 23.217 | -5.694 | 1.00 | 35.60 | S |
| CE | MET | A | 70 | 31.632 | 22.233 | -7.165 | 1.00 | 35.07 | C |
| N | ASP | A | 71 | 29.633 | 28.071 | -3.536 | 1.00 | 29.01 | N |
| CA | ASP | A | 71 | 29.750 | 28.647 | -2.186 | 1.00 | 27.17 | C |
| C | ASP | A | 71 | 30.244 | 27.526 | -1.274 | 1.00 | 26.77 | C |
| O | ASP | A | 71 | 30.018 | 26.329 | -1.542 | 1.00 | 26.15 | O |
| CB | ASP | A | 71 | 28.432 | 29.242 | -1.766 | 1.00 | 26.38 | C |
| CG | ASP | A | 71 | 28.364 | 29.693 | -0.330 | 1.00 | 26.16 | C |
| OD1 | ASP | A | 71 | 28.165 | 28.817 | 0.549 | 1.00 | 26.10 | O |
| OD2 | ASP | A | 71 | 28.481 | 30.909 | -0.081 | 1.00 | 25.93 | O |
| N | ALA | A | 72 | 30.909 | 27.882 | -0.180 | 1.00 | 25.21 | N |
| CA | ALA | A | 72 | 31.419 | 26.919 | 0.780 | 1.00 | 23.86 | C |
| C | ALA | A | 72 | 30.381 | 25.913 | 1.237 | 1.00 | 23.27 | C |
| O | ALA | A | 72 | 30.727 | 24.742 | 1.469 | 1.00 | 23.23 | O |
| CB | ALA | A | 72 | 32.018 | 27.654 | 1.980 | 1.00 | 24.17 | C |
| N | PHE | A | 73 | 29.111 | 26.282 | 1.386 | 1.00 | 22.52 | N |
| CA | PHE | A | 73 | 28.109 | 25.289 | 1.788 | 1.00 | 22.41 | C |
| C | PHE | A | 73 | 28.012 | 24.159 | 0.777 | 1.00 | 23.21 | C |
| O | PHE | A | 73 | 27.924 | 22.992 | 1.186 | 1.00 | 24.39 | O |
| CB | PHE | A | 73 | 26.774 | 25.940 | 2.069 | 1.00 | 21.58 | C |
| CG | PHE | A | 73 | 25.743 | 25.898 | 0.995 | 1.00 | 20.70 | C |
| CD1 | PHE | A | 73 | 24.736 | 24.944 | 1.023 | 1.00 | 20.86 | C |
| CD2 | PHE | A | 73 | 25.785 | 26.798 | -0.053 | 1.00 | 20.41 | C |
| CE1 | PHE | A | 73 | 23.781 | 24.891 | 0.026 | 1.00 | 21.03 | C |
| CE2 | PHE | A | 73 | 24.823 | 26.765 | -1.046 | 1.00 | 20.99 | C |
| CZ | PHE | A | 73 | 23.822 | 25.810 | -1.008 | 1.00 | 20.90 | C |
| N | ILE | A | 74 | 28.066 | 24.445 | -0.515 | 1.00 | 23.43 | N |
| CA | ILE | A | 74 | 28.063 | 23.404 | -1.537 | 1.00 | 24.79 | C |
| C | ILE | A | 74 | 29.339 | 22.570 | -1.443 | 1.00 | 25.35 | C |
| O | ILE | A | 74 | 29.338 | 21.345 | -1.565 | 1.00 | 25.40 | O |
| CB | ILE | A | 74 | 27.946 | 24.049 | -2.933 | 1.00 | 25.11 | C |
| CG1 | ILE | A | 74 | 26.533 | 24.620 | -3.124 | 1.00 | 23.99 | C |
| CG2 | ILE | A | 74 | 28.280 | 23.077 | -4.053 | 1.00 | 24.54 | C |
| CD1 | ILE | A | 74 | 26.463 | 25.656 | -4.221 | 1.00 | 23.46 | C |
| N | GLN | A | 75 | 30.468 | 23.238 | -1.217 | 1.00 | 25.23 | N |
| CA | GLN | A | 75 | 31.747 | 22.553 | -1.090 | 1.00 | 26.02 | C |
| C | GLN | A | 75 | 31.699 | 21.484 | -0.008 | 1.00 | 25.95 | C |
| O | GLN | A | 75 | 32.145 | 20.358 | -0.216 | 1.00 | 26.78 | O |

Figure 2-9

| | | | | | | | | |
|---|---|---|---|---|---|---|---|---|
| CB | GLN | A | 75 | 32.871 | 23.546 | -0.806 | 1.00 | 26.42 | C |
| CG | GLN | A | 75 | 33.332 | 24.282 | -2.062 | 1.00 | 28.06 | C |
| CD | GLN | A | 75 | 34.302 | 25.389 | -1.689 | 1.00 | 29.61 | C |
| OE1 | GLN | A | 75 | 35.078 | 25.201 | -0.737 | 1.00 | 31.73 | O |
| NE2 | GLN | A | 75 | 34.262 | 26.508 | -2.390 | 1.00 | 28.55 | N |
| N | TYR | A | 76 | 31.183 | 21.843 | 1.155 | 1.00 | 25.75 | N |
| CA | TYR | A | 76 | 31.012 | 20.945 | 2.284 | 1.00 | 24.59 | C |
| C | TYR | A | 76 | 30.091 | 19.783 | 1.905 | 1.00 | 25.40 | C |
| O | TYR | A | 76 | 30.453 | 18.620 | 2.090 | 1.00 | 26.52 | O |
| CB | TYR | A | 76 | 30.418 | 21.710 | 3.456 | 1.00 | 23.32 | C |
| CG | TYR | A | 76 | 31.291 | 22.727 | 4.146 | 1.00 | 23.16 | C |
| CD1 | TYR | A | 76 | 30.789 | 23.430 | 5.249 | 1.00 | 22.41 | C |
| CD2 | TYR | A | 76 | 32.593 | 23.002 | 3.755 | 1.00 | 22.62 | C |
| CE1 | TYR | A | 76 | 31.549 | 24.362 | 5.915 | 1.00 | 22.33 | C |
| CE2 | TYR | A | 76 | 33.366 | 23.944 | 4.395 | 1.00 | 21.92 | C |
| CZ | TYR | A | 76 | 32.842 | 24.622 | 5.477 | 1.00 | 23.20 | C |
| OH | TYR | A | 76 | 33.608 | 25.548 | 6.155 | 1.00 | 22.62 | O |
| N | GLY | A | 77 | 28.927 | 20.091 | 1.335 | 1.00 | 24.29 | N |
| CA | GLY | A | 77 | 27.960 | 19.090 | 0.948 | 1.00 | 23.68 | C |
| C | GLY | A | 77 | 28.532 | 18.017 | 0.040 | 1.00 | 24.17 | C |
| O | GLY | A | 77 | 28.286 | 16.831 | 0.258 | 1.00 | 24.09 | O |
| N | ILE | A | 78 | 29.208 | 18.420 | -1.031 | 1.00 | 24.69 | N |
| CA | ILE | A | 78 | 29.852 | 17.512 | -1.963 | 1.00 | 24.28 | C |
| C | ILE | A | 78 | 30.854 | 16.603 | -1.263 | 1.00 | 24.34 | C |
| O | ILE | A | 78 | 30.693 | 15.382 | -1.276 | 1.00 | 24.29 | O |
| CB | ILE | A | 78 | 30.586 | 18.300 | -3.074 | 1.00 | 24.14 | C |
| CG1 | ILE | A | 78 | 29.568 | 19.116 | -3.859 | 1.00 | 24.40 | C |
| CG2 | ILE | A | 78 | 31.358 | 17.347 | -3.975 | 1.00 | 24.03 | C |
| CD1 | ILE | A | 78 | 30.086 | 19.834 | -5.084 | 1.00 | 24.19 | C |
| N | VAL | A | 79 | 31.854 | 17.194 | -0.603 | 1.00 | 23.70 | N |
| CA | VAL | A | 79 | 32.878 | 16.422 | 0.095 | 1.00 | 23.40 | C |
| C | VAL | A | 79 | 32.243 | 15.394 | 1.017 | 1.00 | 24.44 | C |
| O | VAL | A | 79 | 32.638 | 14.232 | 0.981 | 1.00 | 25.15 | O |
| CB | VAL | A | 79 | 33.858 | 17.307 | 0.874 | 1.00 | 23.00 | C |
| CG1 | VAL | A | 79 | 34.656 | 16.524 | 1.907 | 1.00 | 22.25 | C |
| CG2 | VAL | A | 79 | 34.830 | 18.006 | -0.077 | 1.00 | 22.73 | C |
| N | ALA | A | 80 | 31.258 | 15.787 | 1.820 | 1.00 | 25.12 | N |
| CA | ALA | A | 80 | 30.575 | 14.849 | 2.700 | 1.00 | 25.90 | C |
| C | ALA | A | 80 | 29.765 | 13.840 | 1.895 | 1.00 | 27.36 | C |
| O | ALA | A | 80 | 29.609 | 12.695 | 2.314 | 1.00 | 28.42 | O |
| CB | ALA | A | 80 | 29.689 | 15.571 | 3.690 | 1.00 | 24.87 | C |
| N | GLY | A | 81 | 29.235 | 14.245 | 0.749 | 1.00 | 28.62 | N |
| CA | GLY | A | 81 | 28.466 | 13.337 | -0.097 | 1.00 | 30.56 | C |
| C | GLY | A | 81 | 29.379 | 12.247 | -0.652 | 1.00 | 32.31 | C |
| O | GLY | A | 81 | 29.048 | 11.061 | -0.608 | 1.00 | 32.11 | O |
| N | VAL | A | 82 | 30.556 | 12.667 | -1.132 | 1.00 | 32.99 | N |
| CA | VAL | A | 82 | 31.535 | 11.714 | -1.646 | 1.00 | 33.88 | C |
| C | VAL | A | 82 | 31.827 | 10.661 | -0.586 | 1.00 | 35.83 | C |
| O | VAL | A | 82 | 31.598 | 9.465 | -0.785 | 1.00 | 37.36 | O |
| CB | VAL | A | 82 | 32.826 | 12.415 | -2.082 | 1.00 | 33.65 | C |
| CG1 | VAL | A | 82 | 33.943 | 11.418 | -2.341 | 1.00 | 32.35 | C |
| CG2 | VAL | A | 82 | 32.578 | 13.263 | -3.334 | 1.00 | 33.37 | C |
| N | GLN | A | 83 | 32.170 | 11.110 | 0.617 | 1.00 | 36.36 | N |
| CA | GLN | A | 83 | 32.387 | 10.238 | 1.757 | 1.00 | 36.77 | C |
| C | GLN | A | 83 | 31.271 | 9.199 | 1.851 | 1.00 | 36.63 | C |
| O | GLN | A | 83 | 31.534 | 8.003 | 1.903 | 1.00 | 37.55 | O |
| CB | GLN | A | 83 | 32.437 | 11.041 | 3.056 | 1.00 | 36.97 | C |
| CG | GLN | A | 83 | 33.765 | 11.611 | 3.489 | 1.00 | 36.84 | C |
| CD | GLN | A | 83 | 33.698 | 12.194 | 4.888 | 1.00 | 38.07 | C |
| OE1 | GLN | A | 83 | 33.123 | 11.581 | 5.796 | 1.00 | 39.74 | O |
| NE2 | GLN | A | 83 | 34.247 | 13.375 | 5.119 | 1.00 | 37.60 | N |
| N | ALA | A | 84 | 30.028 | 9.661 | 1.864 | 1.00 | 36.63 | N |
| CA | ALA | A | 84 | 28.872 | 8.782 | 1.983 | 1.00 | 36.65 | C |

Figure 2-10

| C | ALA | A | 84 | 28.805 | 7.776 | 0.849 | 1.00 | 36.36 | C |
|---|---|---|---|---|---|---|---|---|---|
| O | ALA | A | 84 | 28.499 | 6.613 | 1.097 | 1.00 | 35.48 | O |
| CB | ALA | A | 84 | 27.592 | 9.595 | 2.089 | 1.00 | 36.13 | C |
| N | MET | A | 85 | 29.116 | 8.196 | -0.367 | 1.00 | 37.76 | N |
| CA | MET | A | 85 | 29.111 | 7.287 | -1.508 | 1.00 | 39.69 | C |
| C | MET | A | 85 | 30.223 | 6.257 | -1.367 | 1.00 | 41.00 | C |
| O | MET | A | 85 | 30.009 | 5.060 | -1.568 | 1.00 | 41.42 | O |
| CB | MET | A | 85 | 29.264 | 8.053 | -2.820 | 1.00 | 40.12 | C |
| CG | MET | A | 85 | 28.061 | 8.945 | -3.132 | 1.00 | 40.96 | C |
| SD | MET | A | 85 | 26.538 | 8.001 | -3.315 | 1.00 | 41.36 | S |
| CE | MET | A | 85 | 26.973 | 6.931 | -4.683 | 1.00 | 40.65 | C |
| N | GLN | A | 86 | 31.410 | 6.738 | -0.992 | 1.00 | 42.08 | N |
| CA | GLN | A | 86 | 32.553 | 5.840 | -0.817 | 1.00 | 42.74 | C |
| C | GLN | A | 86 | 32.252 | 4.822 | 0.259 | 1.00 | 42.97 | C |
| O | GLN | A | 86 | 32.169 | 3.616 | -0.027 | 1.00 | 43.31 | O |
| CB | GLN | A | 86 | 33.823 | 6.663 | -0.577 | 1.00 | 43.27 | C |
| CG | GLN | A | 86 | 34.312 | 7.257 | -1.888 | 1.00 | 44.50 | C |
| CD | GLN | A | 86 | 35.480 | 8.188 | -1.859 | 1.00 | 45.31 | C |
| OE1 | GLN | A | 86 | 35.978 | 8.671 | -0.844 | 1.00 | 45.76 | O |
| NE2 | GLN | A | 86 | 35.975 | 8.516 | -3.067 | 1.00 | 45.96 | N |
| N | ASP | A | 87 | 31.763 | 5.277 | 1.408 | 1.00 | 43.03 | N |
| CA | ASP | A | 87 | 31.337 | 4.384 | 2.470 | 1.00 | 44.15 | C |
| C | ASP | A | 87 | 30.274 | 3.396 | 2.008 | 1.00 | 45.71 | C |
| O | ASP | A | 87 | 30.250 | 2.245 | 2.453 | 1.00 | 46.35 | O |
| CB | ASP | A | 87 | 30.802 | 5.186 | 3.661 | 1.00 | 43.42 | C |
| CG | ASP | A | 87 | 30.677 | 4.330 | 4.904 | 1.00 | 43.34 | C |
| OD1 | ASP | A | 87 | 31.598 | 3.517 | 5.157 | 1.00 | 44.06 | O |
| OD2 | ASP | A | 87 | 29.677 | 4.458 | 5.632 | 1.00 | 42.70 | O |
| N | SER | A | 88 | 29.370 | 3.825 | 1.135 | 1.00 | 47.04 | N |
| CA | SER | A | 88 | 28.293 | 2.977 | 0.654 | 1.00 | 48.12 | C |
| C | SER | A | 88 | 28.814 | 1.828 | -0.197 | 1.00 | 49.19 | C |
| O | SER | A | 88 | 28.259 | 0.731 | -0.169 | 1.00 | 48.51 | O |
| CB | SER | A | 88 | 27.281 | 3.803 | -0.145 | 1.00 | 47.96 | C |
| OG | SER | A | 88 | 27.686 | 3.947 | -1.492 | 1.00 | 47.71 | O |
| N | GLY | A | 89 | 29.809 | 2.112 | -1.033 | 1.00 | 50.61 | N |
| CA | GLY | A | 89 | 30.381 | 1.147 | -1.945 | 1.00 | 52.39 | C |
| C | GLY | A | 89 | 29.514 | 0.870 | -3.164 | 1.00 | 54.05 | C |
| O | GLY | A | 89 | 29.776 | -0.068 | -3.925 | 1.00 | 54.48 | O |
| N | LEU | A | 90 | 28.453 | 1.639 | -3.374 | 1.00 | 55.16 | N |
| CA | LEU | A | 90 | 27.568 | 1.451 | -4.506 | 1.00 | 56.38 | C |
| C | LEU | A | 90 | 28.365 | 1.603 | -5.807 | 1.00 | 57.19 | C |
| O | LEU | A | 90 | 29.179 | 2.512 | -5.927 | 1.00 | 56.97 | O |
| CB | LEU | A | 90 | 26.450 | 2.479 | -4.548 | 1.00 | 56.95 | C |
| CG | LEU | A | 90 | 25.064 | 2.193 | -4.018 | 1.00 | 57.07 | C |
| CD1 | LEU | A | 90 | 24.119 | 3.328 | -4.430 | 1.00 | 56.91 | C |
| CD2 | LEU | A | 90 | 24.503 | 0.865 | -4.490 | 1.00 | 57.14 | C |
| N | GLU | A | 91 | 28.000 | 0.803 | -6.797 | 1.00 | 58.89 | N |
| CA | GLU | A | 91 | 28.532 | 1.023 | -8.143 | 1.00 | 60.44 | C |
| C | GLU | A | 91 | 27.379 | 1.498 | -9.027 | 1.00 | 60.53 | C |
| O | GLU | A | 91 | 26.318 | 0.874 | -9.032 | 1.00 | 59.77 | O |
| CB | GLU | A | 91 | 29.199 | -0.223 | -8.703 | 1.00 | 61.56 | C |
| CG | GLU | A | 91 | 30.719 | -0.181 | -8.594 | 1.00 | 63.08 | C |
| CD | GLU | A | 91 | 31.404 | -1.257 | -9.414 | 1.00 | 64.10 | C |
| OE1 | GLU | A | 91 | 31.231 | -1.261 | -10.655 | 1.00 | 64.05 | O |
| OE2 | GLU | A | 91 | 32.116 | -2.091 | -8.804 | 1.00 | 64.55 | O |
| N | ILE | A | 92 | 27.572 | 2.650 | -9.658 | 1.00 | 61.08 | N |
| CA | ILE | A | 92 | 26.507 | 3.184 | -10.517 | 1.00 | 61.83 | C |
| C | ILE | A | 92 | 26.734 | 2.696 | -11.938 | 1.00 | 62.69 | C |
| O | ILE | A | 92 | 27.835 | 2.776 | -12.482 | 1.00 | 63.13 | O |
| CB | ILE | A | 92 | 26.414 | 4.708 | -10.424 | 1.00 | 61.36 | C |
| CG1 | ILE | A | 92 | 25.864 | 5.103 | -9.040 | 1.00 | 60.82 | C |
| CG2 | ILE | A | 92 | 25.538 | 5.304 | -11.508 | 1.00 | 61.19 | C |
| CD1 | ILE | A | 92 | 26.892 | 5.752 | -8.144 | 1.00 | 60.43 | C |

Figure 2-11

| | | | | | | | | |
|---|---|---|---|---|---|---|---|---|
| N | THR | A | 93 | 25.717 | 2.047 | -12.489 | 1.00 | 63.87 | N |
| CA | THR | A | 93 | 25.781 | 1.551 | -13.860 | 1.00 | 65.29 | C |
| C | THR | A | 93 | 24.654 | 2.175 | -14.672 | 1.00 | 66.26 | C |
| O | THR | A | 93 | 23.741 | 2.769 | -14.099 | 1.00 | 66.46 | O |
| CB | THR | A | 93 | 25.634 | 0.023 | -13.923 | 1.00 | 65.14 | C |
| OG1 | THR | A | 93 | 24.503 | -0.374 | -13.130 | 1.00 | 65.30 | O |
| CG2 | THR | A | 93 | 26.882 | -0.667 | -13.413 | 1.00 | 65.19 | C |
| N | GLU | A | 94 | 24.678 | 2.020 | -15.992 | 1.00 | 67.78 | N |
| CA | GLU | A | 94 | 23.619 | 2.572 | -16.839 | 1.00 | 68.67 | C |
| C | GLU | A | 94 | 22.280 | 1.938 | -16.473 | 1.00 | 68.05 | C |
| O | GLU | A | 94 | 21.220 | 2.554 | -16.551 | 1.00 | 67.97 | O |
| CB | GLU | A | 94 | 23.929 | 2.362 | -18.315 | 1.00 | 70.29 | C |
| CG | GLU | A | 94 | 22.964 | 3.053 | -19.266 | 1.00 | 72.04 | C |
| CD | GLU | A | 94 | 23.583 | 4.206 | -20.025 | 1.00 | 73.06 | C |
| OE1 | GLU | A | 94 | 22.821 | 5.037 | -20.570 | 1.00 | 73.57 | O |
| OE2 | GLU | A | 94 | 24.827 | 4.302 | -20.098 | 1.00 | 73.83 | O |
| N | GLU | A | 95 | 22.325 | 0.700 | -15.999 | 1.00 | 67.33 | N |
| CA | GLU | A | 95 | 21.188 | -0.051 | -15.531 | 1.00 | 66.97 | C |
| C | GLU | A | 95 | 20.796 | 0.344 | -14.109 | 1.00 | 64.95 | C |
| O | GLU | A | 95 | 19.856 | -0.224 | -13.548 | 1.00 | 65.38 | O |
| CB | GLU | A | 95 | 21.506 | -1.555 | -15.548 | 1.00 | 69.25 | C |
| CG | GLU | A | 95 | 21.836 | -2.102 | -16.930 | 1.00 | 71.96 | C |
| CD | GLU | A | 95 | 22.091 | -3.597 | -16.938 | 1.00 | 73.58 | C |
| OE1 | GLU | A | 95 | 22.000 | -4.233 | -15.861 | 1.00 | 74.24 | O |
| OE2 | GLU | A | 95 | 22.396 | -4.174 | -18.011 | 1.00 | 74.44 | O |
| N | ASN | A | 96 | 21.515 | 1.286 | -13.522 | 1.00 | 61.76 | N |
| CA | ASN | A | 96 | 21.332 | 1.731 | -12.162 | 1.00 | 58.00 | C |
| C | ASN | A | 96 | 20.938 | 3.195 | -12.036 | 1.00 | 55.15 | C |
| O | ASN | A | 96 | 20.028 | 3.537 | -11.278 | 1.00 | 54.98 | O |
| CB | ASN | A | 96 | 22.673 | 1.537 | -11.409 | 1.00 | 57.96 | C |
| CG | ASN | A | 96 | 22.424 | 1.041 | -10.004 | 1.00 | 58.40 | C |
| OD1 | ASN | A | 96 | 21.416 | 0.373 | -9.766 | 1.00 | 59.02 | O |
| ND2 | ASN | A | 96 | 23.319 | 1.367 | -9.087 | 1.00 | 58.61 | N |
| N | ALA | A | 97 | 21.635 | 4.072 | -12.739 | 1.00 | 51.18 | N |
| CA | ALA | A | 97 | 21.488 | 5.508 | -12.680 | 1.00 | 47.79 | C |
| C | ALA | A | 97 | 20.095 | 6.010 | -12.346 | 1.00 | 45.31 | C |
| O | ALA | A | 97 | 19.902 | 6.772 | -11.399 | 1.00 | 45.01 | O |
| CB | ALA | A | 97 | 21.961 | 6.128 | -13.996 | 1.00 | 47.88 | C |
| N | THR | A | 98 | 19.100 | 5.621 | -13.091 | 1.00 | 42.91 | N |
| CA | THR | A | 98 | 17.699 | 5.931 | -13.000 | 1.00 | 40.62 | C |
| C | THR | A | 98 | 17.037 | 5.703 | -11.661 | 1.00 | 39.36 | C |
| O | THR | A | 98 | 16.042 | 6.378 | -11.339 | 1.00 | 38.34 | O |
| CB | THR | A | 98 | 17.005 | 5.048 | -14.090 | 1.00 | 40.57 | C |
| OG1 | THR | A | 98 | 17.234 | 5.712 | -15.349 | 1.00 | 41.06 | O |
| CG2 | THR | A | 98 | 15.543 | 4.807 | -13.860 | 1.00 | 39.73 | C |
| N | ARG | A | 99 | 17.519 | 4.763 | -10.855 | 1.00 | 38.10 | N |
| CA | ARG | A | 99 | 16.920 | 4.456 | -9.569 | 1.00 | 37.30 | C |
| C | ARG | A | 99 | 17.598 | 5.091 | -8.368 | 1.00 | 36.58 | C |
| O | ARG | A | 99 | 17.145 | 4.876 | -7.234 | 1.00 | 36.97 | O |
| CB | ARG | A | 99 | 16.875 | 2.928 | -9.394 | 1.00 | 37.24 | C |
| CG | ARG | A | 99 | 16.088 | 2.202 | -10.470 | 1.00 | 37.24 | C |
| CD | ARG | A | 99 | 14.607 | 2.503 | -10.421 | 1.00 | 37.11 | C |
| NE | ARG | A | 99 | 13.916 | 1.972 | -9.256 | 1.00 | 37.06 | N |
| CZ | ARG | A | 99 | 12.751 | 2.448 | -8.809 | 1.00 | 37.39 | C |
| NH1 | ARG | A | 99 | 12.158 | 3.460 | -9.430 | 1.00 | 36.88 | N |
| NH2 | ARG | A | 99 | 12.152 | 1.939 | -7.737 | 1.00 | 37.54 | N |
| N | ILE | A | 100 | 18.679 | 5.822 | -8.561 | 1.00 | 35.14 | N |
| CA | ILE | A | 100 | 19.406 | 6.480 | -7.488 | 1.00 | 34.64 | C |
| C | ILE | A | 100 | 19.191 | 7.990 | -7.556 | 1.00 | 34.51 | C |
| O | ILE | A | 100 | 19.417 | 8.578 | -8.618 | 1.00 | 34.55 | O |
| CB | ILE | A | 100 | 20.922 | 6.224 | -7.582 | 1.00 | 34.85 | C |
| CG1 | ILE | A | 100 | 21.234 | 4.747 | -7.853 | 1.00 | 34.72 | C |
| CG2 | ILE | A | 100 | 21.624 | 6.691 | -6.318 | 1.00 | 34.69 | C |

Figure 2-12

| | | | | | | | | | |
|---|---|---|---|---|---|---|---|---|---|
| CD1 | ILE | A | 100 | 22.465 | 4.568 | -8.720 | 1.00 | 34.52 | C |
| N | GLY | A | 101 | 18.781 | 8.612 | -6.457 | 1.00 | 34.35 | N |
| CA | GLY | A | 101 | 18.555 | 10.059 | -6.465 | 1.00 | 33.77 | C |
| C | GLY | A | 101 | 19.240 | 10.769 | -5.308 | 1.00 | 33.33 | C |
| O | GLY | A | 101 | 20.126 | 10.214 | -4.654 | 1.00 | 33.58 | O |
| N | ALA | A | 102 | 18.803 | 11.995 | -5.024 | 1.00 | 32.06 | N |
| CA | ALA | A | 102 | 19.383 | 12.798 | -3.953 | 1.00 | 30.82 | C |
| C | ALA | A | 102 | 18.332 | 13.668 | -3.284 | 1.00 | 29.70 | C |
| O | ALA | A | 102 | 17.363 | 14.086 | -3.909 | 1.00 | 31.01 | O |
| CB | ALA | A | 102 | 20.516 | 13.678 | -4.479 | 1.00 | 30.53 | C |
| N | ALA | A | 103 | 18.512 | 13.933 | -1.999 | 1.00 | 28.03 | N |
| CA | ALA | A | 103 | 17.575 | 14.753 | -1.230 | 1.00 | 25.22 | C |
| C | ALA | A | 103 | 18.363 | 15.540 | -0.184 | 1.00 | 23.85 | C |
| O | ALA | A | 103 | 18.559 | 15.134 | 0.952 | 1.00 | 23.10 | O |
| CB | ALA | A | 103 | 16.497 | 13.910 | -0.595 | 1.00 | 24.51 | C |
| N | ILE | A | 104 | 19.019 | 16.587 | -0.671 | 1.00 | 23.05 | N |
| CA | ILE | A | 104 | 19.908 | 17.401 | 0.135 | 1.00 | 22.38 | C |
| C | ILE | A | 104 | 19.394 | 18.834 | 0.207 | 1.00 | 22.22 | C |
| O | ILE | A | 104 | 19.072 | 19.399 | -0.839 | 1.00 | 22.93 | O |
| CB | ILE | A | 104 | 21.327 | 17.415 | -0.478 | 1.00 | 21.90 | C |
| CG1 | ILE | A | 104 | 21.877 | 15.989 | -0.520 | 1.00 | 21.01 | C |
| CG2 | ILE | A | 104 | 22.239 | 18.354 | 0.291 | 1.00 | 21.57 | C |
| CD1 | ILE | A | 104 | 22.977 | 15.754 | -1.509 | 1.00 | 19.64 | C |
| N | GLY | A | 105 | 19.352 | 19.406 | 1.402 | 1.00 | 21.16 | N |
| CA | GLY | A | 105 | 18.934 | 20.783 | 1.569 | 1.00 | 20.18 | C |
| C | GLY | A | 105 | 19.941 | 21.613 | 2.354 | 1.00 | 19.37 | C |
| O | GLY | A | 105 | 21.043 | 21.222 | 2.690 | 1.00 | 19.81 | O |
| N | SER | A | 106 | 19.528 | 22.815 | 2.693 | 1.00 | 19.13 | N |
| CA | SER | A | 106 | 20.275 | 23.799 | 3.448 | 1.00 | 18.03 | C |
| C | SER | A | 106 | 19.252 | 24.795 | 4.004 | 1.00 | 19.00 | C |
| O | SER | A | 106 | 18.175 | 24.921 | 3.419 | 1.00 | 19.81 | O |
| CB | SER | A | 106 | 21.271 | 24.488 | 2.526 | 1.00 | 17.16 | C |
| OG | SER | A | 106 | 22.092 | 25.439 | 3.156 | 1.00 | 15.90 | O |
| N | GLY | A | 107 | 19.547 | 25.475 | 5.095 | 1.00 | 19.19 | N |
| CA | GLY | A | 107 | 18.639 | 26.453 | 5.655 | 1.00 | 18.05 | C |
| C | GLY | A | 107 | 18.625 | 27.702 | 4.781 | 1.00 | 18.77 | C |
| O | GLY | A | 107 | 17.531 | 28.123 | 4.418 | 1.00 | 18.68 | O |
| N | ILE | A | 108 | 19.781 | 28.295 | 4.496 | 1.00 | 19.98 | N |
| CA | ILE | A | 108 | 19.854 | 29.517 | 3.697 | 1.00 | 21.92 | C |
| C | ILE | A | 108 | 20.795 | 29.409 | 2.502 | 1.00 | 22.33 | C |
| O | ILE | A | 108 | 20.837 | 30.295 | 1.645 | 1.00 | 22.50 | O |
| CB | ILE | A | 108 | 20.293 | 30.744 | 4.526 | 1.00 | 22.68 | C |
| CG1 | ILE | A | 108 | 19.999 | 32.067 | 3.812 | 1.00 | 22.56 | C |
| CG2 | ILE | A | 108 | 21.790 | 30.677 | 4.834 | 1.00 | 22.23 | C |
| CD1 | ILE | A | 108 | 18.740 | 32.773 | 4.209 | 1.00 | 22.91 | C |
| N | GLY | A | 109 | 21.596 | 28.356 | 2.417 | 1.00 | 23.23 | N |
| CA | GLY | A | 109 | 22.490 | 28.191 | 1.282 | 1.00 | 22.77 | C |
| C | GLY | A | 109 | 23.618 | 29.206 | 1.299 | 1.00 | 23.95 | C |
| O | GLY | A | 109 | 24.325 | 29.369 | 2.302 | 1.00 | 24.99 | O |
| N | GLY | A | 110 | 23.968 | 29.728 | 0.119 | 1.00 | 22.53 | N |
| CA | GLY | A | 110 | 25.186 | 30.444 | -0.086 | 1.00 | 21.57 | C |
| C | GLY | A | 110 | 25.295 | 31.872 | 0.353 | 1.00 | 21.34 | C |
| O | GLY | A | 110 | 25.779 | 32.717 | -0.426 | 1.00 | 20.36 | O |
| N | LEU | A | 111 | 25.141 | 32.142 | 1.646 | 1.00 | 21.33 | N |
| CA | LEU | A | 111 | 25.285 | 33.486 | 2.183 | 1.00 | 21.06 | C |
| C | LEU | A | 111 | 26.612 | 34.144 | 1.839 | 1.00 | 19.97 | C |
| O | LEU | A | 111 | 26.655 | 35.343 | 1.573 | 1.00 | 19.87 | O |
| CB | LEU | A | 111 | 25.107 | 33.458 | 3.709 | 1.00 | 21.38 | C |
| CG | LEU | A | 111 | 23.849 | 34.136 | 4.252 | 1.00 | 21.04 | C |
| CD1 | LEU | A | 111 | 23.966 | 34.302 | 5.758 | 1.00 | 21.27 | C |
| CD2 | LEU | A | 111 | 23.605 | 35.470 | 3.584 | 1.00 | 20.64 | C |
| N | GLY | A | 112 | 27.706 | 33.399 | 1.864 | 1.00 | 19.90 | N |
| CA | GLY | A | 112 | 29.025 | 33.909 | 1.563 | 1.00 | 19.57 | C |

Figure 2-13

| C | GLY | A | 112 | 29.093 | 34.582 | 0.202 | 1.00 | 19.83 | C |
|---|---|---|---|---|---|---|---|---|---|
| O | GLY | A | 112 | 29.436 | 35.763 | 0.110 | 1.00 | 19.16 | O |
| N | LEU | A | 113 | 28.660 | 33.865 | -0.835 | 1.00 | 20.37 | N |
| CA | LEU | A | 113 | 28.717 | 34.373 | -2.195 | 1.00 | 21.45 | C |
| C | LEU | A | 113 | 27.667 | 35.432 | -2.470 | 1.00 | 22.87 | C |
| O | LEU | A | 113 | 27.887 | 36.287 | -3.349 | 1.00 | 24.10 | O |
| CB | LEU | A | 113 | 28.668 | 33.257 | -3.233 | 1.00 | 21.15 | C |
| CG | LEU | A | 113 | 29.966 | 32.437 | -3.379 | 1.00 | 21.11 | C |
| CD1 | LEU | A | 113 | 29.850 | 31.447 | -4.527 | 1.00 | 20.06 | C |
| CD2 | LEU | A | 113 | 31.172 | 33.342 | -3.549 | 1.00 | 20.34 | C |
| N | ILE | A | 114 | 26.567 | 35.437 | -1.726 | 1.00 | 23.17 | N |
| CA | ILE | A | 114 | 25.566 | 36.481 | -1.922 | 1.00 | 23.67 | C |
| C | ILE | A | 114 | 26.153 | 37.807 | -1.442 | 1.00 | 24.59 | C |
| O | ILE | A | 114 | 26.093 | 38.806 | -2.156 | 1.00 | 24.19 | O |
| CB | ILE | A | 114 | 24.246 | 36.209 | -1.205 | 1.00 | 23.59 | C |
| CG1 | ILE | A | 114 | 23.614 | 34.926 | -1.749 | 1.00 | 23.20 | C |
| CG2 | ILE | A | 114 | 23.293 | 37.390 | -1.373 | 1.00 | 23.46 | C |
| CD1 | ILE | A | 114 | 22.368 | 34.488 | -1.014 | 1.00 | 22.82 | C |
| N | GLU | A | 115 | 26.791 | 37.773 | -0.274 | 1.00 | 26.24 | N |
| CA | GLU | A | 115 | 27.382 | 38.995 | 0.283 | 1.00 | 28.37 | C |
| C | GLU | A | 115 | 28.485 | 39.536 | -0.625 | 1.00 | 29.01 | C |
| O | GLU | A | 115 | 28.597 | 40.732 | -0.855 | 1.00 | 28.40 | O |
| CB | GLU | A | 115 | 27.927 | 38.748 | 1.682 | 1.00 | 28.58 | C |
| CG | GLU | A | 115 | 26.918 | 38.301 | 2.723 | 1.00 | 29.16 | C |
| CD | GLU | A | 115 | 27.594 | 38.057 | 4.056 | 1.00 | 30.83 | C |
| OE1 | GLU | A | 115 | 27.136 | 37.229 | 4.861 | 1.00 | 31.28 | O |
| OE2 | GLU | A | 115 | 28.643 | 38.695 | 4.293 | 1.00 | 32.63 | O |
| N | GLU | A | 116 | 29.313 | 38.632 | -1.139 | 1.00 | 30.70 | N |
| CA | GLU | A | 116 | 30.396 | 38.976 | -2.041 | 1.00 | 31.25 | C |
| C | GLU | A | 116 | 29.865 | 39.618 | -3.315 | 1.00 | 29.86 | C |
| O | GLU | A | 116 | 30.328 | 40.689 | -3.701 | 1.00 | 29.96 | O |
| CB | GLU | A | 116 | 31.211 | 37.729 | -2.396 | 1.00 | 33.77 | C |
| CG | GLU | A | 116 | 32.443 | 38.037 | -3.238 | 1.00 | 37.37 | C |
| CD | GLU | A | 116 | 33.380 | 36.848 | -3.326 | 1.00 | 39.87 | C |
| OE1 | GLU | A | 116 | 33.652 | 36.249 | -2.253 | 1.00 | 41.44 | O |
| OE2 | GLU | A | 116 | 33.825 | 36.519 | -4.447 | 1.00 | 40.97 | O |
| N | ASN | A | 117 | 28.893 | 38.962 | -3.954 | 1.00 | 27.58 | N |
| CA | ASN | A | 117 | 28.342 | 39.520 | -5.195 | 1.00 | 25.34 | C |
| C | ASN | A | 117 | 27.694 | 40.865 | -4.966 | 1.00 | 25.27 | C |
| O | ASN | A | 117 | 28.025 | 41.830 | -5.663 | 1.00 | 25.06 | O |
| CB | ASN | A | 117 | 27.401 | 38.518 | -5.849 | 1.00 | 23.78 | C |
| CG | ASN | A | 117 | 28.223 | 37.458 | -6.584 | 1.00 | 23.22 | C |
| OD1 | ASN | A | 117 | 28.593 | 37.682 | -7.736 | 1.00 | 23.18 | O |
| ND2 | ASN | A | 117 | 28.516 | 36.354 | -5.929 | 1.00 | 22.14 | N |
| N | HIS | A | 118 | 26.877 | 40.991 | -3.922 | 1.00 | 25.45 | N |
| CA | HIS | A | 118 | 26.234 | 42.236 | -3.569 | 1.00 | 25.44 | C |
| C | HIS | A | 118 | 27.235 | 43.361 | -3.319 | 1.00 | 26.62 | C |
| O | HIS | A | 118 | 27.016 | 44.496 | -3.749 | 1.00 | 26.46 | O |
| CB | HIS | A | 118 | 25.330 | 42.060 | -2.335 | 1.00 | 24.14 | C |
| CG | HIS | A | 118 | 24.462 | 43.273 | -2.164 | 1.00 | 23.03 | C |
| ND1 | HIS | A | 118 | 24.589 | 44.116 | -1.095 | 1.00 | 23.14 | N |
| CD2 | HIS | A | 118 | 23.480 | 43.774 | -2.955 | 1.00 | 22.09 | C |
| CE1 | HIS | A | 118 | 23.700 | 45.101 | -1.220 | 1.00 | 22.98 | C |
| NE2 | HIS | A | 118 | 23.026 | 44.916 | -2.342 | 1.00 | 22.18 | N |
| N | THR | A | 119 | 28.347 | 43.054 | -2.668 | 1.00 | 27.91 | N |
| CA | THR | A | 119 | 29.438 | 43.991 | -2.456 | 1.00 | 29.63 | C |
| C | THR | A | 119 | 29.983 | 44.489 | -3.790 | 1.00 | 30.90 | C |
| O | THR | A | 119 | 29.968 | 45.696 | -4.060 | 1.00 | 32.10 | O |
| CB | THR | A | 119 | 30.574 | 43.315 | -1.665 | 1.00 | 29.98 | C |
| OG1 | THR | A | 119 | 30.019 | 42.865 | -0.421 | 1.00 | 30.86 | O |
| CG2 | THR | A | 119 | 31.718 | 44.270 | -1.392 | 1.00 | 29.85 | C |
| N | SER | A | 120 | 30.316 | 43.565 | -4.687 | 1.00 | 31.36 | N |
| CA | SER | A | 120 | 30.777 | 43.912 | -6.021 | 1.00 | 33.00 | C |

Figure 2-14

| | | | | | | | | |
|---|---|---|---|---|---|---|---|---|
| C | SER | A | 120 | 29.769 | 44.800 | -6.743 | 1.00 | 35.01 | C |
| O | SER | A | 120 | 30.150 | 45.758 | -7.410 | 1.00 | 35.40 | O |
| CB | SER | A | 120 | 31.031 | 42.671 | -6.875 | 1.00 | 32.36 | C |
| OG | SER | A | 120 | 32.030 | 41.846 | -6.313 | 1.00 | 31.75 | O |
| N | LEU | A | 121 | 28.484 | 44.470 | -6.627 | 1.00 | 36.66 | N |
| CA | LEU | A | 121 | 27.455 | 45.262 | -7.285 | 1.00 | 38.56 | C |
| C | LEU | A | 121 | 27.368 | 46.653 | -6.674 | 1.00 | 40.19 | C |
| O | LEU | A | 121 | 27.089 | 47.641 | -7.348 | 1.00 | 40.35 | O |
| CB | LEU | A | 121 | 26.106 | 44.542 | -7.201 | 1.00 | 37.83 | C |
| CG | LEU | A | 121 | 24.865 | 45.415 | -7.442 | 1.00 | 36.97 | C |
| CD1 | LEU | A | 121 | 24.528 | 45.466 | -8.921 | 1.00 | 36.28 | C |
| CD2 | LEU | A | 121 | 23.708 | 44.901 | -6.611 | 1.00 | 36.72 | C |
| N | MET | A | 122 | 27.576 | 46.750 | -5.367 | 1.00 | 43.04 | N |
| CA | MET | A | 122 | 27.496 | 48.051 | -4.707 | 1.00 | 46.33 | C |
| C | MET | A | 122 | 28.683 | 48.923 | -5.108 | 1.00 | 46.71 | C |
| O | MET | A | 122 | 28.549 | 50.140 | -5.220 | 1.00 | 47.31 | O |
| CB | MET | A | 122 | 27.431 | 47.875 | -3.198 | 1.00 | 48.07 | C |
| CG | MET | A | 122 | 26.196 | 48.466 | -2.532 | 1.00 | 50.31 | C |
| SD | MET | A | 122 | 26.330 | 48.350 | -0.728 | 1.00 | 53.75 | S |
| CE | MET | A | 122 | 26.105 | 50.064 | -0.250 | 1.00 | 53.18 | C |
| N | ASN | A | 123 | 29.831 | 48.291 | -5.337 | 1.00 | 46.45 | N |
| CA | ASN | A | 123 | 31.042 | 48.999 | -5.682 | 1.00 | 46.36 | C |
| C | ASN | A | 123 | 31.412 | 49.047 | -7.142 | 1.00 | 45.60 | C |
| O | ASN | A | 123 | 32.302 | 49.845 | -7.489 | 1.00 | 46.39 | O |
| CB | ASN | A | 123 | 32.212 | 48.384 | -4.869 | 1.00 | 47.24 | C |
| CG | ASN | A | 123 | 32.091 | 48.822 | -3.415 | 1.00 | 48.06 | C |
| OD1 | ASN | A | 123 | 32.236 | 48.009 | -2.502 | 1.00 | 48.53 | O |
| ND2 | ASN | A | 123 | 31.799 | 50.105 | -3.213 | 1.00 | 48.27 | N |
| N | GLY | A | 124 | 30.776 | 48.295 | -8.026 | 1.00 | 44.54 | N |
| CA | GLY | A | 124 | 31.149 | 48.300 | -9.427 | 1.00 | 42.78 | C |
| C | GLY | A | 124 | 29.989 | 48.188 | -10.386 | 1.00 | 42.39 | C |
| O | GLY | A | 124 | 30.226 | 48.129 | -11.606 | 1.00 | 43.03 | O |
| N | GLY | A | 125 | 28.756 | 48.163 | -9.898 | 1.00 | 41.26 | N |
| CA | GLY | A | 125 | 27.592 | 48.015 | -10.773 | 1.00 | 40.34 | C |
| C | GLY | A | 125 | 27.381 | 46.551 | -11.133 | 1.00 | 40.27 | C |
| O | GLY | A | 125 | 28.175 | 45.678 | -10.790 | 1.00 | 38.53 | O |
| N | PRO | A | 126 | 26.332 | 46.262 | -11.900 | 1.00 | 41.29 | N |
| CA | PRO | A | 126 | 25.971 | 44.928 | -12.314 | 1.00 | 41.55 | C |
| C | PRO | A | 126 | 26.927 | 44.186 | -13.211 | 1.00 | 42.21 | C |
| O | PRO | A | 126 | 26.762 | 42.964 | -13.385 | 1.00 | 42.68 | O |
| CB | PRO | A | 126 | 24.624 | 45.099 | -13.027 | 1.00 | 41.13 | C |
| CG | PRO | A | 126 | 24.577 | 46.524 | -13.423 | 1.00 | 41.26 | C |
| CD | PRO | A | 126 | 25.328 | 47.272 | -12.341 | 1.00 | 41.11 | C |
| N | ARG | A | 127 | 27.971 | 44.787 | -13.754 | 1.00 | 43.43 | N |
| CA | ARG | A | 127 | 28.910 | 44.074 | -14.616 | 1.00 | 44.73 | C |
| C | ARG | A | 127 | 29.967 | 43.347 | -13.802 | 1.00 | 44.18 | C |
| O | ARG | A | 127 | 30.718 | 42.517 | -14.326 | 1.00 | 44.09 | O |
| CB | ARG | A | 127 | 29.542 | 45.013 | -15.649 | 1.00 | 46.61 | C |
| CG | ARG | A | 127 | 28.687 | 45.176 | -16.901 | 1.00 | 48.61 | C |
| CD | ARG | A | 127 | 29.498 | 45.033 | -18.186 | 1.00 | 50.41 | C |
| NE | ARG | A | 127 | 29.125 | 46.076 | -19.138 | 1.00 | 51.94 | N |
| CZ | ARG | A | 127 | 29.848 | 47.140 | -19.462 | 1.00 | 52.60 | C |
| NH1 | ARG | A | 127 | 31.051 | 47.369 | -18.951 | 1.00 | 52.07 | N |
| NH2 | ARG | A | 127 | 29.335 | 48.004 | -20.340 | 1.00 | 53.61 | N |
| N | LYS | A | 128 | 30.019 | 43.644 | -12.504 | 1.00 | 43.09 | N |
| CA | LYS | A | 128 | 30.981 | 42.988 | -11.625 | 1.00 | 42.41 | C |
| C | LYS | A | 128 | 30.360 | 41.793 | -10.914 | 1.00 | 40.89 | C |
| O | LYS | A | 128 | 31.045 | 41.117 | -10.140 | 1.00 | 41.77 | O |
| CB | LYS | A | 128 | 31.576 | 43.992 | -10.640 | 1.00 | 43.33 | C |
| CG | LYS | A | 128 | 32.325 | 45.130 | -11.322 | 1.00 | 44.91 | C |
| CD | LYS | A | 128 | 33.747 | 45.254 | -10.788 | 1.00 | 46.28 | C |
| CE | LYS | A | 128 | 34.769 | 45.362 | -11.907 | 1.00 | 46.86 | C |
| NZ | LYS | A | 128 | 35.099 | 44.039 | -12.514 | 1.00 | 47.29 | N |

Figure 2-15

| | N | ILE | A | 129 | 29.092 | 41.484 | -11.181 | 1.00 | 38.34 | N |
|---|---|---|---|---|---|---|---|---|---|---|
| | CA | ILE | A | 129 | 28.474 | 40.313 | -10.586 | 1.00 | 36.66 | C |
| | C | ILE | A | 129 | 28.951 | 39.043 | -11.299 | 1.00 | 35.18 | C |
| | O | ILE | A | 129 | 28.755 | 38.876 | -12.499 | 1.00 | 35.66 | O |
| | CB | ILE | A | 129 | 26.935 | 40.318 | -10.646 | 1.00 | 36.26 | C |
| | CG1 | ILE | A | 129 | 26.323 | 41.520 | -9.942 | 1.00 | 35.86 | C |
| | CG2 | ILE | A | 129 | 26.398 | 39.016 | -10.035 | 1.00 | 35.70 | C |
| | CD1 | ILE | A | 129 | 24.803 | 41.547 | -9.968 | 1.00 | 35.30 | C |
| | N | SER | A | 130 | 29.478 | 38.080 | -10.560 | 1.00 | 33.85 | N |
| | CA | SER | A | 130 | 29.883 | 36.813 | -11.140 | 1.00 | 31.89 | C |
| | C | SER | A | 130 | 28.789 | 36.177 | -11.986 | 1.00 | 32.13 | C |
| | O | SER | A | 130 | 27.620 | 36.054 | -11.582 | 1.00 | 33.21 | O |
| | CB | SER | A | 130 | 30.240 | 35.819 | -10.023 | 1.00 | 30.42 | C |
| | OG | SER | A | 130 | 30.389 | 34.519 | -10.587 | 1.00 | 30.47 | O |
| | N | PRO | A | 131 | 29.191 | 35.552 | -13.092 | 1.00 | 30.65 | N |
| | CA | PRO | A | 131 | 28.299 | 34.765 | -13.917 | 1.00 | 29.11 | C |
| | C | PRO | A | 131 | 27.785 | 33.528 | -13.200 | 1.00 | 29.02 | C |
| | O | PRO | A | 131 | 26.776 | 32.955 | -13.637 | 1.00 | 30.14 | O |
| | CB | PRO | A | 131 | 29.124 | 34.375 | -15.126 | 1.00 | 28.44 | C |
| | CG | PRO | A | 131 | 30.409 | 35.087 | -15.033 | 1.00 | 28.97 | C |
| | CD | PRO | A | 131 | 30.581 | 35.557 | -13.612 | 1.00 | 29.65 | C |
| | N | PHE | A | 132 | 28.441 | 33.063 | -12.136 | 1.00 | 27.36 | N |
| | CA | PHE | A | 132 | 27.960 | 31.926 | -11.380 | 1.00 | 27.08 | C |
| | C | PHE | A | 132 | 27.173 | 32.321 | -10.138 | 1.00 | 26.08 | C |
| | O | PHE | A | 132 | 26.759 | 31.457 | -9.349 | 1.00 | 26.45 | O |
| | CB | PHE | A | 132 | 29.120 | 30.991 | -10.982 | 1.00 | 27.86 | C |
| | CG | PHE | A | 132 | 29.895 | 30.505 | -12.182 | 1.00 | 28.13 | C |
| | CD1 | PHE | A | 132 | 31.227 | 30.847 | -12.339 | 1.00 | 27.90 | C |
| | CD2 | PHE | A | 132 | 29.289 | 29.734 | -13.149 | 1.00 | 27.70 | C |
| | CE1 | PHE | A | 132 | 31.920 | 30.424 | -13.452 | 1.00 | 28.55 | C |
| | CE2 | PHE | A | 132 | 29.991 | 29.306 | -14.261 | 1.00 | 27.80 | C |
| | CZ | PHE | A | 132 | 31.308 | 29.658 | -14.413 | 1.00 | 27.46 | C |
| | N | PHE | A | 133 | 26.852 | 33.592 | -9.954 | 1.00 | 24.74 | N |
| | CA | PHE | A | 133 | 26.121 | 34.021 | -8.776 | 1.00 | 24.54 | C |
| | C | PHE | A | 133 | 24.964 | 33.090 | -8.439 | 1.00 | 24.38 | C |
| | O | PHE | A | 133 | 24.861 | 32.706 | -7.272 | 1.00 | 24.96 | O |
| | CB | PHE | A | 133 | 25.593 | 35.451 | -8.914 | 1.00 | 24.48 | C |
| | CG | PHE | A | 133 | 24.493 | 35.771 | -7.943 | 1.00 | 23.58 | C |
| | CD1 | PHE | A | 133 | 24.769 | 35.949 | -6.603 | 1.00 | 23.84 | C |
| | CD2 | PHE | A | 133 | 23.184 | 35.882 | -8.375 | 1.00 | 23.84 | C |
| | CE1 | PHE | A | 133 | 23.751 | 36.246 | -5.709 | 1.00 | 23.71 | C |
| | CE2 | PHE | A | 133 | 22.167 | 36.173 | -7.492 | 1.00 | 23.70 | C |
| | CZ | PHE | A | 133 | 22.450 | 36.356 | -6.148 | 1.00 | 23.57 | C |
| | N | VAL | A | 134 | 24.050 | 32.868 | -9.381 | 1.00 | 23.61 | N |
| | CA | VAL | A | 134 | 22.876 | 32.053 | -9.096 | 1.00 | 22.99 | C |
| | C | VAL | A | 134 | 23.105 | 30.617 | -8.725 | 1.00 | 22.25 | C |
| | O | VAL | A | 134 | 22.843 | 30.189 | -7.616 | 1.00 | 22.24 | O |
| | CB | VAL | A | 134 | 21.848 | 32.123 | -10.242 | 1.00 | 22.72 | C |
| | CG1 | VAL | A | 134 | 20.659 | 31.215 | -9.955 | 1.00 | 22.55 | C |
| | CG2 | VAL | A | 134 | 21.386 | 33.553 | -10.432 | 1.00 | 22.11 | C |
| | N | PRO | A | 135 | 23.800 | 29.826 | -9.581 | 1.00 | 22.78 | N |
| | CA | PRO | A | 135 | 24.084 | 28.420 | -9.339 | 1.00 | 22.59 | C |
| | C | PRO | A | 135 | 25.084 | 28.127 | -8.241 | 1.00 | 22.00 | C |
| | O | PRO | A | 135 | 25.281 | 26.982 | -7.813 | 1.00 | 20.80 | O |
| 1000 | CB | PRO | A | 135 | 24.618 | 27.904 | -10.681 | 1.00 | 22.31 | C |
| 1001 | CG | PRO | A | 135 | 25.145 | 29.121 | -11.356 | 1.00 | 21.93 | C |
| 1002 | CD | PRO | A | 135 | 24.211 | 30.240 | -10.954 | 1.00 | 22.09 | C |
| 1003 | N | SER | A | 136 | 25.773 | 29.170 | -7.770 | 1.00 | 21.31 | |
| 1004 | CA | SER | A | 136 | 26.758 | 29.002 | -6.719 | 1.00 | 20.34 | |
| 1005 | C | SER | A | 136 | 26.155 | 29.251 | -5.348 | 1.00 | 19.91 | |
| 1006 | O | SER | A | 136 | 26.823 | 28.970 | -4.356 | 1.00 | 21.13 | |
| 1007 | CB | SER | A | 136 | 27.926 | 29.958 | -6.967 | 1.00 | 19.97 | |
| 1008 | OG | SER | A | 136 | 27.646 | 31.272 | -6.556 | 1.00 | 19.96 | |

Figure 2-16

| 1009 | N | THR | A | 137 | 24.936 | 29.770 | -5.285 | 1.00 | 18.88 |
|---|---|---|---|---|---|---|---|---|---|
| 1010 | CA | THR | A | 137 | 24.280 | 30.087 | -4.040 | 1.00 | 18.15 |
| 1011 | C | THR | A | 137 | 22.985 | 29.351 | -3.757 | 1.00 | 18.90 |
| 1012 | O | THR | A | 137 | 22.581 | 29.274 | -2.581 | 1.00 | 18.18 |
| 1013 | CB | THR | A | 137 | 23.916 | 31.604 | -3.999 | 1.00 | 17.20 |
| 1014 | OG1 | THR | A | 137 | 23.015 | 31.883 | -5.079 | 1.00 | 15.95 |
| 1015 | CG2 | THR | A | 137 | 25.142 | 32.469 | -4.124 | 1.00 | 17.33 |
| 1016 | N | ILE | A | 138 | 22.213 | 29.041 | -4.804 | 1.00 | 19.45 |
| 1017 | CA | ILE | A | 138 | 20.877 | 28.482 | -4.541 | 1.00 | 19.38 |
| 1018 | C | ILE | A | 138 | 21.020 | 27.139 | -3.844 | 1.00 | 19.57 |
| 1019 | O | ILE | A | 138 | 21.852 | 26.292 | -4.159 | 1.00 | 20.13 |
| 1020 | CB | ILE | A | 138 | 19.979 | 28.411 | -5.760 | 1.00 | 19.43 |
| 1021 | CG1 | ILE | A | 138 | 20.656 | 27.763 | -6.974 | 1.00 | 20.56 |
| 1022 | CG2 | ILE | A | 138 | 19.521 | 29.812 | -6.159 | 1.00 | 20.24 |
| 1023 | CD1 | ILE | A | 138 | 19.620 | 27.294 | -7.992 | 1.00 | 21.35 |
| 1024 | N | VAL | A | 139 | 20.169 | 26.936 | -2.869 | 1.00 | 19.63 |
| 1025 | CA | VAL | A | 139 | 20.091 | 25.787 | -2.011 | 1.00 | 19.91 |
| 1026 | C | VAL | A | 139 | 20.157 | 24.438 | -2.666 | 1.00 | 20.52 |
| 1027 | O | VAL | A | 139 | 20.631 | 23.510 | -1.962 | 1.00 | 23.00 |
| 1028 | CB | VAL | A | 139 | 18.802 | 25.907 | -1.153 | 1.00 | 19.95 |
| 1029 | CG1 | VAL | A | 139 | 18.110 | 24.594 | -0.875 | 1.00 | 20.14 |
| 1030 | CG2 | VAL | A | 139 | 19.171 | 26.598 | 0.161 | 1.00 | 20.44 |
| 1031 | N | ASN | A | 140 | 19.684 | 24.204 | -3.870 | 1.00 | 19.62 |
| 1032 | CA | ASN | A | 140 | 19.595 | 22.851 | -4.407 | 1.00 | 20.62 |
| 1033 | C | ASN | A | 140 | 20.832 | 22.390 | -5.143 | 1.00 | 22.05 |
| 1034 | O | ASN | A | 140 | 20.998 | 21.205 | -5.505 | 1.00 | 22.79 |
| 1035 | CB | ASN | A | 140 | 18.333 | 22.766 | -5.279 | 1.00 | 20.75 |
| 1036 | CG | ASN | A | 140 | 18.373 | 23.691 | -6.475 | 1.00 | 21.68 |
| 1037 | OD1 | ASN | A | 140 | 18.428 | 24.917 | -6.348 | 1.00 | 22.22 |
| 1038 | ND2 | ASN | A | 140 | 18.366 | 23.136 | -7.680 | 1.00 | 21.47 |
| 1039 | N | MET | A | 141 | 21.844 | 23.243 | -5.265 | 1.00 | 22.68 |
| 1040 | CA | MET | A | 141 | 23.058 | 22.907 | -6.003 | 1.00 | 22.86 |
| 1041 | C | MET | A | 141 | 23.939 | 21.864 | -5.363 | 1.00 | 23.14 |
| 1042 | O | MET | A | 141 | 24.860 | 21.356 | -6.043 | 1.00 | 23.70 |
| 1043 | CB | MET | A | 141 | 23.793 | 24.197 | -6.361 | 1.00 | 23.57 |
| 1044 | CG | MET | A | 141 | 22.939 | 25.084 | -7.273 | 1.00 | 24.80 |
| 1045 | SD | MET | A | 141 | 22.306 | 24.187 | -8.701 | 1.00 | 26.52 |
| 1046 | CE | MET | A | 141 | 23.795 | 23.997 | -9.681 | 1.00 | 25.92 |
| 1047 | N | VAL | A | 142 | 23.717 | 21.457 | -4.114 | 1.00 | 22.25 |
| 1048 | CA | VAL | A | 142 | 24.512 | 20.395 | -3.526 | 1.00 | 22.45 |
| 1049 | C | VAL | A | 142 | 24.079 | 19.083 | -4.204 | 1.00 | 22.89 |
| 1050 | O | VAL | A | 142 | 24.896 | 18.297 | -4.674 | 1.00 | 22.97 |
| 1051 | CB | VAL | A | 142 | 24.360 | 20.211 | -2.019 | 1.00 | 23.14 |
| 1052 | CG1 | VAL | A | 142 | 25.179 | 19.008 | -1.546 | 1.00 | 22.56 |
| 1053 | CG2 | VAL | A | 142 | 24.799 | 21.460 | -1.269 | 1.00 | 24.17 |
| 1054 | N | ALA | A | 143 | 22.756 | 18.911 | -4.309 | 1.00 | 22.65 |
| 1055 | CA | ALA | A | 143 | 22.230 | 17.712 | -4.972 | 1.00 | 21.73 |
| 1056 | C | ALA | A | 143 | 22.517 | 17.765 | -6.474 | 1.00 | 21.76 |
| 1057 | O | ALA | A | 143 | 22.745 | 16.729 | -7.096 | 1.00 | 20.55 |
| 1058 | CB | ALA | A | 143 | 20.755 | 17.536 | -4.701 | 1.00 | 20.45 |
| 1059 | N | GLY | A | 144 | 22.521 | 18.971 | -7.035 | 1.00 | 22.30 |
| 1060 | CA | GLY | A | 144 | 22.787 | 19.154 | -8.455 | 1.00 | 23.35 |
| 1061 | C | GLY | A | 144 | 24.162 | 18.611 | -8.800 | 1.00 | 25.42 |
| 1062 | O | GLY | A | 144 | 24.296 | 17.682 | -9.596 | 1.00 | 25.76 |
| 1063 | N | HIS | A | 145 | 25.196 | 19.154 | -8.144 | 1.00 | 26.63 |
| 1064 | CA | HIS | A | 145 | 26.554 | 18.700 | -8.407 | 1.00 | 26.89 |
| 1065 | C | HIS | A | 145 | 26.729 | 17.227 | -8.086 | 1.00 | 28.15 |
| 1066 | O | HIS | A | 145 | 27.448 | 16.535 | -8.832 | 1.00 | 30.31 |
| 1067 | CB | HIS | A | 145 | 27.585 | 19.534 | -7.650 | 1.00 | 26.46 |
| 1068 | CG | HIS | A | 145 | 27.805 | 20.892 | -8.244 | 1.00 | 26.84 |
| 1069 | ND1 | HIS | A | 145 | 27.292 | 22.047 | -7.675 | 1.00 | 27.40 |
| 1070 | CD2 | HIS | A | 145 | 28.472 | 21.290 | -9.348 | 1.00 | 26.01 |
| 1071 | CE1 | HIS | A | 145 | 27.648 | 23.093 | -8.405 | 1.00 | 26.74 |

Figure 2-17

| | | | | | | | | |
|---|---|---|---|---|---|---|---|---|
| 1072 | NE2 | HIS | A | 145 | 28.366 | 22.655 | -9.424 | 1.00 | 25.68 |
| 1073 | N | LEU | A | 146 | 26.131 | 16.715 | -7.008 | 1.00 | 27.39 |
| 1074 | CA | LEU | A | 146 | 26.354 | 15.300 | -6.698 | 1.00 | 27.60 |
| 1075 | C | LEU | A | 146 | 25.747 | 14.423 | -7.779 | 1.00 | 27.47 |
| 1076 | O | LEU | A | 146 | 26.404 | 13.496 | -8.264 | 1.00 | 27.20 |
| 1077 | CB | LEU | A | 146 | 25.858 | 14.921 | -5.309 | 1.00 | 28.44 |
| 1078 | CG | LEU | A | 146 | 26.876 | 15.053 | -4.170 | 1.00 | 28.92 |
| 1079 | CD1 | LEU | A | 146 | 26.181 | 15.129 | -2.814 | 1.00 | 28.98 |
| 1080 | CD2 | LEU | A | 146 | 27.861 | 13.895 | -4.189 | 1.00 | 28.98 |
| 1081 | N | THR | A | 147 | 24.508 | 14.709 | -8.180 | 1.00 | 27.23 |
| 1082 | CA | THR | A | 147 | 23.882 | 13.907 | -9.228 | 1.00 | 27.05 |
| 1083 | C | THR | A | 147 | 24.791 | 13.868 | -10.457 | 1.00 | 28.80 |
| 1084 | O | THR | A | 147 | 25.146 | 12.771 | -10.910 | 1.00 | 30.40 |
| 1085 | CB | THR | A | 147 | 22.496 | 14.423 | -9.619 | 1.00 | 25.46 |
| 1086 | OG1 | THR | A | 147 | 22.616 | 15.783 | -10.043 | 1.00 | 25.22 |
| 1087 | CG2 | THR | A | 147 | 21.525 | 14.349 | -8.457 | 1.00 | 24.87 |
| 1088 | N | ILE | A | 148 | 25.193 | 15.019 | -10.977 | 1.00 | 28.90 |
| 1089 | CA | ILE | A | 148 | 26.106 | 15.077 | -12.110 | 1.00 | 29.46 |
| 1090 | C | ILE | A | 148 | 27.356 | 14.247 | -11.854 | 1.00 | 30.29 |
| 1091 | O | ILE | A | 148 | 27.645 | 13.327 | -12.620 | 1.00 | 30.71 |
| 1092 | CB | ILE | A | 148 | 26.522 | 16.527 | -12.426 | 1.00 | 29.60 |
| 1093 | CG1 | ILE | A | 148 | 25.279 | 17.399 | -12.625 | 1.00 | 28.38 |
| 1094 | CG2 | ILE | A | 148 | 27.434 | 16.568 | -13.644 | 1.00 | 29.51 |
| 1095 | CD1 | ILE | A | 148 | 25.560 | 18.880 | -12.562 | 1.00 | 27.09 |
| 1096 | N | MET | A | 149 | 28.092 | 14.530 | -10.789 | 1.00 | 31.24 |
| 1097 | CA | MET | A | 149 | 29.290 | 13.793 | -10.437 | 1.00 | 32.79 |
| 1098 | C | MET | A | 149 | 29.123 | 12.277 | -10.514 | 1.00 | 32.64 |
| 1099 | O | MET | A | 149 | 30.014 | 11.601 | -11.042 | 1.00 | 33.82 |
| 1100 | CB | MET | A | 149 | 29.743 | 14.124 | -9.017 | 1.00 | 35.34 |
| 1101 | CG | MET | A | 149 | 30.335 | 15.489 | -8.763 | 1.00 | 37.46 |
| 1102 | SD | MET | A | 149 | 31.040 | 15.582 | -7.096 | 1.00 | 39.92 |
| 1103 | CE | MET | A | 149 | 32.783 | 15.753 | -7.480 | 1.00 | 39.57 |
| 1104 | N | TYR | A | 150 | 28.089 | 11.691 | -9.929 | 1.00 | 31.98 |
| 1105 | CA | TYR | A | 150 | 27.938 | 10.243 | -9.929 | 1.00 | 32.50 |
| 1106 | C | TYR | A | 150 | 26.979 | 9.745 | -10.996 | 1.00 | 32.78 |
| 1107 | O | TYR | A | 150 | 26.625 | 8.561 | -11.031 | 1.00 | 32.62 |
| 1108 | CB | TYR | A | 150 | 27.487 | 9.741 | -8.543 | 1.00 | 32.88 |
| 1109 | CG | TYR | A | 150 | 28.616 | 9.791 | -7.531 | 1.00 | 33.65 |
| 1110 | CD1 | TYR | A | 150 | 28.787 | 10.878 | -6.689 | 1.00 | 33.91 |
| 1111 | CD2 | TYR | A | 150 | 29.523 | 8.745 | -7.442 | 1.00 | 34.07 |
| 1112 | CE1 | TYR | A | 150 | 29.824 | 10.921 | -5.775 | 1.00 | 34.19 |
| 1113 | CE2 | TYR | A | 150 | 30.562 | 8.780 | -6.533 | 1.00 | 34.79 |
| 1114 | CZ | TYR | A | 150 | 30.712 | 9.871 | -5.702 | 1.00 | 34.49 |
| 1115 | OH | TYR | A | 150 | 31.754 | 9.899 | -4.809 | 1.00 | 34.71 |
| 1116 | N | GLY | A | 151 | 26.504 | 10.638 | -11.857 | 1.00 | 32.74 |
| 1117 | CA | GLY | A | 151 | 25.539 | 10.272 | -12.881 | 1.00 | 33.16 |
| 1118 | C | GLY | A | 151 | 24.236 | 9.746 | -12.295 | 1.00 | 33.99 |
| 1119 | O | GLY | A | 151 | 23.721 | 8.729 | -12.764 | 1.00 | 33.51 |
| 1120 | N | LEU | A | 152 | 23.684 | 10.448 | -11.306 | 1.00 | 34.49 |
| 1121 | CA | LEU | A | 152 | 22.410 | 10.038 | -10.710 | 1.00 | 35.95 |
| 1122 | C | LEU | A | 152 | 21.234 | 10.598 | -11.501 | 1.00 | 36.26 |
| 1123 | O | LEU | A | 152 | 21.235 | 11.778 | -11.880 | 1.00 | 36.43 |
| 1124 | CB | LEU | A | 152 | 22.350 | 10.461 | -9.241 | 1.00 | 36.93 |
| 1125 | CG | LEU | A | 152 | 23.622 | 10.233 | -8.413 | 1.00 | 37.72 |
| 1126 | CD1 | LEU | A | 152 | 23.500 | 10.893 | -7.044 | 1.00 | 38.07 |
| 1127 | CD2 | LEU | A | 152 | 23.921 | 8.752 | -8.251 | 1.00 | 37.08 |
| 1128 | N | ARG | A | 153 | 20.282 | 9.734 | -11.869 | 1.00 | 35.94 |
| 1129 | CA | ARG | A | 153 | 19.153 | 10.166 | -12.686 | 1.00 | 35.63 |
| 1130 | C | ARG | A | 153 | 17.825 | 9.995 | -11.954 | 1.00 | 33.77 |
| 1131 | O | ARG | A | 153 | 16.778 | 10.303 | -12.533 | 1.00 | 33.81 |
| 1132 | CB | ARG | A | 153 | 19.085 | 9.447 | -14.033 | 1.00 | 37.46 |
| 1133 | CG | ARG | A | 153 | 20.399 | 9.116 | -14.690 | 1.00 | 39.69 |
| 1134 | CD | ARG | A | 153 | 20.431 | 9.337 | -16.176 | 1.00 | 41.60 |

Figure 2-18

| 1135 | NE | ARG | A | 153 | 19.403 | 8.616 | -16.922 | 1.00 | 44.39 |
|---|---|---|---|---|---|---|---|---|---|
| 1136 | CZ | ARG | A | 153 | 18.686 | 9.211 | -17.887 | 1.00 | 45.81 |
| 1137 | NH1 | ARG | A | 153 | 18.912 | 10.499 | -18.149 | 1.00 | 46.89 |
| 1138 | NH2 | ARG | A | 153 | 17.756 | 8.573 | -18.571 | 1.00 | 45.33 |
| 1139 | N | GLY | A | 154 | 17.858 | 9.525 | -10.711 | 1.00 | 30.89 |
| 1140 | CA | GLY | A | 154 | 16.596 | 9.388 | -9.976 | 1.00 | 29.41 |
| 1141 | C | GLY | A | 154 | 16.126 | 10.755 | -9.479 | 1.00 | 28.32 |
| 1142 | O | GLY | A | 154 | 16.662 | 11.805 | -9.842 | 1.00 | 27.72 |
| 1143 | N | PRO | A | 155 | 15.114 | 10.743 | -8.622 | 1.00 | 27.50 |
| 1144 | CA | PRO | A | 155 | 14.569 | 11.943 | -8.024 | 1.00 | 27.96 |
| 1145 | C | PRO | A | 155 | 15.587 | 12.845 | -7.363 | 1.00 | 28.74 |
| 1146 | O | PRO | A | 155 | 16.486 | 12.456 | -6.620 | 1.00 | 28.70 |
| 1147 | CB | PRO | A | 155 | 13.558 | 11.412 | -7.002 | 1.00 | 27.50 |
| 1148 | CG | PRO | A | 155 | 13.139 | 10.097 | -7.577 | 1.00 | 26.81 |
| 1149 | CD | PRO | A | 155 | 14.397 | 9.522 | -8.175 | 1.00 | 26.49 |
| 1150 | N | SER | A | 156 | 15.428 | 14.144 | -7.570 | 1.00 | 30.55 |
| 1151 | CA | SER | A | 156 | 16.307 | 15.171 | -7.057 | 1.00 | 31.21 |
| 1152 | C | SER | A | 156 | 15.549 | 16.270 | -6.329 | 1.00 | 31.29 |
| 1153 | O | SER | A | 156 | 15.151 | 17.240 | -6.995 | 1.00 | 32.20 |
| 1154 | CB | SER | A | 156 | 17.001 | 15.840 | -8.265 | 1.00 | 32.95 |
| 1155 | OG | SER | A | 156 | 18.380 | 15.560 | -8.281 | 1.00 | 36.38 |
| 1156 | N | ILE | A | 157 | 15.342 | 16.183 | -5.026 | 1.00 | 30.79 |
| 1157 | CA | ILE | A | 157 | 14.683 | 17.270 | -4.316 | 1.00 | 30.48 |
| 1158 | C | ILE | A | 157 | 15.620 | 17.914 | -3.290 | 1.00 | 29.11 |
| 1159 | O | ILE | A | 157 | 16.697 | 17.404 | -3.002 | 1.00 | 29.37 |
| 1160 | CB | ILE | A | 157 | 13.403 | 16.871 | -3.567 | 1.00 | 31.29 |
| 1161 | CG1 | ILE | A | 157 | 13.573 | 15.532 | -2.850 | 1.00 | 31.57 |
| 1162 | CG2 | ILE | A | 157 | 12.213 | 16.868 | -4.511 | 1.00 | 30.63 |
| 1163 | CD1 | ILE | A | 157 | 12.682 | 15.412 | -1.625 | 1.00 | 31.50 |
| 1164 | N | SER | A | 158 | 15.176 | 19.043 | -2.753 | 1.00 | 27.18 |
| 1165 | CA | SER | A | 158 | 15.892 | 19.794 | -1.739 | 1.00 | 25.03 |
| 1166 | C | SER | A | 158 | 14.893 | 20.515 | -0.823 | 1.00 | 23.56 |
| 1167 | O | SER | A | 158 | 14.220 | 21.451 | -1.244 | 1.00 | 23.34 |
| 1168 | CB | SER | A | 158 | 16.836 | 20.827 | -2.322 | 1.00 | 25.63 |
| 1169 | OG | SER | A | 158 | 17.772 | 20.304 | -3.231 | 1.00 | 27.19 |
| 1170 | N | ILE | A | 159 | 14.791 | 20.079 | 0.421 | 1.00 | 22.08 |
| 1171 | CA | ILE | A | 159 | 13.877 | 20.732 | 1.364 | 1.00 | 21.08 |
| 1172 | C | ILE | A | 159 | 14.610 | 21.800 | 2.162 | 1.00 | 21.52 |
| 1173 | O | ILE | A | 159 | 15.714 | 21.582 | 2.690 | 1.00 | 22.88 |
| 1174 | CB | ILE | A | 159 | 13.225 | 19.698 | 2.295 | 1.00 | 19.94 |
| 1175 | CG1 | ILE | A | 159 | 12.349 | 18.764 | 1.451 | 1.00 | 18.45 |
| 1176 | CG2 | ILE | A | 159 | 12.423 | 20.370 | 3.386 | 1.00 | 19.41 |
| 1177 | CD1 | ILE | A | 159 | 11.674 | 17.668 | 2.231 | 1.00 | 18.07 |
| 1178 | N | ALA | A | 160 | 14.032 | 22.986 | 2.213 | 1.00 | 20.71 |
| 1179 | CA | ALA | A | 160 | 14.620 | 24.115 | 2.917 | 1.00 | 20.75 |
| 1180 | C | ALA | A | 160 | 13.679 | 24.596 | 4.021 | 1.00 | 21.65 |
| 1181 | O | ALA | A | 160 | 12.925 | 25.547 | 3.818 | 1.00 | 21.95 |
| 1182 | CB | ALA | A | 160 | 14.891 | 25.245 | 1.943 | 1.00 | 21.36 |
| 1183 | N | THR | A | 161 | 13.742 | 23.921 | 5.166 | 1.00 | 20.97 |
| 1184 | CA | THR | A | 161 | 12.891 | 24.251 | 6.299 | 1.00 | 20.26 |
| 1185 | C | THR | A | 161 | 13.702 | 24.702 | 7.504 | 1.00 | 20.52 |
| 1186 | O | THR | A | 161 | 13.595 | 24.136 | 8.594 | 1.00 | 20.22 |
| 1187 | CB | THR | A | 161 | 12.021 | 23.032 | 6.676 | 1.00 | 19.65 |
| 1188 | OG1 | THR | A | 161 | 12.783 | 21.838 | 6.532 | 1.00 | 17.83 |
| 1189 | CG2 | THR | A | 161 | 10.807 | 22.936 | 5.759 | 1.00 | 19.91 |
| 1190 | N | ALA | A | 162 | 14.588 | 25.679 | 7.284 | 1.00 | 20.21 |
| 1191 | CA | ALA | A | 162 | 15.388 | 26.216 | 8.382 | 1.00 | 19.96 |
| 1192 | C | ALA | A | 162 | 16.121 | 25.080 | 9.083 | 1.00 | 21.41 |
| 1193 | O | ALA | A | 162 | 16.612 | 24.164 | 8.414 | 1.00 | 21.12 |
| 1194 | CB | ALA | A | 162 | 14.479 | 26.948 | 9.353 | 1.00 | 19.07 |
| 1195 | N | CYS | A | 163 | 16.122 | 25.066 | 10.415 | 1.00 | 21.82 |
| 1196 | CA | CYS | A | 163 | 16.785 | 24.038 | 11.185 | 1.00 | 23.27 |
| 1197 | C | CYS | A | 163 | 16.148 | 22.662 | 11.143 | 1.00 | 22.15 |

Figure 2-19

| 1198 | O | CYS | A | 163 | 16.067 | 21.756 | 11.814 | 1.00 | 21.45 |
|---|---|---|---|---|---|---|---|---|---|
| 1199 | CB | CYS | A | 163 | 16.880 | 24.441 | 12.673 | 1.00 | 24.71 |
| 1200 | SG | CYS | A | 163 | 17.913 | 25.911 | 12.915 | 1.00 | 28.93 |
| 1201 | N | THR | A | 164 | 15.037 | 22.488 | 10.446 | 1.00 | 21.76 |
| 1202 | CA | THR | A | 164 | 14.453 | 21.156 | 10.329 | 1.00 | 21.16 |
| 1203 | C | THR | A | 164 | 14.888 | 20.517 | 9.020 | 1.00 | 20.59 |
| 1204 | O | THR | A | 164 | 14.714 | 19.323 | 8.840 | 1.00 | 20.83 |
| 1205 | CB | THR | A | 164 | 12.927 | 21.172 | 10.433 | 1.00 | 20.78 |
| 1206 | OG1 | THR | A | 164 | 12.549 | 22.030 | 11.519 | 1.00 | 21.06 |
| 1207 | CG2 | THR | A | 164 | 12.396 | 19.772 | 10.675 | 1.00 | 20.38 |
| 1208 | N | SER | A | 165 | 15.513 | 21.302 | 8.153 | 1.00 | 21.25 |
| 1209 | CA | SER | A | 165 | 15.984 | 20.830 | 6.858 | 1.00 | 21.35 |
| 1210 | C | SER | A | 165 | 16.609 | 19.451 | 6.925 | 1.00 | 21.57 |
| 1211 | O | SER | A | 165 | 16.155 | 18.544 | 6.235 | 1.00 | 21.53 |
| 1212 | CB | SER | A | 165 | 17.007 | 21.809 | 6.265 | 1.00 | 20.98 |
| 1213 | OG | SER | A | 165 | 16.371 | 23.066 | 6.071 | 1.00 | 21.82 |
| 1214 | N | GLY | A | 166 | 17.618 | 19.286 | 7.774 | 1.00 | 22.48 |
| 1215 | CA | GLY | A | 166 | 18.315 | 18.020 | 7.925 | 1.00 | 22.79 |
| 1216 | C | GLY | A | 166 | 17.388 | 16.830 | 8.069 | 1.00 | 22.94 |
| 1217 | O | GLY | A | 166 | 17.567 | 15.809 | 7.409 | 1.00 | 22.55 |
| 1218 | N | VAL | A | 167 | 16.444 | 16.936 | 9.004 | 1.00 | 23.72 |
| 1219 | CA | VAL | A | 167 | 15.506 | 15.848 | 9.271 | 1.00 | 24.29 |
| 1220 | C | VAL | A | 167 | 14.558 | 15.638 | 8.109 | 1.00 | 24.54 |
| 1221 | O | VAL | A | 167 | 14.389 | 14.509 | 7.627 | 1.00 | 26.12 |
| 1222 | CB | VAL | A | 167 | 14.767 | 16.094 | 10.592 | 1.00 | 24.57 |
| 1223 | CG1 | VAL | A | 167 | 13.442 | 15.358 | 10.672 | 1.00 | 25.23 |
| 1224 | CG2 | VAL | A | 167 | 15.675 | 15.663 | 11.743 | 1.00 | 24.67 |
| 1225 | N | HIS | A | 168 | 13.991 | 16.711 | 7.572 | 1.00 | 24.23 |
| 1226 | CA | HIS | A | 168 | 13.060 | 16.594 | 6.455 | 1.00 | 23.72 |
| 1227 | C | HIS | A | 168 | 13.671 | 15.915 | 5.243 | 1.00 | 23.37 |
| 1228 | O | HIS | A | 168 | 13.003 | 15.055 | 4.637 | 1.00 | 24.37 |
| 1229 | CB | HIS | A | 168 | 12.494 | 17.964 | 6.099 | 1.00 | 23.34 |
| 1230 | CG | HIS | A | 168 | 11.429 | 18.457 | 7.027 | 1.00 | 23.31 |
| 1231 | ND1 | HIS | A | 168 | 11.102 | 19.797 | 7.120 | 1.00 | 22.78 |
| 1232 | CD2 | HIS | A | 168 | 10.613 | 17.813 | 7.897 | 1.00 | 22.79 |
| 1233 | CE1 | HIS | A | 168 | 10.138 | 19.951 | 8.014 | 1.00 | 22.01 |
| 1234 | NE2 | HIS | A | 168 | 9.823 | 18.768 | 8.491 | 1.00 | 21.89 |
| 1235 | N | ASN | A | 169 | 14.898 | 16.225 | 4.857 | 1.00 | 22.74 |
| 1236 | CA | ASN | A | 169 | 15.502 | 15.616 | 3.663 | 1.00 | 23.00 |
| 1237 | C | ASN | A | 169 | 15.656 | 14.107 | 3.822 | 1.00 | 23.66 |
| 1238 | O | ASN | A | 169 | 15.361 | 13.299 | 2.934 | 1.00 | 23.83 |
| 1239 | CB | ASN | A | 169 | 16.826 | 16.291 | 3.343 | 1.00 | 22.66 |
| 1240 | CG | ASN | A | 169 | 16.710 | 17.635 | 2.662 | 1.00 | 22.82 |
| 1241 | OD1 | ASN | A | 169 | 16.286 | 17.729 | 1.503 | 1.00 | 23.41 |
| 1242 | ND2 | ASN | A | 169 | 17.107 | 18.717 | 3.315 | 1.00 | 21.89 |
| 1243 | N | ILE | A | 170 | 16.075 | 13.671 | 5.005 | 1.00 | 23.82 |
| 1244 | CA | ILE | A | 170 | 16.178 | 12.241 | 5.309 | 1.00 | 23.18 |
| 1245 | C | ILE | A | 170 | 14.784 | 11.637 | 5.275 | 1.00 | 22.89 |
| 1246 | O | ILE | A | 170 | 14.532 | 10.695 | 4.507 | 1.00 | 22.87 |
| 1247 | CB | ILE | A | 170 | 16.917 | 12.046 | 6.638 | 1.00 | 23.01 |
| 1248 | CG1 | ILE | A | 170 | 18.322 | 12.677 | 6.508 | 1.00 | 22.40 |
| 1249 | CG2 | ILE | A | 170 | 17.081 | 10.591 | 7.028 | 1.00 | 23.08 |
| 1250 | CD1 | ILE | A | 170 | 18.989 | 12.935 | 7.825 | 1.00 | 22.78 |
| 1251 | N | GLY | A | 171 | 13.831 | 12.245 | 5.971 | 1.00 | 21.80 |
| 1252 | CA | GLY | A | 171 | 12.455 | 11.775 | 5.969 | 1.00 | 22.22 |
| 1253 | C | GLY | A | 171 | 11.908 | 11.490 | 4.579 | 1.00 | 22.83 |
| 1254 | O | GLY | A | 171 | 11.509 | 10.362 | 4.256 | 1.00 | 22.22 |
| 1255 | N | HIS | A | 172 | 11.918 | 12.497 | 3.702 | 1.00 | 23.21 |
| 1256 | CA | HIS | A | 172 | 11.335 | 12.357 | 2.369 | 1.00 | 22.97 |
| 1257 | C | HIS | A | 172 | 12.167 | 11.493 | 1.464 | 1.00 | 23.20 |
| 1258 | O | HIS | A | 172 | 11.668 | 10.866 | 0.520 | 1.00 | 23.49 |
| 1259 | CB | HIS | A | 172 | 11.036 | 13.753 | 1.771 | 1.00 | 22.55 |
| 1260 | CG | HIS | A | 172 | 9.823 | 14.271 | 2.506 | 1.00 | 22.55 |

Figure 2-20

| 1261 | ND1 | HIS | A | 172 | 9.944 | 15.054 | 3.631 | 1.00 | 23.32 |
|---|---|---|---|---|---|---|---|---|---|
| 1262 | CD2 | HIS | A | 172 | 8.513 | 14.044 | 2.327 | 1.00 | 22.72 |
| 1263 | CE1 | HIS | A | 172 | 8.734 | 15.323 | 4.101 | 1.00 | 23.47 |
| 1264 | NE2 | HIS | A | 172 | 7.844 | 14.717 | 3.329 | 1.00 | 23.29 |
| 1265 | N | ALA | A | 173 | 13.468 | 11.384 | 1.760 | 1.00 | 23.72 |
| 1266 | CA | ALA | A | 173 | 14.295 | 10.496 | 0.929 | 1.00 | 23.93 |
| 1267 | C | ALA | A | 173 | 13.810 | 9.058 | 1.148 | 1.00 | 23.83 |
| 1268 | O | ALA | A | 173 | 13.592 | 8.348 | 0.172 | 1.00 | 22.86 |
| 1269 | CB | ALA | A | 173 | 15.756 | 10.702 | 1.222 | 1.00 | 23.75 |
| 1270 | N | ALA | A | 174 | 13.506 | 8.691 | 2.390 | 1.00 | 23.88 |
| 1271 | CA | ALA | A | 174 | 12.985 | 7.375 | 2.714 | 1.00 | 24.96 |
| 1272 | C | ALA | A | 174 | 11.596 | 7.165 | 2.100 | 1.00 | 26.35 |
| 1273 | O | ALA | A | 174 | 11.326 | 6.134 | 1.482 | 1.00 | 26.24 |
| 1274 | CB | ALA | A | 174 | 12.865 | 7.184 | 4.215 | 1.00 | 24.24 |
| 1275 | N | ARG | A | 175 | 10.748 | 8.179 | 2.291 | 1.00 | 26.16 |
| 1276 | CA | ARG | A | 175 | 9.394 | 8.145 | 1.742 | 1.00 | 25.10 |
| 1277 | C | ARG | A | 175 | 9.481 | 7.878 | 0.245 | 1.00 | 27.12 |
| 1278 | O | ARG | A | 175 | 9.021 | 6.838 | -0.251 | 1.00 | 28.18 |
| 1279 | CB | ARG | A | 175 | 8.673 | 9.443 | 2.042 | 1.00 | 23.30 |
| 1280 | CG | ARG | A | 175 | 8.348 | 9.684 | 3.507 | 1.00 | 23.23 |
| 1281 | CD | ARG | A | 175 | 7.206 | 8.809 | 3.977 | 1.00 | 23.38 |
| 1282 | NE | ARG | A | 175 | 6.465 | 9.357 | 5.099 | 1.00 | 24.63 |
| 1283 | CZ | ARG | A | 175 | 6.601 | 8.994 | 6.376 | 1.00 | 24.68 |
| 1284 | NH1 | ARG | A | 175 | 7.476 | 8.054 | 6.731 | 1.00 | 24.38 |
| 1285 | NH2 | ARG | A | 175 | 5.855 | 9.564 | 7.315 | 1.00 | 23.89 |
| 1286 | N | ILE | A | 176 | 10.257 | 8.703 | -0.472 | 1.00 | 27.46 |
| 1287 | CA | ILE | A | 176 | 10.475 | 8.452 | -1.893 | 1.00 | 27.19 |
| 1288 | C | ILE | A | 176 | 10.815 | 6.991 | -2.141 | 1.00 | 28.06 |
| 1289 | O | ILE | A | 176 | 10.169 | 6.352 | -2.971 | 1.00 | 29.01 |
| 1290 | CB | ILE | A | 176 | 11.568 | 9.372 | -2.460 | 1.00 | 26.47 |
| 1291 | CG1 | ILE | A | 176 | 11.036 | 10.812 | -2.486 | 1.00 | 26.78 |
| 1292 | CG2 | ILE | A | 176 | 12.020 | 8.935 | -3.838 | 1.00 | 24.93 |
| 1293 | CD1 | ILE | A | 176 | 11.966 | 11.826 | -3.111 | 1.00 | 26.82 |
| 1294 | N | ILE | A | 177 | 11.823 | 6.460 | -1.463 | 1.00 | 28.98 |
| 1295 | CA | ILE | A | 177 | 12.249 | 5.076 | -1.652 | 1.00 | 29.01 |
| 1296 | C | ILE | A | 177 | 11.104 | 4.111 | -1.387 | 1.00 | 29.49 |
| 1297 | O | ILE | A | 177 | 10.698 | 3.373 | -2.290 | 1.00 | 30.21 |
| 1298 | CB | ILE | A | 177 | 13.483 | 4.745 | -0.802 | 1.00 | 28.06 |
| 1299 | CG1 | ILE | A | 177 | 14.718 | 5.428 | -1.400 | 1.00 | 27.28 |
| 1300 | CG2 | ILE | A | 177 | 13.712 | 3.245 | -0.714 | 1.00 | 28.49 |
| 1301 | CD1 | ILE | A | 177 | 15.924 | 5.483 | -0.490 | 1.00 | 26.54 |
| 1302 | N | ALA | A | 178 | 10.479 | 4.215 | -0.232 | 1.00 | 29.79 |
| 1303 | CA | ALA | A | 178 | 9.318 | 3.437 | 0.141 | 1.00 | 30.54 |
| 1304 | C | ALA | A | 178 | 8.251 | 3.453 | -0.942 | 1.00 | 33.08 |
| 1305 | O | ALA | A | 178 | 7.640 | 2.422 | -1.259 | 1.00 | 35.55 |
| 1306 | CB | ALA | A | 178 | 8.744 | 3.986 | 1.448 | 1.00 | 28.37 |
| 1307 | N | TYR | A | 179 | 7.975 | 4.621 | -1.514 | 1.00 | 33.83 |
| 1308 | CA | TYR | A | 179 | 6.967 | 4.771 | -2.546 | 1.00 | 33.95 |
| 1309 | C | TYR | A | 179 | 7.321 | 3.984 | -3.798 | 1.00 | 33.95 |
| 1310 | O | TYR | A | 179 | 6.399 | 3.530 | -4.495 | 1.00 | 35.65 |
| 1311 | CB | TYR | A | 179 | 6.779 | 6.254 | -2.886 | 1.00 | 34.35 |
| 1312 | CG | TYR | A | 179 | 5.600 | 6.559 | -3.781 | 1.00 | 34.82 |
| 1313 | CD1 | TYR | A | 179 | 4.368 | 6.895 | -3.228 | 1.00 | 35.00 |
| 1314 | CD2 | TYR | A | 179 | 5.715 | 6.518 | -5.167 | 1.00 | 34.57 |
| 1315 | CE1 | TYR | A | 179 | 3.283 | 7.174 | -4.034 | 1.00 | 35.41 |
| 1316 | CE2 | TYR | A | 179 | 4.636 | 6.794 | -5.976 | 1.00 | 34.96 |
| 1317 | CZ | TYR | A | 179 | 3.423 | 7.119 | -5.404 | 1.00 | 35.48 |
| 1318 | OH | TYR | A | 179 | 2.338 | 7.399 | -6.205 | 1.00 | 36.21 |
| 1319 | N | GLY | A | 180 | 8.590 | 3.866 | -4.149 | 1.00 | 33.30 |
| 1320 | CA | GLY | A | 180 | 8.991 | 3.165 | -5.356 | 1.00 | 33.89 |
| 1321 | C | GLY | A | 180 | 9.629 | 4.044 | -6.418 | 1.00 | 34.58 |
| 1322 | O | GLY | A | 180 | 10.091 | 3.541 | -7.461 | 1.00 | 34.05 |
| 1323 | N | ASP | A | 181 | 9.796 | 5.342 | -6.136 | 1.00 | 34.25 |

Figure 2-21

| 1324 | CA | ASP | A | 181 | 10.383 | 6.259 | -7.105 | 1.00 | 34.14 |
|---|---|---|---|---|---|---|---|---|---|
| 1325 | C | ASP | A | 181 | 11.898 | 6.108 | -7.189 | 1.00 | 34.08 |
| 1326 | O | ASP | A | 181 | 12.531 | 6.521 | -8.164 | 1.00 | 32.76 |
| 1327 | CB | ASP | A | 181 | 10.023 | 7.712 | -6.773 | 1.00 | 34.55 |
| 1328 | CG | ASP | A | 181 | 8.564 | 8.032 | -7.022 | 1.00 | 35.35 |
| 1329 | OD1 | ASP | A | 181 | 7.996 | 8.921 | -6.347 | 1.00 | 35.15 |
| 1330 | OD2 | ASP | A | 181 | 7.975 | 7.377 | -7.915 | 1.00 | 36.69 |
| 1331 | N | ALA | A | 182 | 12.486 | 5.534 | -6.145 | 1.00 | 34.99 |
| 1332 | CA | ALA | A | 182 | 13.926 | 5.339 | -6.075 | 1.00 | 35.64 |
| 1333 | C | ALA | A | 182 | 14.284 | 4.134 | -5.210 | 1.00 | 36.12 |
| 1334 | O | ALA | A | 182 | 13.482 | 3.675 | -4.395 | 1.00 | 36.49 |
| 1335 | CB | ALA | A | 182 | 14.594 | 6.592 | -5.527 | 1.00 | 34.86 |
| 1336 | N | ASP | A | 183 | 15.496 | 3.630 | -5.413 | 1.00 | 37.16 |
| 1337 | CA | ASP | A | 183 | 15.993 | 2.489 | -4.644 | 1.00 | 37.73 |
| 1338 | C | ASP | A | 183 | 17.068 | 2.946 | -3.662 | 1.00 | 37.03 |
| 1339 | O | ASP | A | 183 | 17.237 | 2.401 | -2.575 | 1.00 | 37.13 |
| 1340 | CB | ASP | A | 183 | 16.558 | 1.416 | -5.579 | 1.00 | 38.47 |
| 1341 | CG | ASP | A | 183 | 15.452 | 0.660 | -6.299 | 1.00 | 39.28 |
| 1342 | OD1 | ASP | A | 183 | 15.650 | 0.298 | -7.477 | 1.00 | 39.31 |
| 1343 | OD2 | ASP | A | 183 | 14.382 | 0.452 | -5.672 | 1.00 | 39.27 |
| 1344 | N | VAL | A | 184 | 17.870 | 3.907 | -4.112 | 1.00 | 35.93 |
| 1345 | CA | VAL | A | 184 | 18.906 | 4.529 | -3.313 | 1.00 | 34.94 |
| 1346 | C | VAL | A | 184 | 18.726 | 6.051 | -3.354 | 1.00 | 34.49 |
| 1347 | O | VAL | A | 184 | 18.388 | 6.611 | -4.397 | 1.00 | 34.37 |
| 1348 | CB | VAL | A | 184 | 20.329 | 4.191 | -3.783 | 1.00 | 34.92 |
| 1349 | CG1 | VAL | A | 184 | 21.361 | 4.899 | -2.904 | 1.00 | 34.98 |
| 1350 | CG2 | VAL | A | 184 | 20.598 | 2.699 | -3.774 | 1.00 | 34.24 |
| 1351 | N | MET | A | 185 | 18.909 | 6.700 | -2.208 | 1.00 | 33.85 |
| 1352 | CA | MET | A | 185 | 18.808 | 8.150 | -2.102 | 1.00 | 32.05 |
| 1353 | C | MET | A | 185 | 19.974 | 8.691 | -1.280 | 1.00 | 30.49 |
| 1354 | O | MET | A | 185 | 20.234 | 8.138 | -0.210 | 1.00 | 31.31 |
| 1355 | CB | MET | A | 185 | 17.503 | 8.560 | -1.421 | 1.00 | 32.72 |
| 1356 | CG | MET | A | 185 | 16.248 | 8.454 | -2.273 | 1.00 | 32.82 |
| 1357 | SD | MET | A | 185 | 16.312 | 9.494 | -3.751 | 1.00 | 32.53 |
| 1358 | CE | MET | A | 185 | 15.762 | 11.052 | -3.035 | 1.00 | 33.06 |
| 1359 | N | VAL | A | 186 | 20.675 | 9.701 | -1.759 | 1.00 | 29.07 |
| 1360 | CA | VAL | A | 186 | 21.696 | 10.370 | -0.952 | 1.00 | 27.75 |
| 1361 | C | VAL | A | 186 | 20.996 | 11.510 | -0.206 | 1.00 | 26.95 |
| 1362 | O | VAL | A | 186 | 20.426 | 12.381 | -0.880 | 1.00 | 28.34 |
| 1363 | CB | VAL | A | 186 | 22.846 | 10.975 | -1.755 | 1.00 | 27.97 |
| 1364 | CG1 | VAL | A | 186 | 24.006 | 11.307 | -0.815 | 1.00 | 27.63 |
| 1365 | CG2 | VAL | A | 186 | 23.324 | 10.065 | -2.869 | 1.00 | 28.61 |
| 1366 | N | ALA | A | 187 | 20.997 | 11.526 | 1.114 | 1.00 | 24.74 |
| 1367 | CA | ALA | A | 187 | 20.259 | 12.588 | 1.793 | 1.00 | 24.07 |
| 1368 | C | ALA | A | 187 | 21.001 | 13.252 | 2.926 | 1.00 | 24.02 |
| 1369 | O | ALA | A | 187 | 21.836 | 12.664 | 3.607 | 1.00 | 24.74 |
| 1370 | CB | ALA | A | 187 | 18.942 | 12.013 | 2.304 | 1.00 | 23.14 |
| 1371 | N | GLY | A | 188 | 20.682 | 14.533 | 3.152 | 1.00 | 23.56 |
| 1372 | CA | GLY | A | 188 | 21.322 | 15.219 | 4.282 | 1.00 | 22.93 |
| 1373 | C | GLY | A | 188 | 21.198 | 16.719 | 4.107 | 1.00 | 21.97 |
| 1374 | O | GLY | A | 188 | 20.352 | 17.169 | 3.340 | 1.00 | 21.88 |
| 1375 | N | GLY | A | 189 | 22.084 | 17.456 | 4.773 | 1.00 | 21.27 |
| 1376 | CA | GLY | A | 189 | 22.026 | 18.915 | 4.623 | 1.00 | 20.91 |
| 1377 | C | GLY | A | 189 | 23.423 | 19.489 | 4.781 | 1.00 | 20.13 |
| 1378 | O | GLY | A | 189 | 24.305 | 18.799 | 5.280 | 1.00 | 20.88 |
| 1379 | N | ALA | A | 190 | 23.609 | 20.703 | 4.295 | 1.00 | 19.89 |
| 1380 | CA | ALA | A | 190 | 24.906 | 21.374 | 4.431 | 1.00 | 19.71 |
| 1381 | C | ALA | A | 190 | 24.625 | 22.835 | 4.771 | 1.00 | 19.51 |
| 1382 | O | ALA | A | 190 | 23.617 | 23.366 | 4.289 | 1.00 | 19.85 |
| 1383 | CB | ALA | A | 190 | 25.739 | 21.242 | 3.172 | 1.00 | 19.10 |
| 1384 | N | GLU | A | 191 | 25.446 | 23.431 | 5.617 | 1.00 | 19.12 |
| 1385 | CA | GLU | A | 191 | 25.249 | 24.825 | 5.981 | 1.00 | 19.12 |
| 1386 | C | GLU | A | 191 | 26.585 | 25.504 | 6.260 | 1.00 | 18.78 |

Figure 2-22

| 1387 | O | GLU | A | 191 | 27.522 | 24.903 | 6.772 | 1.00 | 18.20 |
|---|---|---|---|---|---|---|---|---|---|
| 1388 | CB | GLU | A | 191 | 24.313 | 24.973 | 7.186 | 1.00 | 18.97 |
| 1389 | CG | GLU | A | 191 | 23.760 | 26.391 | 7.329 | 1.00 | 20.04 |
| 1390 | CD | GLU | A | 191 | 22.420 | 26.607 | 6.662 | 1.00 | 20.10 |
| 1391 | OE1 | GLU | A | 191 | 22.312 | 27.479 | 5.775 | 1.00 | 20.35 |
| 1392 | OE2 | GLU | A | 191 | 21.423 | 25.921 | 6.984 | 1.00 | 19.18 |
| 1393 | N | LYS | A | 192 | 26.650 | 26.784 | 5.942 | 1.00 | 18.47 |
| 1394 | CA | LYS | A | 192 | 27.831 | 27.586 | 6.205 | 1.00 | 18.91 |
| 1395 | C | LYS | A | 192 | 27.392 | 29.047 | 6.334 | 1.00 | 19.50 |
| 1396 | O | LYS | A | 192 | 27.558 | 29.853 | 5.424 | 1.00 | 18.72 |
| 1397 | CB | LYS | A | 192 | 28.882 | 27.398 | 5.129 | 1.00 | 20.21 |
| 1398 | CG | LYS | A | 192 | 30.311 | 27.620 | 5.611 | 1.00 | 21.28 |
| 1399 | CD | LYS | A | 192 | 30.626 | 29.114 | 5.727 | 1.00 | 20.99 |
| 1400 | CE | LYS | A | 192 | 32.101 | 29.304 | 6.035 | 1.00 | 21.43 |
| 1401 | NZ | LYS | A | 192 | 32.369 | 30.319 | 7.082 | 1.00 | 20.87 |
| 1402 | N | ALA | A | 193 | 26.769 | 29.332 | 7.486 | 1.00 | 19.33 |
| 1403 | CA | ALA | A | 193 | 26.218 | 30.651 | 7.745 | 1.00 | 18.76 |
| 1404 | C | ALA | A | 193 | 27.125 | 31.471 | 8.633 | 1.00 | 20.38 |
| 1405 | O | ALA | A | 193 | 26.765 | 32.618 | 8.971 | 1.00 | 22.59 |
| 1406 | CB | ALA | A | 193 | 24.820 | 30.556 | 8.351 | 1.00 | 16.60 |
| 1407 | N | SER | A | 194 | 28.319 | 31.002 | 8.993 | 1.00 | 20.01 |
| 1408 | CA | SER | A | 194 | 29.212 | 31.816 | 9.822 | 1.00 | 19.73 |
| 1409 | C | SER | A | 194 | 29.827 | 32.946 | 9.010 | 1.00 | 19.70 |
| 1410 | O | SER | A | 194 | 31.018 | 32.969 | 8.692 | 1.00 | 19.94 |
| 1411 | CB | SER | A | 194 | 30.324 | 30.953 | 10.417 | 1.00 | 20.42 |
| 1412 | OG | SER | A | 194 | 31.139 | 30.457 | 9.359 | 1.00 | 20.95 |
| 1413 | N | THR | A | 195 | 29.005 | 33.897 | 8.600 | 1.00 | 19.16 |
| 1414 | CA | THR | A | 195 | 29.367 | 35.036 | 7.795 | 1.00 | 19.39 |
| 1415 | C | THR | A | 195 | 28.812 | 36.284 | 8.470 | 1.00 | 19.65 |
| 1416 | O | THR | A | 195 | 27.838 | 36.181 | 9.227 | 1.00 | 21.37 |
| 1417 | CB | THR | A | 195 | 28.757 | 34.967 | 6.382 | 1.00 | 20.32 |
| 1418 | OG1 | THR | A | 195 | 27.366 | 35.354 | 6.457 | 1.00 | 21.29 |
| 1419 | CG2 | THR | A | 195 | 28.843 | 33.585 | 5.772 | 1.00 | 19.40 |
| 1420 | N | PRO | A | 196 | 29.327 | 37.442 | 8.125 | 1.00 | 19.54 |
| 1421 | CA | PRO | A | 196 | 28.846 | 38.693 | 8.699 | 1.00 | 19.97 |
| 1422 | C | PRO | A | 196 | 27.341 | 38.754 | 8.825 | 1.00 | 19.83 |
| 1423 | O | PRO | A | 196 | 26.816 | 38.911 | 9.924 | 1.00 | 20.28 |
| 1424 | CB | PRO | A | 196 | 29.417 | 39.747 | 7.753 | 1.00 | 19.47 |
| 1425 | CG | PRO | A | 196 | 30.666 | 39.142 | 7.224 | 1.00 | 17.90 |
| 1426 | CD | PRO | A | 196 | 30.447 | 37.658 | 7.185 | 1.00 | 18.39 |
| 1427 | N | LEU | A | 197 | 26.601 | 38.575 | 7.744 | 1.00 | 21.07 |
| 1428 | CA | LEU | A | 197 | 25.156 | 38.631 | 7.691 | 1.00 | 21.15 |
| 1429 | C | LEU | A | 197 | 24.471 | 37.549 | 8.504 | 1.00 | 22.25 |
| 1430 | O | LEU | A | 197 | 23.391 | 37.781 | 9.057 | 1.00 | 22.33 |
| 1431 | CB | LEU | A | 197 | 24.696 | 38.550 | 6.235 | 1.00 | 20.97 |
| 1432 | CG | LEU | A | 197 | 23.530 | 39.417 | 5.781 | 1.00 | 20.00 |
| 1433 | CD1 | LEU | A | 197 | 23.781 | 40.878 | 6.083 | 1.00 | 19.91 |
| 1434 | CD2 | LEU | A | 197 | 23.283 | 39.197 | 4.290 | 1.00 | 19.18 |
| 1435 | N | GLY | A | 198 | 25.069 | 36.366 | 8.579 | 1.00 | 22.88 |
| 1436 | CA | GLY | A | 198 | 24.470 | 35.281 | 9.356 | 1.00 | 23.85 |
| 1437 | C | GLY | A | 198 | 24.739 | 35.506 | 10.839 | 1.00 | 26.11 |
| 1438 | O | GLY | A | 198 | 23.874 | 35.251 | 11.681 | 1.00 | 26.78 |
| 1439 | N | VAL | A | 199 | 25.956 | 35.969 | 11.160 | 1.00 | 26.93 |
| 1440 | CA | VAL | A | 199 | 26.250 | 36.222 | 12.587 | 1.00 | 27.85 |
| 1441 | C | VAL | A | 199 | 25.514 | 37.487 | 13.008 | 1.00 | 27.33 |
| 1442 | O | VAL | A | 199 | 24.683 | 37.455 | 13.926 | 1.00 | 27.42 |
| 1443 | CB | VAL | A | 199 | 27.746 | 36.267 | 12.877 | 1.00 | 28.42 |
| 1444 | CG1 | VAL | A | 199 | 28.068 | 36.897 | 14.220 | 1.00 | 27.28 |
| 1445 | CG2 | VAL | A | 199 | 28.327 | 34.844 | 12.826 | 1.00 | 27.96 |
| 1446 | N | GLY | A | 200 | 25.717 | 38.569 | 12.268 | 1.00 | 25.86 |
| 1447 | CA | GLY | A | 200 | 24.993 | 39.806 | 12.549 | 1.00 | 25.88 |
| 1448 | C | GLY | A | 200 | 23.493 | 39.535 | 12.646 | 1.00 | 25.97 |
| 1449 | O | GLY | A | 200 | 22.870 | 39.851 | 13.652 | 1.00 | 26.80 |

Figure 2-23

| | | | | | | | | | |
|---|---|---|---|---|---|---|---|---|---|
| 1450 | N | GLY | A | 201 | 22.885 | 38.974 | 11.615 | 1.00 | 25.48 |
| 1451 | CA | GLY | A | 201 | 21.478 | 38.693 | 11.546 | 1.00 | 25.31 |
| 1452 | C | GLY | A | 201 | 20.889 | 37.981 | 12.738 | 1.00 | 25.85 |
| 1453 | O | GLY | A | 201 | 19.849 | 38.418 | 13.259 | 1.00 | 25.85 |
| 1454 | N | PHE | A | 202 | 21.504 | 36.891 | 13.204 | 1.00 | 25.57 |
| 1455 | CA | PHE | A | 202 | 20.975 | 36.198 | 14.378 | 1.00 | 26.27 |
| 1456 | C | PHE | A | 202 | 21.237 | 37.041 | 15.627 | 1.00 | 27.19 |
| 1457 | O | PHE | A | 202 | 20.509 | 36.959 | 16.608 | 1.00 | 28.35 |
| 1458 | CB | PHE | A | 202 | 21.580 | 34.811 | 14.551 | 1.00 | 26.19 |
| 1459 | CG | PHE | A | 202 | 20.943 | 33.711 | 13.752 | 1.00 | 25.12 |
| 1460 | CD1 | PHE | A | 202 | 21.643 | 33.073 | 12.738 | 1.00 | 24.21 |
| 1461 | CD2 | PHE | A | 202 | 19.632 | 33.332 | 13.996 | 1.00 | 24.42 |
| 1462 | CE1 | PHE | A | 202 | 21.051 | 32.076 | 11.991 | 1.00 | 23.44 |
| 1463 | CE2 | PHE | A | 202 | 19.038 | 32.320 | 13.267 | 1.00 | 24.39 |
| 1464 | CZ | PHE | A | 202 | 19.752 | 31.695 | 12.257 | 1.00 | 23.79 |
| 1465 | N | GLY | A | 203 | 22.305 | 37.834 | 15.611 | 1.00 | 28.07 |
| 1466 | CA | GLY | A | 203 | 22.617 | 38.752 | 16.703 | 1.00 | 28.36 |
| 1467 | C | GLY | A | 203 | 21.489 | 39.776 | 16.825 | 1.00 | 29.38 |
| 1468 | O | GLY | A | 203 | 20.966 | 40.052 | 17.911 | 1.00 | 30.32 |
| 1469 | N | ALA | A | 204 | 21.089 | 40.312 | 15.677 | 1.00 | 28.66 |
| 1470 | CA | ALA | A | 204 | 20.027 | 41.289 | 15.581 | 1.00 | 28.43 |
| 1471 | C | ALA | A | 204 | 18.768 | 40.815 | 16.294 | 1.00 | 28.66 |
| 1472 | O | ALA | A | 204 | 18.131 | 41.610 | 16.982 | 1.00 | 29.26 |
| 1473 | CB | ALA | A | 204 | 19.743 | 41.609 | 14.117 | 1.00 | 28.52 |
| 1474 | N | ALA | A | 205 | 18.435 | 39.539 | 16.198 | 1.00 | 29.22 |
| 1475 | CA | ALA | A | 205 | 17.292 | 38.917 | 16.821 | 1.00 | 29.54 |
| 1476 | C | ALA | A | 205 | 17.532 | 38.582 | 18.293 | 1.00 | 30.76 |
| 1477 | O | ALA | A | 205 | 16.604 | 38.153 | 18.987 | 1.00 | 31.16 |
| 1478 | CB | ALA | A | 205 | 16.930 | 37.619 | 16.106 | 1.00 | 28.27 |
| 1479 | N | ARG | A | 206 | 18.779 | 38.677 | 18.735 | 1.00 | 31.45 |
| 1480 | CA | ARG | A | 206 | 19.159 | 38.399 | 20.110 | 1.00 | 32.71 |
| 1481 | C | ARG | A | 206 | 19.060 | 36.919 | 20.439 | 1.00 | 32.08 |
| 1482 | O | ARG | A | 206 | 18.810 | 36.532 | 21.575 | 1.00 | 32.74 |
| 1483 | CB | ARG | A | 206 | 18.299 | 39.212 | 21.090 | 1.00 | 33.69 |
| 1484 | CG | ARG | A | 206 | 18.709 | 40.680 | 21.147 | 1.00 | 35.43 |
| 1485 | CD | ARG | A | 206 | 18.168 | 41.326 | 22.416 | 1.00 | 37.32 |
| 1486 | NE | ARG | A | 206 | 18.714 | 40.674 | 23.601 | 1.00 | 38.75 |
| 1487 | CZ | ARG | A | 206 | 18.015 | 40.193 | 24.619 | 1.00 | 39.28 |
| 1488 | NH1 | ARG | A | 206 | 18.676 | 39.617 | 25.623 | 1.00 | 40.09 |
| 1489 | NH2 | ARG | A | 206 | 16.692 | 40.273 | 24.653 | 1.00 | 39.00 |
| 1490 | N | ALA | A | 207 | 19.351 | 36.086 | 19.459 | 1.00 | 31.89 |
| 1491 | CA | ALA | A | 207 | 19.203 | 34.651 | 19.541 | 1.00 | 30.97 |
| 1492 | C | ALA | A | 207 | 20.506 | 33.926 | 19.828 | 1.00 | 29.87 |
| 1493 | O | ALA | A | 207 | 20.485 | 32.707 | 20.028 | 1.00 | 30.21 |
| 1494 | CB | ALA | A | 207 | 18.657 | 34.153 | 18.183 | 1.00 | 30.74 |
| 1495 | N | LEU | A | 208 | 21.630 | 34.631 | 19.784 | 1.00 | 28.48 |
| 1496 | CA | LEU | A | 208 | 22.909 | 33.963 | 19.961 | 1.00 | 29.11 |
| 1497 | C | LEU | A | 208 | 23.516 | 34.215 | 21.336 | 1.00 | 29.38 |
| 1498 | O | LEU | A | 208 | 23.357 | 35.310 | 21.857 | 1.00 | 29.54 |
| 1499 | CB | LEU | A | 208 | 23.948 | 34.424 | 18.927 | 1.00 | 28.64 |
| 1500 | CG | LEU | A | 208 | 23.703 | 33.986 | 17.481 | 1.00 | 28.52 |
| 1501 | CD1 | LEU | A | 208 | 24.704 | 34.659 | 16.558 | 1.00 | 27.66 |
| 1502 | CD2 | LEU | A | 208 | 23.763 | 32.470 | 17.372 | 1.00 | 28.39 |
| 1503 | N | SER | A | 209 | 24.285 | 33.229 | 21.813 | 1.00 | 28.67 |
| 1504 | CA | SER | A | 209 | 24.999 | 33.395 | 23.072 | 1.00 | 27.73 |
| 1505 | C | SER | A | 209 | 26.090 | 34.453 | 22.903 | 1.00 | 27.76 |
| 1506 | O | SER | A | 209 | 26.493 | 34.797 | 21.800 | 1.00 | 26.99 |
| 1507 | CB | SER | A | 209 | 25.577 | 32.082 | 23.574 | 1.00 | 27.07 |
| 1508 | OG | SER | A | 209 | 26.481 | 32.291 | 24.653 | 1.00 | 26.06 |
| 1509 | N | THR | A | 210 | 26.482 | 35.063 | 24.008 | 1.00 | 29.62 |
| 1510 | CA | THR | A | 210 | 27.378 | 36.244 | 23.938 | 1.00 | 31.15 |
| 1511 | C | THR | A | 210 | 28.562 | 36.040 | 24.849 | 1.00 | 31.71 |
| 1512 | O | THR | A | 210 | 29.417 | 36.890 | 25.097 | 1.00 | 30.55 |

Figure 2-24

| 1513 | CB | THR | A | 210 | 26.495 | 37.458 | 24.255 | 1.00 | 31.98 |
|------|-----|-----|---|-----|--------|--------|--------|------|-------|
| 1514 | OG1 | THR | A | 210 | 26.238 | 38.187 | 23.037 | 1.00 | 32.30 |
| 1515 | CG2 | THR | A | 210 | 27.039 | 38.393 | 25.302 | 1.00 | 32.74 |
| 1516 | N | ARG | A | 211 | 28.724 | 34.788 | 25.303 | 1.00 | 32.86 |
| 1517 | CA | ARG | A | 211 | 29.800 | 34.414 | 26.204 | 1.00 | 34.98 |
| 1518 | C | ARG | A | 211 | 31.142 | 34.331 | 25.505 | 1.00 | 35.34 |
| 1519 | O | ARG | A | 211 | 31.736 | 33.260 | 25.391 | 1.00 | 35.29 |
| 1520 | CB | ARG | A | 211 | 29.440 | 33.084 | 26.873 | 1.00 | 36.96 |
| 1521 | CG | ARG | A | 211 | 30.276 | 32.715 | 28.078 | 1.00 | 38.63 |
| 1522 | CD | ARG | A | 211 | 29.809 | 31.412 | 28.695 | 1.00 | 40.89 |
| 1523 | NE | ARG | A | 211 | 28.812 | 31.617 | 29.748 | 1.00 | 43.18 |
| 1524 | CZ | ARG | A | 211 | 27.497 | 31.538 | 29.556 | 1.00 | 44.37 |
| 1525 | NH1 | ARG | A | 211 | 27.003 | 31.259 | 28.347 | 1.00 | 44.55 |
| 1526 | NH2 | ARG | A | 211 | 26.676 | 31.740 | 30.581 | 1.00 | 44.44 |
| 1527 | N | ASN | A | 212 | 31.697 | 35.456 | 25.076 | 1.00 | 36.69 |
| 1528 | CA | ASN | A | 212 | 32.967 | 35.519 | 24.386 | 1.00 | 38.57 |
| 1529 | C | ASN | A | 212 | 34.172 | 35.285 | 25.283 | 1.00 | 40.78 |
| 1530 | O | ASN | A | 212 | 35.272 | 35.059 | 24.758 | 1.00 | 41.25 |
| 1531 | CB | ASN | A | 212 | 33.125 | 36.873 | 23.686 | 1.00 | 38.25 |
| 1532 | CG | ASN | A | 212 | 31.919 | 37.286 | 22.873 | 1.00 | 38.78 |
| 1533 | OD1 | ASN | A | 212 | 31.326 | 36.500 | 22.126 | 1.00 | 38.93 |
| 1534 | ND2 | ASN | A | 212 | 31.525 | 38.552 | 23.005 | 1.00 | 38.26 |
| 1535 | N | ASP | A | 213 | 34.018 | 35.328 | 26.601 | 1.00 | 43.10 |
| 1536 | CA | ASP | A | 213 | 35.130 | 35.122 | 27.525 | 1.00 | 45.40 |
| 1537 | C | ASP | A | 213 | 35.433 | 33.638 | 27.704 | 1.00 | 45.34 |
| 1538 | O | ASP | A | 213 | 36.540 | 33.257 | 28.080 | 1.00 | 44.99 |
| 1539 | CB | ASP | A | 213 | 34.896 | 35.821 | 28.858 | 1.00 | 47.21 |
| 1540 | CG | ASP | A | 213 | 33.652 | 35.405 | 29.603 | 1.00 | 49.21 |
| 1541 | OD1 | ASP | A | 213 | 32.526 | 35.562 | 29.072 | 1.00 | 50.18 |
| 1542 | OD2 | ASP | A | 213 | 33.789 | 34.906 | 30.749 | 1.00 | 50.24 |
| 1543 | N | ASN | A | 214 | 34.465 | 32.787 | 27.385 | 1.00 | 45.48 |
| 1544 | CA | ASN | A | 214 | 34.649 | 31.342 | 27.426 | 1.00 | 45.22 |
| 1545 | C | ASN | A | 214 | 33.840 | 30.670 | 26.316 | 1.00 | 43.77 |
| 1546 | O | ASN | A | 214 | 32.803 | 30.045 | 26.541 | 1.00 | 43.50 |
| 1547 | CB | ASN | A | 214 | 34.289 | 30.771 | 28.789 | 1.00 | 46.06 |
| 1548 | CG | ASN | A | 214 | 34.875 | 29.392 | 29.028 | 1.00 | 46.69 |
| 1549 | OD1 | ASN | A | 214 | 35.114 | 29.005 | 30.174 | 1.00 | 47.37 |
| 1550 | ND2 | ASN | A | 214 | 35.114 | 28.633 | 27.966 | 1.00 | 46.96 |
| 1551 | N | PRO | A | 215 | 34.345 | 30.763 | 25.089 | 1.00 | 42.47 |
| 1552 | CA | PRO | A | 215 | 33.653 | 30.271 | 23.911 | 1.00 | 41.85 |
| 1553 | C | PRO | A | 215 | 33.196 | 28.836 | 23.992 | 1.00 | 40.97 |
| 1554 | O | PRO | A | 215 | 32.078 | 28.509 | 23.586 | 1.00 | 40.92 |
| 1555 | CB | PRO | A | 215 | 34.665 | 30.467 | 22.785 | 1.00 | 41.51 |
| 1556 | CG | PRO | A | 215 | 35.519 | 31.597 | 23.234 | 1.00 | 41.27 |
| 1557 | CD | PRO | A | 215 | 35.569 | 31.517 | 24.730 | 1.00 | 41.71 |
| 1558 | N | GLN | A | 216 | 34.006 | 27.940 | 24.542 | 1.00 | 40.36 |
| 1559 | CA | GLN | A | 216 | 33.689 | 26.536 | 24.662 | 1.00 | 40.03 |
| 1560 | C | GLN | A | 216 | 32.649 | 26.243 | 25.736 | 1.00 | 38.52 |
| 1561 | O | GLN | A | 216 | 32.207 | 25.093 | 25.842 | 1.00 | 38.43 |
| 1562 | CB | GLN | A | 216 | 34.948 | 25.709 | 24.953 | 1.00 | 42.11 |
| 1563 | CG | GLN | A | 216 | 36.081 | 25.871 | 23.963 | 1.00 | 44.52 |
| 1564 | CD | GLN | A | 216 | 36.980 | 27.057 | 24.241 | 1.00 | 46.34 |
| 1565 | OE1 | GLN | A | 216 | 36.910 | 27.707 | 25.293 | 1.00 | 47.64 |
| 1566 | NE2 | GLN | A | 216 | 37.842 | 27.386 | 23.279 | 1.00 | 46.74 |
| 1567 | N | ALA | A | 217 | 32.268 | 27.225 | 26.536 | 1.00 | 36.20 |
| 1568 | CA | ALA | A | 217 | 31.303 | 27.017 | 27.608 | 1.00 | 34.50 |
| 1569 | C | ALA | A | 217 | 29.987 | 27.715 | 27.287 | 1.00 | 33.15 |
| 1570 | O | ALA | A | 217 | 28.997 | 27.578 | 28.001 | 1.00 | 32.25 |
| 1571 | CB | ALA | A | 217 | 31.880 | 27.557 | 28.914 | 1.00 | 34.14 |
| 1572 | N | ALA | A | 218 | 29.996 | 28.465 | 26.196 | 1.00 | 32.07 |
| 1573 | CA | ALA | A | 218 | 28.856 | 29.223 | 25.721 | 1.00 | 31.43 |
| 1574 | C | ALA | A | 218 | 27.613 | 28.361 | 25.529 | 1.00 | 31.15 |
| 1575 | O | ALA | A | 218 | 26.539 | 28.709 | 26.018 | 1.00 | 31.19 |

Figure 2-25

| 1576 | CB | ALA | A | 218 | 29.199 | 29.923 | 24.407 | 1.00 | 30.76 |
|---|---|---|---|---|---|---|---|---|---|
| 1577 | N | SER | A | 219 | 27.771 | 27.274 | 24.795 | 1.00 | 30.96 |
| 1578 | CA | SER | A | 219 | 26.679 | 26.362 | 24.487 | 1.00 | 31.23 |
| 1579 | C | SER | A | 219 | 26.385 | 25.476 | 25.684 | 1.00 | 31.50 |
| 1580 | O | SER | A | 219 | 27.187 | 24.600 | 26.008 | 1.00 | 30.63 |
| 1581 | CB | SER | A | 219 | 27.062 | 25.535 | 23.257 | 1.00 | 31.35 |
| 1582 | OG | SER | A | 219 | 25.973 | 24.795 | 22.745 | 1.00 | 31.74 |
| 1583 | N | ARG | A | 220 | 25.240 | 25.687 | 26.343 | 1.00 | 32.52 |
| 1584 | CA | ARG | A | 220 | 24.930 | 24.859 | 27.519 | 1.00 | 33.84 |
| 1585 | C | ARG | A | 220 | 23.463 | 24.496 | 27.638 | 1.00 | 34.32 |
| 1586 | O | ARG | A | 220 | 22.727 | 24.975 | 28.505 | 1.00 | 34.48 |
| 1587 | CB | ARG | A | 220 | 25.426 | 25.582 | 28.776 | 1.00 | 33.63 |
| 1588 | CG | ARG | A | 220 | 25.147 | 27.069 | 28.796 | 1.00 | 34.24 |
| 1589 | CD | ARG | A | 220 | 25.618 | 27.735 | 30.070 | 1.00 | 35.88 |
| 1590 | NE | ARG | A | 220 | 27.023 | 27.517 | 30.346 | 1.00 | 37.22 |
| 1591 | CZ | ARG | A | 220 | 27.541 | 26.815 | 31.336 | 1.00 | 37.40 |
| 1592 | NH1 | ARG | A | 220 | 26.758 | 26.220 | 32.219 | 1.00 | 37.56 |
| 1593 | NH2 | ARG | A | 220 | 28.863 | 26.708 | 31.450 | 1.00 | 38.33 |
| 1594 | N | PRO | A | 221 | 22.988 | 23.595 | 26.782 | 1.00 | 34.72 |
| 1595 | CA | PRO | A | 221 | 21.610 | 23.177 | 26.771 | 1.00 | 35.12 |
| 1596 | C | PRO | A | 221 | 21.070 | 22.782 | 28.127 | 1.00 | 36.33 |
| 1597 | O | PRO | A | 221 | 21.575 | 21.905 | 28.822 | 1.00 | 36.73 |
| 1598 | CB | PRO | A | 221 | 21.556 | 22.019 | 25.790 | 1.00 | 34.23 |
| 1599 | CG | PRO | A | 221 | 22.935 | 21.743 | 25.355 | 1.00 | 34.39 |
| 1600 | CD | PRO | A | 221 | 23.771 | 22.941 | 25.702 | 1.00 | 34.79 |
| 1601 | N | TRP | A | 222 | 19.982 | 23.430 | 28.537 | 1.00 | 37.81 |
| 1602 | CA | TRP | A | 222 | 19.253 | 23.204 | 29.764 | 1.00 | 38.35 |
| 1603 | C | TRP | A | 222 | 19.870 | 23.783 | 31.021 | 1.00 | 40.00 |
| 1604 | O | TRP | A | 222 | 19.244 | 23.803 | 32.087 | 1.00 | 40.39 |
| 1605 | CB | TRP | A | 222 | 18.989 | 21.704 | 29.960 | 1.00 | 37.21 |
| 1606 | CG | TRP | A | 222 | 18.017 | 21.170 | 28.940 | 1.00 | 36.16 |
| 1607 | CD1 | TRP | A | 222 | 16.705 | 21.496 | 28.811 | 1.00 | 35.54 |
| 1608 | CD2 | TRP | A | 222 | 18.304 | 20.213 | 27.913 | 1.00 | 35.39 |
| 1609 | NE1 | TRP | A | 222 | 16.151 | 20.796 | 27.769 | 1.00 | 35.19 |
| 1610 | CE2 | TRP | A | 222 | 17.111 | 20.004 | 27.203 | 1.00 | 35.06 |
| 1611 | CE3 | TRP | A | 222 | 19.453 | 19.511 | 27.533 | 1.00 | 35.46 |
| 1612 | CZ2 | TRP | A | 222 | 17.030 | 19.127 | 26.123 | 1.00 | 35.14 |
| 1613 | CZ3 | TRP | A | 222 | 19.370 | 18.638 | 26.460 | 1.00 | 35.39 |
| 1614 | CH2 | TRP | A | 222 | 18.165 | 18.456 | 25.770 | 1.00 | 35.07 |
| 1615 | N | ASP | A | 223 | 21.097 | 24.269 | 30.942 | 1.00 | 41.44 |
| 1616 | CA | ASP | A | 223 | 21.747 | 24.939 | 32.048 | 1.00 | 42.07 |
| 1617 | C | ASP | A | 223 | 21.001 | 26.228 | 32.378 | 1.00 | 43.35 |
| 1618 | O | ASP | A | 223 | 20.401 | 26.868 | 31.510 | 1.00 | 42.75 |
| 1619 | CB | ASP | A | 223 | 23.201 | 25.239 | 31.680 | 1.00 | 41.91 |
| 1620 | CG | ASP | A | 223 | 23.978 | 25.779 | 32.868 | 1.00 | 42.02 |
| 1621 | OD1 | ASP | A | 223 | 24.089 | 27.022 | 32.965 | 1.00 | 41.30 |
| 1622 | OD2 | ASP | A | 223 | 24.459 | 24.948 | 33.668 | 1.00 | 41.89 |
| 1623 | N | LYS | A | 224 | 21.083 | 26.633 | 33.640 | 1.00 | 44.97 |
| 1624 | CA | LYS | A | 224 | 20.452 | 27.832 | 34.149 | 1.00 | 45.85 |
| 1625 | C | LYS | A | 224 | 21.037 | 29.102 | 33.551 | 1.00 | 45.90 |
| 1626 | O | LYS | A | 224 | 20.369 | 30.142 | 33.550 | 1.00 | 45.61 |
| 1627 | CB | LYS | A | 224 | 20.612 | 27.872 | 35.684 | 1.00 | 47.34 |
| 1628 | CG | LYS | A | 224 | 22.069 | 28.062 | 36.100 | 1.00 | 49.04 |
| 1629 | CD | LYS | A | 224 | 22.200 | 28.799 | 37.419 | 1.00 | 50.57 |
| 1630 | CE | LYS | A | 224 | 22.329 | 30.304 | 37.224 | 1.00 | 51.48 |
| 1631 | NZ | LYS | A | 224 | 23.739 | 30.756 | 37.419 | 1.00 | 52.02 |
| 1632 | N | GLU | A | 225 | 22.281 | 29.047 | 33.071 | 1.00 | 45.79 |
| 1633 | CA | GLU | A | 225 | 22.912 | 30.222 | 32.498 | 1.00 | 45.61 |
| 1634 | C | GLU | A | 225 | 22.934 | 30.253 | 30.980 | 1.00 | 43.95 |
| 1635 | O | GLU | A | 225 | 23.804 | 30.950 | 30.441 | 1.00 | 43.88 |
| 1636 | CB | GLU | A | 225 | 24.348 | 30.358 | 33.009 | 1.00 | 47.52 |
| 1637 | CG | GLU | A | 225 | 24.465 | 30.295 | 34.527 | 1.00 | 49.63 |
| 1638 | CD | GLU | A | 225 | 25.931 | 30.264 | 34.930 | 1.00 | 51.27 |

Figure 2-26

| 1639 | OE1 | GLU | A | 225 | 26.658 | 31.171 | 34.461 | 1.00 | 52.70 |
|---|---|---|---|---|---|---|---|---|---|
| 1640 | OE2 | GLU | A | 225 | 26.323 | 29.336 | 35.663 | 1.00 | 52.08 |
| 1641 | N | ARG | A | 226 | 22.030 | 29.558 | 30.316 | 1.00 | 42.31 |
| 1642 | CA | ARG | A | 226 | 21.854 | 29.621 | 28.870 | 1.00 | 40.38 |
| 1643 | C | ARG | A | 226 | 21.618 | 31.059 | 28.409 | 1.00 | 38.31 |
| 1644 | O | ARG | A | 226 | 20.851 | 31.766 | 29.076 | 1.00 | 38.79 |
| 1645 | CB | ARG | A | 226 | 20.595 | 28.839 | 28.463 | 1.00 | 41.11 |
| 1646 | CG | ARG | A | 226 | 20.733 | 27.358 | 28.276 | 1.00 | 42.80 |
| 1647 | CD | ARG | A | 226 | 19.386 | 26.645 | 28.252 | 1.00 | 44.07 |
| 1648 | NE | ARG | A | 226 | 18.414 | 27.281 | 29.116 | 1.00 | 46.50 |
| 1649 | CZ | ARG | A | 226 | 17.366 | 26.721 | 29.696 | 1.00 | 47.73 |
| 1650 | NH1 | ARG | A | 226 | 17.078 | 25.440 | 29.522 | 1.00 | 48.79 |
| 1651 | NH2 | ARG | A | 226 | 16.571 | 27.446 | 30.475 | 1.00 | 48.31 |
| 1652 | N | ASP | A | 227 | 22.171 | 31.480 | 27.286 | 1.00 | 36.03 |
| 1653 | CA | ASP | A | 227 | 21.891 | 32.830 | 26.791 | 1.00 | 33.63 |
| 1654 | C | ASP | A | 227 | 21.674 | 32.838 | 25.285 | 1.00 | 32.31 |
| 1655 | O | ASP | A | 227 | 21.554 | 33.919 | 24.700 | 1.00 | 32.59 |
| 1656 | CB | ASP | A | 227 | 22.967 | 33.825 | 27.192 | 1.00 | 32.84 |
| 1657 | CG | ASP | A | 227 | 24.334 | 33.499 | 26.637 | 1.00 | 33.33 |
| 1658 | OD1 | ASP | A | 227 | 24.627 | 32.286 | 26.529 | 1.00 | 34.69 |
| 1659 | OD2 | ASP | A | 227 | 25.120 | 34.414 | 26.307 | 1.00 | 32.44 |
| 1660 | N | GLY | A | 228 | 21.550 | 31.672 | 24.654 | 1.00 | 30.62 |
| 1661 | CA | GLY | A | 228 | 21.366 | 31.677 | 23.188 | 1.00 | 28.87 |
| 1662 | C | GLY | A | 228 | 22.125 | 30.526 | 22.548 | 1.00 | 27.72 |
| 1663 | O | GLY | A | 228 | 23.023 | 29.955 | 23.172 | 1.00 | 28.88 |
| 1664 | N | PHE | A | 229 | 21.754 | 30.147 | 21.330 | 1.00 | 25.72 |
| 1665 | CA | PHE | A | 229 | 22.412 | 29.027 | 20.666 | 1.00 | 22.79 |
| 1666 | C | PHE | A | 229 | 23.772 | 29.488 | 20.159 | 1.00 | 22.85 |
| 1667 | O | PHE | A | 229 | 24.077 | 30.672 | 20.162 | 1.00 | 21.95 |
| 1668 | CB | PHE | A | 229 | 21.550 | 28.413 | 19.591 | 1.00 | 21.43 |
| 1669 | CG | PHE | A | 229 | 21.327 | 29.142 | 18.316 | 1.00 | 20.46 |
| 1670 | CD1 | PHE | A | 229 | 22.236 | 29.069 | 17.275 | 1.00 | 19.91 |
| 1671 | CD2 | PHE | A | 229 | 20.191 | 29.920 | 18.131 | 1.00 | 20.66 |
| 1672 | CE1 | PHE | A | 229 | 22.025 | 29.759 | 16.087 | 1.00 | 19.15 |
| 1673 | CE2 | PHE | A | 229 | 19.969 | 30.605 | 16.944 | 1.00 | 19.34 |
| 1674 | CZ | PHE | A | 229 | 20.894 | 30.517 | 15.928 | 1.00 | 18.75 |
| 1675 | N | VAL | A | 230 | 24.597 | 28.526 | 19.795 | 1.00 | 24.11 |
| 1676 | CA | VAL | A | 230 | 25.926 | 28.768 | 19.252 | 1.00 | 24.59 |
| 1677 | C | VAL | A | 230 | 25.972 | 28.253 | 17.810 | 1.00 | 24.91 |
| 1678 | O | VAL | A | 230 | 25.540 | 27.150 | 17.497 | 1.00 | 23.86 |
| 1679 | CB | VAL | A | 230 | 27.024 | 28.118 | 20.106 | 1.00 | 24.60 |
| 1680 | CG1 | VAL | A | 230 | 28.392 | 28.206 | 19.448 | 1.00 | 23.60 |
| 1681 | CG2 | VAL | A | 230 | 27.076 | 28.781 | 21.486 | 1.00 | 23.95 |
| 1682 | N | LEU | A | 231 | 26.347 | 29.141 | 16.910 | 1.00 | 26.19 |
| 1683 | CA | LEU | A | 231 | 26.347 | 28.898 | 15.471 | 1.00 | 27.19 |
| 1684 | C | LEU | A | 231 | 27.458 | 27.932 | 15.080 | 1.00 | 27.61 |
| 1685 | O | LEU | A | 231 | 28.575 | 28.038 | 15.608 | 1.00 | 27.83 |
| 1686 | CB | LEU | A | 231 | 26.532 | 30.244 | 14.786 | 1.00 | 27.96 |
| 1687 | CG | LEU | A | 231 | 26.207 | 30.468 | 13.329 | 1.00 | 29.21 |
| 1688 | CD1 | LEU | A | 231 | 25.563 | 29.269 | 12.659 | 1.00 | 29.75 |
| 1689 | CD2 | LEU | A | 231 | 25.315 | 31.702 | 13.176 | 1.00 | 29.24 |
| 1690 | N | GLY | A | 232 | 27.171 | 27.010 | 14.159 | 1.00 | 26.20 |
| 1691 | CA | GLY | A | 232 | 28.192 | 26.067 | 13.714 | 1.00 | 24.72 |
| 1692 | C | GLY | A | 232 | 28.023 | 25.702 | 12.248 | 1.00 | 23.99 |
| 1693 | O | GLY | A | 232 | 26.901 | 25.451 | 11.800 | 1.00 | 24.18 |
| 1694 | N | ASP | A | 233 | 29.117 | 25.550 | 11.512 | 1.00 | 23.28 |
| 1695 | CA | ASP | A | 233 | 29.061 | 25.134 | 10.117 | 1.00 | 22.60 |
| 1696 | C | ASP | A | 233 | 29.340 | 23.637 | 9.959 | 1.00 | 21.54 |
| 1697 | O | ASP | A | 233 | 29.988 | 23.027 | 10.810 | 1.00 | 20.87 |
| 1698 | CB | ASP | A | 233 | 30.079 | 25.883 | 9.261 | 1.00 | 23.15 |
| 1699 | CG | ASP | A | 233 | 30.103 | 27.370 | 9.485 | 1.00 | 24.40 |
| 1700 | OD1 | ASP | A | 233 | 29.054 | 27.994 | 9.749 | 1.00 | 24.44 |
| 1701 | OD2 | ASP | A | 233 | 31.216 | 27.933 | 9.398 | 1.00 | 26.06 |

Figure 2-27

| 1702 | N | GLY | A | 234 | 28.918 | 23.080 | 8.825 | 1.00 | 20.29 |
|---|---|---|---|---|---|---|---|---|---|
| 1703 | CA | GLY | A | 234 | 29.210 | 21.686 | 8.549 | 1.00 | 21.48 |
| 1704 | C | GLY | A | 234 | 28.252 | 21.018 | 7.587 | 1.00 | 22.09 |
| 1705 | O | GLY | A | 234 | 27.397 | 21.042 | 6.971 | 1.00 | 22.10 |
| 1706 | N | ALA | A | 235 | 28.367 | 19.694 | 7.476 | 1.00 | 23.04 |
| 1707 | CA | ALA | A | 235 | 27.488 | 18.924 | 6.612 | 1.00 | 24.26 |
| 1708 | C | ALA | A | 235 | 27.550 | 17.452 | 7.013 | 1.00 | 25.10 |
| 1709 | O | ALA | A | 235 | 28.601 | 16.959 | 7.413 | 1.00 | 25.69 |
| 1710 | CB | ALA | A | 235 | 27.839 | 19.064 | 5.141 | 1.00 | 24.12 |
| 1711 | N | GLY | A | 236 | 26.406 | 16.810 | 6.904 | 1.00 | 25.31 |
| 1712 | CA | GLY | A | 236 | 26.263 | 15.399 | 7.203 | 1.00 | 25.96 |
| 1713 | C | GLY | A | 236 | 25.401 | 14.764 | 6.106 | 1.00 | 27.84 |
| 1714 | O | GLY | A | 236 | 24.292 | 15.232 | 5.828 | 1.00 | 28.18 |
| 1715 | N | MET | A | 237 | 25.956 | 13.732 | 5.480 | 1.00 | 27.94 |
| 1716 | CA | MET | A | 237 | 25.264 | 13.032 | 4.412 | 1.00 | 28.58 |
| 1717 | C | MET | A | 237 | 25.021 | 11.579 | 4.791 | 1.00 | 29.18 |
| 1718 | O | MET | A | 237 | 25.840 | 10.946 | 5.457 | 1.00 | 30.25 |
| 1719 | CB | MET | A | 237 | 26.058 | 13.121 | 3.111 | 1.00 | 29.09 |
| 1720 | CG | MET | A | 237 | 26.241 | 14.540 | 2.584 | 1.00 | 30.84 |
| 1721 | SD | MET | A | 237 | 24.689 | 15.275 | 2.005 | 1.00 | 31.49 |
| 1722 | CE | MET | A | 237 | 23.983 | 13.854 | 1.197 | 1.00 | 32.58 |
| 1723 | N | LEU | A | 238 | 23.861 | 11.059 | 4.432 | 1.00 | 29.03 |
| 1724 | CA | LEU | A | 238 | 23.455 | 9.697 | 4.647 | 1.00 | 28.93 |
| 1725 | C | LEU | A | 238 | 23.154 | 9.058 | 3.274 | 1.00 | 30.08 |
| 1726 | O | LEU | A | 238 | 22.641 | 9.736 | 2.395 | 1.00 | 30.53 |
| 1727 | CB | LEU | A | 238 | 22.174 | 9.573 | 5.445 | 1.00 | 29.18 |
| 1728 | CG | LEU | A | 238 | 21.953 | 9.963 | 6.879 | 1.00 | 28.28 |
| 1729 | CD1 | LEU | A | 238 | 21.343 | 8.806 | 7.674 | 1.00 | 28.10 |
| 1730 | CD2 | LEU | A | 238 | 23.203 | 10.416 | 7.588 | 1.00 | 28.92 |
| 1731 | N | VAL | A | 239 | 23.389 | 7.769 | 3.139 | 1.00 | 31.20 |
| 1732 | CA | VAL | A | 239 | 22.950 | 7.027 | 1.966 | 1.00 | 31.08 |
| 1733 | C | VAL | A | 239 | 21.801 | 6.122 | 2.442 | 1.00 | 31.88 |
| 1734 | O | VAL | A | 239 | 21.972 | 5.326 | 3.365 | 1.00 | 31.48 |
| 1735 | CB | VAL | A | 239 | 24.047 | 6.189 | 1.317 | 1.00 | 30.98 |
| 1736 | CG1 | VAL | A | 239 | 23.493 | 5.297 | 0.207 | 1.00 | 30.65 |
| 1737 | CG2 | VAL | A | 239 | 25.150 | 7.069 | 0.756 | 1.00 | 30.59 |
| 1738 | N | LEU | A | 240 | 20.614 | 6.367 | 1.910 | 1.00 | 32.81 |
| 1739 | CA | LEU | A | 240 | 19.465 | 5.539 | 2.267 | 1.00 | 34.06 |
| 1740 | C | LEU | A | 240 | 19.197 | 4.602 | 1.091 | 1.00 | 35.24 |
| 1741 | O | LEU | A | 240 | 19.377 | 5.025 | -0.056 | 1.00 | 35.94 |
| 1742 | CB | LEU | A | 240 | 18.233 | 6.367 | 2.568 | 1.00 | 34.52 |
| 1743 | CG | LEU | A | 240 | 18.327 | 7.391 | 3.694 | 1.00 | 34.89 |
| 1744 | CD1 | LEU | A | 240 | 17.392 | 8.562 | 3.424 | 1.00 | 35.01 |
| 1745 | CD2 | LEU | A | 240 | 18.007 | 6.741 | 5.029 | 1.00 | 34.67 |
| 1746 | N | GLU | A | 241 | 18.858 | 3.355 | 1.376 | 1.00 | 36.34 |
| 1747 | CA | GLU | A | 241 | 18.549 | 2.426 | 0.288 | 1.00 | 37.40 |
| 1748 | C | GLU | A | 241 | 17.604 | 1.337 | 0.790 | 1.00 | 38.22 |
| 1749 | O | GLU | A | 241 | 17.459 | 1.156 | 1.997 | 1.00 | 37.42 |
| 1750 | CB | GLU | A | 241 | 19.775 | 1.860 | -0.376 | 1.00 | 37.02 |
| 1751 | CG | GLU | A | 241 | 20.414 | 0.626 | 0.198 | 1.00 | 36.23 |
| 1752 | CD | GLU | A | 241 | 21.624 | 0.198 | -0.629 | 1.00 | 36.50 |
| 1753 | OE1 | GLU | A | 241 | 22.743 | 0.616 | -0.277 | 1.00 | 36.26 |
| 1754 | OE2 | GLU | A | 241 | 21.457 | -0.538 | -1.624 | 1.00 | 36.05 |
| 1755 | N | GLU | A | 242 | 16.839 | 0.808 | -0.161 | 1.00 | 39.24 |
| 1756 | CA | GLU | A | 242 | 15.825 | -0.196 | 0.151 | 1.00 | 40.59 |
| 1757 | C | GLU | A | 242 | 16.502 | -1.471 | 0.625 | 1.00 | 42.13 |
| 1758 | O | GLU | A | 242 | 17.499 | -1.913 | 0.049 | 1.00 | 42.65 |
| 1759 | CB | GLU | A | 242 | 14.947 | -0.425 | -1.073 | 1.00 | 40.67 |
| 1760 | CG | GLU | A | 242 | 13.767 | -1.365 | -0.852 | 1.00 | 40.14 |
| 1761 | CD | GLU | A | 242 | 14.158 | -2.796 | -1.182 | 1.00 | 40.03 |
| 1762 | OE1 | GLU | A | 242 | 15.061 | -2.964 | -2.033 | 1.00 | 40.30 |
| 1763 | OE2 | GLU | A | 242 | 13.583 | -3.715 | -0.577 | 1.00 | 40.12 |
| 1764 | N | TYR | A | 243 | 15.985 | -2.050 | 1.688 | 1.00 | 44.48 |

Figure 2-28

| 1765 | CA | TYR | A | 243 | 16.528 | -3.249 | 2.295 | 1.00 | 47.55 |
|---|---|---|---|---|---|---|---|---|---|
| 1766 | C | TYR | A | 243 | 16.969 | -4.314 | 1.312 | 1.00 | 49.06 |
| 1767 | O | TYR | A | 243 | 18.165 | -4.612 | 1.194 | 1.00 | 48.62 |
| 1768 | CB | TYR | A | 243 | 15.501 | -3.828 | 3.281 | 1.00 | 49.37 |
| 1769 | CG | TYR | A | 243 | 16.082 | -4.940 | 4.129 | 1.00 | 51.38 |
| 1770 | CD1 | TYR | A | 243 | 16.964 | -4.671 | 5.162 | 1.00 | 51.69 |
| 1771 | CD2 | TYR | A | 243 | 15.741 | -6.264 | 3.873 | 1.00 | 52.26 |
| 1772 | CE1 | TYR | A | 243 | 17.492 | -5.698 | 5.921 | 1.00 | 52.76 |
| 1773 | CE2 | TYR | A | 243 | 16.261 | -7.293 | 4.635 | 1.00 | 52.69 |
| 1774 | CZ | TYR | A | 243 | 17.141 | -7.004 | 5.652 | 1.00 | 52.88 |
| 1775 | OH | TYR | A | 243 | 17.668 | -8.024 | 6.409 | 1.00 | 53.60 |
| 1776 | N | GLU | A | 244 | 16.023 | -4.912 | 0.584 | 1.00 | 50.65 |
| 1777 | CA | GLU | A | 244 | 16.323 | -5.960 | -0.383 | 1.00 | 51.25 |
| 1778 | C | GLU | A | 244 | 17.448 | -5.559 | 1.325 | 1.00 | 51.58 |
| 1779 | O | GLU | A | 244 | 18.371 | -6.345 | -1.534 | 1.00 | 51.59 |
| 1780 | CB | GLU | A | 244 | 15.091 | -6.361 | -1.191 | 1.00 | 51.54 |
| 1781 | CG | GLU | A | 244 | 13.925 | -6.882 | -0.386 | 1.00 | 52.35 |
| 1782 | CD | GLU | A | 244 | 14.242 | -8.097 | 0.454 | 1.00 | 53.32 |
| 1783 | OE1 | GLU | A | 244 | 15.188 | -8.845 | 0.125 | 1.00 | 53.91 |
| 1784 | OE2 | GLU | A | 244 | 13.535 | -8.312 | 1.464 | 1.00 | 53.96 |
| 1785 | N | HIS | A | 245 | 17.376 | -4.358 | -1.889 | 1.00 | 52.37 |
| 1786 | CA | HIS | A | 245 | 18.422 | -3.872 | -2.788 | 1.00 | 53.53 |
| 1787 | C | HIS | A | 245 | 19.776 | -3.940 | -2.079 | 1.00 | 54.72 |
| 1788 | O | HIS | A | 245 | 20.741 | -4.460 | -2.619 | 1.00 | 54.26 |
| 1789 | CB | HIS | A | 245 | 18.120 | -2.454 | -3.239 | 1.00 | 53.08 |
| 1790 | CG | HIS | A | 245 | 19.042 | -1.894 | -4.277 | 1.00 | 52.59 |
| 1791 | ND1 | HIS | A | 245 | 20.337 | -1.511 | -4.003 | 1.00 | 52.62 |
| 1792 | CD2 | HIS | A | 245 | 18.841 | -1.610 | -5.584 | 1.00 | 52.43 |
| 1793 | CE1 | HIS | A | 245 | 20.899 | -1.032 | -5.096 | 1.00 | 52.61 |
| 1794 | NE2 | HIS | A | 245 | 20.012 | -1.087 | -6.075 | 1.00 | 52.66 |
| 1795 | N | ALA | A | 246 | 19.814 | -3.419 | -0.859 | 1.00 | 56.49 |
| 1796 | CA | ALA | A | 246 | 20.984 | -3.410 | -0.006 | 1.00 | 58.02 |
| 1797 | C | ALA | A | 246 | 21.414 | -4.832 | 0.362 | 1.00 | 59.33 |
| 1798 | O | ALA | A | 246 | 22.605 | -5.134 | 0.342 | 1.00 | 59.12 |
| 1799 | CB | ALA | A | 246 | 20.685 | -2.632 | 1.276 | 1.00 | 57.55 |
| 1800 | N | LYS | A | 247 | 20.452 | -5.691 | 0.677 | 1.00 | 60.88 |
| 1801 | CA | LYS | A | 247 | 20.736 | -7.079 | 1.017 | 1.00 | 62.53 |
| 1802 | C | LYS | A | 247 | 21.478 | -7.785 | -0.112 | 1.00 | 63.46 |
| 1803 | O | LYS | A | 247 | 22.586 | -8.299 | 0.062 | 1.00 | 64.16 |
| 1804 | CB | LYS | A | 247 | 19.444 | -7.828 | 1.336 | 1.00 | 62.93 |
| 1805 | CG | LYS | A | 247 | 19.190 | -8.093 | 2.806 | 1.00 | 63.75 |
| 1806 | CD | LYS | A | 247 | 18.323 | -9.329 | 3.008 | 1.00 | 64.65 |
| 1807 | CE | LYS | A | 247 | 18.834 | -10.207 | 4.137 | 1.00 | 65.11 |
| 1808 | NZ | LYS | A | 247 | 17.770 | -11.078 | 4.710 | 1.00 | 65.33 |
| 1809 | N | LYS | A | 248 | 20.890 | -7.806 | -1.300 | 1.00 | 63.98 |
| 1810 | CA | LYS | A | 248 | 21.459 | -8.440 | -2.475 | 1.00 | 64.52 |
| 1811 | C | LYS | A | 248 | 22.870 | -7.995 | -2.808 | 1.00 | 64.22 |
| 1812 | O | LYS | A | 248 | 23.676 | -8.794 | -3.305 | 1.00 | 64.61 |
| 1813 | CB | LYS | A | 248 | 20.526 | -8.201 | -3.673 | 1.00 | 65.73 |
| 1814 | CG | LYS | A | 248 | 21.041 | -8.731 | -4.997 | 1.00 | 67.49 |
| 1815 | CD | LYS | A | 248 | 19.933 | -9.335 | -5.847 | 1.00 | 68.99 |
| 1816 | CE | LYS | A | 248 | 19.422 | -10.650 | -5.279 | 1.00 | 69.64 |
| 1817 | NZ | LYS | A | 248 | 18.013 | -10.943 | -5.671 | 1.00 | 69.80 |
| 1818 | N | ARG | A | 249 | 23.220 | -6.740 | -2.582 | 1.00 | 63.72 |
| 1819 | CA | ARG | A | 249 | 24.542 | -6.222 | -2.893 | 1.00 | 63.29 |
| 1820 | C | ARG | A | 249 | 25.520 | -6.419 | -1.743 | 1.00 | 62.36 |
| 1821 | O | ARG | A | 249 | 26.712 | -6.136 | -1.891 | 1.00 | 62.39 |
| 1822 | CB | ARG | A | 249 | 24.449 | -4.730 | -3.260 | 1.00 | 63.82 |
| 1823 | CG | ARG | A | 249 | 23.678 | -3.920 | -2.231 | 1.00 | 64.36 |
| 1824 | CD | ARG | A | 249 | 23.874 | -2.430 | -2.376 | 1.00 | 64.71 |
| 1825 | NE | ARG | A | 249 | 25.279 | -2.056 | -2.335 | 1.00 | 64.93 |
| 1826 | CZ | ARG | A | 249 | 25.762 | -0.961 | -1.772 | 1.00 | 64.91 |
| 1827 | NH1 | ARG | A | 249 | 24.951 | -0.101 | -1.182 | 1.00 | 64.78 |

Figure 2-29

| 1828 | NH2 | ARG | A | 249 | 27.067 | -0.745 | -1.812 | 1.00 | 65.38 |
|---|---|---|---|---|---|---|---|---|---|
| 1829 | N | GLY | A | 250 | 25.040 | -6.911 | -0.607 | 1.00 | 60.87 |
| 1830 | CA | GLY | A | 250 | 25.913 | -7.131 | 0.548 | 1.00 | 59.90 |
| 1831 | C | GLY | A | 250 | 26.469 | -5.794 | 1.037 | 1.00 | 58.77 |
| 1832 | O | GLY | A | 250 | 27.666 | -5.532 | 0.986 | 1.00 | 58.78 |
| 1833 | N | ALA | A | 251 | 25.565 | -4.945 | 1.522 | 1.00 | 57.41 |
| 1834 | CA | ALA | A | 251 | 25.944 | -3.621 | 1.977 | 1.00 | 55.66 |
| 1835 | C | ALA | A | 251 | 26.096 | -3.568 | 3.491 | 1.00 | 54.72 |
| 1836 | O | ALA | A | 251 | 25.302 | -4.138 | 4.231 | 1.00 | 55.01 |
| 1837 | CB | ALA | A | 251 | 24.901 | -2.602 | 1.531 | 1.00 | 55.46 |
| 1838 | N | LYS | A | 252 | 27.088 | -2.814 | 3.936 | 1.00 | 53.10 |
| 1839 | CA | LYS | A | 252 | 27.217 | -2.428 | 5.336 | 1.00 | 51.33 |
| 1840 | C | LYS | A | 252 | 25.891 | -1.818 | 5.792 | 1.00 | 49.96 |
| 1841 | O | LYS | A | 252 | 25.612 | -0.691 | 5.346 | 1.00 | 50.79 |
| 1842 | CB | LYS | A | 252 | 28.294 | -1.349 | 5.418 | 1.00 | 51.97 |
| 1843 | CG | LYS | A | 252 | 29.460 | -1.544 | 6.340 | 1.00 | 52.61 |
| 1844 | CD | LYS | A | 252 | 30.208 | -0.239 | 6.593 | 1.00 | 53.01 |
| 1845 | CE | LYS | A | 252 | 30.836 | 0.346 | 5.343 | 1.00 | 52.98 |
| 1846 | NZ | LYS | A | 252 | 32.219 | -0.157 | 5.097 | 1.00 | 53.69 |
| 1847 | N | ILE | A | 253 | 25.090 | -2.482 | 6.604 | 1.00 | 47.12 |
| 1848 | CA | ILE | A | 253 | 23.840 | -1.881 | 7.062 | 1.00 | 44.71 |
| 1849 | C | ILE | A | 253 | 24.020 | -1.246 | 8.435 | 1.00 | 43.36 |
| 1850 | O | ILE | A | 253 | 24.012 | -1.935 | 9.462 | 1.00 | 44.22 |
| 1851 | CB | ILE | A | 253 | 22.674 | -2.884 | 7.110 | 1.00 | 45.09 |
| 1852 | CG1 | ILE | A | 253 | 22.284 | -3.326 | 5.694 | 1.00 | 44.84 |
| 1853 | CG2 | ILE | A | 253 | 21.477 | -2.282 | 7.844 | 1.00 | 44.25 |
| 1854 | CD1 | ILE | A | 253 | 20.932 | -4.007 | 5.591 | 1.00 | 44.67 |
| 1855 | N | TYR | A | 254 | 24.049 | 0.082 | 8.495 | 1.00 | 41.00 |
| 1856 | CA | TYR | A | 254 | 24.201 | 0.773 | 9.772 | 1.00 | 38.50 |
| 1857 | C | TYR | A | 254 | 22.948 | 0.731 | 10.628 | 1.00 | 37.38 |
| 1858 | O | TYR | A | 254 | 23.010 | 0.615 | 11.853 | 1.00 | 38.15 |
| 1859 | CB | TYR | A | 254 | 24.571 | 2.235 | 9.557 | 1.00 | 37.33 |
| 1860 | CG | TYR | A | 254 | 25.979 | 2.477 | 9.071 | 1.00 | 36.11 |
| 1861 | CD1 | TYR | A | 254 | 26.250 | 2.657 | 7.726 | 1.00 | 35.30 |
| 1862 | CD2 | TYR | A | 254 | 27.031 | 2.550 | 9.972 | 1.00 | 35.51 |
| 1863 | CE1 | TYR | A | 254 | 27.538 | 2.899 | 7.292 | 1.00 | 35.59 |
| 1864 | CE2 | TYR | A | 254 | 28.322 | 2.787 | 9.545 | 1.00 | 34.81 |
| 1865 | CZ | TYR | A | 254 | 28.567 | 2.969 | 8.209 | 1.00 | 35.14 |
| 1866 | OH | TYR | A | 254 | 29.845 | 3.209 | 7.764 | 1.00 | 35.01 |
| 1867 | N | ALA | A | 255 | 21.792 | 0.886 | 10.004 | 1.00 | 36.44 |
| 1868 | CA | ALA | A | 255 | 20.536 | 0.899 | 10.748 | 1.00 | 35.71 |
| 1869 | C | ALA | A | 255 | 19.367 | 0.917 | 9.769 | 1.00 | 35.68 |
| 1870 | O | ALA | A | 255 | 19.573 | 0.959 | 8.558 | 1.00 | 34.91 |
| 1871 | CB | ALA | A | 255 | 20.481 | 2.114 | 11.662 | 1.00 | 35.22 |
| 1872 | N | GLU | A | 256 | 18.168 | 0.899 | 10.321 | 1.00 | 36.53 |
| 1873 | CA | GLU | A | 256 | 16.945 | 0.951 | 9.552 | 1.00 | 37.42 |
| 1874 | C | GLU | A | 256 | 16.152 | 2.209 | 9.902 | 1.00 | 37.04 |
| 1875 | O | GLU | A | 256 | 15.941 | 2.490 | 11.086 | 1.00 | 36.85 |
| 1876 | CB | GLU | A | 256 | 16.054 | -0.267 | 9.831 | 1.00 | 39.31 |
| 1877 | CG | GLU | A | 256 | 15.103 | -0.594 | 8.690 | 1.00 | 42.01 |
| 1878 | CD | GLU | A | 256 | 14.074 | -1.643 | 9.048 | 1.00 | 43.86 |
| 1879 | OE1 | GLU | A | 256 | 12.853 | -1.395 | 8.910 | 1.00 | 44.65 |
| 1880 | OE2 | GLU | A | 256 | 14.479 | -2.750 | 9.478 | 1.00 | 45.17 |
| 1881 | N | LEU | A | 257 | 15.723 | 2.931 | 8.874 | 1.00 | 36.43 |
| 1882 | CA | LEU | A | 257 | 14.882 | 4.120 | 9.112 | 1.00 | 35.83 |
| 1883 | C | LEU | A | 257 | 13.456 | 3.603 | 9.292 | 1.00 | 35.09 |
| 1884 | O | LEU | A | 257 | 12.950 | 2.950 | 8.368 | 1.00 | 35.81 |
| 1885 | CB | LEU | A | 257 | 14.990 | 5.075 | 7.952 | 1.00 | 36.17 |
| 1886 | CG | LEU | A | 257 | 14.474 | 6.497 | 8.023 | 1.00 | 36.62 |
| 1887 | CD1 | LEU | A | 257 | 14.176 | 6.980 | 9.428 | 1.00 | 36.47 |
| 1888 | CD2 | LEU | A | 257 | 15.503 | 7.434 | 7.371 | 1.00 | 36.59 |
| 1889 | N | VAL | A | 258 | 12.898 | 3.663 | 10.496 | 1.00 | 34.38 |
| 1890 | CA | VAL | A | 258 | 11.603 | 3.034 | 10.719 | 1.00 | 34.14 |

Figure 2-30

| 1891 | C | VAL | A | 258 | 10.495 | 4.012 | 11.049 | 1.00 | 33.65 |
|---|---|---|---|---|---|---|---|---|---|
| 1892 | O | VAL | A | 258 | 9.349 | 3.561 | 11.194 | 1.00 | 34.38 |
| 1893 | CB | VAL | A | 258 | 11.619 | 1.965 | 11.845 | 1.00 | 34.54 |
| 1894 | CG1 | VAL | A | 258 | 12.689 | 0.913 | 11.602 | 1.00 | 33.95 |
| 1895 | CG2 | VAL | A | 258 | 11.761 | 2.594 | 13.219 | 1.00 | 32.70 |
| 1896 | N | GLY | A | 259 | 10.787 | 5.287 | 11.243 | 1.00 | 33.01 |
| 1897 | CA | GLY | A | 259 | 9.718 | 6.223 | 11.594 | 1.00 | 32.64 |
| 1898 | C | GLY | A | 259 | 10.094 | 7.640 | 11.195 | 1.00 | 33.38 |
| 1899 | O | GLY | A | 259 | 11.260 | 8.010 | 11.307 | 1.00 | 34.33 |
| 1900 | N | PHE | A | 260 | 9.104 | 8.408 | 10.758 | 1.00 | 32.82 |
| 1901 | CA | PHE | A | 260 | 9.288 | 9.793 | 10.342 | 1.00 | 31.11 |
| 1902 | C | PHE | A | 260 | 8.028 | 10.607 | 10.608 | 1.00 | 30.38 |
| 1903 | O | PHE | A | 260 | 6.958 | 10.321 | 10.062 | 1.00 | 30.80 |
| 1904 | CB | PHE | A | 260 | 9.666 | 9.859 | 8.864 | 1.00 | 30.74 |
| 1905 | CG | PHE | A | 260 | 9.673 | 11.244 | 8.289 | 1.00 | 30.39 |
| 1906 | CD1 | PHE | A | 260 | 10.339 | 12.272 | 8.939 | 1.00 | 30.56 |
| 1907 | CD2 | PHE | A | 260 | 9.014 | 11.518 | 7.103 | 1.00 | 30.06 |
| 1908 | CE1 | PHE | A | 260 | 10.344 | 13.552 | 8.419 | 1.00 | 30.43 |
| 1909 | CE2 | PHE | A | 260 | 9.023 | 12.791 | 6.566 | 1.00 | 29.90 |
| 1910 | CZ | PHE | A | 260 | 9.687 | 13.803 | 7.227 | 1.00 | 30.57 |
| 1911 | N | GLY | A | 261 | 8.141 | 11.610 | 11.470 | 1.00 | 29.70 |
| 1912 | CA | GLY | A | 261 | 7.008 | 12.434 | 11.837 | 1.00 | 28.92 |
| 1913 | C | GLY | A | 261 | 7.223 | 13.919 | 11.616 | 1.00 | 29.15 |
| 1914 | O | GLY | A | 261 | 8.264 | 14.502 | 11.927 | 1.00 | 28.06 |
| 1915 | N | MET | A | 262 | 6.195 | 14.568 | 11.075 | 1.00 | 29.65 |
| 1916 | CA | MET | A | 262 | 6.234 | 16.006 | 10.832 | 1.00 | 30.20 |
| 1917 | C | MET | A | 262 | 5.070 | 16.647 | 11.590 | 1.00 | 30.06 |
| 1918 | O | MET | A | 262 | 4.076 | 15.969 | 11.820 | 1.00 | 30.13 |
| 1919 | CB | MET | A | 262 | 6.108 | 16.345 | 9.363 | 1.00 | 30.45 |
| 1920 | CG | MET | A | 262 | 7.201 | 15.870 | 8.440 | 1.00 | 30.83 |
| 1921 | SD | MET | A | 262 | 6.528 | 15.370 | 6.839 | 1.00 | 33.07 |
| 1922 | CE | MET | A | 262 | 6.552 | 16.931 | 5.973 | 1.00 | 33.59 |
| 1923 | N | SER | A | 263 | 5.220 | 17.898 | 11.968 | 1.00 | 30.55 |
| 1924 | CA | SER | A | 263 | 4.195 | 18.630 | 12.684 | 1.00 | 31.14 |
| 1925 | C | SER | A | 263 | 4.371 | 20.143 | 12.513 | 1.00 | 31.88 |
| 1926 | O | SER | A | 263 | 5.461 | 20.618 | 12.178 | 1.00 | 31.41 |
| 1927 | CB | SER | A | 263 | 4.271 | 18.315 | 14.184 | 1.00 | 31.36 |
| 1928 | OG | SER | A | 263 | 5.026 | 19.356 | 14.817 | 1.00 | 32.23 |
| 1929 | N | SER | A | 264 | 3.304 | 20.883 | 12.800 | 1.00 | 32.27 |
| 1930 | CA | SER | A | 264 | 3.383 | 22.344 | 12.751 | 1.00 | 33.13 |
| 1931 | C | SER | A | 264 | 2.953 | 22.913 | 14.107 | 1.00 | 33.50 |
| 1932 | O | SER | A | 264 | 2.190 | 22.277 | 14.843 | 1.00 | 34.89 |
| 1933 | CB | SER | A | 264 | 2.563 | 22.928 | 11.619 | 1.00 | 33.19 |
| 1934 | OG | SER | A | 264 | 3.245 | 22.889 | 10.378 | 1.00 | 32.30 |
| 1935 | N | ASP | A | 265 | 3.549 | 24.024 | 14.495 | 1.00 | 32.03 |
| 1936 | CA | ASP | A | 265 | 3.310 | 24.635 | 15.783 | 1.00 | 31.81 |
| 1937 | C | ASP | A | 265 | 2.084 | 25.546 | 15.757 | 1.00 | 33.26 |
| 1938 | O | ASP | A | 265 | 1.225 | 25.499 | 16.637 | 1.00 | 33.79 |
| 1939 | CB | ASP | A | 265 | 4.523 | 25.457 | 16.231 | 1.00 | 29.59 |
| 1940 | CG | ASP | A | 265 | 5.554 | 24.701 | 17.034 | 1.00 | 27.79 |
| 1941 | OD1 | ASP | A | 265 | 5.426 | 23.486 | 17.253 | 1.00 | 25.02 |
| 1942 | OD2 | ASP | A | 265 | 6.556 | 25.343 | 17.450 | 1.00 | 27.38 |
| 1943 | N | ALA | A | 266 | 2.039 | 26.413 | 14.753 | 1.00 | 34.80 |
| 1944 | CA | ALA | A | 266 | 0.929 | 27.352 | 14.616 | 1.00 | 36.45 |
| 1945 | C | ALA | A | 266 | 0.882 | 28.274 | 15.829 | 1.00 | 38.12 |
| 1946 | O | ALA | A | 266 | -0.183 | 28.542 | 16.390 | 1.00 | 39.22 |
| 1947 | CB | ALA | A | 266 | -0.366 | 26.578 | 14.412 | 1.00 | 35.63 |
| 1948 | N | TYR | A | 267 | 2.047 | 28.804 | 16.209 | 1.00 | 39.02 |
| 1949 | CA | TYR | A | 267 | 2.138 | 29.676 | 17.365 | 1.00 | 40.82 |
| 1950 | C | TYR | A | 267 | 2.858 | 30.985 | 17.074 | 1.00 | 40.11 |
| 1951 | O | TYR | A | 267 | 2.279 | 32.071 | 17.056 | 1.00 | 40.09 |
| 1952 | CB | TYR | A | 267 | 2.853 | 28.938 | 18.513 | 1.00 | 42.94 |
| 1953 | CG | TYR | A | 267 | 2.995 | 29.795 | 19.754 | 1.00 | 45.78 |

Figure 2-31

| 1954 | CD1 | TYR | A | 267 | 1.870 | 30.187 | 20.475 | 1.00 | 46.70 |
|---|---|---|---|---|---|---|---|---|---|
| 1955 | CD2 | TYR | A | 267 | 4.240 | 30.225 | 20.194 | 1.00 | 46.17 |
| 1956 | CE1 | TYR | A | 267 | 1.997 | 30.980 | 21.598 | 1.00 | 47.78 |
| 1957 | CE2 | TYR | A | 267 | 4.369 | 31.016 | 21.316 | 1.00 | 46.66 |
| 1958 | CZ | TYR | A | 267 | 3.246 | 31.393 | 22.012 | 1.00 | 47.81 |
| 1959 | OH | TYR | A | 267 | 3.352 | 32.177 | 23.146 | 1.00 | 49.51 |
| 1960 | N | HIS | A | 268 | 4.167 | 30.890 | 16.898 | 1.00 | 39.39 |
| 1961 | CA | HIS | A | 268 | 4.985 | 32.066 | 16.641 | 1.00 | 38.82 |
| 1962 | C | HIS | A | 268 | 5.976 | 31.797 | 15.519 | 1.00 | 38.25 |
| 1963 | O | HIS | A | 268 | 6.275 | 30.640 | 15.227 | 1.00 | 37.62 |
| 1964 | CB | HIS | A | 268 | 5.684 | 32.479 | 17.942 | 1.00 | 38.89 |
| 1965 | CG | HIS | A | 268 | 6.302 | 33.838 | 17.821 | 1.00 | 38.92 |
| 1966 | ND1 | HIS | A | 268 | 7.602 | 34.018 | 17.404 | 1.00 | 39.06 |
| 1967 | CD2 | HIS | A | 268 | 5.784 | 35.065 | 18.025 | 1.00 | 39.28 |
| 1968 | CE1 | HIS | A | 268 | 7.871 | 35.309 | 17.376 | 1.00 | 39.76 |
| 1969 | NE2 | HIS | A | 268 | 6.783 | 35.966 | 17.743 | 1.00 | 40.01 |
| 1970 | N | MET | A | 269 | 6.475 | 32.851 | 14.890 | 1.00 | 38.43 |
| 1971 | CA | MET | A | 269 | 7.351 | 32.732 | 13.739 | 1.00 | 39.01 |
| 1972 | C | MET | A | 269 | 8.749 | 32.275 | 14.107 | 1.00 | 39.15 |
| 1973 | O | MET | A | 269 | 9.426 | 31.657 | 13.275 | 1.00 | 39.25 |
| 1974 | CB | MET | A | 269 | 7.386 | 34.016 | 12.910 | 1.00 | 38.43 |
| 1975 | CG | MET | A | 269 | 7.675 | 35.291 | 13.655 | 1.00 | 38.54 |
| 1976 | SD | MET | A | 269 | 8.284 | 36.624 | 12.597 | 1.00 | 39.05 |
| 1977 | CE | MET | A | 269 | 6.747 | 37.295 | 11.973 | 1.00 | 38.85 |
| 1978 | N | THR | A | 270 | 9.206 | 32.554 | 15.318 | 1.00 | 39.79 |
| 1979 | CA | THR | A | 270 | 10.544 | 32.142 | 15.738 | 1.00 | 39.79 |
| 1980 | C | THR | A | 270 | 10.491 | 31.386 | 17.061 | 1.00 | 39.73 |
| 1981 | O | THR | A | 270 | 11.262 | 30.461 | 17.286 | 1.00 | 40.16 |
| 1982 | CB | THR | A | 270 | 11.500 | 33.336 | 15.909 | 1.00 | 39.47 |
| 1983 | OG1 | THR | A | 270 | 10.849 | 34.378 | 16.650 | 1.00 | 38.86 |
| 1984 | CG2 | THR | A | 270 | 11.946 | 33.850 | 14.549 | 1.00 | 39.41 |
| 1985 | N | SER | A | 271 | 9.562 | 31.784 | 17.912 | 1.00 | 39.92 |
| 1986 | CA | SER | A | 271 | 9.368 | 31.191 | 19.218 | 1.00 | 40.15 |
| 1987 | C | SER | A | 271 | 8.529 | 29.923 | 19.208 | 1.00 | 39.41 |
| 1988 | O | SER | A | 271 | 7.519 | 29.833 | 18.522 | 1.00 | 38.39 |
| 1989 | CB | SER | A | 271 | 8.655 | 32.218 | 20.122 | 1.00 | 40.93 |
| 1990 | OG | SER | A | 271 | 9.597 | 32.892 | 20.930 | 1.00 | 42.94 |
| 1991 | N | PRO | A | 272 | 8.916 | 28.967 | 20.033 | 1.00 | 39.55 |
| 1992 | CA | PRO | A | 272 | 8.149 | 27.755 | 20.264 | 1.00 | 39.89 |
| 1993 | C | PRO | A | 272 | 7.144 | 27.989 | 21.382 | 1.00 | 40.70 |
| 1994 | O | PRO | A | 272 | 7.253 | 28.945 | 22.155 | 1.00 | 40.74 |
| 1995 | CB | PRO | A | 272 | 9.213 | 26.763 | 20.710 | 1.00 | 39.54 |
| 1996 | CG | PRO | A | 272 | 10.251 | 27.585 | 21.378 | 1.00 | 39.69 |
| 1997 | CD | PRO | A | 272 | 10.104 | 29.011 | 20.924 | 1.00 | 39.50 |
| 1998 | N | PRO | A | 273 | 6.128 | 27.155 | 21.451 | 1.00 | 41.57 |
| 1999 | CA | PRO | A | 273 | 5.155 | 27.209 | 22.529 | 1.00 | 41.97 |
| 2000 | C | PRO | A | 273 | 5.763 | 26.687 | 23.815 | 1.00 | 42.79 |
| 2001 | O | PRO | A | 273 | 6.367 | 25.604 | 23.834 | 1.00 | 42.22 |
| 2002 | CB | PRO | A | 273 | 4.021 | 26.336 | 22.032 | 1.00 | 41.91 |
| 2003 | CG | PRO | A | 273 | 4.442 | 25.701 | 20.769 | 1.00 | 41.49 |
| 2004 | CD | PRO | A | 273 | 5.908 | 25.976 | 20.573 | 1.00 | 41.55 |
| 2005 | N | GLU | A | 274 | 5.557 | 27.355 | 24.947 | 1.00 | 44.77 |
| 2006 | CA | GLU | A | 274 | 6.113 | 26.899 | 26.229 | 1.00 | 46.56 |
| 2007 | C | GLU | A | 274 | 5.820 | 25.427 | 26.481 | 1.00 | 45.89 |
| 2008 | O | GLU | A | 274 | 6.614 | 24.681 | 27.049 | 1.00 | 46.05 |
| 2009 | CB | GLU | A | 274 | 5.598 | 27.763 | 27.382 | 1.00 | 48.17 |
| 2010 | CG | GLU | A | 274 | 6.173 | 29.169 | 27.404 | 1.00 | 49.92 |
| 2011 | CD | GLU | A | 274 | 6.416 | 29.712 | 28.793 | 1.00 | 51.48 |
| 2012 | OE1 | GLU | A | 274 | 5.443 | 30.190 | 29.421 | 1.00 | 52.14 |
| 2013 | OE2 | GLU | A | 274 | 7.573 | 29.677 | 29.280 | 1.00 | 52.45 |
| 2014 | N | ASN | A | 275 | 4.655 | 24.997 | 26.094 | 1.00 | 45.72 |
| 2015 | CA | ASN | A | 275 | 4.102 | 23.686 | 26.059 | 1.00 | 46.22 |
| 2016 | C | ASN | A | 275 | 4.974 | 22.643 | 25.375 | 1.00 | 45.27 |

Figure 2-32

| 2017 | O | ASN | A | 275 | 5.181 | 21.540 | 25.870 | 1.00 | 45.50 |
|---|---|---|---|---|---|---|---|---|---|
| 2018 | CB | ASN | A | 275 | 2.792 | 23.832 | 25.226 | 1.00 | 48.36 |
| 2019 | CG | ASN | A | 275 | 1.786 | 22.757 | 25.501 | 1.00 | 50.56 |
| 2020 | OD1 | ASN | A | 275 | 0.610 | 23.052 | 25.746 | 1.00 | 51.89 |
| 2021 | ND2 | ASN | A | 275 | 2.222 | 21.499 | 25.461 | 1.00 | 51.68 |
| 2022 | N | GLY | A | 276 | 5.404 | 22.926 | 24.142 | 1.00 | 43.78 |
| 2023 | CA | GLY | A | 276 | 6.162 | 21.984 | 23.332 | 1.00 | 41.18 |
| 2024 | C | GLY | A | 276 | 5.229 | 21.052 | 22.558 | 1.00 | 39.94 |
| 2025 | O | GLY | A | 276 | 5.630 | 19.999 | 22.057 | 1.00 | 38.60 |
| 2026 | N | ALA | A | 277 | 3.960 | 21.444 | 22.429 | 1.00 | 38.88 |
| 2027 | CA | ALA | A | 277 | 2.943 | 20.651 | 21.765 | 1.00 | 38.13 |
| 2028 | C | ALA | A | 277 | 3.282 | 20.243 | 20.338 | 1.00 | 37.49 |
| 2029 | O | ALA | A | 277 | 2.921 | 19.138 | 19.911 | 1.00 | 37.45 |
| 2030 | CB | ALA | A | 277 | 1.602 | 21.380 | 21.780 | 1.00 | 37.64 |
| 2031 | N | GLY | A | 278 | 3.871 | 21.144 | 19.562 | 1.00 | 36.32 |
| 2032 | CA | GLY | A | 278 | 4.257 | 20.831 | 18.183 | 1.00 | 34.59 |
| 2033 | C | GLY | A | 278 | 5.357 | 19.776 | 18.211 | 1.00 | 33.11 |
| 2034 | O | GLY | A | 278 | 5.263 | 18.743 | 17.545 | 1.00 | 32.66 |
| 2035 | N | ALA | A | 279 | 6.362 | 20.011 | 19.051 | 1.00 | 31.37 |
| 2036 | CA | ALA | A | 279 | 7.431 | 19.025 | 19.215 | 1.00 | 31.33 |
| 2037 | C | ALA | A | 279 | 6.857 | 17.681 | 19.660 | 1.00 | 31.17 |
| 2038 | O | ALA | A | 279 | 7.231 | 16.611 | 19.159 | 1.00 | 31.33 |
| 2039 | CB | ALA | A | 279 | 8.444 | 19.546 | 20.212 | 1.00 | 31.56 |
| 2040 | N | ALA | A | 280 | 5.884 | 17.714 | 20.562 | 1.00 | 30.93 |
| 2041 | CA | ALA | A | 280 | 5.212 | 16.518 | 21.041 | 1.00 | 31.18 |
| 2042 | C | ALA | A | 280 | 4.505 | 15.758 | 19.932 | 1.00 | 31.56 |
| 2043 | O | ALA | A | 280 | 4.626 | 14.536 | 19.788 | 1.00 | 31.58 |
| 2044 | CB | ALA | A | 280 | 4.227 | 16.911 | 22.141 | 1.00 | 30.59 |
| 2045 | N | LEU | A | 281 | 3.781 | 16.482 | 19.078 | 1.00 | 31.84 |
| 2046 | CA | LEU | A | 281 | 2.989 | 15.831 | 18.031 | 1.00 | 32.50 |
| 2047 | C | LEU | A | 281 | 3.840 | 15.238 | 16.924 | 1.00 | 32.77 |
| 2048 | O | LEU | A | 281 | 3.402 | 14.330 | 16.205 | 1.00 | 32.06 |
| 2049 | CB | LEU | A | 281 | 1.958 | 16.823 | 17.508 | 1.00 | 33.11 |
| 2050 | CG | LEU | A | 281 | 1.157 | 16.429 | 16.271 | 1.00 | 34.64 |
| 2051 | CD1 | LEU | A | 281 | 0.256 | 15.241 | 16.556 | 1.00 | 33.87 |
| 2052 | CD2 | LEU | A | 281 | 0.351 | 17.623 | 15.767 | 1.00 | 34.77 |
| 2053 | N | ALA | A | 282 | 5.072 | 15.723 | 16.774 | 1.00 | 32.69 |
| 2054 | CA | ALA | A | 282 | 5.988 | 15.209 | 15.765 | 1.00 | 31.83 |
| 2055 | C | ALA | A | 282 | 6.667 | 13.936 | 16.256 | 1.00 | 31.20 |
| 2056 | O | ALA | A | 282 | 6.953 | 13.060 | 15.448 | 1.00 | 29.68 |
| 2057 | CB | ALA | A | 282 | 7.022 | 16.256 | 15.397 | 1.00 | 32.01 |
| 2058 | N | MET | A | 283 | 6.927 | 13.865 | 17.571 | 1.00 | 31.55 |
| 2059 | CA | MET | A | 283 | 7.522 | 12.619 | 18.101 | 1.00 | 32.09 |
| 2060 | C | MET | A | 283 | 6.415 | 11.558 | 18.038 | 1.00 | 32.78 |
| 2061 | O | MET | A | 283 | 6.510 | 10.526 | 17.386 | 1.00 | 32.13 |
| 2062 | CB | MET | A | 283 | 8.041 | 12.793 | 19.507 | 1.00 | 31.89 |
| 2063 | CG | MET | A | 283 | 9.262 | 13.684 | 19.646 | 1.00 | 31.94 |
| 2064 | SD | MET | A | 283 | 9.783 | 13.914 | 21.342 | 1.00 | 31.98 |
| 2065 | CE | MET | A | 283 | 8.955 | 15.399 | 21.846 | 1.00 | 31.11 |
| 2066 | N | ALA | A | 284 | 5.274 | 11.947 | 18.604 | 1.00 | 33.35 |
| 2067 | CA | ALA | A | 284 | 4.038 | 11.207 | 18.566 | 1.00 | 33.77 |
| 2068 | C | ALA | A | 284 | 3.757 | 10.601 | 17.196 | 1.00 | 34.98 |
| 2069 | O | ALA | A | 284 | 3.547 | 9.387 | 17.080 | 1.00 | 36.92 |
| 2070 | CB | ALA | A | 284 | 2.907 | 12.160 | 18.950 | 1.00 | 33.34 |
| 2071 | N | ASN | A | 285 | 3.789 | 11.409 | 16.147 | 1.00 | 35.09 |
| 2072 | CA | ASN | A | 285 | 3.535 | 10.975 | 14.782 | 1.00 | 34.98 |
| 2073 | C | ASN | A | 285 | 4.601 | 10.009 | 14.281 | 1.00 | 35.26 |
| 2074 | O | ASN | A | 285 | 4.339 | 9.059 | 13.540 | 1.00 | 35.45 |
| 2075 | CB | ASN | A | 285 | 3.433 | 12.196 | 13.863 | 1.00 | 34.80 |
| 2076 | CG | ASN | A | 285 | 2.128 | 12.946 | 13.906 | 1.00 | 35.23 |
| 2077 | OD1 | ASN | A | 285 | 1.075 | 12.436 | 14.290 | 1.00 | 36.24 |
| 2078 | ND2 | ASN | A | 285 | 2.126 | 14.219 | 13.505 | 1.00 | 34.94 |
| 2079 | N | ALA | A | 286 | 5.854 | 10.220 | 14.671 | 1.00 | 35.27 |

Figure 2-33

| 2080 | CA | ALA | A | 286 | 6.964 | 9.362 | 14.285 | 1.00 | 34.55 |
|---|---|---|---|---|---|---|---|---|---|
| 2081 | C | ALA | A | 286 | 6.742 | 7.970 | 14.874 | 1.00 | 35.42 |
| 2082 | O | ALA | A | 286 | 6.960 | 6.935 | 14.264 | 1.00 | 34.04 |
| 2083 | CB | ALA | A | 286 | 8.268 | 9.936 | 14.818 | 1.00 | 33.75 |
| 2084 | N | LEU | A | 287 | 6.321 | 7.995 | 16.143 | 1.00 | 37.17 |
| 2085 | CA | LEU | A | 287 | 6.018 | 6.780 | 16.884 | 1.00 | 38.32 |
| 2086 | C | LEU | A | 287 | 4.957 | 5.967 | 16.164 | 1.00 | 39.73 |
| 2087 | O | LEU | A | 287 | 5.158 | 4.784 | 15.877 | 1.00 | 38.69 |
| 2088 | CB | LEU | A | 287 | 5.600 | 7.154 | 18.313 | 1.00 | 37.88 |
| 2089 | CG | LEU | A | 287 | 6.795 | 7.426 | 19.249 | 1.00 | 37.80 |
| 2090 | CD1 | LEU | A | 287 | 6.334 | 7.877 | 20.616 | 1.00 | 37.05 |
| 2091 | CD2 | LEU | A | 287 | 7.683 | 6.190 | 19.347 | 1.00 | 37.58 |
| 2092 | N | ARG | A | 288 | 3.851 | 6.632 | 15.806 | 1.00 | 41.38 |
| 2093 | CA | ARG | A | 288 | 2.769 | 5.969 | 15.083 | 1.00 | 42.96 |
| 2094 | C | ARG | A | 288 | 3.269 | 5.379 | 13.774 | 1.00 | 42.65 |
| 2095 | O | ARG | A | 288 | 3.015 | 4.219 | 13.465 | 1.00 | 42.61 |
| 2096 | CB | ARG | A | 288 | 1.613 | 6.940 | 14.836 | 1.00 | 45.04 |
| 2097 | CG | ARG | A | 288 | 0.425 | 6.321 | 14.128 | 1.00 | 48.66 |
| 2098 | CD | ARG | A | 288 | -0.811 | 7.210 | 14.128 | 1.00 | 51.29 |
| 2099 | NE | ARG | A | 288 | -0.651 | 8.364 | 13.243 | 1.00 | 53.75 |
| 2100 | CZ | ARG | A | 288 | -0.499 | 9.617 | 13.668 | 1.00 | 54.99 |
| 2101 | NH1 | ARG | A | 288 | -0.514 | 9.916 | 14.964 | 1.00 | 54.93 |
| 2102 | NH2 | ARG | A | 288 | -0.326 | 10.579 | 12.762 | 1.00 | 56.01 |
| 2103 | N | ASP | A | 289 | 4.067 | 6.129 | 13.025 | 1.00 | 42.95 |
| 2104 | CA | ASP | A | 289 | 4.620 | 5.710 | 11.751 | 1.00 | 42.81 |
| 2105 | C | ASP | A | 289 | 5.494 | 4.477 | 11.897 | 1.00 | 43.26 |
| 2106 | O | ASP | A | 289 | 5.539 | 3.627 | 11.010 | 1.00 | 43.44 |
| 2107 | CB | ASP | A | 289 | 5.428 | 6.850 | 11.122 | 1.00 | 43.06 |
| 2108 | CG | ASP | A | 289 | 5.762 | 6.635 | 9.663 | 1.00 | 43.34 |
| 2109 | OD1 | ASP | A | 289 | 6.926 | 6.875 | 9.262 | 1.00 | 43.42 |
| 2110 | OD2 | ASP | A | 289 | 4.871 | 6.222 | 8.888 | 1.00 | 43.16 |
| 2111 | N | ALA | A | 290 | 6.219 | 4.383 | 13.006 | 1.00 | 44.10 |
| 2112 | CA | ALA | A | 290 | 7.082 | 3.243 | 13.279 | 1.00 | 44.21 |
| 2113 | C | ALA | A | 290 | 6.287 | 2.108 | 13.921 | 1.00 | 44.87 |
| 2114 | O | ALA | A | 290 | 6.659 | 0.944 | 13.787 | 1.00 | 45.98 |
| 2115 | CB | ALA | A | 290 | 8.234 | 3.653 | 14.178 | 1.00 | 43.78 |
| 2116 | N | GLY | A | 291 | 5.218 | 2.444 | 14.636 | 1.00 | 44.81 |
| 2117 | CA | GLY | A | 291 | 4.362 | 1.476 | 15.281 | 1.00 | 44.46 |
| 2118 | C | GLY | A | 291 | 4.864 | 1.013 | 16.634 | 1.00 | 44.95 |
| 2119 | O | GLY | A | 291 | 4.471 | -0.051 | 17.128 | 1.00 | 45.58 |
| 2120 | N | ILE | A | 292 | 5.742 | 1.778 | 17.273 | 1.00 | 44.88 |
| 2121 | CA | ILE | A | 292 | 6.300 | 1.395 | 18.562 | 1.00 | 44.50 |
| 2122 | C | ILE | A | 292 | 5.816 | 2.343 | 19.650 | 1.00 | 45.65 |
| 2123 | O | ILE | A | 292 | 5.155 | 3.335 | 19.342 | 1.00 | 46.14 |
| 2124 | CB | ILE | A | 292 | 7.833 | 1.360 | 18.544 | 1.00 | 43.75 |
| 2125 | CG1 | ILE | A | 292 | 8.408 | 2.772 | 18.452 | 1.00 | 43.53 |
| 2126 | CG2 | ILE | A | 292 | 8.345 | 0.488 | 17.399 | 1.00 | 43.48 |
| 2127 | CD1 | ILE | A | 292 | 9.919 | 2.823 | 18.411 | 1.00 | 43.81 |
| 2128 | N | GLU | A | 293 | 6.139 | 2.028 | 20.896 | 1.00 | 46.56 |
| 2129 | CA | GLU | A | 293 | 5.750 | 2.864 | 22.029 | 1.00 | 47.85 |
| 2130 | C | GLU | A | 293 | 6.937 | 3.673 | 22.527 | 1.00 | 47.03 |
| 2131 | O | GLU | A | 293 | 8.089 | 3.286 | 22.313 | 1.00 | 46.47 |
| 2132 | CB | GLU | A | 293 | 5.186 | 1.973 | 23.133 | 1.00 | 50.62 |
| 2133 | CG | GLU | A | 293 | 3.680 | 1.735 | 23.051 | 1.00 | 53.57 |
| 2134 | CD | GLU | A | 293 | 3.132 | 1.252 | 24.385 | 1.00 | 55.85 |
| 2135 | OE1 | GLU | A | 293 | 3.663 | 0.235 | 24.895 | 1.00 | 56.88 |
| 2136 | OE2 | GLU | A | 293 | 2.191 | 1.876 | 24.929 | 1.00 | 56.96 |
| 2137 | N | ALA | A | 294 | 6.708 | 4.773 | 23.233 | 1.00 | 46.80 |
| 2138 | CA | ALA | A | 294 | 7.797 | 5.618 | 23.718 | 1.00 | 47.26 |
| 2139 | C | ALA | A | 294 | 8.843 | 4.831 | 24.484 | 1.00 | 47.74 |
| 2140 | O | ALA | A | 294 | 10.056 | 5.007 | 24.289 | 1.00 | 48.22 |
| 2141 | CB | ALA | A | 294 | 7.260 | 6.780 | 24.546 | 1.00 | 46.78 |
| 2142 | N | SER | A | 295 | 8.436 | 3.892 | 25.316 | 1.00 | 48.05 |

Figure 2-34

| 2143 | CA | SER | A | 295 | 9.257 | 3.037 | 26.133 | 1.00 | 47.63 |
|------|-----|-----|---|-----|--------|--------|--------|------|-------|
| 2144 | C | SER | A | 295 | 10.346 | 2.265 | 25.410 | 1.00 | 46.97 |
| 2145 | O | SER | A | 295 | 11.303 | 1.793 | 26.057 | 1.00 | 47.56 |
| 2146 | CB | SER | A | 295 | 8.340 | 2.003 | 26.837 | 1.00 | 48.01 |
| 2147 | OG | SER | A | 295 | 8.027 | 0.966 | 25.905 | 1.00 | 48.28 |
| 2148 | N | GLN | A | 296 | 10.256 | 2.092 | 24.102 | 1.00 | 45.19 |
| 2149 | CA | GLN | A | 296 | 11.275 | 1.355 | 23.359 | 1.00 | 44.36 |
| 2150 | C | GLN | A | 296 | 12.408 | 2.264 | 22.917 | 1.00 | 42.95 |
| 2151 | O | GLN | A | 296 | 13.471 | 1.798 | 22.505 | 1.00 | 42.77 |
| 2152 | CB | GLN | A | 296 | 10.617 | 0.635 | 22.180 | 1.00 | 45.62 |
| 2153 | CG | GLN | A | 296 | 9.237 | 0.075 | 22.532 | 1.00 | 46.57 |
| 2154 | CD | GLN | A | 296 | 8.730 | -0.897 | 21.494 | 1.00 | 47.79 |
| 2155 | OE1 | GLN | A | 296 | 7.551 | -0.881 | 21.125 | 1.00 | 48.74 |
| 2156 | NE2 | GLN | A | 296 | 9.609 | -1.763 | 21.001 | 1.00 | 48.30 |
| 2157 | N | ILE | A | 297 | 12.205 | 3.573 | 23.038 | 1.00 | 41.44 |
| 2158 | CA | ILE | A | 297 | 13.219 | 4.559 | 22.695 | 1.00 | 39.95 |
| 2159 | C | ILE | A | 297 | 14.281 | 4.624 | 23.787 | 1.00 | 38.41 |
| 2160 | O | ILE | A | 297 | 14.009 | 4.967 | 24.934 | 1.00 | 37.64 |
| 2161 | CB | ILE | A | 297 | 12.625 | 5.963 | 22.469 | 1.00 | 40.09 |
| 2162 | CG1 | ILE | A | 297 | 11.659 | 5.978 | 21.279 | 1.00 | 39.62 |
| 2163 | CG2 | ILE | A | 297 | 13.728 | 6.994 | 22.250 | 1.00 | 39.76 |
| 2164 | CD1 | ILE | A | 297 | 12.247 | 5.455 | 19.990 | 1.00 | 39.49 |
| 2165 | N | GLY | A | 298 | 15.515 | 4.307 | 23.421 | 1.00 | 37.84 |
| 2166 | CA | GLY | A | 298 | 16.599 | 4.327 | 24.404 | 1.00 | 37.21 |
| 2167 | C | GLY | A | 298 | 17.183 | 5.719 | 24.557 | 1.00 | 37.35 |
| 2168 | O | GLY | A | 298 | 17.381 | 6.216 | 25.665 | 1.00 | 37.77 |
| 2169 | N | TYR | A | 299 | 17.447 | 6.354 | 23.420 | 1.00 | 37.03 |
| 2170 | CA | TYR | A | 299 | 18.092 | 7.654 | 23.391 | 1.00 | 35.98 |
| 2171 | C | TYR | A | 299 | 17.388 | 8.622 | 22.447 | 1.00 | 35.82 |
| 2172 | O | TYR | A | 299 | 17.030 | 8.314 | 21.312 | 1.00 | 35.55 |
| 2173 | CB | TYR | A | 299 | 19.551 | 7.463 | 22.983 | 1.00 | 36.16 |
| 2174 | CG | TYR | A | 299 | 20.319 | 8.708 | 22.633 | 1.00 | 36.96 |
| 2175 | CD1 | TYR | A | 299 | 20.929 | 8.828 | 21.390 | 1.00 | 37.22 |
| 2176 | CD2 | TYR | A | 299 | 20.456 | 9.757 | 23.535 | 1.00 | 37.10 |
| 2177 | CE1 | TYR | A | 299 | 21.648 | 9.957 | 21.048 | 1.00 | 37.84 |
| 2178 | CE2 | TYR | A | 299 | 21.165 | 10.893 | 23.204 | 1.00 | 37.79 |
| 2179 | CZ | TYR | A | 299 | 21.770 | 10.981 | 21.966 | 1.00 | 38.60 |
| 2180 | OH | TYR | A | 299 | 22.504 | 12.096 | 21.627 | 1.00 | 39.51 |
| 2181 | N | VAL | A | 300 | 17.222 | 9.841 | 22.938 | 1.00 | 34.63 |
| 2182 | CA | VAL | A | 300 | 16.664 | 10.948 | 22.185 | 1.00 | 33.18 |
| 2183 | C | VAL | A | 300 | 17.784 | 11.965 | 21.929 | 1.00 | 32.63 |
| 2184 | O | VAL | A | 300 | 18.255 | 12.605 | 22.871 | 1.00 | 32.19 |
| 2185 | CB | VAL | A | 300 | 15.524 | 11.660 | 22.938 | 1.00 | 32.62 |
| 2186 | CG1 | VAL | A | 300 | 15.214 | 13.020 | 22.333 | 1.00 | 32.40 |
| 2187 | CG2 | VAL | A | 300 | 14.269 | 10.800 | 22.975 | 1.00 | 32.13 |
| 2188 | N | ASN | A | 301 | 18.193 | 12.099 | 20.675 | 1.00 | 32.15 |
| 2189 | CA | ASN | A | 301 | 19.069 | 13.226 | 20.309 | 1.00 | 31.41 |
| 2190 | C | ASN | A | 301 | 18.178 | 14.464 | 20.181 | 1.00 | 30.53 |
| 2191 | O | ASN | A | 301 | 17.442 | 14.640 | 19.215 | 1.00 | 31.07 |
| 2192 | CB | ASN | A | 301 | 19.859 | 12.951 | 19.048 | 1.00 | 31.30 |
| 2193 | CG | ASN | A | 301 | 20.806 | 14.085 | 18.713 | 1.00 | 31.98 |
| 2194 | OD1 | ASN | A | 301 | 21.995 | 14.005 | 19.010 | 1.00 | 31.87 |
| 2195 | ND2 | ASN | A | 301 | 20.263 | 15.136 | 18.093 | 1.00 | 32.95 |
| 2196 | N | ALA | A | 302 | 18.200 | 15.291 | 21.205 | 1.00 | 29.64 |
| 2197 | CA | ALA | A | 302 | 17.376 | 16.466 | 21.312 | 1.00 | 29.90 |
| 2198 | C | ALA | A | 302 | 17.724 | 17.596 | 20.361 | 1.00 | 29.88 |
| 2199 | O | ALA | A | 302 | 18.820 | 17.710 | 19.818 | 1.00 | 30.09 |
| 2200 | CB | ALA | A | 302 | 17.484 | 17.001 | 22.755 | 1.00 | 29.38 |
| 2201 | N | HIS | A | 303 | 16.747 | 18.500 | 20.201 | 1.00 | 29.39 |
| 2202 | CA | HIS | A | 303 | 17.001 | 19.687 | 19.382 | 1.00 | 29.72 |
| 2203 | C | HIS | A | 303 | 17.906 | 20.605 | 20.225 | 1.00 | 29.85 |
| 2204 | O | HIS | A | 303 | 18.944 | 21.062 | 19.777 | 1.00 | 29.00 |
| 2205 | CB | HIS | A | 303 | 15.719 | 20.388 | 18.976 | 1.00 | 29.67 |

Figure 2-35

| 2206 | CG | HIS | A | 303 | 15.963 | 21.570 | 18.080 | 1.00 | 29.65 |
|---|---|---|---|---|---|---|---|---|---|
| 2207 | ND1 | HIS | A | 303 | 16.740 | 21.478 | 16.942 | 1.00 | 30.47 |
| 2208 | CD2 | HIS | A | 303 | 15.552 | 22.850 | 18.160 | 1.00 | 29.32 |
| 2209 | CE1 | HIS | A | 303 | 16.792 | 22.660 | 16.355 | 1.00 | 30.67 |
| 2210 | NE2 | HIS | A | 303 | 16.084 | 23.516 | 17.084 | 1.00 | 30.18 |
| 2211 | N | GLY | A | 304 | 17.545 | 20.716 | 21.499 | 1.00 | 30.19 |
| 2212 | CA | GLY | A | 304 | 18.260 | 21.378 | 22.551 | 1.00 | 31.04 |
| 2213 | C | GLY | A | 304 | 19.387 | 22.299 | 22.113 | 1.00 | 30.87 |
| 2214 | O | GLY | A | 304 | 20.568 | 21.962 | 22.172 | 1.00 | 30.26 |
| 2215 | N | THR | A | 305 | 19.016 | 23.502 | 21.704 | 1.00 | 30.59 |
| 2216 | CA | THR | A | 305 | 19.924 | 24.486 | 21.163 | 1.00 | 30.95 |
| 2217 | C | THR | A | 305 | 20.526 | 25.444 | 22.160 | 1.00 | 30.62 |
| 2218 | O | THR | A | 305 | 21.218 | 26.374 | 21.730 | 1.00 | 31.05 |
| 2219 | CB | THR | A | 305 | 19.167 | 25.300 | 20.073 | 1.00 | 31.44 |
| 2220 | OG1 | THR | A | 305 | 18.143 | 26.079 | 20.709 | 1.00 | 32.41 |
| 2221 | CG2 | THR | A | 305 | 18.511 | 24.357 | 19.074 | 1.00 | 30.77 |
| 2222 | N | SER | A | 306 | 20.310 | 25.280 | 23.448 | 1.00 | 30.65 |
| 2223 | CA | SER | A | 306 | 20.823 | 26.156 | 24.492 | 1.00 | 29.52 |
| 2224 | C | SER | A | 306 | 20.129 | 27.510 | 24.521 | 1.00 | 29.40 |
| 2225 | O | SER | A | 306 | 20.713 | 28.556 | 24.800 | 1.00 | 28.21 |
| 2226 | CB | SER | A | 306 | 22.333 | 26.315 | 24.382 | 1.00 | 29.55 |
| 2227 | OG | SER | A | 306 | 22.887 | 26.873 | 25.564 | 1.00 | 29.38 |
| 2228 | N | THR | A | 307 | 18.828 | 27.513 | 24.218 | 1.00 | 30.00 |
| 2229 | CA | THR | A | 307 | 18.054 | 28.750 | 24.287 | 1.00 | 30.62 |
| 2230 | C | THR | A | 307 | 17.049 | 28.601 | 25.429 | 1.00 | 31.06 |
| 2231 | O | THR | A | 307 | 16.500 | 27.519 | 25.623 | 1.00 | 30.43 |
| 2232 | CB | THR | A | 307 | 17.330 | 29.115 | 22.986 | 1.00 | 29.95 |
| 2233 | OG1 | THR | A | 307 | 16.320 | 28.137 | 22.714 | 1.00 | 29.62 |
| 2234 | CG2 | THR | A | 307 | 18.318 | 29.199 | 21.834 | 1.00 | 29.18 |
| 2235 | N | PRO | A | 308 | 16.948 | 29.632 | 26.249 | 1.00 | 32.42 |
| 2236 | CA | PRO | A | 308 | 16.079 | 29.618 | 27.413 | 1.00 | 33.00 |
| 2237 | C | PRO | A | 308 | 14.725 | 29.019 | 27.109 | 1.00 | 34.60 |
| 2238 | O | PRO | A | 308 | 14.429 | 27.899 | 27.560 | 1.00 | 36.16 |
| 2239 | CB | PRO | A | 308 | 15.998 | 31.083 | 27.808 | 1.00 | 32.75 |
| 2240 | CG | PRO | A | 308 | 17.304 | 31.659 | 27.359 | 1.00 | 32.45 |
| 2241 | CD | PRO | A | 308 | 17.600 | 30.954 | 26.056 | 1.00 | 32.33 |
| 2242 | N | ALA | A | 309 | 13.936 | 29.674 | 26.262 | 1.00 | 35.22 |
| 2243 | CA | ALA | A | 309 | 12.602 | 29.191 | 25.929 | 1.00 | 35.74 |
| 2244 | C | ALA | A | 309 | 12.598 | 27.867 | 25.185 | 1.00 | 35.62 |
| 2245 | O | ALA | A | 309 | 11.768 | 26.998 | 25.490 | 1.00 | 36.25 |
| 2246 | CB | ALA | A | 309 | 11.839 | 30.245 | 25.132 | 1.00 | 36.27 |
| 2247 | N | GLY | A | 310 | 13.473 | 27.703 | 24.205 | 1.00 | 35.30 |
| 2248 | CA | GLY | A | 310 | 13.536 | 26.509 | 23.394 | 1.00 | 34.58 |
| 2249 | C | GLY | A | 310 | 13.761 | 25.233 | 24.178 | 1.00 | 35.19 |
| 2250 | O | GLY | A | 310 | 13.020 | 24.257 | 24.002 | 1.00 | 34.63 |
| 2251 | N | ASP | A | 311 | 14.748 | 25.228 | 25.076 | 1.00 | 36.16 |
| 2252 | CA | ASP | A | 311 | 15.095 | 24.027 | 25.837 | 1.00 | 37.35 |
| 2253 | C | ASP | A | 311 | 13.984 | 23.622 | 26.798 | 1.00 | 37.28 |
| 2254 | O | ASP | A | 311 | 13.703 | 22.442 | 26.979 | 1.00 | 35.57 |
| 2255 | CB | ASP | A | 311 | 16.425 | 24.187 | 26.566 | 1.00 | 38.20 |
| 2256 | CG | ASP | A | 311 | 17.609 | 24.388 | 25.642 | 1.00 | 39.32 |
| 2257 | OD1 | ASP | A | 311 | 18.776 | 24.372 | 26.101 | 1.00 | 38.85 |
| 2258 | OD2 | ASP | A | 311 | 17.397 | 24.571 | 24.423 | 1.00 | 40.40 |
| 2259 | N | LYS | A | 312 | 13.300 | 24.604 | 27.377 | 1.00 | 38.66 |
| 2260 | CA | LYS | A | 312 | 12.173 | 24.347 | 28.260 | 1.00 | 39.64 |
| 2261 | C | LYS | A | 312 | 11.110 | 23.515 | 27.545 | 1.00 | 39.36 |
| 2262 | O | LYS | A | 312 | 10.686 | 22.467 | 28.007 | 1.00 | 39.26 |
| 2263 | CB | LYS | A | 312 | 11.532 | 25.663 | 28.693 | 1.00 | 41.64 |
| 2264 | CG | LYS | A | 312 | 12.133 | 26.320 | 29.920 | 1.00 | 43.75 |
| 2265 | CD | LYS | A | 312 | 11.035 | 26.838 | 30.841 | 1.00 | 45.48 |
| 2266 | CE | LYS | A | 312 | 11.461 | 28.114 | 31.550 | 1.00 | 47.04 |
| 2267 | NZ | LYS | A | 312 | 10.296 | 28.741 | 32.255 | 1.00 | 48.24 |
| 2268 | N | ALA | A | 313 | 10.680 | 24.032 | 26.398 | 1.00 | 39.30 |

Figure 2-36

| 2269 | CA | ALA | A | 313 | 9.625 | 23.450 | 25.595 | 1.00 | 38.76 |
|---|---|---|---|---|---|---|---|---|---|
| 2270 | C | ALA | A | 313 | 9.893 | 22.012 | 25.216 | 1.00 | 39.23 |
| 2271 | O | ALA | A | 313 | 9.032 | 21.158 | 25.441 | 1.00 | 40.34 |
| 2272 | CB | ALA | A | 313 | 9.401 | 24.290 | 24.340 | 1.00 | 38.69 |
| 2273 | N | GLU | A | 314 | 11.061 | 21.713 | 24.651 | 1.00 | 39.89 |
| 2274 | CA | GLU | A | 314 | 11.354 | 20.344 | 24.246 | 1.00 | 40.45 |
| 2275 | C | GLU | A | 314 | 11.322 | 19.373 | 25.418 | 1.00 | 40.84 |
| 2276 | O | GLU | A | 314 | 10.768 | 18.279 | 25.320 | 1.00 | 40.97 |
| 2277 | CB | GLU | A | 314 | 12.721 | 20.240 | 23.564 | 1.00 | 40.99 |
| 2278 | CG | GLU | A | 314 | 12.961 | 18.830 | 23.011 | 1.00 | 40.54 |
| 2279 | CD | GLU | A | 314 | 14.188 | 18.798 | 22.132 | 1.00 | 40.81 |
| 2280 | OE1 | GLU | A | 314 | 14.953 | 19.783 | 22.149 | 1.00 | 40.94 |
| 2281 | OE2 | GLU | A | 314 | 14.361 | 17.791 | 21.423 | 1.00 | 41.62 |
| 2282 | N | ALA | A | 315 | 11.963 | 19.767 | 26.514 | 1.00 | 41.04 |
| 2283 | CA | ALA | A | 315 | 11.937 | 18.989 | 27.740 | 1.00 | 41.54 |
| 2284 | C | ALA | A | 315 | 10.495 | 18.632 | 28.093 | 1.00 | 41.87 |
| 2285 | O | ALA | A | 315 | 10.175 | 17.464 | 28.313 | 1.00 | 41.76 |
| 2286 | CB | ALA | A | 315 | 12.588 | 19.759 | 28.877 | 1.00 | 41.38 |
| 2287 | N | GLN | A | 316 | 9.621 | 19.640 | 28.103 | 1.00 | 42.34 |
| 2288 | CA | GLN | A | 316 | 8.217 | 19.395 | 28.399 | 1.00 | 43.86 |
| 2289 | C | GLN | A | 316 | 7.595 | 18.404 | 27.423 | 1.00 | 44.27 |
| 2290 | O | GLN | A | 316 | 6.988 | 17.400 | 27.803 | 1.00 | 43.96 |
| 2291 | CB | GLN | A | 316 | 7.412 | 20.695 | 28.386 | 1.00 | 44.58 |
| 2292 | CG | GLN | A | 316 | 5.971 | 20.493 | 28.849 | 1.00 | 46.52 |
| 2293 | CD | GLN | A | 316 | 5.893 | 20.074 | 30.312 | 1.00 | 47.74 |
| 2294 | OE1 | GLN | A | 316 | 6.524 | 20.669 | 31.190 | 1.00 | 47.58 |
| 2295 | NE2 | GLN | A | 316 | 5.130 | 19.006 | 30.546 | 1.00 | 47.69 |
| 2296 | N | ALA | A | 317 | 7.864 | 18.596 | 26.130 | 1.00 | 44.25 |
| 2297 | CA | ALA | A | 317 | 7.349 | 17.688 | 25.118 | 1.00 | 44.89 |
| 2298 | C | ALA | A | 317 | 7.812 | 16.258 | 25.346 | 1.00 | 44.92 |
| 2299 | O | ALA | A | 317 | 7.103 | 15.311 | 24.979 | 1.00 | 44.45 |
| 2300 | CB | ALA | A | 317 | 7.760 | 18.188 | 23.734 | 1.00 | 45.79 |
| 2301 | N | VAL | A | 318 | 9.008 | 16.071 | 25.897 | 1.00 | 45.09 |
| 2302 | CA | VAL | A | 318 | 9.525 | 14.735 | 26.187 | 1.00 | 45.96 |
| 2303 | C | VAL | A | 318 | 8.773 | 14.126 | 27.372 | 1.00 | 46.69 |
| 2304 | O | VAL | A | 318 | 8.442 | 12.943 | 27.383 | 1.00 | 46.39 |
| 2305 | CB | VAL | A | 318 | 11.038 | 14.753 | 26.459 | 1.00 | 45.52 |
| 2306 | CG1 | VAL | A | 318 | 11.526 | 13.458 | 27.096 | 1.00 | 45.04 |
| 2307 | CG2 | VAL | A | 318 | 11.806 | 15.009 | 25.166 | 1.00 | 44.92 |
| 2308 | N | LYS | A | 319 | 8.439 | 14.958 | 28.352 | 1.00 | 47.66 |
| 2309 | CA | LYS | A | 319 | 7.685 | 14.521 | 29.517 | 1.00 | 49.06 |
| 2310 | C | LYS | A | 319 | 6.271 | 14.119 | 29.128 | 1.00 | 49.78 |
| 2311 | O | LYS | A | 319 | 5.722 | 13.163 | 29.680 | 1.00 | 50.92 |
| 2312 | CB | LYS | A | 319 | 7.689 | 15.604 | 30.598 | 1.00 | 49.56 |
| 2313 | CG | LYS | A | 319 | 9.083 | 15.838 | 31.176 | 1.00 | 50.90 |
| 2314 | CD | LYS | A | 319 | 9.067 | 16.783 | 32.366 | 1.00 | 52.01 |
| 2315 | CE | LYS | A | 319 | 9.207 | 16.011 | 33.668 | 1.00 | 53.29 |
| 2316 | NZ | LYS | A | 319 | 9.356 | 16.912 | 34.850 | 1.00 | 53.92 |
| 2317 | N | THR | A | 320 | 5.698 | 14.790 | 28.141 | 1.00 | 49.61 |
| 2318 | CA | THR | A | 320 | 4.377 | 14.478 | 27.627 | 1.00 | 49.41 |
| 2319 | C | THR | A | 320 | 4.383 | 13.153 | 26.878 | 1.00 | 50.24 |
| 2320 | O | THR | A | 320 | 3.445 | 12.365 | 27.009 | 1.00 | 51.00 |
| 2321 | CB | THR | A | 320 | 3.874 | 15.591 | 26.688 | 1.00 | 48.97 |
| 2322 | OG1 | THR | A | 320 | 3.544 | 16.754 | 27.464 | 1.00 | 48.43 |
| 2323 | CG2 | THR | A | 320 | 2.655 | 15.160 | 25.895 | 1.00 | 48.62 |
| 2324 | N | ILE | A | 321 | 5.396 | 12.928 | 26.060 | 1.00 | 51.08 |
| 2325 | CA | ILE | A | 321 | 5.482 | 11.731 | 25.236 | 1.00 | 52.44 |
| 2326 | C | ILE | A | 321 | 5.988 | 10.521 | 25.994 | 1.00 | 53.78 |
| 2327 | O | ILE | A | 321 | 5.453 | 9.413 | 25.850 | 1.00 | 54.21 |
| 2328 | CB | ILE | A | 321 | 6.389 | 11.992 | 24.012 | 1.00 | 52.16 |
| 2329 | CG1 | ILE | A | 321 | 5.814 | 13.143 | 23.185 | 1.00 | 52.52 |
| 2330 | CG2 | ILE | A | 321 | 6.559 | 10.745 | 23.168 | 1.00 | 51.63 |
| 2331 | CD1 | ILE | A | 321 | 4.434 | 12.868 | 22.619 | 1.00 | 53.06 |

Figure 2-37

| 2332 | N | PHE | A | 322 | 7.062 | 10.686 | 26.764 | 1.00 | 55.32 |
|---|---|---|---|---|---|---|---|---|---|
| 2333 | CA | PHE | A | 322 | 7.623 | 9.536 | 27.482 | 1.00 | 57.01 |
| 2334 | C | PHE | A | 322 | 6.854 | 9.233 | 28.751 | 1.00 | 58.22 |
| 2335 | O | PHE | A | 322 | 6.709 | 8.063 | 29.131 | 1.00 | 58.09 |
| 2336 | CB | PHE | A | 322 | 9.129 | 9.740 | 27.695 | 1.00 | 56.37 |
| 2337 | CG | PHE | A | 322 | 9.837 | 9.510 | 26.375 | 1.00 | 56.26 |
| 2338 | CD1 | PHE | A | 322 | 9.909 | 10.521 | 25.438 | 1.00 | 56.23 |
| 2339 | CD2 | PHE | A | 322 | 10.364 | 8.269 | 26.073 | 1.00 | 56.06 |
| 2340 | CE1 | PHE | A | 322 | 10.527 | 10.306 | 24.219 | 1.00 | 56.27 |
| 2341 | CE2 | PHE | A | 322 | 10.981 | 8.052 | 24.857 | 1.00 | 56.46 |
| 2342 | CZ | PHE | A | 322 | 11.063 | 9.069 | 23.926 | 1.00 | 56.24 |
| 2343 | N | GLY | A | 323 | 6.262 | 10.257 | 29.358 | 1.00 | 59.40 |
| 2344 | CA | GLY | A | 323 | 5.449 | 10.098 | 30.548 | 1.00 | 61.56 |
| 2345 | C | GLY | A | 323 | 6.205 | 9.479 | 31.715 | 1.00 | 63.08 |
| 2346 | O | GLY | A | 323 | 7.035 | 10.135 | 32.346 | 1.00 | 62.72 |
| 2347 | N | GLU | A | 324 | 5.911 | 8.211 | 31.997 | 1.00 | 64.65 |
| 2348 | CA | GLU | A | 324 | 6.532 | 7.504 | 33.112 | 1.00 | 66.18 |
| 2349 | C | GLU | A | 324 | 7.932 | 7.025 | 32.757 | 1.00 | 65.94 |
| 2350 | O | GLU | A | 324 | 8.799 | 6.936 | 33.631 | 1.00 | 66.15 |
| 2351 | CB | GLU | A | 324 | 5.653 | 6.337 | 33.561 | 1.00 | 67.61 |
| 2352 | CG | GLU | A | 324 | 4.724 | 6.673 | 34.715 | 1.00 | 69.11 |
| 2353 | CD | GLU | A | 324 | 3.266 | 6.766 | 34.309 | 1.00 | 70.22 |
| 2354 | OE1 | GLU | A | 324 | 2.919 | 7.668 | 33.508 | 1.00 | 70.44 |
| 2355 | OE2 | GLU | A | 324 | 2.459 | 5.940 | 34.799 | 1.00 | 70.43 |
| 2356 | N | ALA | A | 325 | 8.170 | 6.761 | 31.475 | 1.00 | 65.16 |
| 2357 | CA | ALA | A | 325 | 9.469 | 6.309 | 31.002 | 1.00 | 64.72 |
| 2358 | C | ALA | A | 325 | 10.416 | 7.477 | 30.754 | 1.00 | 64.29 |
| 2359 | O | ALA | A | 325 | 11.505 | 7.276 | 30.360 | 1.00 | 63.88 |
| 2360 | CB | ALA | A | 325 | 9.326 | 5.470 | 29.739 | 1.00 | 64.73 |
| 2361 | N | ALA | A | 326 | 9.977 | 8.690 | 31.052 | 1.00 | 63.99 |
| 2362 | CA | ALA | A | 326 | 10.745 | 9.905 | 30.917 | 1.00 | 63.96 |
| 2363 | C | ALA | A | 326 | 12.013 | 9.906 | 31.759 | 1.00 | 64.59 |
| 2364 | O | ALA | A | 326 | 12.982 | 10.590 | 31.423 | 1.00 | 65.46 |
| 2365 | CB | ALA | A | 326 | 9.892 | 11.111 | 31.296 | 1.00 | 63.23 |
| 2366 | N | SER | A | 327 | 12.034 | 9.169 | 32.856 | 1.00 | 64.91 |
| 2367 | CA | SER | A | 327 | 13.195 | 9.076 | 33.724 | 1.00 | 64.87 |
| 2368 | C | SER | A | 327 | 14.168 | 8.006 | 33.253 | 1.00 | 64.31 |
| 2369 | O | SER | A | 327 | 15.363 | 8.062 | 33.553 | 1.00 | 65.08 |
| 2370 | CB | SER | A | 327 | 12.725 | 8.745 | 35.152 | 1.00 | 65.49 |
| 2371 | OG | SER | A | 327 | 11.692 | 7.767 | 35.086 | 1.00 | 65.92 |
| 2372 | N | ARG | A | 328 | 13.663 | 7.014 | 32.526 | 1.00 | 63.15 |
| 2373 | CA | ARG | A | 328 | 14.520 | 5.936 | 32.040 | 1.00 | 61.76 |
| 2374 | C | ARG | A | 328 | 15.101 | 6.250 | 30.671 | 1.00 | 59.76 |
| 2375 | O | ARG | A | 328 | 16.033 | 5.564 | 30.233 | 1.00 | 60.32 |
| 2376 | CB | ARG | A | 328 | 13.764 | 4.609 | 32.025 | 1.00 | 62.86 |
| 2377 | CG | ARG | A | 328 | 12.866 | 4.373 | 30.827 | 1.00 | 64.26 |
| 2378 | CD | ARG | A | 328 | 11.855 | 3.269 | 31.095 | 1.00 | 65.68 |
| 2379 | NE | ARG | A | 328 | 11.950 | 2.167 | 30.144 | 1.00 | 66.47 |
| 2380 | CZ | ARG | A | 328 | 11.064 | 1.187 | 30.020 | 1.00 | 66.85 |
| 2381 | NH1 | ARG | A | 328 | 9.983 | 1.158 | 30.792 | 1.00 | 67.11 |
| 2382 | NH2 | ARG | A | 328 | 11.246 | 0.229 | 29.119 | 1.00 | 67.06 |
| 2383 | N | VAL | A | 329 | 14.570 | 7.262 | 29.985 | 1.00 | 56.58 |
| 2384 | CA | VAL | A | 329 | 15.070 | 7.594 | 28.651 | 1.00 | 52.91 |
| 2385 | C | VAL | A | 329 | 16.235 | 8.569 | 28.713 | 1.00 | 51.13 |
| 2386 | O | VAL | A | 329 | 16.259 | 9.466 | 29.550 | 1.00 | 50.77 |
| 2387 | CB | VAL | A | 329 | 13.964 | 8.144 | 27.740 | 1.00 | 52.48 |
| 2388 | CG1 | VAL | A | 329 | 13.541 | 9.544 | 28.160 | 1.00 | 51.82 |
| 2389 | CG2 | VAL | A | 329 | 14.411 | 8.119 | 26.284 | 1.00 | 51.86 |
| 2390 | N | LEU | A | 330 | 17.217 | 8.350 | 27.844 | 1.00 | 48.78 |
| 2391 | CA | LEU | A | 330 | 18.386 | 9.205 | 27.748 | 1.00 | 46.67 |
| 2392 | C | LEU | A | 330 | 18.182 | 10.298 | 26.701 | 1.00 | 45.85 |
| 2393 | O | LEU | A | 330 | 17.791 | 10.038 | 25.560 | 1.00 | 45.82 |
| 2394 | CB | LEU | A | 330 | 19.627 | 8.379 | 27.404 | 1.00 | 46.55 |

Figure 2-38

| 2395 | CG | LEU | A | 330 | 20.032 | 7.297 | 28.410 | 1.00 | 46.63 |
|------|-----|-----|---|-----|--------|--------|--------|------|-------|
| 2396 | CD1 | LEU | A | 330 | 21.221 | 6.501 | 27.896 | 1.00 | 46.07 |
| 2397 | CD2 | LEU | A | 330 | 20.345 | 7.902 | 29.769 | 1.00 | 45.97 |
| 2398 | N | VAL | A | 331 | 18.358 | 11.547 | 27.118 | 1.00 | 43.84 |
| 2399 | CA | VAL | A | 331 | 18.211 | 12.702 | 26.266 | 1.00 | 42.46 |
| 2400 | C | VAL | A | 331 | 19.460 | 13.580 | 26.316 | 1.00 | 41.99 |
| 2401 | O | VAL | A | 331 | 19.603 | 14.358 | 27.267 | 1.00 | 41.78 |
| 2402 | CB | VAL | A | 331 | 17.022 | 13.610 | 26.674 | 1.00 | 42.13 |
| 2403 | CG1 | VAL | A | 331 | 16.686 | 14.548 | 25.519 | 1.00 | 41.88 |
| 2404 | CG2 | VAL | A | 331 | 15.797 | 12.845 | 27.111 | 1.00 | 41.37 |
| 2405 | N | SER | A | 332 | 20.281 | 13.610 | 25.269 | 1.00 | 41.05 |
| 2406 | CA | SER | A | 332 | 21.423 | 14.534 | 25.294 | 1.00 | 39.11 |
| 2407 | C | SER | A | 332 | 21.364 | 15.492 | 24.113 | 1.00 | 38.45 |
| 2408 | O | SER | A | 332 | 20.643 | 15.253 | 23.151 | 1.00 | 38.77 |
| 2409 | CB | SER | A | 332 | 22.754 | 13.797 | 25.309 | 1.00 | 38.87 |
| 2410 | OG | SER | A | 332 | 22.976 | 13.032 | 24.140 | 1.00 | 38.04 |
| 2411 | N | SER | A | 333 | 22.152 | 16.557 | 24.185 | 1.00 | 37.37 |
| 2412 | CA | SER | A | 333 | 22.327 | 17.480 | 23.081 | 1.00 | 35.80 |
| 2413 | C | SER | A | 333 | 23.808 | 17.578 | 22.713 | 1.00 | 35.02 |
| 2414 | O | SER | A | 333 | 24.608 | 18.160 | 23.448 | 1.00 | 34.17 |
| 2415 | CB | SER | A | 333 | 21.803 | 18.883 | 23.391 | 1.00 | 35.80 |
| 2416 | OG | SER | A | 333 | 22.173 | 19.787 | 22.353 | 1.00 | 34.77 |
| 2417 | N | THR | A | 334 | 24.153 | 17.125 | 21.506 | 1.00 | 33.66 |
| 2418 | CA | THR | A | 334 | 25.523 | 17.226 | 21.031 | 1.00 | 32.68 |
| 2419 | C | THR | A | 334 | 25.890 | 18.626 | 20.566 | 1.00 | 31.79 |
| 2420 | O | THR | A | 334 | 27.042 | 18.855 | 20.175 | 1.00 | 32.24 |
| 2421 | CB | THR | A | 334 | 25.794 | 16.248 | 19.874 | 1.00 | 33.55 |
| 2422 | OG1 | THR | A | 334 | 24.632 | 16.210 | 19.035 | 1.00 | 35.08 |
| 2423 | CG2 | THR | A | 334 | 26.091 | 14.854 | 20.395 | 1.00 | 33.98 |
| 2424 | N | LYS | A | 335 | 24.966 | 19.571 | 20.620 | 1.00 | 29.86 |
| 2425 | CA | LYS | A | 335 | 25.130 | 20.954 | 20.255 | 1.00 | 28.11 |
| 2426 | C | LYS | A | 335 | 25.909 | 21.722 | 21.323 | 1.00 | 28.33 |
| 2427 | O | LYS | A | 335 | 26.403 | 22.833 | 21.112 | 1.00 | 28.49 |
| 2428 | CB | LYS | A | 335 | 23.766 | 21.632 | 20.065 | 1.00 | 27.41 |
| 2429 | CG | LYS | A | 335 | 22.985 | 21.211 | 18.848 | 1.00 | 26.22 |
| 2430 | CD | LYS | A | 335 | 21.797 | 22.117 | 18.573 | 1.00 | 25.45 |
| 2431 | CE | LYS | A | 335 | 21.096 | 21.719 | 17.274 | 1.00 | 24.18 |
| 2432 | NZ | LYS | A | 335 | 20.513 | 20.357 | 17.370 | 1.00 | 22.35 |
| 2433 | N | SER | A | 336 | 26.063 | 21.085 | 22.485 | 1.00 | 27.13 |
| 2434 | CA | SER | A | 336 | 26.898 | 21.586 | 23.553 | 1.00 | 26.20 |
| 2435 | C | SER | A | 336 | 28.357 | 21.641 | 23.098 | 1.00 | 25.15 |
| 2436 | O | SER | A | 336 | 29.092 | 22.541 | 23.491 | 1.00 | 24.26 |
| 2437 | CB | SER | A | 336 | 26.778 | 20.723 | 24.803 | 1.00 | 26.48 |
| 2438 | OG | SER | A | 336 | 26.951 | 19.355 | 24.499 | 1.00 | 26.89 |
| 2439 | N | MET | A | 337 | 28.738 | 20.692 | 22.253 | 1.00 | 24.47 |
| 2440 | CA | MET | A | 337 | 30.088 | 20.611 | 21.733 | 1.00 | 25.03 |
| 2441 | C | MET | A | 337 | 30.227 | 21.244 | 20.352 | 1.00 | 25.59 |
| 2442 | O | MET | A | 337 | 31.126 | 22.030 | 20.063 | 1.00 | 27.27 |
| 2443 | CB | MET | A | 337 | 30.505 | 19.123 | 21.646 | 1.00 | 23.76 |
| 2444 | CG | MET | A | 337 | 30.336 | 18.420 | 22.987 | 1.00 | 22.85 |
| 2445 | SD | MET | A | 337 | 30.647 | 16.670 | 22.961 | 1.00 | 22.05 |
| 2446 | CE | MET | A | 337 | 29.019 | 15.966 | 22.795 | 1.00 | 20.77 |
| 2447 | N | THR | A | 338 | 29.335 | 20.877 | 19.481 | 1.00 | 24.93 |
| 2448 | CA | THR | A | 338 | 29.336 | 21.064 | 18.043 | 1.00 | 24.13 |
| 2449 | C | THR | A | 338 | 28.770 | 22.406 | 17.637 | 1.00 | 24.84 |
| 2450 | O | THR | A | 338 | 29.244 | 23.073 | 16.706 | 1.00 | 25.40 |
| 2451 | CB | THR | A | 338 | 28.506 | 19.864 | 17.512 | 1.00 | 23.52 |
| 2452 | OG1 | THR | A | 338 | 29.316 | 18.985 | 16.726 | 1.00 | 22.42 |
| 2453 | CG2 | THR | A | 338 | 27.262 | 20.277 | 16.790 | 1.00 | 23.55 |
| 2454 | N | GLY | A | 339 | 27.753 | 22.870 | 18.368 | 1.00 | 24.13 |
| 2455 | CA | GLY | A | 339 | 27.098 | 24.144 | 18.051 | 1.00 | 21.84 |
| 2456 | C | GLY | A | 339 | 25.883 | 23.812 | 17.178 | 1.00 | 21.27 |
| 2457 | O | GLY | A | 339 | 25.688 | 22.635 | 16.865 | 1.00 | 21.79 |

Figure 2-39

| 2458 | N | HIS | A | 340 | 25.078 | 24.779 | 16.805 | 1.00 | 20.63 |
|---|---|---|---|---|---|---|---|---|---|
| 2459 | CA | HIS | A | 340 | 23.911 | 24.536 | 15.968 | 1.00 | 21.54 |
| 2460 | C | HIS | A | 340 | 24.257 | 24.569 | 14.493 | 1.00 | 21.15 |
| 2461 | O | HIS | A | 340 | 24.500 | 25.668 | 13.973 | 1.00 | 21.62 |
| 2462 | CB | HIS | A | 340 | 22.858 | 25.630 | 16.248 | 1.00 | 23.15 |
| 2463 | CG | HIS | A | 340 | 21.477 | 25.188 | 15.873 | 1.00 | 24.70 |
| 2464 | ND1 | HIS | A | 340 | 21.254 | 24.220 | 14.915 | 1.00 | 25.46 |
| 2465 | CD2 | HIS | A | 340 | 20.258 | 25.566 | 16.319 | 1.00 | 24.88 |
| 2466 | CE1 | HIS | A | 340 | 19.955 | 24.014 | 14.797 | 1.00 | 25.60 |
| 2467 | NE2 | HIS | A | 340 | 19.332 | 24.819 | 15.640 | 1.00 | 25.55 |
| 2468 | N | LEU | A | 341 | 24.136 | 23.463 | 13.765 | 1.00 | 21.78 |
| 2469 | CA | LEU | A | 341 | 24.425 | 23.446 | 12.332 | 1.00 | 21.51 |
| 2470 | C | LEU | A | 341 | 23.246 | 23.864 | 11.455 | 1.00 | 20.67 |
| 2471 | O | LEU | A | 341 | 23.264 | 23.596 | 10.245 | 1.00 | 20.80 |
| 2472 | CB | LEU | A | 341 | 24.939 | 22.111 | 11.840 | 1.00 | 22.08 |
| 2473 | CG | LEU | A | 341 | 26.253 | 21.519 | 12.279 | 1.00 | 23.06 |
| 2474 | CD1 | LEU | A | 341 | 27.036 | 20.962 | 11.093 | 1.00 | 22.21 |
| 2475 | CD2 | LEU | A | 341 | 27.124 | 22.487 | 13.058 | 1.00 | 23.72 |
| 2476 | N | LEU | A | 342 | 22.235 | 24.517 | 12.005 | 1.00 | 19.56 |
| 2477 | CA | LEU | A | 342 | 21.091 | 24.989 | 11.221 | 1.00 | 18.26 |
| 2478 | C | LEU | A | 342 | 20.559 | 23.973 | 10.240 | 1.00 | 18.01 |
| 2479 | O | LEU | A | 342 | 20.095 | 22.884 | 10.652 | 1.00 | 18.33 |
| 2480 | CB | LEU | A | 342 | 21.537 | 26.296 | 10.539 | 1.00 | 17.17 |
| 2481 | CG | LEU | A | 342 | 22.146 | 27.319 | 11.515 | 1.00 | 16.80 |
| 2482 | CD1 | LEU | A | 342 | 22.711 | 28.519 | 10.799 | 1.00 | 16.76 |
| 2483 | CD2 | LEU | A | 342 | 21.099 | 27.764 | 12.537 | 1.00 | 17.23 |
| 2484 | N | GLY | A | 343 | 20.749 | 24.167 | 8.940 | 1.00 | 16.41 |
| 2485 | CA | GLY | A | 343 | 20.241 | 23.256 | 7.937 | 1.00 | 15.90 |
| 2486 | C | GLY | A | 343 | 20.886 | 21.889 | 7.985 | 1.00 | 17.08 |
| 2487 | O | GLY | A | 343 | 20.296 | 20.916 | 7.502 | 1.00 | 18.05 |
| 2488 | N | ALA | A | 344 | 22.065 | 21.769 | 8.575 | 1.00 | 17.39 |
| 2489 | CA | ALA | A | 344 | 22.809 | 20.531 | 8.651 | 1.00 | 18.18 |
| 2490 | C | ALA | A | 344 | 22.583 | 19.807 | 9.966 | 1.00 | 19.20 |
| 2491 | O | ALA | A | 344 | 22.784 | 18.593 | 10.077 | 1.00 | 20.60 |
| 2492 | CB | ALA | A | 344 | 24.297 | 20.832 | 8.466 | 1.00 | 18.23 |
| 2493 | N | ALA | A | 345 | 22.134 | 20.542 | 10.974 | 1.00 | 19.41 |
| 2494 | CA | ALA | A | 345 | 21.900 | 19.977 | 12.300 | 1.00 | 19.17 |
| 2495 | C | ALA | A | 345 | 21.211 | 18.626 | 12.284 | 1.00 | 19.03 |
| 2496 | O | ALA | A | 345 | 21.746 | 17.655 | 12.825 | 1.00 | 19.54 |
| 2497 | CB | ALA | A | 345 | 21.118 | 20.990 | 13.127 | 1.00 | 19.37 |
| 2498 | N | GLY | A | 346 | 20.031 | 18.481 | 11.700 | 1.00 | 19.05 |
| 2499 | CA | GLY | A | 346 | 19.302 | 17.240 | 11.616 | 1.00 | 18.25 |
| 2500 | C | GLY | A | 346 | 20.038 | 16.124 | 10.895 | 1.00 | 18.83 |
| 2501 | O | GLY | A | 346 | 19.819 | 14.936 | 11.171 | 1.00 | 18.01 |
| 2502 | N | ALA | A | 347 | 20.907 | 16.443 | 9.944 | 1.00 | 19.83 |
| 2503 | CA | ALA | A | 347 | 21.683 | 15.439 | 9.228 | 1.00 | 21.04 |
| 2504 | C | ALA | A | 347 | 22.782 | 14.842 | 10.108 | 1.00 | 22.71 |
| 2505 | O | ALA | A | 347 | 22.859 | 13.614 | 10.275 | 1.00 | 23.84 |
| 2506 | CB | ALA | A | 347 | 22.311 | 16.035 | 7.979 | 1.00 | 19.88 |
| 2507 | N | VAL | A | 348 | 23.650 | 15.698 | 10.660 | 1.00 | 21.96 |
| 2508 | CA | VAL | A | 348 | 24.717 | 15.167 | 11.500 | 1.00 | 22.97 |
| 2509 | C | VAL | A | 348 | 24.116 | 14.420 | 12.684 | 1.00 | 24.48 |
| 2510 | O | VAL | A | 348 | 24.481 | 13.283 | 12.973 | 1.00 | 24.55 |
| 2511 | CB | VAL | A | 348 | 25.723 | 16.226 | 11.966 | 1.00 | 22.43 |
| 2512 | CG1 | VAL | A | 348 | 26.341 | 16.954 | 10.786 | 1.00 | 20.44 |
| 2513 | CG2 | VAL | A | 348 | 25.108 | 17.219 | 12.947 | 1.00 | 22.09 |
| 2514 | N | GLU | A | 349 | 23.120 | 14.982 | 13.349 | 1.00 | 26.69 |
| 2515 | CA | GLU | A | 349 | 22.474 | 14.348 | 14.490 | 1.00 | 29.09 |
| 2516 | C | GLU | A | 349 | 21.792 | 13.035 | 14.192 | 1.00 | 29.44 |
| 2517 | O | GLU | A | 349 | 21.603 | 12.239 | 15.125 | 1.00 | 29.84 |
| 2518 | CB | GLU | A | 349 | 21.503 | 15.364 | 15.131 | 1.00 | 30.54 |
| 2519 | CG | GLU | A | 349 | 22.309 | 16.556 | 15.629 | 1.00 | 33.46 |
| 2520 | CD | GLU | A | 349 | 21.540 | 17.774 | 16.041 | 1.00 | 35.00 |

Figure 2-40

| 2521 | OE1 | GLU | A | 349 | 20.333 | 17.684 | 16.369 | 1.00 | 36.57 |
|------|-----|-----|---|-----|--------|--------|--------|------|-------|
| 2522 | OE2 | GLU | A | 349 | 22.176 | 18.863 | 16.064 | 1.00 | 35.08 |
| 2523 | N | SER | A | 350 | 21.411 | 12.764 | 12.952 | 1.00 | 29.09 |
| 2524 | CA | SER | A | 350 | 20.905 | 11.481 | 12.516 | 1.00 | 28.77 |
| 2525 | C | SER | A | 350 | 22.049 | 10.458 | 12.529 | 1.00 | 29.04 |
| 2526 | O | SER | A | 350 | 21.839 | 9.297 | 12.841 | 1.00 | 29.05 |
| 2527 | CB | SER | A | 350 | 20.348 | 11.539 | 11.089 | 1.00 | 28.76 |
| 2528 | OG | SER | A | 350 | 19.043 | 12.076 | 11.069 | 1.00 | 28.97 |
| 2529 | N | ILE | A | 351 | 23.246 | 10.918 | 12.176 | 1.00 | 28.95 |
| 2530 | CA | ILE | A | 351 | 24.426 | 10.066 | 12.186 | 1.00 | 29.01 |
| 2531 | C | ILE | A | 351 | 24.801 | 9.724 | 13.627 | 1.00 | 29.32 |
| 2532 | O | ILE | A | 351 | 25.060 | 8.551 | 13.918 | 1.00 | 29.82 |
| 2533 | CB | ILE | A | 351 | 25.611 | 10.703 | 11.453 | 1.00 | 28.57 |
| 2534 | CG1 | ILE | A | 351 | 25.423 | 10.556 | 9.941 | 1.00 | 28.77 |
| 2535 | CG2 | ILE | A | 351 | 26.940 | 10.091 | 11.861 | 1.00 | 28.44 |
| 2536 | CD1 | ILE | A | 351 | 26.265 | 11.488 | 9.099 | 1.00 | 28.88 |
| 2537 | N | TYR | A | 352 | 24.714 | 10.695 | 14.530 | 1.00 | 28.96 |
| 2538 | CA | TYR | A | 352 | 25.000 | 10.452 | 15.938 | 1.00 | 29.99 |
| 2539 | C | TYR | A | 352 | 24.004 | 9.479 | 16.562 | 1.00 | 30.75 |
| 2540 | O | TYR | A | 352 | 24.407 | 8.671 | 17.391 | 1.00 | 32.84 |
| 2541 | CB | TYR | A | 352 | 25.012 | 11.723 | 16.779 | 1.00 | 28.66 |
| 2542 | CG | TYR | A | 352 | 25.850 | 12.864 | 16.269 | 1.00 | 26.47 |
| 2543 | CD1 | TYR | A | 352 | 25.545 | 14.168 | 16.639 | 1.00 | 26.55 |
| 2544 | CD2 | TYR | A | 352 | 26.948 | 12.650 | 15.451 | 1.00 | 25.98 |
| 2545 | CE1 | TYR | A | 352 | 26.313 | 15.236 | 16.196 | 1.00 | 26.27 |
| 2546 | CE2 | TYR | A | 352 | 27.708 | 13.705 | 14.984 | 1.00 | 26.13 |
| 2547 | CZ | TYR | A | 352 | 27.385 | 14.991 | 15.359 | 1.00 | 25.70 |
| 2548 | OH | TYR | A | 352 | 28.157 | 16.019 | 14.896 | 1.00 | 25.41 |
| 2549 | N | SER | A | 353 | 22.744 | 9.528 | 16.167 | 1.00 | 31.38 |
| 2550 | CA | SER | A | 353 | 21.742 | 8.592 | 16.666 | 1.00 | 32.24 |
| 2551 | C | SER | A | 353 | 21.926 | 7.201 | 16.064 | 1.00 | 32.63 |
| 2552 | O | SER | A | 353 | 21.565 | 6.189 | 16.681 | 1.00 | 32.93 |
| 2553 | CB | SER | A | 353 | 20.337 | 9.125 | 16.385 | 1.00 | 32.06 |
| 2554 | OG | SER | A | 353 | 20.266 | 10.510 | 16.706 | 1.00 | 32.40 |
| 2555 | N | ILE | A | 354 | 22.497 | 7.136 | 14.866 | 1.00 | 31.79 |
| 2556 | CA | ILE | A | 354 | 22.761 | 5.860 | 14.218 | 1.00 | 31.51 |
| 2557 | C | ILE | A | 354 | 23.987 | 5.200 | 14.844 | 1.00 | 32.97 |
| 2558 | O | ILE | A | 354 | 23.951 | 4.012 | 15.168 | 1.00 | 33.27 |
| 2559 | CB | ILE | A | 354 | 22.935 | 6.018 | 12.703 | 1.00 | 29.87 |
| 2560 | CG1 | ILE | A | 354 | 21.576 | 6.159 | 12.009 | 1.00 | 29.52 |
| 2561 | CG2 | ILE | A | 354 | 23.698 | 4.848 | 12.116 | 1.00 | 30.35 |
| 2562 | CD1 | ILE | A | 354 | 21.606 | 6.908 | 10.688 | 1.00 | 27.41 |
| 2563 | N | LEU | A | 355 | 25.055 | 5.970 | 15.066 | 1.00 | 33.53 |
| 2564 | CA | LEU | A | 355 | 26.290 | 5.432 | 15.639 | 1.00 | 33.26 |
| 2565 | C | LEU | A | 355 | 26.082 | 4.959 | 17.072 | 1.00 | 33.69 |
| 2566 | O | LEU | A | 355 | 26.622 | 3.935 | 17.510 | 1.00 | 32.84 |
| 2567 | CB | LEU | A | 355 | 27.439 | 6.436 | 15.553 | 1.00 | 32.20 |
| 2568 | CG | LEU | A | 355 | 27.931 | 6.753 | 14.130 | 1.00 | 31.40 |
| 2569 | CD1 | LEU | A | 355 | 28.833 | 7.978 | 14.145 | 1.00 | 31.15 |
| 2570 | CD2 | LEU | A | 355 | 28.643 | 5.566 | 13.506 | 1.00 | 29.67 |
| 2571 | N | ALA | A | 356 | 25.232 | 5.673 | 17.809 | 1.00 | 33.95 |
| 2572 | CA | ALA | A | 356 | 24.883 | 5.298 | 19.175 | 1.00 | 34.20 |
| 2573 | C | ALA | A | 356 | 24.327 | 3.879 | 19.202 | 1.00 | 35.31 |
| 2574 | O | ALA | A | 356 | 24.632 | 3.095 | 20.103 | 1.00 | 35.75 |
| 2575 | CB | ALA | A | 356 | 23.883 | 6.300 | 19.720 | 1.00 | 33.94 |
| 2576 | N | LEU | A | 357 | 23.556 | 3.497 | 18.178 | 1.00 | 36.14 |
| 2577 | CA | LEU | A | 357 | 23.049 | 2.136 | 18.063 | 1.00 | 36.56 |
| 2578 | C | LEU | A | 357 | 24.201 | 1.160 | 17.855 | 1.00 | 37.61 |
| 2579 | O | LEU | A | 357 | 24.258 | 0.103 | 18.490 | 1.00 | 39.13 |
| 2580 | CB | LEU | A | 357 | 22.020 | 2.012 | 16.933 | 1.00 | 35.23 |
| 2581 | CG | LEU | A | 357 | 20.692 | 2.753 | 17.197 | 1.00 | 34.83 |
| 2582 | CD1 | LEU | A | 357 | 19.880 | 2.899 | 15.923 | 1.00 | 33.45 |
| 2583 | CD2 | LEU | A | 357 | 19.892 | 2.060 | 18.281 | 1.00 | 33.22 |

Figure 2-41

| 2584 | N | ARG | A | 358 | 25.135 | 1.515 | 16.982 | 1.00 | 37.51 |
|---|---|---|---|---|---|---|---|---|---|
| 2585 | CA | ARG | A | 358 | 26.271 | 0.683 | 16.685 | 1.00 | 37.58 |
| 2586 | C | ARG | A | 358 | 27.129 | 0.376 | 17.910 | 1.00 | 38.26 |
| 2587 | O | ARG | A | 358 | 27.577 | -0.751 | 18.097 | 1.00 | 39.24 |
| 2588 | CB | ARG | A | 358 | 27.197 | 1.380 | 15.656 | 1.00 | 37.33 |
| 2589 | CG | ARG | A | 358 | 28.337 | 0.451 | 15.242 | 1.00 | 37.76 |
| 2590 | CD | ARG | A | 358 | 29.272 | 1.085 | 14.228 | 1.00 | 37.44 |
| 2591 | NE | ARG | A | 358 | 30.034 | 2.160 | 14.848 | 1.00 | 38.18 |
| 2592 | CZ | ARG | A | 358 | 30.884 | 2.965 | 14.221 | 1.00 | 38.70 |
| 2593 | NH1 | ARG | A | 358 | 31.108 | 2.831 | 12.917 | 1.00 | 38.32 |
| 2594 | NH2 | ARG | A | 358 | 31.479 | 3.932 | 14.919 | 1.00 | 38.15 |
| 2595 | N | ASP | A | 359 | 27.448 | 1.410 | 18.670 | 1.00 | 37.94 |
| 2596 | CA | ASP | A | 359 | 28.406 | 1.368 | 19.746 | 1.00 | 37.27 |
| 2597 | C | ASP | A | 359 | 27.808 | 1.313 | 21.132 | 1.00 | 38.02 |
| 2598 | O | ASP | A | 359 | 28.521 | 1.217 | 22.136 | 1.00 | 37.65 |
| 2599 | CB | ASP | A | 359 | 29.231 | 2.675 | 19.670 | 1.00 | 36.75 |
| 2600 | CG | ASP | A | 359 | 30.238 | 2.668 | 18.549 | 1.00 | 36.38 |
| 2601 | OD1 | ASP | A | 359 | 30.280 | 1.693 | 17.771 | 1.00 | 36.72 |
| 2602 | OD2 | ASP | A | 359 | 30.991 | 3.661 | 18.460 | 1.00 | 36.33 |
| 2603 | N | GLN | A | 360 | 26.491 | 1.483 | 21.216 | 1.00 | 38.96 |
| 2604 | CA | GLN | A | 360 | 25.810 | 1.516 | 22.509 | 1.00 | 39.05 |
| 2605 | C | GLN | A | 360 | 26.538 | 2.465 | 23.461 | 1.00 | 39.38 |
| 2606 | O | GLN | A | 360 | 26.698 | 2.168 | 24.643 | 1.00 | 39.53 |
| 2607 | CB | GLN | A | 360 | 25.660 | 0.130 | 23.099 | 1.00 | 39.41 |
| 2608 | CG | GLN | A | 360 | 24.973 | -0.898 | 22.217 | 1.00 | 39.76 |
| 2609 | CD | GLN | A | 360 | 23.466 | -0.769 | 22.178 | 1.00 | 40.29 |
| 2610 | OE1 | GLN | A | 360 | 22.782 | -0.477 | 23.159 | 1.00 | 39.32 |
| 2611 | NE2 | GLN | A | 360 | 22.893 | -0.991 | 20.988 | 1.00 | 40.99 |
| 2612 | N | ALA | A | 361 | 26.886 | 3.644 | 22.959 | 1.00 | 39.00 |
| 2613 | CA | ALA | A | 361 | 27.461 | 4.728 | 23.751 | 1.00 | 38.72 |
| 2614 | C | ALA | A | 361 | 26.683 | 6.012 | 23.442 | 1.00 | 38.04 |
| 2615 | O | ALA | A | 361 | 26.357 | 6.270 | 22.275 | 1.00 | 38.26 |
| 2616 | CB | ALA | A | 361 | 28.937 | 4.883 | 23.455 | 1.00 | 38.95 |
| 2617 | N | VAL | A | 362 | 26.325 | 6.779 | 24.460 | 1.00 | 35.95 |
| 2618 | CA | VAL | A | 362 | 25.509 | 7.982 | 24.250 | 1.00 | 33.68 |
| 2619 | C | VAL | A | 362 | 26.293 | 9.242 | 24.568 | 1.00 | 32.65 |
| 2620 | O | VAL | A | 362 | 26.684 | 9.490 | 25.703 | 1.00 | 31.11 |
| 2621 | CB | VAL | A | 362 | 24.215 | 7.874 | 25.077 | 1.00 | 33.18 |
| 2622 | CG1 | VAL | A | 362 | 23.575 | 9.209 | 25.387 | 1.00 | 32.96 |
| 2623 | CG2 | VAL | A | 362 | 23.209 | 6.988 | 24.346 | 1.00 | 32.67 |
| 2624 | N | PRO | A | 363 | 26.535 | 10.050 | 23.534 | 1.00 | 32.66 |
| 2625 | CA | PRO | A | 363 | 27.283 | 11.285 | 23.645 | 1.00 | 31.67 |
| 2626 | C | PRO | A | 363 | 26.671 | 12.173 | 24.705 | 1.00 | 31.09 |
| 2627 | O | PRO | A | 363 | 25.449 | 12.194 | 24.869 | 1.00 | 32.64 |
| 2628 | CB | PRO | A | 363 | 27.199 | 11.941 | 22.285 | 1.00 | 32.07 |
| 2629 | CG | PRO | A | 363 | 26.641 | 10.940 | 21.360 | 1.00 | 32.96 |
| 2630 | CD | PRO | A | 363 | 26.096 | 9.789 | 22.139 | 1.00 | 32.89 |
| 2631 | N | PRO | A | 364 | 27.495 | 12.901 | 25.434 | 1.00 | 30.09 |
| 2632 | CA | PRO | A | 364 | 27.032 | 13.733 | 26.516 | 1.00 | 29.72 |
| 2633 | C | PRO | A | 364 | 26.553 | 15.120 | 26.123 | 1.00 | 29.59 |
| 2634 | O | PRO | A | 364 | 26.782 | 15.591 | 25.016 | 1.00 | 28.83 |
| 2635 | CB | PRO | A | 364 | 28.284 | 13.863 | 27.386 | 1.00 | 29.18 |
| 2636 | CG | PRO | A | 364 | 29.418 | 13.799 | 26.423 | 1.00 | 29.36 |
| 2637 | CD | PRO | A | 364 | 28.974 | 12.883 | 25.323 | 1.00 | 29.95 |
| 2638 | N | THR | A | 365 | 25.950 | 15.787 | 27.100 | 1.00 | 28.90 |
| 2639 | CA | THR | A | 365 | 25.536 | 17.166 | 27.039 | 1.00 | 29.34 |
| 2640 | C | THR | A | 365 | 26.515 | 17.969 | 27.909 | 1.00 | 29.33 |
| 2641 | O | THR | A | 365 | 26.271 | 18.122 | 29.106 | 1.00 | 28.44 |
| 2642 | CB | THR | A | 365 | 24.119 | 17.418 | 27.589 | 1.00 | 30.33 |
| 2643 | OG1 | THR | A | 365 | 23.174 | 16.540 | 26.967 | 1.00 | 31.73 |
| 2644 | CG2 | THR | A | 365 | 23.680 | 18.864 | 27.360 | 1.00 | 29.24 |
| 2645 | N | ILE | A | 366 | 27.654 | 18.366 | 27.362 | 1.00 | 29.73 |
| 2646 | CA | ILE | A | 366 | 28.650 | 19.040 | 28.203 | 1.00 | 30.00 |

Figure 2-42

| | | | | | | | | |
|---|---|---|---|---|---|---|---|---|
| 2647 | C | ILE | A | 366 | 28.162 | 20.419 | 28.621 | 1.00 | 31.27 |
| 2648 | O | ILE | A | 366 | 27.219 | 20.981 | 28.067 | 1.00 | 30.39 |
| 2649 | CB | ILE | A | 366 | 30.025 | 19.120 | 27.528 | 1.00 | 29.07 |
| 2650 | CG1 | ILE | A | 366 | 30.052 | 20.205 | 26.451 | 1.00 | 29.20 |
| 2651 | CG2 | ILE | A | 366 | 30.405 | 17.769 | 26.927 | 1.00 | 27.75 |
| 2652 | CD1 | ILE | A | 366 | 31.415 | 20.552 | 25.913 | 1.00 | 28.17 |
| 2653 | N | ASN | A | 367 | 28.785 | 20.975 | 29.652 | 1.00 | 32.72 |
| 2654 | CA | ASN | A | 367 | 28.511 | 22.285 | 30.190 | 1.00 | 34.91 |
| 2655 | C | ASN | A | 367 | 27.251 | 22.403 | 31.019 | 1.00 | 36.61 |
| 2656 | O | ASN | A | 367 | 26.871 | 23.504 | 31.450 | 1.00 | 36.20 |
| 2657 | CB | ASN | A | 367 | 28.483 | 23.311 | 29.038 | 1.00 | 35.89 |
| 2658 | CG | ASN | A | 367 | 29.871 | 23.565 | 28.480 | 1.00 | 36.26 |
| 2659 | OD1 | ASN | A | 367 | 30.866 | 23.259 | 29.146 | 1.00 | 37.27 |
| 2660 | ND2 | ASN | A | 367 | 29.952 | 24.113 | 27.279 | 1.00 | 35.83 |
| 2661 | N | LEU | A | 368 | 26.596 | 21.297 | 31.326 | 1.00 | 39.08 |
| 2662 | CA | LEU | A | 368 | 25.351 | 21.292 | 32.094 | 1.00 | 41.70 |
| 2663 | C | LEU | A | 368 | 25.647 | 21.267 | 33.592 | 1.00 | 44.25 |
| 2664 | O | LEU | A | 368 | 25.388 | 20.294 | 34.299 | 1.00 | 44.89 |
| 2665 | CB | LEU | A | 368 | 24.506 | 20.106 | 31.655 | 1.00 | 40.63 |
| 2666 | CG | LEU | A | 368 | 23.160 | 19.841 | 32.309 | 1.00 | 40.11 |
| 2667 | CD1 | LEU | A | 368 | 22.287 | 21.085 | 32.347 | 1.00 | 40.15 |
| 2668 | CD2 | LEU | A | 368 | 22.447 | 18.702 | 31.590 | 1.00 | 38.98 |
| 2669 | N | ASP | A | 369 | 26.196 | 22.375 | 34.085 | 1.00 | 46.52 |
| 2670 | CA | ASP | A | 369 | 26.643 | 22.493 | 35.460 | 1.00 | 48.49 |
| 2671 | C | ASP | A | 369 | 25.472 | 22.540 | 36.426 | 1.00 | 49.89 |
| 2672 | O | ASP | A | 369 | 25.518 | 21.893 | 37.476 | 1.00 | 50.35 |
| 2673 | CB | ASP | A | 369 | 27.544 | 23.715 | 35.641 | 1.00 | 48.44 |
| 2674 | CG | ASP | A | 369 | 28.783 | 23.682 | 34.769 | 1.00 | 48.89 |
| 2675 | OD1 | ASP | A | 369 | 29.283 | 24.771 | 34.401 | 1.00 | 49.53 |
| 2676 | OD2 | ASP | A | 369 | 29.284 | 22.587 | 34.435 | 1.00 | 48.33 |
| 2677 | N | ASN | A | 370 | 24.430 | 23.299 | 36.104 | 1.00 | 51.52 |
| 2678 | CA | ASN | A | 370 | 23.261 | 23.423 | 36.964 | 1.00 | 52.70 |
| 2679 | C | ASN | A | 370 | 21.951 | 23.438 | 36.185 | 1.00 | 53.77 |
| 2680 | O | ASN | A | 370 | 21.512 | 24.515 | 35.756 | 1.00 | 53.47 |
| 2681 | CB | ASN | A | 370 | 23.326 | 24.734 | 37.759 | 1.00 | 52.88 |
| 2682 | CG | ASN | A | 370 | 24.420 | 24.856 | 38.775 | 1.00 | 53.02 |
| 2683 | OD1 | ASN | A | 370 | 25.288 | 25.726 | 38.676 | 1.00 | 52.97 |
| 2684 | ND2 | ASN | A | 370 | 24.419 | 23.967 | 39.766 | 1.00 | 53.88 |
| 2685 | N | PRO | A | 371 | 21.289 | 22.302 | 36.046 | 1.00 | 55.26 |
| 2686 | CA | PRO | A | 371 | 20.009 | 22.231 | 35.356 | 1.00 | 57.50 |
| 2687 | C | PRO | A | 371 | 19.056 | 23.295 | 35.870 | 1.00 | 60.20 |
| 2688 | O | PRO | A | 371 | 19.124 | 23.621 | 37.064 | 1.00 | 61.29 |
| 2689 | CB | PRO | A | 371 | 19.481 | 20.849 | 35.667 | 1.00 | 56.46 |
| 2690 | CG | PRO | A | 371 | 20.611 | 20.064 | 36.190 | 1.00 | 56.02 |
| 2691 | CD | PRO | A | 371 | 21.728 | 20.992 | 36.542 | 1.00 | 55.51 |
| 2692 | N | ASP | A | 372 | 18.181 | 23.849 | 35.029 | 1.00 | 63.07 |
| 2693 | CA | ASP | A | 372 | 17.273 | 24.869 | 35.590 | 1.00 | 66.12 |
| 2694 | C | ASP | A | 372 | 16.119 | 24.159 | 36.301 | 1.00 | 67.48 |
| 2695 | O | ASP | A | 372 | 15.977 | 22.938 | 36.253 | 1.00 | 67.01 |
| 2696 | CB | ASP | A | 372 | 16.848 | 25.919 | 34.606 | 1.00 | 66.67 |
| 2697 | CG | ASP | A | 372 | 16.102 | 25.455 | 33.384 | 1.00 | 67.57 |
| 2698 | OD1 | ASP | A | 372 | 16.051 | 24.235 | 33.120 | 1.00 | 67.94 |
| 2699 | OD2 | ASP | A | 372 | 15.548 | 26.313 | 32.657 | 1.00 | 67.93 |
| 2700 | N | GLU | A | 373 | 15.370 | 24.916 | 37.074 | 1.00 | 69.63 |
| 2701 | CA | GLU | A | 373 | 14.336 | 24.473 | 37.968 | 1.00 | 71.38 |
| 2702 | C | GLU | A | 373 | 13.674 | 23.139 | 37.710 | 1.00 | 71.44 |
| 2703 | O | GLU | A | 373 | 13.781 | 22.240 | 38.570 | 1.00 | 71.34 |
| 2704 | CB | GLU | A | 373 | 13.255 | 25.573 | 38.067 | 1.00 | 72.68 |
| 2705 | CG | GLU | A | 373 | 13.293 | 26.290 | 39.420 | 1.00 | 74.09 |
| 2706 | CD | GLU | A | 373 | 11.900 | 26.805 | 39.766 | 1.00 | 75.02 |
| 2707 | OE1 | GLU | A | 373 | 11.719 | 28.038 | 39.754 | 1.00 | 75.05 |
| 2708 | OE2 | GLU | A | 373 | 11.025 | 25.946 | 40.020 | 1.00 | 75.57 |
| 2709 | N | GLY | A | 374 | 12.842 | 23.002 | 36.683 | 1.00 | 71.36 |

Figure 2-43

| 2710 | CA | GLY | A | 374 | 12.019 | 21.821 | 36.531 | 1.00 | 71.79 |
|---|---|---|---|---|---|---|---|---|---|
| 2711 | C | GLY | A | 374 | 12.488 | 20.762 | 35.569 | 1.00 | 72.06 |
| 2712 | O | GLY | A | 374 | 11.663 | 19.944 | 35.116 | 1.00 | 72.74 |
| 2713 | N | CYS | A | 375 | 13.776 | 20.705 | 35.244 | 1.00 | 71.14 |
| 2714 | CA | CYS | A | 375 | 14.273 | 19.700 | 34.302 | 1.00 | 70.11 |
| 2715 | C | CYS | A | 375 | 14.845 | 18.495 | 35.029 | 1.00 | 69.27 |
| 2716 | O | CYS | A | 375 | 16.026 | 18.445 | 35.367 | 1.00 | 69.95 |
| 2717 | CB | CYS | A | 375 | 15.295 | 20.356 | 33.373 | 1.00 | 70.22 |
| 2718 | SG | CYS | A | 375 | 14.615 | 21.786 | 32.484 | 1.00 | 70.33 |
| 2719 | N | ASP | A | 376 | 14.003 | 17.492 | 35.257 | 1.00 | 67.38 |
| 2720 | CA | ASP | A | 376 | 14.353 | 16.293 | 35.989 | 1.00 | 65.40 |
| 2721 | C | ASP | A | 376 | 14.761 | 15.117 | 35.118 | 1.00 | 63.43 |
| 2722 | O | ASP | A | 376 | 14.848 | 13.977 | 35.602 | 1.00 | 63.21 |
| 2723 | CB | ASP | A | 376 | 13.144 | 15.872 | 36.851 | 1.00 | 66.52 |
| 2724 | CG | ASP | A | 376 | 11.940 | 15.452 | 36.031 | 1.00 | 67.35 |
| 2725 | OD1 | ASP | A | 376 | 11.974 | 15.549 | 34.786 | 1.00 | 67.44 |
| 2726 | OD2 | ASP | A | 376 | 10.925 | 15.017 | 36.628 | 1.00 | 67.75 |
| 2727 | N | LEU | A | 377 | 14.953 | 15.337 | 33.820 | 1.00 | 60.30 |
| 2728 | CA | LEU | A | 377 | 15.263 | 14.233 | 32.913 | 1.00 | 56.65 |
| 2729 | C | LEU | A | 377 | 16.745 | 13.893 | 32.912 | 1.00 | 54.35 |
| 2730 | O | LEU | A | 377 | 17.586 | 14.727 | 33.248 | 1.00 | 54.22 |
| 2731 | CB | LEU | A | 377 | 14.804 | 14.587 | 31.496 | 1.00 | 56.05 |
| 2732 | CG | LEU | A | 377 | 13.342 | 14.988 | 31.318 | 1.00 | 55.48 |
| 2733 | CD1 | LEU | A | 377 | 13.151 | 15.780 | 30.034 | 1.00 | 55.31 |
| 2734 | CD2 | LEU | A | 377 | 12.450 | 13.755 | 31.324 | 1.00 | 55.45 |
| 2735 | N | ASP | A | 378 | 17.072 | 12.669 | 32.518 | 1.00 | 51.50 |
| 2736 | CA | ASP | A | 378 | 18.466 | 12.246 | 32.405 | 1.00 | 49.45 |
| 2737 | C | ASP | A | 378 | 19.063 | 12.822 | 31.118 | 1.00 | 47.99 |
| 2738 | O | ASP | A | 378 | 18.941 | 12.271 | 30.023 | 1.00 | 47.05 |
| 2739 | CB | ASP | A | 378 | 18.579 | 10.724 | 32.418 | 1.00 | 49.34 |
| 2740 | CG | ASP | A | 378 | 19.988 | 10.196 | 32.572 | 1.00 | 48.74 |
| 2741 | OD1 | ASP | A | 378 | 20.188 | 8.963 | 32.538 | 1.00 | 48.13 |
| 2742 | OD2 | ASP | A | 378 | 20.931 | 11.003 | 32.733 | 1.00 | 49.41 |
| 2743 | N | PHE | A | 379 | 19.757 | 13.945 | 31.255 | 1.00 | 46.19 |
| 2744 | CA | PHE | A | 379 | 20.293 | 14.689 | 30.135 | 1.00 | 44.78 |
| 2745 | C | PHE | A | 379 | 21.708 | 14.267 | 29.762 | 1.00 | 44.38 |
| 2746 | O | PHE | A | 379 | 22.392 | 14.967 | 29.015 | 1.00 | 44.31 |
| 2747 | CB | PHE | A | 379 | 20.289 | 16.185 | 30.455 | 1.00 | 44.27 |
| 2748 | CG | PHE | A | 379 | 18.959 | 16.872 | 30.410 | 1.00 | 43.99 |
| 2749 | CD1 | PHE | A | 379 | 18.592 | 17.747 | 31.419 | 1.00 | 43.84 |
| 2750 | CD2 | PHE | A | 379 | 18.069 | 16.671 | 29.370 | 1.00 | 44.12 |
| 2751 | CE1 | PHE | A | 379 | 17.374 | 18.397 | 31.397 | 1.00 | 43.77 |
| 2752 | CE2 | PHE | A | 379 | 16.850 | 17.315 | 29.337 | 1.00 | 44.24 |
| 2753 | CZ | PHE | A | 379 | 16.497 | 18.184 | 30.358 | 1.00 | 43.96 |
| 2754 | N | VAL | A | 380 | 22.144 | 13.120 | 30.252 | 1.00 | 43.74 |
| 2755 | CA | VAL | A | 380 | 23.491 | 12.604 | 30.043 | 1.00 | 42.47 |
| 2756 | C | VAL | A | 380 | 24.485 | 13.738 | 30.306 | 1.00 | 42.16 |
| 2757 | O | VAL | A | 380 | 25.133 | 14.254 | 29.412 | 1.00 | 41.83 |
| 2758 | CB | VAL | A | 380 | 23.717 | 11.953 | 28.690 | 1.00 | 41.28 |
| 2759 | CG1 | VAL | A | 380 | 25.002 | 11.135 | 28.721 | 1.00 | 40.26 |
| 2760 | CG2 | VAL | A | 380 | 22.530 | 11.071 | 28.317 | 1.00 | 41.05 |
| 2761 | N | PRO | A | 381 * | 24.545 | 14.148 | 31.578 | 1.00 | 42.27 |
| 2762 | CA | PRO | A | 381 | 25.180 | 15.367 | 31.990 | 1.00 | 42.11 |
| 2763 | C | PRO | A | 381 | 26.599 | 15.644 | 31.608 | 1.00 | 41.67 |
| 2764 | O | PRO | A | 381 | 26.806 | 16.781 | 31.118 | 1.00 | 43.27 |
| 2765 | CB | PRO | A | 381 | 25.021 | 15.391 | 33.511 | 1.00 | 42.44 |
| 2766 | CG | PRO | A | 381 | 23.830 | 14.555 | 33.781 | 1.00 | 42.72 |
| 2767 | CD | PRO | A | 381 | 23.743 | 13.541 | 32.680 | 1.00 | 42.38 |
| 2768 | N | HIS | A | 382 | 27.641 | 14.854 | 31.837 | 1.00 | 40.46 |
| 2769 | CA | HIS | A | 382 | 28.972 | 15.361 | 31.463 | 1.00 | 40.21 |
| 2770 | C | HIS | A | 382 | 29.808 | 14.418 | 30.635 | 1.00 | 41.00 |
| 2771 | O | HIS | A | 382 | 30.612 | 14.846 | 29.797 | 1.00 | 39.92 |
| 2772 | CB | HIS | A | 382 | 29.745 | 15.751 | 32.740 | 1.00 | 39.82 |

Figure 2-44

| 2773 | CG | HIS | A | 382 | 29.317 | 17.068 | 33.305 | 1.00 | 39.32 |
|---|---|---|---|---|---|---|---|---|---|
| 2774 | ND1 | HIS | A | 382 | 29.629 | 18.266 | 32.705 | 1.00 | 39.09 |
| 2775 | CD2 | HIS | A | 382 | 28.543 | 17.367 | 34.375 | 1.00 | 39.39 |
| 2776 | CE1 | HIS | A | 382 | 29.086 | 19.250 | 33.393 | 1.00 | 39.48 |
| 2777 | NE2 | HIS | A | 382 | 28.422 | 18.738 | 34.413 | 1.00 | 39.23 |
| 2778 | N | GLU | A | 383 | 29.706 | 13.118 | 30.916 | 1.00 | 42.14 |
| 2779 | CA | GLU | A | 383 | 30.521 | 12.126 | 30.227 | 1.00 | 43.32 |
| 2780 | C | GLU | A | 383 | 29.638 | 11.155 | 29.456 | 1.00 | 42.41 |
| 2781 | O | GLU | A | 383 | 28.503 | 10.903 | 29.847 | 1.00 | 41.73 |
| 2782 | CB | GLU | A | 383 | 31.403 | 11.362 | 31.220 | 1.00 | 45.87 |
| 2783 | CG | GLU | A | 383 | 32.071 | 12.198 | 32.299 | 1.00 | 48.56 |
| 2784 | CD | GLU | A | 383 | 33.412 | 12.759 | 31.859 | 1.00 | 50.99 |
| 2785 | OE1 | GLU | A | 383 | 34.217 | 12.003 | 31.260 | 1.00 | 51.92 |
| 2786 | OE2 | GLU | A | 383 | 33.672 | 13.962 | 32.105 | 1.00 | 52.07 |
| 2787 | N | ALA | A | 384 | 30.166 | 10.620 | 28.357 | 1.00 | 42.07 |
| 2788 | CA | ALA | A | 384 | 29.437 | 9.632 | 27.575 | 1.00 | 41.28 |
| 2789 | C | ALA | A | 384 | 28.935 | 8.511 | 28.488 | 1.00 | 41.42 |
| 2790 | O | ALA | A | 384 | 29.646 | 8.072 | 29.392 | 1.00 | 40.84 |
| 2791 | CB | ALA | A | 384 | 30.318 | 9.038 | 26.491 | 1.00 | 40.98 |
| 2792 | N | ARG | A | 385 | 27.719 | 8.050 | 28.221 | 1.00 | 41.17 |
| 2793 | CA | ARG | A | 385 | 27.134 | 6.969 | 28.987 | 1.00 | 41.16 |
| 2794 | C | ARG | A | 385 | 27.155 | 5.663 | 28.204 | 1.00 | 41.68 |
| 2795 | O | ARG | A | 385 | 26.740 | 5.612 | 27.048 | 1.00 | 43.05 |
| 2796 | CB | ARG | A | 385 | 25.688 | 7.287 | 29.379 | 1.00 | 41.25 |
| 2797 | CG | ARG | A | 385 | 25.008 | 6.145 | 30.128 | 1.00 | 41.15 |
| 2798 | CD | ARG | A | 385 | 24.890 | 6.475 | 31.600 | 1.00 | 40.96 |
| 2799 | NE | ARG | A | 385 | 23.866 | 7.495 | 31.831 | 1.00 | 41.21 |
| 2800 | CZ | ARG | A | 385 | 24.175 | 8.720 | 32.233 | 1.00 | 41.50 |
| 2801 | NH1 | ARG | A | 385 | 25.455 | 9.016 | 32.428 | 1.00 | 41.34 |
| 2802 | NH2 | ARG | A | 385 | 23.211 | 9.609 | 32.418 | 1.00 | 42.12 |
| 2803 | N | GLN | A | 386 | 27.568 | 4.596 | 28.867 | 1.00 | 41.57 |
| 2804 | CA | GLN | A | 386 | 27.548 | 3.262 | 28.264 | 1.00 | 40.47 |
| 2805 | C | GLN | A | 386 | 26.152 | 2.680 | 28.446 | 1.00 | 39.88 |
| 2806 | O | GLN | A | 386 | 25.497 | 2.999 | 29.451 | 1.00 | 39.50 |
| 2807 | CB | GLN | A | 386 | 28.622 | 2.417 | 28.935 | 1.00 | 41.01 |
| 2808 | CG | GLN | A | 386 | 28.533 | 0.926 | 28.674 | 1.00 | 40.91 |
| 2809 | CD | GLN | A | 386 | 29.158 | 0.575 | 27.341 | 1.00 | 41.24 |
| 2810 | OE1 | GLN | A | 386 | 30.355 | 0.781 | 27.144 | 1.00 | 41.99 |
| 2811 | NE2 | GLN | A | 386 | 28.338 | 0.075 | 26.430 | 1.00 | 41.97 |
| 2812 | N | VAL | A | 387 | 25.622 | 1.979 | 27.446 | 1.00 | 38.93 |
| 2813 | CA | VAL | A | 387 | 24.293 | 1.392 | 27.543 | 1.00 | 38.54 |
| 2814 | C | VAL | A | 387 | 24.315 | -0.048 | 27.017 | 1.00 | 38.79 |
| 2815 | O | VAL | A | 387 | 25.250 | -0.473 | 26.346 | 1.00 | 38.11 |
| 2816 | CB | VAL | A | 387 | 23.166 | 2.146 | 26.817 | 1.00 | 37.66 |
| 2817 | CG1 | VAL | A | 387 | 22.938 | 3.547 | 27.358 | 1.00 | 36.33 |
| 2818 | CG2 | VAL | A | 387 | 23.414 | 2.193 | 25.311 | 1.00 | 37.03 |
| 2819 | N | SER | A | 388 | 23.234 | -0.770 | 27.273 | 1.00 | 39.59 |
| 2820 | CA | SER | A | 388 | 23.106 | -2.146 | 26.786 | 1.00 | 40.66 |
| 2821 | C | SER | A | 388 | 21.701 | -2.390 | 26.241 | 1.00 | 40.21 |
| 2822 | O | SER | A | 388 | 20.723 | -1.842 | 26.761 | 1.00 | 40.50 |
| 2823 | CB | SER | A | 388 | 23.421 | -3.127 | 27.922 | 1.00 | 41.01 |
| 2824 | OG | SER | A | 388 | 23.601 | -4.451 | 27.431 | 1.00 | 41.76 |
| 2825 | N | GLY | A | 389 | 21.562 | -3.180 | 25.192 | 1.00 | 39.76 |
| 2826 | CA | GLY | A | 389 | 20.284 | -3.503 | 24.608 | 1.00 | 41.14 |
| 2827 | C | GLY | A | 389 | 19.426 | -2.359 | 24.114 | 1.00 | 41.70 |
| 2828 | O | GLY | A | 389 | 18.189 | -2.390 | 24.235 | 1.00 | 41.06 |
| 2829 | N | MET | A | 390 | 20.032 | -1.330 | 23.533 | 1.00 | 42.05 |
| 2830 | CA | MET | A | 390 | 19.265 | -0.199 | 23.001 | 1.00 | 42.20 |
| 2831 | C | MET | A | 390 | 18.906 | -0.488 | 21.545 | 1.00 | 42.88 |
| 2832 | O | MET | A | 390 | 19.802 | -0.610 | 20.705 | 1.00 | 42.82 |
| 2833 | CB | MET | A | 390 | 20.065 | 1.080 | 23.159 | 1.00 | 41.46 |
| 2834 | CG | MET | A | 390 | 19.354 | 2.345 | 22.696 | 1.00 | 40.33 |
| 2835 | SD | MET | A | 390 | 20.300 | 3.828 | 23.053 | 1.00 | 39.24 |

Figure 2-45

| 2836 | CE | MET | A | 390 | 21.765 | 3.567 | 22.063 | 1.00 | 37.25 |
|---|---|---|---|---|---|---|---|---|---|
| 2837 | N | GLU | A | 391 | 17.620 | -0.654 | 21.248 | 1.00 | 43.99 |
| 2838 | CA | GLU | A | 391 | 17.201 | -1.001 | 19.892 | 1.00 | 46.08 |
| 2839 | C | GLU | A | 391 | 16.864 | 0.206 | 19.024 | 1.00 | 45.41 |
| 2840 | O | GLU | A | 391 | 17.167 | 0.247 | 17.826 | 1.00 | 44.59 |
| 2841 | CB | GLU | A | 391 | 16.005 | -1.963 | 19.929 | 1.00 | 48.01 |
| 2842 | CG | GLU | A | 391 | 16.255 | -3.301 | 20.576 | 1.00 | 51.25 |
| 2843 | CD | GLU | A | 391 | 16.345 | -4.482 | 19.632 | 1.00 | 53.60 |
| 2844 | OE1 | GLU | A | 391 | 15.617 | -4.540 | 18.607 | 1.00 | 54.36 |
| 2845 | OE2 | GLU | A | 391 | 17.166 | -5.391 | 19.930 | 1.00 | 54.27 |
| 2846 | N | TYR | A | 392 | 16.214 | 1.215 | 19.591 | 1.00 | 44.78 |
| 2847 | CA | TYR | A | 392 | 15.787 | 2.388 | 18.871 | 1.00 | 44.24 |
| 2848 | C | TYR | A | 392 | 16.312 | 3.695 | 19.477 | 1.00 | 43.65 |
| 2849 | O | TYR | A | 392 | 16.257 | 3.870 | 20.701 | 1.00 | 43.45 |
| 2850 | CB | TYR | A | 392 | 14.257 | 2.501 | 18.881 | 1.00 | 44.89 |
| 2851 | CG | TYR | A | 392 | 13.475 | 1.323 | 18.387 | 1.00 | 45.69 |
| 2852 | CD1 | TYR | A | 392 | 12.942 | 0.403 | 19.287 | 1.00 | 46.27 |
| 2853 | CD2 | TYR | A | 392 | 13.246 | 1.120 | 17.032 | 1.00 | 45.96 |
| 2854 | CE1 | TYR | A | 392 | 12.202 | -0.678 | 18.851 | 1.00 | 46.79 |
| 2855 | CE2 | TYR | A | 392 | 12.515 | 0.037 | 16.588 | 1.00 | 46.86 |
| 2856 | CZ | TYR | A | 392 | 11.991 | -0.857 | 17.499 | 1.00 | 47.26 |
| 2857 | OH | TYR | A | 392 | 11.240 | -1.930 | 17.071 | 1.00 | 47.84 |
| 2858 | N | THR | A | 393 | 16.527 | 4.677 | 18.599 | 1.00 | 41.43 |
| 2859 | CA | THR | A | 393 | 16.763 | 6.049 | 18.998 | 1.00 | 40.27 |
| 2860 | C | THR | A | 393 | 15.896 | 7.031 | 18.195 | 1.00 | 39.59 |
| 2861 | O | THR | A | 393 | 15.601 | 6.863 | 17.017 | 1.00 | 39.19 |
| 2862 | CB | THR | A | 393 | 18.227 | 6.496 | 18.876 | 1.00 | 40.35 |
| 2863 | OG1 | THR | A | 393 | 18.792 | 6.069 | 17.624 | 1.00 | 40.81 |
| 2864 | CG2 | THR | A | 393 | 19.062 | 5.964 | 20.019 | 1.00 | 39.93 |
| 2865 | N | LEU | A | 394 | 15.488 | 8.104 | 18.846 | 1.00 | 39.00 |
| 2866 | CA | LEU | A | 394 | 14.695 | 9.169 | 18.264 | 1.00 | 38.29 |
| 2867 | C | LEU | A | 394 | 15.567 | 10.401 | 18.030 | 1.00 | 37.46 |
| 2868 | O | LEU | A | 394 | 16.480 | 10.682 | 18.814 | 1.00 | 36.71 |
| 2869 | CB | LEU | A | 394 | 13.533 | 9.523 | 19.189 | 1.00 | 39.52 |
| 2870 | CG | LEU | A | 394 | 12.508 | 10.542 | 18.696 | 1.00 | 40.53 |
| 2871 | CD1 | LEU | A | 394 | 11.158 | 9.876 | 18.456 | 1.00 | 40.54 |
| 2872 | CD2 | LEU | A | 394 | 12.360 | 11.689 | 19.690 | 1.00 | 40.98 |
| 2873 | N | CYS | A | 395 | 15.300 | 11.120 | 16.940 | 1.00 | 36.66 |
| 2874 | CA | CYS | A | 395 | 16.095 | 12.310 | 16.628 | 1.00 | 35.56 |
| 2875 | C | CYS | A | 395 | 15.238 | 13.530 | 16.318 | 1.00 | 34.76 |
| 2876 | O | CYS | A | 395 | 14.505 | 13.532 | 15.328 | 1.00 | 34.93 |
| 2877 | CB | CYS | A | 395 | 17.014 | 12.019 | 15.441 | 1.00 | 34.91 |
| 2878 | SG | CYS | A | 395 | 17.954 | 13.469 | 14.915 | 1.00 | 35.28 |
| 2879 | N | ASN | A | 396 | 15.362 | 14.594 | 17.099 | 1.00 | 33.67 |
| 2880 | CA | ASN | A | 396 | 14.583 | 15.799 | 16.915 | 1.00 | 33.78 |
| 2881 | C | ASN | A | 396 | 15.283 | 16.976 | 16.256 | 1.00 | 32.51 |
| 2882 | O | ASN | A | 396 | 16.488 | 17.152 | 16.339 | 1.00 | 33.78 |
| 2883 | CB | ASN | A | 396 | 14.115 | 16.318 | 18.292 | 1.00 | 35.61 |
| 2884 | CG | ASN | A | 396 | 12.854 | 15.629 | 18.754 | 1.00 | 37.03 |
| 2885 | OD1 | ASN | A | 396 | 12.208 | 14.917 | 17.979 | 1.00 | 36.89 |
| 2886 | ND2 | ASN | A | 396 | 12.542 | 15.844 | 20.031 | 1.00 | 37.90 |
| 2887 | N | SER | A | 397 | 14.501 | 17.847 | 15.645 | 1.00 | 31.24 |
| 2888 | CA | SER | A | 397 | 14.937 | 19.065 | 14.990 | 1.00 | 30.08 |
| 2889 | C | SER | A | 397 | 13.728 | 19.999 | 14.871 | 1.00 | 29.36 |
| 2890 | O | SER | A | 397 | 12.686 | 19.517 | 14.403 | 1.00 | 28.86 |
| 2891 | CB | SER | A | 397 | 15.460 | 18.847 | 13.579 | 1.00 | 29.66 |
| 2892 | OG | SER | A | 397 | 16.795 | 18.440 | 13.514 | 1.00 | 30.44 |
| 2893 | N | PHE | A | 398 | 13.798 | 21.220 | 15.377 | 1.00 | 28.10 |
| 2894 | CA | PHE | A | 398 | 12.630 | 22.116 | 15.262 | 1.00 | 28.51 |
| 2895 | C | PHE | A | 398 | 13.071 | 23.370 | 14.525 | 1.00 | 28.82 |
| 2896 | O | PHE | A | 398 | 14.295 | 23.555 | 14.417 | 1.00 | 30.86 |
| 2897 | CB | PHE | A | 398 | 12.006 | 22.417 | 16.613 | 1.00 | 28.54 |
| 2898 | CG | PHE | A | 398 | 11.817 | 21.230 | 17.522 | 1.00 | 28.25 |

Figure 2-46

| 2899 | CD1 | PHE | A | 398 | 12.295 | 21.264 | 18.818 | 1.00 | 28.38 |
|---|---|---|---|---|---|---|---|---|---|
| 2900 | CD2 | PHE | A | 398 | 11.174 | 20.084 | 17.096 | 1.00 | 27.71 |
| 2901 | CE1 | PHE | A | 398 | 12.163 | 20.173 | 19.651 | 1.00 | 29.51 |
| 2902 | CE2 | PHE | A | 398 | 11.073 | 18.976 | 17.897 | 1.00 | 28.62 |
| 2903 | CZ | PHE | A | 398 | 11.556 | 19.013 | 19.188 | 1.00 | 29.57 |
| 2904 | N | GLY | A | 399 | 12.192 | 24.182 | 13.950 | 1.00 | 27.59 |
| 2905 | CA | GLY | A | 399 | 12.635 | 25.341 | 13.198 | 1.00 | 26.19 |
| 2906 | C | GLY | A | 399 | 11.652 | 26.491 | 13.079 | 1.00 | 26.07 |
| 2907 | O | GLY | A | 399 | 10.445 | 26.378 | 13.285 | 1.00 | 25.91 |
| 2908 | N | PHE | A | 400 | 12.188 | 27.658 | 12.745 | 1.00 | 25.06 |
| 2909 | CA | PHE | A | 400 | 11.482 | 28.899 | 12.529 | 1.00 | 24.03 |
| 2910 | C | PHE | A | 400 | 10.259 | 28.629 | 11.651 | 1.00 | 24.31 |
| 2911 | O | PHE | A | 400 | 10.354 | 27.971 | 10.616 | 1.00 | 23.63 |
| 2912 | CB | PHE | A | 400 | 12.387 | 29.922 | 11.850 | 1.00 | 24.14 |
| 2913 | CG | PHE | A | 400 | 13.306 | 30.718 | 12.718 | 1.00 | 25.15 |
| 2914 | CD1 | PHE | A | 400 | 13.533 | 30.424 | 14.055 | 1.00 | 24.96 |
| 2915 | CD2 | PHE | A | 400 | 13.974 | 31.813 | 12.170 | 1.00 | 25.57 |
| 2916 | CE1 | PHE | A | 400 | 14.385 | 31.188 | 14.826 | 1.00 | 24.16 |
| 2917 | CE2 | PHE | A | 400 | 14.806 | 32.600 | 12.940 | 1.00 | 25.43 |
| 2918 | CZ | PHE | A | 400 | 15.018 | 32.276 | 14.270 | 1.00 | 25.18 |
| 2919 | N | GLY | A | 401 | 9.099 | 29.086 | 12.115 | 1.00 | 24.50 |
| 2920 | CA | GLY | A | 401 | 7.842 | 28.848 | 11.405 | 1.00 | 23.46 |
| 2921 | C | GLY | A | 401 | 7.129 | 27.661 | 12.040 | 1.00 | 23.34 |
| 2922 | O | GLY | A | 401 | 6.228 | 27.052 | 11.467 | 1.00 | 22.92 |
| 2923 | N | GLY | A | 402 | 7.634 | 27.221 | 13.198 | 1.00 | 23.63 |
| 2924 | CA | GLY | A | 402 | 7.103 | 26.072 | 13.900 | 1.00 | 23.42 |
| 2925 | C | GLY | A | 402 | 7.077 | 24.803 | 13.068 | 1.00 | 24.44 |
| 2926 | O | GLY | A | 402 | 6.208 | 23.954 | 13.285 | 1.00 | 24.84 |
| 2927 | N | THR | A | 403 | 8.060 | 24.585 | 12.203 | 1.00 | 24.96 |
| 2928 | CA | THR | A | 403 | 8.122 | 23.374 | 11.385 | 1.00 | 25.60 |
| 2929 | C | THR | A | 403 | 8.923 | 22.313 | 12.123 | 1.00 | 25.97 |
| 2930 | O | THR | A | 403 | 10.091 | 22.525 | 12.445 | 1.00 | 26.03 |
| 2931 | CB | THR | A | 403 | 8.711 | 23.664 | 10.000 | 1.00 | 26.33 |
| 2932 | OG1 | THR | A | 403 | 8.834 | 22.465 | 9.225 | 1.00 | 26.55 |
| 2933 | CG2 | THR | A | 403 | 10.078 | 24.329 | 10.102 | 1.00 | 26.08 |
| 2934 | N | ASN | A | 404 | 8.267 | 21.206 | 12.481 | 1.00 | 26.32 |
| 2935 | CA | ASN | A | 404 | 8.883 | 20.161 | 13.278 | 1.00 | 25.93 |
| 2936 | C | ASN | A | 404 | 9.004 | 18.827 | 12.553 | 1.00 | 26.08 |
| 2937 | O | ASN | A | 404 | 8.216 | 18.461 | 11.678 | 1.00 | 25.83 |
| 2938 | CB | ASN | A | 404 | 8.105 | 19.908 | 14.575 | 1.00 | 26.10 |
| 2939 | CG | ASN | A | 404 | 7.872 | 21.156 | 15.387 | 1.00 | 27.31 |
| 2940 | OD1 | ASN | A | 404 | 8.801 | 21.721 | 15.968 | 1.00 | 27.66 |
| 2941 | ND2 | ASN | A | 404 | 6.620 | 21.607 | 15.422 | 1.00 | 28.28 |
| 2942 | N | GLY | A | 405 | 10.005 | 18.064 | 12.990 | 1.00 | 25.82 |
| 2943 | CA | GLY | A | 405 | 10.265 | 16.759 | 12.411 | 1.00 | 27.49 |
| 2944 | C | GLY | A | 405 | 11.035 | 15.853 | 13.369 | 1.00 | 27.89 |
| 2945 | O | GLY | A | 405 | 11.823 | 16.310 | 14.199 | 1.00 | 28.48 |
| 2946 | N | SER | A | 406 | 10.834 | 14.555 | 13.213 | 1.00 | 26.92 |
| 2947 | CA | SER | A | 406 | 11.477 | 13.559 | 14.029 | 1.00 | 27.03 |
| 2948 | C | SER | A | 406 | 11.774 | 12.300 | 13.211 | 1.00 | 28.11 |
| 2949 | O | SER | A | 406 | 10.962 | 11.914 | 12.365 | 1.00 | 28.49 |
| 2950 | CB | SER | A | 406 | 10.563 | 13.146 | 15.182 | 1.00 | 27.63 |
| 2951 | OG | SER | A | 406 | 10.349 | 14.156 | 16.132 | 1.00 | 28.47 |
| 2952 | N | LEU | A | 407 | 12.897 | 11.661 | 13.493 | 1.00 | 28.14 |
| 2953 | CA | LEU | A | 407 | 13.261 | 10.416 | 12.830 | 1.00 | 29.52 |
| 2954 | C | LEU | A | 407 | 13.559 | 9.328 | 13.861 | 1.00 | 30.74 |
| 2955 | O | LEU | A | 407 | 14.165 | 9.583 | 14.910 | 1.00 | 31.02 |
| 2956 | CB | LEU | A | 407 | 14.464 | 10.657 | 11.925 | 1.00 | 29.92 |
| 2957 | CG | LEU | A | 407 | 14.168 | 11.373 | 10.595 | 1.00 | 30.15 |
| 2958 | CD1 | LEU | A | 407 | 15.461 | 11.704 | 9.874 | 1.00 | 28.71 |
| 2959 | CD2 | LEU | A | 407 | 13.247 | 10.526 | 9.725 | 1.00 | 29.57 |
| 2960 | N | ILE | A | 408 | 13.073 | 8.116 | 13.633 | 1.00 | 31.35 |
| 2961 | CA | ILE | A | 408 | 13.309 | 7.003 | 14.552 | 1.00 | 31.21 |

Figure 2-47

| 2962 | C | ILE | A | 408 | 14.199 | 5.975 | 13.852 | 1.00 | 32.25 |
|---|---|---|---|---|---|---|---|---|---|
| 2963 | O | ILE | A | 408 | 13.896 | 5.536 | 12.746 | 1.00 | 31.08 |
| 2964 | CB | ILE | A | 408 | 12.025 | 6.322 | 15.033 | 1.00 | 30.12 |
| 2965 | CG1 | ILE | A | 408 | 11.353 | 7.157 | 16.132 | 1.00 | 29.79 |
| 2966 | CG2 | ILE | A | 408 | 12.305 | 4.920 | 15.557 | 1.00 | 29.58 |
| 2967 | CD1 | ILE | A | 408 | 9.895 | 6.798 | 16.326 | 1.00 | 29.42 |
| 2968 | N | PHE | A | 409 | 15.284 | 5.614 | 14.523 | 1.00 | 34.35 |
| 2969 | CA | PHE | A | 409 | 16.214 | 4.642 | 13.950 | 1.00 | 36.66 |
| 2970 | C | PHE | A | 409 | 16.134 | 3.342 | 14.724 | 1.00 | 38.51 |
| 2971 | O | PHE | A | 409 | 15.690 | 3.343 | 15.874 | 1.00 | 38.95 |
| 2972 | CB | PHE | A | 409 | 17.635 | 5.215 | 13.925 | 1.00 | 36.47 |
| 2973 | CG | PHE | A | 409 | 17.789 | 6.215 | 12.808 | 1.00 | 36.23 |
| 2974 | CD1 | PHE | A | 409 | 17.643 | 7.567 | 13.065 | 1.00 | 36.49 |
| 2975 | CD2 | PHE | A | 409 | 17.991 | 5.788 | 11.505 | 1.00 | 35.84 |
| 2976 | CE1 | PHE | A | 409 | 17.755 | 8.487 | 12.036 | 1.00 | 36.42 |
| 2977 | CE2 | PHE | A | 409 | 18.093 | 6.696 | 10.475 | 1.00 | 36.01 |
| 2978 | CZ | PHE | A | 409 | 17.977 | 8.051 | 10.745 | 1.00 | 36.45 |
| 2979 | N | LYS | A | 410 | 16.465 | 2.241 | 14.066 | 1.00 | 40.81 |
| 2980 | CA | LYS | A | 410 | 16.395 | 0.937 | 14.720 | 1.00 | 42.76 |
| 2981 | C | LYS | A | 410 | 17.648 | 0.123 | 14.412 | 1.00 | 43.74 |
| 2982 | O | LYS | A | 410 | 18.141 | 0.139 | 13.281 | 1.00 | 42.97 |
| 2983 | CB | LYS | A | 410 | 15.147 | 0.184 | 14.279 | 1.00 | 43.67 |
| 2984 | CG | LYS | A | 410 | 15.072 | -1.261 | 14.749 | 1.00 | 45.15 |
| 2985 | CD | LYS | A | 410 | 13.842 | -1.944 | 14.178 | 1.00 | 46.70 |
| 2986 | CE | LYS | A | 410 | 13.728 | -3.393 | 14.600 | 1.00 | 47.69 |
| 2987 | NZ | LYS | A | 410 | 13.392 | -3.506 | 16.051 | 1.00 | 48.43 |
| 2988 | N | LYS | A | 411 | 18.133 | -0.567 | 15.439 | 1.00 | 45.19 |
| 2989 | CA | LYS | A | 411 | 19.314 | -1.409 | 15.301 | 1.00 | 47.01 |
| 2990 | C | LYS | A | 411 | 18.931 | -2.679 | 14.539 | 1.00 | 48.00 |
| 2991 | O | LYS | A | 411 | 17.858 | -3.221 | 14.794 | 1.00 | 47.64 |
| 2992 | CB | LYS | A | 411 | 19.882 | -1.782 | 16.661 | 1.00 | 47.51 |
| 2993 | CG | LYS | A | 411 | 21.236 | -2.461 | 16.610 | 1.00 | 48.43 |
| 2994 | CD | LYS | A | 411 | 21.829 | -2.606 | 18.008 | 1.00 | 49.25 |
| 2995 | CE | LYS | A | 411 | 21.660 | -4.036 | 18.505 | 1.00 | 49.84 |
| 2996 | NZ | LYS | A | 411 | 22.313 | -4.225 | 19.835 | 1.00 | 50.37 |
| 2997 | N | ILE | A | 412 | 19.767 | -3.087 | 13.601 | 1.00 | 49.72 |
| 2998 | CA | ILE | A | 412 | 19.469 | -4.274 | 12.799 | 1.00 | 51.86 |
| 2999 | C | ILE | A | 412 | 20.459 | -5.392 | 13.085 | 1.00 | 52.16 |
| 3000 | O | ILE | A | 412 | 20.167 | -6.540 | 12.754 | 1.00 | 52.95 |
| 3001 | CB | ILE | A | 412 | 19.422 | -3.917 | 11.307 | 1.00 | 53.06 |
| 3002 | CG1 | ILE | A | 412 | 18.129 | -4.459 | 10.671 | 1.00 | 53.46 |
| 3003 | CG2 | ILE | A | 412 | 20.640 | -4.413 | 10.543 | 1.00 | 53.46 |
| 3004 | CD1 | ILE | A | 412 | 17.892 | -3.896 | 9.278 | 1.00 | 53.36 |
| 3005 | OXT | ILE | A | 412 | 21.521 | -5.114 | 13.639 | 1.00 | 52.95 |
| 3006 | | ILE | A | 412 | | | | | |
| 3007 | C1 | CER | A | 413 | 16.270 | 27.008 | 14.939 | 1.00 | 42.62 |
| 3008 | N1 | CER | A | 413 | 15.405 | 28.001 | 15.549 | 1.00 | 43.68 |
| 3009 | O1 | CER | A | 413 | 16.728 | 30.271 | 11.664 | 1.00 | 41.32 |
| 3010 | C2 | CER | A | 413 | 16.925 | 27.331 | 13.561 | 1.00 | 38.73 |
| 3011 | O2 | CER | A | 413 | 16.493 | 25.921 | 15.481 | 1.00 | 43.30 |
| 3012 | C3 | CER | A | 413 | 15.986 | 28.354 | 12.880 | 1.00 | 40.31 |
| 3013 | O3 | CER | A | 413 | 14.813 | 27.662 | 12.446 | 1.00 | 40.48 |
| 3014 | C4 | CER | A | 413 | 16.661 | 29.036 | 11.703 | 1.00 | 40.39 |
| 3015 | C5 | CER | A | 413 | 17.226 | 28.267 | 10.507 | 1.00 | 40.11 |
| 3016 | C6 | CER | A | 413 | 17.265 | 29.232 | 9.297 | 1.00 | 39.90 |
| 3017 | C7 | CER | A | 413 | 18.711 | 29.652 | 9.103 | 1.00 | 40.02 |
| 3018 | C8 | CER | A | 413 | 19.383 | 29.404 | 7.982 | 1.00 | 39.25 |
| 3019 | C9 | CER | A | 413 | 20.833 | 29.912 | 7.969 | 1.00 | 39.77 |
| 3020 | C10 | CER | A | 413 | 20.766 | 31.443 | 7.867 | 1.00 | 39.44 |
| 3021 | C11 | CER | A | 413 | 21.590 | 32.160 | 8.641 | 1.00 | 39.99 |
| 3022 | C12 | CER | A | 413 | 21.550 | 33.685 | 8.529 | 1.00 | 40.81 |
| 3023 | O | HOH | | 501 | 21.907 | 17.399 | 19.574 | 1.00 | 18.60 | O |
| 3024 | O | HOH | | 502 | 21.318 | 20.702 | -2.438 | 1.00 | 24.78 | O |

Figure 2-48

| 3025 | O | HOH | 503 | 26.523 | 32.326 | 19.940 | 1.00 | 34.45 | O |
|---|---|---|---|---|---|---|---|---|---|
| 3026 | O | HOH | 504 | 28.449 | 30.874 | 3.017 | 1.00 | 33.79 | O |
| 3027 | O | HOH | 505 | 24.668 | 28.038 | 4.445 | 1.00 | 18.32 | O |
| 3028 | O | HOH | 507 | 15.042 | 27.512 | 5.199 | 1.00 | 17.31 | O |
| 3029 | O | HOH | 508 | 29.925 | 26.579 | 22.947 | 1.00 | 40.78 | O |
| 3030 | O | HOH | 511 | 23.439 | 42.041 | 15.173 | 1.00 | 71.80 | O |
| 3031 | O | HOH | 512 | 22.342 | 38.099 | 20.418 | 1.00 | 32.70 | O |
| 3032 | O | HOH | 516 | 10.030 | 4.324 | 6.316 | 1.00 | 46.02 | O |
| 3033 | O | HOH | 520 | 13.286 | 7.231 | -11.806 | 1.00 | 52.47 | O |
| 3034 | O | HOH | 600 | 4.344 | 28.171 | 14.312 | 1.00 | 34.33 | O |
| 3035 | O | HOH | 601 | 8.984 | 29.158 | 15.330 | 1.00 | 19.89 | O |
| 3036 | O | HOH | 602 | 23.826 | 20.969 | 14.788 | 1.00 | 27.55 | O |
| 3037 | O | HOH | 604 | 35.933 | 26.827 | 5.038 | 1.00 | 38.80 | O |
| 3038 | O | HOH | 605 | 32.286 | 37.853 | -6.692 | 1.00 | 46.37 | O |
| 3039 | O | HOH | 606 | 3.089 | 3.720 | 8.561 | 1.00 | 61.24 | O |
| 3040 | O | HOH | 607 | 16.239 | -0.824 | 25.960 | 1.00 | 37.31 | O |
| 3041 | O | HOH | 608 | 6.142 | 22.763 | 19.648 | 1.00 | 44.37 | O |
| 3042 | O | HOH | 609 | 6.225 | 28.059 | 17.075 | 1.00 | 32.61 | O |
| 3043 | O | HOH | 611 | 32.315 | 7.695 | 30.119 | 1.00 | 51.98 | O |
| 3044 | O | HOH | 612 | 32.210 | 7.634 | 6.284 | 1.00 | 35.28 | O |
| 3045 | O | HOH | 613 | 17.070 | 38.017 | 12.044 | 1.00 | 22.73 | O |
| 3046 | O | HOH | 614 | 31.176 | 19.825 | 30.843 | 1.00 | 37.36 | O |
| 3047 | O | HOH | 615 | 27.957 | 31.368 | 17.445 | 1.00 | 32.76 | O |
| 3048 | O | HOH | 616 | 32.966 | 30.345 | -2.158 | 1.00 | 56.05 | O |
| 3049 | O | HOH | 618 | 11.323 | -4.259 | 1.793 | 1.00 | 38.53 | O |
| 3050 | O | HOH | 620 | 26.925 | 5.604 | -18.307 | 1.00 | 53.90 | O |
| 3051 | O | HOH | 621 | 16.279 | 30.145 | 2.670 | 1.00 | 31.13 | O |
| 3052 | O | HOH | 622 | 38.595 | 8.716 | 10.273 | 1.00 | 46.13 | O |
| 3053 | O | HOH | 623 | 33.582 | 26.804 | 8.900 | 1.00 | 21.60 | O |
| 3054 | O | HOH | 624 | 21.151 | 45.870 | -3.906 | 1.00 | 28.41 | O |
| 3055 | O | HOH | 625 | 23.504 | 29.447 | 25.903 | 1.00 | 17.43 | O |
| 3056 | O | HOH | 626 | 26.368 | 1.855 | -19.938 | 1.00 | 44.00 | O |
| 3057 | O | HOH | 627 | 2.152 | 6.256 | 9.459 | 1.00 | 47.04 | O |
| 3058 | O | HOH | 628 | 6.809 | 19.529 | 9.383 | 1.00 | 29.11 | O |
| 3059 | O | HOH | 629 | 15.379 | 11.563 | 30.794 | 1.00 | 48.45 | O |
| 3060 | O | HOH | 630 | 27.712 | 4.338 | -20.522 | 1.00 | 45.95 | O |
| 3061 | O | HOH | 631 | 18.721 | 20.451 | 10.277 | 1.00 | 22.11 | O |
| 3062 | O | HOH | 632 | 31.228 | 24.084 | 23.545 | 1.00 | 32.43 | O |
| 3063 | O | HOH | 634 | 39.583 | 12.746 | 19.869 | 1.00 | 49.30 | O |
| 3064 | O | HOH | 635 | 25.064 | 38.355 | 18.750 | 1.00 | 31.27 | O |
| 3065 | O | HOH | 636 | 28.974 | 33.743 | -7.396 | 1.00 | 25.15 | O |
| 3066 | O | HOH | 637 | 26.250 | 41.318 | 16.894 | 1.00 | 47.65 | O |
| 3067 | O | HOH | 638 | 11.568 | 27.419 | 17.240 | 1.00 | 50.15 | O |
| 3068 | O | HOH | 639 | 18.706 | -6.969 | 8.775 | 1.00 | 47.69 | O |
| 3069 | O | HOH | 640 | 19.374 | -8.885 | 10.540 | 1.00 | 90.15 | O |
| 3070 | O | HOH | 641 | 22.107 | -2.476 | 12.466 | 1.00 | 58.99 | O |
| 3071 | O | HOH | 642 | 31.157 | 0.866 | 24.564 | 1.00 | 73.54 | O |
| 3072 | O | HOH | 643 | 11.493 | 22.417 | 31.837 | 1.00 | 62.07 | O |
| 3073 | O | HOH | 644 | 20.933 | 16.056 | -12.243 | 1.00 | 35.36 | O |
| 3074 | O | HOH | 645 | 15.004 | 40.860 | 22.656 | 1.00 | 47.29 | O |
| 3075 | O | HOH | 646 | 16.452 | -8.745 | 9.506 | 1.00 | 93.19 | O |

Figure 2-49

| Decreasing the Length | Increasing the Length |
|---|---|
| I108F | L111A |
| I108L | F133A |
| A193I | L111A, F133A |
| A193M | I108A, L111A, I114A |
| I108F, A193I | L197A |
| I108F, A193M | F133A, L197A |
| I108L, A193I | I108A, L111A, I114A, F133A, L197A |
| I108L, A193M | |

Mutations Introduced into *E. coli* KAS II

FIGURE 7

| E.coli Kas II | C.pu KAS IV |
|---|---|
| I108 | M110 |
| L111 | M113 |
| L113 | V115 |
| I114 | F116 |
| F133 | C134 |
| I138 | T139 |
| L197 | I198 |
| G203 | V204 |

**Sequence Differences in the Hydrophobic Pockets of *E.coli* KAS II and *C.pu* KAS IV**

```
                          490       500
At KASI.pro      SNSFGFGGHNSSVVAFAPFK--         431
Br Kas 50.pro    SNSFGFGGHNSVVAFSAFK-P          429
Ch KAS I .pro    SNSFGFGGHNSVVAFSAFK-P          350
Ch KASI-1.pro    SNSFGFGGHNSVVAFSAFK-P          441
Cpu KAS I.PRO    SNSFGFGGHNSVVAFSAFK-P          430
cpuKASI-1.PRO    SNSFGFGGHNSVVAFSAFK-P          428
Hv Kas12.pro     SNSFGFGGHNSVVFAPFK-P           427
RcKas50.pro      SNSFGFGGHNSVAFSAFK             428
Cc Kas.pro       SNSFGFGGHNSVVFAPYK-P           420
Ch KAS IV-1.pro  SNSFGFGGHNSSILFAPY--N          420
Ch KASIV.pro     SNSFGFGGHNSSILFAPCN            420
Cpu KASIV.pro    SNSFGFGGHNSSILFAPY--I          421
Cw KASA-1.pro    SNSFGFGGHNSSILFAPCN-V          420
Cw KasA-2.pro    SNSFGFGGHNSSILFAPCN            420
Hv KasORF22(KAS I) SNSFGFGGHNSSILFAPFK          419
Hv KasORF25(KAS I) SNSFGFGGHNSSILFAPF           420
RcKas46.pro      SNSFGFGGHNSSIIFAPYK            414
Ce.KAS.PRO       CNSFGFGATNASLILKQF.            442
CEM.pro          CNSFGFGGVNTSLLFKKWEGS          410
Ec KAS II.pro    CNSFGFGGTNGSLIF                406
Ec KasI.pro      SNSFGFGGTNATLVMRKLK-D          416
M.tub.KasA.pro   NNSFGFGGHNVALAFGRY             438
M.tub.KasB.PRO   NNSFGFGGHNVAIAFGRY             418
Rat. Kas.PRO     -NSFGFGGANVHVILQP-NAS          401
RtNodE.pro       SNAFAMGTNAVLAFRQV              419
StrepPolyk.pro   TVGSGFGFQSAMLLSRLE-R           416
SYN KAS.pro      SNSFGFGGHNVTLAFKKYQ            441
V.pro            SNSFGFGGTNGSLLFKKAD
```

Figure 12-5

Bgl II site *Sal I site*
CTGAGATCT*GTCGAC*ATGGCGACCGCTTCTCGCATGGTTGCGTCCCCTTTCTGTACGTGGC
TCGTAGCTGCATGCATGCCCACTTCATCCGACAACGACCCACGTTCCCTTTCCCACAAGCGGCT
CCGCCTCTCCCGTCGCCGGAGGACTCTCTCCTCCCATTGCTCCCTCCGCGGATCCACCTTCCAA
TGCCTCGATCCTTGCAACCAGCAACGCTTCCTCGGGGATAACGGATTCGCTTCCCTCTTCGGAT
CCAAGCCTCTTCGTTCAAATCGCGGCCACCTGAGGCTCGGCCGCACTTCCCATTCCGGGGAGG
TCATGGCTGTGGCTATGCAACCTGCACAGGAAGTCTCCACAAGATCTGTC
                                                            Bgl II site

Figure 14

ENGINEERING β-KETOACYL ACP SYNTHASE FOR NOVEL SUBSTRATE SPECIFICITY

This application claims the benefit of U.S. Provisional Application No. 60/138,308 filed Jun. 9, 1999.

INCORPORATION OF SEQUENCE LISTING

A paper copy of the Sequence Listing and a computer readable form of the sequence listing on diskette, containing the file named SeqList.txt, which is 103 kilobytes in size (measured in MS-DOS), and which was created on Apr. 11, 2002.

TECHNICAL FIELD

The present invention is directed to proteins, nucleic acid sequences and constructs, and methods related thereto.

BACKGROUND

Fatty acids are organic acids having a hydrocarbon chain of from about 4 to 24 carbons. Many different kinds of fatty acids are known which differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bonds.

The production of fatty acids in plants begins in the plastid with the reaction between acetyl-CoA and malonyl-ACP to produce acetoacetyl-ACP catalyzed by the enzyme, β-ketoacyl-ACP synthase III. Elongation of acetyl-ACP to 16- and 18-carbon fatty acids involves the following cycle of reactions: condensation with a two-carbon unit from malonyl-ACP to form a β-ketoacyl-ACP (β-ketoacyl-ACP synthase), reduction of the keto-function to an alcohol (β-ketoacyl-ACP reductase), dehydration to form an enoyl-ACP (β-hydroxyacyl-ACP dehydrase), and finally reduction of the enoyl-ACP to form the elongated saturated acyl-ACP (enoyl-ACP reductase). β-ketoacyl-ACP synthase I, catalyzes elongation up to palmitoyl-ACP (C16:0), whereas β-ketoacyl-ACP synthase II catalyzes the final elongation to stearoyl-ACP (C18:0). The longest chain fatty acids produced by the FAS are typically 18 carbons long. Additional biochemical steps in the cell produce specific fatty acid constituents, for example through desaturation and elongation.

β-ketoacyl synthases, condensing enzymes, comprise a structurally and functionally related family that play critical roles in the biosynthesis of a variety of natural products, including fatty acids, and the polyketide precursors leading to antibiotics, toxins, and other secondary metabolites. β-ketoacyl synthases catalyze carbon-carbon bond forming reactions by condenisng a variety of acyl chain precursors with an elongating carbon source, usually malonyl or methyl malonyl moieties, that are covalently attached through a thioester linkage to an acyl carrier protein. Condensing enzymes can be part of multienzyme complexes, domains of large, multifunctional polypeptide chains as the mammalian fatty acid synthase, or single enzymes as the β-ketoacyl synthases in plants and most bacteria.

Condensing enzymes have been identified with properties subject to exploitation in the areas of plant oil modification, polyketide engineering, and ultimately design anti-cancer and anti-tuberculosis agents. One of the molecular targets of isoniazid, which is widely used in the treatment of tuberculosis, is KAS. Cerulinin, a mycotoxin produced by the fungus *Cephalosporium caerulens*, acts as a potent inhibitor of KAS by covalent modification of the active cysteine thiol. Condensing enzymes from many other pathways and sources have all been shown to be inactivated by this antibiotic with the exception of the synthase from *C. caerulens* and KAS III, the isozyme responsible for the initial condensation of malonyl-ACP with acetyl-CoA in plant and bacterial fatty acid biosynthesis. Inhibition of the KAS domain of fatty acid synthase by cerulinin is selectively cytotoxic to certain cancer cells.

SUMMARY OF THE INVENTION

The present invention is directed to β-ketoacyl ACP synthase (KAS), and in particular to engineered KAS polypeptides and polynucleotides encoding engineered KAS proteins having a modified substrate specificity with respect to the native (also referred to herein as wild-type) KAS protein. The engineered polypeptides and polynucleotides of the present invention include those derived from plant and bacterial sources.

In another aspect of the invention polynucleotide encoding engineered polypeptides, particularly, polynucleotides that encode a KAS protein with a modified substrate specificity with respect to the native KAS protein, are provided.

In a further aspect the invention relates to oligonucleotides derived from the engineered KAS proteins and oligonucleotides which include partial or complete engineered KAS encoding sequences.

It is also an aspect of the present invention to provide recombinant DNA constructs which can be used for transcription or transcription and translation (expression) of an engineered KAS protein having an altered substrate specificity with respect to the native KAS protein. In particular, constructs are provided which are capable of transcription or transcription and translation in host cells. Particularly preferred constructs are those capable of transcription or transcription and translation in plant cells.

In another aspect of the present invention, methods are provided for production of engineered KAS proteins having a modified substrate specificity with respect to the native KAS in a host cell or progeny thereof. In particular, host cells are transformed or transfected with a DNA construct which can be used for transcription or transcription and translation of an engineered KAS. The recombinant cells which contain engineered KAS are also part of the present invention.

In a further aspect, the present invention relates to methods of using the engineered polynucleotide and polypeptide sequences of the present invention to modify the fatty acid composition in a host cell, as well as to modify the composition and/or structure of triglyceride molecules, particularly in seed oil of oilseed crops. Plant cells having such a modified triglyceride content are also contemplated herein.

The modified plants, seeds and oils obtained by the expression of the plant engineered KAS proteins are also considered part of the invention.

DESCRIPTION OF THE FIGURES

FIGS. 1-1 to 1-48 provides the coordinates of the crystal structure of the *E. coli* KAS protein. The first column provides the Type of atom (N=Nitrogen, O=oxygen, C=Carbon, CA=alpha carbon, CB=beta carbon, CG=gamma carbon, CD=delta carbon, CE=epsilon carbon, NZ=zeta nitrogen, NH=amino group), the second column provides the amino acid residue type (three letter abbreviation), the third column provides the subunit in which the amino acid is located, the forth column provides the amino acid position in the protein sequence base don the mature unprocessed protein, columns seven through nine provide the x, y and z coordinates, respectively, of the three dimensional location of the respective atom in the crystal structure.

FIGS. 2-1 to 2-49 provides the profile of the crystal structure of the *E. coli* KAS-cerulenin complex. The first column provides the Type of atom (N=Nitrogen, O=oxygen, C=Carbon, CA=alpha carbon, CB=beta carbon, CG=gamma carbon, CD=delta carbon, CE=epsilon carbon, NZ=zeta nitrogen, NH=amino group), the second column provides the amino acid residue type (three letter abbreviation), the third column provides the subunit in which the amino acid is located, the forth column provides the amino acid position in the protein sequence base don the mature unprocessed protein, columns seven through nine provide the x, y and z coordinates, respectively, of the three dimensional location of the respective atom in the crystal structure.

FIG. 3 provides the effects of KAS II mutations on the fatty acid composition of *E. coli*.

FIG. 4 shows that mutations I108F, I108L and A193M all cause significant reduction in the activity of KAS II on 8:0-ACP as compared to 6:0-ACP (38, 31 and 12 fold reductions respectively), without significantly reducing the activity on 6:0-ACP.

FIG. 5 shows that the combined mutations at I108 and A193 have the effect of reducing the activity of KAS II on 6:0-ACP substrates.

FIG. 6 shows that the combined effect of two or more mutations had a greater effect on the activity with acyl-ACPs 8:0 and longer (14:0) substrates.

FIG. 7 shows the complete list of mutations that were generated.

FIG. 8 provides the structure of the Cpu KAS I homodimer.

FIG. 9 provides the structure of the Cpu KAS IV homodimer.

FIG. 10 provides the structure of the Cpu KAS I/Cpu KAS IV heterodimer.

FIG. 11 provides the sequence differences in the hydrophobic pocket of the *E. coli* KASII and *C. pu* KASIV.

FIGS. 12-1 to 12-5 provide an amino acid sequence alignment of KAS protein sequences from plant (Arabidopsis, Brassica, *Cuphea hookeriana* and *pullcherima*, Hordeum, Riccinus), bacterial (*E. coli*, streptococcus, tuberculosis), mammalian (rat, mouse) and others (*C. elegans*).

FIG. 13 provides a bar graph representing the results of fatty acid analysis of seeds from transformed Arabidopsis lines containing pCGN11058, pCGN11062, pCGN11041, or nontransformed control lines (AT002-44). For each line, bars represent, from left to right, C12:0, C14:0, C16:0, C16:1, C18:0, C18:1 (delta9), C18:1 (delta 11), C18:2, C18:3, C20:0, C20:1 (delta 11), C20:1 (delta 13), C20:2, C20:3, C22:0, C22:1, C22:2, C22:3, C24:0, and C24:1 fatty acids.

FIG. 14 provides the nucleotide sequence of the plastid targeting sequence from *Cuphea hookeriana* KASII-7.

DETAILED DESCRIPTION OF THE INVENTION

Figure 3:
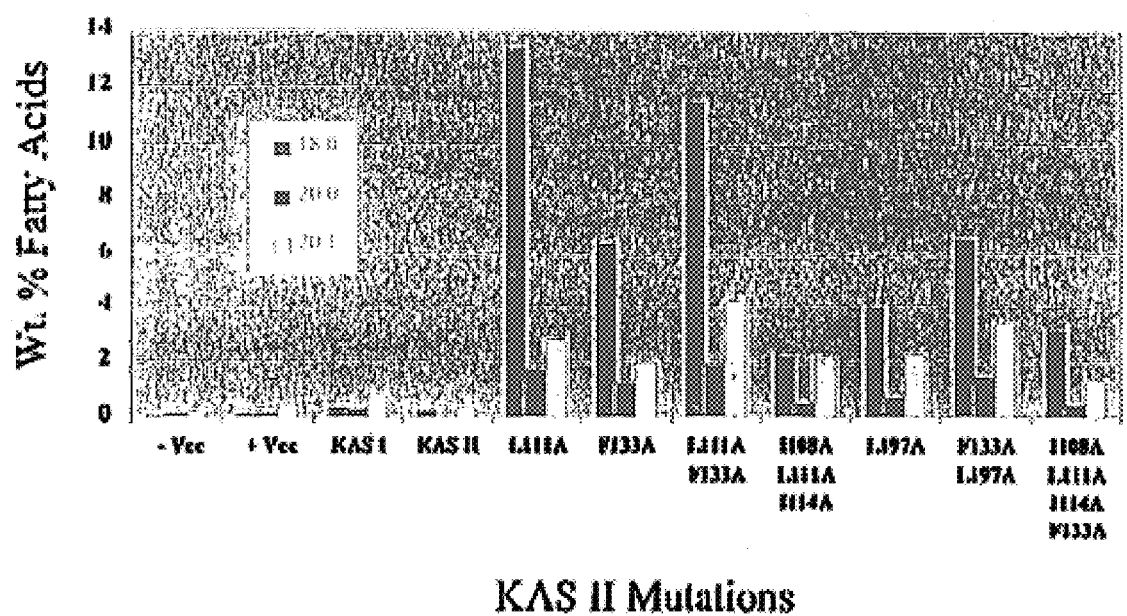

In accordance with the subject invention, engineered nucleotide sequences are provided which are capable of coding sequences of amino acids, such as, a protein, polypeptide or peptide. The engineered nucleotide sequences encode β-ketoacyl-ACP synthase (KAS) proteins with a modified substrate specificity compared to the native KAS protein (also referred to herein as the wild-type KAS protein) under enzyme reaction conditions. Such sequences are referred to herein as engineered β-ketoacyl-ACP synthase (also referred to as engineered KAS) proteins. The engineered nucleic acid sequences find use in the preparation of constructs to direct their expression in a host cell. Furthermore, the engineered nucleic acid sequences find use in the preparation of plant expression constructs to alter the fatty acid composition of a plant cell. By "enzyme reactive conditions" is meant that any necessary conditions are available in an environment (for example, such factors as temperature, pH, lack of inhibiting substances) which will permit the enzyme to function.

An engineered β-ketoacyl-ACP synthase nucleic acid sequence of this invention includes any nucleic acid sequence coding a β-ketoacyl-ACP synthase having altered substrate specificity relative to the native KAS in a host cell, including but not limited to, in vivo, or in a cell-like environment, for example, in vitro. By altered, or modified, substrate specificity is meant an alteration in the acyl-ACP substrates elongated by the KAS enzyme or an alteration in the elongator molecule used by the KAS to elongate the acyl-ACP relative to the native or unaltered KAS protein. An alteration in the acyl-ACP substrate elongated by the KAS enzymes includes, but is not limited to, elongation of an acyl-ACP substrate not elongated by the wild-type KAS, the inability to elongate an acyl-ACP substrate elongated by the wild-type KAS, and a preference for elongating acyl-ACP substrates not normally preferred by the wild-type KAS. An alteration in the elongator molecule used by the engineered KAS for the elongation of the acyl-ACP substrate includes, but is not limited to, methyl-malonyl ACP for the production of branched chain fatty acids.

A first aspect of the present invention relates to engineered β-ketoacyl-ACP synthase polypeptides. In particular, engineered KAS II polypeptides are provided. Preferred peptides include those found in the hydrophobic fatty acid/cerulenin binding pocket of the KAS protein. Such polypeptides include the engineered polypeptides set forth in the Sequence Listing, as well as polypeptides and fragments thereof, particularly those polypeptides which exhibit a modified substrate specificity with respect to the wild-type KAS polypeptide. Particularly preferred polypeptides include those having engineered amino acid residues 105 to 120, 130–140, 190–200 and 340–400. Most preferred polypeptides include those having engineered amino acid residues I108A, I108F, I108G, I108L, L111A, I114A, F133A, V134A, V134G, I138A, I138G, A162G, A193G, A193I, A193M, L197A, F202L, F202I, F202G, L342A, and L342G. Amino acid positions, as used herein, refer to the amino acid residue position in the active or processed protein.

Engineered β-ketoacyl-ACP synthases can be prepared by random (via chemical mutagenesis or DNA shuffling) or specific mutagenesis of a β-ketoacyl-ACP synthase encoding sequence to provide for one or more amino acid substitutions in the translated amino acid sequence. Alternatively, an engineered β-ketoacyl-ACP synthase can be prepared by domain swapping between related β-ketoacyl-ACP synthases, wherein extensive regions of the native β-ketoacyl-ACP synthase encoding sequence arc replaced with the corresponding region from a different β-ketoacyl-ACP synthase.

Altered substrate specificities of an engineered β-ketoacyl-ACP synthase can be reflected by the elongation of an acyl-ACP substrates of particular chain length fatty acyl-ACP groups which are not elongated by the native β-ketoacyl-ACP synthase enzyme. In addition, altered substrate specificities can be reflected by the in ability to elongate an acyl-ACP substrate of particular chain length fatty acyl-ACP groups which are not normally preferred by the native β-ketoacyl-ACP synthase enzyme. The newly recognized acyl-ACP substrate can differ from native substrates of the enzyme in various ways, such as by having a shorter or longer carbon chain length (usually reflected by the addition or deletion of one or more 2-carbon units), as well as by degrees of unsaturation.

Another aspect of the present invention relates to engineered β-ketoacyl-ACP synthase polynucleotides. In particular, engineered β-ketoacyl-ACP synthase II polynucleotides are provided. The polynucleotide sequences of the present invention include engineered polynucleotides that encode the polypeptides of the invention having a deduced amino acid sequence selected from the group of sequences set forth in the Sequence Listing.

The invention provides a polynucleotide sequence identical over its entire length to each coding sequence as set forth in the Sequence Listing. The invention also provides the coding sequence for the mature polypeptide or a fragment thereof, as well as the coding sequence for the mature engineered polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

As described herein, analysis of the KAS II/cerulinin crystal structure complex is performed using modeling software to produce a profile of the complex, as well as the KAS II protein alone. Based on comparisons of the two profiles, amino acid residues are identified, which when mutagenized, alter the fatty acyl substrate specificities. As demonstrated herein, engineering of the nucleic acid sequence to modify the amino acid sequence in particular regions of the KAS protein effectively modify the substrate specificity of the engineered KAS. Particular ranges for the engineering of the protein include amino acid residues 105 to 120, 130–140, 190–200 and 340–345. Particularly, engineering of residues 108, 111, 114, 133, 193 and 197 can alter the length of the fatty acids synthesized by the engineered KAS II protein. More particularly, engineering of residues 108, 111, 114, 133, 193 and 197 with variously sized hydrophobic residues will alter the length of the fatty acids synthesized by the engineered KAS II protein. Furthermore, engineering the amino acid residue at position 400 can also have an effect on the substrate specificity.

As demonstrated more fully in the following examples, the acyl-ACP substrate specificity of b-ketoacyl-ACP synthases may be modified by various amino acid changes to the protein sequence, such as amino acid substitutions, insertions or deletions in the mature protein portion of the b-ketoacyl-ACP synthases. Modified substrate specificity can be detected by expression of the engineered b-ketoacyl-ACP synthase s in $E.$ $coli$ and assaying to detect enzyme activity or by using purified protein in in vitro assays.

Modified substrate specificity can be indicted by a shift in acyl-ACP substrate preference such that the engineered b-ketoacyl-ACP synthase is newly capable of utilizing a substrate not recognized by the native b-ketoacyl-ACP synthase. The newly recognized substrate can vary from substrates of the native enzyme by carbon chain length and/or degree of saturation of the fatty acyl portion of the substrate. Additionally, modified substrate specificity can be reflected by a shift in the relative b-ketoacyl-ACP synthase activity on two or more substrates of the native b-ketoacyl-ACP synthase such that an engineered b-ketoacyl-ACP synthase exhibits a different order of preference for the acyl-ACP substrates.

Furthermore, provided herein are KAS proteins with an altered elongator molecule preference. For example, by widening the hydrophobic fatty acid binding different elongator molecules, other than Malonyl-ACP, can be utilized by the KAS protein. For example Methyl-malonyl-ACP can be utilized by the engineered KAS resulting in the synthesis of branched chained fatty acid. The mutations that lengthen the pocket may to some degree also widen it, in addition mutations A193G, I108G, L342A or G, V134A or G,F202L,I or G may well cause widening of the pocket sufficiently to allow Methyl-malonyl-ACP to be accepted as an elongator.

As described in more detail herein, alterations in the nucleic acid sequence of the $E.$ $coli$ KAS II, particularly, I108F, I108L, A193I, A193M, as well as combinations thereof, are prepared for the production of shorter chain length fatty acids. Furthermore, alterations of I108A, L111A, I114A, F133A, L197A, and combinations thereof, are prepared for increasing the length of fatty acids produced by the host cell.

Thus, as the result of modifications to the substrate specificity of b-ketoacyl-ACP synthases, it can he seen that the relative amounts of the fatty acids produced in a cell where various substrates are available for hydrolysis may be altered. Furthermore, molecules which are formed from available free fatty acids, such as plant seed triglycerides, may also be altered as a result of expression of engineered b-ketoacyl-ACP synthase s having altered substrate specificities.

It is anticipated that the ranges of mutations provided herein can also be engineered in plant KAS proteins as well as to other polyketide synthases. Such plant KAS proteins are known in the art, and are described for example in PCT Publication WO 98/46776, and in U.S. Pat. No. 5,475,099, the entireties of which are incorporated herein by reference.

Plant Constructs and Methods of Use

Of particular interest is the use of the nucleotide sequences, or polynucleotides, in recombinant DNA constructs to direct the transcription or transcription and translation (expression) of the engineered KAS sequences of the present invention in a host plant cell. The expression constructs generally comprise a promoter functional in a host plant cell operably linked to a nucleic acid sequence encoding a engineered KAS of the present invention and a transcriptional termination region functional in a host plant cell.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313:810–812; Rogers, U.S. Pat. No. 5,378,619). In addition, it may also be preferred to brine about expression of the engineered KAS in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res.* 1:209:219 (1991)), phaseolin, zein, soybean trypsin inhibitor, ACP, stearoyl-ACP desaturase, soybean α' subunit of β-conglycinin (soy 7s, (Chen et al., *Proc. Natl. Acad. Sci.*, 83:8560–8564 (1986))) and oleosin.

It may be advantageous to direct the localization of proteins to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the protein of interest is not directly inserted into the plastid, the expression construct will additionally contain a gene encoding a transit peptide to direct the protein of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481. Additional transit peptides for the translocation of the engineered KAS protein to the endoplasmic reticulum (ER), or vacuole may also find use in the constructs of the present invention.

Depending upon the intended use, additional constructs can be employed containing the nucleic acid sequence which provides for the suppression of the host cell's endogenous KAS protein. Where antisense inhibition of a host cells native KAS protein is desired, the entire wild-type KAS sequence is not required.

The skilled artisan will recognize that there are various methods for the inhibition of expression of endogenous sequences in a host cell. Such methods include, but are not limited to antisense suppression (Smith, et al. (1988) *Nature* 334:724–726), co-suppression (Napoli, et al. (1989) *Plant Cell* 2:279–289), ribozymes (PCT Publication WO 97/10328), and combinations of sense and antisense Waterhouse, et al. (1998) *Proc. Natl. Acad. Sci. USA* 95:13959–13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the wild-type KAS or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the engineered KAS sequences directly from the host plant cell plastid. Such constructs and methods are known in the art and are generally described, for example, in Svab, et al. (1990) *Proc. Natl. Acad. Sci. USA* 87:8526–8530 and Svab and Maliga (1993) *Proc. Natl. Acad. Sci. USA* 90:913–917 and in U.S. Pat. No. 5,693,507.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a engineered KAS nucleic acid sequence.

Plant expression or transcription constructs having an engineered KAS as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of engineered KAS constructs in plants which have been genetically engineered to produce a particular fatty acid in the plant seed oil, where TAG in the seeds of nonengineered plants of the engineered species, do not naturally contain that particular fatty acid.

The engineered KAS constructs of the present invention can also be used to provide a means for the production of plants having resistance to plant pathogens. Engineered KAS constructs providing for an increased production of particular fatty acids involved in the biosynthesis of pathogen response signals or inhibitors. For example, engineered KAS constructs providing for the increased production of C:8 fatty acids allows for the production of transgenic plants having an increased tolerance to fungal pathogens.

It is contemplated that the gene sequences may be synthesized, either completely or in part, especially where it is desirable to provide plant-preferred sequences. Thus, all or a portion of the desired structural gene (that portion of the gene which encodes the engineered protein) may be synthesized using codons preferred by a selected host. Host-preferred codons may be determined, for example, from the codons used most frequently in the proteins expressed in a desired host species.

Once the desired engineered KAS nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding an engineered KAS of this invention may be combined with other non-native, or "heterologous", sequences in a variety of ways. By "heterologous" sequences is meant any sequence which is not naturally found joined to the engineered KAS, including, for example, combinations of nucleic acid sequences from the same plant which are not naturally found joined together.

The DNA sequence encoding an engineered KAS of this invention may be employed in conjunction with all or part of the gene sequences normally associated with the wild-type KAS. In its component parts, a DNA sequence encoding engineered KAS is combined in a DNA construct having, in the 5' to 3' direction of transcription, a transcription initiation control region capable of promoting transcription and translation in a host cell, the DNA sequence encoding engineered KAS and a transcription and translation termination region.

Potential host cells include both prokaryotic and eukaryotic cells. A host cell may be unicellular or found in a multicellular differentiated or undifferentiated organism depending upon the intended use. Cells of this invention may be distinguished by having an engineered KAS foreign to the wild-type cell present therein, for example, by having a recombinant nucleic acid construct encoding an engineered KAS therein.

The methods used for the transformation of the host plant cell are not critical to the present invention. The transformation of the plant is preferably permanent, i.e. by integration of the introduced expression constructs into the host plant genome, so that the introduced constructs are passed onto successive plant generations. The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to calcium-phosphate-DNA co-precipitations, electroporation, microinjection, Agrobacterium infection, liposomes or microprojectile transformation. The skilled artisan can refer to the literature for details and select suitable techniques for use in the methods of the present invention.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming host plant cells, the expression or transcription construct bordered by the T-DNA border region (s) will he inserted into a broad host range vector capable of replication in E. coli and Agrobacterium), there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in E. coli, and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Included with the expression construct and the T-DNA will be one or more markers, which allow for selection of transformed Agrobacterium and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

There are several possible ways to obtain the plant cells of this invention which contain multiple expression constructs. Any means for producing a plant comprising a construct having a DNA sequence encoding the engineered KAS of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the engineered KAS expression construct, or alternatively, transformed plants, one expressing the engineered KAS construct and one expressing the second construct, can be crossed to bring the constructs together in the same plant.

Other Constructs and Methods of Use

The invention also relates to vectors that include a polynucleotide or polynucleotides of the invention, host cells that are genetically engineered with vectors of the invention and the production of polypeptides of the invention by recombinant techniques. Cell free translation systems can be employed to produce such protein using RNAs derived from the DNA constructs of the invention.

For recombinant production, host cells can be genetically engineered to incorporate expression systems or portions thereof or polynucleotides of the present invention. Introduction of a polynucleotide into a host cell can be effected by methods described in many standard laboratory manuals, such as Davis et al., Basic Methods in Molecular Biology, (1986) and Sambrook et al, Molecular Cloning: A Laboratory Manual. $2^{nd}$ Edition. Cold Spring Harbor Laboratory Press, Cold Spring Harbor N.Y. (1989). Such methods include, but are not limited to, calcium phosphate transfection, DEAE dextran mediated transfection, transvection, microinjection, cationic lipid-mediated transfection, electroporation, transduction, scrape loading ballistic introduction and infection.

Representative examples of appropriate hosts include bacterial cells, such as streptococci, staphylococci, enterococci, E. coli, streptomyces, and Bacillus subtilis cells; fungal cells, such as yeast cells and Aspergillus cells; insect cells, such as Drosophila S2 and Spodoptera Sf9 cells; animal cells such as CHO, COS, HeLa, C127, 3T3, BHK, 293 and Bowes melanoma cells: and plant cells as described above.

A variety of expression systems can be used to produce the polypeptides of the invention. Such vectors include, but are not limited to, chromosomal, episomal, and virus derived vectors, for example vectors from bacterial plasmids, bacteriophage, transposons, yeast episomes, insertion elements, yeast chromosomal elements, viruses such as baculoviruses, papova viruses, such as SB40, vaccinia viruses, adenoviruses, fowl pox viruses, pseudorabies viruses and retroviruses, and vectors derived from combinations of such viruses, such as those derived from plasmid and bacteriophage genetic elements, such as cosmids and phagemids. The expression system constructs may contain control regions that regulate as well as engender expression. Generally, any system or vector which is suitable to maintain, propagate or express polynucleotides and/or to express a polypeptide in a host can be used for expression. The appropriate DNA sequence can be inserted into the chosen expression by any of a variety of well-known and routine techniques, such as, for example, those set forth in Sambrook et al. *Molecular Cloning. A Laboratory Manual.* (*supra*).

Appropriate secretion signals, either homologous or heterologous, can be incorporated into the expressed polypeptide to allow the secretion of the protein into the lumen of the endoplasmic reticulum, the periplasmic space or the extracellular environment.

The polypeptides of the present invention can be recovered and purified from recombinant cell cultures by any of a number of well known methods, including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. It is most preferable to use high performance liquid chromatography (HPLC) for purification. Any of the well known techniques for protein refolding can be used to regenerate an active confirmation if the polypeptide is denatured during isolation and/or purification.

The engineered KAS polynucleotides and polypeptides of the present invention find use in a variety of applications.

The engineered KAS polynucleotides and polypeptides as well as the constructs containing such engineered KAS polynucleotides and polypeptides find use in the alteration of fatty acid composition. Furthermore, the engineered KAS polynucleotides and polypeptides of the present invention find use in the production of particular fatty acid components. For example, an engineered KAS having a preference for elongating 6, 8, 10, and 12 carbon acyl-ACP substrates can be used in the production of medium chain fatty acids. Such engineered KAS polynucleotides and polypeptides can also be used with additional sequences for the production of medium chain fatty acids, including, but not limited to, medium chain specific thioesterases (see for example U.S. Pat. No. 5,512,482).

The present invention further provides methods for the engineering of polyketides and for the identification of molecules useful in cancer therapy, immunosuppressants, anti-parasite, and antibiotic production.

Thus, the present invention permits the use of molecular design techniques to design, select and synthesize chemical entities and compounds, including inhibitory compounds, capable of binding to the active site or substrate binding site of KAS, in whole or in part.

A first approach enabled by this invention, is to use the structure coordinates of KAS to design compounds that bind to the enzyme and alter the physical properties of the compounds in different ways, e.g., solubility. For example, this invention enables the design of compounds that act as competitive inhibitors of the KAS enzyme by binding to, all or a portion of, the active site of KAS. This invention also enables the design of compounds that act as uncompetitive inhibitors of the KAS enzyme. These inhibitors may bind to, all or a portion of, the substrate binding site of KAS already bound to its substrate and may be more potent and less non-specific than known competitive inhibitors that compete only for the KAS active site. Similarly, non-competitive inhibitors that bind to and inhibit KAS whether or not it is bound to another chemical entity may be designed using the structure coordinates of KAS of this invention. Additionally, reversible and irreversible inhibitors can also be designed.

A second design approach is to probe KAS with molecules composed of a variety of different chemical entities to determine optimal sites for interaction between candidate ICE inhibitors and the enzyme. For example, high resolution X-ray diffraction data collected from crystals saturated with solvent allows the determination of where each type of solvent molecule sticks. Small molecules that bind tightly to those sites can then be designed and synthesized and tested for their KAS inhibitor activity. Travis, J., *Science*, 262, p. 1374 (1993).

This invention also enables the development of compounds that can isomerize to short-lived reaction intermediates in the chemical reaction of a substrate or other compound that binds to KAS, with KAS. Thus, the time-dependent analysis of structural changes in KAS during its interaction with other molecules is enabled. The reaction intermediates of KAS can also be deduced from the reaction product in co-complex with KAS. Such information is useful to design improved analogues of known KAS inhibitors or to design novel classes of inhibitors based on the reaction intermediates of the KAS enzyme and KAS-inhibitor co-complex. This provides a novel route for designing KAS inhibitors with both high specificity and stability.

Another approach made possible and enabled by this invention, is to screen computationally small molecule data bases for chemical entities or compounds that can bind in whole, or in part, to the KAS enzyme. In this screening, the quality of fit of such entities or compounds to the binding site may be judged either by shape complementarity or by estimated interaction energy. Meng, E. C. et al., *J. Comp. Chem.*, 13. pp. 505–524 (1992).

The invention now being generally described, it will be more readily understood by reference to the following examples which are included for purposes of illustration only and are not intended to limit the present invention.

EXAMPLES

Example 1

Determination of the KAS II-Cerulenin Complex Structure

The KASII-cerulenin complex was prepared as described previously (Edwards, et al. (1997) *FEBS Lett*. 402:62–66). Crystals of the complex were grown by the hanging drop method. Droplets consisting of equal amounts of protein solution (6 mg ml$^{-1}$, 21 protein, 0.3 M NaCl, 25 mM Tris, pH 8.0, 5 mM imidazole, and 10% v/v glycerol) and reservoir solution were equilibrated against 26% w/v polyethylene glycol 8000 and 0.1% v/v 2-mercaptoethanol in water. Data from two crystals were collected at 298 K at the synchrotron in MAX-lab, beamline I711, in Lund. The data was processed with DENZO (Otwinowski (1993) *Proceedings of the Collaborative Computating Project 4 Study Weekend: Data Collection and Processing* (Sawyer, L., Isaacs, N., and Bailey, S. S., eds.) pp 56–62, SERC Daresbury Laboratory, Warrington) and programs from the Collaborative Computating Project 4 Suite (Collaborative Computating Project 4 (1994) *Acta Crystallagr. Sect. D Biol. Crystallogr*. 50:760–763) and the two data sets were scaled together in SCALA (Eavans, (1993) *Proceedings of the Collaborative Computating Project 4 Study Weekend: Data Collection and Processing* (Sawyer, L., Isaacs, N., and Bailey, S. S., eds.) pp 56–62, SERC Daresbury Laboratory, Warrington). The crystals are very radiation-sensitive, but cannot be frozen in a cryostream. Due to non-isomorphism, data of only two crystals could be merged. The crystals of the complex have space group P321 with similar cell dimensions as the native enzyme. The coordinates of the native enzyme (Huang, et al. (1998) *EMBO J*. 17:1183–1191) were used to calculate initial electron density maps with SIGMAA (Read (1986) *Acta Crystallogr*. 42:140–149). All data were used in the refinement: no sigma cutoff was applied. After an initial cycle of positional refinement, the model was rebuilt and a model of cerulenin was included. Further cycles of refinement of the complex were carried out using the program REFMAC (Murshudov, et al. (1997) *Acta Crystallagr. Sect. D Biol. Crystallogr* 53:240–253) including a bulk solvent correction, interspersed with inspection and correction of the model using O (Jones, et al. (1991) *Acta Crystallagr. Sect. A* 47:100–119). OOPS (Kleywegt, et al. (1996) *Acta Crystallagr. Sect. D Biol. Crystallogr* 52:829–832), and PROCHECK (Laskowski, et al. (1993) *J. Appl. Crystallogr*. 26:282–291). Structure comparisons were performed using O (Jones, et al. (1991) supra) with default parameters.

The complex of KASII from *E. coli* with cerulenin crystallized in space group P3$_1$21 isomorphously with the native enzyme (Huang, et al. (1998) supra), and the crystal structure was determined to 2.65-Å resolution by difference Fourier methods. The final protein model after refinement (R-factor 5 0.213 and R$_{Inv}$ 5 0.270 with good stereochemistry) contains 411 out of the 412 residues of the subunit; no electron density for the N-terminal residue was found. The overall real-space correlation coefficient (Jones, et al. (1991) supra) is 0.92, and there is well defined electron density for the polypeptide chain except for some side chains on the molecular surface. The inhibitor molecule is well defined by the electron density. However, there is weaker than average electron density for the amide group and no electron density for the last carbon atom of the hydrocarbon tail, indicating considerable flexibility for the terminal methyl group.

The overall structure of the KAS dimer is unchanged upon binding of cerulenin; the root mean square deviations for the 411 Cα atoms of the subunit is 0.23 Å between the two structures. These differences are mainly localized in the active site, in particular in the loop comprising residues 398–401. The main differences in structure between the native enzyme and the cerulenin complex are in the conformation of the side chains of Phe-400 (which was anticipated already from the native structure) and of Ile-108, which have completely new rotamer conformations, and in the positions of the side chains of Cys-163, His-340, and Leu-342, which also have moved substantially. These conformational changes provide access for cerulenin to the active site cysteine and open a hydrophobic pocket for the hydrophobic tail of the inhibitor. From the initial F,2F, electron density map these structural changes could he readily seen as well as the binding site for the inhibitor). Cerulenin is bound covalently through its C2 carbon atom to the Cys-163 Sγ atom. Its hydrocarbon tail fits in a hydrophobic pocket formed at the dimer interface. The structure of the adduct of cerulenin and cysteine, isolated by tryptic digestion of the cerulenin-fatty acid synthase complex, has been determined by NMR and mass spectroscopy (Funabashi, et al. (1989) *J. Biochem*.(Tokyo) 105:751–755). This study revealed that the inhibitor reacts at its C2-epoxide carbon with the SH group of cysteine and that cerulenin formed a hydroxylactam ring. The electron density observed in the KASII-cerulenin complex is not consistent with this structure. It was not possible to model bound cerulenin in the closed ring form but the open form of the inhibitor could readily be fitted to the electron density map. The hydroxylactam ring, which is formed preferably in protic solvents (Funabashi, et al. (1989) supra), is not present in the hydrophobic environment of the protein.

In the KASII-cerulenin complex, the inhibitor amide carbonyl oxygen is within hydrogen bond distance to the N∈ atoms of the side chains of His-340 and His-303, while the amide NH$_2$ group does not make any close interactions. It is, however, not possible from the structure to exclude the opposite conformation and interactions for the amide group. The hydroxyl group at C3 forms a hydrogen bond to the main chain NH of Phe-400. The carbonyl oxygen at C4 does not form any polar interactions, in fact, it is located in a very hydrophobic pocket formed by side chains Phe-400, Phe-202, and Val-134 from the other subunit in the dimer. The binding site for the hydrophobic part of the inhibitor is also lined with hydrophobic residues: Ala-162, Gly-107, Leu-342, Phe-202, Leu-1 II, Ile-108, Ala-193, Gly-198; and from the second subunit in the dimer, Ile-138, Val-134, and Phe-133. The two double bonds with trans configuration give the hydrophobic tail a shape that fits to the hydrophobic groove once residue Ile-108 has changed rotamer. In comparison, binding of tetrahydrocerulenin would cost entropy, and as expected it shows more than 2 orders of magnitude less inhibitory activity (D'Agnolo, et al.(1973) Biochim. Biophys. Acta 326:155–156). The influence of the length of the hydrocarbon chain, maintaining the double bond positions, has been studied using fatty acid synthase from Saccharomyces cerevisiae (Morisaki, et al. (1993) J. Biol. Chem. 211:111–115). Cerulenin (12 carbons) had the highest inhibitory activity, with slightly decreasing binding strength upon increase in chain length. However, when increasing the length from 16 to 18 carbon atoms, the inhibition decreased by 2 orders of magnitude. The size of the hydrophobic pocket in KASII, which binds the hydrocarbon tail of cerulenin, suggests that there is space for a longer hydrophobic tail only if the side chains of Leu-111 and of Phe-133 in the second subunit change their conformation. Thus, possible differences in the sensitivity of condensing enzymes toward cerulenin might be controlled by the size of this cavity.

The structure of the cerulenin complex can be considered to mimic the intermediate formed upon reaction of KAS with the acyl-ACP. In such a complex the hydrophobic cavity would harbor the hydrocarbon tail of the acyl intermediate. The acyl hydrophobic tails will not be restricted by two double bonds (as in the case of cerulenin), and this will allow longer acyl chains to be buried in this pocket. Inspection of the active site cavity suggests that it would not be possible to harbor a linear acyl chain longer than 14 carbon atoms without structural changes. Such conformational changes must occur since KASII is able to elongate 16:1 to 18:1 (Garwin, et al. (1980) J. Biol. Chem. 255:3263–3265).

Coordinates for the KAS II crystal structure as well as the KAS-cerulenin complex were produced and are presented in FIGS. 1 and 2 respectively.

Example 2

Engineering KAS II Proteins

The structure of the E.coli KAS II-cerulenin complex was analyzed using the Swiss Pdb Viewer (SPV) modeling program, and by stereo viewing of printouts of the structure in different orientations. Using SPV each of the hydrophobic residues surrounding the bound cerulenin residue were changed to all the possible larger hydrophobic residues, and each of the rotamers for the mutant amino acids were examined for steric clashes (SPV rotamer score) with adjacent amino acids and the bound cerulenin molecule. The identified amino acids were targeted for mutagenesis for decreasing tile fatty acid chain length specificity of the KAS II protein. The candidate chain length shortening mutations chosen were those that made the least steric clashes with neighboring amino acids while having the most clashes with the end 1 to 6 carbons of cerulenin.

The structure of the E.coli KAS II/cerulenin complex was studied as described above and the hydrophobic amino acid residues near the end of the cerulenin binding "pocket" were identified. These amino acids were identified for mutagenesis for the increase in fatty acid chain length recognition. The large hydrophobic residues positioned beyond the end of the cerulenin potentially preventing longer fatty acids from occupying this pocket were chosen for mutagenesis to smaller (alanine) residues.

PCR site-directed mutagenesis was performed using the Quick-Change™ site-directed mutagenesis kit (Stratagene) following the manufacturers protocol. For the preparation of the specific mutations listed in Table 1, the following oligonucleotide primers were used in the reactions.

TABLE 1

| | | | |
|---|---|---|---|
| I108F | Sense | 5'-GTGCCGCAATTGGATCCGGGTTTGGCGGCCTCGGAC | (SEQ ID NO:1) |
| | Antisense | 5'-GTCCGAGGCCGCCAAACCCGGATCCAATTGCGGCAC | (SEQ ID NO:2) |
| I108L | Sense | 5'-GTGCCGCAATTGGCTCCGGGCTTGGAGGCCTCGGACTGATCG | (SEQ ID NO:3) |
| | Antisense | 5'-CGATCAGTCCGAGGCCTCCAAGCCCGGAGCCAATTGCGGCAC | (SEQ ID NO:4) |
| A193I | Sense | 5'-GCAGGTGGCGCCGAGAAAATCAGTACGCCGCTGGGC | (SEQ ID NO:5) |
| | Antisense | 5'-GCCCAGCGGCGTACTGATTTTCTCGGCGCCACCTGC | (SEQ ID NO:6) |
| A193M | Sense | 5'-GGTGGCGCAGAGAAAATGAGTACTCCGCTGGGCGTTG | (SEQ ID NO:7) |
| | Antisense | 5'-CAACGCCCAGCGGAGTACTCATTTTCTCTGCGCCACC | (SEQ ID NO:8) |
| I108A, L111A, I114A | Sense | 5'-GCAATTGGCTCCGGGGCTGGCGGCGCCGGACTGGCCGAAG AAAACCACAC | (SEQ ID NO:9) |
| | Antisense | 5'-GTGTGGTTTTCTTCGGCCAGTCCGGCGCCGCCAGCCCCGG AGCCAATTGC | (SEQ ID NO:10) |
| L111A | Sense | 5'-GGGATTGGCGGCGCCGGACTGATCGAAG | (SEQ ID NO:11) |
| | Antisense | 5'-CTTCGATCAGTCCGGCGCCGCCAATCCC | (SEQ ID NO:12) |
| F133A | Sense | 5'-GATCAGCCCATTCGCGGTACCGTCAACGATTGTG | (SEQ ID NO:13) |
| | Antisense | 5'-CACAATCGTTGACGGTACCGCGAATGGGCTGATC | (SEQ ID NO:14) |
| I197A | Sense | 5'-GAGAAAGCCAGTACTCCGGCGGGCGTTGGTGG | (SEQ ID NO:15) |
| | Antisense | 5'-CCACCAACGCCCGCCGGAGTACTGGCTTTCTC | (SEQ ID NO:16) |

Example 3

Construct Preparation

3A. E. coli Expression Constructs

A series of constructs are prepared to direct the expression of the engineered KAS sequences in E. coli.

A series of constructs are prepared to direct the expression of the various engineered KAS sequences in host plant cells.

The construct pCGN10440 contains the I108F mutant expressed from the pQE30 (Qiagen) vector for expression in a host *E. coli* cell.

The construct pCGN10441 contains the I108L mutant expressed from the pQE30 (Qiagen) vector for expression in a host *E. coli* cell.

The construct pCGN10442 contains the A193I mutant expressed from the pQE30 (Qiagen) vector for expression in a host *E. coli* cell.

The construct pCGN10443 contains the I108F, A193I mutant expressed from the pQE30 (Qiagen) vector for expression in a host *E. coli* cell.

The construct pCGN10444 contains the I108L, A193I mutant expressed from the pQE30 (Qiagen) vector for expression in a host *E. coli* cell.

The construct pCGN10445 contains the A193M mutant expressed from the pQE30 (Qiagen) vector for expression in a host *E. coli* cell.

The construct pCGN10446 contains the I108F, A193M mutant expressed from the pQE30 (Qiagen) vector for expression in a host *E. coli* cell.

The construct pCGN10447 contains the I108L, A193M mutant expressed from the pQE30 (Qiagen) vector for expression in a host *E. coli* cell.

The construct pCGN10448 contains the L111A mutant expressed from the pQE30 (Qiagen) vector for expression in a host *E. coli* cell.

The construct pCGN10449 contains the F133A mutant expressed from the pQE30 (Qiagen) vector for expression in a host *E. coli* cell.

The construct pCGN10450 contains the L111A, F133A mutant expressed from the pQE30 (Qiagen) vector for expression in a host *E. coli* cell.

The construct pCGN10451 contains the I108A, L11A, I114A mutant expressed from the pQE30 (Qiagen) vector for expression in a host *E. coli* cell.

The construct pCGN10452 contains the F133A, L197A mutant expressed from the pQE30 (Qiagen) vector for expression in a host *E. coli* cell.

The construct pCGN10453 contains the I108A, L11A, I114A, F133A, L197A mutant expressed from the pQE30 (Qiagen) vector for expression in a host *E. coli* cell.

The construct pCGN10454 contains the L197A mutant expressed from the pQE30 (Qiagen) vector for expression in a host *E. coli* cell.

3B. Preparation of Plant Expression Constructs

A series of constructs are prepared to direct the expression of the engineered KAS sequences in plant host cells, both alone and in combination with additional sequences encoding proteins involved in fatty acid biosynthesis.

A plasmid containing the napin cassette derived from pCGN3223 (described in U.S. Pat. No. 5,639,790, the entirety of which is incorporated herein by reference) was modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATG-GCGCGCCCTGCAGGCGGCCGCCTG-CAGGGCGCGCCATTTAAAT (SEQ ID NO: ) was ligated into the cloning vector pBC SK+(Stratagene) after digestion with the restriction endonuclease BssHII to construct vector pCGN7765. Plamids pCGN3223 and pCGN7765 were digested with NotI and ligated together. The resultant vector, pCGN7770, contains the pCGN7765 backbone with the napin seed specific expression cassette from pCGN3223.

A binary vector for plant transformation, pCGN5139, was constructed from pCGN1558 (McBride and Summerfelt, (1990) Plant Molecular Biology, 14:269–276). The polylinker of pCGN1558 was replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139.

A binary vector, pCGN8642 was constructed to allow for the rapid cloning of various expression cassettes into the vector for use in plant transformation. The construct contains a multiple cloning region located between the right and left borders of the Agrobacterium transfer DNA. The construct also contains the Tn5 gene expressed from the 35S promoter between the multiple cloning site and the left border for selection of transformed plants on kanamycin.

A 354 bp BgIII fragment containing the *Cuphea hookeriana* KASII-7 plastid targeting sequence (FIG. 14) (SEQ ID NO: ) was cloned into the BamHI site of the various pQE30 constructs containing the *E. coli* KASII (FabF) wild type or mutant KAS sequences. The resultant chimeric KAS II targeting sequence/FabF) encoding sequence were cloned as HindIII/SalI fragments into filled-in SalI/XhoI sites of the napin expression cassette, pCGN7770. The resulting napin/KAS cassettes were cloned as NotI fragments into the NotI sites of various plant binary constructs as described below.

A napin cassette containing the coding sequence of the *Cuphea hookeriana* FatB2 protein (described in PCT Publication WO 98/46776, the entirety of which is incorporated herein by reference) was cloned as a NotI fragment into the NotI site of pCGN8642 to create pCGN11000.

A napin cassette containing the coding sequence of the Garm FatAI protein (described in PCT Publication WO 97/12047, the entirety of which is incorporated herein by reference) was cloned into the NotI site of pCGN8642 to create pCGN11003.

A napin cassette containing the native (wild-type) *E.coli* KAS II coding sequence was cloned into the NotI site of pCGN11003 to create pCGN11040.

A napin cassette containing the native (wild-type) *E. coli* KAS II coding sequence was cloned into the NotI site of pCGN11003 to create pCGN11040.

A napin cassette containing the native (wild-type) *E.coli* KAS II coding sequence was cloned into the NotI site of pCGN8642 to create pCGN11041.

A napin cassette containing the native (wild-type) *E. coli* KAS II coding sequence was cloned into the NotI site of PCGN11000 to create pCGN11042.

A napin cassette containing the L111A KAS II mutant coding sequence was cloned into the NotI site of pCGN11003 to create pCGN11045.

A napin cassette containing the L111A KAS II mutant coding sequence was cloned into the NotI site of pCGN8642 to create pCGN11046.

A napin cassette containing the F133A KAS II mutant coding sequence was cloned into the NotI site of pCGN11003 to create pCGN11049.

A napin cassette containing the F133A KAS II mutant coding sequence was cloned into the NotI site of pCGN11003 to create pCGN11050.

A napin cassette containing the L111A, F133A KAS II double mutant coding sequence was cloned into the NotI site of pCGN11003 to create pCGN11053.

A napin cassette containing the L111A, F133A KAS II double mutant coding sequence was cloned into the NotI site of pCGN8642 to create pCGN11054.

A napin cassette containing the I108A, L111A, I114A KAS II triple mutant coding sequence was cloned into the NotI site of pCGN11003 to create pCGN11057.

A napin cassette containing the I108A, L111A, I114A KAS II triple mutant coding sequence was cloned into the NotI site of pCGN8642 to create pCGN11058.

A napin cassette containing the I108A, L111A, I114A, F133A, L197A KAS II multiple mutant coding sequence was cloned into the NotI site of pCGN11003 to create pCGN11061.

A napin cassette containing the I108A, L111A, I114A, F133A, L197A KAS II multiple mutant coding sequence was cloned into the NotI site of pCGN8642 to create pCGN11062.

A napin cassette containing the I108F KAS II mutant coding sequence was cloned into the NotI site of pCGN11000 to create pCGN11065.

A napin cassette containing the I108F KAS II mutant coding sequence was cloned into the NotI site of pCGN8642 to create pCGN11066.

A napin cassette containing the I108F, A193I KAS II double mutant coding sequence was cloned into the NotI site of pCGN11000 to create pCGN11069.

A napin cassette containing the I108F, A193I KAS II double mutant coding sequence was cloned into the NotI site of pCGN8642 to create pCGN11070.

A napin cassette containing the A193M KAS II mutant coding sequence was cloned into the NotI site of pCGN11000 to create pCGN11073.

A napin cassette containing the A193M KAS II mutant coding sequence was cloned into the NotI site of pCGN8642 to create pCGN11074.

Example 4

Analysis of Engineered KAS II Proteins Expression in E. coli

FIG. 7 shows the complete list of mutations that were generated in E.coli KAS II using the Stratagene Quick-Change™ site-directed mutagenesis kit, and confirmed by DNA sequencing. The mutant KAS II genes cloned behind an IPTG inducible T5 promoter (pQE30 vector, Qiagen) were transformed into E.coli strain M15/pREP4. The effect of the expression of these KAS II mutants on the fatty acid composition of E.coli is shown in FIG. 3. E.coli M15/pREP4 strains containing no vector (−Vec), vector without insert (+Vec), or vectors expression wild-type KAS I or II or single or multiple engineered forms of KASII were grown to mid-log phase in LB media at 30° C. Expression was induced for 2 hours with IPTG (0.75 mM), cells were harvested, lyophilzed, and the lipids were extracted into toluene and derivatized by sodium methoxide and analyzed for fatty acid content by GC FAME analysis as described in Dehesh, et al. (1998) Plant J. 15:383–390.

The mutations prepared to increase the length of the end product fatty acids lead to the accumulation of abnormally long fatty acids in E.coli (FIG. 3). Wild-type E.coli membranes contain no stearic acid and barely detectable levels of 20:0 and 20:1. Whereas L197, F133A and L111A all resulted in further elongation of the normal membrane components 16.0, and 18:1 resulting in the accumulation of 4, 7 and 13% 18:0 respectively, and 1 to 3% 20:0 and 20:1. KAS II/L111A produced the highest level of 18:0 (13%) while KAS II/L111A-F133A accumulated the highest levels of 20:0 and 20:1 (2 and 4% respectively). Mutations I108A and I114A appeared to decrease the long chain fatty acid accumulation due to L111A and F133A.

The KAS II mutants prepared to shorten the maximum fatty acids were analyzed in vitro for the ability to utilize various chain length acyl-ACP substrates. Results of the in vitro assays (FIGS. 4, 5, and 6) demonstrates that the mutants I108F, I108L, A193M, and A193I have a reduced ability to utilize C8-ACP and longer substrates for condensation. However, these mutations are able to utilize C6-ACP substrates for elongation to produce C8 fatty acids. Furthermore, at least one mutation, A193M, had an increased ability to utilize C6-ACP substrates compared to the wild-type KAS for elongation.

Figure 4:
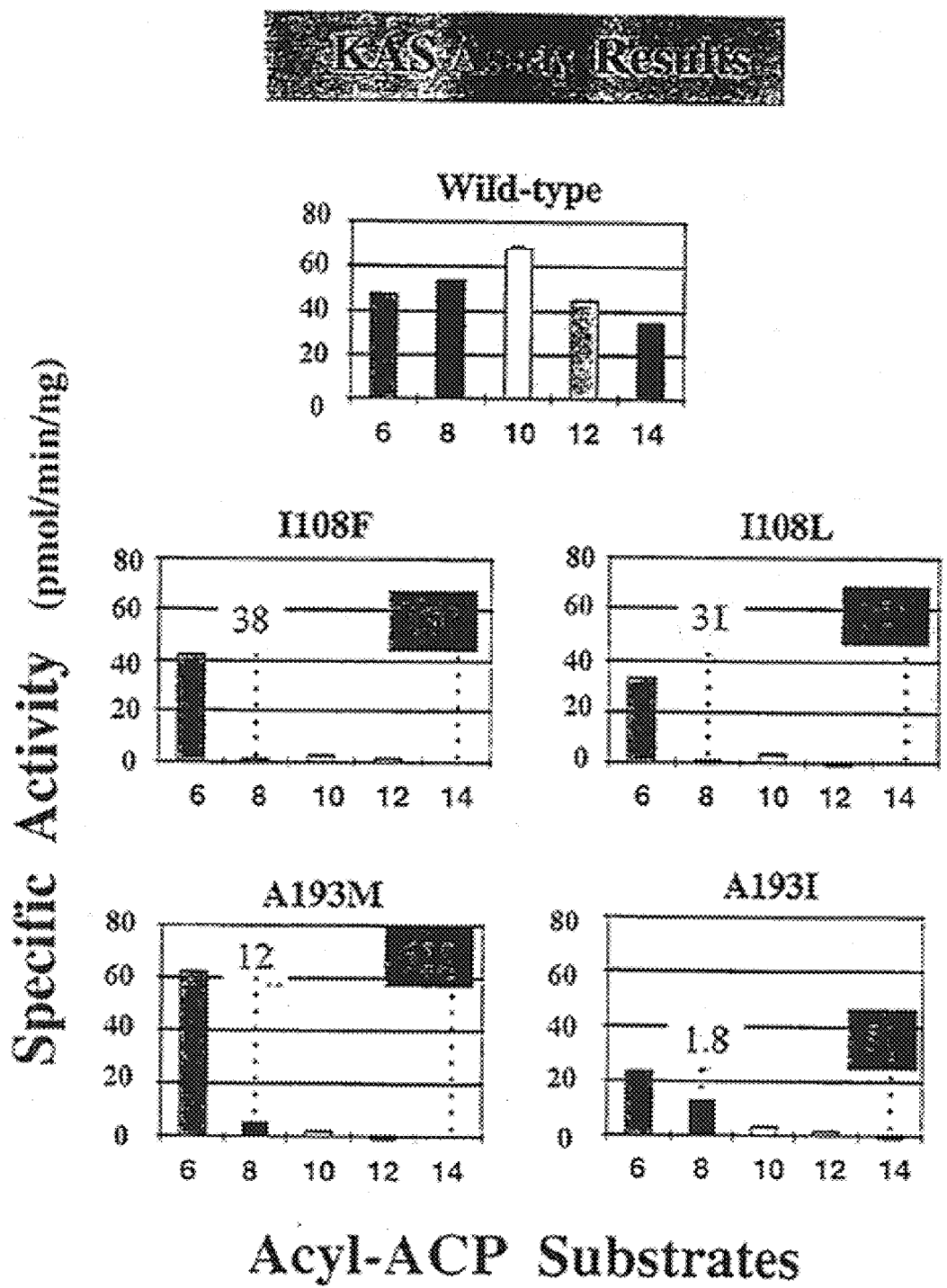
Figure 5:
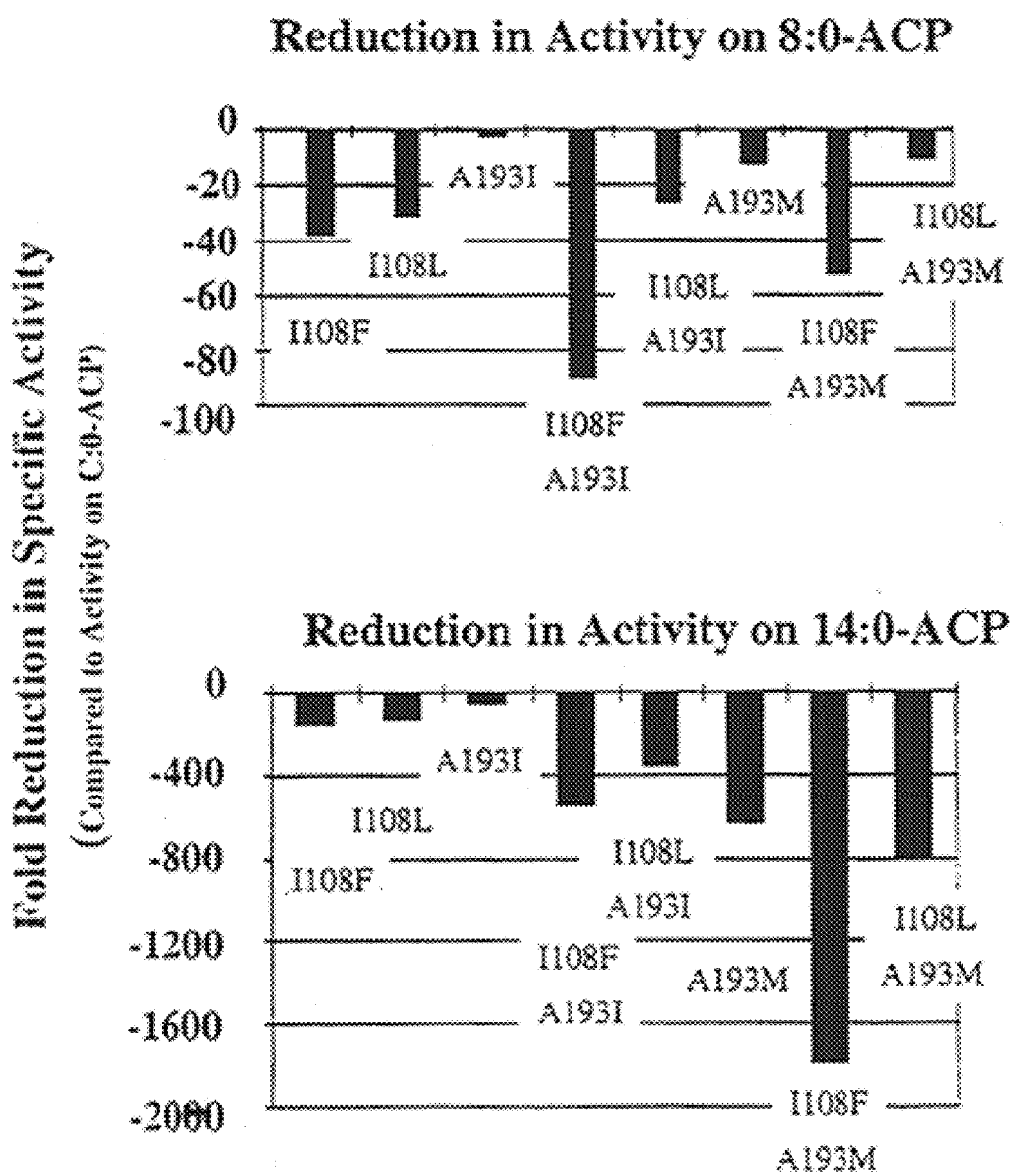
Figure 6:
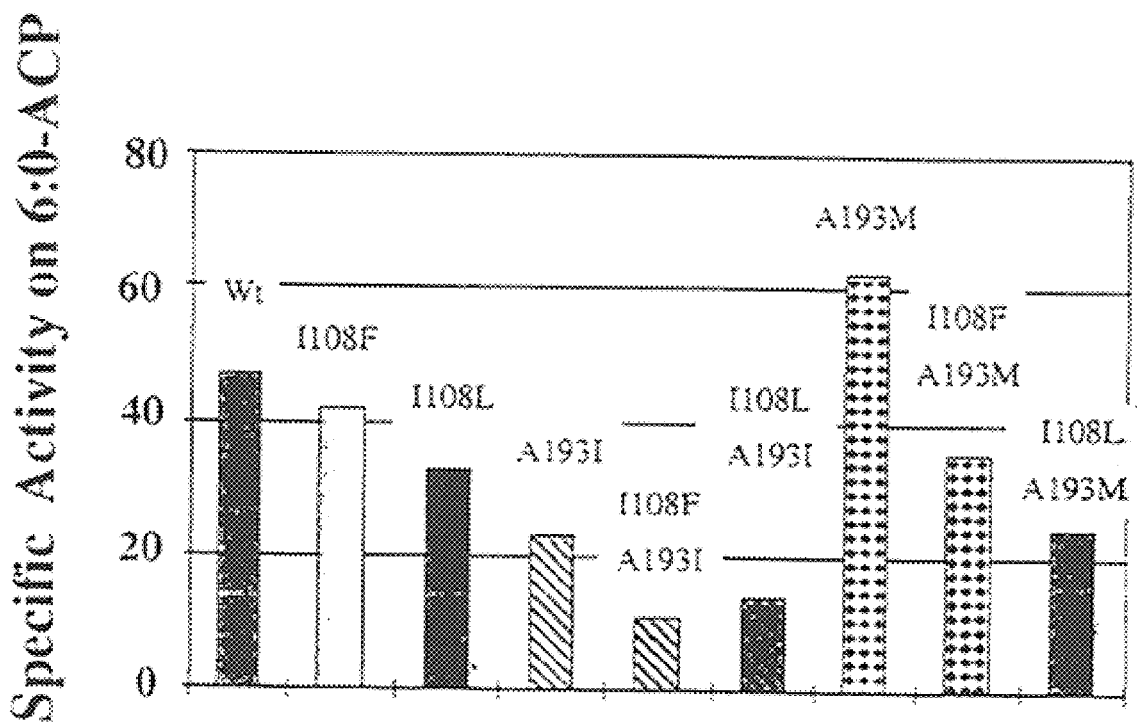

The data showing the effect of mutations I108F, I108L, A193I and A193M (together or separately) on the enzymatic activity of KAS II are summarized in FIGS. 4, 5 and 6. FIG. 4 shows that mutations I108F, I108L and A193M all cause significant reduction in the activity of KAS II on 8:0-ACP as compared to 6:0-ACP (38, 31 and 12 fold reductions respectively), without significantly reducing the activity on 6:0-ACP. In other words they have effectively changed KAS II into an enzyme capable of making fatty acids up to a maximum of 8 carbons in length. Mutation A193I only causes a 1.8 fold decrease in activity on 8:0-ACP as compared to 6:0-ACP. FIG. 5 shows that the combined mutations at I108 and A193 have the effect of reducing the activity of KAS II on 6:0-ACP somewhat, but FIG. 6 shows that the combined effect was much greater effect on the activity with acyl-ACPs 8:0 and longer (14:0).

Consequently the double mutants are even more specific for the synthesis of 8 carbon fatty acids. The most specific is KAS II I108F/A193 KAS II which is 90X more active on 6:0-ACP than it is on 8:0-ACP suggesting that it is now an enzyme highly specific for the synthesis of fatty acids only up to 8 carbons in length.

Example 5

Structural Comparisons of a Plant Medium-Chain Specific KAS with E.coli KAS II

Figure 8:
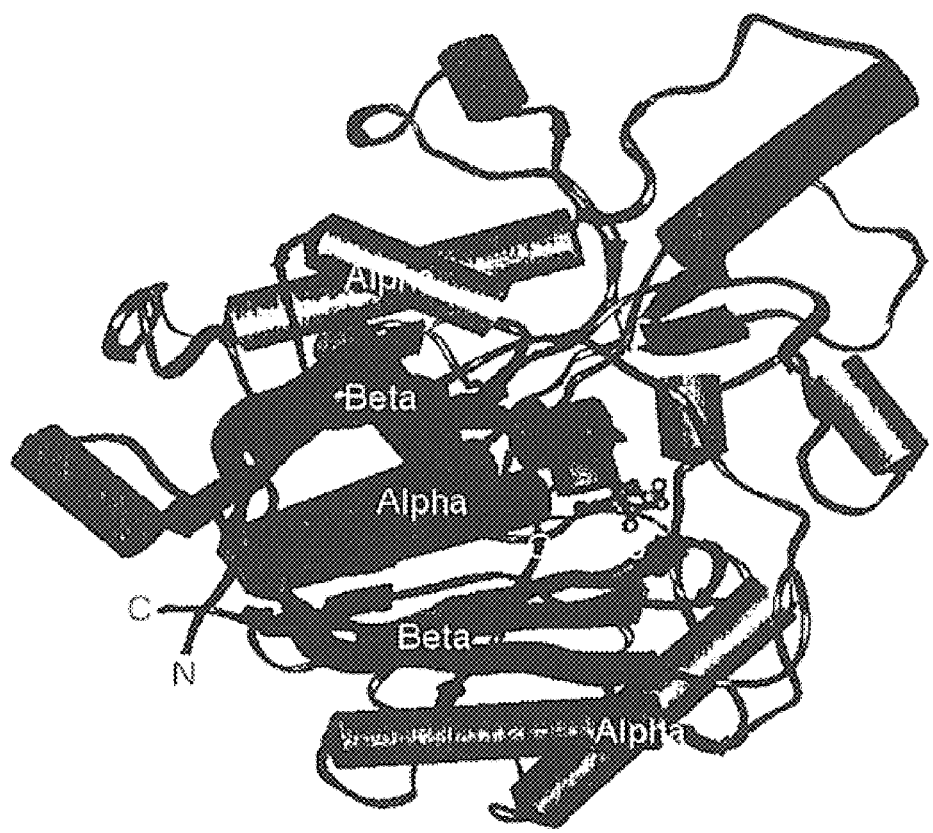
Figure 9:
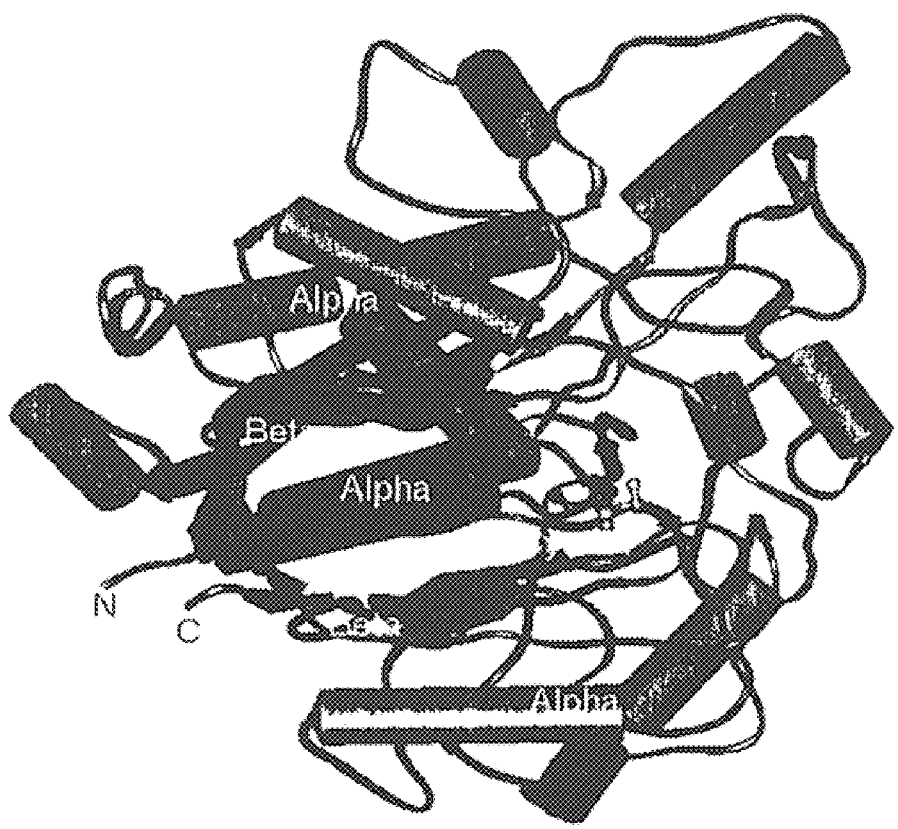
Figure 10:
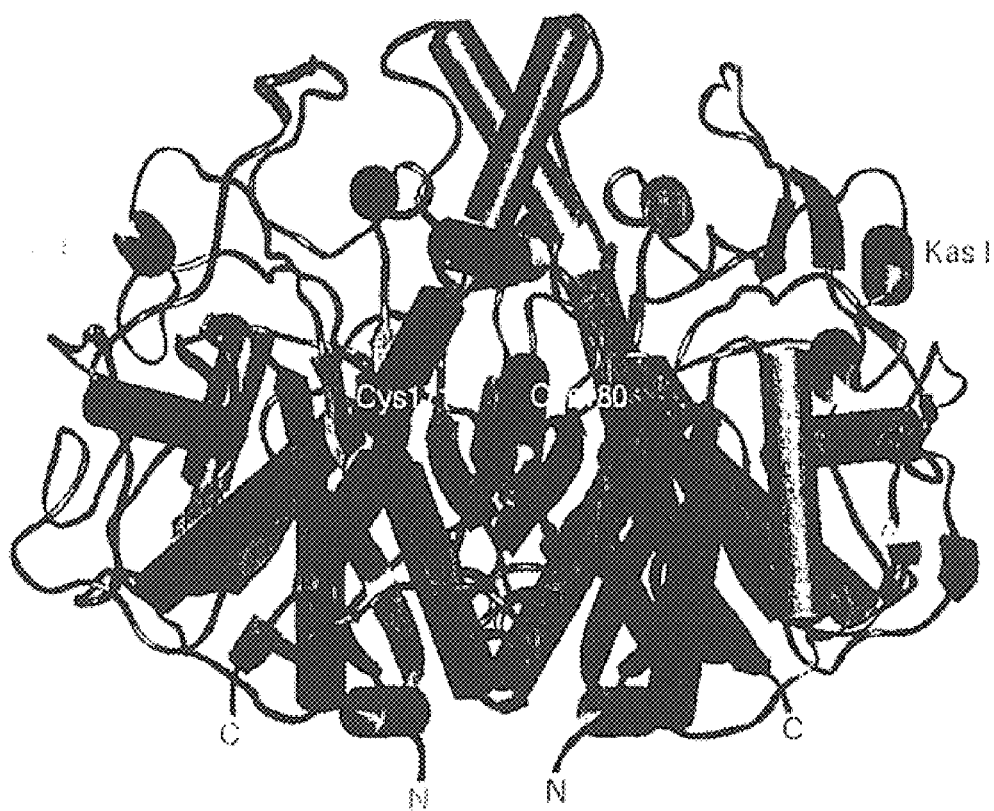

To further characterize the structure-function relationships of KAS fatty acid binding pockets the modeled structure of a plant medium-chain (8:0, 10:0) specific KAS [Cuphea, pulcherrima, (C.pu) KASIV] (Dehesh et al. (1998) Plant J. 15:383–390) was compared with the crystal structure of E.coli KAS II. FIG. 8 shows that C.pu KAS I is predicted to share essentially the same folding pattern as E.coli KAS II with the exception of a few loop regions, as might be expected given the structural similarity between KAS enzymes. Furthermore, Cpu KAS IV also has a similar structure (FIG. 9). The general structure for the KAS family of proteins follows the α-β-α-β-α folding pattern. Indeed at the amino acid sequence level, all but 7 of the 55 highly conserved residues among KAS enzymes are identical (87% identity). However there is only 60% identity in hydrophobic fatty acid binding pocket region with 8 of the 20 amino acids being different consistent with this region of the protein being responsible for the differences in the enzymes specificity. Furthermore the model shows no stearic hinderance in the formation of KASI and KASIV heterodimer (FIG. 10). In addition, amino acid sequence comparisons between plant, mammalian, bacterial.

Example 6

Plant Transformation and Analysis

The expression constructs described in Example 3B above were used to transform Arabidopsis thaliana (Columbia) and/or Columbia mutants fab1, fae1-1, and fae1-2.

Figure 13:
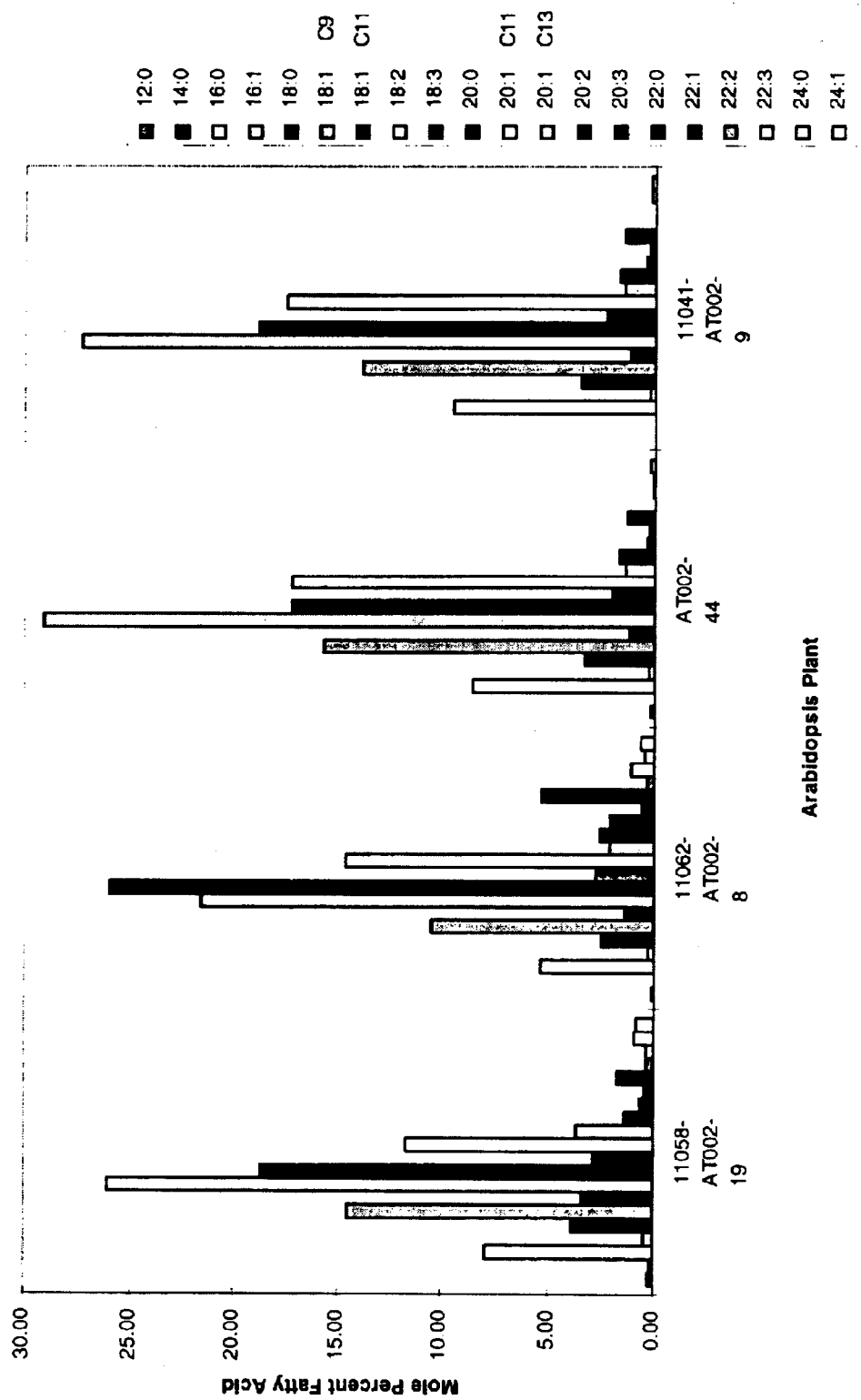

Seeds from transformed Arabidopsis lines were analyzed for fatty acid composition and are provided in Table 2 below and shown in FIG. 13. Fatty acid methyl esters (FAME) extracted in hexane were resolved by gas chromatography (GC) on a Hewlett Packard model 6890 GC.

TABLE 2

| Fatty Acid | 12:0 | 14:0 | 16:0 | 16:1 | 18:0 | 18:1 C9 | 18:1 C11 | 18:2 | 18:3 | 20:0 | 20:1 C11 | 20:1 C13 |
|---|---|---|---|---|---|---|---|---|---|---|---|---|
| 11058-AT002-19 | 0.29 | 0.17 | 7.86 | 0.50 | 3.85 | 14.53 | 3.37 | 26.02 | 18.72 | 2.83 | 11.61 | 3.71 |
| 11062-AT002-8 | 0.12 | 0.00 | 5.30 | 0.23 | 2.49 | 10.47 | 1.34 | 21.55 | 25.97 | 2.75 | 14.55 | 2.11 |
| AT002-44 | 0.17 | 0.00 | 8.53 | 0.26 | 3.35 | 15.65 | 1.21 | 29.06 | 17.22 | 2.06 | 17.22 | 1.36 |
| 11041-AT002-9 | 0.00 | 0.00 | 9.46 | 0.29 | 3.49 | 13.87 | 1.18 | 27.32 | 18.88 | 2.28 | 17.52 | 1.43 |

| Fatty Acid | 20:2 | 20:3 | 22:0 | 22:1 | 22:2 | 22:3 | 24:0 | 24:1 |
|---|---|---|---|---|---|---|---|---|
| 11058-AT002-19 | 1.39 | 0.67 | 0.41 | 1.71 | 0.33 | 0.33 | 0.90 | 0.81 |
| 11062-AT002-8 | 2.56 | 2.07 | 0.55 | 5.36 | 0.40 | 1.13 | 0.42 | 0.63 |
| AT002-44 | 1.63 | 0.36 | 0.29 | 1.26 | 0.02 | 0.07 | 0.14 | 0.14 |
| 11041-AT002-9 | 1.69 | 0.48 | 0.30 | 1.46 | 0.00 | 0.00 | 0.18 | 0.16 |

T2 pooled seeds from transgenic Arabidopsis lines containing pCGN11041 (11041-AT002-9) expressing the native E.coli KAS II protein in the seed tissue demonstrated nearly the same fatty acid composition as the nontransformed control Arabidopsis plants (AT002-44).

T2 pooled seeds from transgenic Arabidopsis var Columbia containing the construct pCGN11058 demonstrated the ability to synthesize longer carbon chain fatty acids compared to the nontransformed control plants as well as transgenic plants containing the wild-type E. coli KAS II protein. Particular increases in the production of 18:1 c11, 20:1 c13, 24:0 and 24:1 are observed in transgenic plants containing pCGN11058. Increases of 18:1 c11, 20:1 c13, 24:0 and 24:1 of 2 to 3 fold are obtained compared to nontransformed control plants. The fact that these levels were not higher may he due to the fact that there are many enzymatic steps downstream from the condensation step catalyzed by KAS enzymes which affect the longer chain acyl-ACPs produced incorporation into triglycerides.

T2 pooled seeds from transgenic Arabidopsis vis var Columbia containing the construct pCGN11062 also demonstrated the ability to synthesize longer chain fatty acids compared to nontransformed control plants and transgenic plants containing the wild-type E.coli KAS II protein construct. The T2 pooled seeds of I1062 transgenic lines were found to have a 3 to 4 fold increase in 22:1 as well as increased amounts of 20:2, 20:3 and 22:3, consistent with the presence of a KAS II protein being present in the plastid.

The above results demonstrate the ability to modify β-ketoacyl-ACP synthase sequences such that engineered β-ketoacyl-ACP synthases having altered substrate specificity may be produced. Such β-ketoacyl-ACP synthases may be expressed in host cells to provide a supply of the engineered β-ketoacyl-ACP synthase and to modify the existing pathway of fatty acid synthesis such that novel compositions of fatty acids are obtained. In particular, the engineered β-ketoacyl-ACP synthases may be expressed in the seeds of oilseed plants to provide a natural source of desirable TAG molecules.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An engineered β-Ketoacyl-acyl carrier protein synthase protein comprising an amino acid sequence (i) wherein said amino acid sequence of said engineered β-Ketoacyl-acyl carrier protein synthase protein has a substitution of at least one amino acid residue selected from the group consisting of amino acid residues at a position corresponding to residue 108, 111, 114, 133, and 197 of SEQ ID NO: 47, and (ii) wherein said substitution is of a hydrophobic residue to a smaller residue, and (iii) wherein said engineered β-Ketoacyl-acyl carrier protein synthase protein increases long chain fatty acid accumulation compared to a β-Ketoacyl-acyl carrier protein synthase protein having at least one unaltered amino acid residue selected from the group consisting of amino acid residues at a position corresponding to residue 108, 111, 114, 133, and 197 of SEQ ID NO: 47.

2. The engineered β-Ketoacyl-acyl carrier protein synthase protein of claim 1, wherein said β-Ketoacyl-acyl carrier protein synthase protein is obtained from a prokaryotic source.

3. The engineered β-Ketoacyl-acyl carrier protein synthase protein of claim 1, wherein said β-Ketoacyl-acyl carrier protein synthase protein is obtained from *Escherichia coli*.

4. The engineered β-Ketoacyl-acyl carrier protein synthase protein of claim 1, wherein said β-Ketoacyl-acyl carrier protein synthase protein is obtained from a plant source.

5. The engineered β-Ketoacyl-acyl carrier protein synthase protein of claim 1, wherein fatty acid production of said engineered β-Ketoacyl-acyl carrier protein synthase protein is altered such that short chain fatty acid accumulation is decreased compared to a β-Ketoacyl-acyl carrier protein synthase protein having said at least one unaltered residue.

6. An engineered β-Ketoacyl-acyl carrier protein synthase protein comprising an amino acid sequence (i) wherein said amino acid sequence of said engineered β-Ketoacyl-acyl carrier protein synthase protein has a substitution of at least one amino acid selected from the group consisting of amino acid residues at a position corresponding to residue 108 and 193 of SEQ ID NO: 47, and (ii) wherein said substitution is of a hydrophobic residue to a different hydrophobic residue, and (iii) wherein said engineered β-Ketoacyl-acyl carrier protein synthase protein preferentially accumulates fatty acids having a shorter chain length compared to a β-Ketoacyl-acyl carrier protein synthase protein having at least one unaltered amino acid residue selected from the group consisting of amino acid residues at a position corresponding to residue 108 and 193 of SEQ ID NO: 47.

7. The engineered β-Ketoacyl-acyl carrier protein synthase protein of claim 6, wherein said β-Ketoacyl-acyl carrier protein synthase protein is obtained from a prokaryotic source.

8. The engineered β-Ketoacyl-acyl carrier protein synthase protein of claim 6, wherein said β-Ketoacyl-acyl carrier protein synthase protein is obtained from *Escherichia coli*.

9. The engineered β-Ketoacyl-acyl carrier protein synthase protein of claim 6, wherein said β-Ketoacyl-acyl carrier protein synthase protein is obtained from a plant source.

10. The engineered β-Ketoacyl-acyl carrier protein synthase protein of claim 6, wherein fatty acid production of said engineered β-Ketoacyl-acyl carrier protein synthase protein is altered such that long chain fatty acid accumulation is decreased compared to a β-Ketoacyl-acyl carrier protein synthase protein having said at least one unaltered residue.

11. The engineered β-Ketoacyl-acyl carrier protein synthase protein of claim 6, wherein (i) said amino acid residue corresponding to the residue at position 108 of SEQ ID NO: 47 is selected from the group consisting of isoleucine, leucine, and methionine and wherein (ii) said amino acid residue is substituted with phenylalanine.

12. The engineered β-Ketoacyl-acyl carrier protein synthase protein of claim 6, wherein (i) said amino acid residue corresponding to the residue at position 108 of SEQ ID NO: 47 is selected from the group consisting of isoleucine and methionine and wherein (ii) said amino acid residue is substituted with leucine.

13. The engineered β-Ketoacyl-acyl carrier protein synthase protein of claim 6, wherein (i) said amino acid residue corresponding to the residue at position 193 of SEQ ID NO: 47 is selected from the group consisting of alanine, phenylalanine, valine, and leucine and wherein (ii) said amino acid residue is substituted with isoleucine.

14. The engineered β-Ketoacyl-acyl carrier protein synthase protein of claim 6, wherein (i) said amino acid residue corresponding to the residue at position 193 of SEQ ID NO: 47 is selected from the group consisting of alanine, phenylalanine, valine, and leucine and wherein (ii) said amino acid residue is substituted with methionine.

15. The engineered β-Ketoacyl-acyl carrier protein synthase protein of claim 1, wherein (i) said amino acid residue corresponding to the residue at position 108 of SEQ ID NO: 47 is selected from the group consisting of valine, leucine, isoleucine, and methionine, and wherein (ii) said amino acid residue is substituted with alanine.

16. The engineered β-Ketoacyl-acyl carrier protein synthase protein of claim 1, wherein (i) said amino acid residue corresponding to the residue at position 111 of SEQ ID NO: 47 is selected from the group consisting of phenylalanine, isoleucine, and leucine, and wherein (ii) said amino acid residue is substituted with alanine.

17. The engineered β-Ketoacyl-acyl carrier protein synthase protein of claim 1, wherein (i) said amino acid residue corresponding to the residue at position 114 of SEQ ID NO: 47 is selected from the group consisting of valine, leucine, isoleucine, and methionine, and wherein (ii) said amino acid residue is substituted with alanine.

18. The engineered β-Ketoacyl-acyl carrier protein synthase protein of claim 1, wherein (i) said amino acid residue corresponding to the residue at position 133 of SEQ ID) NO: 47 is selected from the group consisting of phenylalanine, isoleucine, and leucine and wherein (ii) said amino acid residue is substituted with alanine.

19. The engineered β-Ketoacyl-acyl carrier protein synthase protein of claim 1, wherein (i) said amino acid residue corresponding to the residue at position 197 of SEQ ID NO: 47 is selected from the group consisting of leucine and isoleucine and wherein (ii) said amino acid residue is substituted with alanine.

20. The engineered β-Ketoacyl-acyl carrier protein synthase protein of claim 1, wherein said engineered β-Ketoacyl-acyl carrier protein synthase protein accumulates normal membrane components compared to a β-Ketoacyl-acyl carrier protein synthase protein having said at least one unaltered residue.

21. The engineered β-Ketoacyl-acyl carrier protein synthase protein of claim 1, wherein said engineered β-Ketoacyl-acyl carrier protein synthase protein accumulates longer than normal membrane components compared to a β-Ketoacyl-acyl carrier protein synthase protein having said at least one unaltered residue.

22. The engineered β-Ketoacyl-acyl carrier protein synthase protein of claim 1, wherein said engineered β-Ketoacyl-acyl carrier protein synthase protein is more specific for the synthesis of eight carbon fatty acids compared to a β-Ketoacyl-acyl carrier protein synthase protein having said at least one unaltered residue.

23. The engineered β-Ketoacyl-acyl carrier protein synthase protein of claim 1, wherein said engineered β-Ketoacyl-acyl carrier protein synthase protein (i) has an alanine substitution at positions corresponding to residues 108, 111, and 114 of SEQ ID NO: 47 and (ii) wherein said engineered β-Ketoacyl-acyl carrier protein synthase protein synthesizes longer carbon chain fatty acids in transgenic plants compared to wild-type plants.

24. The engineered β-Ketoacyl-acyl carrier protein synthase protein of claim 1, wherein said engineered β-Ketoacyl-acyl carrier protein synthase protein (i) has an alanine substitution at positions corresponding to residues 108, 111, and 114 of SEQ ID NO: 47 and (ii) wherein said engineered β-Ketoacyl-acyl carrier protein synthase protein synthesizes longer carbon chain fatty acids in transgenic plants compared to a β-Ketoacyl-acyl carrier protein synthase protein having said at least one unaltered residue in transgenic plants.

25. The engineered β-Ketoacyl-acyl carrier protein synthase protein of claim 1, wherein said engineered β-Ketoacyl-acyl carrier protein synthase protein (i) has an alanine substitution at positions corresponding to residues 108, 111, 114, 133, and 197 of SEQ ID NO: 47 and (ii) wherein said engineered β-Ketoacyl-acyl carrier protein synthase protein synthesizes longer carbon chain fatty acids in transgenic plants compared to wild-type plants.

26. The engineered β-Ketoacyl-acyl carrier protein synthase protein of claim 1, wherein said engineered β-Ketoacyl-acyl carrier protein synthase protein (i) has an alanine substitution at positions corresponding to residues 108, 111, 114, 133, and 197 of SEQ ID NO: 47 and (ii) wherein said engineered β-Ketoacyl-acyl carrier protein synthase protein synthesizes longer carbon chain fatty acids in transgenic plants compared to a β-Ketoacyl-acyl carrier protein synthase protein having said at least one unaltered residue in transgenic plants.

27. The engineered β-Ketoacyl-acyl carrier protein synthase protein of claim 6, wherein said engineered β-Ketoacyl-acyl carrier protein synthase protein has a reduced ability to utilize C8-ACP and longer substrates for condensation while still able to use the C6-ACP for elongation to produce C8 fatty acids.

28. The engineered β-Ketoacyl-acyl carrier protein synthase protein of claim 6, wherein said engineered β-Ketoacyl-acyl carrier protein synthase protein has an increased ability to utilize C6-ACP substrates for elongation compared to a β-Ketoacyl-acyl carrier protein synthase protein having said at least one unaltered residue.

29. An engineered β-Ketoacyl-acyl carrier protein synthase protein comprising an amino acid sequence (i) wherein said amino acid sequence of said engineered β-Ketoacyl-acyl carrier protein synthase protein has a substitution of at least one amino acid residue selected from the group consisting of amino acid residues at a position corresponding to residue 108, 134, 193, 202 and 342 of SEQ ID NO: 47, and (ii) wherein said substitution widens the hydrophobic fatty acid binding pocket, and (iii) wherein said engineered β-Ketoacyl-acyl carrier protein synthase protein has an altered substrate preference compared to a β-Ketoacyl-acyl carrier protein synthase protein having at least one unaltered amino acid residue selected from the group consisting of amino acid residues at a position corresponding to residue 108, 134, 193, 202 and 342 of SEQ ID NO: 47.

30. The engineered β-Ketoacyl-acyl carrier protein synthase protein of claim 29, wherein said β-Ketoacyl-acyl carrier protein synthase protein is obtained from a prokaryotic source.

31. The engineered β-Ketoacyl-acyl carrier protein synthase protein of claim 29, wherein said β-Ketoacyl-acyl carrier protein synthase protein is obtained from *Escherichia coil.*

32. The engineered β-Ketoacyl-acyl carrier protein synthase protein of claim 29, wherein said β-Ketoacyl-acyl carrier protein synthase protein is obtained from a plant source.

33. The engineered β-Ketoacyl-acyl carrier protein synthase protein of claim 29, wherein a substrate is a molecule other than Malonyl-ACP.

34. The amino acid sequence of claim 29, wherein said engineered β-Ketoacyl-acyl carrier protein synthase protein produces a branched chain fatty acid.

35. The engineered β-Ketoacyl-acyl carrier protein synthase protein of claim 29, wherein (i) said amino acid residue corresponding to the residue at position 108 of SEQ ID NO: 47 is selected from the group consisting of alanine, valine, leucine, isoleucine, and methionine, and wherein (ii) said amino acid residue is substituted with glycine.

36. The engineered β-Ketoacyl-acyl carrier protein synthase protein of claim 29, wherein (i) said amino acid residue corresponding to the residue at position 134 of SEQ ID NO: 47 is selected from the group consisting of valine and isoleucine and wherein (ii) said amino acid residue is substituted with glycine.

37. The engineered β-Ketoacyl-acyl carrier protein synthase protein of claim 29, wherein (i) said amino acid residue corresponding to the residue at position 134 of SEQ ID NO: 47 is selected from the group consisting of valine and isoleucine and wherein (ii) said amino acid residue is substituted with alanine.

38. The engineered β-Ketoacyl-acyl carrier protein synthase protein of claim 29, wherein (i) said amino acid residue corresponding to the residue at position 193 of SEQ ID NO: 47 is selected from the group consisting of alanine, phenylalanine, valine, and leucine and wherein (ii) said amino acid residue is substituted with glycine.

39. The engineered β-Ketoacyl-acyl carrier protein synthase protein of claim 29, wherein (i) said amino acid residue corresponding to the residue at position 202 of SEQ ID NO: 47 is a phenylalanine and wherein (ii) said phenylalanine is substituted with an amino acid residue selected from the group consisting of isoleucine, leucine, and glycine.

40. The engineered β-Ketoacyl-acyl carrier protein synthase protein of claim 29, wherein (i) said amino acid residue corresponding to the residue at position 342 of SEQ ID NO: 47 is a leucine and wherein (ii) said leucine is substituted with an amino acid residue selected from the group consisting of alanine and glycine.

41. The engineered β-Ketoacyl-acyl carrier protein synthase protein of claim 6, wherein (i) wherein said amino acid sequence of said engineered β-Ketoacyl-acyl carrier protein synthase protein has a substitution of at least one amino acid selected from the group consisting of amino acid residues at a position corresponding to residue 108 and 193 of SEQ ID NO: 47, and (ii) wherein said substitution is of a hydrophobic residue to a larger hydrophobic residue, and (iii) wherein said engineered β-Ketoacyl-acyl carrier protein synthase protein preferentially accumulates fatty acids having a shorter chain length compared to a β-Ketoacyl-acyl carrier protein synthase protein having at least one unaltered amino acid residue selected from the group consisting of amino acid residues at a position corresponding to residue 108 and 193 of SEQ ID NO: 47.

42. The engineered β-Ketoacyl-acyl carrier protein synthase protein of claim 6, wherein (i) said amino acid residue corresponding to the residue at position 108 of SEQ ID NO: 47 is isoleucine, and wherein (ii) said amino acid residue is substituted with phenylalanine.

43. The engineered β-Ketoacyl-acyl carrier protein synthase protein of claim 6, wherein (i) said amino acid residue corresponding to the residue at position 108 of SEQ ID NO: 47 is isoleucine, and wherein (ii) said amino acid residue is substituted with leucine.

44. The engineered β-Ketoacyl-acyl carrier protein synthase protein of claim 6, wherein (i) said amino acid residue corresponding to the residue at position 193 of SEQ ID NO: 47 is alanine, and wherein (ii) said amino acid residue is substituted with isoleucine.

45. The engineered β-Ketoacyl-acyl carrier protein synthase protein of claim 6, wherein (i) said amino acid residue corresponding to the residue at position 193 of SEQ ID NO: 47 is alanine, and wherein (ii) said amino acid residue is substituted with methionine.

46. The engineered β-Ketoacyl-acyl carrier protein synthase protein of claim 1, wherein (i) said amino acid residue corresponding to the residue at position 108 of SEQ ID NO: 47 is isoleucine, and wherein (ii) said amino acid residue is substituted with alanine.

47. The engineered β-Ketoacyl-acyl carrier protein synthase protein of claim 1, wherein (i) said amino acid residue corresponding to the residue at position 111 of SEQ ID NO: 47 is leucine, and wherein (ii) said amino acid residue is substituted with alanine.

48. The engineered β-Ketoacyl-acyl carrier protein synthase protein of claim 1, wherein (i) said amino acid residue corresponding to the residue at position 114 of SEQ ID NO: 47 is isoleucine, and wherein (ii) said amino acid residue is substituted with alanine.

49. The engineered β-Ketoacyl-acyl carrier protein synthase protein of claim 1, wherein (i) said amino acid residue corresponding to the residue at position 133 of SEQ ID NO: 47 is phenylalanine, and wherein (ii) said amino acid residue is substituted with alanine.

50. The engineered β-Ketoacyl-acyl carrier protein synthase protein of claim 1, wherein (i) said amino acid residue corresponding to the residue at position 197 of SEQ ID NO: 47 is leucine, and wherein (ii) said amino acid residue is substituted with alanine.

51. The engineered β-Ketoacyl-acyl carrier protein synthase protein of claim 29, wherein (i) said amino acid residue corresponding to the residue at position 108 of SEQ ID NO: 47 is isoleucine, and wherein (ii) said amino acid residue is substituted with glycine.

52. The engineered β-Ketoacyl-acyl carrier protein synthase protein of claim 29, wherein (i) said amino acid residue corresponding to the residue at position 134 of SEQ ID NO: 47 is valine and wherein (ii) said amino acid residue is substituted with glycine.

53. The engineered β-Ketoacyl-acyl carrier protein synthase protein of claim 29, wherein (i) said amino acid residue corresponding to the residue at position 134 of SEQ ID NO: 47 is valine and wherein (ii) said amino acid residue is substituted with alanine.

54. The engineered β-Ketoacyl-acyl carrier protein synthase protein of claim 29, wherein (i) said amino acid residue corresponding to the residue at position 193 of SEQ ID NO: 47 is alanine and wherein (ii) said amino acid residue is substituted with glycine.

* * * * *

SEQUENCE LISTING

```
<160> NUMBER OF SEQ ID NOS: 47

<210> SEQ ID NO 1
<211> LENGTH: 36
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer I108F Sense

<400> SEQUENCE: 1
gtgccgcaat tggatccggg tttggcggcc tcggac                            36

<210> SEQ ID NO 2
<211> LENGTH: 36
<212> TYPE: DNA
<213> ORGANISM: Artificial Sequence
<220> FEATURE:
<221> NAME/KEY: misc_feature
```

-continued

```
<222> LOCATION: ()..()
<223> OTHER INFORMATION: Oligonucleotide Primer I108F Antisense

<400> SEQUENCE: 2
gtccgaggcc gccaaacccg gatccaattg cggcac                                    36

<210> SEQ ID NO 3
<211> LENGTH: 42
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer I108L Sense

<400> SEQUENCE: 3
gtgccgcaat tggctccggg cttggaggcc tcggactgat cg                             42

<210> SEQ ID NO 4
<211> LENGTH: 42
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer I108L Antisense

<400> SEQUENCE: 4
cgatcagtcc gaggcctcca agcccggagc caattgcggc ac                             42

<210> SEQ ID NO 5
<211> LENGTH: 36
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer A193I Sense

<400> SEQUENCE: 5
gcaggtggcg ccgagaaaat cagtacgccg ctgggc                                    36

<210> SEQ ID NO 6
<211> LENGTH: 35
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer A193I Antisense

<400> SEQUENCE: 6
gcccagcggc gtactgattt tctcggcgcc acctg                                     35

<210> SEQ ID NO 7
<211> LENGTH: 37
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer A193M Sense

<400> SEQUENCE: 7
ggtggcgcag agaaaatgag tactccgctg gcgttg                                    37

<210> SEQ ID NO 8
```

```
<211> LENGTH: 37
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer A193M Antisense

<400> SEQUENCE: 8
caacgcccag cggagtactc attttctctg cgccacc                              37

<210> SEQ ID NO 9
<211> LENGTH: 50
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer I108A,L111A, I114A Sense

<400> SEQUENCE: 9
gcaattggct ccggggctgg cggcgccgga ctggccgaag aaaaccacac                50

<210> SEQ ID NO 10
<211> LENGTH: 50
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer I108A,L111A, I114A
      Antisense

<400> SEQUENCE: 10
gtgtggtttt cttcggccag tccggcgccg ccagccccgg agccaattgc                50

<210> SEQ ID NO 11
<211> LENGTH: 28
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer L111A Sense

<400> SEQUENCE: 11
gggattggcg gcgccggact gatcgaag                                        28

<210> SEQ ID NO 12
<211> LENGTH: 28
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer L111A Antisense

<400> SEQUENCE: 12
cttcgatcag tccggcgccg ccaatccc                                        28

<210> SEQ ID NO 13
<211> LENGTH: 34
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer F133A Sense
```

```
<400> SEQUENCE: 13
gatcagccca ttcgcggtac cgtcaacgat tgtg                                    34

<210> SEQ ID NO 14
<211> LENGTH: 34
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer F133A Antisense

<400> SEQUENCE: 14
cacaatcgtt gacggtaccg cgaatgggct gatc                                    34

<210> SEQ ID NO 15
<211> LENGTH: 32
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer L197A Sense

<400> SEQUENCE: 15
gagaaagcca gtactccggc gggcgttggt gg                                      32

<210> SEQ ID NO 16
<211> LENGTH: 32
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligonucleotide Primer L197A Antisense

<400> SEQUENCE: 16
ccaccaacgc ccgccggagt actggctttc tc                                      32

<210> SEQ ID NO 17
<211> LENGTH: 56
<212> TYPE: DNA
<213> ORGANISM: Artificial sequence
<220> FEATURE:
<221> NAME/KEY: misc_feature
<222> LOCATION: ()..()
<223> OTHER INFORMATION: Self annealed oligonucleotide primer

<400> SEQUENCE: 17
cgcgatttaa atggcgcgcc ctgcaggcgg ccgcctgcag ggcgcgccat ttaaat            56

<210> SEQ ID NO 18
<211> LENGTH: 366
<212> TYPE: DNA
<213> ORGANISM: Cuphea hookeriana

<400> SEQUENCE: 18
ctgagatctg tcgacatggc gaccgcttct cgcatggttg cgtccccttt ctgtacgtgg        60
ctcgtagctg catgcatgcc cacttcatcc gacaacgacc cacgttccct ttcccacaag      120
cggctccgcc tctcccgtcg ccggaggact ctctcctccc attgctccct ccgcggatcc      180
accttccaat gcctcgatcc ttgcaaccag caacgcttcc tcgggataa cggattcgct       240 tccctcttcg gatccaagcc tcttcgttca aatcgcggcc acctgaggct cggccgcact      300
tcccattccg gggaggtcat ggctgtggct atgcaacctg cacaggaagt ctccacaaga      360
```

```
tctgtc                                                    366
```

<210> SEQ ID NO 19
<211> LENGTH: 431
<212> TYPE: PRT
<213> ORGANISM: Arabidopsis thaliana

<400> SEQUENCE: 19

```
Ile Ser Ala Ser Ala Ser Thr Val Ser Ala Pro Lys Arg Glu Thr Asp
 1               5                  10                  15

Pro Lys Lys Arg Val Val Ile Thr Gly Met Gly Leu Val Ser Val Cys
            20                  25                  30

Gly Asn Asp Val Asp Ala Tyr Tyr Glu Lys Leu Leu Ser Gly Glu Ser
        35                  40                  45

Gly Ile Ser Leu Ile Asp Arg Phe Asp Ala Ser Lys Phe Pro Thr Arg
    50                  55                  60

Phe Gly Gly Gln Ile Arg Gly Phe Ser Ser Glu Gly Tyr Ile Asp Gly
65                  70                  75                  80

Lys Asn Glu Arg Arg Leu Asp Asp Cys Leu Lys Tyr Cys Ile Val Ala
                85                  90                  95

Gly Lys Lys Ala Leu Glu Ser Ala Asn Leu Gly Gly Asp Lys Leu Asn
            100                 105                 110

Thr Ile Asp Lys Arg Lys Ala Gly Val Leu Val Gly Thr Gly Met Gly
        115                 120                 125

Gly Leu Thr Val Phe Ser Glu Gly Val Gln Asn Leu Ile Glu Lys Gly
    130                 135                 140

His Arg Arg Ile Ser Pro Phe Phe Ile Pro Tyr Ala Ile Thr Asn Met
145                 150                 155                 160

Gly Ser Ala Leu Leu Ala Ile Asp Leu Gly Leu Met Gly Pro Asn Tyr
                165                 170                 175

Ser Ile Ser Thr Ala Cys Ala Thr Ser Asn Tyr Cys Phe Tyr Ala Ala
            180                 185                 190

Ala Asn His Asn His Arg Gly Glu Ala Asp Met Met Ile Ala Gly Gly
        195                 200                 205

Thr Glu Ala Ala Ile Ile Pro Ile Gly Leu Gly Gly Phe Val Ala Cys
    210                 215                 220

Arg Ala Leu Ser Gln Arg Asn Asp Asp Pro Gln Thr Ala Ser Arg Pro
225                 230                 235                 240

Trp Asp Lys Ala Arg Asp Gly Phe Val Met Gly Glu Gly Ala Gly Val
                245                 250                 255

Leu Val Met Glu Ser Leu Glu His Ala Met Lys Arg Gly Ala Pro Ile
            260                 265                 270

Val Ala Glu Tyr Leu Gly Gly Ala Val Asn Cys Asp Ala His His Met
        275                 280                 285

Thr Asp Pro Arg Ala Asp Gly Leu Gly Val Ser Ser Cys Ile Glu Arg
    290                 295                 300

Cys Leu Glu Asp Ala Gly Val Ser Pro Glu Glu Val Asn Tyr Ile Asn
305                 310                 315                 320

Ala His Ala Thr Ser Thr Leu Ala Gly Asp Leu Ala Glu Ile Asn Ala
                325                 330                 335

Ile Lys Lys Val Phe Lys Ser Thr Ser Gly Ile Lys Ile Asn Ala Thr
            340                 345                 350

Lys Ser Met Ile Gly His Cys Leu Gly Ala Ala Gly Gly Leu Glu Ala
        355                 360                 365
```

```
Ile Ala Thr Val Lys Ala Ile Asn Thr Gly Trp Leu His Pro Ser Ile
    370                 375                 380

Asn Gln Phe Asn Pro Glu Gln Ala Val Asp Phe Asp Thr Val Pro Asn
385                 390                 395                 400

Glu Lys Lys Gln His Glu Val Asp Val Ala Ile Ser Asn Ser Phe Gly
                405                 410                 415

Phe Gly Gly His Asn Ser Val Val Ala Phe Ser Ala Phe Lys Pro
                420                 425                 430

<210> SEQ ID NO 20
<211> LENGTH: 429
<212> TYPE: PRT
<213> ORGANISM: Brassica napus

<400> SEQUENCE: 20

Ala Ser Ser Ser Ala Val Ser Ala Pro Lys Arg Glu Thr Asp Pro Lys
1               5                   10                  15

Lys Arg Val Val Ile Thr Gly Met Gly Leu Val Ser Val Phe Gly Asn
                20                  25                  30

Asp Val Asp Ala Tyr Tyr Glu Lys Leu Leu Ser Gly Glu Ser Gly Ile
            35                  40                  45

Ser Leu Ile Asp Arg Phe Asp Ala Ser Lys Phe Pro Thr Arg Phe Gly
        50                  55                  60

Gly Gln Ile Arg Gly Phe Ser Ser Glu Gly Tyr Ile Asp Gly Lys Asn
65                  70                  75                  80

Glu Arg Arg Leu Asp Asp Cys Leu Lys Tyr Cys Ile Val Ala Gly Lys
                85                  90                  95

Lys Ala Leu Glu Ser Ala Asn Leu Gly Gly Asp Lys Leu Asn Thr Ile
                100                 105                 110

Asp Lys Gln Lys Ala Gly Val Leu Val Gly Thr Gly Met Gly Gly Leu
            115                 120                 125

Thr Val Phe Ser Asp Gly Val Gln Ala Leu Ile Glu Lys Gly His Arg
130                 135                 140

Arg Ile Ser Pro Phe Phe Ile Pro Tyr Ala Ile Thr Asn Met Gly Ser
145                 150                 155                 160

Ala Leu Leu Ala Ile Asp Leu Gly Leu Met Gly Pro Asn Tyr Ser Ile
                165                 170                 175

Ser Thr Ala Cys Ala Thr Ser Asn Tyr Cys Phe Tyr Ala Ala Ala Asn
            180                 185                 190

His Ile Arg Arg Gly Glu Ala Asp Met Met Ile Ala Gly Gly Thr Glu
        195                 200                 205

Ala Ala Ile Ile Pro Ile Gly Leu Gly Gly Phe Val Ala Cys Arg Ala
    210                 215                 220

Leu Ser Gln Arg Asn Asp Asp Pro Gln Thr Ala Ser Arg Pro Trp Asp
225                 230                 235                 240

Lys Gln Arg Asp Gly Phe Val Met Gly Glu Gly Ala Gly Val Leu Val
                245                 250                 255

Met Glu Ser Leu Glu His Ala Met Lys Arg Gly Ala Pro Ile Val Ala
            260                 265                 270

Glu Tyr Leu Gly Gly Ala Val Asn Cys Asp Ala His His Met Thr Asp
        275                 280                 285

Pro Arg Ala Asp Gly Leu Gly Val Ser Ser Cys Ile Glu Ser Cys Leu
    290                 295                 300

Glu Asp Ala Gly Val Ser Pro Glu Glu Val Asn Tyr Ile Asn Ala His
```

-continued

```
                305                 310                 315                 320
Ala Thr Ser Thr Leu Ala Gly Asp Leu Ala Glu Ile Asn Ala Ile Lys
                    325                 330                 335

Lys Val Phe Lys Ser Thr Ser Gly Ile Lys Ile Asn Ala Thr Lys Ser
                340                 345                 350

Met Ile Gly His Cys Leu Gly Ala Ala Gly Gly Leu Glu Ala Ile Ala
            355                 360                 365

Thr Val Lys Ala Ile Asn Thr Gly Trp Leu His Pro Ser Ile Asn Gln
        370                 375                 380

Phe Asn Pro Glu Pro Ala Val Asp Phe Asp Thr Val Ala Asn Glu Lys
385                 390                 395                 400

Lys Gln His Glu Val Asn Val Ala Ile Ser Asn Ser Phe Gly Phe Gly
                405                 410                 415

Gly His Asn Ser Val Val Ala Phe Ser Ala Phe Lys Pro
                420                 425

<210> SEQ ID NO 21
<211> LENGTH: 350
<212> TYPE: PRT
<213> ORGANISM: Cuphea hookeriana

<400> SEQUENCE: 21

Ser Ser Thr Ala Val Ala Ala Leu Glu Leu Val Asp Pro Pro Gly
1               5                   10                  15

Cys Arg Asn Ser Ala Arg Ala Asp Leu Gly Ala Asp Arg Leu Ser Lys
                20                  25                  30

Ile Asp Lys Glu Arg Ala Gly Val Leu Val Gly Thr Gly Met Gly Gly
            35                  40                  45

Leu Thr Val Phe Ser Asp Gly Val Gln Ser Leu Ile Glu Lys Gly His
        50                  55                  60

Arg Lys Ile Thr Pro Phe Phe Ile Pro Tyr Ala Ile Thr Asn Met Gly
65                  70                  75                  80

Ser Ala Leu Leu Ala Ile Glu Phe Gly Leu Met Gly Pro Asn Tyr Ser
                85                  90                  95

Ile Ser Thr Ala Cys Ala Thr Ser Asn Tyr Cys Phe His Ala Ala Ala
                100                 105                 110

Asn His Ile Arg Arg Gly Glu Ala Asp Leu Met Ile Ala Gly Gly Thr
            115                 120                 125

Glu Ala Ala Ile Ile Pro Ile Gly Leu Gly Gly Phe Val Ala Cys Arg
        130                 135                 140

Ala Leu Ser Gln Arg Asn Asp Asp Pro Gln Thr Ala Ser Arg Pro Trp
145                 150                 155                 160

Asp Lys Asp Arg Asp Gly Phe Val Met Gly Glu Gly Ala Gly Val Leu
                165                 170                 175

Val Met Glu Ser Leu Glu His Ala Met Arg Arg Gly Ala Pro Ile Ile
                180                 185                 190

Ala Glu Tyr Leu Gly Gly Ala Ile Asn Cys Asp Ala Tyr His Met Thr
            195                 200                 205

Asp Pro Arg Ala Asp Gly Leu Gly Val Ser Ser Cys Ile Glu Ser Ser
        210                 215                 220

Leu Glu Asp Ala Gly Val Ser Pro Glu Glu Val Asn Tyr Ile Asn Ala
225                 230                 235                 240

His Ala Thr Ser Thr Leu Ala Gly Asp Leu Ala Glu Ile Asn Ala Ile
                245                 250                 255
```

```
Lys Lys Val Phe Lys Asn Thr Lys Asp Ile Lys Ile Asn Ala Thr Lys
            260                 265                 270

Ser Met Ile Gly His Cys Leu Gly Ala Ser Gly Gly Leu Glu Ala Ile
            275                 280                 285

Ala Thr Ile Lys Gly Ile Asn Thr Gly Trp Leu His Pro Ser Ile Asn
            290                 295                 300

Gln Phe Asn Pro Glu Pro Ser Val Glu Phe Asp Thr Val Ala Asn Lys
305                 310                 315                 320

Lys Gln Gln His Glu Val Asn Val Ala Ile Ser Asn Ser Phe Gly Phe
            325                 330                 335

Gly Gly His Asn Ser Val Val Ala Phe Ser Ala Phe Lys Pro
            340                 345                 350

<210> SEQ ID NO 22
<211> LENGTH: 441
<212> TYPE: PRT
<213> ORGANISM: Cuphea hookeriana
<220> FEATURE:
<221> NAME/KEY: misc_feature
<222> LOCATION: (15)..(15)
<223> OTHER INFORMATION: Xaa at position 15 is unknown.

<400> SEQUENCE: 22

Lys Leu Thr Leu Thr Lys Gly Asn Lys Ser Trp Ser Ser Thr Xaa Val
1               5                   10                  15

Ala Ala Ala Leu Glu Leu Val Asp Pro Pro Gly Cys Arg Asn Ser Ala
            20                  25                  30

Arg Ala Gly Met Gly Leu Val Ser Val Phe Gly Ser Asp Val Asp Ser
            35                  40                  45

Tyr Tyr Glu Lys Leu Leu Ser Gly Glu Ser Gly Ile Ser Leu Ile Asp
        50                  55                  60

Arg Phe Asp Ala Ser Lys Phe Pro Thr Arg Phe Gly Gly Gln Ile Arg
65                  70                  75                  80

Gly Phe Asn Ala Thr Gly Tyr Ile Asp Gly Lys Asn Asp Arg Arg Leu
            85                  90                  95

Asp Asp Cys Leu Arg Tyr Cys Ile Val Ala Gly Lys Lys Ala Leu Glu
            100                 105                 110

Asn Ser Asp Leu Gly Gly Glu Ser Leu Ser Lys Ile Asp Lys Glu Arg
            115                 120                 125

Ala Gly Val Leu Val Gly Thr Gly Met Gly Gly Leu Thr Val Phe Ser
130                 135                 140

Asp Gly Val Gln Asn Leu Ile Glu Lys Gly His Arg Lys Ile Ser Pro
145                 150                 155                 160

Phe Phe Ile Pro Tyr Ala Ile Thr Asn Met Gly Ser Ala Leu Leu Ala
            165                 170                 175

Ile Asp Leu Gly Leu Met Gly Pro Asn Tyr Ser Ile Ser Thr Ala Cys
            180                 185                 190

Ala Thr Ser Asn Tyr Cys Phe Tyr Ala Ala Ala Asn His Ile Arg Arg
            195                 200                 205

Gly Glu Ala Asp Leu Met Ile Ala Gly Gly Thr Glu Ala Ala Ile Ile
            210                 215                 220

Pro Ile Gly Leu Gly Gly Phe Val Ala Cys Arg Ala Leu Ser Gln Arg
225                 230                 235                 240

Asn Asp Asp Pro Gln Thr Ala Ser Arg Pro Trp Asp Lys Asp Arg Asp
            245                 250                 255

Gly Phe Val Met Gly Glu Gly Ala Gly Val Leu Val Met Glu Ser Leu
```

```
                    260                 265                 270
Glu His Ala Met Lys Arg Gly Ala Pro Ile Ile Ala Glu Tyr Leu Gly
                275                 280                 285

Gly Ala Val Asn Cys Asp Ala Tyr His Met Thr Asp Pro Arg Ala Asp
            290                 295                 300

Gly Leu Gly Val Ser Ser Cys Ile Glu Ser Ser Leu Glu Asp Ala Gly
305                 310                 315                 320

Val Ser Pro Glu Glu Val Asn Tyr Ile Asn Ala His Ala Thr Ser Thr
                325                 330                 335

Leu Ala Gly Asp Leu Ala Glu Ile Asn Ala Ile Lys Lys Val Phe Lys
                340                 345                 350

Asn Thr Lys Glu Ile Thr Ile Asn Ala Thr Lys Ser Met Ile Gly His
                355                 360                 365

Cys Leu Gly Ala Ser Gly Gly Leu Glu Ala Ile Ala Thr Ile Lys Gly
            370                 375                 380

Ile Thr Thr Gly Trp Leu His Pro Ser Ile Asn Gln Phe Asn Pro Glu
385                 390                 395                 400

Pro Ser Val Glu Phe Asp Thr Val Ala Asn Lys Lys Gln Gln His Glu
                405                 410                 415

Val Asn Val Ala Ile Ser Asn Ser Phe Gly Phe Gly Gly His Asn Ser
                420                 425                 430

Val Val Ala Phe Ser Ala Phe Lys Pro
            435                 440

<210> SEQ ID NO 23
<211> LENGTH: 430
<212> TYPE: PRT
<213> ORGANISM: Cuphea pullcherima

<400> SEQUENCE: 23

Arg Ala Ala Ser Pro Thr Val Ser Ala Pro Lys Arg Glu Thr Asp Pro
1               5                   10                  15

Lys Lys Arg Val Val Ile Thr Gly Met Gly Leu Val Ser Val Phe Gly
                20                  25                  30

Ser Asp Val Asp Ala Tyr Tyr Asp Lys Leu Leu Ser Gly Glu Ser Gly
            35                  40                  45

Ile Gly Pro Ile Asp Arg Phe Asp Ala Ser Lys Phe Pro Thr Arg Phe
        50                  55                  60

Gly Gly Gln Ile Arg Gly Phe Asn Ser Met Gly Tyr Ile Asp Gly Lys
65              70                  75                  80

Asn Asp Arg Arg Leu Asp Asp Cys Leu Arg Tyr Cys Ile Val Ala Gly
                85                  90                  95

Lys Lys Ser Leu Glu Asp Ala Asp Leu Gly Ala Asp Arg Leu Ser Lys
                100                 105                 110

Ile Asp Lys Glu Arg Ala Gly Val Leu Val Gly Thr Gly Met Gly Gly
            115                 120                 125

Leu Thr Val Phe Ser Asp Gly Val Gln Ser Leu Ile Glu Lys Gly His
130                 135                 140

Arg Lys Ile Thr Pro Phe Phe Ile Pro Tyr Ala Ile Thr Asn Met Gly
145                 150                 155                 160

Ser Ala Leu Leu Ala Ile Glu Leu Gly Leu Met Gly Pro Asn Tyr Ser
                165                 170                 175

Ile Ser Thr Ala Cys Ala Thr Ser Asn Tyr Cys Phe His Ala Ala Ala
            180                 185                 190
```

```
Asn His Ile Arg Arg Gly Glu Ala Asp Leu Met Ile Ala Gly Gly Thr
            195                 200                 205

Glu Ala Ala Ile Ile Pro Ile Gly Leu Gly Gly Phe Val Ala Cys Arg
        210                 215                 220

Ala Leu Ser Gln Arg Asn Asp Pro Gln Thr Ala Ser Arg Pro Trp
225                 230                 235                 240

Asp Lys Asp Arg Asp Gly Phe Val Met Gly Glu Gly Ala Gly Val Leu
                245                 250                 255

Val Leu Glu Ser Leu Glu His Ala Met Lys Arg Gly Ala Pro Ile Ile
            260                 265                 270

Ala Glu Tyr Leu Gly Gly Ala Ile Asn Cys Asp Ala Tyr His Met Thr
        275                 280                 285

Asp Pro Arg Ala Asp Gly Leu Gly Val Ser Ser Cys Ile Glu Ser Ser
290                 295                 300

Leu Glu Asp Ala Gly Val Ser Pro Glu Glu Val Asn Tyr Ile Asn Ala
305                 310                 315                 320

His Ala Thr Ser Thr Leu Ala Gly Asp Leu Ala Glu Ile Asn Ala Ile
                325                 330                 335

Lys Lys Val Phe Lys Asn Thr Lys Asp Ile Lys Ile Asn Ala Thr Lys
            340                 345                 350

Ser Met Ile Gly His Cys Leu Gly Ala Ser Gly Gly Leu Glu Ala Ile
        355                 360                 365

Ala Thr Ile Lys Gly Ile Asn Thr Gly Trp Leu His Pro Ser Ile Asn
370                 375                 380

Gln Phe Asn Pro Glu Pro Ser Val Glu Phe Asp Thr Val Ala Asn Lys
385                 390                 395                 400

Lys Gln Gln His Glu Val Asn Val Ala Ile Ser Asn Ser Phe Gly Phe
                405                 410                 415

Gly Gly His Asn Ser Val Val Ala Phe Ser Ala Phe Lys Pro
                420                 425                 430

<210> SEQ ID NO 24
<211> LENGTH: 428
<212> TYPE: PRT
<213> ORGANISM: Cuphea pullcherima

<400> SEQUENCE: 24

Arg Ala Ala Thr Ala Ser Ala Pro Lys Arg Glu Ser Asp Pro Lys Lys
1               5                   10                  15

Arg Val Val Ile Thr Gly Met Gly Leu Val Ser Val Phe Gly Ser Asp
                20                  25                  30

Val Asp Ala Tyr Tyr Asp Lys Leu Leu Ser Gly Glu Ser Gly Ile Ser
            35                  40                  45

Leu Ile Asp Arg Phe Asp Ala Ser Lys Phe Pro Thr Arg Phe Ala Gly
        50                  55                  60

Gln Ile Arg Gly Phe Asn Ala Thr Gly Tyr Ile Asp Gly Lys Asn Asp
65                  70                  75                  80

Arg Arg Leu Asp Asp Cys Leu Arg Tyr Cys Ile Val Ala Gly Lys Lys
                85                  90                  95

Ala Leu Glu Asp Ala Asp Leu Ala Gly Gln Ser Leu Ser Lys Ile Asp
            100                 105                 110

Lys Glu Arg Ala Gly Val Leu Val Gly Thr Gly Met Gly Gly Leu Thr
        115                 120                 125

Val Phe Ser Asp Gly Val Gln Asn Leu Ile Glu Lys Gly His Arg Lys
130                 135                 140
```

```
Ile Ser Pro Phe Phe Ile Pro Tyr Ala Ile Thr Asn Met Gly Ser Ala
145                 150                 155                 160

Leu Leu Ala Ile Asp Leu Gly Leu Met Gly Pro Asn Tyr Ser Ile Ser
            165                 170                 175

Thr Ala Cys Ala Thr Ser Asn Tyr Cys Phe Tyr Ala Ala Ala Asn His
        180                 185                 190

Ile Arg Arg Gly Glu Ala Asp Leu Met Ile Ala Gly Thr Glu Ala
    195                 200                 205

Ala Val Ile Pro Ile Gly Leu Gly Gly Phe Val Ala Cys Arg Ala Leu
    210                 215                 220

Ser Gln Arg Asn Asp Asp Pro Gln Thr Ala Ser Arg Pro Trp Asp Lys
225                 230                 235                 240

Asp Arg Asp Gly Phe Val Met Gly Glu Gly Ala Gly Val Leu Val Met
                245                 250                 255

Glu Ser Leu Glu His Ala Met Lys Arg Gly Ala Pro Ile Ile Ala Glu
            260                 265                 270

Tyr Leu Gly Gly Ala Val Asn Cys Asp Ala Tyr His Met Thr Asp Pro
        275                 280                 285

Arg Ala Asp Gly Leu Gly Val Ser Ser Cys Ile Glu Ser Ser Leu Glu
    290                 295                 300

Asp Ala Gly Val Ser Pro Glu Glu Val Asn Tyr Ile Asn Ala His Ala
305                 310                 315                 320

Thr Ser Thr Leu Ala Gly Asp Leu Ala Glu Ile Asn Ala Ile Lys Lys
                325                 330                 335

Val Phe Lys Asn Thr Lys Glu Ile Lys Ile Asn Ala Thr Lys Ser Met
            340                 345                 350

Ile Gly His Cys Leu Gly Ala Ser Gly Gly Leu Glu Ala Ile Ala Thr
        355                 360                 365

Ile Lys Gly Ile Thr Thr Gly Trp Leu His Pro Ser Ile Asn Gln Phe
    370                 375                 380

Asn Pro Glu Pro Ser Val Asp Phe Asn Thr Val Ala Asn Lys Lys Gln
385                 390                 395                 400

Gln His Glu Val Asn Val Ala Ile Ser Asn Ser Phe Gly Phe Gly Gly
                405                 410                 415

His Asn Ser Val Val Ala Phe Ser Ala Phe Lys Pro
            420                 425

<210> SEQ ID NO 25
<211> LENGTH: 427
<212> TYPE: PRT
<213> ORGANISM: Hordeum vulgare

<400> SEQUENCE: 25

Thr Ser Ala Ala Pro Gln Arg Glu Thr Asp Pro Arg Lys Arg Val Val
1               5                   10                  15

Ile Thr Gly Met Gly Leu Ala Ser Val Phe Gly Ser Asp Val Asp Thr
                20                  25                  30

Phe Tyr Asp Arg Leu Leu Ala Gly Glu Ser Gly Val Gly Pro Ile Asp
            35                  40                  45

Arg Phe Asp Ala Ser Ser Phe Pro Thr Arg Phe Ala Gly Gln Ile Arg
    50                  55                  60

Gly Phe Ser Ser Glu Gly Tyr Ile Asp Gly Lys Asn Asp Arg Arg Leu
65                  70                  75                  80

Asp Asp Cys Ile Arg Tyr Cys Ile Leu Ser Gly Lys Lys Ala Leu Glu
```

```
                    85                  90                  95
Ser Ala Gly Leu Gly Ala Gly Ser Asp Ala His Val Lys Leu Asp Val
            100                 105                 110
Gly Arg Ala Gly Val Leu Val Gly Thr Gly Met Gly Gly Leu Ser Val
            115                 120                 125
Phe Ser Asp Gly Val Gln Asn Leu Ile Glu Lys Gly Tyr Arg Lys Ile
            130                 135                 140
Ser Pro Phe Phe Ile Pro Tyr Ala Ile Thr Asn Met Gly Ser Ala Leu
145                 150                 155                 160
Leu Ala Ile Asp Val Gly Phe Met Gly Pro Asn Tyr Ser Ile Ser Thr
                165                 170                 175
Ala Cys Ala Thr Ser Asn Tyr Cys Phe Tyr Ala Ala Ala Asn His Ile
            180                 185                 190
Arg Arg Gly Glu Ala Asp Ile Ile Val Ala Gly Gly Thr Glu Ala Ala
            195                 200                 205
Ile Ile Pro Ile Gly Leu Gly Gly Phe Val Ala Cys Arg Ala Leu Ser
            210                 215                 220
Gln Arg Asn Asp Asp Pro Ile Thr Ala Cys Arg Pro Trp Asp Lys Glu
225                 230                 235                 240
Arg Asp Gly Phe Val Met Gly Glu Gly Ala Gly Val Leu Val Met Glu
                245                 250                 255
Ser Leu Glu His Ala Met Lys Arg Asp Ala Pro Ile Ile Ala Glu Tyr
            260                 265                 270
Leu Gly Gly Ala Val Asn Cys Asp Ala Tyr His Met Thr Asp Pro Arg
            275                 280                 285
Ala Asp Gly Leu Gly Val Ser Ser Cys Ile Thr Met Ser Leu Arg Asp
290                 295                 300
Ala Gly Val Ala Pro Glu Glu Val Asn Tyr Ile Asn Ala His Ala Thr
305                 310                 315                 320
Ser Thr Leu Ala Gly Asp Leu Ala Glu Val Arg Ala Ile Lys Gln Val
                325                 330                 335
Phe Lys Asn Pro Ser Glu Ile Lys Ile Asn Ser Thr Lys Ser Met Ile
            340                 345                 350
Gly His Cys Leu Gly Ala Ala Gly Gly Leu Glu Ala Ile Ala Thr Ile
            355                 360                 365
Lys Ser Ile Thr Thr Gly Trp Val His Pro Thr Ile Asn Gln Phe Asn
            370                 375                 380
Pro Glu Pro Glu Val Asp Phe Asp Thr Val Ala Asn Glu Lys Lys Gln
385                 390                 395                 400
His Glu Val Asn Val Gly Ile Ser Asn Ser Phe Gly Phe Gly Gly His
                405                 410                 415
Asn Ser Val Val Val Phe Ala Pro Phe Lys Pro
            420                 425

<210> SEQ ID NO 26
<211> LENGTH: 428
<212> TYPE: PRT
<213> ORGANISM: Ricinus communis

<400> SEQUENCE: 26

Asn Asn Asn Thr Thr Ile Ser Ala Pro Lys Arg Glu Lys Asp Pro Arg
1               5                   10                  15
Lys Arg Val Val Ile Thr Gly Thr Gly Leu Val Ser Val Phe Gly Asn
            20                  25                  30
```

Asp Val Asp Thr Tyr Tyr Asp Lys Leu Leu Ala Gly Glu Ser Gly Ile
        35                  40                  45

Gly Leu Ile Asp Arg Phe Asp Ala Ser Lys Phe Pro Thr Arg Phe Gly
    50                  55                  60

Gly Gln Ile Arg Gly Phe Asn Ser Gln Gly Tyr Ile Asp Gly Lys Asn
65                  70                  75                  80

Asp Arg Arg Leu Asp Asp Cys Leu Arg Tyr Cys Ile Val Ala Gly Lys
                85                  90                  95

Lys Ala Leu Glu His Ala Asp Leu Gly Gly Asp Lys Leu Ser Lys Ile
            100                 105                 110

Asp Lys Glu Arg Ala Gly Val Leu Val Gly Thr Gly Met Gly Gly Leu
        115                 120                 125

Thr Val Phe Ser Asp Gly Val Gln Ala Leu Ile Glu Lys Gly His Arg
    130                 135                 140

Lys Ile Thr Pro Phe Phe Ile Pro Tyr Ala Ile Thr Asn Met Gly Ser
145                 150                 155                 160

Ala Leu Leu Ala Ile Glu Leu Gly Leu Met Gly Pro Asn Tyr Ser Ile
                165                 170                 175

Ser Thr Ala Cys Ala Thr Ser Asn Tyr Cys Phe Tyr Ala Ala Ala Asn
            180                 185                 190

His Ile Arg Arg Gly Glu Ala Glu Leu Met Ile Ala Gly Gly Thr Glu
        195                 200                 205

Ala Ala Ile Ile Pro Ile Gly Leu Gly Gly Phe Val Ala Cys Arg Ala
    210                 215                 220

Leu Ser Gln Arg Asn Asp Asp Pro Gln Thr Ala Ser Arg Pro Trp Asp
225                 230                 235                 240

Lys Asp Arg Asp Gly Phe Val Met Gly Glu Gly Ala Gly Val Leu Val
                245                 250                 255

Met Glu Ser Leu Glu His Ala Met Lys Arg Gly Ala Pro Ile Ile Ala
            260                 265                 270

Glu Tyr Leu Gly Gly Ala Val Asn Cys Asp Ala Tyr His Met Thr Asp
        275                 280                 285

Pro Arg Ala Asp Gly Leu Gly Val Ser Ser Cys Ile Glu Arg Ser Leu
    290                 295                 300

Glu Asp Ala Gly Val Ser Pro Glu Gln Val Asn Tyr Ile Asn Ala His
305                 310                 315                 320

Ala Thr Ser Thr Leu Ala Gly Asp Leu Ala Glu Ile Asn Ala Ile Lys
                325                 330                 335

Lys Val Phe Lys Asn Thr Ser Asp Ile Lys Ile Asn Ala Thr Lys Ser
            340                 345                 350

Met Ile Gly His Cys Leu Gly Ala Ala Gly Gly Leu Glu Ala Ile Ala
        355                 360                 365

Cys Val Lys Ala Ile Thr Thr Gly Trp Leu His Pro Thr Ile Asn Gln
    370                 375                 380

Phe Asn Pro Glu Pro Ser Val Glu Phe Asp Thr Val Ala Asn Lys Lys
385                 390                 395                 400

Gln Gln His Glu Val Asn Val Ala Ile Ser Asn Ser Phe Gly Phe Gly
                405                 410                 415

Gly His Asn Ser Val Val Ala Phe Ser Ala Phe Lys
            420                 425

<210> SEQ ID NO 27
<211> LENGTH: 420
<212> TYPE: PRT

<213> ORGANISM: Capsicum chinense

<400> SEQUENCE: 27

| | | | | | | | | | | | | | | |
|---|---|---|---|---|---|---|---|---|---|---|---|---|---|---|
| Lys | Arg | Glu | Thr | Asp | Pro | Lys | Arg | Ile | Val | Ile | Thr | Gly | Met | Gly |
| 1 | | | | 5 | | | | | 10 | | | | | 15 |
| Leu | Val | Ser | Val | Phe | Gly | Ser | Asp | Ile | Asp | Asn | Phe | Tyr | Asn | Lys | Leu |
| | | | 20 | | | | | 25 | | | | | 30 | | |
| Leu | Glu | Gly | Gln | Ser | Gly | Ile | Ser | Leu | Ile | Asp | Arg | Phe | Asp | Ala | Ser |
| | | 35 | | | | | 40 | | | | | 45 | | | |
| Ser | Tyr | Thr | Val | Arg | Phe | Ala | Gly | Gln | Ile | Arg | Asp | Phe | Ser | Ser | Glu |
| | 50 | | | | | 55 | | | | | 60 | | | | |
| Gly | Tyr | Ile | Asp | Gly | Lys | Asn | Asp | Arg | Arg | Leu | Asp | Asp | Cys | Trp | Arg |
| 65 | | | | | 70 | | | | | 75 | | | | | 80 |
| Tyr | Cys | Leu | Val | Ala | Gly | Lys | Arg | Ala | Leu | Glu | Asp | Ala | Asn | Leu | Gly |
| | | | | 85 | | | | | 90 | | | | | 95 | |
| Gln | Gln | Val | Leu | Asp | Thr | Met | Asp | Lys | Thr | Arg | Ile | Gly | Val | Leu | Val |
| | | | 100 | | | | | 105 | | | | | 110 | | |
| Gly | Ser | Ser | Met | Gly | Gly | Ser | Lys | Val | Phe | Ala | Asp | Ala | Val | Glu | Ala |
| | | 115 | | | | | 120 | | | | | 125 | | | |
| Leu | Val | Gln | Arg | Gly | Tyr | Lys | Lys | Ile | Asn | Pro | Phe | Phe | Ile | Pro | Tyr |
| | | 130 | | | | | 135 | | | | | 140 | | | |
| Ser | Ile | Thr | Asn | Met | Gly | Ser | Ala | Leu | Leu | Ala | Ile | Asp | Thr | Gly | Leu |
| 145 | | | | | 150 | | | | | 155 | | | | | 160 |
| Met | Gly | Pro | Thr | Tyr | Ser | Ile | Ser | Thr | Ala | Cys | Ala | Thr | Ala | Asn | Tyr |
| | | | | 165 | | | | | 170 | | | | | 175 | |
| Cys | Phe | Tyr | Ala | Ser | Ala | Asn | His | Ile | Arg | Arg | Gly | Glu | Ala | Asp | Ile |
| | | | 180 | | | | | 185 | | | | | 190 | | |
| Met | Val | Ala | Gly | Gly | Thr | Asp | Ala | Phe | Ile | Ser | Ala | Ile | Gly | Val | Gly |
| | | 195 | | | | | 200 | | | | | 205 | | | |
| Gly | Leu | Ile | Ala | Cys | Arg | Ala | Leu | Ser | Gln | Arg | Asn | Asp | Glu | Tyr | Glu |
| | 210 | | | | | 215 | | | | | 220 | | | | |
| Lys | Ala | Ser | Arg | Pro | Trp | Asp | Arg | Asn | Arg | Asp | Gly | Phe | Val | Ile | Gly |
| 225 | | | | | 230 | | | | | 235 | | | | | 240 |
| Glu | Gly | Ser | Gly | Val | Leu | Val | Met | Glu | Asn | Leu | Glu | His | Ala | Leu | Lys |
| | | | | 245 | | | | | 250 | | | | | 255 | |
| Arg | Gly | Ala | Pro | Ile | Ile | Ala | Glu | Tyr | Leu | Gly | Gly | Ala | Ile | Thr | Cys |
| | | | 260 | | | | | 265 | | | | | 270 | | |
| Asp | Ala | His | His | Ile | Thr | Asp | Pro | Arg | Ala | Asp | Gly | Leu | Gly | Val | Ser |
| | | 275 | | | | | 280 | | | | | 285 | | | |
| Ser | Cys | Ile | Val | Met | Ser | Leu | Val | Asp | Ala | Gly | Val | Ser | Pro | Glu | Glu |
| | 290 | | | | | 295 | | | | | 300 | | | | |
| Val | Asn | Tyr | Ile | Asn | Ala | His | Ala | Thr | Ser | Thr | Leu | Ala | Gly | Asp | Leu |
| 305 | | | | | 310 | | | | | 315 | | | | | 320 |
| Ala | Glu | Val | Asn | Ala | Ile | Lys | Lys | Val | Phe | Lys | Asp | Thr | Ser | Glu | Ile |
| | | | | 325 | | | | | 330 | | | | | 335 | |
| Lys | Met | Asn | Gly | Thr | Lys | Ser | Met | Ile | Gly | His | Gly | Leu | Gly | Ala | Ser |
| | | | 340 | | | | | 345 | | | | | 350 | | |
| Gly | Gly | Leu | Glu | Ala | Ile | Ala | Thr | Ile | Lys | Ala | Ile | Thr | Thr | Gly | Trp |
| | | 355 | | | | | 360 | | | | | 365 | | | |
| Leu | His | Pro | Thr | Ile | Asn | Gln | Tyr | Asp | Leu | Glu | Pro | Gln | Val | Thr | Ile |
| | 370 | | | | | 375 | | | | | 380 | | | | |
| Asp | Thr | Val | Pro | Asn | Val | Lys | Lys | Gln | His | Glu | Val | Asn | Val | Gly | Ile |
| 385 | | | | | 390 | | | | | 395 | | | | | 400 |

```
Ser Asn Ser Phe Gly Phe Gly Gly His Asn Ser Val Val Phe Ala
                405                 410                 415
Pro Tyr Lys Pro
            420

<210> SEQ ID NO 28
<211> LENGTH: 420
<212> TYPE: PRT
<213> ORGANISM: Cuphea hookeriana

<400> SEQUENCE: 28

Lys Lys Lys Pro Ser Ile Lys Gln Arg Val Val Val Thr Gly Met
1               5                   10                  15

Gly Val Val Thr Pro Leu Gly His Asp Pro Asp Val Phe Tyr Asn Asn
                20                  25                  30

Leu Leu Asp Gly Thr Ser Gly Ile Ser Glu Ile Glu Thr Phe Asp Cys
                35                  40                  45

Ala Gln Phe Pro Thr Arg Ile Ala Gly Glu Ile Lys Ser Phe Ser Thr
            50                  55                  60

Asp Gly Trp Val Ala Pro Lys Leu Ser Lys Arg Met Asp Lys Phe Met
65                  70                  75                  80

Leu Tyr Met Leu Thr Ala Gly Lys Lys Ala Leu Thr Asn Gly Gly Ile
                    85                  90                  95

Thr Glu Asp Val Met Lys Glu Leu Asp Lys Arg Lys Cys Gly Val Leu
                100                 105                 110

Ile Gly Ser Ala Met Gly Gly Met Lys Val Phe Asn Asp Ala Ile Glu
                115                 120                 125

Ala Leu Arg Ile Ser Tyr Lys Lys Met Asn Pro Phe Cys Val Pro Phe
            130                 135                 140

Ala Thr Thr Asn Met Gly Ser Ala Met Leu Ala Met Asp Leu Gly Trp
145                 150                 155                 160

Met Gly Pro Asn Tyr Ser Ile Ser Thr Ala Cys Ala Thr Ser Asn Phe
                165                 170                 175

Cys Ile Leu Asn Ala Ala Asn His Ile Ile Arg Gly Glu Ala Asp Val
                180                 185                 190

Met Leu Cys Gly Gly Ser Asp Ala Val Ile Ile Pro Ile Gly Met Gly
            195                 200                 205

Gly Phe Val Ala Cys Arg Ala Leu Ser Gln Arg Asn Ala Asp Pro Thr
            210                 215                 220

Lys Ala Ser Arg Pro Trp Asp Ser Asn Arg Asp Gly Phe Val Met Gly
225                 230                 235                 240

Glu Gly Ala Gly Val Leu Leu Leu Glu Glu Leu Glu His Ala Lys Lys
                245                 250                 255

Arg Gly Ala Thr Ile Tyr Ala Glu Phe Leu Gly Gly Ser Phe Thr Cys
                260                 265                 270

Asp Ala Tyr His Met Thr Glu Pro His Pro Asp Gly Ala Gly Val Ile
            275                 280                 285

Leu Cys Ile Glu Lys Ala Leu Ala Gln Ser Gly Val Ser Arg Glu Asp
290                 295                 300

Val Asn Tyr Ile Asn Ala His Ala Thr Ser Thr Pro Ala Gly Asp Ile
305                 310                 315                 320

Lys Glu Tyr Gln Ala Leu Ile His Cys Phe Gly Gln Asn Asn Glu Leu
                325                 330                 335

Lys Val Asn Ser Thr Lys Ser Met Ile Gly His Leu Leu Gly Ala Ala
            340                 345                 350
```

-continued

```
Gly Gly Val Glu Ala Val Ser Val Gln Ala Ile Arg Thr Gly Trp
            355                 360                 365
Ile His Pro Asn Ile Asn Leu Glu Asn Pro Asp Glu Gly Val Asp Thr
        370                 375                 380
Lys Leu Leu Val Gly Pro Lys Lys Glu Arg Leu Asn Ile Lys Val Gly
385                 390                 395                 400
Leu Ser Asn Ser Phe Gly Phe Gly Gly His Asn Ser Ser Ile Leu Phe
                405                 410                 415
Ala Pro Tyr Asn
            420

<210> SEQ ID NO 29
<211> LENGTH: 420
<212> TYPE: PRT
<213> ORGANISM: Cuphea hookeriana

<400> SEQUENCE: 29

Asn Lys Lys Pro Ala Thr Lys Gln Arg Arg Val Val Thr Gly Met
1               5                   10                  15
Gly Val Val Thr Pro Leu Gly His Asp Pro Asp Val Tyr Tyr Asn Asn
                20                  25                  30
Leu Leu Asp Gly Ile Ser Gly Ile Ser Glu Ile Glu Asn Phe Asp Cys
            35                  40                  45
Ser Gln Phe Pro Thr Arg Ile Ala Gly Glu Ile Lys Ser Phe Ser Thr
        50                  55                  60
Asp Gly Trp Val Ala Pro Lys Phe Ser Glu Arg Met Asp Lys Phe Met
65                  70                  75                  80
Leu Tyr Met Leu Thr Ala Gly Lys Lys Ala Leu Ala Asp Gly Gly Ile
                85                  90                  95
Thr Glu Asp Ala Met Lys Glu Leu Asn Lys Arg Lys Cys Gly Val Leu
            100                 105                 110
Ile Gly Ser Gly Leu Gly Gly Met Lys Val Phe Ser Asp Ser Ile Glu
        115                 120                 125
Ala Leu Arg Thr Ser Tyr Lys Lys Ile Ser Pro Phe Cys Val Pro Phe
    130                 135                 140
Ser Thr Thr Asn Met Gly Ser Ala Ile Leu Ala Met Asp Leu Gly Trp
145                 150                 155                 160
Met Gly Pro Asn Tyr Ser Ile Ser Thr Ala Cys Ala Thr Ser Asn Phe
                165                 170                 175
Cys Ile Leu Asn Ala Ala Asn His Ile Ile Lys Gly Glu Ala Asp Met
            180                 185                 190
Met Leu Cys Gly Gly Ser Asp Ala Ala Val Leu Pro Val Gly Leu Gly
        195                 200                 205
Gly Phe Val Ala Cys Arg Ala Leu Ser Gln Arg Asn Asn Asp Pro Thr
    210                 215                 220
Lys Ala Ser Arg Pro Trp Asp Ser Asn Arg Asp Gly Phe Val Met Gly
225                 230                 235                 240
Glu Gly Ala Gly Val Leu Leu Leu Glu Glu Leu Glu His Ala Lys Lys
                245                 250                 255
Arg Gly Ala Thr Ile Tyr Ala Glu Phe Leu Gly Gly Ser Phe Thr Cys
            260                 265                 270
Asp Ala Tyr His Met Thr Glu Pro His Pro Glu Gly Ala Gly Val Ile
        275                 280                 285
Leu Cys Ile Glu Lys Ala Leu Ala Gln Ser Gly Val Ser Arg Glu Asp
```

```
          290                 295                 300
Val Asn Tyr Ile Asn Ala His Ala Thr Ser Thr Pro Ala Gly Asp Ile
305                 310                 315                 320

Lys Glu Tyr Gln Ala Leu Ala His Cys Phe Gly Gln Asn Ser Glu Leu
                325                 330                 335

Arg Val Asn Ser Thr Lys Ser Met Ile Gly His Leu Leu Gly Gly Ala
                340                 345                 350

Gly Gly Val Glu Ala Val Ala Val Gln Ala Ile Arg Thr Gly Trp
                355                 360                 365

Ile His Pro Asn Ile Asn Leu Glu Asp Pro Asp Glu Gly Val Asp Ala
370                 375                 380

Lys Leu Leu Val Gly Pro Lys Glu Lys Leu Lys Val Lys Val Gly
385                 390                 395                 400

Leu Ser Asn Ser Phe Gly Phe Gly Gly His Asn Ser Ser Ile Leu Phe
                405                 410                 415

Ala Pro Cys Asn
            420

<210> SEQ ID NO 30
<211> LENGTH: 420
<212> TYPE: PRT
<213> ORGANISM: Cuphea pullcherima

<400> SEQUENCE: 30

Lys Lys Lys Pro Ser Ile Lys Gln Arg Arg Val Val Thr Gly Met
1               5                   10                  15

Gly Val Val Thr Pro Leu Gly His Asp Pro Asp Val Phe Tyr Asn Asn
                20                  25                  30

Leu Leu Asp Gly Thr Ser Gly Ile Ser Glu Ile Glu Thr Phe Asp Cys
                35                  40                  45

Ala Gln Phe Pro Thr Arg Ile Ala Gly Glu Ile Lys Ser Phe Ser Thr
50                  55                  60

Asp Gly Trp Val Ala Pro Lys Leu Ser Lys Arg Met Asp Lys Phe Met
65                  70                  75                  80

Leu Tyr Met Leu Thr Ala Gly Lys Lys Ala Leu Thr Asp Gly Gly Ile
                85                  90                  95

Thr Glu Asp Val Met Lys Glu Leu Asp Lys Arg Lys Cys Gly Val Leu
                100                 105                 110

Ile Gly Ser Ala Met Gly Gly Met Lys Val Phe Asn Asp Ala Ile Glu
                115                 120                 125

Ala Leu Arg Ile Ser Tyr Lys Lys Met Asn Pro Phe Cys Val Pro Phe
130                 135                 140

Ala Thr Thr Asn Met Gly Ser Ala Met Leu Ala Met Asp Leu Gly Trp
145                 150                 155                 160

Met Gly Pro Asn Tyr Ser Ile Ser Thr Ala Cys Ala Thr Ser Asn Phe
                165                 170                 175

Cys Ile Met Asn Ala Ala Asn His Ile Ile Arg Gly Glu Ala Asp Val
                180                 185                 190

Met Leu Cys Gly Gly Ser Asp Ala Val Ile Ile Pro Ile Gly Met Gly
                195                 200                 205

Gly Phe Val Ala Cys Arg Ala Leu Ser Gln Arg Asn Ser Asp Pro Thr
                210                 215                 220

Lys Ala Ser Arg Pro Trp Asp Ser Asn Arg Asp Gly Phe Val Met Gly
225                 230                 235                 240
```

```
Glu Gly Ala Gly Val Leu Leu Glu Glu Leu His Ala Lys Lys
            245                 250                 255

Arg Gly Ala Thr Ile Tyr Ala Glu Phe Leu Gly Gly Ser Phe Thr Cys
            260                 265                 270

Asp Ala Tyr His Met Thr Glu Pro His Pro Asp Gly Ala Gly Val Ile
            275                 280                 285

Leu Cys Ile Glu Lys Ala Leu Ala Gln Ser Gly Val Ser Arg Glu Asp
290                 295                 300

Val Asn Tyr Ile Asn Ala His Ala Thr Ser Thr Pro Ala Gly Asp Ile
305                 310                 315                 320

Lys Glu Tyr Gln Ala Leu Ile His Cys Phe Gly Gln Asn Arg Glu Leu
                325                 330                 335

Lys Val Asn Ser Thr Lys Ser Met Ile Gly His Leu Leu Gly Ala Ala
            340                 345                 350

Gly Gly Val Glu Ala Val Ser Val Val Gln Ala Ile Arg Thr Gly Trp
            355                 360                 365

Ile His Pro Asn Ile Asn Leu Glu Asn Pro Asp Glu Gly Val Asp Thr
            370                 375                 380

Lys Leu Leu Val Gly Pro Lys Lys Glu Arg Leu Asn Val Lys Val Gly
385                 390                 395                 400

Leu Ser Asn Ser Phe Gly Phe Gly Gly His Asn Ser Ser Ile Leu Phe
                405                 410                 415

Ala Pro Tyr Ile
            420

<210> SEQ ID NO 31
<211> LENGTH: 421
<212> TYPE: PRT
<213> ORGANISM: Cuphea wrightii

<400> SEQUENCE: 31

Lys Lys Lys Pro Val Ile Lys Gln Arg Arg Val Val Thr Gly Met
1               5                   10                  15

Gly Val Val Thr Pro Leu Gly His Glu Pro Asp Val Phe Tyr Asn Asn
            20                  25                  30

Leu Leu Asp Gly Val Ser Gly Ile Ser Glu Ile Glu Thr Phe Asp Cys
            35                  40                  45

Thr Gln Phe Pro Thr Arg Ile Ala Gly Glu Ile Lys Ser Phe Ser Thr
        50                  55                  60

Asp Gly Trp Val Ala Pro Lys Leu Ser Lys Arg Met Asp Lys Phe Met
65                  70                  75                  80

Leu Tyr Leu Leu Thr Ala Gly Lys Lys Ala Leu Ala Asp Gly Gly Ile
                85                  90                  95

Thr Asp Glu Val Met Lys Glu Leu Asp Lys Arg Lys Cys Gly Val Leu
            100                 105                 110

Ile Gly Ser Gly Met Gly Gly Met Lys Val Phe Asn Asp Ala Ile Glu
            115                 120                 125

Ala Leu Arg Val Ser Tyr Lys Lys Met Asn Pro Phe Cys Val Pro Phe
130                 135                 140

Ala Thr Thr Asn Met Gly Ser Ala Met Leu Ala Met Asp Leu Gly Trp
145                 150                 155                 160

Met Gly Pro Asn Tyr Ser Ile Ser Thr Ala Cys Ala Thr Ser Asn Phe
                165                 170                 175

Cys Ile Leu Asn Ala Ala Asn His Ile Ile Arg Gly Glu Ala Asp Met
            180                 185                 190
```

```
Met Leu Cys Gly Gly Ser Asp Ala Val Ile Ile Pro Ile Gly Leu Gly
            195                 200                 205

Gly Phe Val Ala Cys Arg Ala Leu Ser Gln Arg Asn Ser Asp Pro Thr
    210                 215                 220

Lys Ala Ser Arg Pro Trp Asp Ser Asn Arg Asp Gly Phe Val Met Gly
225                 230                 235                 240

Glu Gly Ala Gly Val Leu Leu Glu Glu Leu Glu His Ala Lys Lys
                245                 250                 255

Arg Gly Ala Thr Ile Tyr Ala Glu Phe Leu Gly Gly Ser Phe Thr Cys
            260                 265                 270

Asp Ala Tyr His Met Thr Glu Pro His Pro Glu Gly Ala Gly Val Ile
            275                 280                 285

Leu Cys Ile Glu Lys Ala Leu Ala Gln Ala Gly Val Ser Lys Glu Asp
        290                 295                 300

Val Asn Tyr Ile Asn Ala His Ala Thr Ser Thr Ser Ala Gly Asp Ile
305                 310                 315                 320

Lys Glu Tyr Gln Ala Leu Ala Arg Cys Phe Gly Gln Asn Ser Glu Leu
                325                 330                 335

Arg Val Asn Ser Thr Lys Ser Met Ile Gly His Leu Leu Gly Ala Ala
            340                 345                 350

Gly Gly Val Glu Ala Val Thr Val Val Gln Ala Ile Arg Thr Gly Trp
        355                 360                 365

Ile His Pro Asn Leu Asn Leu Glu Asp Pro Asp Lys Ala Val Asp Ala
    370                 375                 380

Lys Leu Leu Val Gly Pro Lys Lys Glu Arg Leu Asn Val Lys Val Gly
385                 390                 395                 400

Leu Ser Asn Ser Phe Gly Phe Gly Gly His Asn Ser Ser Ile Leu Phe
                405                 410                 415

Ala Pro Cys Asn Val
            420

<210> SEQ ID NO 32
<211> LENGTH: 420
<212> TYPE: PRT
<213> ORGANISM: Cuphea wrightii

<400> SEQUENCE: 32

Lys Lys Lys Pro Val Thr Lys Gln Arg Arg Val Val Thr Gly Met
1               5                   10                  15

Gly Val Val Thr Pro Leu Gly His Asp Pro Asp Val Phe Tyr Asn Asn
                20                  25                  30

Leu Leu Asp Gly Val Ser Gly Ile Ser Glu Ile Glu Thr Phe Asp Cys
            35                  40                  45

Thr Gln Phe Pro Thr Arg Ile Ala Gly Glu Ile Lys Ser Phe Ser Thr
        50                  55                  60

Asp Gly Trp Val Ala Pro Lys Leu Ser Lys Arg Met Asp Lys Phe Met
65                  70                  75                  80

Leu Tyr Met Leu Thr Ala Gly Lys Lys Ala Leu Ala Asp Ala Gly Ile
                85                  90                  95

Thr Glu Asp Val Met Lys Glu Leu Asp Lys Arg Lys Cys Gly Val Leu
            100                 105                 110

Ile Gly Ser Gly Met Gly Gly Met Lys Leu Phe Asn Asp Ser Ile Glu
        115                 120                 125

Ala Leu Arg Ile Ser Tyr Lys Lys Met Asn Pro Phe Cys Val Pro Phe
```

```
            130                 135                 140
Ala Thr Thr Asn Met Gly Ser Ala Met Leu Ala Met Asp Leu Gly Trp
145                 150                 155                 160

Met Gly Pro Asn Tyr Ser Ile Ser Thr Ala Cys Ala Thr Ser Asn Phe
                165                 170                 175

Cys Ile Leu Asn Ala Ala Asn His Ile Ile Arg Gly Glu Ala Asp Met
            180                 185                 190

Met Leu Cys Gly Gly Ser Asp Ala Ala Ile Ile Pro Ile Gly Leu Gly
        195                 200                 205

Gly Phe Val Ala Cys Arg Ala Leu Ser Gln Arg Asn Asn Asp Pro Thr
    210                 215                 220

Lys Ala Ser Arg Pro Trp Asp Ser Asn Arg Asp Gly Phe Val Met Gly
225                 230                 235                 240

Glu Gly Ala Gly Val Leu Leu Leu Glu Glu Leu Glu His Ala Lys Lys
                245                 250                 255

Arg Gly Ala Thr Ile Tyr Ala Glu Phe Leu Gly Gly Ser Phe Thr Cys
                260                 265                 270

Asp Ala Tyr His Met Thr Glu Pro His Pro Glu Gly Ala Gly Val Ile
            275                 280                 285

Leu Cys Ile Glu Arg Ala Leu Ala Gln Ser Gly Val Ser Lys Glu Asp
        290                 295                 300

Val Asn Tyr Ile Asn Ala His Ala Thr Ser Thr Pro Ala Gly Asp Ile
305                 310                 315                 320

Lys Glu Tyr Gln Ala Leu Ala Arg Ile Phe Ser Gln Asn Ser Glu Leu
                325                 330                 335

Arg Val Asn Ser Thr Lys Ser Met Ile Gly His Leu Leu Gly Ala Ala
                340                 345                 350

Gly Gly Val Glu Ala Val Thr Val Val Gln Ala Ile Arg Thr Gly Trp
            355                 360                 365

Ile His Pro Asn Ile Asn Leu Glu Asn Pro Asp Asp Gly Val Asp Ala
        370                 375                 380

Lys Leu Leu Val Gly Pro Lys Lys Glu Lys Leu Lys Val Lys Val Gly
385                 390                 395                 400

Leu Ser Asn Ser Phe Gly Phe Gly Gly His Asn Ser Ser Ile Leu Phe
                405                 410                 415

Ala Pro Cys Asn
            420

<210> SEQ ID NO 33
<211> LENGTH: 420
<212> TYPE: PRT
<213> ORGANISM: Hordeum vulgare

<400> SEQUENCE: 33

Lys Lys Arg Pro Asp Val Lys Gln Arg Val Val Val Thr Gly Met
1               5                   10                  15

Gly Val Val Thr Pro Leu Gly His Asp Pro Asp Val Phe Tyr Thr Asn
                20                  25                  30

Leu Leu Asp Gly His Ser Gly Ile Ser Glu Ile Glu Thr Phe Asp Cys
            35                  40                  45

Ser Lys Phe Pro Thr Arg Ile Ala Gly Glu Ile Lys Ser Phe Ser Thr
        50                  55                  60

Glu Gly Trp Val Val Pro Lys Leu Ser Lys Arg Met Asp Lys Phe Met
65                  70                  75                  80
```

```
Leu Tyr Leu Ile Thr Ala Gly Lys Lys Ala Leu Glu Asn Gly Gly Leu
                85                  90                  95

Thr Glu Glu Val Arg Asn Glu Leu Asp Lys Thr Arg Cys Gly Val Leu
            100                 105                 110

Ile Gly Ser Ala Met Gly Gly Met Lys Val Phe Asn Asp Ala Ile Glu
        115                 120                 125

Ala Leu Arg Val Ser Tyr Arg Lys Met Asn Pro Phe Cys Val Pro Phe
    130                 135                 140

Ala Thr Thr Asn Met Gly Ser Ala Ile Leu Ala Met Asp Leu Gly Trp
145                 150                 155                 160

Met Gly Pro Asn Tyr Ser Ile Ser Thr Ala Cys Ala Thr Ser Asn Phe
                165                 170                 175

Cys Ile Leu Asn Ala Ala Asn His Ile Arg Arg Gly Glu Ala Asp Val
            180                 185                 190

Met Leu Cys Gly Gly Ser Asp Ala Pro Leu Ile Pro Ile Gly Leu Gly
        195                 200                 205

Gly Phe Val Ala Cys Arg Ala Leu Ser Gln Arg Asn Ser Asp Pro Thr
    210                 215                 220

Lys Ala Ser Arg Pro Trp Asp Met Asp Arg Asp Gly Phe Val Met Gly
225                 230                 235                 240

Glu Gly Ala Gly Val Leu Val Leu Glu Glu Leu Glu His Ala Lys Gln
                245                 250                 255

Arg Gly Ala Thr Ile Tyr Ala Glu Phe Leu Gly Gly Ser Phe Thr Cys
            260                 265                 270

Asp Ala Tyr His Met Thr Glu Pro His Pro Glu Gly Thr Gly Ile Thr
        275                 280                 285

Leu Cys Ile Glu Lys Ala Leu Ala Asp Ser Gly Val Ala Arg Glu Glu
    290                 295                 300

Ile Asn Tyr Val Asn Ala His Ala Thr Ser Thr Gln Ser Gly Asp Leu
305                 310                 315                 320

Lys Glu Tyr Glu Ala Ile Val Arg Cys Phe Gly Gln Asn Pro Gln Leu
                325                 330                 335

Arg Val Asn Ser Thr Lys Ser Met Thr Gly His Leu Ile Gly Ala Ala
            340                 345                 350

Gly Gly Ile Glu Ala Val Ala Cys Val Gln Ala Ile Arg Thr Gly Trp
        355                 360                 365

Val His Pro Asn Leu Asn Leu Glu Asn Pro Glu Lys Val Val Asp Val
    370                 375                 380

Gly Val Leu Val Gly Ser Lys Glu Arg Cys Glu Val Lys Val Ala
385                 390                 395                 400

Leu Ser Asn Ser Phe Gly Phe Gly Gly His Asn Ser Ser Ile Leu Phe
                405                 410                 415

Ala Pro Phe Lys
            420

<210> SEQ ID NO 34
<211> LENGTH: 419
<212> TYPE: PRT
<213> ORGANISM: Hordeum vulgare

<400> SEQUENCE: 34

Asn Asn Lys Ser Glu Thr Lys Gln Arg Val Val Thr Gly Met
1               5                   10                  15

Gly Val Val Thr Pro Leu Gly His Glu Pro Asp Glu Phe Tyr Asn Asn
                20                  25                  30
```

Leu Leu Gln Gly Val Ser Gly Val Ser Glu Ile Glu Ala Phe Asp Cys
         35                  40                  45

Ser Ser Tyr Pro Thr Arg Ile Ala Gly Glu Ile Lys Ser Phe Ser Thr
 50                  55                  60

Asp Gly Trp Val Ala Pro Lys Leu Ala Lys Arg Met Asp Lys Phe Met
 65                  70                  75                  80

Gln Tyr Leu Ile Val Ala Gly Lys Lys Ala Leu Asp Asn Gly Gly Val
                 85                  90                  95

Thr Glu Asp Ile Met Asn Glu Leu Asp Lys Ser Arg Cys Gly Val Leu
                100                 105                 110

Ile Gly Ser Gly Met Gly Met Lys Val Phe Ser Asp Ala Ile Glu
                115                 120                 125

Ala Leu Arg Val Ser Tyr Arg Lys Met Asn Pro Phe Cys Val Pro Phe
        130                 135                 140

Ala Thr Thr Asn Met Gly Ser Ala Val Leu Ala Met Asp Leu Gly Trp
145                 150                 155                 160

Met Gly Pro Asn Tyr Ser Ile Ser Thr Ala Cys Ala Thr Ser Asn Phe
                165                 170                 175

Cys Ile Leu Ser Ala Ala Asn His Ile Met Arg Gly Glu Thr Asp Leu
                180                 185                 190

Met Leu Cys Gly Gly Ser Asp Ala Pro Ile Ile Pro Ile Gly Leu Gly
            195                 200                 205

Gly Phe Val Ala Cys Arg Ala Leu Ser Gln Arg Asn Ser Asp Pro Thr
        210                 215                 220

Lys Ala Ser Arg Pro Trp Asp Val Asp Arg Asp Gly Phe Val Met Gly
225                 230                 235                 240

Glu Gly Ala Gly Val Leu Leu Leu Glu Glu Leu Glu His Ala Lys Gln
                245                 250                 255

Arg Gly Ala Glu Ile Tyr Ala Glu Phe Leu Gly Gly Asn Phe Thr Cys
            260                 265                 270

Asp Ala Tyr His Met Thr Glu Pro His Pro Glu Gly Lys Gly Val Ile
        275                 280                 285

Leu Cys Val Glu Asn Ala Leu Ala Asp Ala Gly Val Thr Arg Gln Asp
290                 295                 300

Ile Asn Tyr Val Asn Ala His Ala Thr Ser Thr Gln Leu Gly Asp Leu
305                 310                 315                 320

Lys Glu Phe Glu Ala Leu Arg Arg Cys Phe Gly Gln Asn Pro Gln Leu
                325                 330                 335

Arg Val Asn Ser Thr Lys Ser Met Thr Gly His Leu Leu Gly Ala Ala
            340                 345                 350

Gly Gly Ile Glu Ala Val Ala Ala Ile Gln Ala Ile Arg Thr Gly Trp
        355                 360                 365

Ile His Pro Asn Ile Asn Leu Asn Asn Pro Lys Asn Val Asp Val
            370                 375                 380

Ser Leu Leu Val Gly Ser Gln Lys Glu Arg Cys Asp Val Lys Val Ala
385                 390                 395                 400

Leu Ser Asn Ser Phe Gly Phe Gly Gly His Asn Ser Ser Ile Leu Phe
                405                 410                 415

Ala Pro Phe

<210> SEQ ID NO 35
<211> LENGTH: 420
<212> TYPE: PRT

<213> ORGANISM: Ricinus communis

<400> SEQUENCE: 35

```
Asn Lys Lys Pro Leu Met Lys Gln Arg Arg Val Val Val Thr Gly Met
1               5                   10                  15

Gly Val Val Ser Pro Leu Gly His Asp Ile Asp Val Tyr Tyr Asn Asn
            20                  25                  30

Leu Leu Asp Gly Ser Ser Gly Ile Ser Gln Ile Asp Ser Phe Asp Cys
        35                  40                  45

Ala Gln Phe Pro Thr Arg Ile Ala Gly Glu Ile Lys Ser Phe Ser Thr
    50                  55                  60

Asp Gly Trp Val Ala Pro Lys Leu Ser Lys Arg Met Asp Lys Phe Met
65                  70                  75                  80

Leu Tyr Met Leu Thr Ala Gly Lys Lys Ala Leu Ala Asp Gly Gly Ile
                85                  90                  95

Thr Glu Asp Met Met Asp Glu Leu Asp Lys Ala Arg Cys Gly Val Leu
            100                 105                 110

Ile Gly Ser Ala Met Gly Gly Met Lys Val Phe Asn Asp Ala Ile Glu
        115                 120                 125

Ala Leu Arg Ile Ser Tyr Arg Lys Met Asn Pro Phe Cys Val Pro Phe
    130                 135                 140

Ala Thr Thr Asn Met Gly Ser Ala Met Leu Ala Met Asp Leu Gly Trp
145                 150                 155                 160

Met Gly Pro Asn Tyr Ser Ile Ser Thr Ala Cys Ala Thr Ser Asn Phe
                165                 170                 175

Cys Ile Leu Asn Ala Ala Asn His Ile Ile Arg Gly Glu Ala Asp Ile
            180                 185                 190

Met Leu Cys Gly Gly Ser Asp Ala Ala Ile Ile Pro Ile Gly Leu Gly
        195                 200                 205

Gly Phe Val Ala Cys Arg Ala Leu Ser Gln Arg Asn Asp Asp Pro Thr
    210                 215                 220

Lys Ala Ser Arg Pro Trp Asp Met Asn Arg Asp Gly Phe Val Met Gly
225                 230                 235                 240

Glu Gly Ala Gly Val Leu Leu Leu Glu Glu Leu Glu His Ala Lys Lys
                245                 250                 255

Arg Gly Ala Asn Ile Tyr Ala Glu Phe Leu Gly Gly Ser Phe Thr Cys
            260                 265                 270

Asp Ala Tyr His Met Thr Glu Pro Arg Pro Asp Gly Val Gly Val Ile
        275                 280                 285

Leu Cys Ile Glu Lys Ala Leu Ala Arg Ser Gly Val Ser Lys Glu Glu
    290                 295                 300

Val Asn Tyr Ile Asn Ala His Ala Thr Ser Thr Pro Ala Gly Asp Leu
305                 310                 315                 320

Lys Glu Tyr Glu Ala Leu Met Arg Cys Phe Ser Gln Asn Pro Asp Leu
                325                 330                 335

Arg Val Asn Ser Thr Lys Ser Met Ile Gly His Leu Leu Gly Ala Ala
            340                 345                 350

Gly Ala Val Glu Ala Ile Ala Thr Ile Gln Ala Ile Arg Thr Gly Trp
        355                 360                 365

Val His Pro Asn Ile Asn Leu Glu Asn Pro Glu Glu Gly Val Asp Thr
    370                 375                 380

Lys Val Leu Val Gly Pro Lys Lys Glu Arg Leu Asp Ile Lys Val Ala
385                 390                 395                 400
```

-continued

```
Leu Ser Asn Ser Phe Gly Phe Gly Gly His Asn Ser Ser Ile Ile Phe
            405                 410                 415
Ala Pro Tyr Lys
            420

<210> SEQ ID NO 36
<211> LENGTH: 413
<212> TYPE: PRT
<213> ORGANISM: Caenorhabditis elegans
<220> FEATURE:
<221> NAME/KEY: misc_feature
<222> LOCATION: (53)..(53)
<223> OTHER INFORMATION: Xaa in position 53 in unknown.

<400> SEQUENCE: 36

Met Lys Leu Lys Ile Asn Lys Asn Phe Glu Met His Arg Val Val Ile
1               5                   10                  15
Thr Gly Met Gly Ala Ile Ser Pro Phe Gly Val Thr Val Asn Ala Leu
            20                  25                  30
Arg Asn Gly Leu Asn Glu Gly Arg Ser Gly Leu Lys Tyr Asp Glu Ile
            35                  40                  45
Leu Lys Phe Val Xaa Gly Ala Val Pro Gly Glu Arg Val Glu Asp Arg
        50                  55                  60
Trp Ser Thr Gly Gln Gln Arg Glu Met Ser Lys Ala Ser Met Phe Val
65                  70                  75                  80
Leu Ala Ala Ser Glu Glu Ala Leu Lys Gln Ala Lys Ala Glu Asp Val
                85                  90                  95
Asp His Asn Glu Thr Leu Val Asn Ile Gly Thr Cys Met Ser Asp Leu
            100                 105                 110
Glu His Ile Gly Glu Thr Ala Gln Lys Val Ser Glu Gly Gln Ser Arg
            115                 120                 125
Arg Val Ser Pro Tyr Phe Val Pro Arg Ile Leu Asn Asn Leu Pro Ala
        130                 135                 140
Gly Tyr Val Ala Met Lys Tyr Lys Met Arg Gly Gly Val Glu Ser Thr
145                 150                 155                 160
Ser Thr Ala Cys Ala Thr Gly Leu His Cys Ile Gly Asn Ser Phe Arg
                165                 170                 175
Ser Ile Arg Tyr Gly Asp Ser Arg Arg Ala Leu Ala Gly Ala Val Glu
            180                 185                 190
Cys Ala Leu Asn Pro Ile Ala Leu Ala Gly Phe Asp Arg Met Arg Ala
            195                 200                 205
Leu Ala Arg Gly Asp Gln Pro Asn Ile Ser Arg Pro Phe Asp Lys Lys
        210                 215                 220
Arg Ala Gly Phe Val Met Ser Glu Gly Val Gly Leu Val Phe Met Glu
225                 230                 235                 240
Arg Leu Glu Asp Ala Gln Ala Arg Gly Ala Gln Ile Leu Ala Glu Val
                245                 250                 255
Val Gly Tyr Gly Ile Ser Ser Asp Cys Tyr His Ile Ser Thr Pro Asp
            260                 265                 270
Pro Ser Ala Ile Gly Ala Val Leu Ser Met Asn Arg Ala Ile Gly Asn
            275                 280                 285
Ala His Leu Glu Pro Lys Asp Ile Gly Tyr Val Asn Ala His Ala Thr
        290                 295                 300
Ser Thr Pro Asn Gly Asp Ser Val Glu Ala Glu Ala Val Arg Gln Val
305                 310                 315                 320
Phe Pro Glu Gln Asn Ile Ala Val Ser Ser Val Lys Gly His Ile Gly
```

```
                       325                 330                 335
His Leu Leu Gly Ala Ala Gly Ser Val Glu Ala Ile Ala Thr Ile Phe
                340                 345                 350

Ala Met Asn Asp Asp Val Leu Pro Ala Asn Arg Asn Leu Glu Glu Thr
            355                 360                 365

Asp Glu Gly Asn Gly Leu Asn Leu Leu Arg Glu Asn Gln Lys Trp Ser
        370                 375                 380

Asp Val Ser Gly Asn Lys Ser Arg Ile Ser Ile Cys Asn Ser Phe Gly
385                 390                 395                 400

Phe Gly Ala Thr Asn Ala Ser Leu Ile Leu Lys Gln Phe
                405                 410

<210> SEQ ID NO 37
<211> LENGTH: 442
<212> TYPE: PRT
<213> ORGANISM: Saccharomyces cerevisiae

<400> SEQUENCE: 37

Met Ser Arg Arg Val Val Ile Thr Gly Leu Gly Cys Val Thr Pro Leu
1               5                   10                  15

Gly Arg Ser Leu Ser Glu Ser Trp Gly Asn Leu Leu Ser Ser Lys Asn
                20                  25                  30

Gly Leu Thr Pro Ile Thr Ser Leu Pro Asn Tyr Asn Glu Asp Tyr Lys
            35                  40                  45

Leu Arg Glu Lys Ser Ile Pro Ser Thr Ile Thr Val Gly Lys Ile Pro
        50                  55                  60

Glu Asn Phe Gln Asn Glu Asn Ser Ala Ile Asn Lys Leu Leu Phe Thr
65                  70                  75                  80

Ser Gln Asp Glu Arg Arg Thr Ser Ser Phe Ile Lys Leu Ala Leu Arg
                85                  90                  95

Thr Thr Tyr Glu Ala Leu His Asn Ala Gly Leu Leu Asn Pro Asn Asp
            100                 105                 110

Ile Thr Ile Asn Thr Ser Leu Cys Asn Leu Asp His Phe Gly Cys Leu
        115                 120                 125

Ile Gly Ser Gly Ile Gly Ser Ile Gln Asp Ile Tyr Gln Thr Ser Leu
    130                 135                 140

Gln Phe His Asn Asp Asn Lys Arg Ile Asn Pro Tyr Phe Val Pro Lys
145                 150                 155                 160

Ile Leu Thr Asn Met Ala Ala Gly Asn Val Ser Ile Lys Phe Asn Leu
                165                 170                 175

Arg Gly Leu Ser His Ser Val Ser Thr Ala Cys Ala Thr Gly Asn Asn
            180                 185                 190

Ser Ile Gly Asp Ala Phe Asn Phe Ile Arg Leu Gly Met Gln Asp Ile
        195                 200                 205

Cys Val Ala Gly Ala Ser Glu Thr Ser Leu His Pro Leu Ser Leu Ala
    210                 215                 220

Gly Phe Ile Arg Ala Lys Ser Ile Thr Thr Asn Gly Ile Ser Arg Pro
225                 230                 235                 240

Phe Asp Thr Gln Arg Ser Gly Phe Val Leu Gly Glu Gly Cys Gly Met
                245                 250                 255

Ile Val Met Glu Ser Leu Glu His Ala Gln Lys Arg Asn Ala Asn Ile
            260                 265                 270

Ile Ser Glu Leu Val Gly Tyr Gly Leu Ser Ser Asp Ala Cys His Ile
        275                 280                 285
```

```
Thr Ser Pro Pro Ala Asp Gly Asn Gly Ala Lys Arg Ala Ile Glu Met
    290                 295                 300

Ala Leu Lys Met Ala Arg Leu Glu Pro Thr Asp Val Asp Tyr Val Asn
305                 310                 315                 320

Ala His Ala Thr Ser Thr Leu Leu Gly Asp Lys Ala Glu Cys Leu Ala
                325                 330                 335

Val Ala Ser Ala Leu Leu Pro Gly Arg Ser Lys Ser Lys Pro Leu Tyr
            340                 345                 350

Ile Ser Ser Asn Lys Gly Ala Ile Gly His Leu Leu Gly Ala Ala Gly
        355                 360                 365

Ala Val Glu Ser Ile Phe Thr Ile Cys Ser Leu Lys Asp Asp Lys Met
    370                 375                 380

Pro His Thr Leu Asn Leu Asp Asn Val Leu Thr Leu Glu Asn Asn Glu
385                 390                 395                 400

Ala Asp Lys Leu His Phe Ile Arg Asp Lys Pro Ile Val Gly Ala Asn
                405                 410                 415

Pro Lys Tyr Ala Leu Cys Asn Ser Phe Gly Phe Gly Val Asn Thr
            420                 425                 430

Ser Leu Leu Phe Lys Lys Trp Glu Gly Ser
        435                 440

<210> SEQ ID NO 38
<211> LENGTH: 410
<212> TYPE: PRT
<213> ORGANISM: Escherichia coli

<400> SEQUENCE: 38

Met Ser Lys Arg Arg Val Val Val Thr Gly Leu Gly Met Leu Ser Pro
1               5                   10                  15

Val Gly Asn Thr Val Glu Ser Thr Trp Lys Ala Leu Leu Ala Gly Gln
            20                  25                  30

Ser Gly Ile Ser Leu Ile Asp His Phe Asp Thr Ser Ala Tyr Ala Thr
        35                  40                  45

Lys Phe Ala Gly Leu Val Lys Asp Phe Asn Cys Glu Asp Ile Ile Ser
50                  55                  60

Arg Lys Glu Gln Arg Lys Met Asp Ala Phe Ile Gln Tyr Gly Ile Val
65                  70                  75                  80

Ala Gly Val Gln Ala Met Gln Asp Ser Gly Leu Glu Ile Thr Glu Glu
                85                  90                  95

Asn Ala Thr Arg Ile Gly Ala Ala Ile Gly Ser Gly Ile Gly Gly Leu
            100                 105                 110

Gly Leu Ile Glu Glu Asn His Thr Ser Leu Met Asn Gly Gly Pro Arg
        115                 120                 125

Lys Ile Ser Pro Phe Phe Val Pro Ser Thr Ile Val Asn Met Val Ala
130                 135                 140

Gly His Leu Thr Ile Met Tyr Gly Leu Arg Gly Pro Ser Ile Ser Ile
145                 150                 155                 160

Ala Thr Ala Cys Thr Ser Gly Val His Asn Ile Gly His Ala Ala Arg
                165                 170                 175

Ile Ile Ala Tyr Gly Asp Ala Asp Val Met Val Ala Gly Gly Ala Glu
            180                 185                 190

Lys Ala Ser Thr Pro Leu Gly Val Gly Gly Phe Gly Ala Ala Arg Ala
        195                 200                 205

Leu Ser Thr Arg Asn Asp Asn Pro Gln Ala Ala Ser Arg Pro Trp Asp
210                 215                 220
```

-continued

```
Lys Glu Arg Asp Gly Phe Val Leu Gly Asp Gly Ala Gly Met Leu Val
225                 230                 235                 240

Leu Glu Glu Tyr Glu His Ala Lys Lys Arg Gly Ala Lys Ile Tyr Ala
            245                 250                 255

Glu Leu Val Gly Phe Gly Met Ser Ser Asp Ala Tyr His Met Thr Ser
        260                 265                 270

Pro Pro Glu Asn Gly Ala Gly Ala Ala Leu Ala Met Ala Asn Ala Leu
    275                 280                 285

Arg Asp Ala Gly Ile Glu Ala Ser Gln Ile Gly Tyr Val Asn Ala His
290                 295                 300

Gly Thr Ser Thr Pro Ala Gly Asp Lys Ala Glu Ala Gln Ala Val Lys
305                 310                 315                 320

Thr Ile Phe Gly Glu Ala Ala Ser Arg Val Leu Val Ser Ser Thr Lys
                325                 330                 335

Ser Met Thr Gly His Leu Leu Gly Ala Ala Gly Ala Val Glu Ser Ile
            340                 345                 350

Tyr Ser Ile Leu Ala Leu Arg Asp Gln Ala Val Pro Pro Thr Ile Asn
        355                 360                 365

Leu Asp Asn Pro Asp Glu Gly Cys Asp Leu Asp Phe Val Pro His Glu
    370                 375                 380

Ala Arg Gln Val Ser Gly Met Glu Tyr Thr Leu Cys Asn Ser Phe Gly
385                 390                 395                 400

Phe Gly Gly Thr Asn Gly Ser Leu Ile Phe
                405                 410

<210> SEQ ID NO 39
<211> LENGTH: 406
<212> TYPE: PRT
<213> ORGANISM: Escherichia coli

<400> SEQUENCE: 39

Met Lys Arg Ala Val Ile Thr Gly Leu Gly Ile Val Ser Ser Ile Gly
1               5                   10                  15

Asn Asn Gln Gln Glu Val Leu Ala Ser Leu Arg Glu Gly Arg Ser Gly
            20                  25                  30

Ile Thr Phe Ser Gln Glu Leu Lys Asp Ser Gly Met Arg Ser His Val
        35                  40                  45

Trp Gly Asn Val Lys Leu Asp Thr Thr Gly Leu Ile Asp Arg Lys Val
    50                  55                  60

Val Arg Phe Met Ser Asp Ala Ser Ile Tyr Ala Phe Leu Ser Met Glu
65                  70                  75                  80

Gln Ala Ile Ala Asp Ala Gly Leu Ser Pro Glu Ala Tyr Gln Asn Asn
                85                  90                  95

Pro Arg Val Gly Leu Ile Ala Gly Ser Gly Gly Gly Ser Pro Arg Phe
            100                 105                 110

Gln Val Phe Gly Ala Asp Ala Met Arg Gly Pro Arg Gly Leu Lys Ala
        115                 120                 125

Val Gly Pro Tyr Val Val Thr Lys Ala Met Ala Ser Gly Val Ser Ala
    130                 135                 140

Cys Leu Ala Thr Pro Phe Lys Ile His Gly Val Asn Tyr Ser Ile Ser
145                 150                 155                 160

Ser Ala Cys Ala Thr Ser Ala His Cys Ile Gly Asn Ala Val Glu Gln
                165                 170                 175

Ile Gln Leu Gly Lys Gln Asp Ile Val Phe Ala Gly Gly Gly Glu Glu
```

-continued

```
            180                 185                 190

Leu Cys Trp Glu Met Ala Cys Glu Phe Asp Ala Met Gly Ala Leu Ser
        195                 200                 205

Thr Lys Tyr Asn Asp Thr Pro Glu Lys Ala Ser Arg Thr Tyr Asp Ala
    210                 215                 220

His Arg Asp Gly Phe Val Ile Ala Gly Gly Gly Gly Met Val Val Val
225                 230                 235                 240

Glu Glu Leu Glu His Ala Leu Ala Arg Gly Ala His Ile Tyr Ala Glu
                245                 250                 255

Ile Val Gly Tyr Gly Ala Thr Ser Asp Gly Ala Asp Met Val Ala Pro
            260                 265                 270

Ser Gly Glu Gly Ala Val Arg Cys Met Lys Met Ala Met His Gly Val
        275                 280                 285

Asp Thr Pro Ile Asp Tyr Leu Asn Ser His Gly Thr Ser Thr Pro Val
    290                 295                 300

Gly Asp Val Lys Glu Leu Ala Ala Ile Arg Glu Val Phe Gly Asp Lys
305                 310                 315                 320

Ser Pro Ala Ile Ser Ala Thr Lys Ala Met Thr Gly His Ser Leu Gly
                325                 330                 335

Ala Ala Gly Val Gln Glu Ala Ile Tyr Ser Leu Leu Met Leu Glu His
            340                 345                 350

Gly Phe Ile Ala Pro Ser Ile Asn Ile Glu Glu Leu Asp Glu Gln Ala
        355                 360                 365

Ala Gly Leu Asn Ile Val Thr Glu Thr Thr Asp Arg Glu Leu Thr Thr
    370                 375                 380

Val Met Ser Asn Ser Phe Gly Phe Gly Gly Thr Asn Ala Thr Leu Val
385                 390                 395                 400

Met Arg Lys Leu Lys Asp
                405

<210> SEQ ID NO 40
<211> LENGTH: 416
<212> TYPE: PRT
<213> ORGANISM: Mycobacterium tuberculosis

<400> SEQUENCE: 40

Met Ser Gln Pro Ser Thr Ala Asn Gly Gly Phe Pro Ser Val Val Val
1               5                   10                  15

Thr Ala Val Thr Ala Thr Thr Ser Ile Ser Pro Asp Ile Glu Ser Thr
            20                  25                  30

Trp Lys Gly Leu Leu Ala Gly Glu Ser Gly Ile His Ala Leu Glu Asp
        35                  40                  45

Glu Phe Val Thr Lys Trp Asp Leu Ala Val Lys Ile Gly Gly His Leu
    50                  55                  60

Lys Asp Pro Val Asp Ser His Met Gly Arg Leu Asp Met Arg Arg Met
65                  70                  75                  80

Ser Tyr Val Gln Arg Met Gly Lys Leu Leu Gly Gly Gln Leu Trp Glu
                85                  90                  95

Ser Ala Gly Ser Pro Glu Val Asp Pro Asp Arg Phe Ala Val Val Val
            100                 105                 110

Gly Thr Gly Leu Gly Gly Ala Glu Arg Ile Val Glu Ser Tyr Asp Leu
        115                 120                 125

Met Asn Ala Gly Gly Pro Arg Lys Val Ser Pro Leu Ala Val Gln Met
    130                 135                 140
```

-continued

```
Ile Met Pro Asn Gly Ala Ala Val Ile Gly Leu Gln Leu Gly Ala
145                 150                 155                 160

Arg Ala Gly Val Met Thr Pro Val Ser Ala Cys Ser Ser Gly Ser Glu
                165                 170                 175

Ala Ile Ala His Ala Trp Arg Gln Ile Val Met Gly Asp Ala Asp Val
            180                 185                 190

Ala Val Cys Gly Gly Val Glu Gly Pro Ile Glu Ala Leu Pro Ile Ala
        195                 200                 205

Ala Phe Ser Met Met Arg Ala Met Ser Thr Arg Asn Asp Glu Pro Glu
    210                 215                 220

Arg Ala Ser Arg Pro Phe Asp Lys Asp Arg Asp Gly Phe Val Phe Gly
225                 230                 235                 240

Glu Ala Gly Ala Leu Met Leu Ile Glu Thr Glu Glu His Ala Lys Ala
                245                 250                 255

Arg Gly Ala Lys Pro Leu Ala Arg Leu Leu Gly Ala Gly Ile Thr Ser
                260                 265                 270

Asp Ala Phe His Met Val Ala Pro Ala Ala Asp Gly Val Arg Ala Gly
            275                 280                 285

Arg Ala Met Thr Arg Ser Leu Glu Leu Ala Gly Leu Ser Pro Ala Asp
    290                 295                 300

Ile Asp His Val Asn Ala His Gly Thr Ala Thr Pro Ile Gly Asp Ala
305                 310                 315                 320

Ala Glu Ala Asn Ala Ile Arg Val Ala Gly Cys Asp Gln Ala Ala Val
                325                 330                 335

Tyr Ala Pro Lys Ser Ala Leu Gly His Ser Ile Gly Ala Val Gly Ala
                340                 345                 350

Leu Glu Ser Val Leu Thr Val Leu Thr Leu Arg Asp Gly Val Ile Pro
            355                 360                 365

Pro Thr Leu Asn Tyr Glu Thr Pro Asp Pro Glu Ile Asp Leu Asp Val
    370                 375                 380

Val Ala Gly Glu Pro Arg Tyr Gly Asp Tyr Arg Tyr Ala Val Asn Asn
385                 390                 395                 400

Ser Phe Gly Phe Gly Gly His Asn Val Ala Leu Ala Phe Gly Arg Tyr
                405                 410                 415

<210> SEQ ID NO 41
<211> LENGTH: 438
<212> TYPE: PRT
<213> ORGANISM: Mycobacterium tuberculosis

<400> SEQUENCE: 41

Met Gly Val Pro Pro Leu Ala Gly Ala Ser Arg Thr Asp Met Glu Gly
1               5                   10                  15

Thr Phe Ala Arg Pro Met Thr Glu Leu Val Thr Gly Lys Ala Phe Pro
                20                  25                  30

Tyr Val Val Thr Gly Ile Ala Met Thr Thr Ala Leu Ala Thr Asp
            35                  40                  45

Ala Glu Thr Thr Trp Lys Leu Leu Leu Asp Arg Gln Ser Gly Ile Arg
    50                  55                  60

Thr Leu Asp Asp Pro Phe Val Glu Glu Phe Asp Leu Pro Val Arg Ile
65                  70                  75                  80

Gly Gly His Leu Leu Glu Glu Phe Asp His Gln Leu Thr Arg Ile Glu
                85                  90                  95

Leu Arg Arg Met Gly Tyr Leu Gln Arg Met Ser Thr Val Leu Ser Arg
                100                 105                 110
```

-continued

Arg Leu Trp Glu Asn Ala Gly Ser Pro Glu Val Asp Thr Asn Arg Leu
            115                 120                 125
Met Val Ser Ile Gly Thr Gly Leu Gly Ser Ala Glu Glu Leu Val Phe
        130                 135                 140
Ser Tyr Asp Asp Met Arg Ala Arg Gly Met Lys Ala Val Ser Pro Leu
145                 150                 155                 160
Thr Val Gln Lys Tyr Met Pro Asn Gly Ala Ala Ala Val Gly Leu
            165                 170                 175
Glu Arg His Ala Lys Ala Gly Val Met Thr Pro Val Ser Ala Cys Ala
            180                 185                 190
Ser Gly Ala Glu Ala Ile Ala Arg Ala Trp Gln Gln Ile Val Leu Gly
            195                 200                 205
Glu Ala Asp Ala Ile Cys Gly Gly Val Glu Thr Arg Ile Glu Ala
            210                 215                 220
Val Pro Ile Ala Gly Phe Ala Gln Met Arg Ile Val Met Ser Thr Asn
225                 230                 235                 240
Asn Asp Asp Pro Ala Gly Ala Cys Arg Pro Phe Asp Arg Asp Arg Asp
            245                 250                 255
Gly Phe Val Phe Gly Glu Gly Gly Ala Leu Leu Leu Ile Glu Thr Glu
            260                 265                 270
Glu His Ala Lys Ala Arg Gly Ala Asn Ile Leu Ala Arg Ile Met Gly
            275                 280                 285
Ala Ser Ile Thr Ser Asp Gly Phe His Met Val Ala Pro Asp Pro Asn
        290                 295                 300
Gly Glu Arg Ala Gly His Ala Ile Thr Arg Ala Ile Gln Leu Ala Gly
305                 310                 315                 320
Leu Ala Pro Gly Asp Ile Asp His Val Asn Ala His Ala Thr Gly Thr
                325                 330                 335
Gln Val Gly Asp Leu Ala Glu Gly Arg Ala Ile Asn Asn Ala Leu Gly
            340                 345                 350
Gly Asn Arg Pro Ala Val Tyr Ala Pro Lys Ser Ala Leu Gly His Ser
            355                 360                 365
Val Gly Ala Val Gly Ala Val Glu Ser Ile Leu Thr Val Leu Ala Leu
        370                 375                 380
Arg Asp Gln Val Ile Pro Pro Thr Leu Asn Leu Val Asn Leu Asp Pro
385                 390                 395                 400
Glu Ile Asp Leu Asp Val Val Ala Gly Glu Pro Arg Pro Gly Asn Tyr
            405                 410                 415
Arg Tyr Ala Ile Asn Asn Ser Phe Gly Phe Gly Gly His Asn Val Ala
            420                 425                 430
Ile Ala Phe Gly Arg Tyr
        435

<210> SEQ ID NO 42
<211> LENGTH: 418
<212> TYPE: PRT
<213> ORGANISM: Rattus norvegicus

<400> SEQUENCE: 42

Ser Arg Ala Ser Arg Gln Arg Ala Met Glu Glu Val Val Ile Ala
1               5                   10                  15
Gly Met Ser Gly Lys Leu Pro Glu Ser Glu Asn Leu Gln Glu Phe Trp
            20                  25                  30
Ala Asn Leu Ile Gly Gly Val Asp Met Val Thr Asp Asp Asp Arg Arg

```
                    35                  40                  45
Trp Lys Ala Gly Leu Tyr Gly Leu Pro Lys Arg Ser Gly Lys Leu Lys
 50                  55                  60

Asp Leu Ser Lys Phe Asp Ala Ser Phe Phe Gly Val His Pro Lys Gln
 65                  70                  75                  80

Ala His Thr Met Asp Pro Gln Leu Arg Leu Leu Glu Val Ser Tyr
                 85                  90                  95

Glu Ala Ile Val Asp Gly Gly Ile Asn Pro Ala Ser Leu Arg Gly Thr
                100                 105                 110

Asn Thr Gly Val Trp Val Gly Val Ser Gly Ser Glu Ala Ser Glu Ala
                115                 120                 125

Leu Ser Arg Asp Pro Glu Thr Leu Leu Gly Tyr Ser Met Val Gly Cys
130                 135                 140

Gln Arg Ala Met Met Ala Asn Arg Leu Ser Phe Phe Phe Asp Phe Lys
145                 150                 155                 160

Gly Pro Ser Ile Ala Leu Asp Thr Ala Cys Ser Ser Ser Leu Leu Ala
                165                 170                 175

Leu Gln Asn Ala Tyr Gln Ala Ile Arg Ser Gly Glu Cys Pro Ala Ala
                180                 185                 190

Ile Val Gly Gly Ile Asn Leu Leu Lys Pro Asn Thr Ser Val Gln
                195                 200                 205

Phe Met Lys Leu Gly Met Leu Ser Pro Asp Gly Thr Cys Arg Ser Phe
210                 215                 220

Asp Asp Ser Gly Asn Gly Tyr Cys Arg Ala Glu Ala Val Val Ala Val
225                 230                 235                 240

Leu Leu Thr Lys Lys Ser Leu Ala Arg Arg Val Tyr Ala Thr Ile Leu
                245                 250                 255

Asn Ala Gly Thr Asn Thr Asp Gly Cys Lys Glu Gln Gly Val Thr Phe
                260                 265                 270

Pro Ser Gly Glu Ala Gln Glu Gln Leu Ile Arg Ser Leu Tyr Gln Pro
                275                 280                 285

Gly Gly Val Ala Pro Glu Ser Leu Glu Tyr Ile Glu Ala His Gly Thr
290                 295                 300

Gly Thr Lys Val Gly Asp Pro Gln Glu Leu Asn Gly Ile Thr Arg Ser
305                 310                 315                 320

Leu Cys Ala Phe Arg Gln Ser Pro Leu Leu Ile Gly Ser Thr Lys Ser
                325                 330                 335

Asn Met Gly His Pro Glu Pro Ala Ser Gly Leu Ala Ala Leu Thr Lys
                340                 345                 350

Val Leu Leu Ser Leu Glu Asn Gly Val Trp Ala Pro Asn Leu His Phe
                355                 360                 365

His Asn Pro Asn Pro Glu Ile Pro Ala Leu Leu Asp Gly Arg Leu Gln
                370                 375                 380

Val Val Asp Arg Pro Leu Pro Val Arg Gly Ile Val Gly Ile Asn
385                 390                 395                 400

Ser Phe Gly Phe Gly Gly Ala Asn Val His Val Ile Leu Gln Pro Asn
                405                 410                 415

Ala Ser

<210> SEQ ID NO 43
<211> LENGTH: 401
<212> TYPE: PRT
<213> ORGANISM: Rhizobium sp. Nodulation Protein E
```

<400> SEQUENCE: 43

```
Met Asp Arg Arg Val Val Ile Thr Gly Ile Gly Leu Cys Gly Leu
 1               5                  10                  15

Gly Thr Asn Ala Ala Ser Ile Trp Lys Glu Met Arg Glu Gly Pro Ser
            20                  25                  30

Ala Ile Ser Pro Ile Ile Thr Thr Asp Leu Tyr Asp Leu Glu Gly Thr
            35                  40                  45

Val Gly Leu Glu Ile Lys Ala Ile Pro Glu His Asp Ile Pro Arg Lys
    50                  55                  60

Gln Leu Val Ser Met Asp Arg Phe Ser Leu Leu Ala Val Ile Ala Ala
 65                  70                  75                  80

Thr Glu Ala Met Lys Gln Ala Gly Leu Ser Cys Asp Glu Gln Asn Ala
                85                  90                  95

His Arg Phe Gly Ala Ala Met Gly Leu Gly Gly Pro Gly Trp Asp Thr
            100                 105                 110

Ile Glu Thr Tyr Arg Ser Ile Leu Leu Asp Gly Val Thr Arg Ala
            115                 120                 125

Arg Ile Phe Thr Ala Pro Lys Gly Met Pro Ser Ala Ala Gly His
130                 135                 140

Val Ser Ile Phe Leu Gly Leu Arg Gly Pro Val Phe Gly Val Thr Ser
145                 150                 155                 160

Ala Cys Ala Ala Gly Asn His Ala Ile Ala Ser Ala Val Asp Gln Ile
                165                 170                 175

Arg Leu Gly Arg Ala Asp Val Met Leu Ala Gly Gly Ser Asp Ala Pro
            180                 185                 190

Leu Thr Trp Gly Val Leu Lys Ser Trp Glu Ala Leu Arg Val Leu Ala
            195                 200                 205

Pro Asp Thr Cys Arg Pro Phe Ser Ala Asp Arg Lys Gly Val Val Leu
    210                 215                 220

Gly Glu Gly Ala Gly Met Ala Val Leu Glu Ser Tyr Glu His Ala Ala
225                 230                 235                 240

Ala Arg Gly Ala Thr Met Leu Ala Glu Val Ala Gly Ile Gly Leu Ser
                245                 250                 255

Gly Asp Ala Tyr Asp Ile Val Met Pro Ser Ile Glu Gly Pro Glu Ala
            260                 265                 270

Ala Met Arg Ser Cys Leu Ala Asp Ala Glu Leu Asn Pro Asp Asp Val
            275                 280                 285

Asp Tyr Leu Asn Ala His Gly Thr Gly Thr Val Ala Asn Asp Glu Met
    290                 295                 300

Glu Thr Ala Ala Ile Lys Arg Val Phe Gly Asp His Ala Phe Gln Met
305                 310                 315                 320

Ser Val Ser Ser Thr Lys Ser Met His Ala His Cys Leu Gly Ala Ala
                325                 330                 335

Ser Ala Leu Glu Met Ile Ala Cys Val Met Ala Ile Gln Glu Gly Val
            340                 345                 350

Ile Pro Pro Thr Ala Asn Tyr Arg Glu Pro Asp Pro Gln Cys Asp Leu
            355                 360                 365

Asp Val Thr Pro Asn Val Pro Arg Glu Gln Arg Cys Gly Ser Met Ser
    370                 375                 380

Asn Ala Phe Ala Met Gly Gly Thr Asn Ala Val Leu Ala Phe Arg Gln
385                 390                 395                 400

Val
```

<210> SEQ ID NO 44
<211> LENGTH: 419
<212> TYPE: PRT
<213> ORGANISM: Streptomyces polyketide synthase

<400> SEQUENCE: 44

```
Val Asn Arg Arg Ile Val Ile Thr Gly Ile Gly Val Val Ala Pro Gly
1               5                   10                  15

Ala Val Gly Thr Lys Pro Phe Trp Glu Leu Leu Ser Gly Thr Thr
            20                  25                  30

Ala Thr Arg Ala Ile Ser Thr Phe Asp Ala Thr Pro Phe Arg Ser Arg
        35                  40                  45

Ile Ala Ala Glu Cys Asp Phe Asp Pro Val Ala Ala Gly Leu Ser Ala
    50                  55                  60

Glu Gln Ala Arg Arg Leu Asp Arg Ala Gly Gln Phe Ala Leu Val Ala
65                  70                  75                  80

Gly Gln Glu Ala Leu Ala Asp Ser Gly Leu Arg Ile Asp Glu Asp Ser
                85                  90                  95

Ala His Arg Val Gly Val Cys Val Gly Thr Ala Val Gly Cys Thr Gln
            100                 105                 110

Lys Leu Glu Ser Glu Tyr Val Ala Leu Ser Ala Gly Gly Ala His Trp
        115                 120                 125

Val Val Asp Pro Gly Arg Gly Ser Pro Glu Leu Tyr Asp Tyr Phe Val
130                 135                 140

Pro Ser Ser Leu Ala Ala Glu Val Ala Trp Leu Ala Gly Ala Glu Gly
145                 150                 155                 160

Pro Val Asn Ile Val Ser Ala Gly Cys Thr Ser Gly Ile Asp Ser Ile
                165                 170                 175

Gly Tyr Ala Cys Glu Leu Ile Arg Glu Gly Thr Val Asp Ala Met Val
            180                 185                 190

Ala Gly Gly Val Asp Ala Pro Ile Ala Pro Ile Thr Val Ala Cys Phe
        195                 200                 205

Asp Ala Ile Arg Ala Thr Ser Asp His Asn Asp Thr Pro Glu Thr Ala
    210                 215                 220

Ser Arg Pro Phe Ser Arg Ser Arg Asn Gly Phe Val Leu Gly Glu Gly
225                 230                 235                 240

Gly Ala Ile Val Val Leu Glu Glu Ala Glu Ala Ala Val Arg Arg Gly
                245                 250                 255

Ala Arg Ile Tyr Ala Glu Ile Gly Gly Tyr Ala Ser Arg Gly Asn Ala
            260                 265                 270

Tyr His Met Thr Gly Leu Arg Ala Asp Gly Ala Glu Met Ala Ala Ala
        275                 280                 285

Ile Thr Ala Ala Leu Asp Glu Ala Arg Arg Asp Pro Ser Asp Val Asp
    290                 295                 300

Tyr Val Asn Ala His Gly Thr Ala Thr Lys Gln Asn Asp Arg His Glu
305                 310                 315                 320

Thr Ser Ala Phe Lys Arg Ser Leu Gly Glu His Ala Tyr Arg Val Pro
                325                 330                 335

Ile Ser Ser Ile Lys Ser Met Ile Gly His Ser Leu Gly Ala Val Gly
            340                 345                 350

Ser Leu Glu Val Ala Ala Thr Ala Leu Ala Val Glu Tyr Gly Val Ile
        355                 360                 365

Pro Pro Thr Ala Asn Leu His Asp Pro Asp Pro Glu Leu Asp Leu Asp
    370                 375                 380
```

Tyr Val Pro Leu Thr Ala Arg Glu Lys Arg Val Arg His Ala Leu Thr
385                 390                 395                 400

Val Gly Ser Gly Phe Gly Phe Gln Ser Ala Met Leu Leu Ser Arg
            405                 410                 415

Leu Glu Arg

<210> SEQ ID NO 45
<211> LENGTH: 416
<212> TYPE: PRT
<213> ORGANISM: Synechocystis sp.

<400> SEQUENCE: 45

Met Ala Asn Leu Glu Lys Lys Arg Val Val Thr Gly Leu Gly Ala
1               5                   10                  15

Ile Thr Pro Ile Gly Asn Thr Leu Gln Asp Tyr Trp Gln Gly Leu Met
                20                  25                  30

Glu Gly Arg Asn Gly Ile Gly Pro Ile Thr Arg Phe Asp Ala Ser Asp
            35                  40                  45

Gln Ala Cys Arg Phe Gly Gly Glu Val Lys Asp Phe Asp Ala Thr Gln
50                  55                  60

Phe Leu Asp Arg Lys Glu Ala Lys Arg Met Asp Arg Phe Cys His Phe
65                  70                  75                  80

Ala Val Cys Ala Ser Gln Gln Ala Ile Asn Asp Ala Lys Leu Val Ile
                85                  90                  95

Asn Glu Leu Asn Ala Asp Glu Ile Gly Val Leu Ile Gly Thr Gly Ile
            100                 105                 110

Gly Gly Leu Lys Val Leu Glu Asp Gln Gln Thr Ile Leu Leu Asp Lys
        115                 120                 125

Gly Pro Ser Arg Cys Ser Pro Phe Met Ile Pro Met Met Ile Ala Asn
130                 135                 140

Met Ala Ser Gly Leu Thr Ala Ile Asn Leu Gly Ala Lys Gly Pro Asn
145                 150                 155                 160

Asn Cys Thr Val Thr Ala Cys Ala Ala Gly Ser Asn Ala Ile Gly Asp
                165                 170                 175

Ala Phe Arg Leu Val Gln Asn Gly Tyr Ala Lys Ala Met Ile Cys Gly
            180                 185                 190

Gly Thr Glu Ala Ala Ile Thr Pro Leu Ser Tyr Ala Gly Phe Ala Ser
        195                 200                 205

Ala Arg Ala Leu Ser Phe Arg Asn Asp Pro Leu His Ala Ser Arg
210                 215                 220

Pro Phe Asp Lys Asp Arg Asp Gly Phe Val Met Gly Glu Gly Ser Gly
225                 230                 235                 240

Ile Leu Ile Leu Glu Glu Leu Glu Ser Ala Leu Ala Arg Gly Ala Lys
                245                 250                 255

Ile Tyr Gly Glu Met Val Gly Tyr Ala Met Thr Cys Asp Ala Tyr His
            260                 265                 270

Ile Thr Ala Pro Val Pro Asp Gly Arg Gly Ala Thr Arg Ala Ile Ala
        275                 280                 285

Trp Ala Leu Lys Asp Ser Gly Leu Lys Pro Glu Met Val Ser Tyr Ile
290                 295                 300

Asn Ala His Gly Thr Ser Thr Pro Ala Asn Asp Val Thr Glu Thr Arg
305                 310                 315                 320

Ala Ile Lys Gln Ala Leu Gly Asn His Ala Tyr Asn Ile Ala Val Ser
                325                 330                 335

-continued

```
Ser Thr Lys Ser Met Thr Gly His Leu Leu Gly Gly Ser Gly Gly Ile
            340                 345                 350
Glu Ala Val Ala Thr Val Met Ala Ile Ala Glu Asp Lys Val Pro Pro
            355                 360                 365
Thr Ile Asn Leu Glu Asn Pro Asp Pro Glu Cys Asp Leu Asp Tyr Val
            370                 375                 380
Pro Gly Gln Ser Arg Ala Leu Ile Val Asp Val Ala Leu Ser Asn Ser
385                 390                 395                 400
Phe Gly Phe Gly Gly His Asn Val Thr Leu Ala Phe Lys Lys Tyr Gln
                    405                 410                 415
```

<210> SEQ ID NO 46
<211> LENGTH: 441
<212> TYPE: PRT
<213> ORGANISM: Vibrio harveyi

<400> SEQUENCE: 46

```
Ser Asp Tyr His Asn His Phe Ile Asn Val Lys Ala Val Ala Arg Pro
1               5                   10                  15
Leu Phe Phe Cys Leu Phe Trp Arg Thr Ser Val Ala Asn Asn Arg Arg
            20                  25                  30
Val Val Ile Thr Gly Leu Gly Ile Val Ser Pro Val Gly Asn Thr Val
            35                  40                  45
Ala Thr Ala Trp Glu Ala Ile Lys Ser Gly Ile Ser Gly Ile Glu Asn
            50                  55                  60
Ile Glu His Phe Asp Thr Thr Asn Phe Ser Thr Lys Phe Ala Gly Leu
65                  70                  75                  80
Val Asn Asp Phe Asp Ala Glu Ser Val Gly Ile Asn Arg Lys Asp Cys
                    85                  90                  95
Arg Lys Met Asp Leu Phe Ile Gln Tyr Gly Ile Ala Ala Ala Glu Gln
            100                 105                 110
Ala Leu Thr Asp Ser Gly Leu Glu Ile Thr Glu Gln Asn Ala Thr Arg
            115                 120                 125
Ile Gly Thr Ala Ile Gly Ser Gly Ile Gly Gly Leu Gly Leu Ile Glu
130                 135                 140
Gln Asn Val His Ser Phe Val Lys Gly Gly Ala Arg Lys Val Ser Pro
145                 150                 155                 160
Phe Phe Val Pro Ala Thr Ile Val Asn Met Val Ala Gly His Val Ser
                    165                 170                 175
Ile Arg Asn Asn Leu Lys Gly Pro Asn Ile Ala Ile Ala Thr Ala Cys
            180                 185                 190
Thr Ser Gly Thr His Cys Ile Gly Gln Ser Ala Arg Met Ile Ala Tyr
            195                 200                 205
Gly Asp Ala Asp Val Met Val Ala Gly Gly Ala Glu Lys Ala Ser Thr
            210                 215                 220
Glu Met Gly Leu Ala Gly Phe Gly Ser Ala Lys Ala Leu Ser Thr Arg
225                 230                 235                 240
Asn Asp Asp Pro Gln Lys Ala Ser Arg Pro Trp Asp Lys Asp Arg Asp
                    245                 250                 255
Gly Phe Val Leu Gly Asp Gly Ala Gly Val Leu Val Met Glu Glu Tyr
            260                 265                 270
Glu His Ala Val Ala Arg Gly Ala Thr Ile Tyr Ala Glu Leu Ala Gly
            275                 280                 285
Phe Gly Met Ser Gly Asp Ala Phe His Met Thr Ser Pro Pro Glu Asp
```

-continued

```
            290                 295                 300

Gly Ala Gly Ala Ala Leu Ser Met Asn Asn Ala Ile Ala Asp Ala Gly
305                 310                 315                 320

Ile Thr Ala Asp Lys Val Gly Tyr Val Asn Ala His Gly Thr Ser Thr
                325                 330                 335

Pro Ala Gly Asp Lys Ala Glu Thr Ala Ala Val Lys Ser Val Phe Gly
                340                 345                 350

Glu His Ala Tyr Thr Leu Ala Val Ser Ser Thr Lys Ser Met Thr Gly
                355                 360                 365

His Leu Leu Gly Ala Ala Gly Ala Ile Glu Ala Ile Phe Thr Ile Leu
                370                 375                 380

Ala Leu Lys Asp Gln Ile Leu Pro Pro Thr Ile Asn Leu Glu Asn Pro
385                 390                 395                 400

Ser Glu Gly Cys Asp Leu Asp Tyr Val Thr Asp Gly Ala Arg Pro Val
                405                 410                 415

Asn Met Glu Tyr Ala Leu Ser Asn Ser Phe Gly Phe Gly Gly Thr Asn
                420                 425                 430

Gly Ser Leu Leu Phe Lys Lys Ala Asp
                435                 440

<210> SEQ ID NO 47
<211> LENGTH: 409
<212> TYPE: PRT
<213> ORGANISM: Escherichia coli

<400> SEQUENCE: 47

Ser Lys Arg Arg Val Val Val Thr Gly Leu Gly Met Leu Ser Pro Val
1               5                   10                  15

Gly Asn Thr Val Glu Ser Thr Trp Lys Ala Leu Leu Ala Gly Gln Ser
                20                  25                  30

Gly Ile Ser Leu Ile Asp His Phe Asp Thr Ser Ala Tyr Ala Thr Lys
            35                  40                  45

Phe Ala Gly Leu Val Lys Asp Phe Asn Cys Glu Asp Ile Ile Ser Arg
    50                  55                  60

Lys Glu Gln Arg Lys Met Asp Ala Phe Ile Gln Tyr Gly Ile Val Ala
65                  70                  75                  80

Gly Val Gln Ala Met Gln Asp Ser Gly Leu Glu Ile Thr Glu Glu Asn
                85                  90                  95

Ala Thr Arg Ile Gly Ala Ala Ile Gly Ser Gly Ile Gly Gly Leu Gly
                100                 105                 110

Leu Ile Glu Glu Asn His Thr Ser Leu Met Asn Gly Gly Pro Arg Lys
            115                 120                 125

Ile Ser Pro Phe Phe Val Pro Ser Thr Ile Val Asn Met Val Ala Gly
    130                 135                 140

His Leu Thr Ile Met Tyr Gly Leu Arg Gly Pro Ser Ile Ser Ile Ala
145                 150                 155                 160

Thr Ala Cys Thr Ser Gly Val His Asn Ile Gly His Ala Ala Arg Ile
                165                 170                 175

Ile Ala Tyr Gly Asp Ala Asp Val Met Val Ala Gly Gly Ala Glu Lys
                180                 185                 190

Ala Ser Thr Pro Leu Gly Val Gly Gly Phe Gly Ala Ala Arg Ala Leu
            195                 200                 205

Ser Thr Arg Asn Asp Asn Pro Gln Ala Ala Ser Arg Pro Trp Asp Lys
    210                 215                 220
```

-continued

| | | | | | | | | | | | | |
|---|---|---|---|---|---|---|---|---|---|---|---|---|
| Glu 225 | Arg | Asp | Gly | Phe 230 | Val | Leu | Gly | Asp | Gly 235 | Ala | Gly | Met | Leu | Val | Leu 240 |
| Glu | Glu | Tyr | Glu 245 | His | Ala | Lys | Lys | Arg 250 | Gly | Ala | Lys | Ile | Tyr 255 | Ala | Glu |
| Leu | Val | Gly | Phe 260 | Gly | Met | Ser | Ser | Asp 265 | Ala | Tyr | His | Met | Thr 270 | Ser | Pro |
| Pro | Glu | Asn 275 | Gly | Ala | Gly | Ala | Ala 280 | Leu | Ala | Met | Ala | Asn 285 | Ala | Leu | Arg |
| Asp | Ala 290 | Gly | Ile | Glu | Ala 295 | Ser | Gln | Ile | Gly | Tyr 300 | Val | Asn | Ala | His | Gly |
| Thr 305 | Ser | Thr | Pro | Ala | Gly 310 | Asp | Lys | Ala | Glu | Ala 315 | Gln | Ala | Val | Lys | Thr 320 |
| Ile | Phe | Gly | Glu | Ala 325 | Ala | Ser | Arg | Val | Leu 330 | Val | Ser | Ser | Thr | Lys 335 | Ser |
| Met | Thr | Gly | His 340 | Leu | Leu | Gly | Ala | Ala 345 | Gly | Ala | Val | Glu | Ser 350 | Ile | Tyr |
| Ser | Ile | Leu 355 | Ala | Leu | Arg | Asp | Gln 360 | Ala | Val | Pro | Pro | Thr 365 | Ile | Asn | Leu |
| Asp | Asn | Pro 370 | Asp | Glu | Gly | Cys 375 | Asp | Leu | Asp | Phe | Val 380 | Pro | His | Glu | Ala |
| Arg 385 | Gln | Val | Ser | Gly | Met 390 | Glu | Tyr | Thr | Leu | Cys 395 | Asn | Ser | Phe | Gly | Phe 400 |
| Gly | Gly | Thr | Asn | Gly 405 | Ser | Leu | Ile | Phe | | | | | | | |